(12) United States Patent
Linge et al.

(10) Patent No.: US 11,466,022 B2
(45) Date of Patent: Oct. 11, 2022

(54) MATERIALS FOR ORGANIC ELECTROLUMINESCENT DEVICES

(71) Applicant: Merck Patent GmbH, Darmstadt (DE)

(72) Inventors: Rouven Linge, Darmstadt (DE); Sebastian Meyer, Frankfurt am Main (DE); Lara-Isabel Rodriguez, Darmstadt (DE); Aaron Lackner, Mannheim (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 17/272,361

(22) PCT Filed: Aug. 26, 2019

(86) PCT No.: PCT/EP2019/072697
§ 371 (c)(1),
(2) Date: Mar. 1, 2021

(87) PCT Pub. No.: WO2020/043657
PCT Pub. Date: Mar. 5, 2020

(65) Prior Publication Data
US 2022/0204520 A1 Jun. 30, 2022

(30) Foreign Application Priority Data

Aug. 28, 2018 (EP) .................... 18191175

(51) Int. Cl.
*C07D 493/00* (2006.01)
*H01L 51/50* (2006.01)
*H01L 51/00* (2006.01)

(52) U.S. Cl.
CPC ........ *C07D 493/00* (2013.01); *H01L 51/0061* (2013.01); *H01L 51/0073* (2013.01); *H01L 51/5012* (2013.01)

(58) Field of Classification Search
CPC ........... H01L 51/50112; H01L 51/0061; H01L 51/5012; H01L 51/0073; H01L 51/006; C07D 403/14; C07D 493/00; C07D 495/04; C07D 487/04; C09K 2211/1044; C09K 2211/1007

See application file for complete search history.

(56) References Cited

U.S. PATENT DOCUMENTS

| | | | |
|---|---|---|---|
| 4,539,507 A | 9/1985 | Vanslyke et al. | |
| 10,879,482 B2 * | 12/2020 | Ogiwara | ............. H01L 51/0059 |
| 2017/0012214 A1 | 1/2017 | Pyo et al. | |
| 2020/0369678 A1 * | 11/2020 | Linge | .................... C07D 493/20 |
| 2021/0269445 A1 * | 9/2021 | Kang | ...................... H01L 51/00 |

FOREIGN PATENT DOCUMENTS

| CN | 107573306 A | 1/2018 |
|---|---|---|
| CN | 107573308 A | 1/2018 |
| CN | 107573925 A | 1/2018 |
| CN | 108017606 A | 5/2018 |
| CN | 108341795 A | 7/2018 |

OTHER PUBLICATIONS

International Preliminary Report on Patentability received for PCT Patent Application No. PCT/EP2019/072697, dated Mar. 11, 2021, 7 pages.
International Search Report and Written Opinion received for PCT Patent Application No. PCT/EP2019/072697, dated Oct. 15, 2019, 8 pages.
Zhao et al., "Horizontal molecular orientation in solution-processed organic light-emitting diodes", Appl. Phys. Lett. vol. 106, 2015, pp. 063301-1-063301-5.

\* cited by examiner

*Primary Examiner* — Caridad Everhart
(74) *Attorney, Agent, or Firm* — Faegre Drinker Biddle & Reath LLP

(57) ABSTRACT

The present invention relates to compounds of the formula (1) which are suitable for use in electronic devices, in particular organic electroluminescent devices, and to electronic devices which comprise these compounds.

21 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2019/072697, filed Aug. 26, 2019, which claims benefit of European Application No. 18191175.1, filed Aug. 28, 2018, both of which are incorporated herein by reference in their entirety.

The present invention relates to a compound of the formula (1), to the use of the compound in an electronic device, and to an electronic device comprising a compound of the formula (1). The present invention furthermore relates to a process for the preparation of a compound of the formula (1) and to a formulation comprising one or more compounds of the formula (1).

The development of functional compounds for use in electronic devices is currently the subject of intensive research. The aim is, in particular, the development of compounds with which improved properties of electronic devices in one or more relevant points can be achieved, such as, for example, power efficiency and lifetime of the device as well as colour coordinates of the emitted light.

In accordance with the present invention, the term electronic device is taken to mean, inter alia, organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs).

Of particular interest is the provision of compounds for use in the last-mentioned electronic devices called OLEDs. The general structure and the functional principle of OLEDs are known to the person skilled in the art and are described, for example, in U.S. Pat. No. 4,539,507.

Further improvements are still necessary with respect to the performance data of OLEDs, in particular with a view to broad commercial use, for example in display devices or as light sources. Of particular importance in this connection are the lifetime, the efficiency and the operating voltage of the OLEDs and as well as the colour values achieved. In particular, in case of blue-emitting OLEDs, there is potential for improvement with respect to the lifetime and the efficiency of the devices.

An important starting point for achieving the said improvements is the choice of the emitter compound and of the host compound employed in the electronic device.

Blue-fluorescent emitters known from the prior art are a multiplicity of compounds. Arylamines containing one or more condensed aryl are known from the prior art. Arylamines containing dibenzofuran groups (as disclosed in US 2017/0012214) or indenodibenzofuran groups (as disclosed in CN 10753308) are also known from the prior art.

However, there is still a need for further fluorescent emitters, especially blue-fluorescent emitters, which may be employed in OLEDs and lead to OLEDs having very good properties in terms of lifetime, color emission and efficiency.

More particularly, there is a need for blue-fluorescent emitters combining very high efficiencies, very good life time and suitable color coordinates as well as high color purity.

Furthermore, it is known that an OLED may comprise different layers, which may be applied either by vapour deposition in a vacuum chamber or by processing from a solution. The processes based on vapour deposition lead to good results, but such processes are complex and expensive. Therefore, there is also a need for OLED materials that can be easily and reliably processed from solution. In this case, the materials should have good solubility properties in the solution that comprises them. Additionally, the OLED materials that are processed from a solution should be able to orientate themselves in the deposited film to improve the overall efficiency of the OLED. The term orientation means here the horizontal molecular orientation of the compounds, as explained in Zhao et al., Horizontal molecular orientation in solution-processed organic light-emitting diodes, Appl. Phys. Lett. 106063301, 2015.

The present invention is thus based on the technical object of providing compounds which are suitable for use in electronic devices, such as OLEDs, more particularly as blue-fluorescent emitters or matrix materials and, which are suitable for vacuum processing or for solution processing.

In investigations on novel compounds for use in electronic devices, it has now been found, that compounds of formula (1) as defined below are eminently suitable for use in electronic devices. In particular, they achieve one or more, preferably all, of the above-mentioned technical objects.

The invention thus relates to compounds of formula (1),

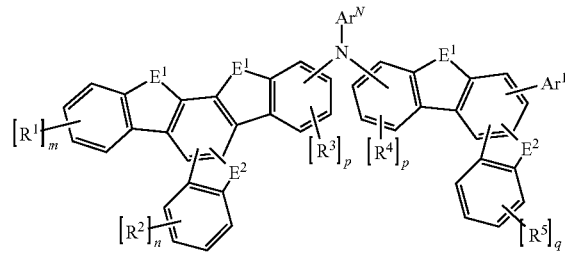

formula (1)

where the following applies to the symbols and indices used:

$Ar^1$, $Ar^N$ are on each occurrence, identically or differently, selected from an aromatic or heteroaromatic ring system having 5 to 60 aromatic ring atoms, which may in each case be substituted by one or more radicals R;

$E^1$ is on each occurrence, identically or differently, selected from —$BR^O$—, —$C(R^O)_2$—, —$C(R^O)_2$—$C(R^O)_2$—, —$C(R^O)_2$—O—, —$C(R^O)_2$—S—, —$R^OC$=$CR^O$—, —$R^OC$=N—, $Si(R^O)_2$, —$Si(R^O)_2$—$Si(R^O)_2$—, —C(=O)—, —C(=$NR^O$)—, —C(=C($R^O)_2$)—, —O—, —S—, —S(=O)—, —$SO_2$—, —N($R^O$)—, —P($R^O$)— and —P((=O)$R^O$)—; or $E^1$ is a group of formula (E-1),

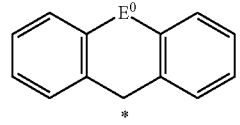

formula (E-1)

where the symbol * in formula (E-1) indicates the corresponding group $E^1$ in formula (1); and $E^O$ is identically or differently on each occurrence, selected from the group consisting of a single bond, —$BR^O$—, —$C(R^O)_2$—, —$C(R^O)_2$—$C(R^O)_2$—, —$C(R^O)_2$—O—, —$C(R^O)_2$—S—, —$R^OC$=$CR^O$—, —$R^OC$=N—, $Si(R^O)_2$, —Si(R⁰)₂—Si(R⁰)₂—, —C(=O)—, —C(=NR⁰)—, —C(=C(R⁰)₂)—, —O—, —S—, —S(=O)—, —SO₂—, —N(R⁰)—, —P(R⁰)— and —P((=O)R⁰)—;

$E^2$ is, identically or differently, on each occurrence, selected from the group consisting of —O—, —S—, —S(=O)— and —SO₂—;

$R^0$ to $R^5$ stand on each occurrence, identically or differently, for H, D, F, Cl, Br, I, CHO, CN, N(Ar)₂, C(=O)Ar, P(=O)(Ar)₂, S(=O)Ar, S(=O)₂Ar, NO₂, Si(R)₃, B(OR)₂, OSO₂R, a straight-chain alkyl, alkoxy or thioalkyl group having 1 to 40 C atoms or branched or cyclic alkyl, alkoxy or thioalkyl group having 3 to 40 C atoms, each of which may be substituted by one or more radicals R, where in each case one or more non-adjacent CH₂ groups may be replaced by RC=CR, C≡C, Si(R)₂, Ge(R)₂, Sn(R)₂, C=O, C=S, C=Se, P(=O)(R), SO, SO₂, O, S or CONR and where one or more H atoms may be replaced by D, F, Cl, Br, I, CN or NO₂, an aromatic or heteroaromatic ring system having 5 to 60 aromatic ring atoms, which may in each case be substituted by one or more radicals R, or an aryloxy group having 5 to 60 aromatic ring atoms, which may be substituted by one or more radicals R, where two adjacent substituents $R^0$, and/or two adjacent substituents $R^1$, and/or two adjacent substituents $R^2$, and/or two adjacent substituents $R^3$, and/or two adjacent substituents $R^4$, and/or two adjacent substituents $R^5$ may form a mono- or polycyclic, aliphatic ring system or aromatic ring system, which may be substituted by one or more radicals R;

m, n, q stand on each occurrence, identically or differently, for an integer selected from 0, 1, 2, 3 or 4;

p stands on each occurrence, identically or differently, for an integer selected from 0, 1, 2 or 3;

R stands on each occurrence, identically or differently, for H, D, F, Cl, Br, I, CHO, CN, N(Ar)₂, C(=O)Ar, P(=O)(Ar)₂, S(=O)Ar, S(=O)₂Ar, NO₂, Si(R')₃, B(OR')₂, OSO₂R', a straight-chain alkyl, alkoxy or thioalkyl group having 1 to 40 C atoms or branched or cyclic alkyl, alkoxy or thioalkyl groups having 3 to 40 C atoms, each of which may be substituted by one or more radicals R', where in each case one or more non-adjacent CH₂ groups may be replaced by R'C=CR', C≡C, Si(R')₂, Ge(R')₂, Sn(R')₂, C=O, C=S, C=Se, P(=O)(R'), SO, SO₂, O, S or CONR' and where one or more H atoms may be replaced by D, F, Cl, Br, I, CN or NO₂, an aromatic or heteroaromatic ring system having 5 to 60 aromatic ring atoms, which may in each case be substituted by one or more radicals R', or an aryloxy group having 5 to 60 aromatic ring atoms, which may be substituted by one or more radicals R', where two adjacent substituents R may form a mono- or polycyclic, aliphatic ring system or aromatic ring system, which may be substituted by one or more radicals R';

Ar is on each occurrence, identically or differently, an aromatic or heteroaromatic ring system having 5 to 24 aromatic ring atoms, which may in each case also be substituted by one or more radicals R';

R' stands on each occurrence, identically or differently, for H, D, F, Cl, Br, I, CN, a straight-chain alkyl, alkoxy or thioalkyl group having 1 to 20 C atoms or branched or cyclic alkyl, alkoxy or thioalkyl group having 3 to 20 C atoms, where in each case one or more non-adjacent CH₂ groups may be replaced by SO, SO₂, O, S and where one or more H atoms may be replaced by D, F, Cl, Br or I, or an aromatic or heteroaromatic ring system having 5 to 24 C atoms.

Adjacent substituents in the sense of the present invention are substituents which are bonded to atoms which are linked directly to one another or which are bonded to the same atom.

Furthermore, the following definitions of chemical groups apply for the purposes of the present application:

An aryl group in the sense of this invention contains 6 to 60 aromatic ring atoms, preferably 6 to 40 aromatic ring atoms, more preferably 6 to 20 aromatic ring atoms; a heteroaryl group in the sense of this invention contains 5 to 60 aromatic ring atoms, preferably 5 to 40 aromatic ring atoms, more preferably 5 to 20 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system, preferably 6 to 40 C atoms, more preferably 6 to 20 C atoms. A heteroaromatic ring system in the sense of this invention contains 5 to 60 aromatic ring atoms, preferably 5 to 40 aromatic ring atoms, more preferably 5 to 20 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an sp$^3$-hybridised C, Si, N or O atom, an sp$^2$-hybridised C or N atom or an sp-hybridised C atom. Thus, for example, systems such as 9,9'-spirobifluorene, 9,9'-diaryl-fluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or CH$_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cyclo-heptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyl-oxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present application, intended to be taken to mean, inter alia, that the two radicals are linked to one another by a chemical bond. This is illustrated by the following schemes:

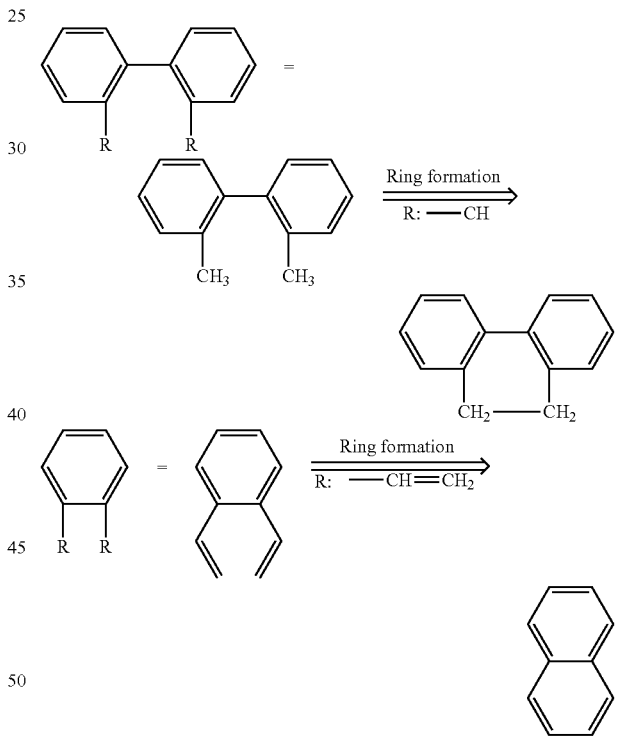

Furthermore, however, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

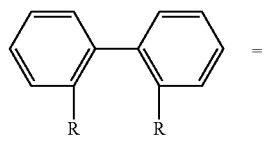

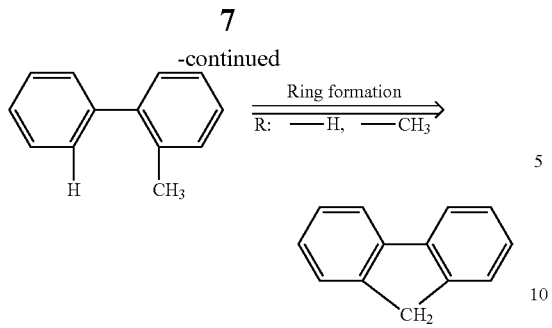

In accordance with a preferred embodiment, the group $E^1$ is on each occurrence, identically or differently, selected from —C(R$^0$)$_2$—, —Si(R$^0$)$_2$—, —O—, —S—, —N(R$^0$)—; or $E^1$ is a group of formula (E-1),

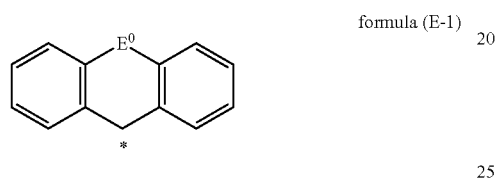

formula (E-1)

where the symbol * in formula (E-1) indicates the corresponding group $E^1$ in formula (1) and where $E^0$ has the same meaning as above.

In accordance with a very preferred embodiment, the group $E^1$ stands for —C(R$^0$)$_2$—.

In accordance with another very preferred embodiment, the group $E^1$ stands for a group of formula (E-1) where, $E^0$ stands for a single bond or —C(R$^0$)$_2$—.

Preferably, the group $E^2$ is on each occurrence, identically or differently, selected from —O— or —S—. Very preferably, the group $E^2$ stands for —O—.

Preferably, Ar$^N$ stands for phenyl, biphenyl, fluorene, spirobifluorene, naphthalene, phenanthrene, dibenzofuran, dibenzothiophene, carbazole, pyridine, pyrimidine, pyrazine, pyridazine, triazine, benzopyridine, benzopyridazine, benzopyrimidine or quinazoline, or for a combination of two to six of these groups, each of which may be substituted by one or more radicals R.

Very preferably, Ar$^N$ stands for phenyl, biphenyl, fluorene, naphthalene, phenanthrene, dibenzofuran, dibenzothiophene, carbazole, or for a combination of two to six of these groups, each of which may be substituted by one or more radicals R.

Particularly preferably, Ar$^N$ stands for a group of one of the formulae (ArN-1) to (ArN-22) as depicted in the table below:

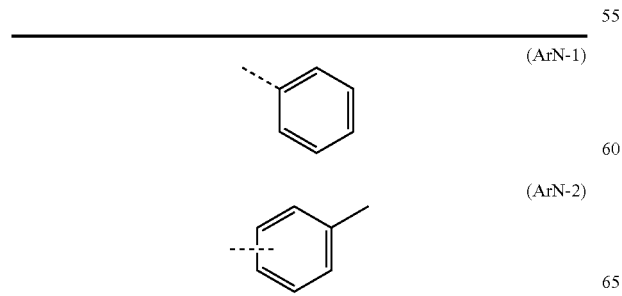

(ArN-1)

(ArN-2)

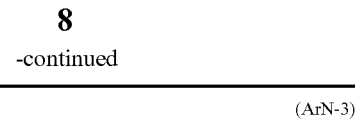
(ArN-3)

(ArN-4)

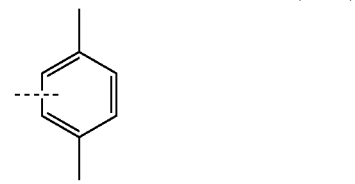
(ArN-5)

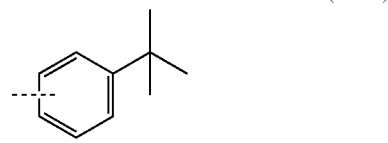
(ArN-6)

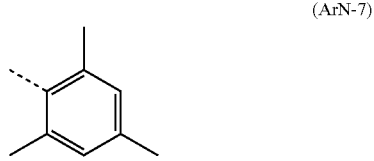
(ArN-7)

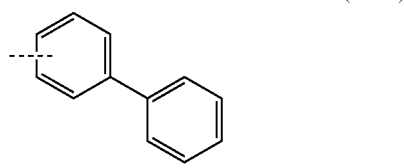
(ArN-8)

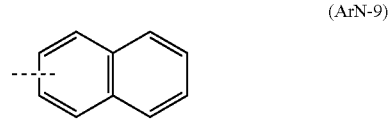
(ArN-9)

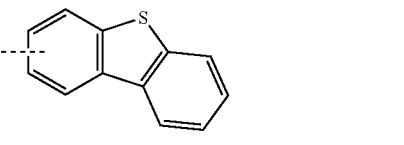
(ArN-10)

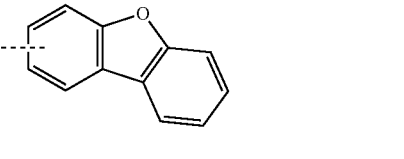
(ArN-11)

(ArN-12)
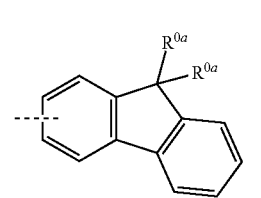
(ArN-13)
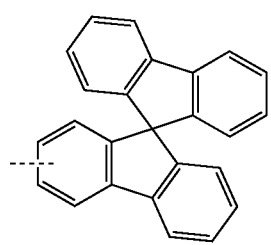
(ArN-14)
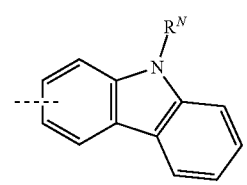
(ArN-15)
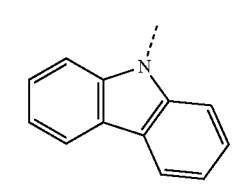
(ArN-16)
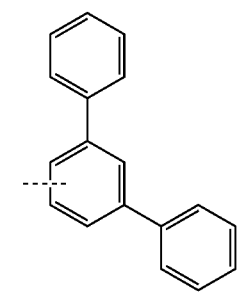
(ArN-17)
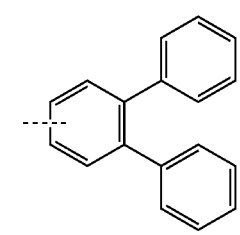
(ArN-18)
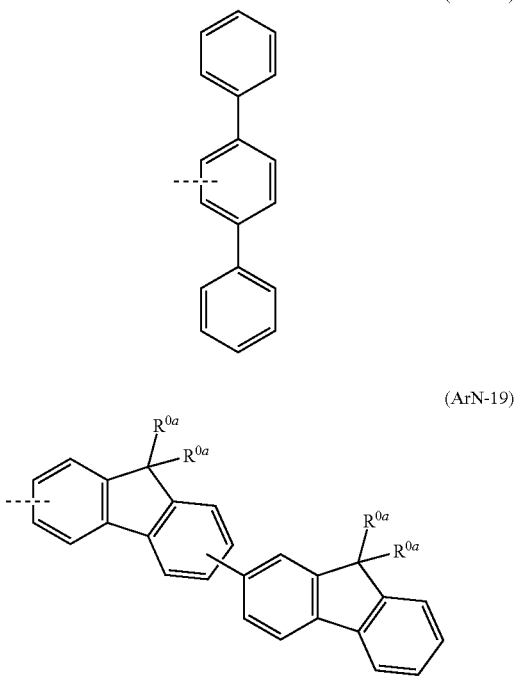
(ArN-19)
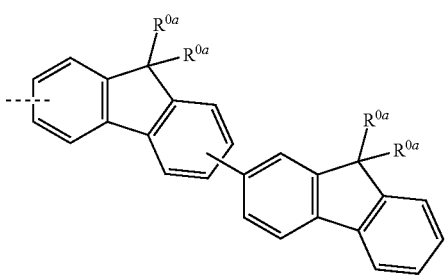
(ArN-20)
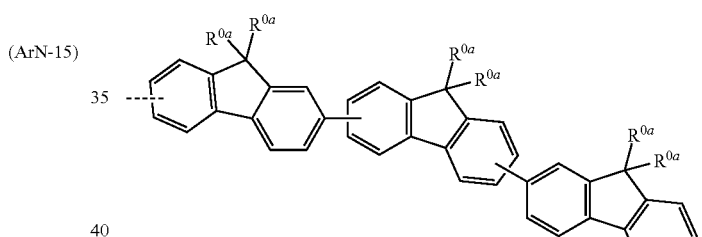
(ArN-21)
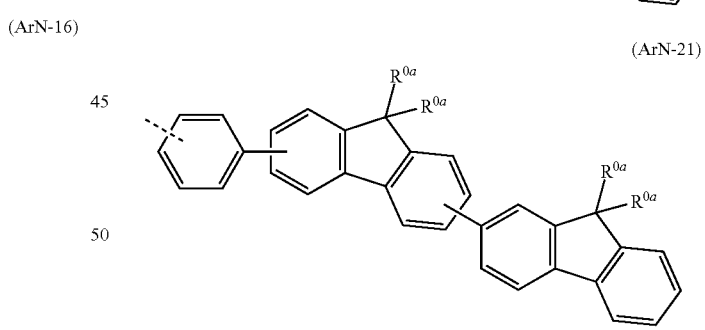
(ArN-22)
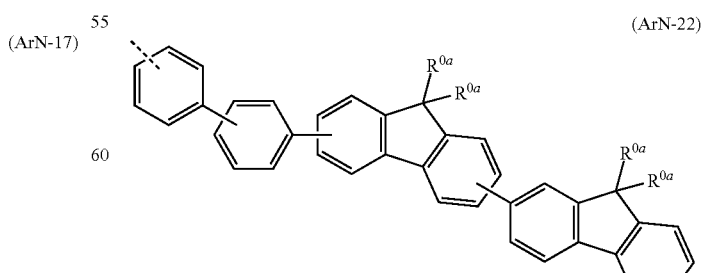

where in formulae (ArN-1) to (ArN-22):

the dashed bond indicates the bonding to the nitrogen of the structure of formula (1);

the group $R^N$ in formula (ArN-14) stands on each occurrence, identically or differently, for H, D, a straight-chain alkyl group having 1 to 40, preferably 1 to 20, more preferably 1 to 10 C atoms or branched or cyclic alkyl group having 3 to 40, preferably 3 to 20, more preferably 3 to 10 C atoms, each of which may be substituted by one or more radicals R, where in each case one or more non-adjacent CH$_2$ groups may be replaced by RC=CR, C≡C, C=O, C=S, SO, SO$_2$, O or S, and where one or more H atoms may be replaced by D, F or CN, an aromatic or heteroaromatic ring system having 5 to 60, preferably 5 to 40, more preferably 5 to 30, particularly preferably 5 to 18 aromatic ring atoms, which may in each case be substituted by one or more radicals R, where two adjacent substituents $R^N$ may form a mono- or polycyclic, aliphatic ring system or aromatic ring system, which may be substituted by one or more radicals R, where R has the same meaning as above;

the group $R^{Oa}$ in formulae (ArN-12) and (ArN-19) to (ArN-22) has the same definition as the group $R^O$ as defined above; and the groups of formulae (ArN-1) to (ArN-22) may be substituted at each free position by a group R, which has the same meaning as above.

In accordance with a preferred embodiment, the group $Ar^1$ stands on each occurrence, identically or differently, for an aromatic or heteroaromatic ring system selected from phenyl, biphenyl, fluorene, spirobifluorene, naphthalene, phenanthrene, dibenzofuran, dibenzothiophene, carbazole, pyridine, pyrimidine, pyrazine, pyridazine, triazine, benzopyridine, benzopyridazine, benzopyrimidine, quinazoline, or for a combination of two to six of these groups, each of which may be substituted by one or more radicals R.

Very preferably, the group $Ar^1$ stands on each occurrence, identically or differently, for an aromatic or heteroaromatic ring system selected from phenyl, biphenyl, fluorene or naphthalene, each of which may be substituted by one or more radicals R, or for a combination of two to six groups selected from phenyl, biphenyl, fluorene or naphthalene, each of which may be substituted by one or more radicals R.

Examples of suitable groups $Ar^1$ are the groups of formulae (Ar1-1) to (Ar1-22) represented below:

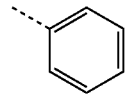

(Ar1-1)

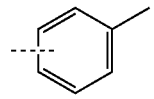

(Ar1-2)

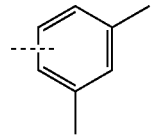

(Ar1-3)

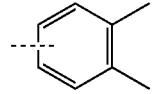

(Ar1-4)

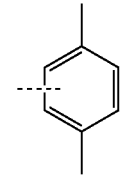

(Ar1-5)

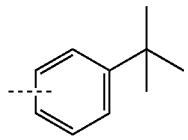

(Ar1-6)

-continued
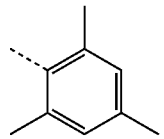
(Ar1-7)
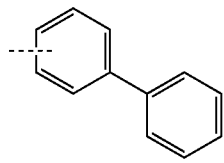
(Ar1-8)
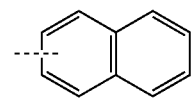
(Ar1-9)
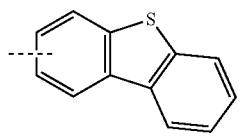
(Ar1-10)
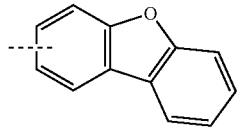
(Ar1-11)
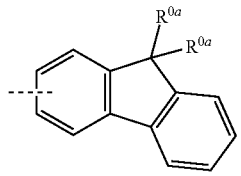
(Ar1-12)
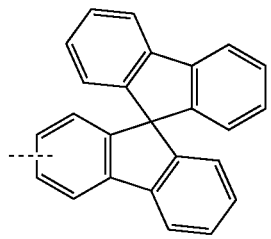
(Ar1-13)
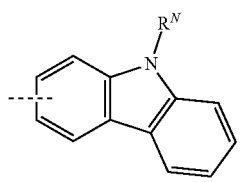
(Ar1-14)

-continued
(Ar1-15)
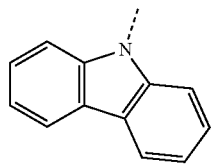
(Ar1-16)
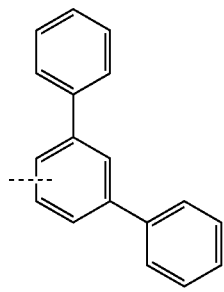
(Ar1-17)
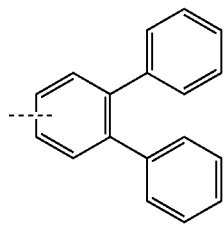
(Ar1-18)
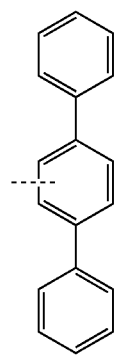
(Ar1-19)
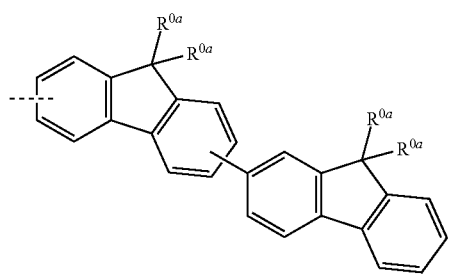

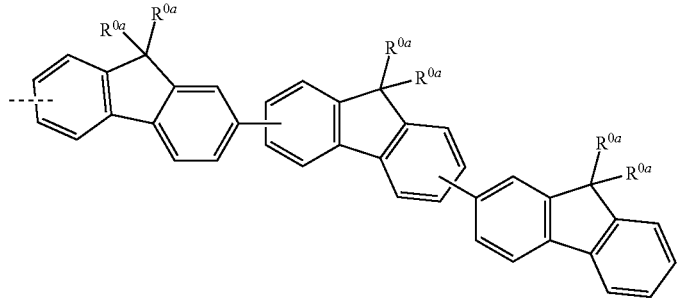

(Ar1-20)

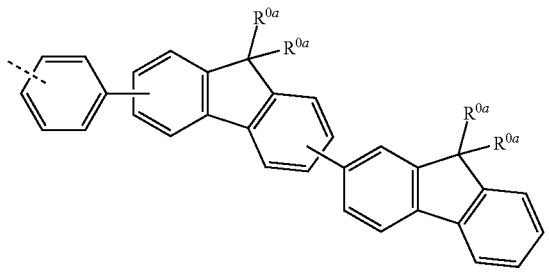

(Ar1-21)

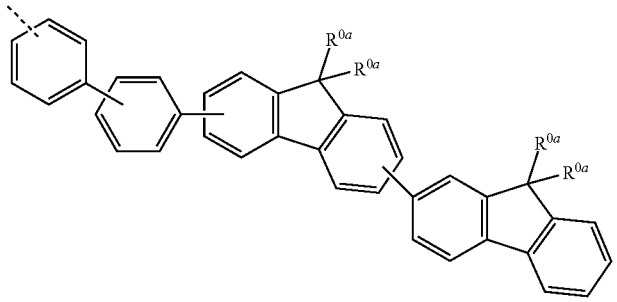

(Ar1-22)

where in formulae (Ar1-1) to (Ar1-22):
the dashed bond indicates the bonding to the structure of formula (1);
the group $R^N$ in formula (Ar1-14) has the same definition as above;
the group $R^{0a}$ has the same definition as above; and
the groups of formulae (Ar1-1) to (Ar1-22) may be substituted at each free position by a group R, which has the same meaning as above.

Preferably, the compounds of formula (1) are selected from compounds of formula (2),

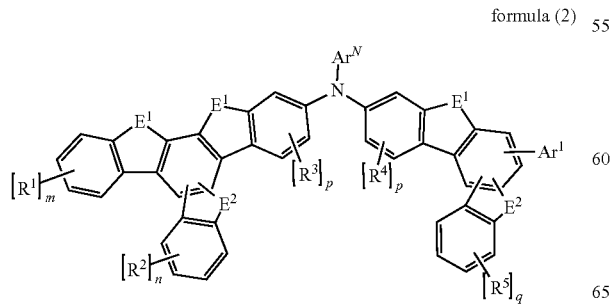

formula (2)

where the symbols $Ar^N$, $E^1$, $E^2$, $Ar^1$, $R^1$ to $R^5$ and the indices m, n, p and q have the same meaning as above.

Very preferably, the compounds of formula (1) are selected from compounds of formula (3),

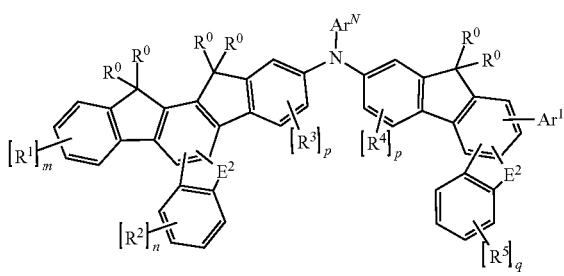

formula (3)

where the symbols $Ar^N$, $E^2$, $Ar^1$, $R^0$, $R^1$ to $R^5$ and the indices m, n, p and q have the same meaning as above.

Particularly preferably, the compounds of formula (1) are selected from compounds of formula (4), formula (4)

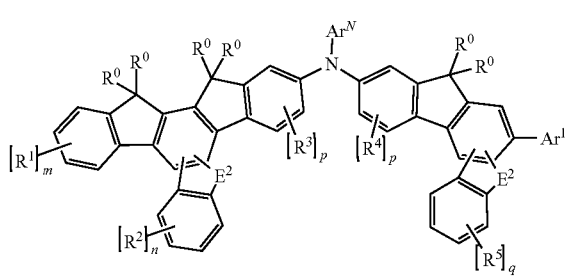

where the symbols $Ar^N$, $E^2$, $Ar^1$, $R^0$, $R^1$ to $R^5$ and the indices m, n, p and q have the same meaning as above.

Very particularly preferably, the compounds of formula (1) are selected from compounds of formulae (4-1) to (4-4), formula (4-1)

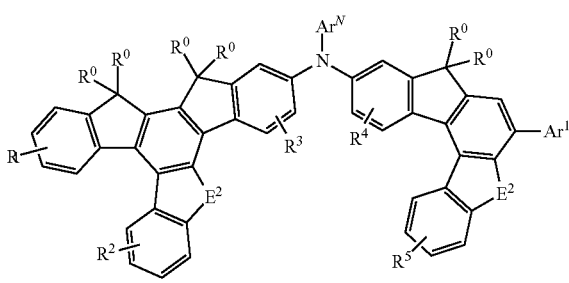

formula (4-2)

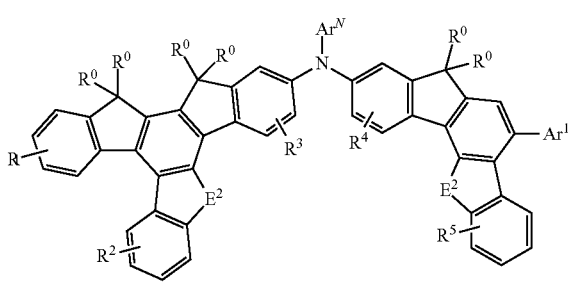

formula (4-3)

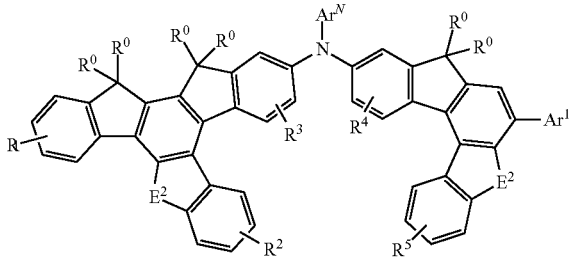

formula (4-4)

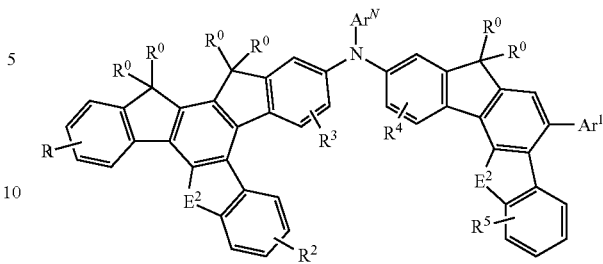

where the symbols $Ar^N$, $E^2$, $Ar^1$, $R^0$, $R^1$ to $R^5$ have the same meaning as above.

In accordance with a preferred embodiment, the compounds of formulae (4-1) to (4-4) are selected from compounds of formulae (4-1a) to (4-4a), formula (4-1a)

formula (4-2a)

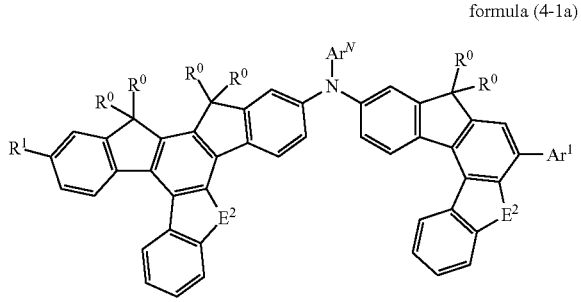

formula (4-3a)

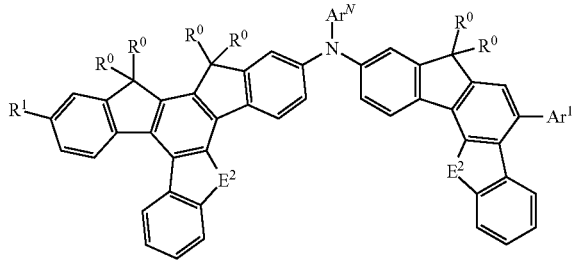

formula (4-4a)

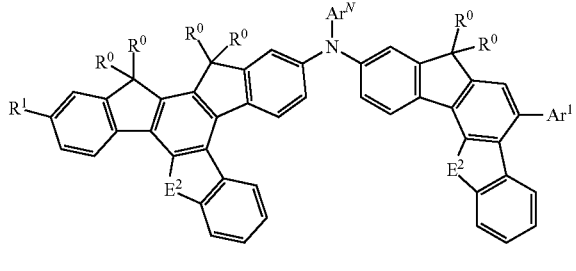

where the symbols Ar$^N$, E$^2$, Ar$^1$, R$^0$ and R$^1$ have the same meaning as above.

In accordance with another preferred embodiment, the compounds of formulae (4-1) to (4-4) are selected from compounds of formulae (4-1 b) to (4-4b),

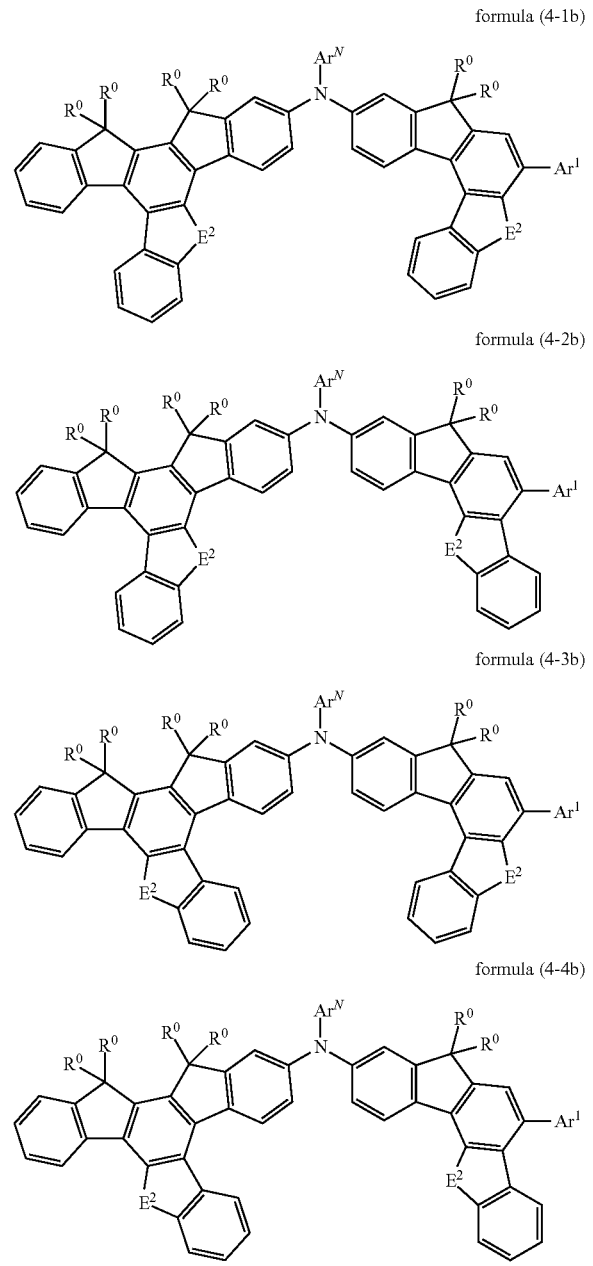

formula (4-1b)

formula (4-2b)

formula (4-3b)

formula (4-4b)

where the symbols Ar$^N$, E$^2$, Ar$^1$ and R$^0$ have the same meaning as above.

Preferably, the group R$^0$ and R$^{0a}$ stand on each occurrence, identically or differently, for H, D, F, CN, a straight-chain alkyl group having 1 to 40, preferably 1 to 20, more preferably 1 to 10 C atoms or branched or cyclic alkyl group having 3 to 40, preferably 3 to 20, more preferably 3 to 10 C atoms, each of which may be substituted by one or more radicals R, where in each case one or more non-adjacent CH$_2$ groups may be replaced by RC=CR, C≡C, C=O, C=S, SO, SO$_2$, O or S and where one or more H atoms may be replaced by D, F, Cl, Br, I, CN or NO$_2$, an aromatic or heteroaromatic ring system having 5 to 60, preferably 5 to 40, more preferably 5 to 25, even more preferably 5 to 18 aromatic ring atoms, which may in each case be substituted by one or more radicals R; where two adjacent substituents R$^0$ and/or R$^{0a}$ may form a mono- or polycyclic, aliphatic ring system or aromatic ring system, which may be substituted by one or more radicals R.

Very preferably, the groups R$^0$ and R$^{0a}$ stand on each occurrence, identically or differently, for H, a straight-chain alkyl group having 1 to 10 C atoms or branched or cyclic alkyl group having 3 to 10 C atoms, each of which may be substituted by one or more radicals R, where one or more H atoms may be replaced by D, F, Cl, Br, I, CN or NO$_2$, an aromatic or heteroaromatic ring system having 5 to 18 aromatic ring atoms, which may in each case be substituted by one or more radicals R, where two adjacent substituents R$^0$ and/or R$^{0a}$ may form a mono- or polycyclic, aliphatic ring system or aromatic ring system, which may be substituted by one or more radicals R.

Particularly preferably, the groups R$^0$ and/or R$^{0a}$ stand on each occurrence, identically or differently, for a straight-chain alkyl group having 1 to 10 C atoms, which may be substituted by one or more radicals R, or an aromatic or heteroaromatic ring system having 5 to 18 aromatic ring atoms, which may in each case be substituted by one or more radicals R, where two adjacent substituents R$^0$ may form a mono- or polycyclic, aliphatic ring system or aromatic ring system, which may be substituted by one or more radicals R.

Very particularly preferably, R$^0$ stands on each occurrence, identically or differently, for a methyl or a phenyl group, which may be substituted by one or more radicals R.

Very particularly preferably, the group R$^{0a}$ stand on each occurrence, identically or differently, for a straight-chain alkyl group having 1 to 10 C atoms, which may be substituted by one or more radicals R.

In accordance with a preferred embodiment, the groups of formulae (ArN-12) and (Ar1-12) comprise 1 or 2 groups R$^{0a}$, which stand(s) for a straight-chain alkyl group having 3 to 10, preferably 5 to 10, more preferably 6 to 10 C atoms and the groups or formulae (ArN-19) to (ArN-22), (Ar1-19) to (Ar1-22) comprise 1, 2, 3 or 4 groups R$^{0a}$, which stand(s) for a straight-chain alkyl group having 3 to 10, preferably 5 to 10, more preferably 6 to 10 C atoms.

Preferably, R$^1$ to R$^5$ stand on each occurrence, identically or differently, for H, D, F, CN, N(Ar)$_2$, Si(R)$_3$, a straight-chain alkyl, alkoxy or thioalkyl group having 1 to 40, preferably 1 to 20, more preferably 1 to 10 C atoms or branched or cyclic alkyl, alkoxy or thioalkyl group having 3 to 40, preferably 3 to 20, more preferably 3 to 10 C atoms, each of which may be substituted by one or more radicals R, where in each case one or more non-adjacent CH$_2$ groups may be replaced by RC=CR, C≡C, C=O, C=S, SO, SO$_2$, O or S and where one or more H atoms may be replaced by D, F, Cl, Br, I, CN or NO$_2$, an aromatic or heteroaromatic ring system having 5 to 60, preferably 5 to 40, more preferably 5 to 25, even more preferably 5 to 18 aromatic ring atoms, which may in each case be substituted by one or more radicals R, or an aryloxy group having 5 to 60, preferably 5 to 40, more preferably 5 to 25, even more preferably 5 to 18 aromatic ring atoms, which may be substituted by one or more radicals R, where two adjacent substituents R$^1$, and/or two adjacent substituents R$^2$, and/or two adjacent substituents R$^3$, and/or two adjacent substituents R$^4$, and/or two adjacent substituents R$^5$ may form a mono- or polycyclic, aliphatic ring system or aromatic ring system, which may be substituted by one or more radicals R.

More preferably, $R^1$ stands on each occurrence, identically or differently, for H, D, F, CN, a straight-chain alkyl group having 1 to 40, preferably 1 to 20, more preferably 1 to 10 C atoms or branched or cyclic alkyl group having 3 to 40, preferably 3 to 20, more preferably 3 to 10 C atoms, each of which may be substituted by one or more radicals R, an aromatic or heteroaromatic ring system having 5 to 60, preferably 5 to 40, more preferably 5 to 25, even more preferably 5 to 18 aromatic ring atoms, which may in each case be substituted by one or more radicals R, which may be substituted by one or more radicals R.

In accordance with a preferred embodiment, $R^1$ is H.

In accordance with another preferred embodiment, the compounds of formula (1) comprise at least one group $R^1$ selected from an aromatic or heteroaromatic ring system having 5 to 60 aromatic ring atoms.

When the compounds of formula (1) comprise at least one group $R^1$ selected from an aromatic or heteroaromatic ring system having 5 to 60 aromatic ring atoms, then $R^1$ stands preferably for a group selected from phenyl, biphenyl, fluorene, spirobifluorene, naphthalene, phenanthrene, dibenzofuran, dibenzothiophene, carbazole, pyridine, pyrimidine, pyrazine, pyridazine, triazine, benzopyridine, benzopyridazine, benzopyrimidine, quinazoline, or a combination of two to six of these groups, each of which may be substituted by one or more radicals R.

When the compounds of formula (1) comprise at least one group $R^1$ selected from an aromatic or heteroaromatic ring system having 5 to 60 aromatic ring atoms, then $R^1$ stands very preferably for a group selected from phenyl, biphenyl, fluorene and naphthalene, each of which may be substituted by one or more radicals R, or for a combination of two to six groups selected from phenyl, biphenyl, fluorene or naphthalene, each of which may be substituted by one or more radicals R.

Particularly preferably, the compounds of formula (1) comprise at least one group $R^1$, which stands for a group selected from formulae (Ar1-1) to (Ar1-22) as represented above. Very particularly preferably, the compounds of formula (1) comprise at least one group $R^1$, which stands for a group selected from formulae (Ar1-19) to (Ar1-22) as represented above.

In accordance with a preferred embodiment, $R^2$ to $R^5$ stand on each occurrence, identically or differently, for H, D, F, CN, a straight-chain alkyl group having 1 to 40, preferably 1 to 20, more preferably 1 to 10 C atoms or a branched or cyclic alkyl group having 3 to 40, preferably 3 to 20, more preferably 3 to 10 C atoms, each of which may be substituted by one or more radicals R, or an aromatic or heteroaromatic ring system having 5 to 18 aromatic ring atoms, which may in each case be substituted by one or more radicals R. Particularly preferably, $R^2$ to $R^5$ stand on each occurrence, identically or differently, for H, a straight-chain alkyl group having 1 to 10 C atoms or a branched or cyclic alkyl group having 3 to 10 C atoms, each of which may be substituted by one or more radicals R, or an aromatic or heteroaromatic ring system having 5 to 18 aromatic ring atoms, which may in each case be substituted by one or more radicals R. Very particularly preferably, $R^2$ to $R^5$ stand for H.

In accordance with a preferred embodiment, R stands on each occurrence, identically or differently, for H, D, F, CN, $N(Ar)_2$, $Si(R')_3$, a straight-chain alkyl, alkoxy or thioalkyl group having 1 to 40, preferably 1 to 20, more preferably 1 to 10 C atoms or branched or cyclic alkyl, alkoxy or thioalkyl group having 3 to 40, preferably 3 to 20, more preferably 3 to 10 C atoms, each of which may be substituted by one or more radicals R', where in each case one or more non-adjacent $CH_2$ groups may be replaced by $R'C=CR'$, $C\equiv C$, $C=O$, $C=S$, SO, $SO_2$, O or S and where one or more H atoms may be replaced by D, F, Cl, Br, I, CN or $NO_2$, an aromatic or heteroaromatic ring system having 5 to 60, preferably 5 to 40, more preferably 5 to 25, even more preferably 5 to 18 aromatic ring atoms, which may in each case be substituted by one or more radicals R', or an aryloxy group having 5 to 60, preferably 5 to 40, more preferably 5 to 25, even more preferably 5 to 18 aromatic ring atoms, which may be substituted by one or more radicals R', where two adjacent substituents R may form a mono- or polycyclic, aliphatic ring system or aromatic ring system, which may be substituted by one or more radicals R'.

In accordance with a preferred embodiment, R' stands on each occurrence, identically or differently, for H, D, F, Cl, Br, I, ON, a straight-chain alkyl group having 1 to 10 C atoms or branched or cyclic alkyl group having 3 to 10 C atoms, or an aromatic or heteroaromatic ring system having 5 to 18 C atoms.

The following compounds are examples of compounds of formula (1):

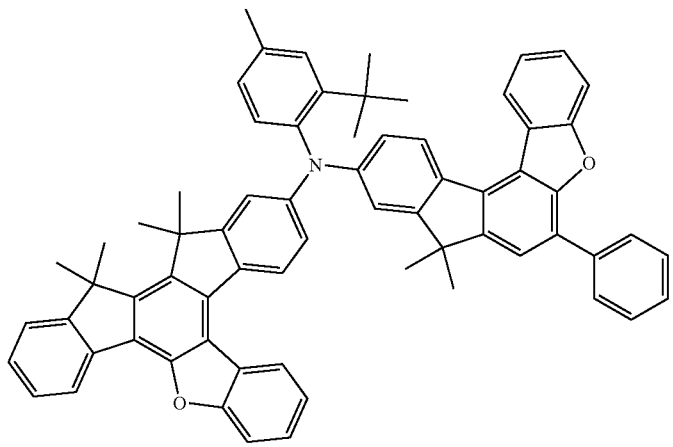 [SMILES: Cc1ccc(N(c2ccc3c(c2)C(C)(C)c2cc(-c4ccccc4)c4oc5ccccc5c4c2-3)c2ccc3c(c2)C(C)(C)c2c4c(c5oc6ccccc6c5c2-3)-c2ccccc2C4(C)C)c(C(C)(C)C)c1]

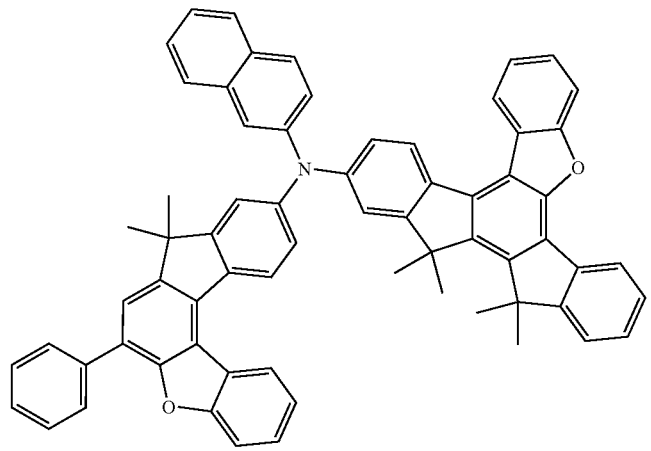 [SMILES: CC1(C)c2cc(N(c3ccc4c(c3)C(C)(C)c3c5c(c6oc7ccccc7c6c3-4)-c3ccccc3C5(C)C)c3ccc4ccccc4c3)ccc2-c2c1cc(-c1ccccc1)c1oc3ccccc3c21]
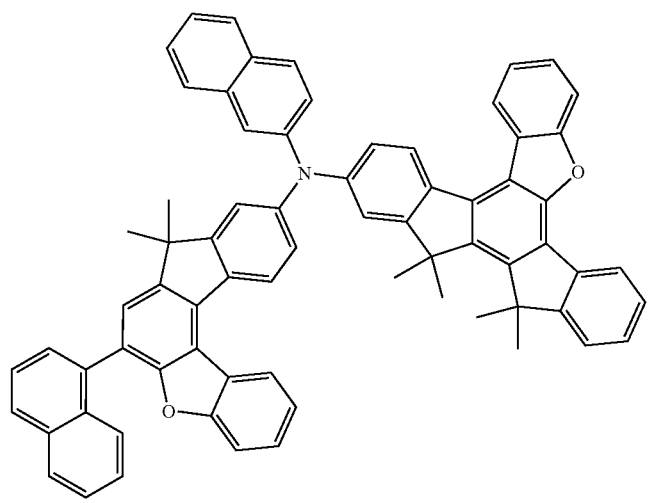 [SMILES: CC1(C)c2cc(N(c3ccc4c(c3)C(C)(C)c3c5c(c6oc7ccccc7c6c3-4)-c3ccccc3C5(C)C)c3ccc4ccccc4c3)ccc2-c2c1cc(-c1cccc3ccccc13)c1oc3ccccc3c21]
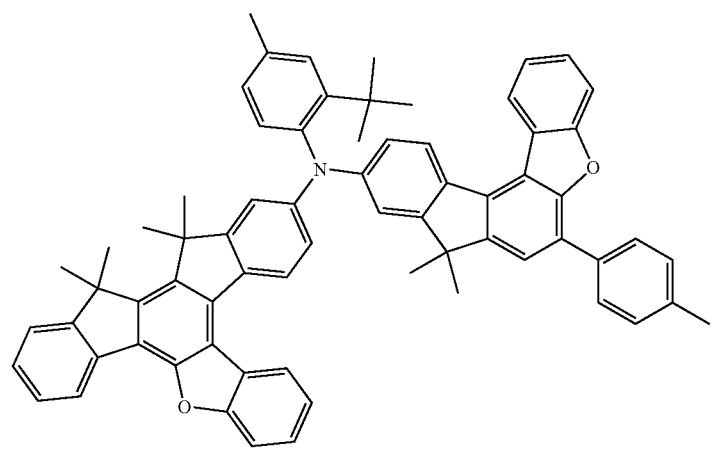 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccc(C)cc4C(C)(C)C)cc2C3(C)C)cc1]

-continued
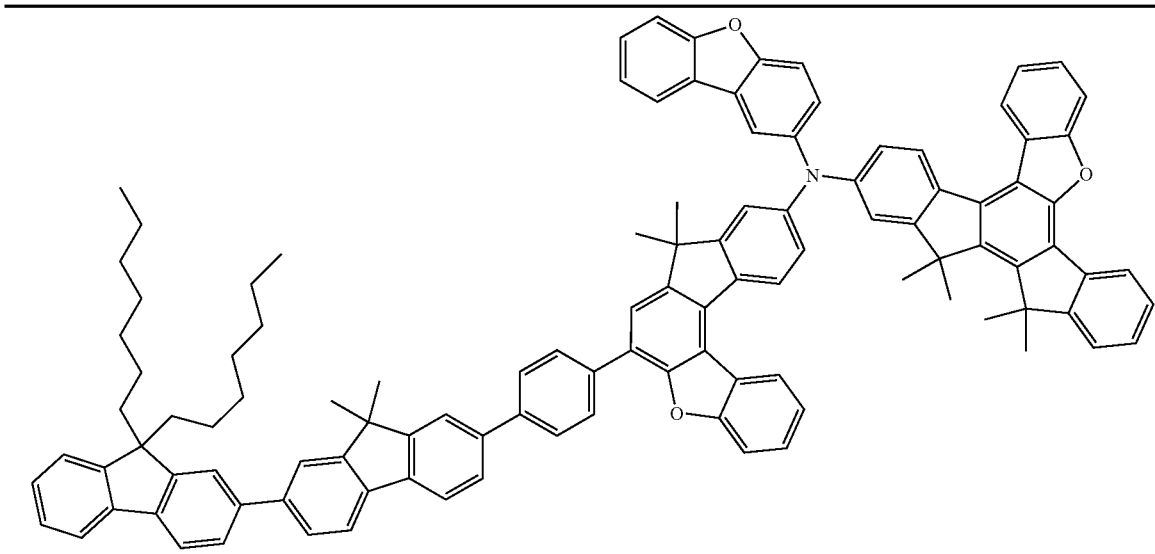
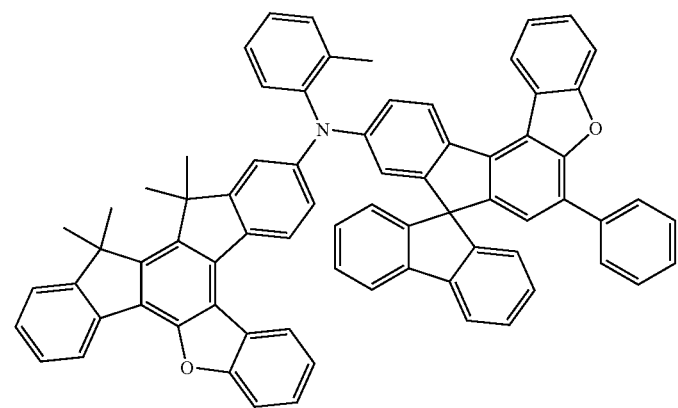 [SMILES: Cc1ccccc1N(c1ccc2c(c1)C(C)(C)c1c3c(c4oc5ccccc5c4c1-2)-c1ccccc1C3(C)C)c1ccc2c(c1)C1(c3ccccc3-c3ccccc31)c1cc(-c3ccccc3)c3oc4ccccc4c3c1-2]
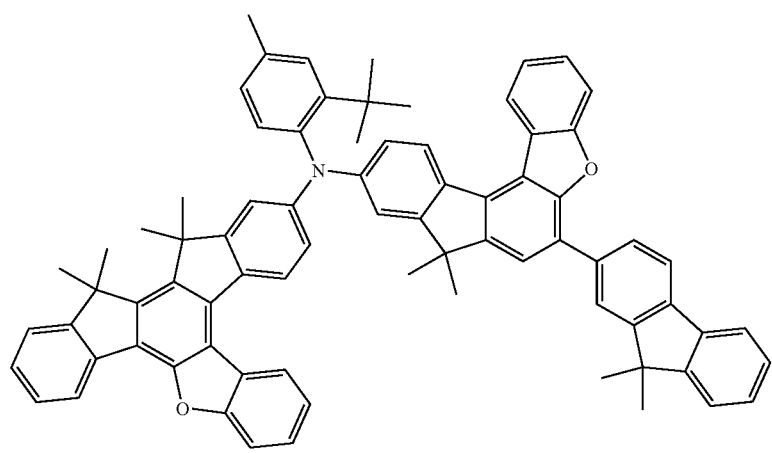 [SMILES: Cc1ccc(N(c2ccc3c(c2)C(C)(C)c2cc(-c4ccc5c(c4)C(C)(C)c4ccccc4-5)c4oc5ccccc5c4c2-3)c2ccc3c(c2)C(C)(C)c2c4c(c5oc6ccccc6c5c2-3)-c2ccccc2C4(C)C)c(C(C)(C)C)c1]

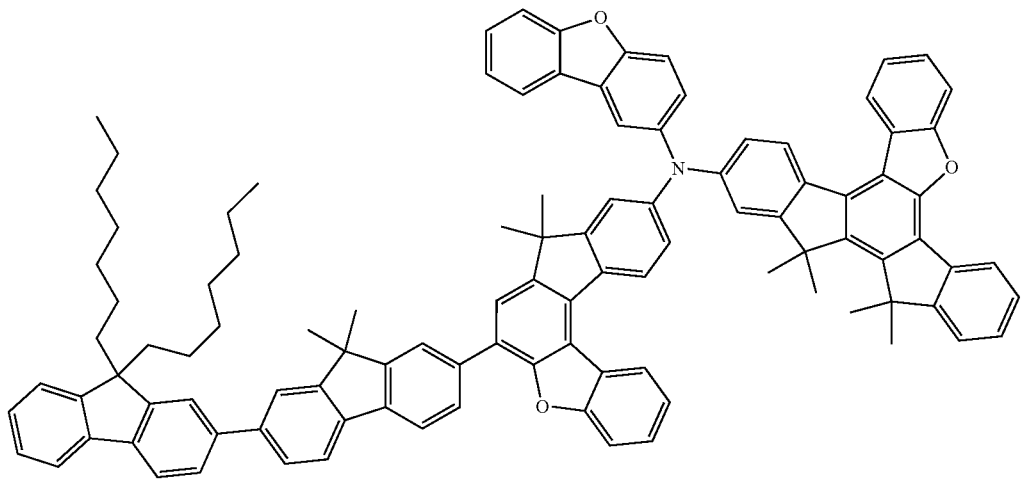 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7ccc8oc9ccccc9c8c7)cc5C6(C)C)ccc3-4)cc21]

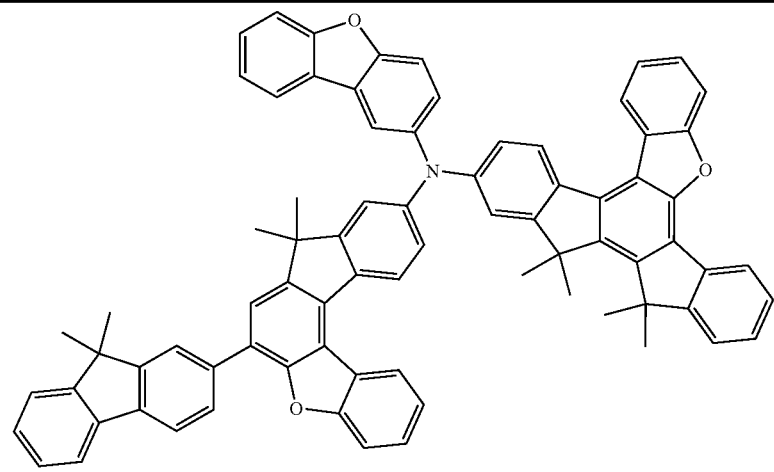
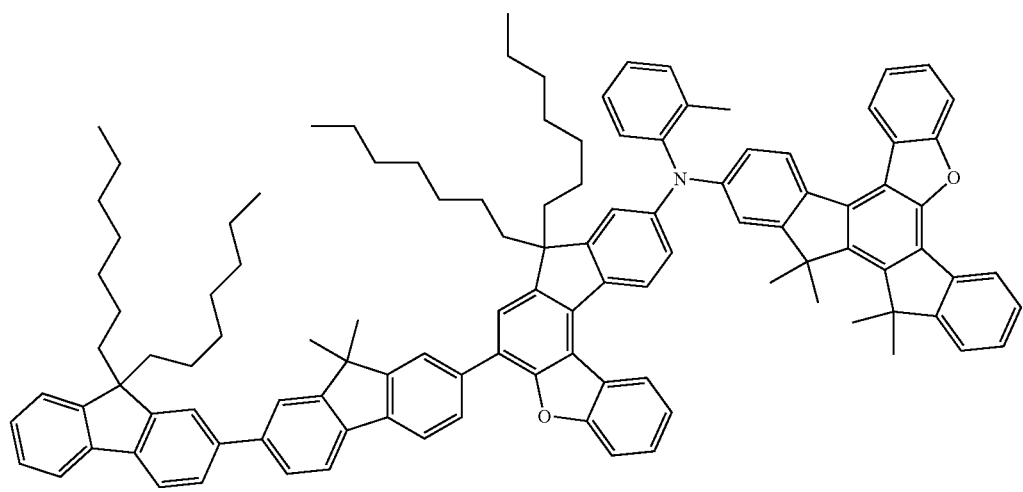 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7ccccc7C)cc5C6(CCCCCCC)CCCCCCC)ccc3-4)cc21]
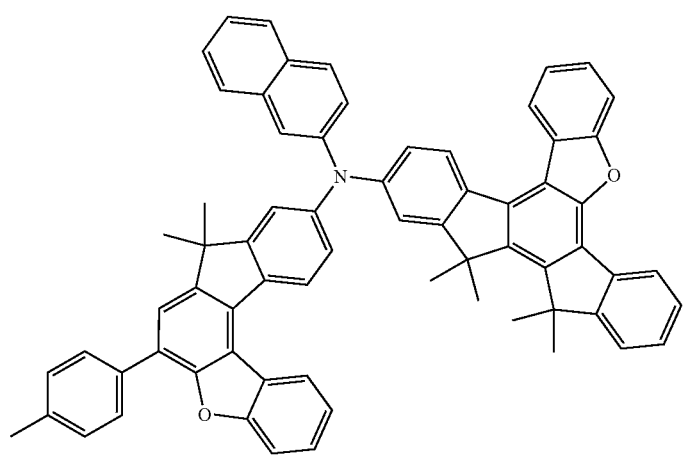 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccc5ccccc5c4)cc2C3(C)C)cc1]

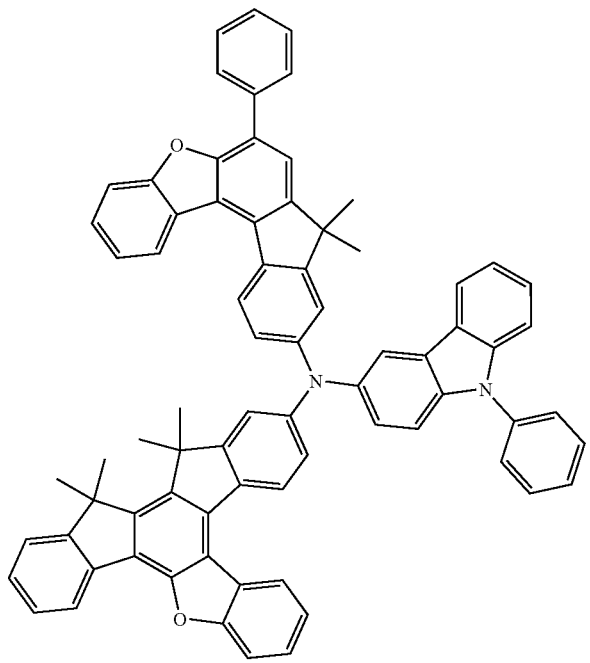 [SMILES: CC1(C)c2cc(N(c3ccc4c(c3)C(C)(C)c3c5c(c6oc7ccccc7c6c3-4)-c3ccccc3C5(C)C)c3ccc4c(c3)c3ccccc3n4-c3ccccc3)ccc2-c2c1cc(-c1ccccc1)c1oc3ccccc3c21]
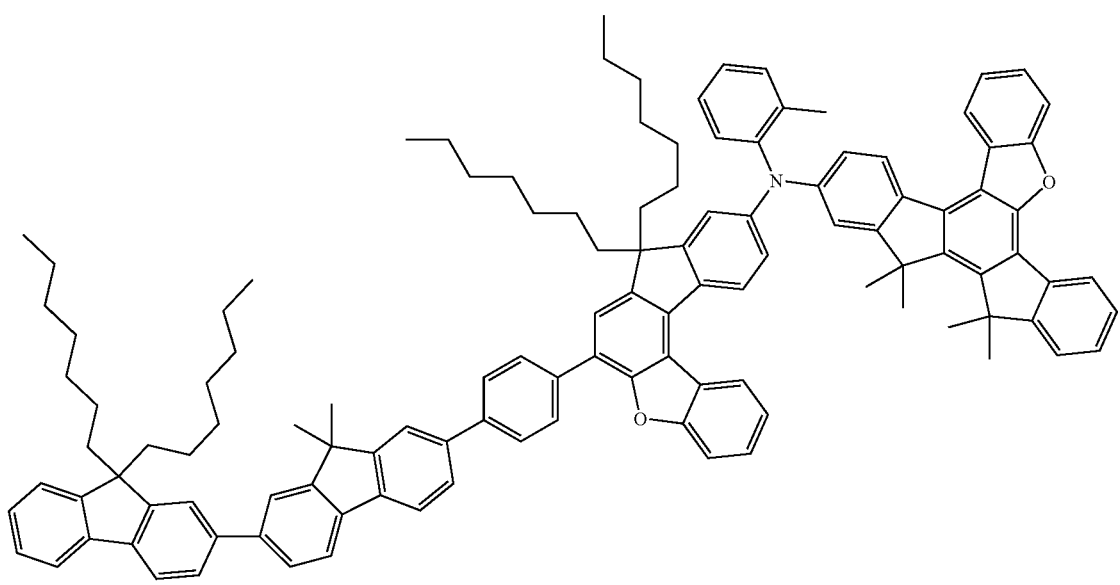 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8ccccc8C)cc6C7(CCCCCCC)CCCCCCC)cc5)ccc3-4)cc21]

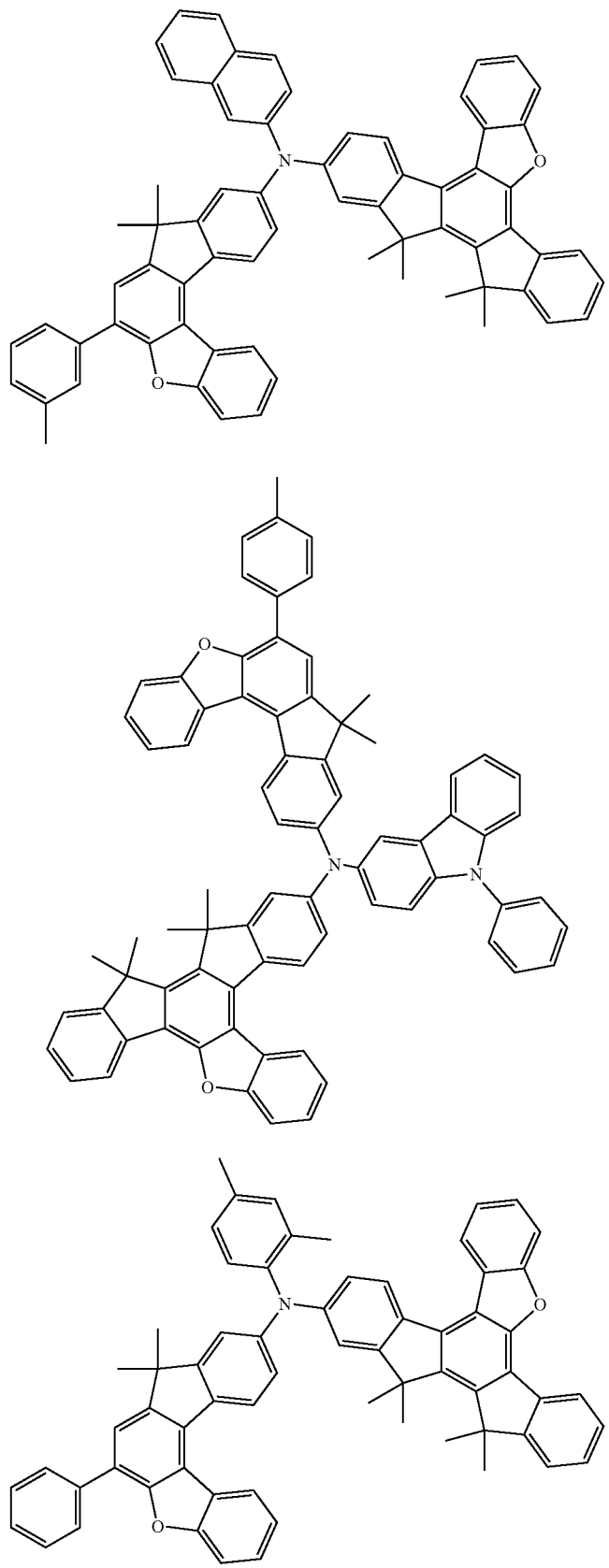

-continued
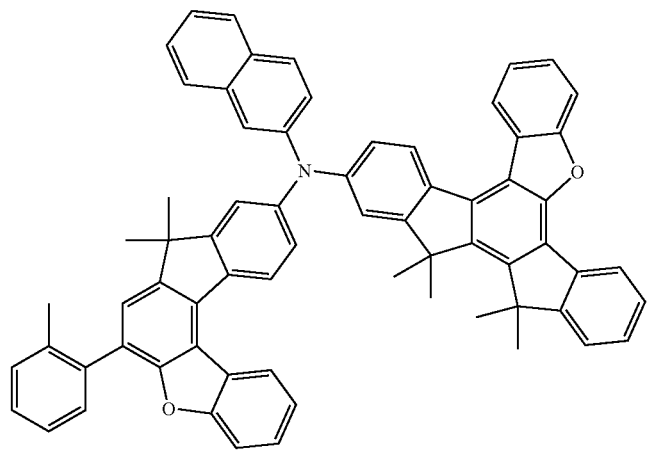 [SMILES: Cc1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3ccc4ccccc4c3)cc1C2(C)C]
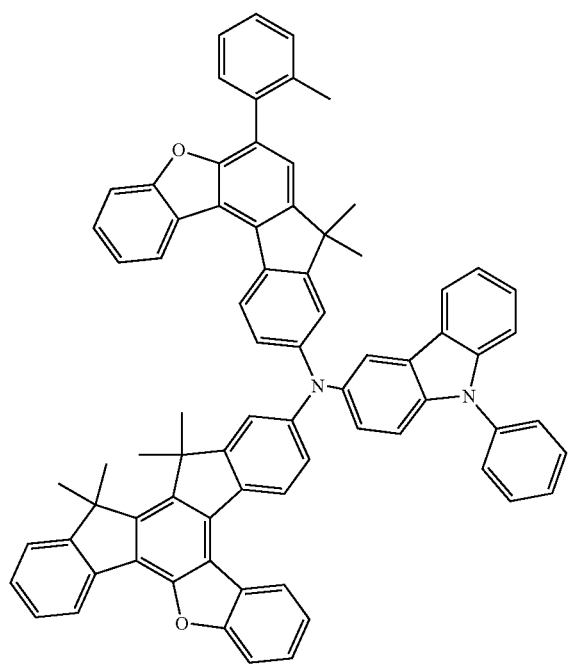 [SMILES: Cc1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3ccc4c(c3)c3ccccc3n4-c3ccccc3)cc1C2(C)C]
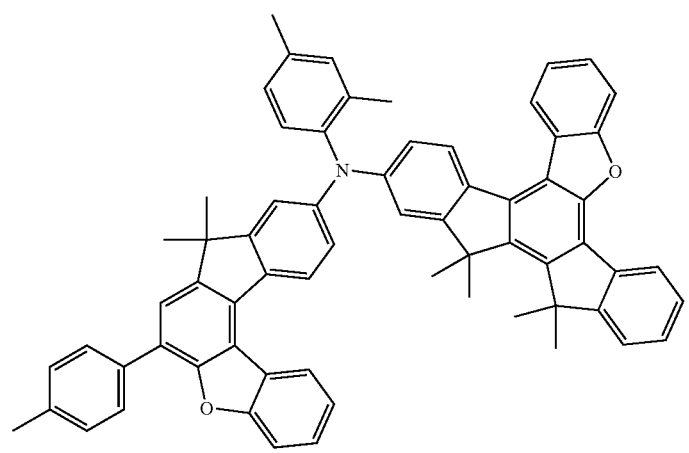 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccc(C)cc4C)cc2C3(C)C)cc1]

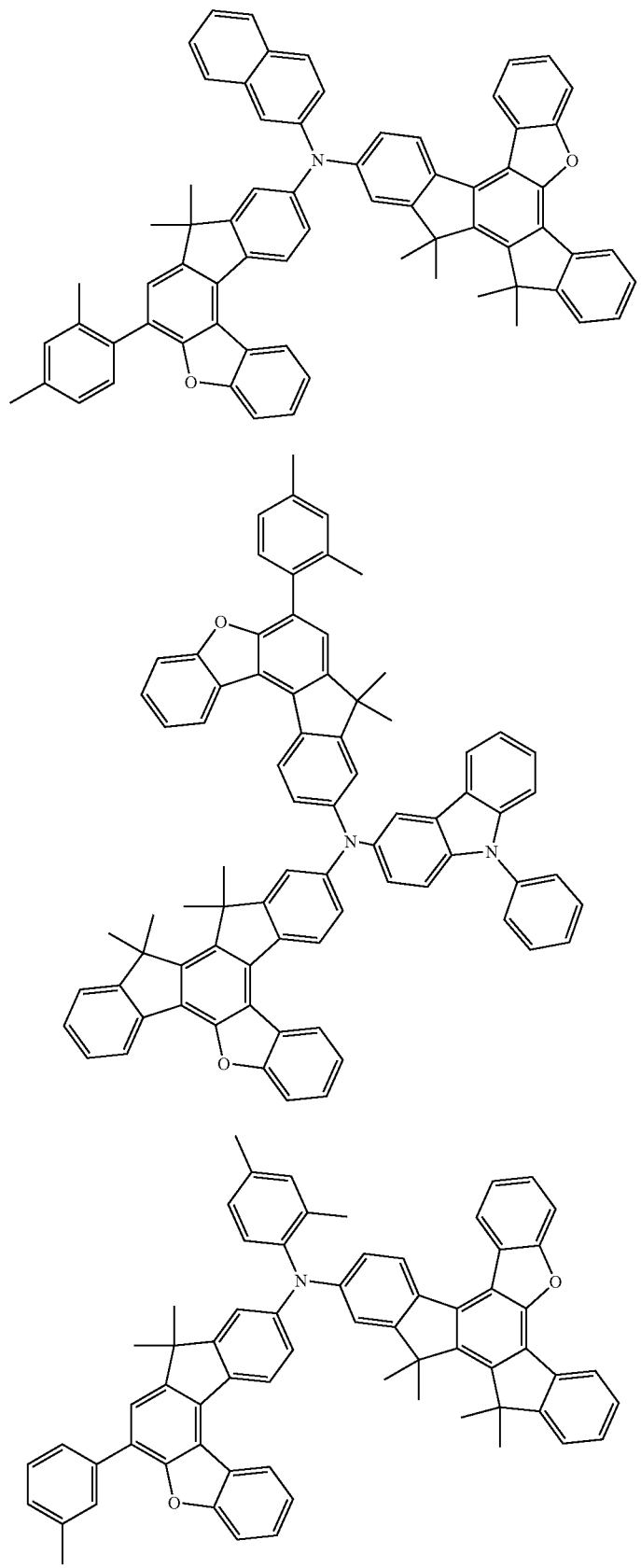

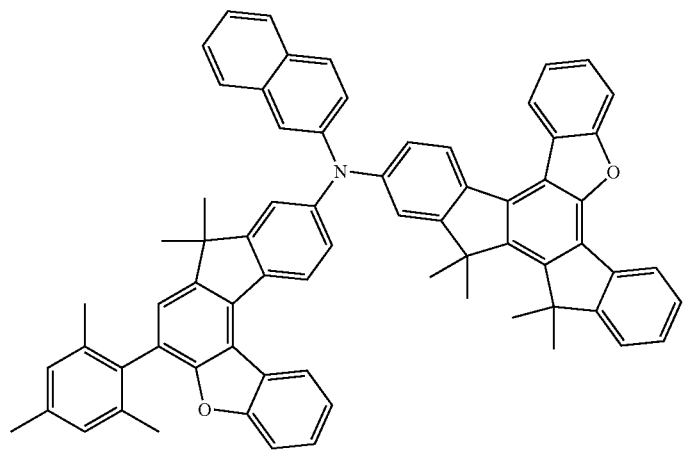 [SMILES: Cc1cc(C)c(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccc5ccccc5c4)cc2C3(C)C)c(C)c1]
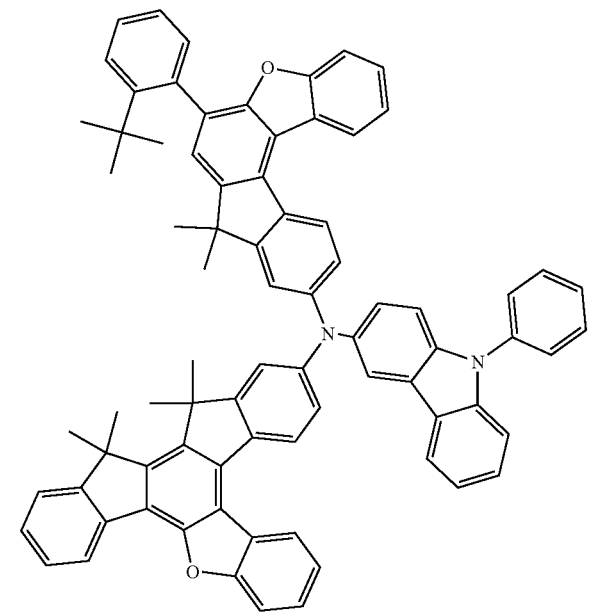 [SMILES: CC(C)(C)c1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3ccc4c(c3)c3ccccc3n4-c3ccccc3)cc1C2(C)C]
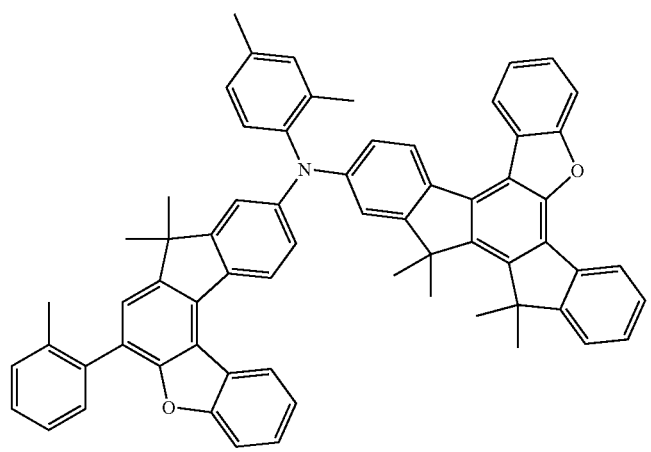 [SMILES: Cc1ccc(N(c2ccc3c(c2)C(C)(C)c2cc(-c4ccccc4C)c4oc5ccccc5c4c2-3)c2ccc3c(c2)C(C)(C)c2c4c(c5oc6ccccc6c5c2-3)-c2ccccc2C4(C)C)c(C)c1]

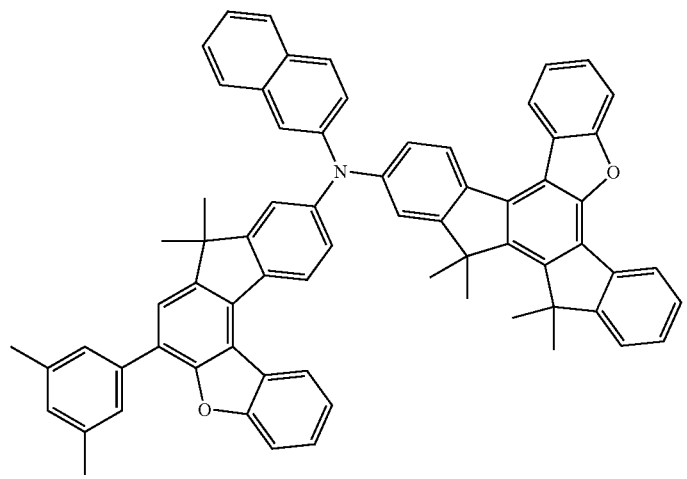 [SMILES: Cc1cc(C)cc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccc5ccccc5c4)cc2C3(C)C)c1]
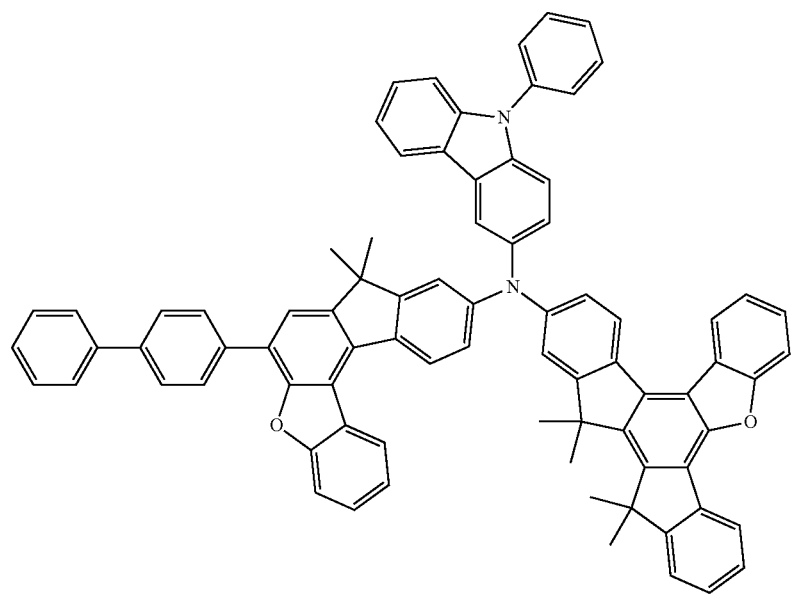 [SMILES: CC1(C)c2cc(N(c3ccc4c(c3)C(C)(C)c3c5c(c6oc7ccccc7c6c3-4)-c3ccccc3C5(C)C)c3ccc4c(c3)c3ccccc3n4-c3ccccc3)ccc2-c2c1cc(-c1ccc(-c3ccccc3)cc1)c1oc3ccccc3c21]
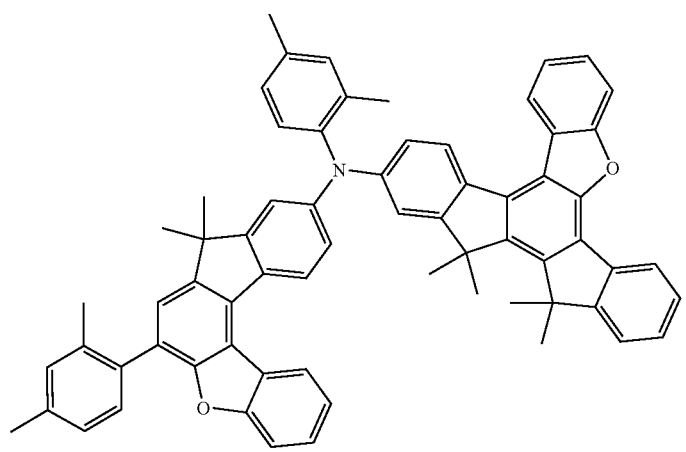 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccc(C)cc4C)cc2C3(C)C)c(C)c1]

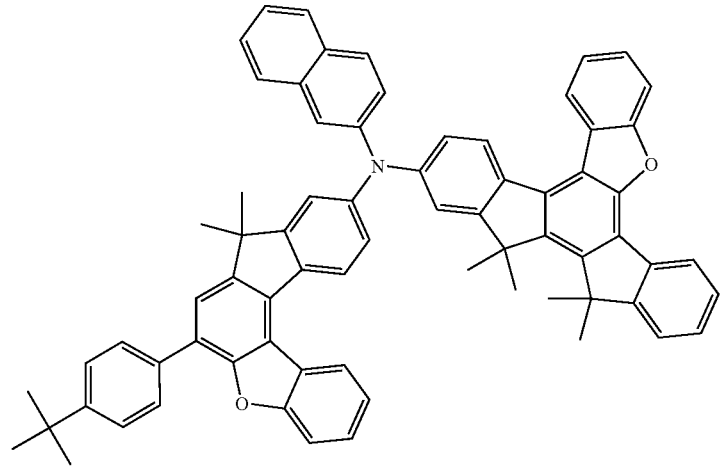 [SMILES: CC(C)(C)c1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccc5ccccc5c4)cc2C3(C)C)cc1]
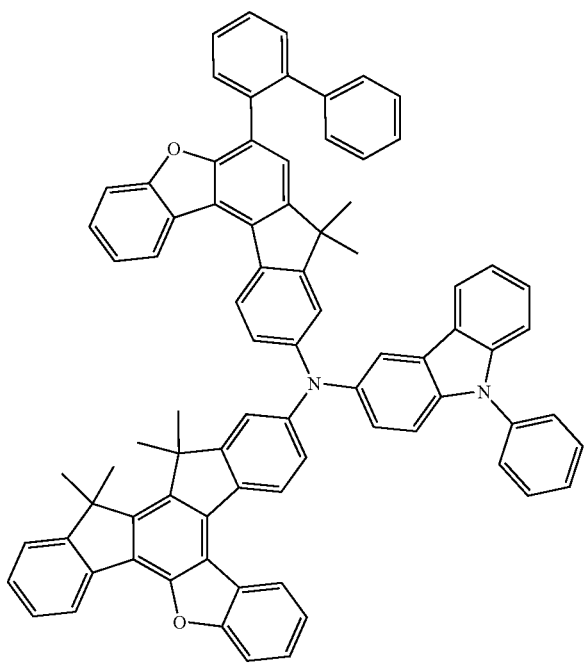 [SMILES: CC1(C)c2cc(N(c3ccc4c(c3)C(C)(C)c3c5c(c6oc7ccccc7c6c3-4)-c3ccccc3C5(C)C)c3ccc4c(c3)c3ccccc3n4-c3ccccc3)ccc2-c2c1cc(-c1ccccc1-c1ccccc1)c1oc3ccccc3c21]
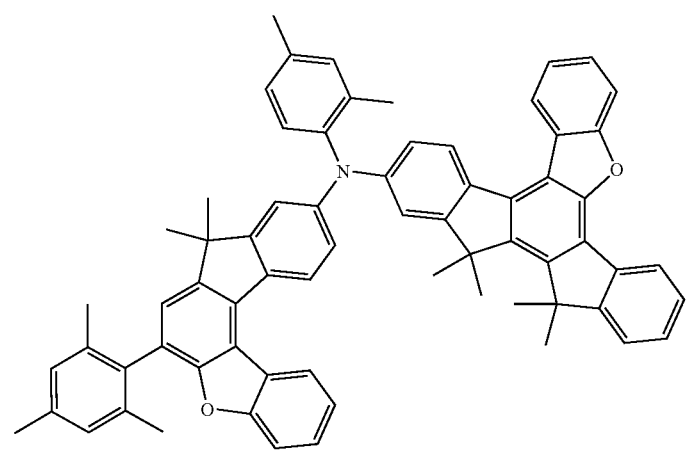 [SMILES: Cc1ccc(N(c2ccc3c(c2)C(C)(C)c2cc(-c4c(C)cc(C)cc4C)c4oc5ccccc5c4c2-3)c2ccc3c(c2)C(C)(C)c2c4c(c5oc6ccccc6c5c2-3)-c2ccccc2C4(C)C)c(C)c1]

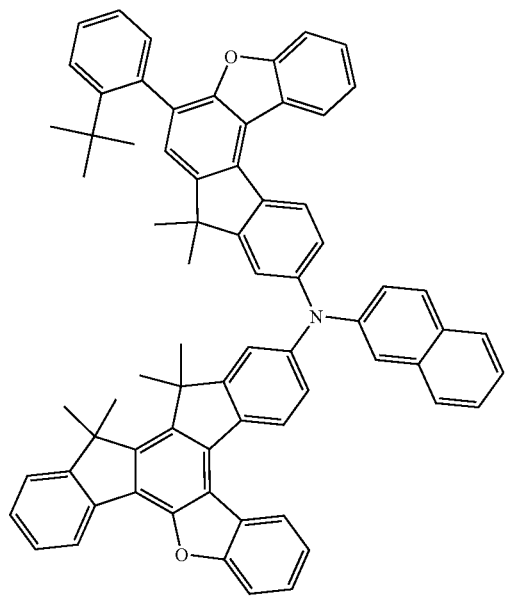 [SMILES: CC(C)(C)c1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3ccc4ccccc4c3)cc1C2(C)C]
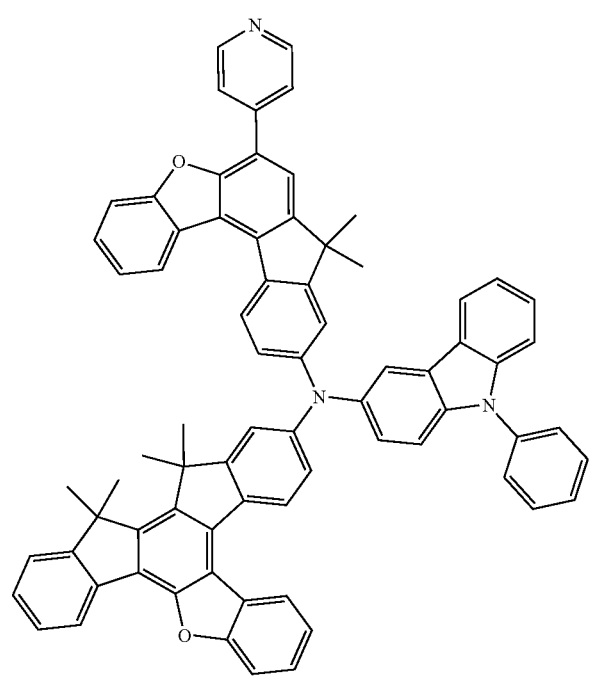 [SMILES: CC1(C)c2cc(N(c3ccc4c(c3)C(C)(C)c3c5c(c6oc7ccccc7c6c3-4)-c3ccccc3C5(C)C)c3ccc4c(c3)c3ccccc3n4-c3ccccc3)ccc2-c2c1cc(-c1ccncc1)c1oc3ccccc3c21]

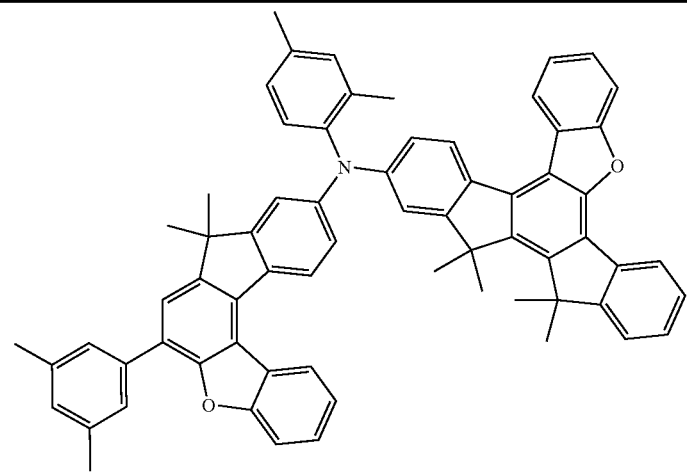
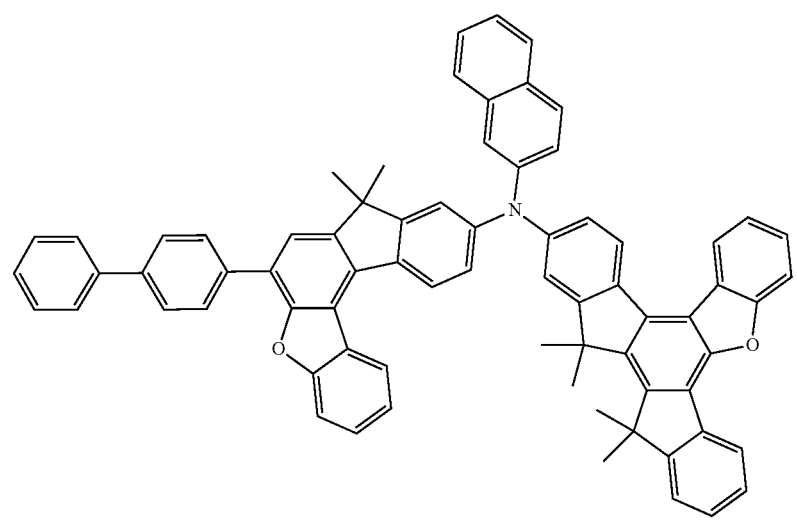 [SMILES: CC1(C)c2cc(N(c3ccc4c(c3)C(C)(C)c3c5c(c6oc7ccccc7c6c3-4)-c3ccccc3C5(C)C)c3ccc4ccccc4c3)ccc2-c2c1cc(-c1ccc(-c3ccccc3)cc1)c1oc3ccccc3c21]
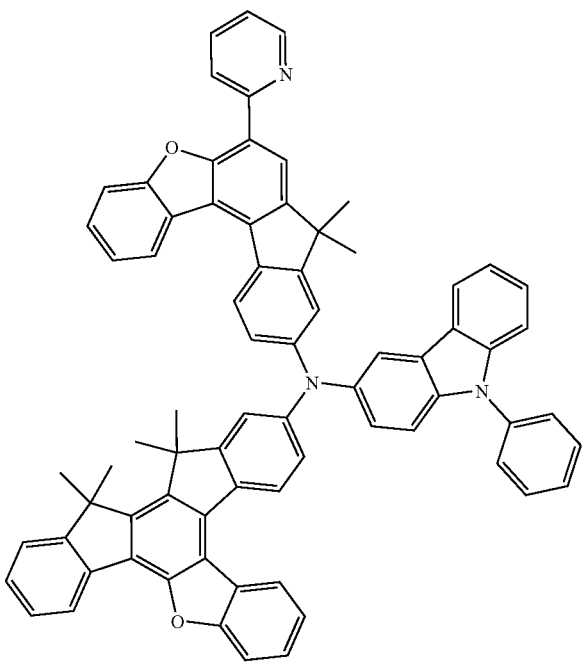 [SMILES: CC1(C)c2cc(N(c3ccc4c(c3)C(C)(C)c3c5c(c6oc7ccccc7c6c3-4)-c3ccccc3C5(C)C)c3ccc4c(c3)c3ccccc3n4-c3ccccc3)ccc2-c2c1cc(-c1ccccn1)c1oc3ccccc3c21]

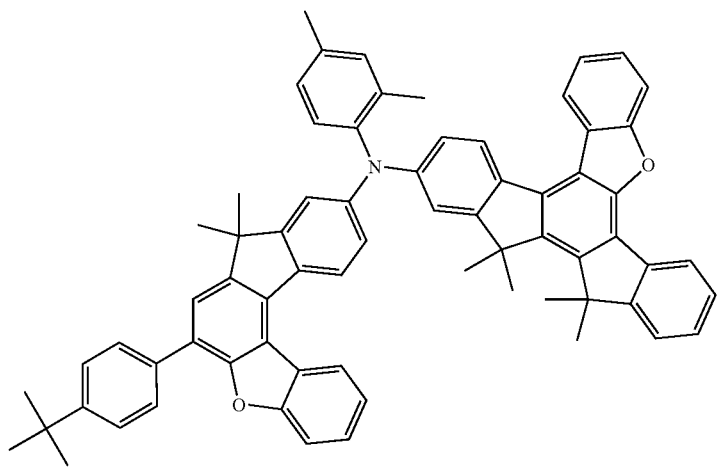 [SMILES: Cc1ccc(N(c2ccc3c(c2)C(C)(C)c2cc(-c4ccc(C(C)(C)C)cc4)c4oc5ccccc5c4c2-3)c2ccc3c(c2)C(C)(C)c2c4c(c5oc6ccccc6c5c2-3)-c2ccccc2C4(C)C)c(C)c1]
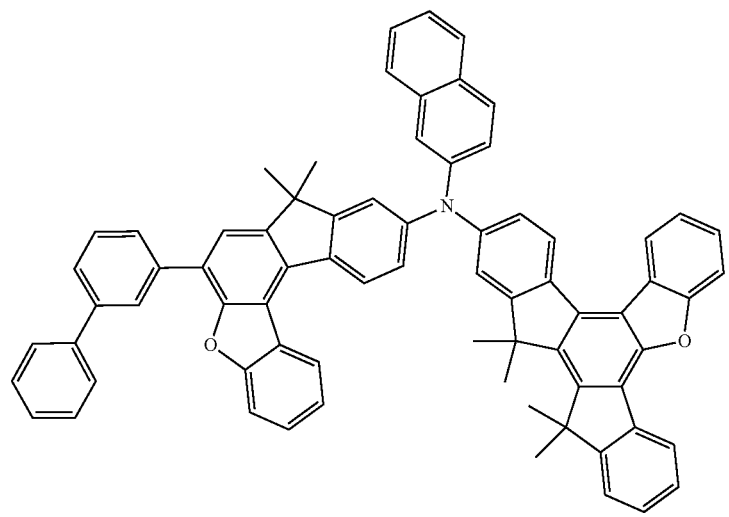 [SMILES: CC1(C)c2cc(N(c3ccc4c(c3)C(C)(C)c3c5c(c6oc7ccccc7c6c3-4)-c3ccccc3C5(C)C)c3ccc4ccccc4c3)ccc2-c2c1cc(-c1cccc(-c3ccccc3)c1)c1oc3ccccc3c21]
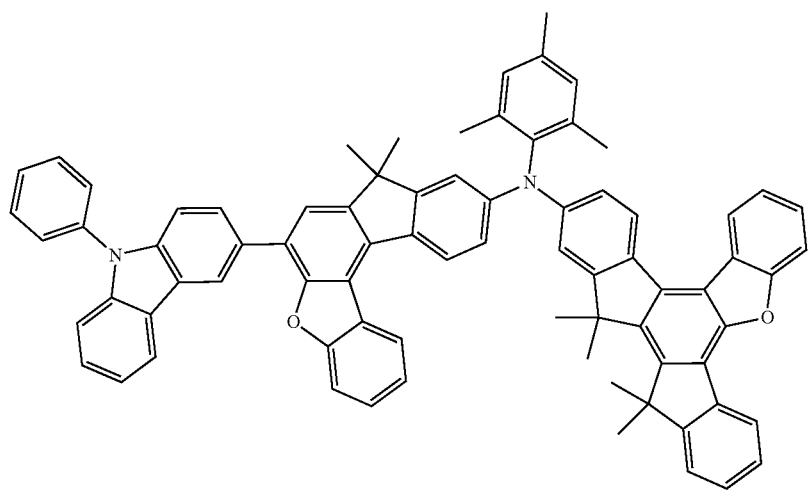 [SMILES: Cc1cc(C)c(N(c2ccc3c(c2)C(C)(C)c2cc(-c4ccc5c(c4)c4ccccc4n5-c4ccccc4)c4oc5ccccc5c4c2-3)c2ccc3c(c2)C(C)(C)c2c4c(c5oc6ccccc6c5c2-3)-c2ccccc2C4(C)C)c(C)c1]

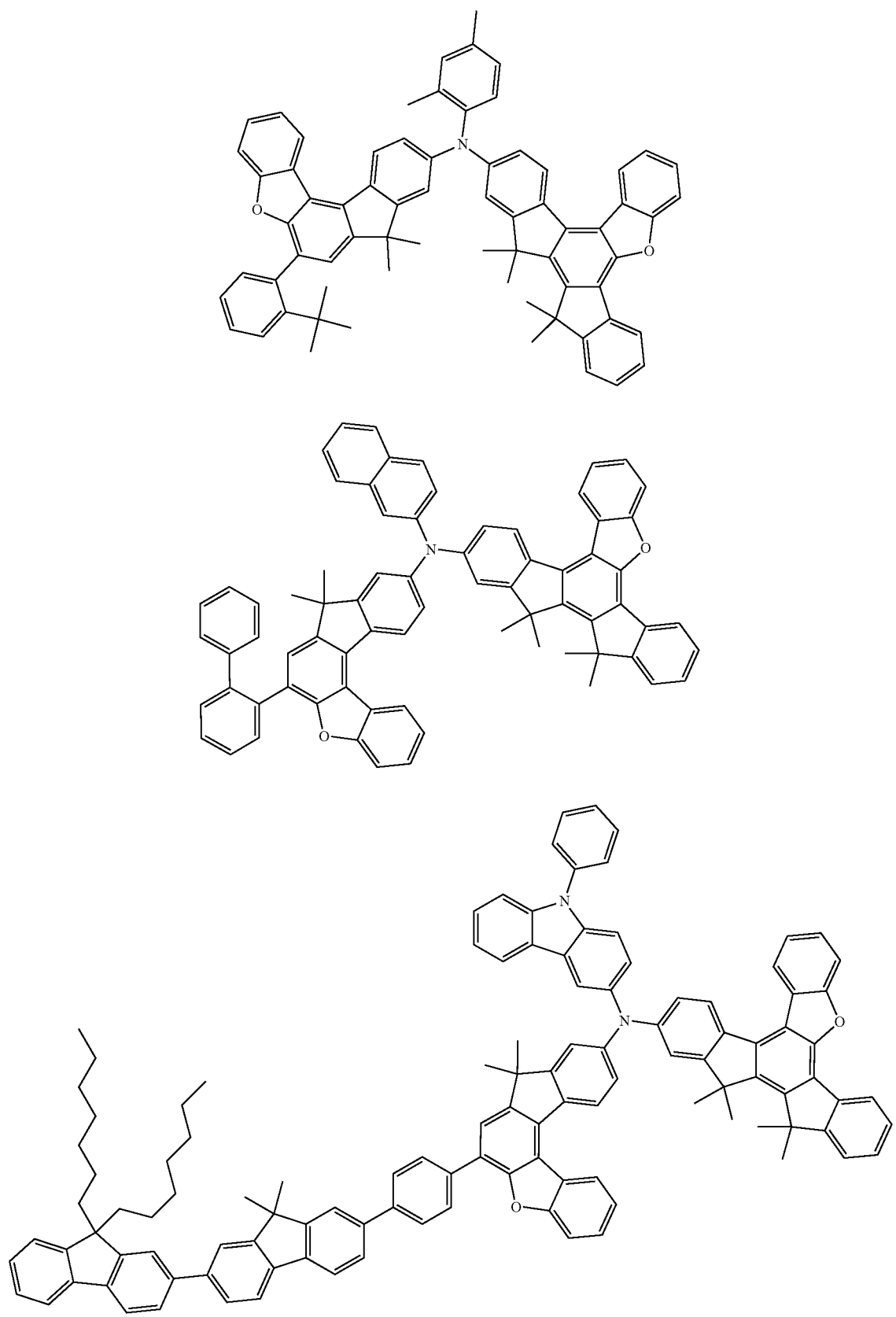

-continued
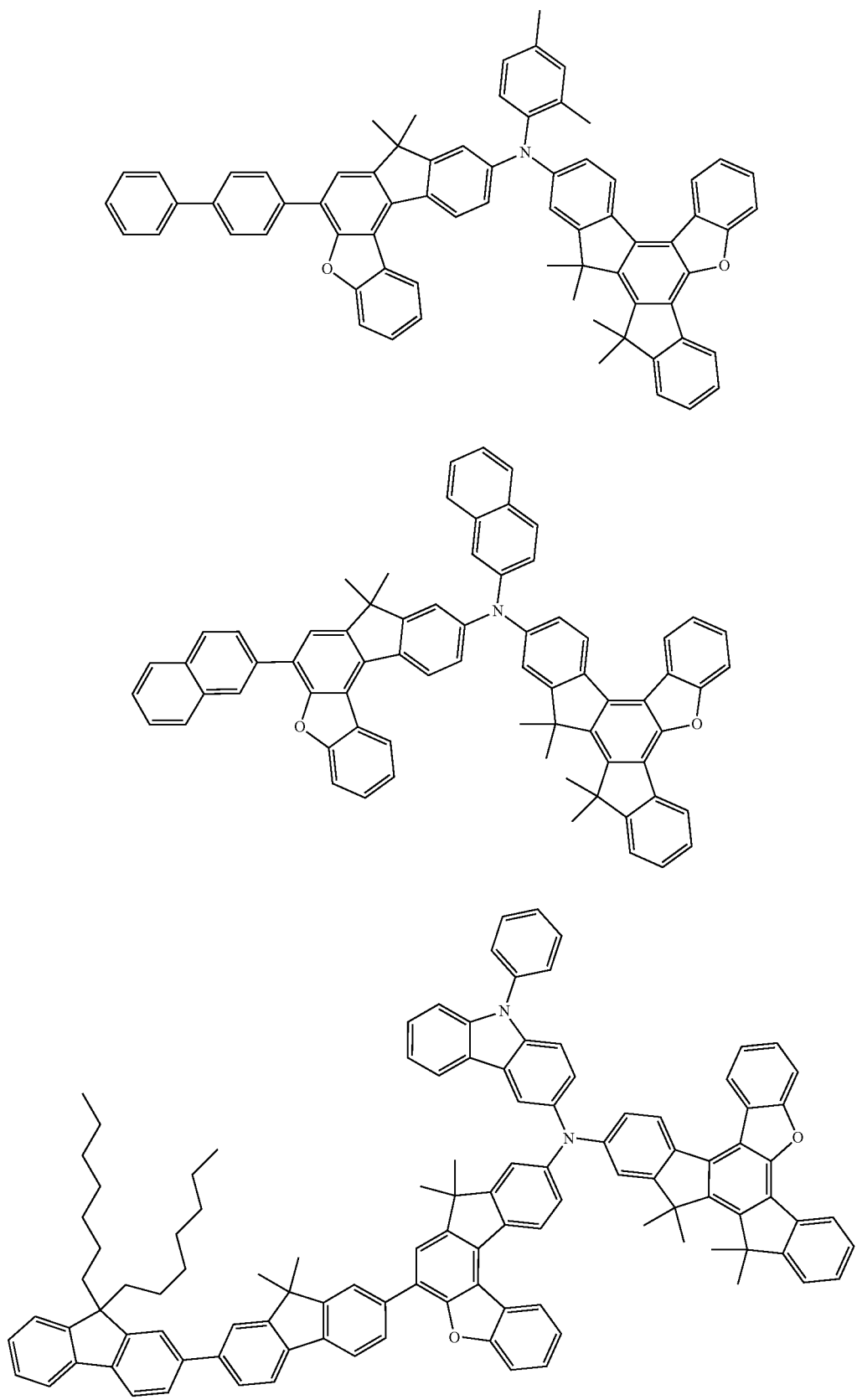

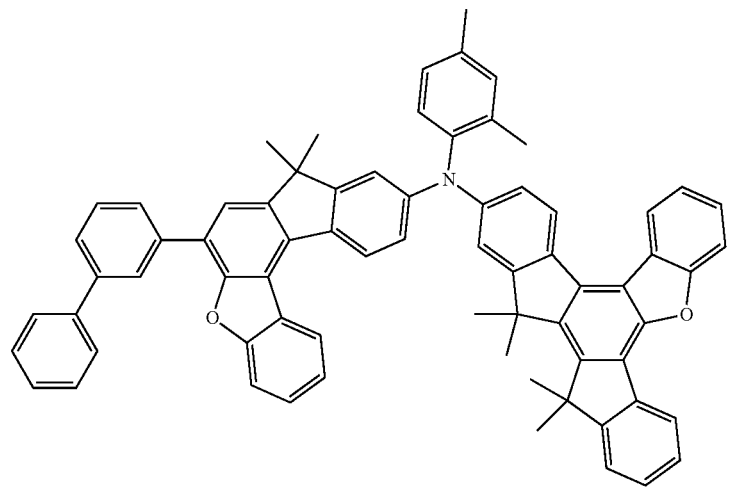 [SMILES: Cc1ccc(N(c2ccc3c(c2)C(C)(C)c2cc(-c4cccc(-c5ccccc5)c4)c4oc5ccccc5c4c2-3)c2ccc3c(c2)C(C)(C)c2c4c(c5oc6ccccc6c5c2-3)-c2ccccc2C4(C)C)c(C)c1]
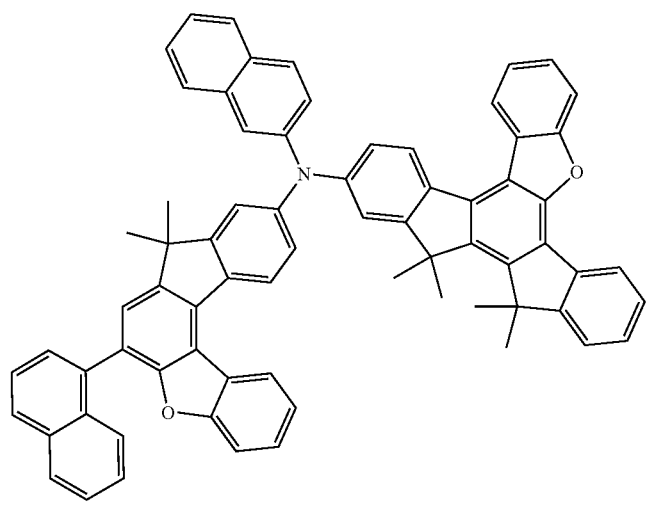 [SMILES: CC1(C)c2cc(N(c3ccc4c(c3)C(C)(C)c3c5c(c6oc7ccccc7c6c3-4)-c3ccccc3C5(C)C)c3ccc4ccccc4c3)ccc2-c2c1cc(-c1cccc3ccccc13)c1oc3ccccc3c21]
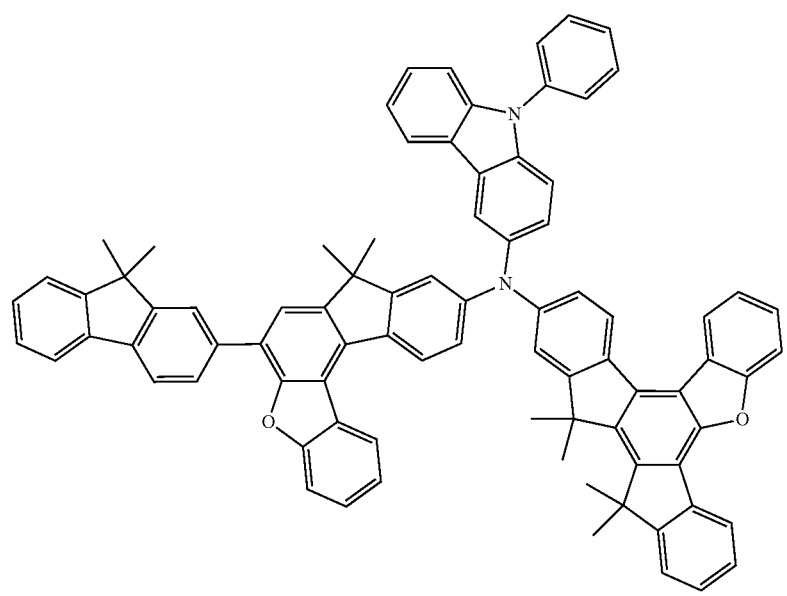 [SMILES: CC1(C)c2ccccc2-c2ccc(-c3cc4c(c5c3oc3ccccc35)-c3ccc(N(c5ccc6c(c5)C(C)(C)c5c7c(c8oc9ccccc9c8c5-6)-c5ccccc5C7(C)C)c5ccc6c(c5)c5ccccc5n6-c5ccccc5)cc3C4(C)C)cc21]

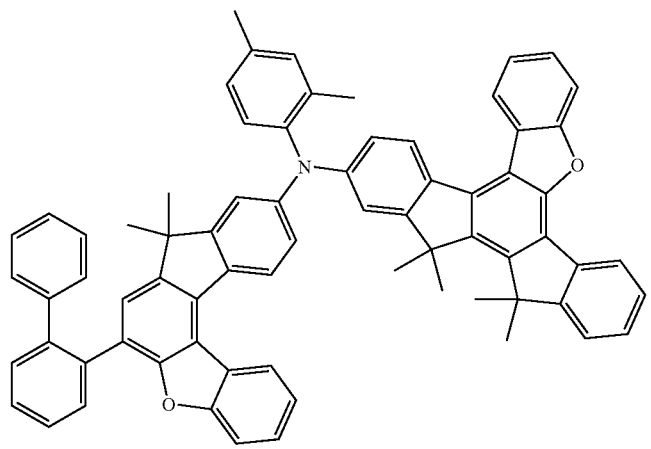 [SMILES: Cc1ccc(N(c2ccc3c(c2)C(C)(C)c2cc(-c4ccccc4-c4ccccc4)c4oc5ccccc5c4c2-3)c2ccc3c(c2)C(C)(C)c2c4c(c5oc6ccccc6c5c2-3)-c2ccccc2C4(C)C)c(C)c1]
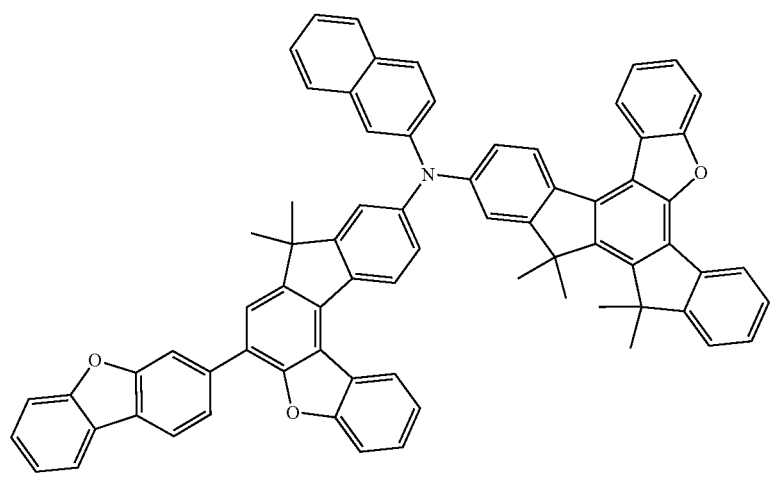 [SMILES: CC1(C)c2cc(N(c3ccc4c(c3)C(C)(C)c3c5c(c6oc7ccccc7c6c3-4)-c3ccccc3C5(C)C)c3ccc4ccccc4c3)ccc2-c2c1cc(-c1ccc3c(c1)oc1ccccc13)c1oc3ccccc3c21]
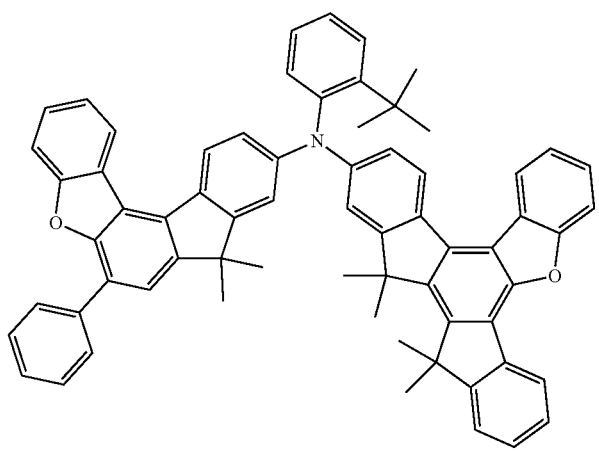 [SMILES: CC(C)(C)c1ccccc1N(c1ccc2c(c1)C(C)(C)c1cc(-c3ccccc3)c3oc4ccccc4c3c1-2)c1ccc2c(c1)C(C)(C)c1c3c(c4oc5ccccc5c4c1-2)-c1ccccc1C3(C)C]

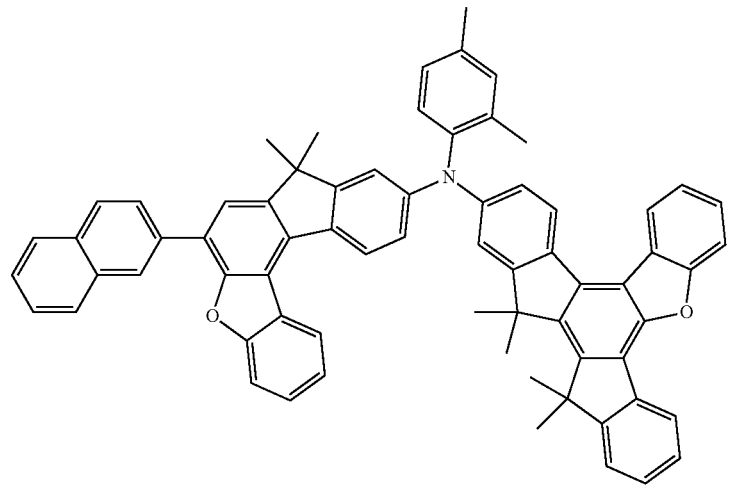 [SMILES: Cc1ccc(N(c2ccc3c(c2)C(C)(C)c2cc(-c4ccc5ccccc5c4)c4oc5ccccc5c4c2-3)c2ccc3c(c2)C(C)(C)c2c4c(c5oc6ccccc6c5c2-3)-c2ccccc2C4(C)C)c(C)c1]
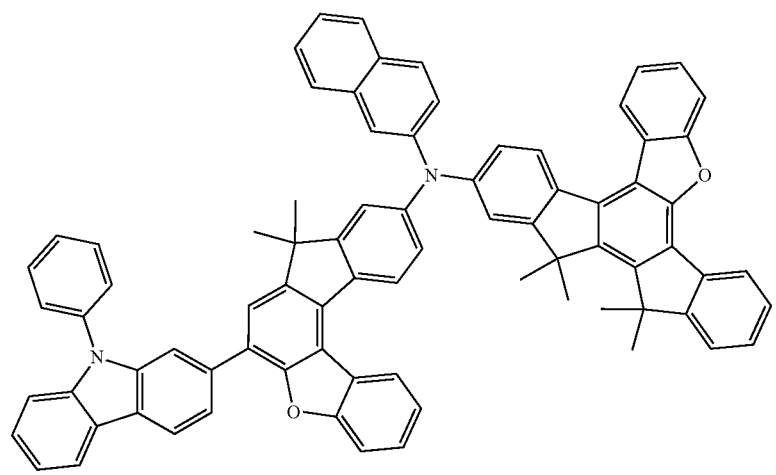 [SMILES: CC1(C)c2cc(N(c3ccc4c(c3)C(C)(C)c3c5c(c6oc7ccccc7c6c3-4)-c3ccccc3C5(C)C)c3ccc4ccccc4c3)ccc2-c2c1cc(-c1ccc3c4ccccc4n(-c4ccccc4)c3c1)c1oc3ccccc3c21]
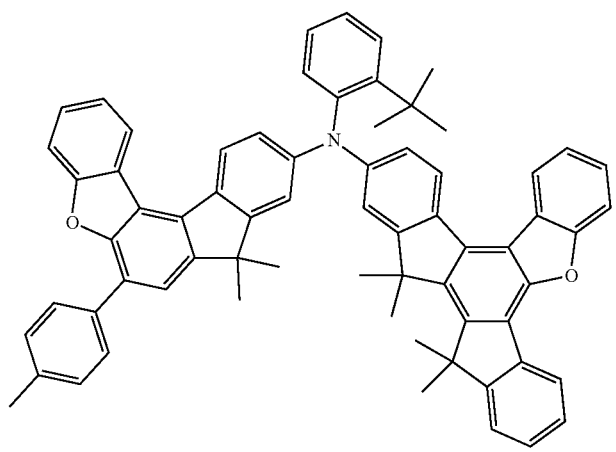 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccccc4C(C)(C)C)cc2C3(C)C)cc1]

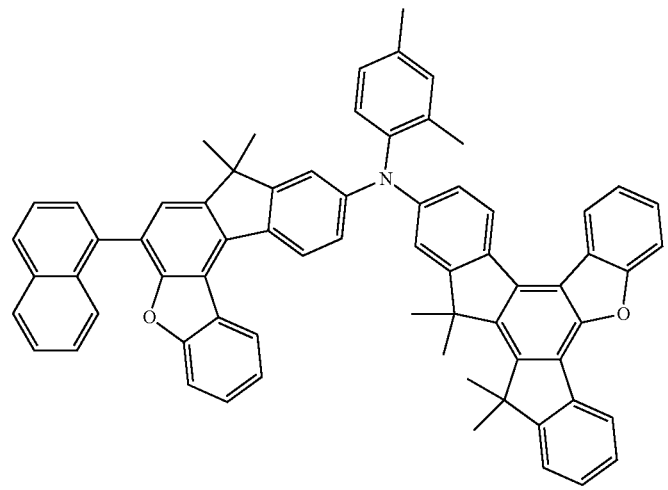 [SMILES: Cc1ccc(N(c2ccc3c(c2)C(C)(C)c2cc(-c4cccc5ccccc45)c4oc5ccccc5c4c2-3)c2ccc3c(c2)C(C)(C)c2c4c(c5oc6ccccc6c5c2-3)-c2ccccc2C4(C)C)c(C)c1]
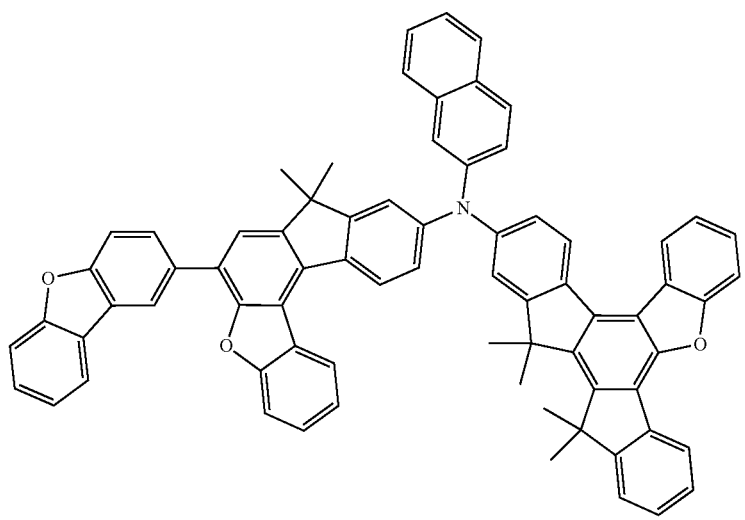 [SMILES: CC1(C)c2cc(N(c3ccc4c(c3)C(C)(C)c3c5c(c6oc7ccccc7c6c3-4)-c3ccccc3C5(C)C)c3ccc4ccccc4c3)ccc2-c2c1cc(-c1ccc3oc4ccccc4c3c1)c1oc3ccccc3c21]
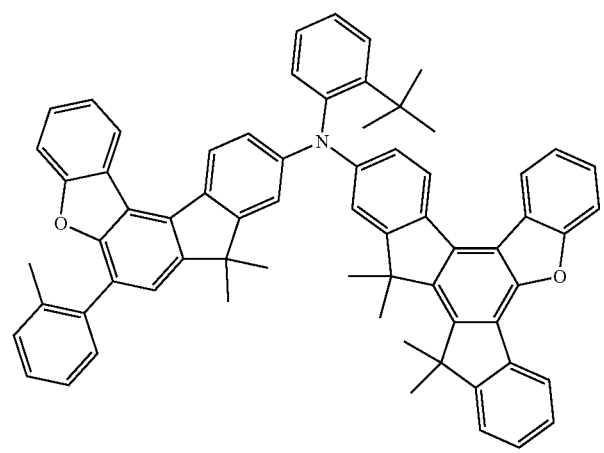 [SMILES: Cc1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3ccccc3C(C)(C)C)cc1C2(C)C]

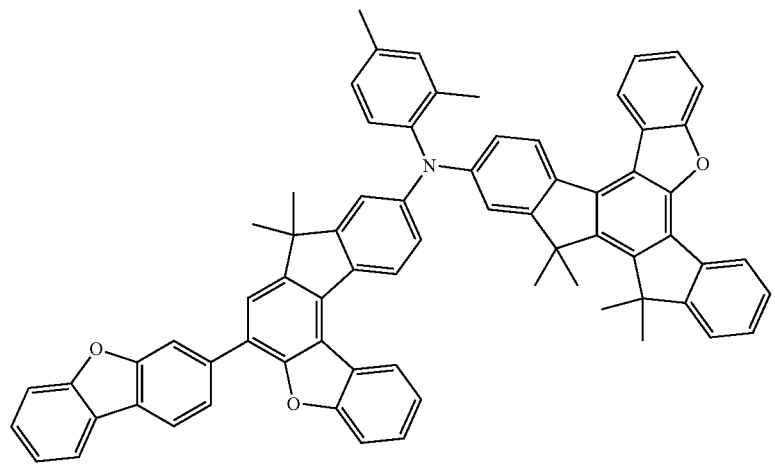 [SMILES: Cc1ccc(N(c2ccc3c(c2)C(C)(C)c2cc(-c4ccc5c(c4)oc4ccccc45)c4oc5ccccc5c4c2-3)c2ccc3c(c2)C(C)(C)c2c4c(c5oc6ccccc6c5c2-3)-c2ccccc2C4(C)C)c(C)c1]
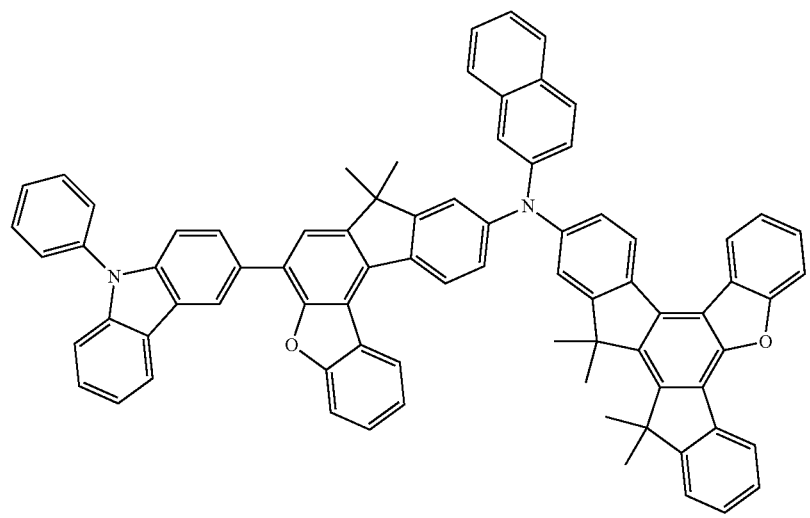 [SMILES: CC1(C)c2cc(N(c3ccc4c(c3)C(C)(C)c3c5c(c6oc7ccccc7c6c3-4)-c3ccccc3C5(C)C)c3ccc4ccccc4c3)ccc2-c2c1cc(-c1ccc3c(c1)c1ccccc1n3-c1ccccc1)c1oc3ccccc3c21]
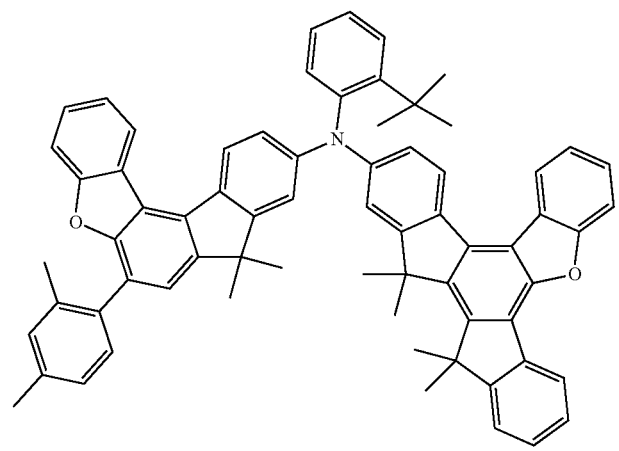 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccccc4C(C)(C)C)cc2C3(C)C)c(C)c1]

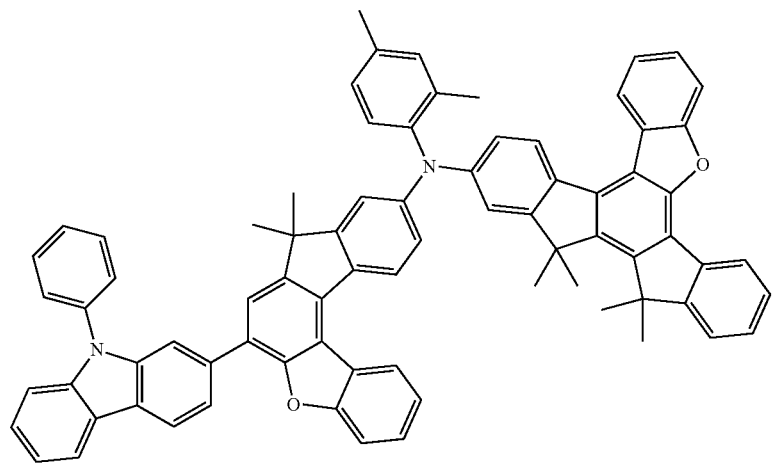 [SMILES: Cc1ccc(N(c2ccc3c(c2)C(C)(C)c2cc(-c4ccc5c6ccccc6n(-c6ccccc6)c5c4)c4oc5ccccc5c4c2-3)c2ccc3c(c2)C(C)(C)c2c4c(c5oc6ccccc6c5c2-3)-c2ccccc2C4(C)C)c(C)c1]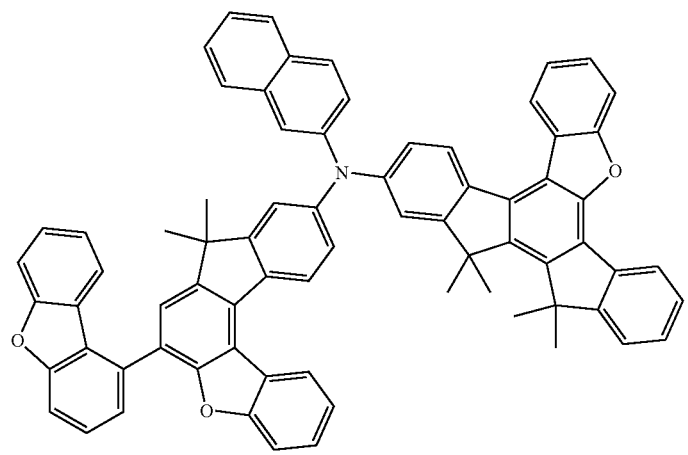 [SMILES: CC1(C)c2cc(N(c3ccc4c(c3)C(C)(C)c3c5c(c6oc7ccccc7c6c3-4)-c3ccccc3C5(C)C)c3ccc4ccccc4c3)ccc2-c2c1cc(-c1cccc3oc4ccccc4c13)c1oc3ccccc3c21]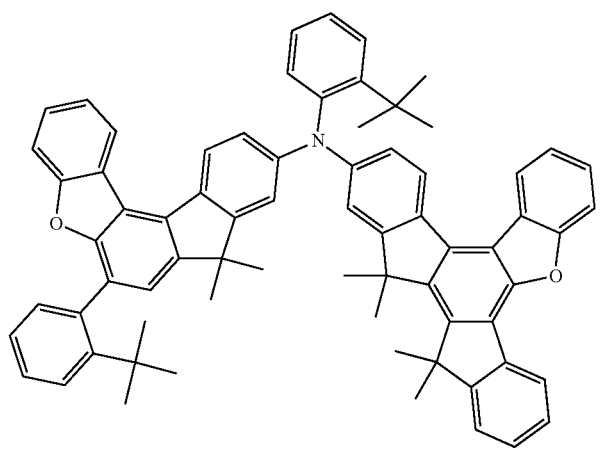 [SMILES: CC(C)(C)c1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3ccccc3C(C)(C)C)cc1C2(C)C]

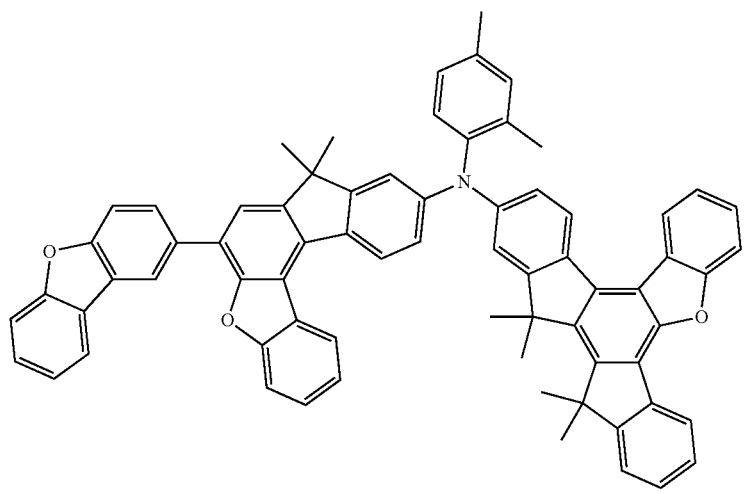 [SMILES: Cc1ccc(N(c2ccc3c(c2)C(C)(C)c2cc(-c4ccc5oc6ccccc6c5c4)c4oc5ccccc5c4c2-3)c2ccc3c(c2)C(C)(C)c2c4c(c5oc6ccccc6c5c2-3)-c2ccccc2C4(C)C)c(C)c1]
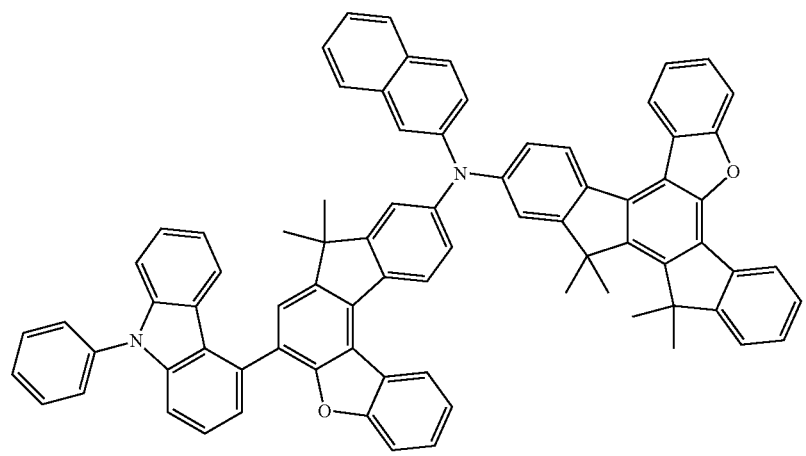 [SMILES: CC1(C)c2cc(N(c3ccc4c(c3)C(C)(C)c3c5c(c6oc7ccccc7c6c3-4)-c3ccccc3C5(C)C)c3ccc4ccccc4c3)ccc2-c2c1cc(-c1cccc3c1c1ccccc1n3-c1ccccc1)c1oc3ccccc3c21]
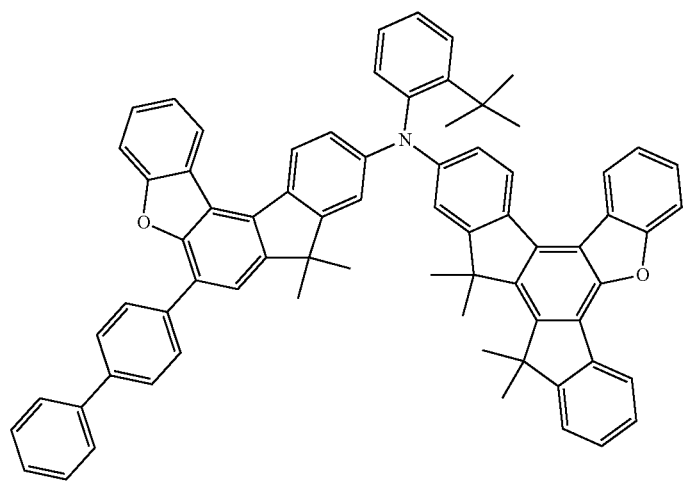 [SMILES: CC(C)(C)c1ccccc1N(c1ccc2c(c1)C(C)(C)c1cc(-c3ccc(-c4ccccc4)cc3)c3oc4ccccc4c3c1-2)c1ccc2c(c1)C(C)(C)c1c3c(c4oc5ccccc5c4c1-2)-c1ccccc1C3(C)C]

-continued
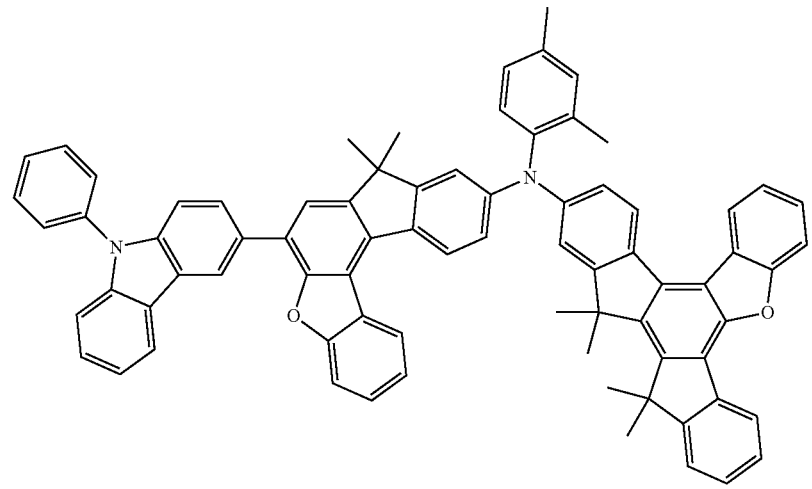 [SMILES: Cc1ccc(N(c2ccc3c(c2)C(C)(C)c2cc(-c4ccc5c(c4)c4ccccc4n5-c4ccccc4)c4oc5ccccc5c4c2-3)c2ccc3c(c2)C(C)(C)c2c4c(c5oc6ccccc6c5c2-3)-c2ccccc2C4(C)C)c(C)c1]
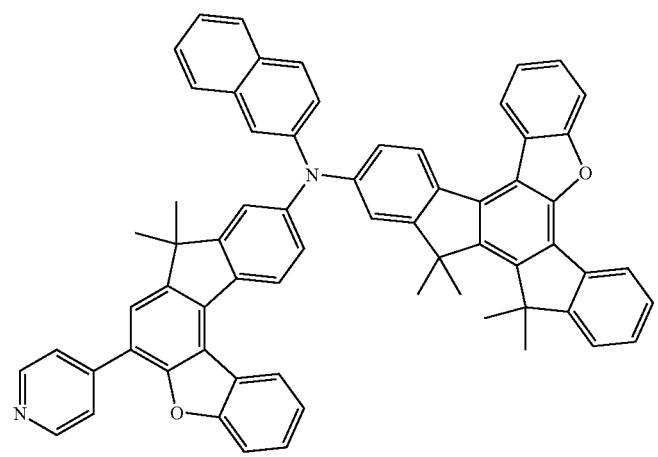 [SMILES: CC1(C)c2cc(N(c3ccc4c(c3)C(C)(C)c3c5c(c6oc7ccccc7c6c3-4)-c3ccccc3C5(C)C)c3ccc4ccccc4c3)ccc2-c2c1cc(-c1ccncc1)c1oc3ccccc3c21]
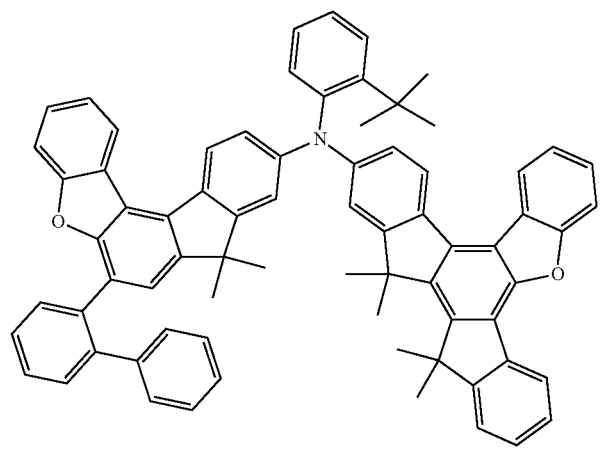 [SMILES: CC(C)(C)c1ccccc1N(c1ccc2c(c1)C(C)(C)c1cc(-c3ccccc3-c3ccccc3)c3oc4ccccc4c3c1-2)c1ccc2c(c1)C(C)(C)c1c3c(c4oc5ccccc5c4c1-2)-c1ccccc1C3(C)C]

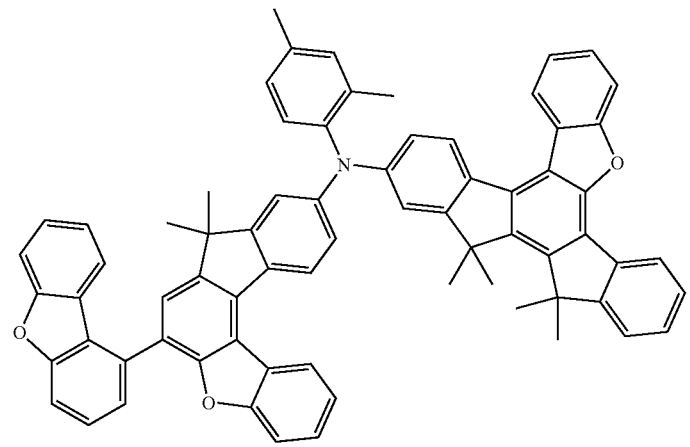 [SMILES: Cc1ccc(N(c2ccc3c(c2)C(C)(C)c2cc(-c4cccc5oc6ccccc6c45)c4oc5ccccc5c4c2-3)c2ccc3c(c2)C(C)(C)c2c4c(c5oc6ccccc6c5c2-3)-c2ccccc2C4(C)C)c(C)c1]
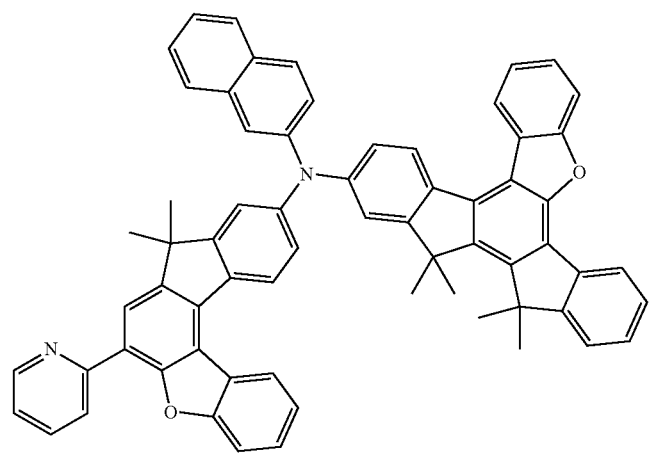 [SMILES: CC1(C)c2cc(N(c3ccc4c(c3)C(C)(C)c3c5c(c6oc7ccccc7c6c3-4)-c3ccccc3C5(C)C)c3ccc4ccccc4c3)ccc2-c2c1cc(-c1ccccn1)c1oc3ccccc3c21]
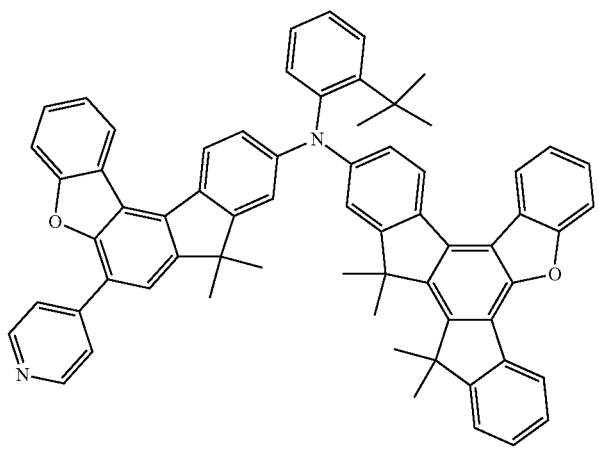 [SMILES: CC(C)(C)c1ccccc1N(c1ccc2c(c1)C(C)(C)c1cc(-c3ccncc3)c3oc4ccccc4c3c1-2)c1ccc2c(c1)C(C)(C)c1c3c(c4oc5ccccc5c4c1-2)-c1ccccc1C3(C)C]

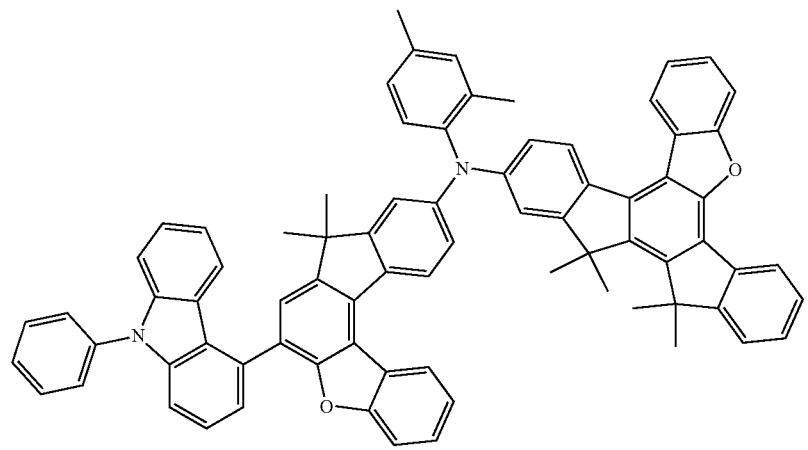 [SMILES: Cc1ccc(N(c2ccc3c(c2)C(C)(C)c2cc(-c4cccc5c4c4ccccc4n5-c4ccccc4)c4oc5ccccc5c4c2-3)c2ccc3c(c2)C(C)(C)c2c4c(c5oc6ccccc6c5c2-3)-c2ccccc2C4(C)C)c(C)c1]
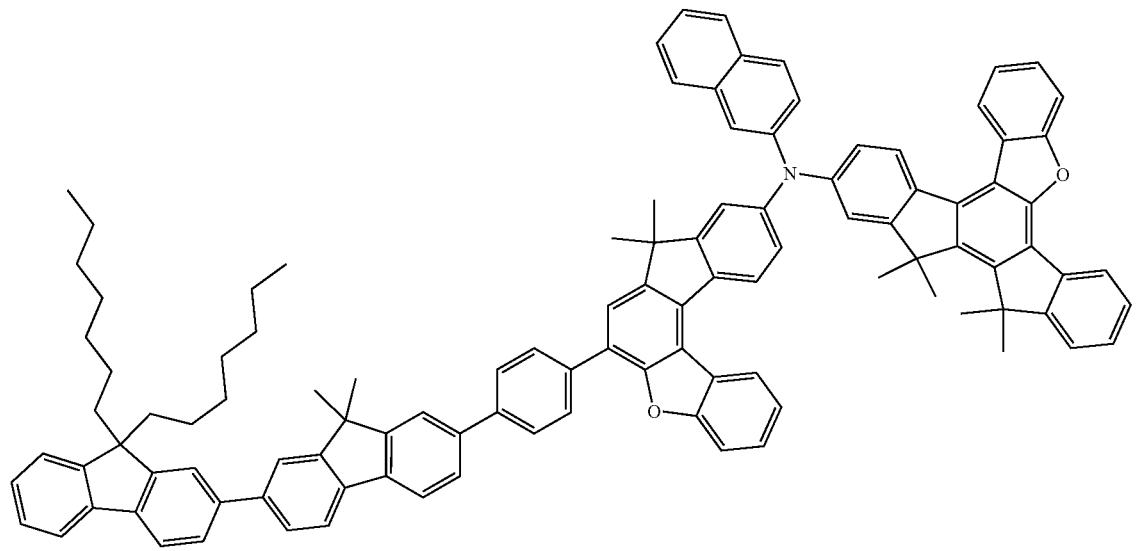 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8ccc9ccccc9c8)cc6C7(C)C)cc5)ccc3-4)cc21]
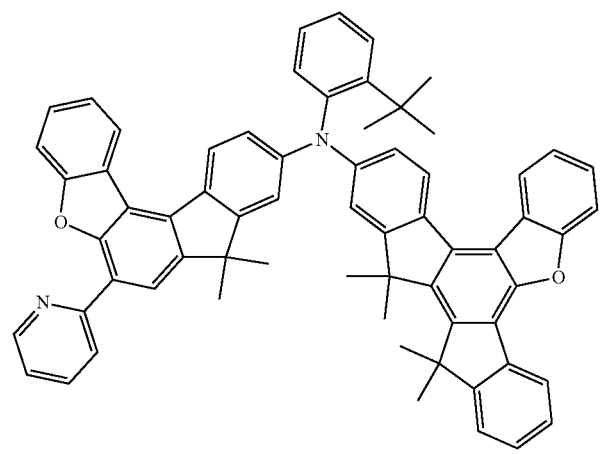 [SMILES: CC(C)(C)c1ccccc1N(c1ccc2c(c1)C(C)(C)c1cc(-c3ccccn3)c3oc4ccccc4c3c1-2)c1ccc2c(c1)C(C)(C)c1c3c(c4oc5ccccc5c4c1-2)-c1ccccc1C3(C)C]

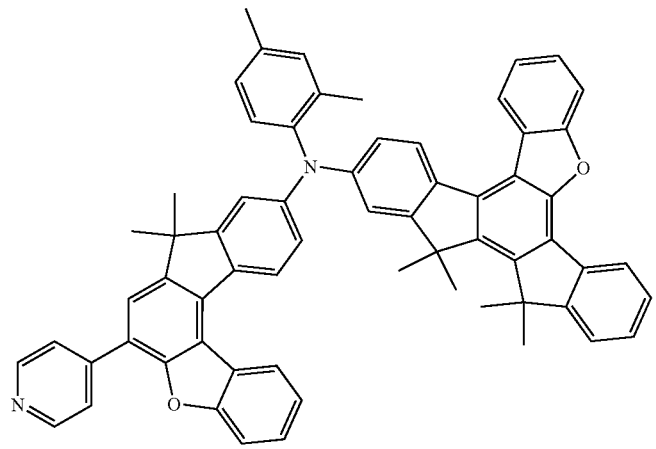 [SMILES: Cc1ccc(N(c2ccc3c(c2)C(C)(C)c2cc(-c4ccncc4)c4oc5ccccc5c4c2-3)c2ccc3c(c2)C(C)(C)c2c4c(c5oc6ccccc6c5c2-3)-c2ccccc2C4(C)C)c(C)c1]
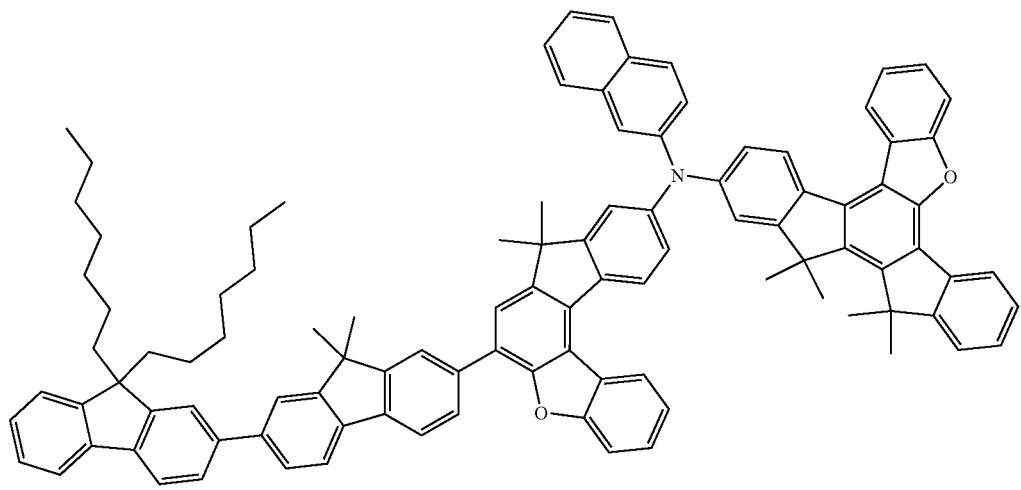 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7ccc8ccccc8c7)cc5C6(C)C)ccc3-4)cc21]
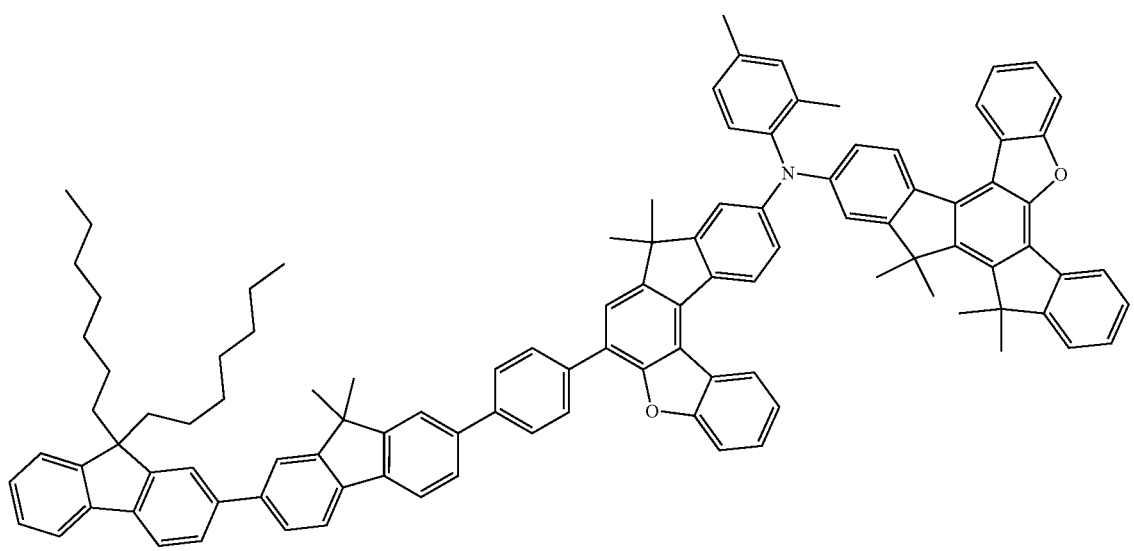 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8ccc(C)cc8C)cc6C7(C)C)cc5)ccc3-4)cc21]

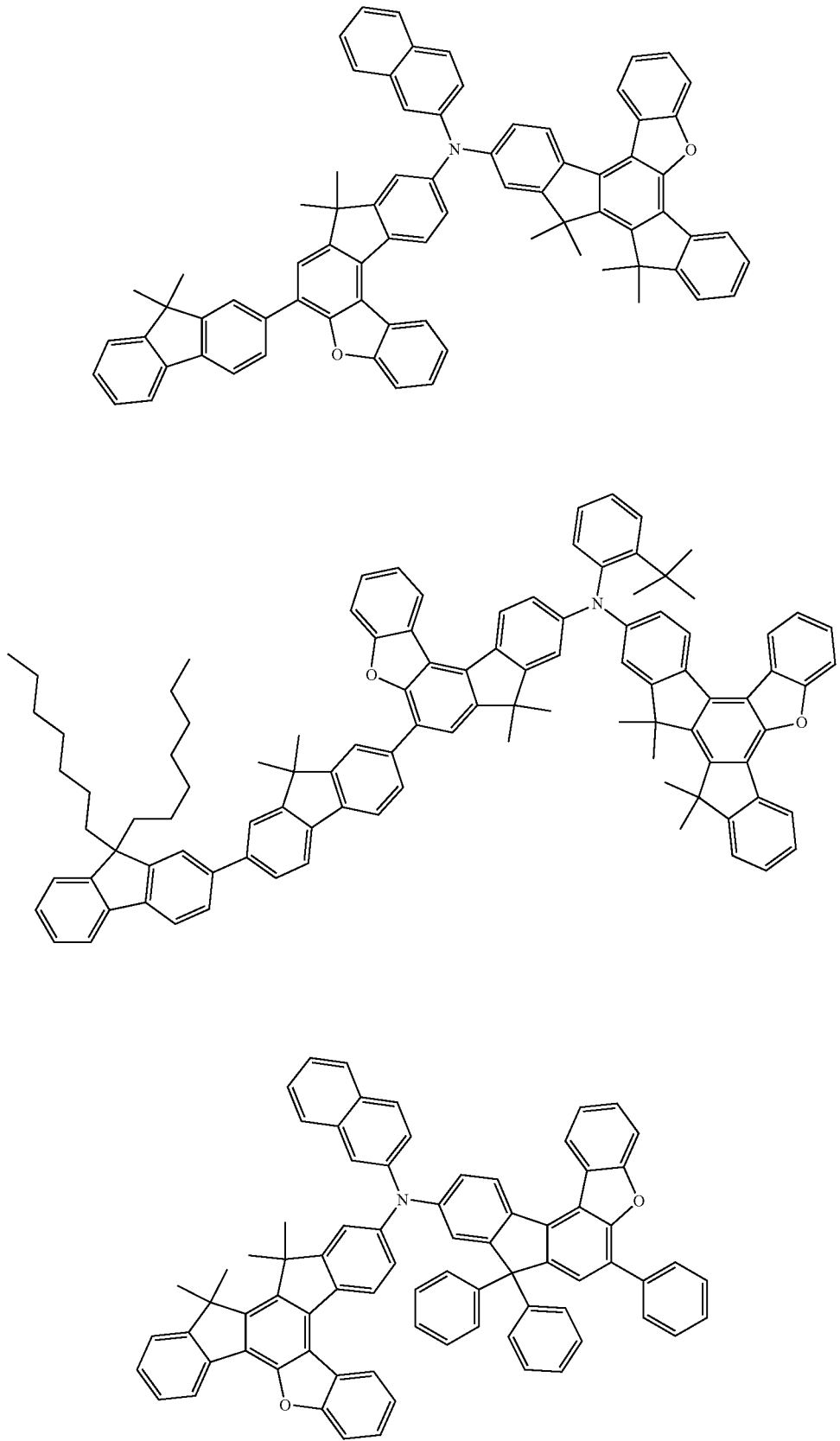

-continued
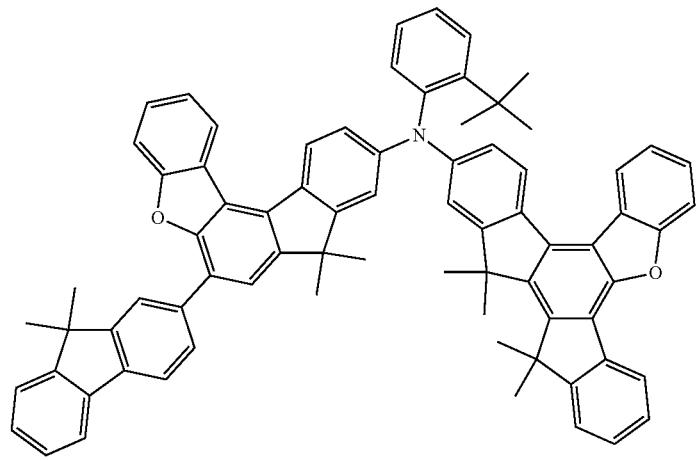 [SMILES: CC(C)(C)c1ccccc1N(c1ccc2c(c1)C(C)(C)c1cc(-c3ccc4c(c3)C(C)(C)c3ccccc3-4)c3oc4ccccc4c3c1-2)c1ccc2c(c1)C(C)(C)c1c3c(c4oc5ccccc5c4c1-2)-c1ccccc1C3(C)C]
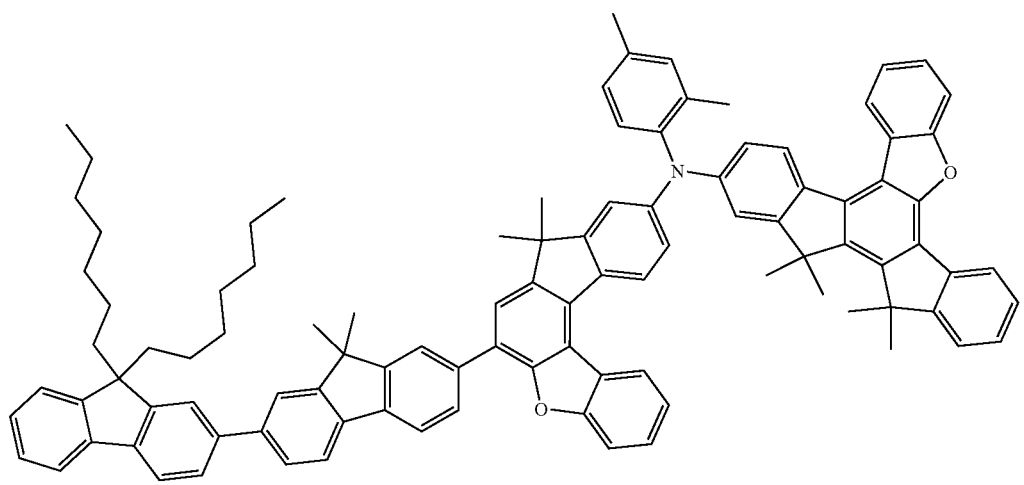 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7ccc(C)cc7C)cc5C6(C)C)ccc3-4)cc21]
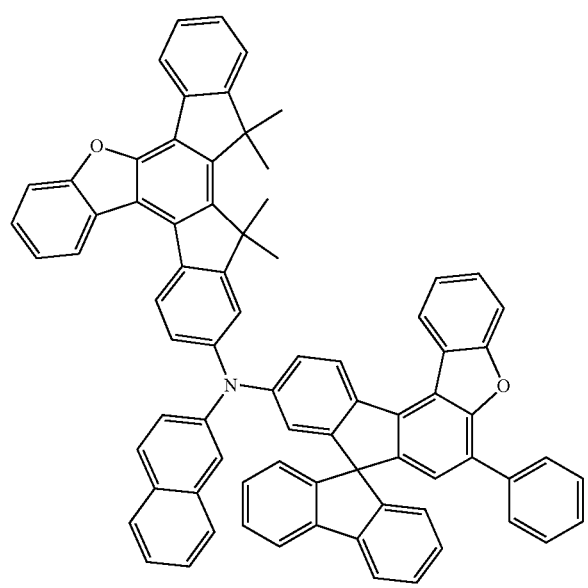 [SMILES: CC1(C)c2ccccc2-c2c1c1c(c3c2oc2ccccc23)-c2ccc(N(c3ccc4c(c3)C3(c5ccccc5-c5ccccc53)c3cc(-c5ccccc5)c5oc6ccccc6c5c3-4)c3ccc4ccccc4c3)cc2C1(C)C]

-continued
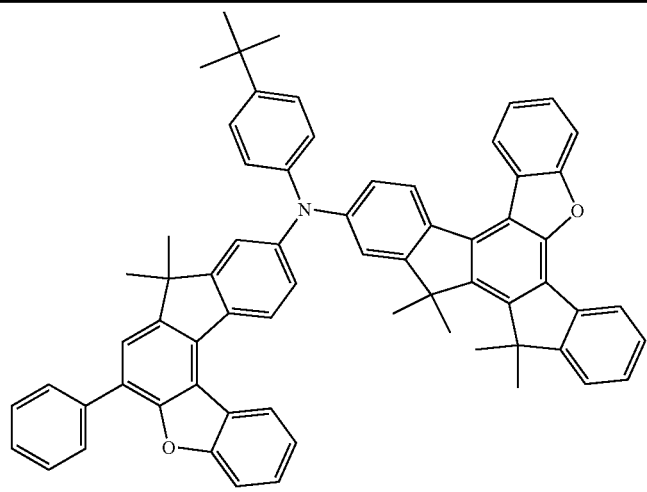
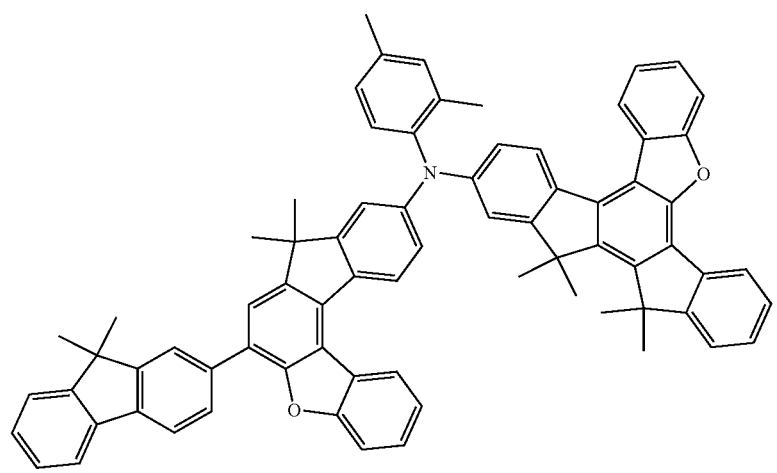 [SMILES: Cc1ccc(N(c2ccc3c(c2)C(C)(C)c2cc(-c4ccc5c(c4)C(C)(C)c4ccccc4-5)c4oc5ccccc5c4c2-3)c2ccc3c(c2)C(C)(C)c2c4c(c5oc6ccccc6c5c2-3)-c2ccccc2C4(C)C)c(C)c1]
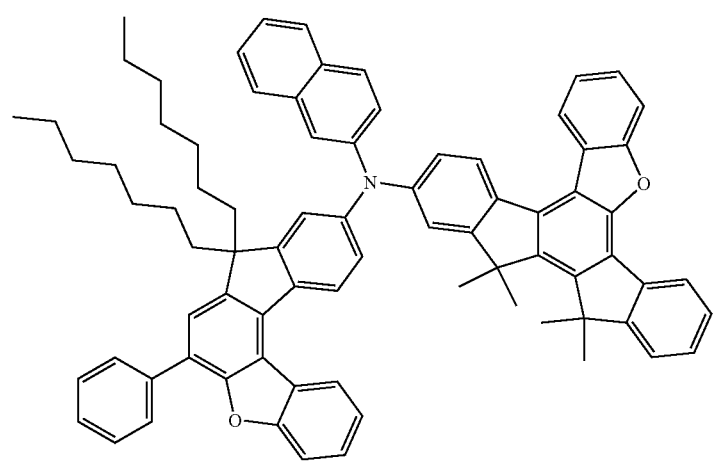 [SMILES: CCCCCCCC1(CCCCCCC)c2cc(N(c3ccc4c(c3)C(C)(C)c3c5c(c6oc7ccccc7c6c3-4)-c3ccccc3C5(C)C)c3ccc4ccccc4c3)ccc2-c2c1cc(-c1ccccc1)c1oc3ccccc3c21]

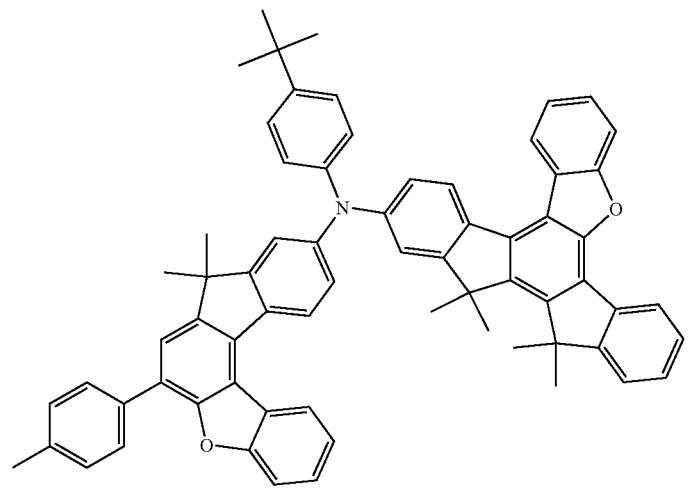 [SMILES: Cc1ccc(-c2cc3c(c4c2oc2ccccc24)-c2ccc(N(c4ccc(C(C)(C)C)cc4)c4ccc5c(c4)C(C)(C)c4c6c(c7oc8ccccc8c7c4-5)-c4ccccc4C6(C)C)cc2C3(C)C)cc1]
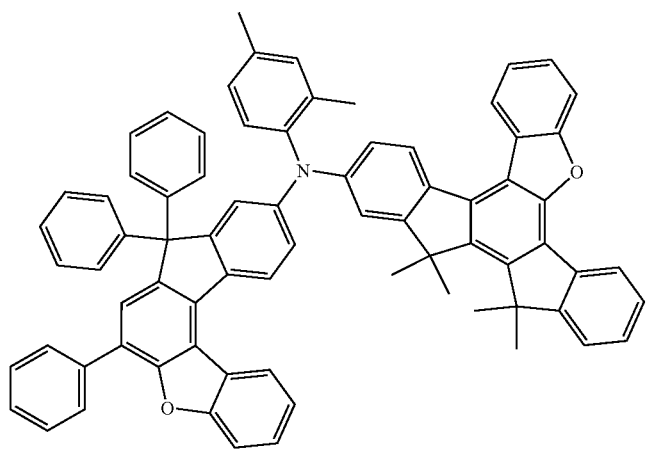 [SMILES: Cc1ccc(N(c2ccc3c(c2)C(C)(C)c2c4c(c5oc6ccccc6c5c2-3)-c2ccccc2C4(C)C)c2ccc3c(c2)C(c2ccccc2)(c2ccccc2)c2cc(-c4ccccc4)c4oc5ccccc5c4c2-3)c(C)c1]
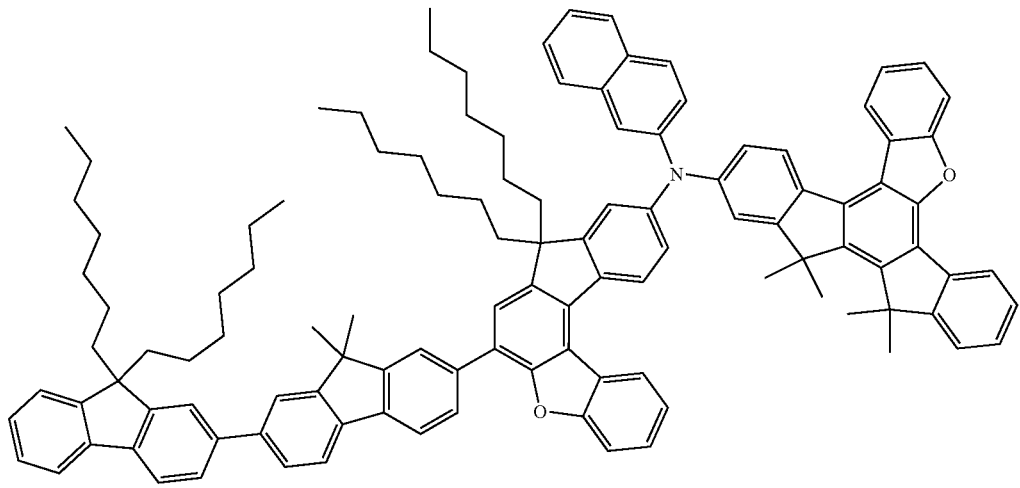 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7ccc8ccccc8c7)cc5C6(CCCCCCC)CCCCCCC)ccc3-4)cc21]

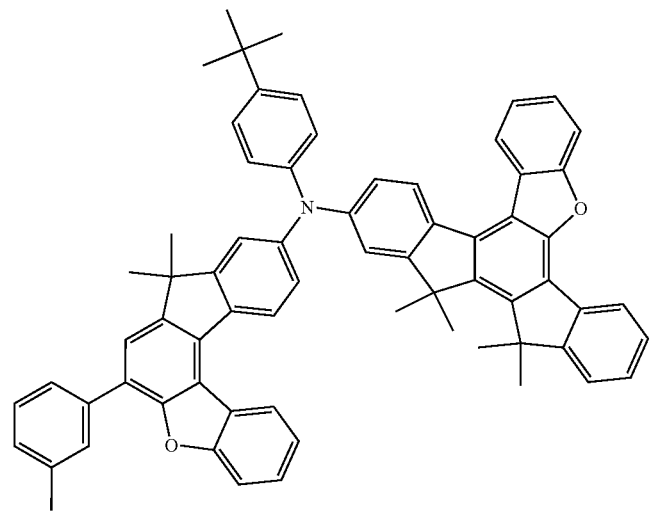 [SMILES: Cc1cccc(-c2cc3c(c4c2oc2ccccc24)-c2ccc(N(c4ccc(C(C)(C)C)cc4)c4ccc5c(c4)C(C)(C)c4c6c(c7oc8ccccc8c7c4-5)-c4ccccc4C6(C)C)cc2C3(C)C)c1]
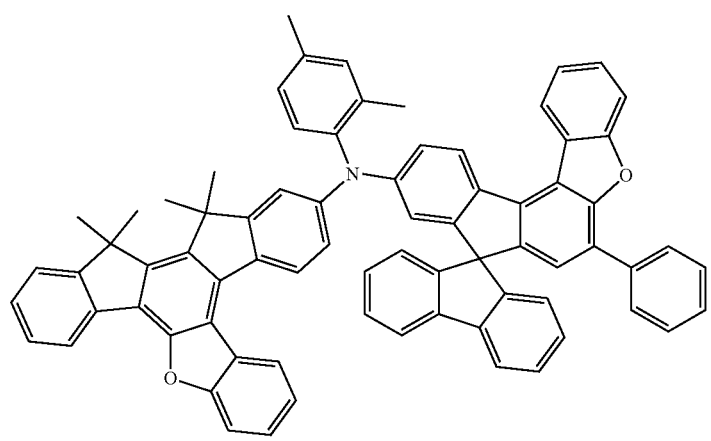 [SMILES: Cc1ccc(N(c2ccc3c(c2)C(C)(C)c2c4c(c5oc6ccccc6c5c2-3)-c2ccccc2C4(C)C)c2ccc3c(c2)C2(c4ccccc4-c4ccccc42)c2cc(-c4ccccc4)c4oc5ccccc5c4c2-3)c(C)c1]
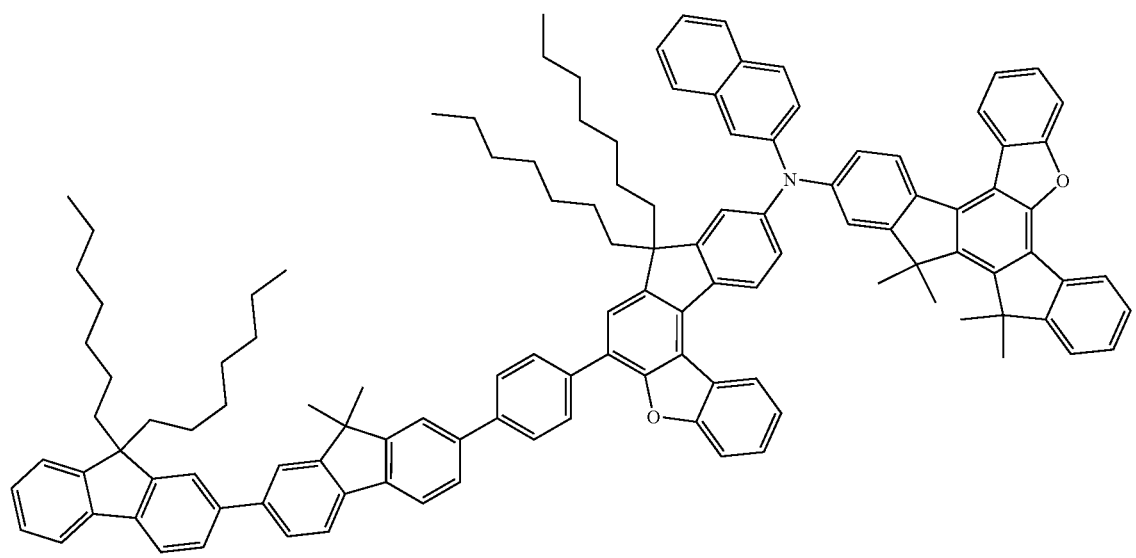 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8ccc9ccccc9c8)cc6C7(CCCCCCC)CCCCCCC)cc5)ccc3-4)cc21]

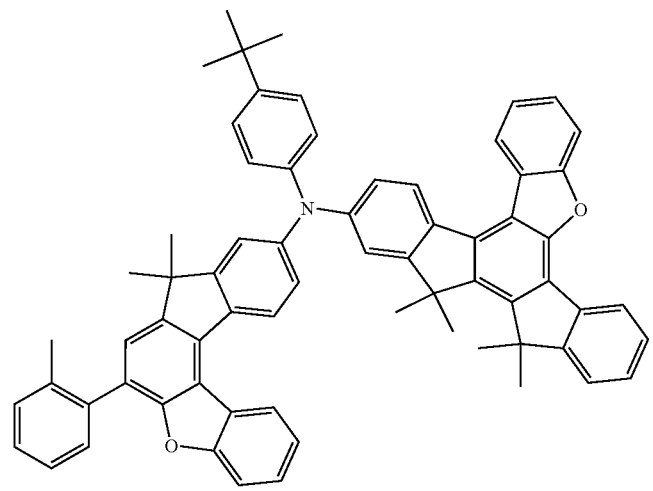 [SMILES: Cc1ccccc1-c1cc2c(c3c1oc1ccccc13)-c1ccc(N(c3ccc(C(C)(C)C)cc3)c3ccc4c(c3)C(C)(C)c3c5c(c6oc7ccccc7c6c3-4)-c3ccccc3C5(C)C)cc1C2(C)C]
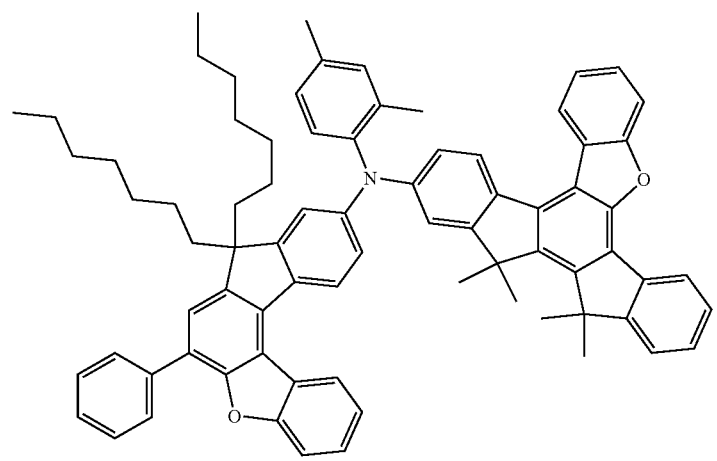 [SMILES: CCCCCCCC1(CCCCCCC)c2cc(N(c3ccc4c(c3)C(C)(C)c3c5c(c6oc7ccccc7c6c3-4)-c3ccccc3C5(C)C)c3ccc(C)cc3C)ccc2-c2c1cc(-c1ccccc1)c1oc3ccccc3c21]
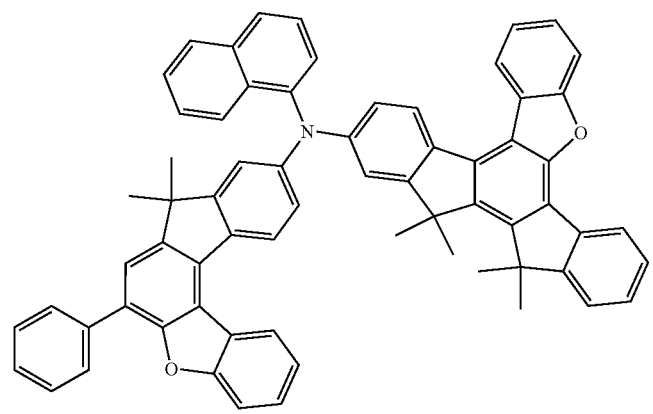 [SMILES: CC1(C)c2cc(N(c3ccc4c(c3)C(C)(C)c3c5c(c6oc7ccccc7c6c3-4)-c3ccccc3C5(C)C)c3cccc4ccccc34)ccc2-c2c1cc(-c1ccccc1)c1oc3ccccc3c21]

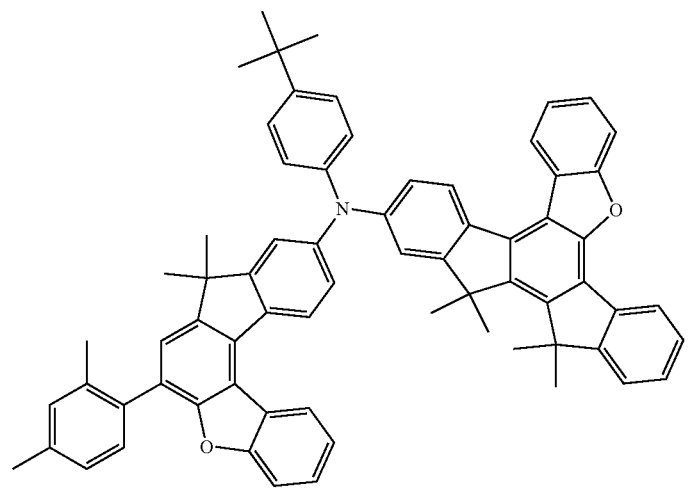 [SMILES: Cc1ccc(-c2cc3c(c4c2oc2ccccc24)-c2ccc(N(c4ccc(C(C)(C)C)cc4)c4ccc5c(c4)C(C)(C)c4c6c(c7oc8ccccc8c7c4-5)-c4ccccc4C6(C)C)cc2C3(C)C)c(C)c1]
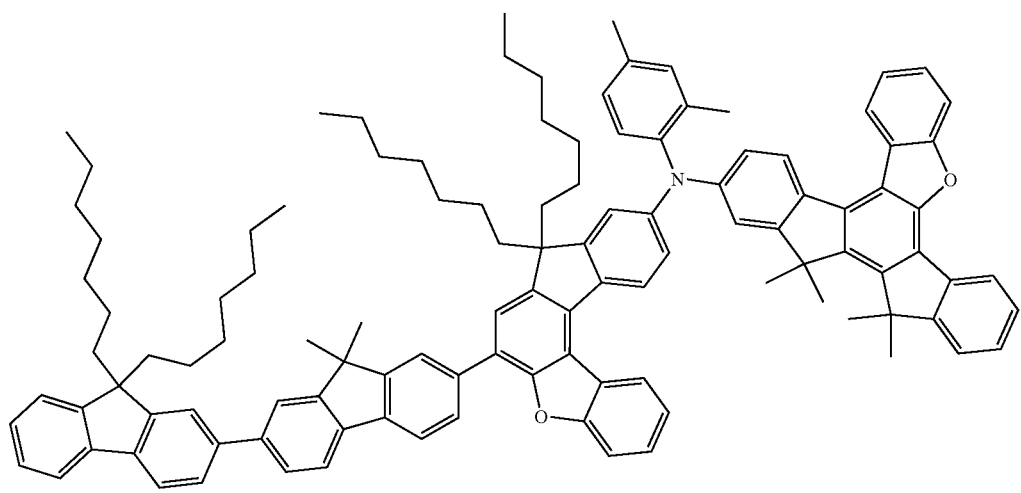 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7ccc(C)cc7C)cc5C6(CCCCCCC)CCCCCCC)ccc3-4)cc21]
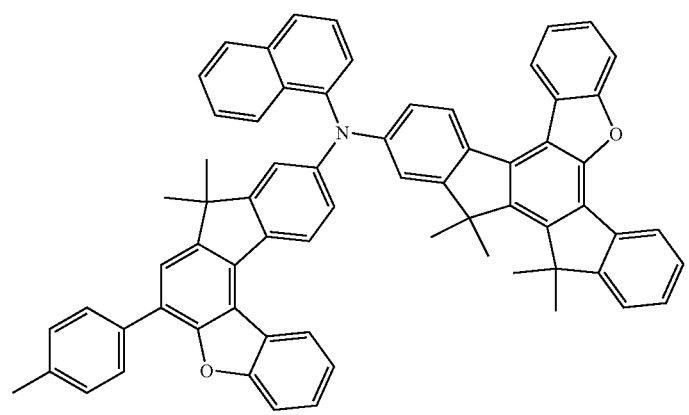 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4cccc5ccccc45)cc2C3(C)C)cc1]

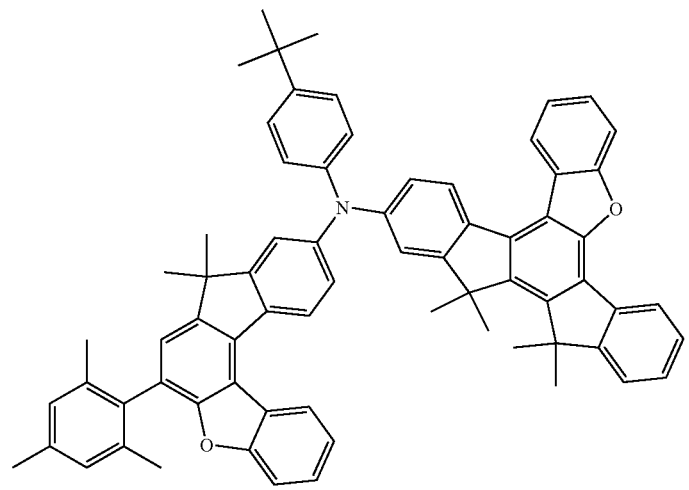 [SMILES: Cc1cc(C)c(-c2cc3c(c4c2oc2ccccc24)-c2ccc(N(c4ccc(C(C)(C)C)cc4)c4ccc5c(c4)C(C)(C)c4c6c(c7oc8ccccc8c7c4-5)-c4ccccc4C6(C)C)cc2C3(C)C)c(C)c1]
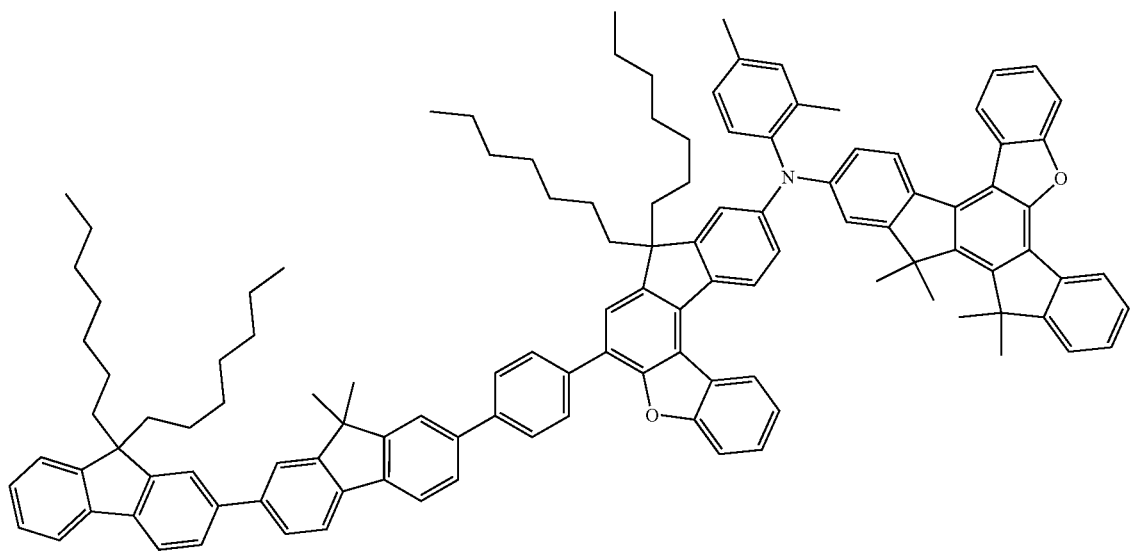 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8ccc(C)cc8C)cc6C7(CCCCCCC)CCCCCCC)cc5)ccc3-4)cc21]
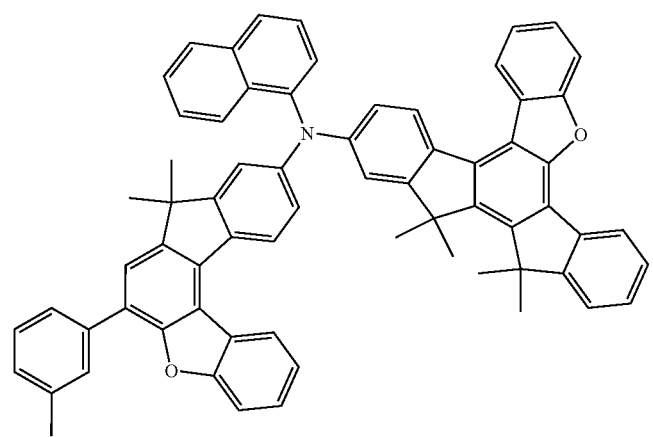 [SMILES: Cc1cccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4cccc5ccccc45)cc2C3(C)C)c1]

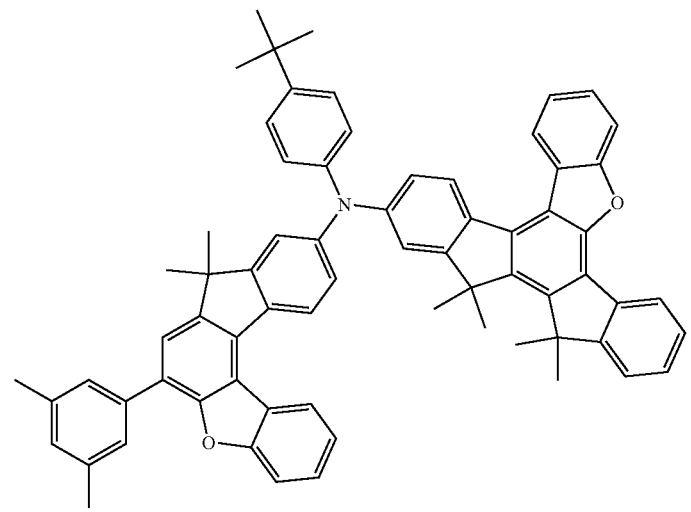 [SMILES: Cc1cc(C)cc(-c2cc3c(c4c2oc2ccccc24)-c2ccc(N(c4ccc(C(C)(C)C)cc4)c4ccc5c(c4)C(C)(C)c4c6c(c7oc8ccccc8c7c4-5)-c4ccccc4C6(C)C)cc2C3(C)C)c1]
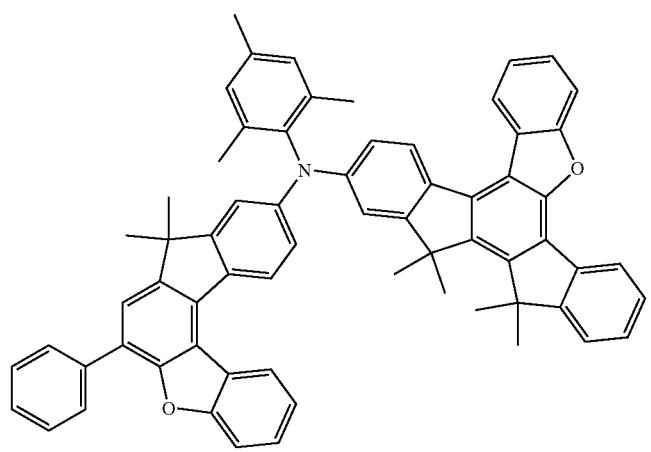 [SMILES: Cc1cc(C)c(N(c2ccc3c(c2)C(C)(C)c2cc(-c4ccccc4)c4oc5ccccc5c4c2-3)c2ccc3c(c2)C(C)(C)c2c4c(c5oc6ccccc6c5c2-3)-c2ccccc2C4(C)C)c(C)c1]
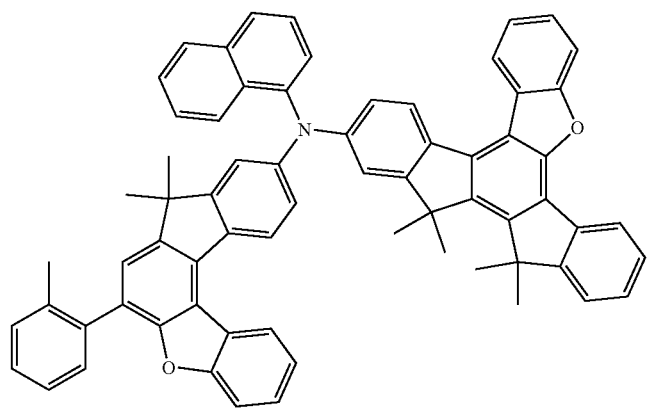 [SMILES: Cc1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3cccc4ccccc34)cc1C2(C)C]

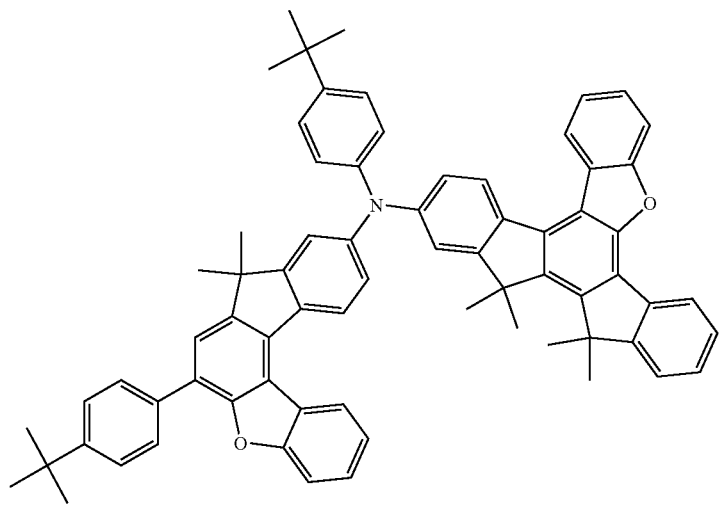 [SMILES: CC(C)(C)c1ccc(-c2cc3c(c4c2oc2ccccc24)-c2ccc(N(c4ccc(C(C)(C)C)cc4)c4ccc5c(c4)C(C)(C)c4c6c(c7oc8ccccc8c7c4-5)-c4ccccc4C6(C)C)cc2C3(C)C)cc1]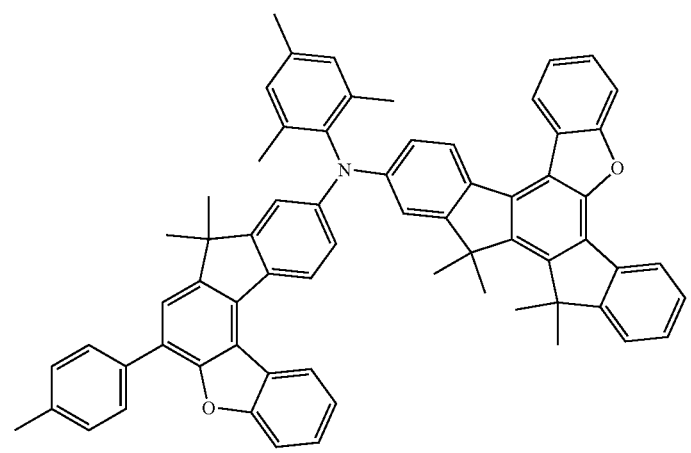 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4c(C)cc(C)cc4C)cc2C3(C)C)cc1]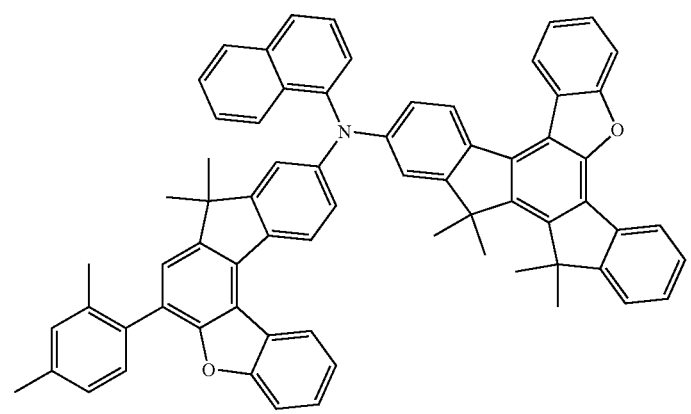 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4cccc5ccccc45)cc2C3(C)C)c(C)c1]

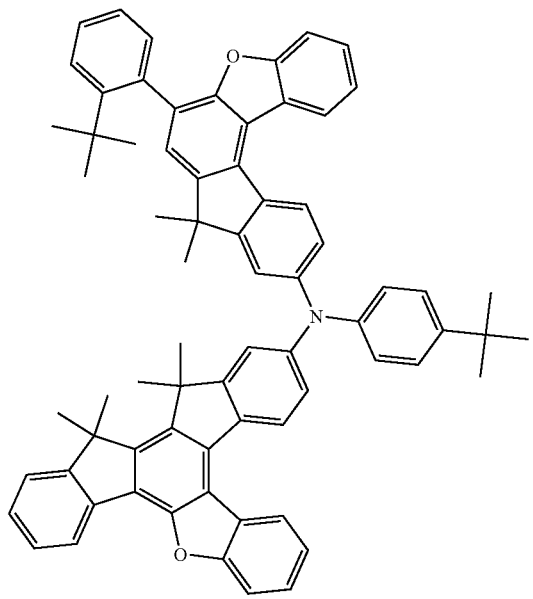 [SMILES: CC(C)(C)c1ccc(N(c2ccc3c(c2)C(C)(C)c2cc(-c4ccccc4C(C)(C)C)c4oc5ccccc5c4c2-3)c2ccc3c(c2)C(C)(C)c2c4c(c5oc6ccccc6c5c2-3)-c2ccccc2C4(C)C)cc1]
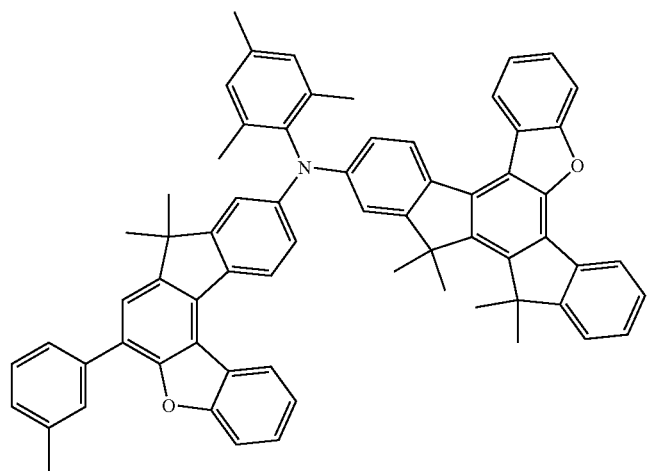 [SMILES: Cc1cccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4c(C)cc(C)cc4C)cc2C3(C)C)c1]
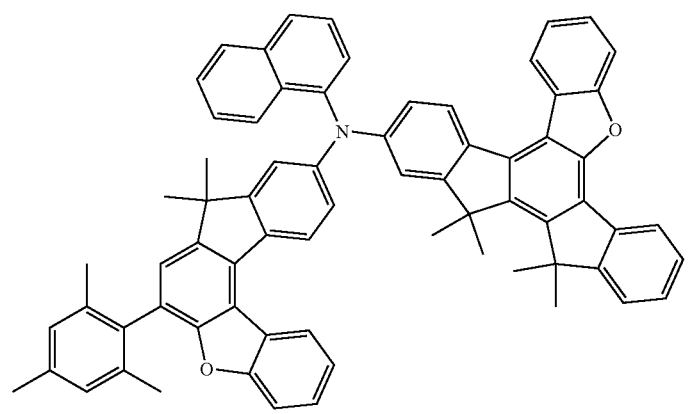 [SMILES: Cc1cc(C)c(-c2cc3c(c4c2oc2ccccc24)-c2ccc(N(c4ccc5c(c4)C(C)(C)c4c6c(c7oc8ccccc8c7c4-5)-c4ccccc4C6(C)C)c4cccc5ccccc45)cc2C3(C)C)c(C)c1]

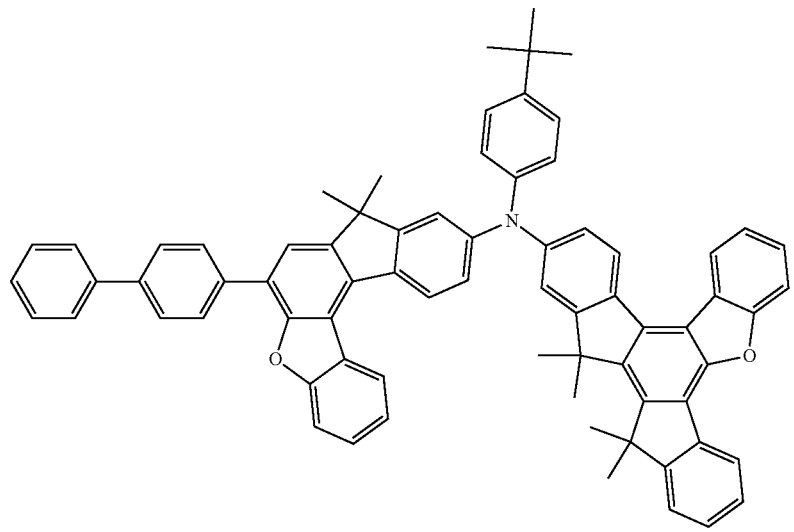 [SMILES: CC(C)(C)c1ccc(N(c2ccc3c(c2)C(C)(C)c2cc(-c4ccc(-c5ccccc5)cc4)c4oc5ccccc5c4c2-3)c2ccc3c(c2)C(C)(C)c2c4c(c5oc6ccccc6c5c2-3)-c2ccccc2C4(C)C)cc1]
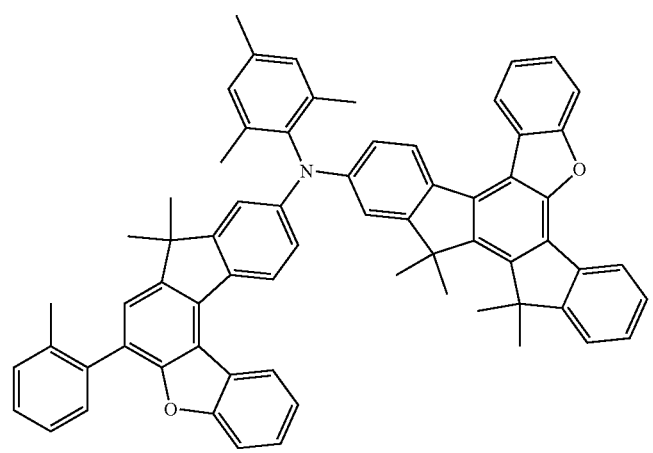 [SMILES: Cc1cc(C)c(N(c2ccc3c(c2)C(C)(C)c2cc(-c4ccccc4C)c4oc5ccccc5c4c2-3)c2ccc3c(c2)C(C)(C)c2c4c(c5oc6ccccc6c5c2-3)-c2ccccc2C4(C)C)c(C)c1]
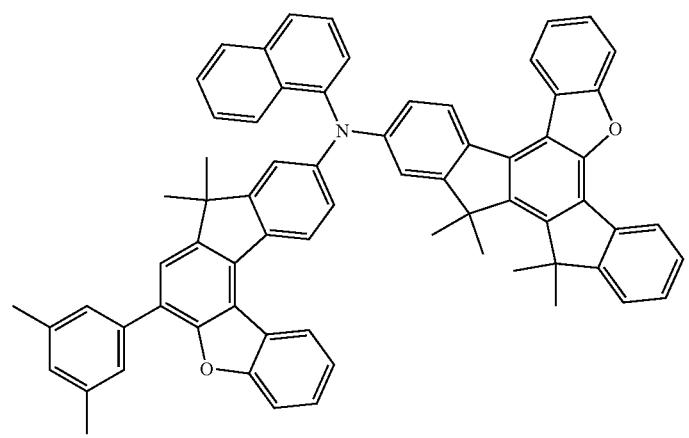 [SMILES: Cc1cc(C)cc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4cccc5ccccc45)cc2C3(C)C)c1]

-continued
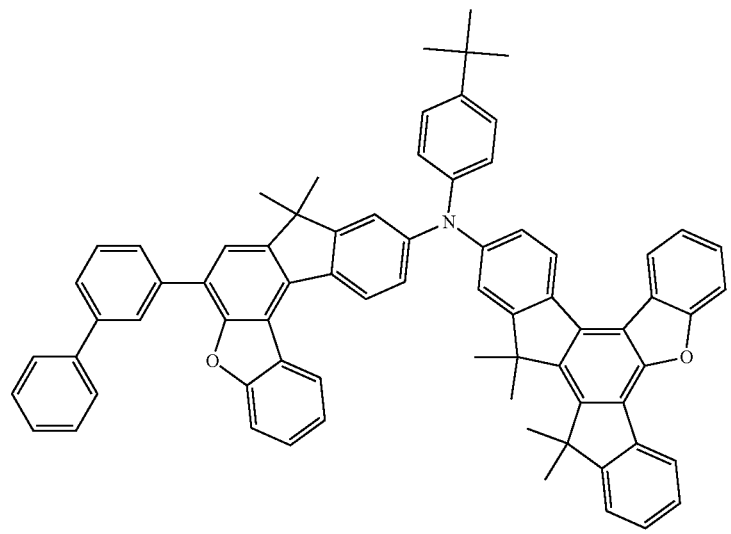 [SMILES: CC(C)(C)c1ccc(N(c2ccc3c(c2)C(C)(C)c2cc(-c4cccc(-c5ccccc5)c4)c4oc5ccccc5c4c2-3)c2ccc3c(c2)C(C)(C)c2c4c(c5oc6ccccc6c5c2-3)-c2ccccc2C4(C)C)cc1]
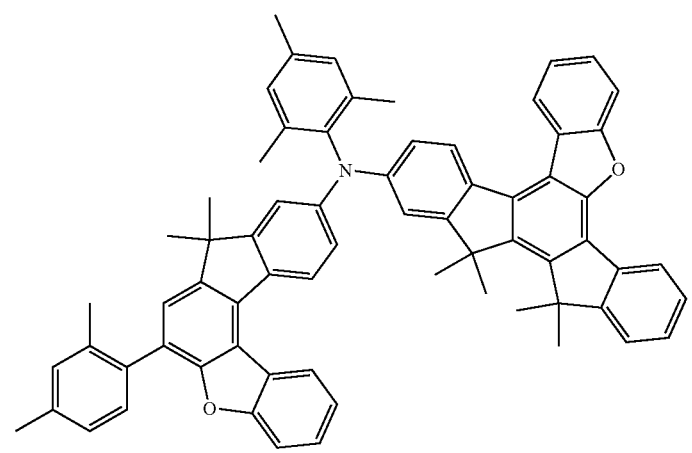 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4c(C)cc(C)cc4C)cc2C3(C)C)c(C)c1]
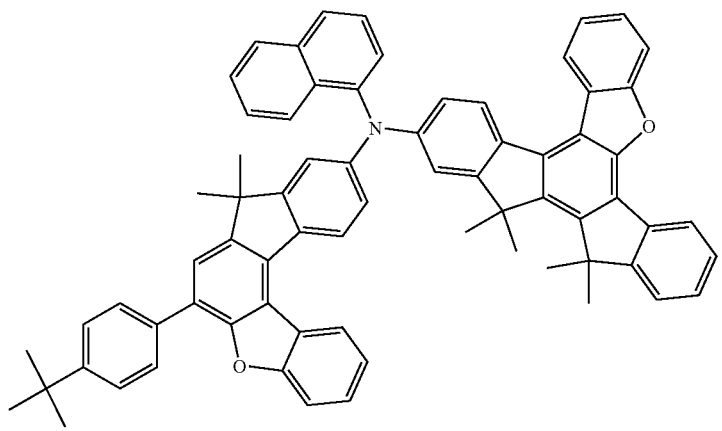 [SMILES: CC(C)(C)c1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4cccc5ccccc45)cc2C3(C)C)cc1]

-continued
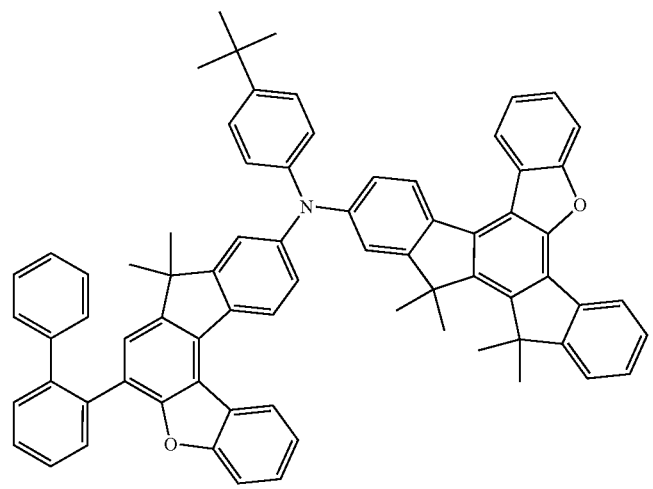 [SMILES: CC(C)(C)c1ccc(N(c2ccc3c(c2)C(C)(C)c2cc(-c4ccccc4-c4ccccc4)c4oc5ccccc5c4c2-3)c2ccc3c(c2)C(C)(C)c2c4c(c5oc6ccccc6c5c2-3)-c2ccccc2C4(C)C)cc1]
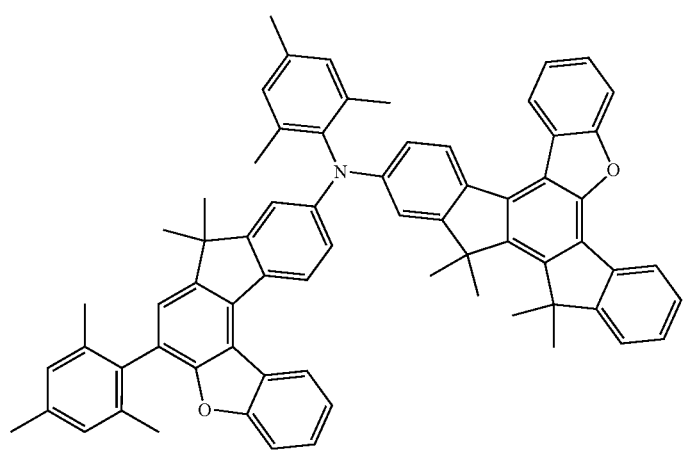 [SMILES: Cc1cc(C)c(-c2cc3c(c4c2oc2ccccc24)-c2ccc(N(c4ccc5c(c4)C(C)(C)c4c6c(c7oc8ccccc8c7c4-5)-c4ccccc4C6(C)C)c4c(C)cc(C)cc4C)cc2C3(C)C)c(C)c1]
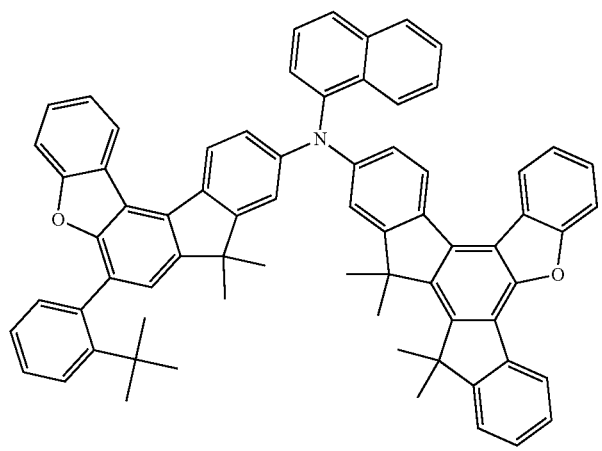 [SMILES: CC(C)(C)c1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3cccc4ccccc34)cc1C2(C)C]

-continued
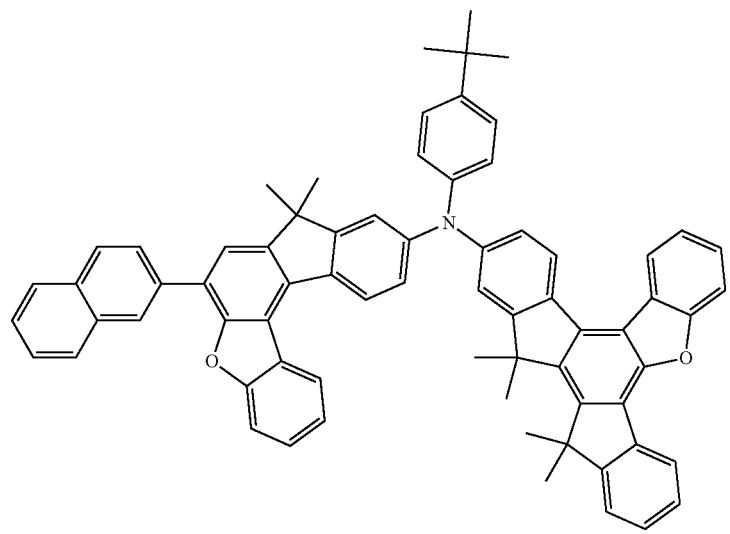 [SMILES: CC(C)(C)c1ccc(N(c2ccc3c(c2)C(C)(C)c2cc(-c4ccc5ccccc5c4)c4oc5ccccc5c4c2-3)c2ccc3c(c2)C(C)(C)c2c4c(c5oc6ccccc6c5c2-3)-c2ccccc2C4(C)C)cc1]
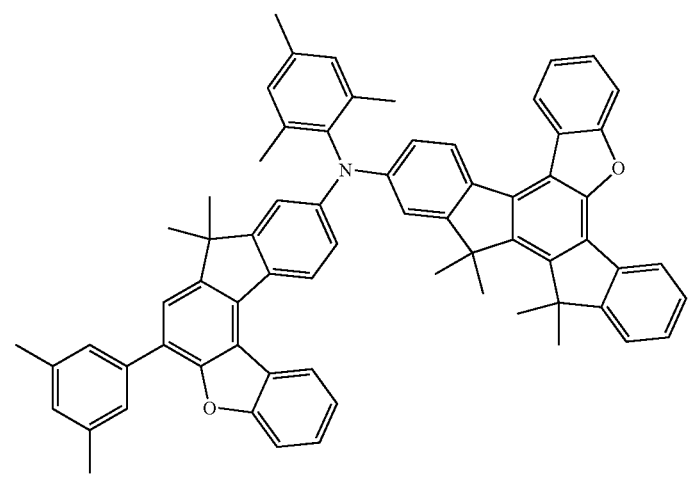 [SMILES: Cc1cc(C)cc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4c(C)cc(C)cc4C)cc2C3(C)C)c1]
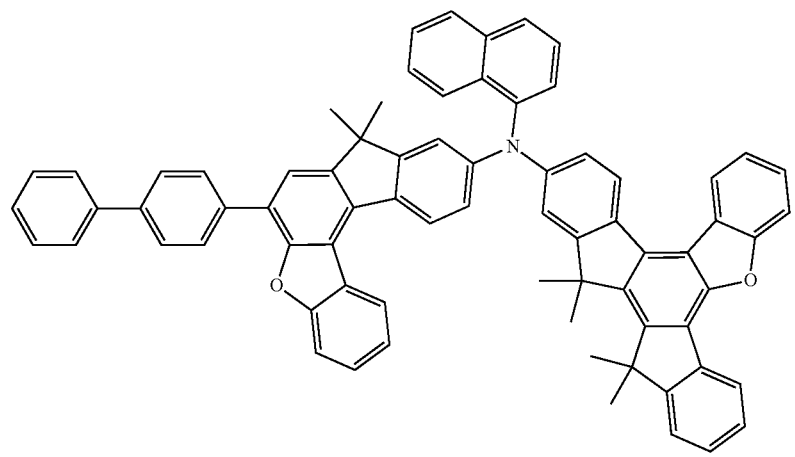 [SMILES: CC1(C)c2cc(N(c3ccc4c(c3)C(C)(C)c3c5c(c6oc7ccccc7c6c3-4)-c3ccccc3C5(C)C)c3cccc4ccccc34)ccc2-c2c1cc(-c1ccc(-c3ccccc3)cc1)c1oc3ccccc3c21]

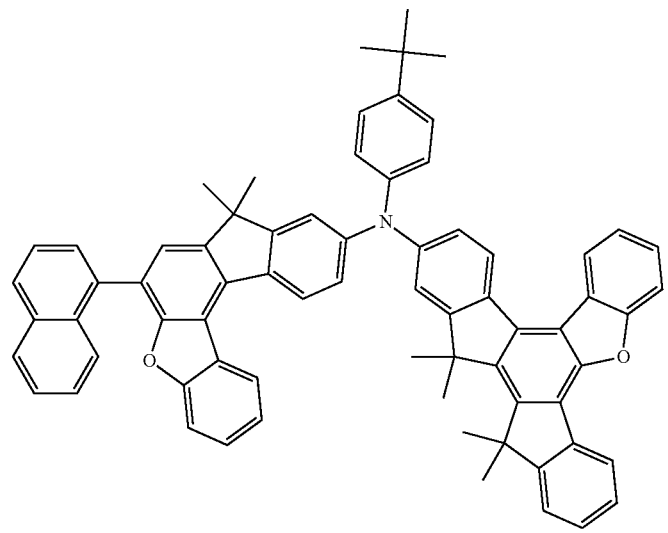 [SMILES: CC(C)(C)c1ccc(N(c2ccc3c(c2)C(C)(C)c2cc(-c4cccc5ccccc45)c4oc5ccccc5c4c2-3)c2ccc3c(c2)C(C)(C)c2c4c(c5oc6ccccc6c5c2-3)-c2ccccc2C4(C)C)cc1]
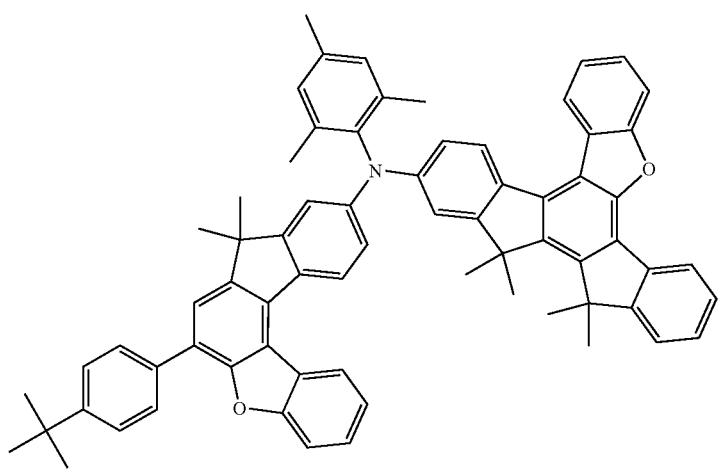 [SMILES: Cc1cc(C)c(N(c2ccc3c(c2)C(C)(C)c2cc(-c4ccc(C(C)(C)C)cc4)c4oc5ccccc5c4c2-3)c2ccc3c(c2)C(C)(C)c2c4c(c5oc6ccccc6c5c2-3)-c2ccccc2C4(C)C)c(C)c1]
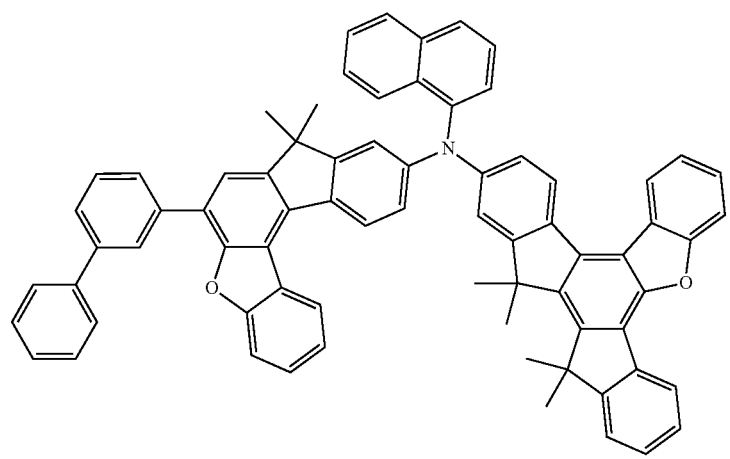 [SMILES: CC1(C)c2cc(N(c3ccc4c(c3)C(C)(C)c3c5c(c6oc7ccccc7c6c3-4)-c3ccccc3C5(C)C)c3cccc4ccccc34)ccc2-c2c1cc(-c1cccc(-c3ccccc3)c1)c1oc3ccccc3c21]

-continued
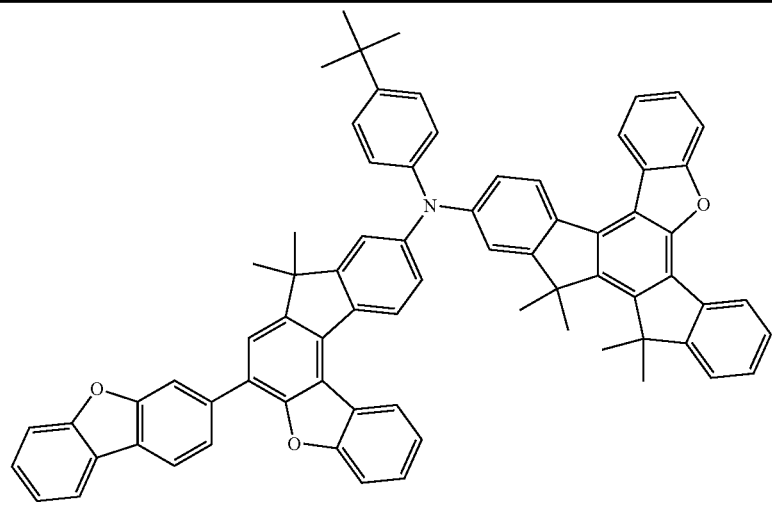
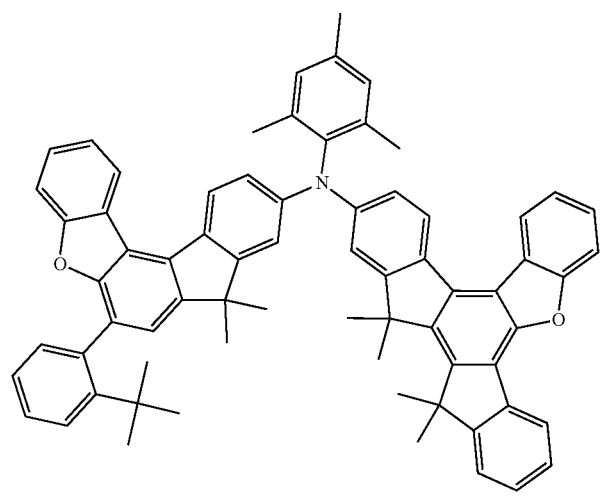 [SMILES: Cc1cc(C)c(N(c2ccc3c(c2)C(C)(C)c2cc(-c4ccccc4C(C)(C)C)c4oc5ccccc5c4c2-3)c2ccc3c(c2)C(C)(C)c2c4c(c5oc6ccccc6c5c2-3)-c2ccccc2C4(C)C)c(C)c1]
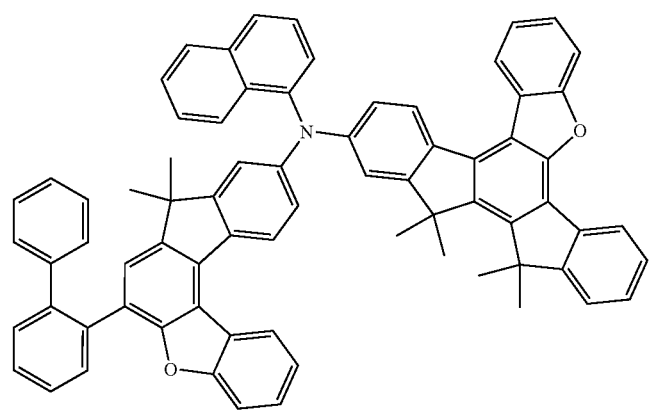 [SMILES: CC1(C)c2cc(N(c3ccc4c(c3)C(C)(C)c3c5c(c6oc7ccccc7c6c3-4)-c3ccccc3C5(C)C)c3cccc4ccccc34)ccc2-c2c1cc(-c1ccccc1-c1ccccc1)c1oc3ccccc3c21]

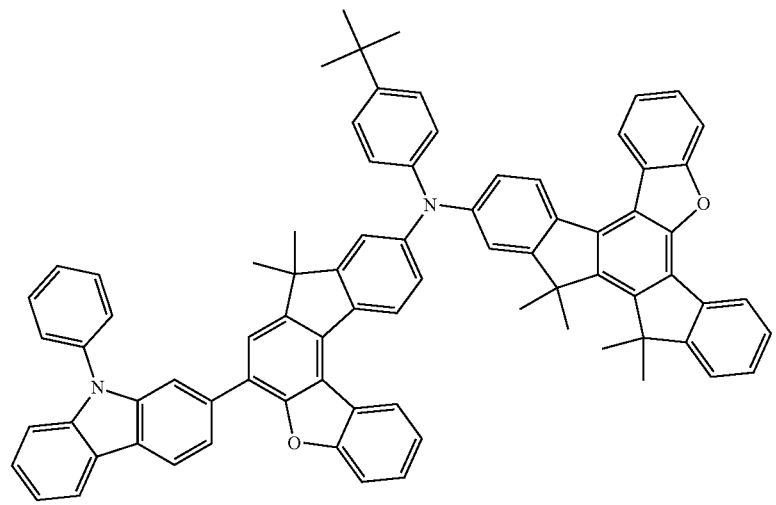 [SMILES: CC(C)(C)c1ccc(N(c2ccc3c(c2)C(C)(C)c2cc(-c4ccc5c6ccccc6n(-c6ccccc6)c5c4)c4oc5ccccc5c4c2-3)c2ccc3c(c2)C(C)(C)c2c4c(c5oc6ccccc6c5c2-3)-c2ccccc2C4(C)C)cc1]
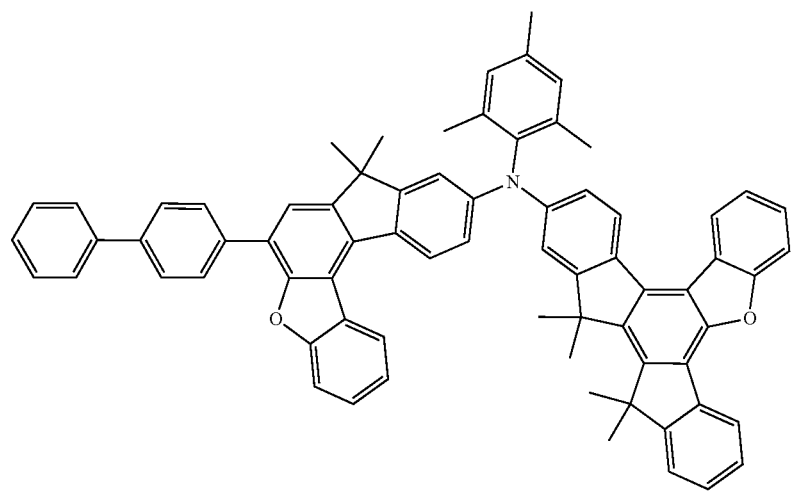 [SMILES: Cc1cc(C)c(N(c2ccc3c(c2)C(C)(C)c2cc(-c4ccc(-c5ccccc5)cc4)c4oc5ccccc5c4c2-3)c2ccc3c(c2)C(C)(C)c2c4c(c5oc6ccccc6c5c2-3)-c2ccccc2C4(C)C)c(C)c1]
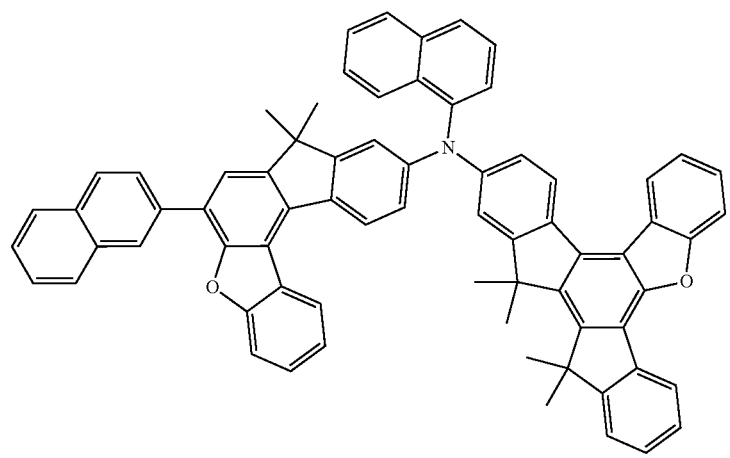 [SMILES: CC1(C)c2cc(N(c3ccc4c(c3)C(C)(C)c3c5c(c6oc7ccccc7c6c3-4)-c3ccccc3C5(C)C)c3cccc4ccccc34)ccc2-c2c1cc(-c1ccc3ccccc3c1)c1oc3ccccc3c21]

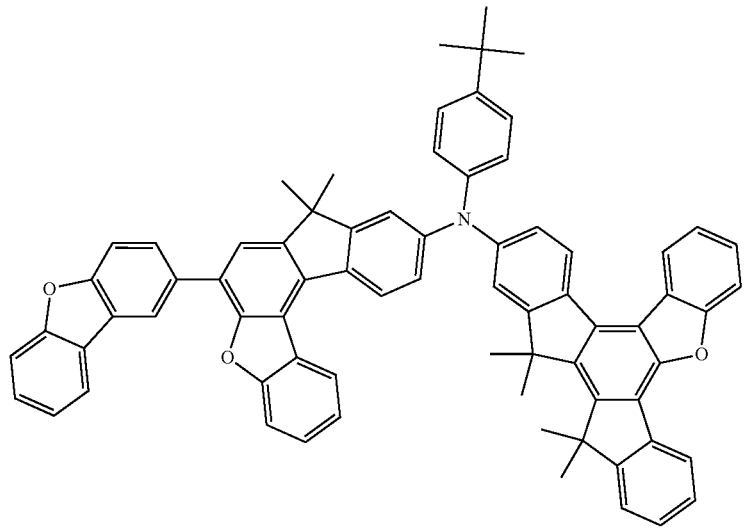 [SMILES: CC(C)(C)c1ccc(N(c2ccc3c(c2)C(C)(C)c2cc(-c4ccc5oc6ccccc6c5c4)c4oc5ccccc5c4c2-3)c2ccc3c(c2)C(C)(C)c2c4c(c5oc6ccccc6c5c2-3)-c2ccccc2C4(C)C)cc1]
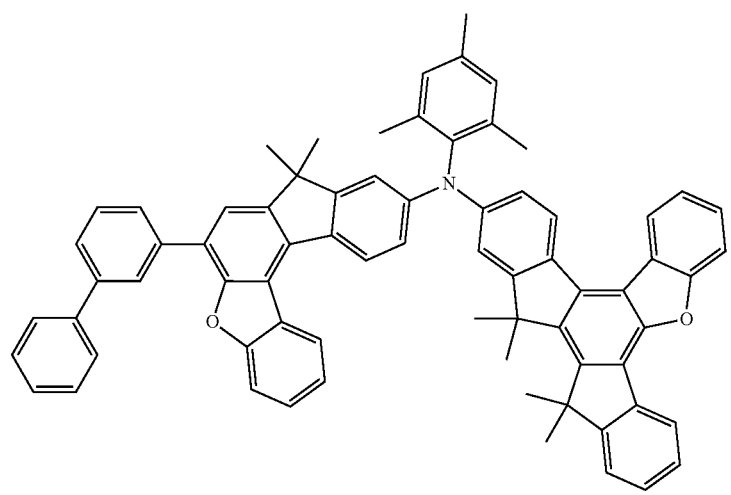 [SMILES: Cc1cc(C)c(N(c2ccc3c(c2)C(C)(C)c2cc(-c4cccc(-c5ccccc5)c4)c4oc5ccccc5c4c2-3)c2ccc3c(c2)C(C)(C)c2c4c(c5oc6ccccc6c5c2-3)-c2ccccc2C4(C)C)c(C)c1]
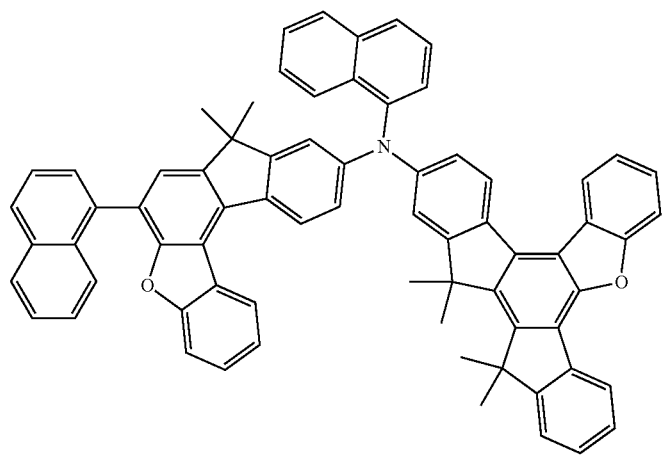 [SMILES: CC1(C)c2cc(N(c3ccc4c(c3)C(C)(C)c3c5c(c6oc7ccccc7c6c3-4)-c3ccccc3C5(C)C)c3cccc4ccccc34)ccc2-c2c1cc(-c1cccc3ccccc13)c1oc3ccccc3c21]

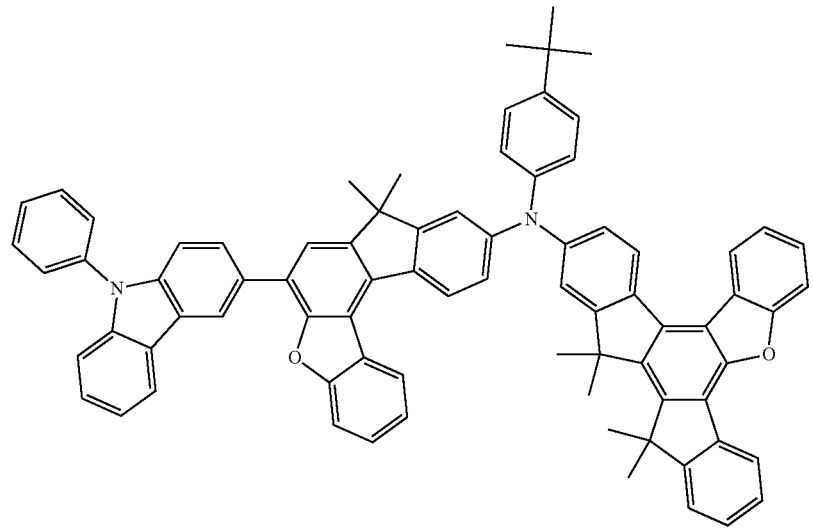 [SMILES: CC(C)(C)c1ccc(N(c2ccc3c(c2)C(C)(C)c2cc(-c4ccc5c(c4)c4ccccc4n5-c4ccccc4)c4oc5ccccc5c4c2-3)c2ccc3c(c2)C(C)(C)c2c4c(c5oc6ccccc6c5c2-3)-c2ccccc2C4(C)C)cc1]
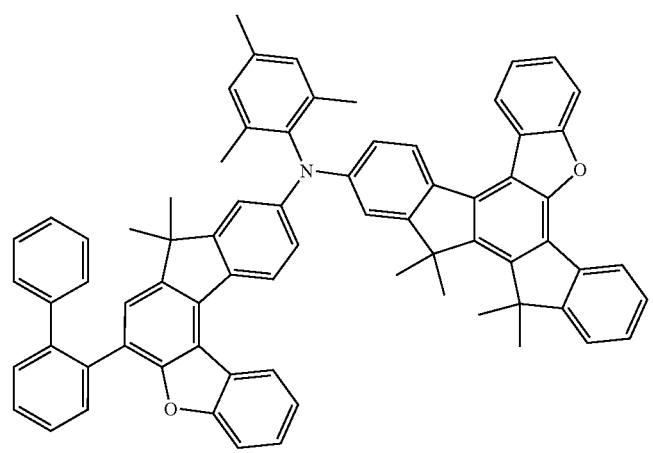 [SMILES: Cc1cc(C)c(N(c2ccc3c(c2)C(C)(C)c2cc(-c4ccccc4-c4ccccc4)c4oc5ccccc5c4c2-3)c2ccc3c(c2)C(C)(C)c2c4c(c5oc6ccccc6c5c2-3)-c2ccccc2C4(C)C)c(C)c1]
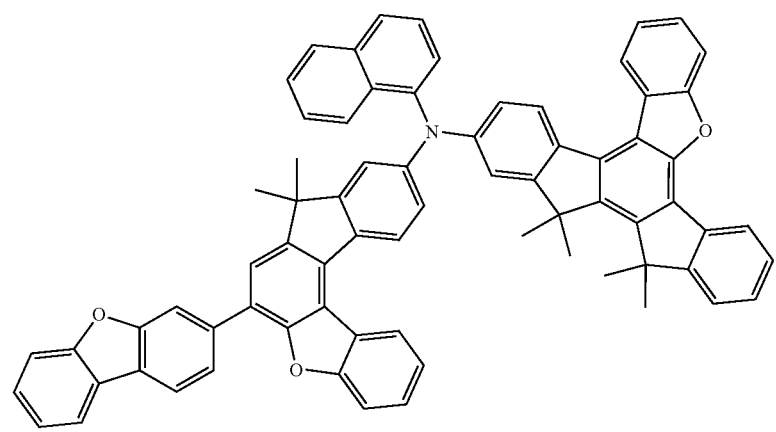 [SMILES: CC1(C)c2cc(N(c3ccc4c(c3)C(C)(C)c3c5c(c6oc7ccccc7c6c3-4)-c3ccccc3C5(C)C)c3cccc4ccccc34)ccc2-c2c1cc(-c1ccc3c(c1)oc1ccccc13)c1oc3ccccc3c21]

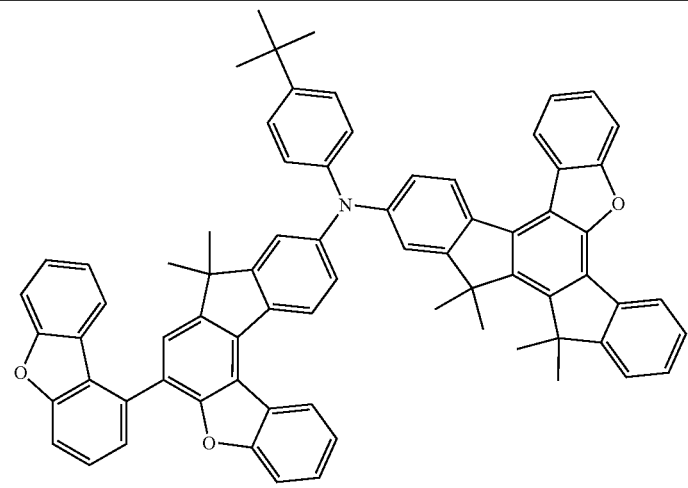
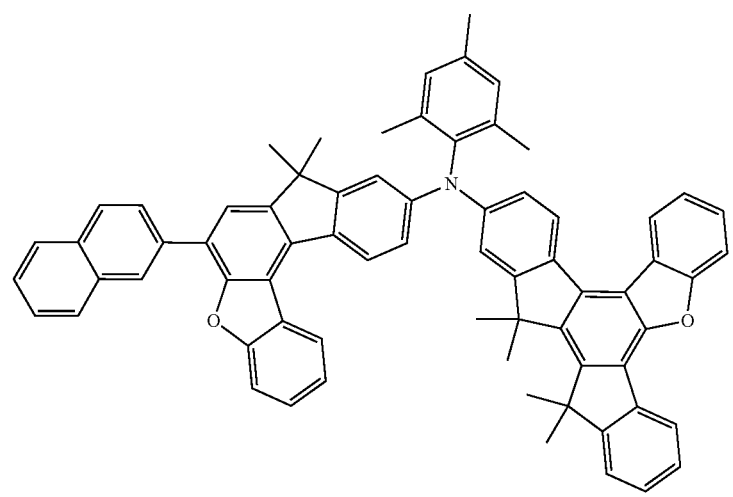 [SMILES: Cc1cc(C)c(N(c2ccc3c(c2)C(C)(C)c2cc(-c4ccc5ccccc5c4)c4oc5ccccc5c4c2-3)c2ccc3c(c2)C(C)(C)c2c4c(c5oc6ccccc6c5c2-3)-c2ccccc2C4(C)C)c(C)c1]
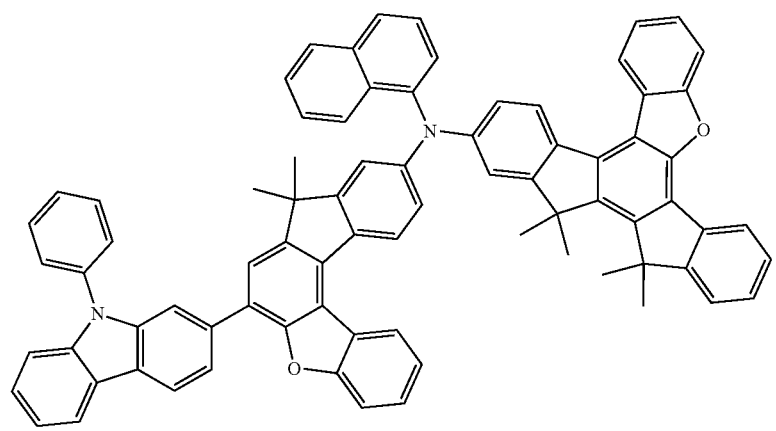 [SMILES: CC1(C)c2cc(N(c3ccc4c(c3)C(C)(C)c3c5c(c6oc7ccccc7c6c3-4)-c3ccccc3C5(C)C)c3cccc4ccccc34)ccc2-c2c1cc(-c1ccc3c4ccccc4n(-c4ccccc4)c3c1)c1oc3ccccc3c21]

-continued
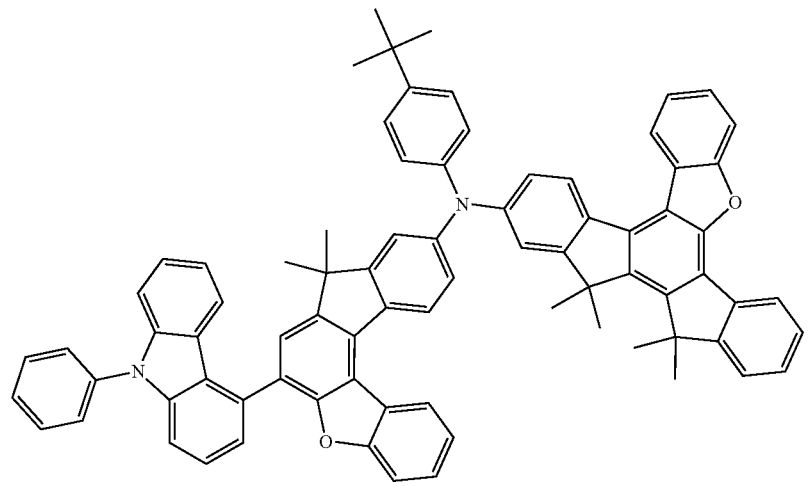 [SMILES: CC(C)(C)c1ccc(N(c2ccc3c(c2)C(C)(C)c2cc(-c4cccc5c4c4ccccc4n5-c4ccccc4)c4oc5ccccc5c4c2-3)c2ccc3c(c2)C(C)(C)c2c4c(c5oc6ccccc6c5c2-3)-c2ccccc2C4(C)C)cc1]
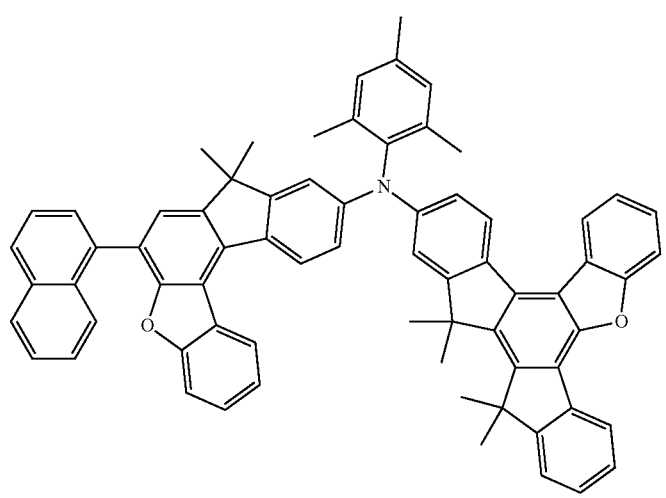 [SMILES: Cc1cc(C)c(N(c2ccc3c(c2)C(C)(C)c2cc(-c4cccc5ccccc45)c4oc5ccccc5c4c2-3)c2ccc3c(c2)C(C)(C)c2c4c(c5oc6ccccc6c5c2-3)-c2ccccc2C4(C)C)c(C)c1]
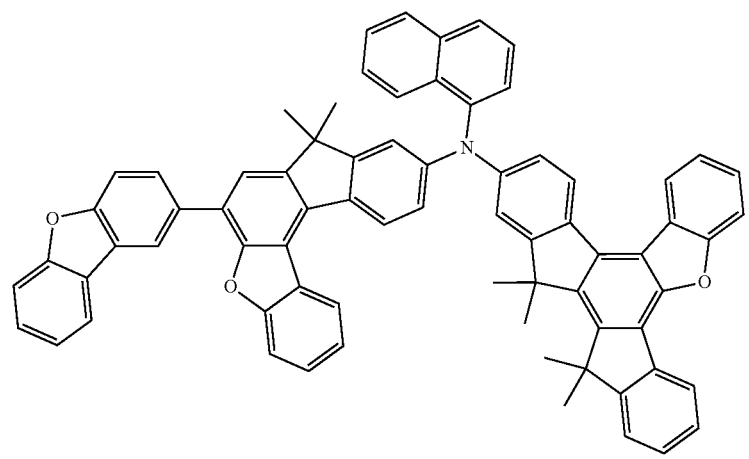 [SMILES: CC1(C)c2cc(N(c3ccc4c(c3)C(C)(C)c3c5c(c6oc7ccccc7c6c3-4)-c3ccccc3C5(C)C)c3cccc4ccccc34)ccc2-c2c1cc(-c1ccc3oc4ccccc4c3c1)c1oc3ccccc3c21]

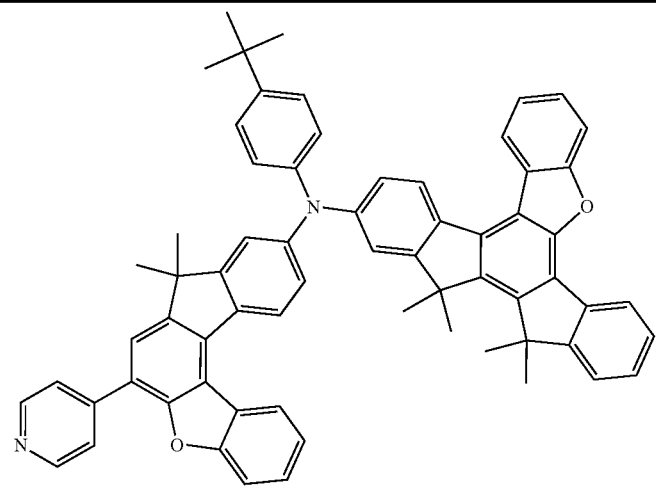
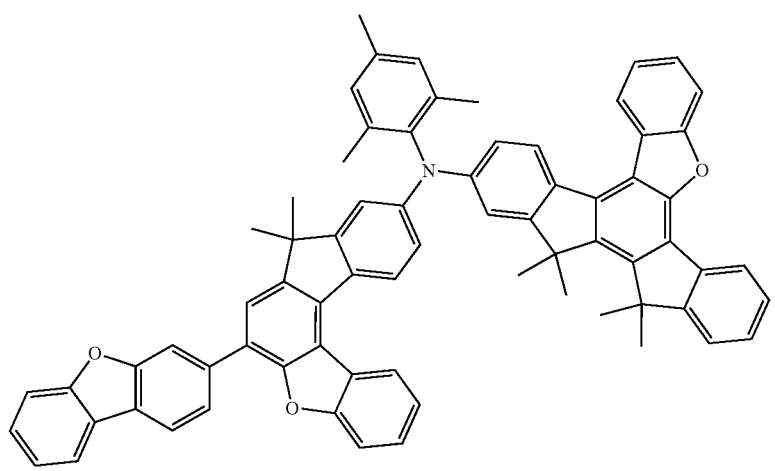 [SMILES: Cc1cc(C)c(N(c2ccc3c(c2)C(C)(C)c2cc(-c4ccc5c(c4)oc4ccccc45)c4oc5ccccc5c4c2-3)c2ccc3c(c2)C(C)(C)c2c4c(c5oc6ccccc6c5c2-3)-c2ccccc2C4(C)C)c(C)c1]
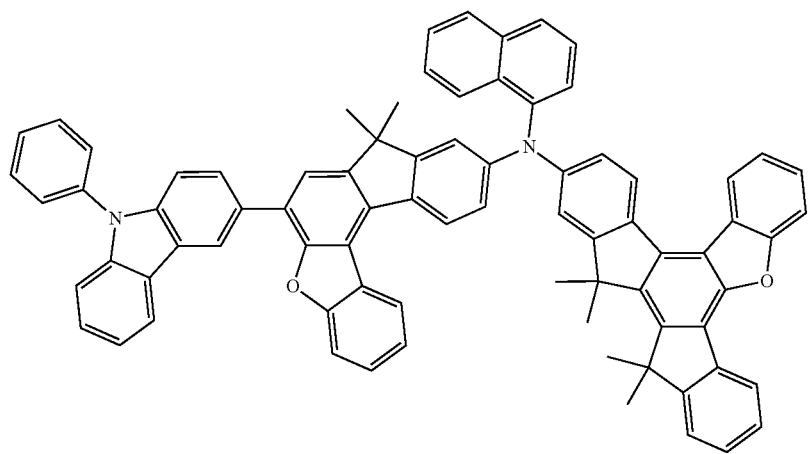 [SMILES: CC1(C)c2cc(N(c3ccc4c(c3)C(C)(C)c3c5c(c6oc7ccccc7c6c3-4)-c3ccccc3C5(C)C)c3cccc4ccccc34)ccc2-c2c1cc(-c1ccc3c(c1)c1ccccc1n3-c1ccccc1)c1oc3ccccc3c21]

-continued
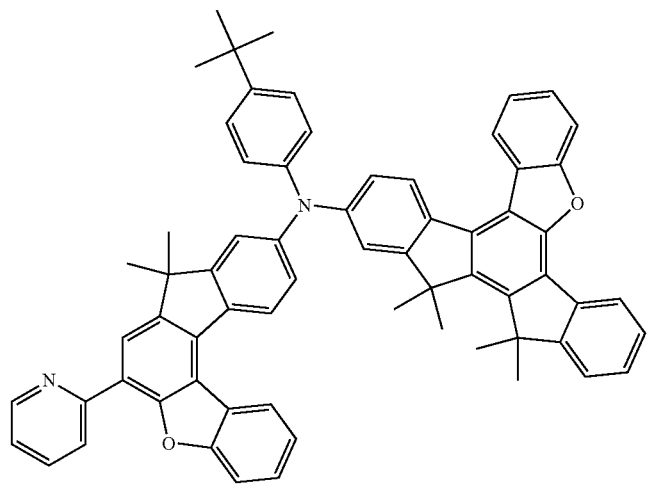 [SMILES: CC(C)(C)c1ccc(N(c2ccc3c(c2)C(C)(C)c2cc(-c4ccccn4)c4oc5ccccc5c4c2-3)c2ccc3c(c2)C(C)(C)c2c4c(c5oc6ccccc6c5c2-3)-c2ccccc2C4(C)C)cc1]
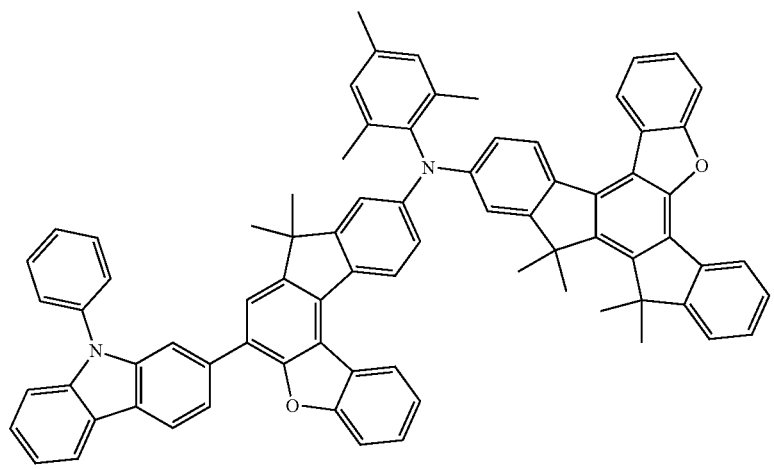 [SMILES: Cc1cc(C)c(N(c2ccc3c(c2)C(C)(C)c2cc(-c4ccc5c6ccccc6n(-c6ccccc6)c5c4)c4oc5ccccc5c4c2-3)c2ccc3c(c2)C(C)(C)c2c4c(c5oc6ccccc6c5c2-3)-c2ccccc2C4(C)C)c(C)c1]
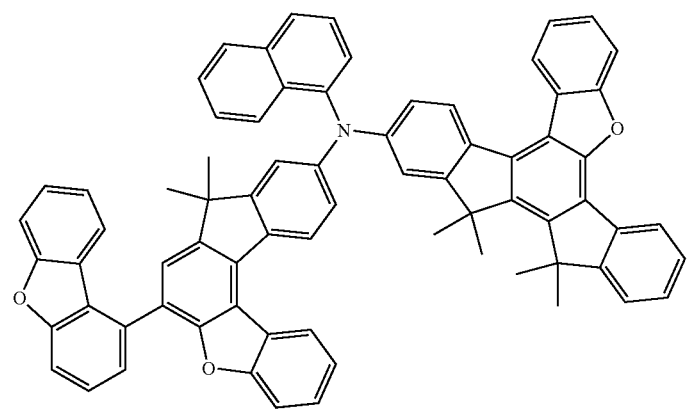 [SMILES: CC1(C)c2cc(N(c3ccc4c(c3)C(C)(C)c3c5c(c6oc7ccccc7c6c3-4)-c3ccccc3C5(C)C)c3cccc4ccccc34)ccc2-c2c1cc(-c1cccc3oc4ccccc4c13)c1oc3ccccc3c21]

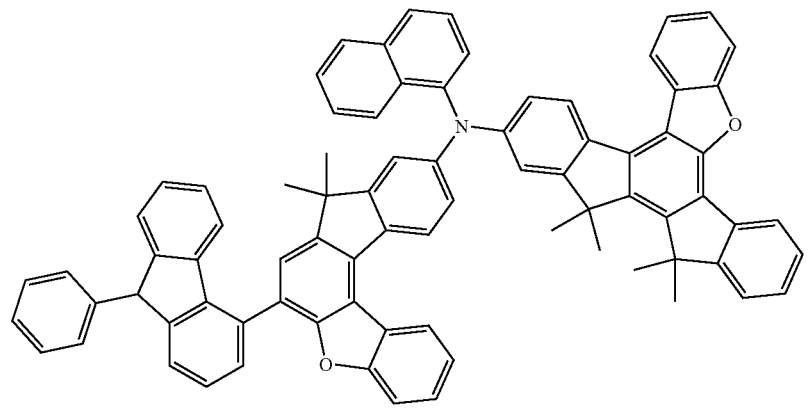 [SMILES: CC1(C)c2cc(N(c3ccc4c(c3)C(C)(C)c3c5c(c6oc7ccccc7c6c3-4)-c3ccccc3C5(C)C)c3cccc4ccccc34)ccc2-c2c1cc(-c1cccc3c1-c1ccccc1C3c1ccccc1)c1oc3ccccc3c21]
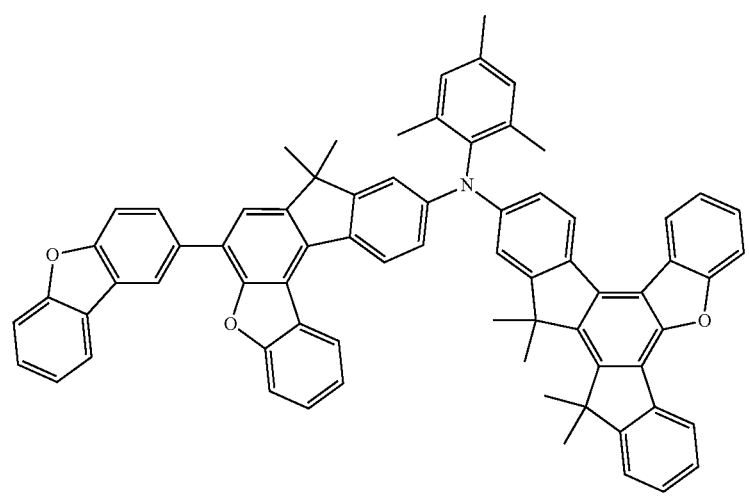 [SMILES: Cc1cc(C)c(N(c2ccc3c(c2)C(C)(C)c2cc(-c4ccc5oc6ccccc6c5c4)c4oc5ccccc5c4c2-3)c2ccc3c(c2)C(C)(C)c2c4c(c5oc6ccccc6c5c2-3)-c2ccccc2C4(C)C)c(C)c1]
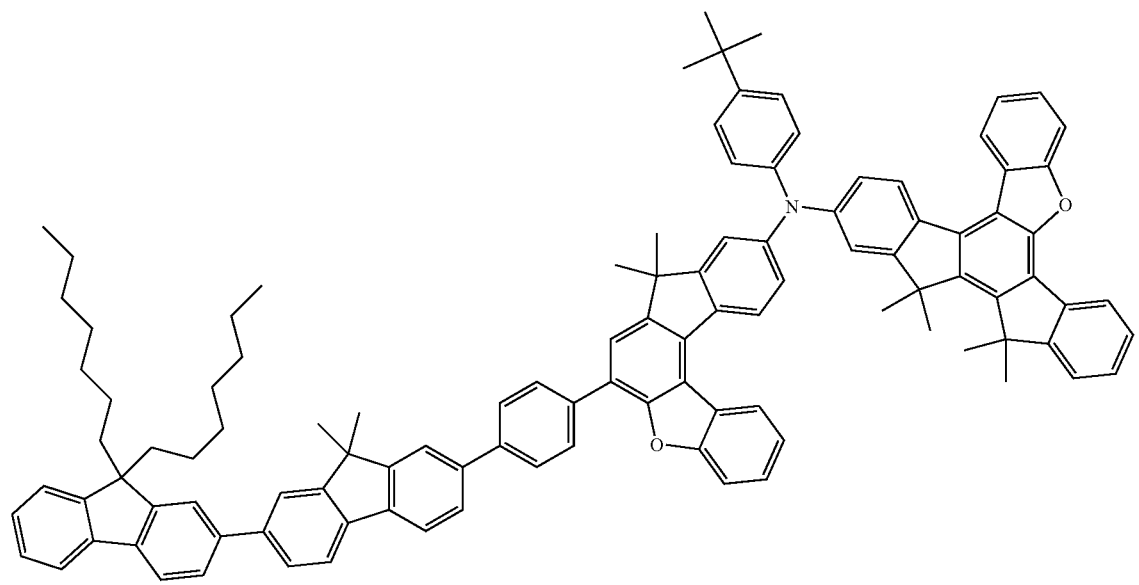 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc(C(C)(C)C)cc8)c8ccc9c(c8)C(C)(C)c8c%10c(c%11oc%12ccccc%12c%11c8-9)-c8ccccc8C%10(C)C)cc6C7(C)C)cc5)ccc3-4)cc21]

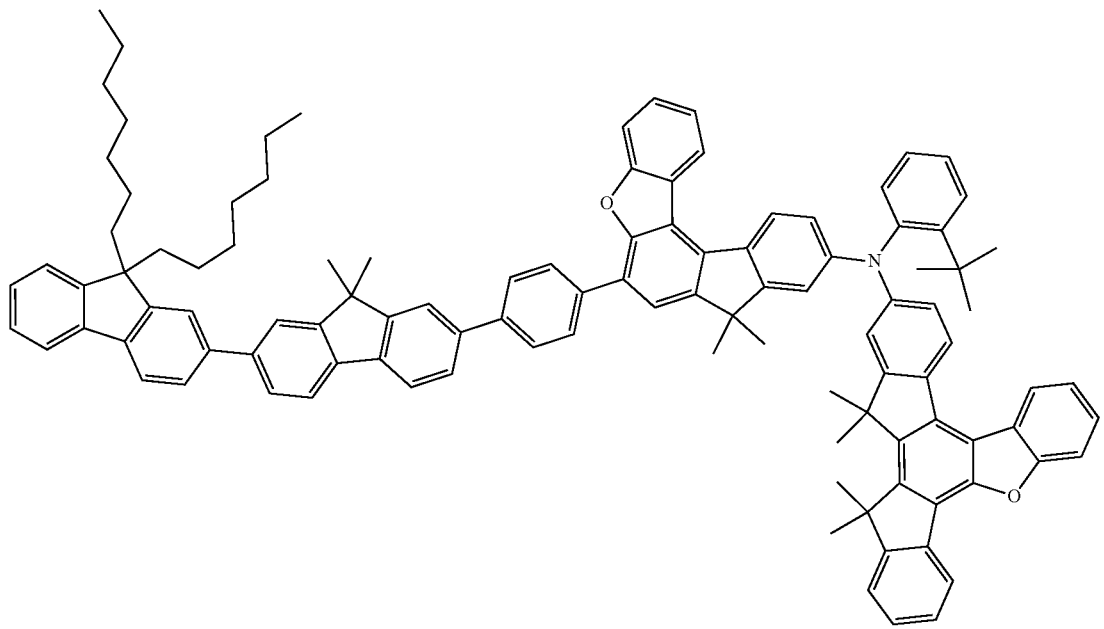 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8ccccc8C(C)(C)C)cc6C7(C)C)cc5)ccc3-4)cc21]
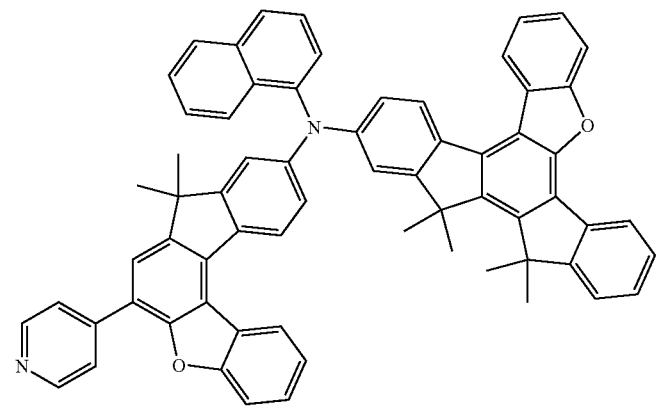 [SMILES: CC1(C)c2cc(N(c3ccc4c(c3)C(C)(C)c3c5c(c6oc7ccccc7c6c3-4)-c3ccccc3C5(C)C)c3cccc4ccccc34)ccc2-c2c1cc(-c1ccncc1)c1oc3ccccc3c21]
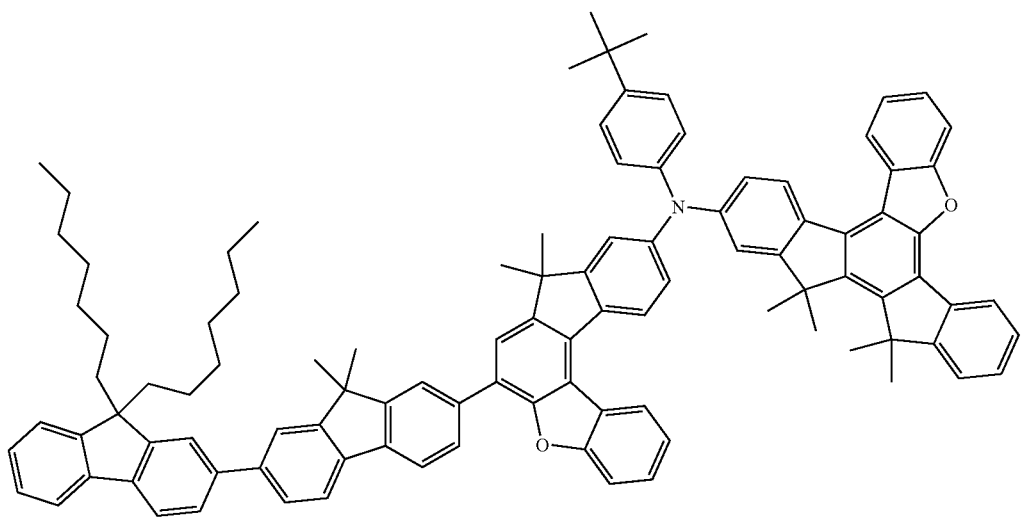 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc(C(C)(C)C)cc7)c7ccc8c(c7)C(C)(C)c7c9c(c%10oc%11ccccc%11c%10c7-8)-c7ccccc7C9(C)C)cc5C6(C)C)ccc3-4)cc21]

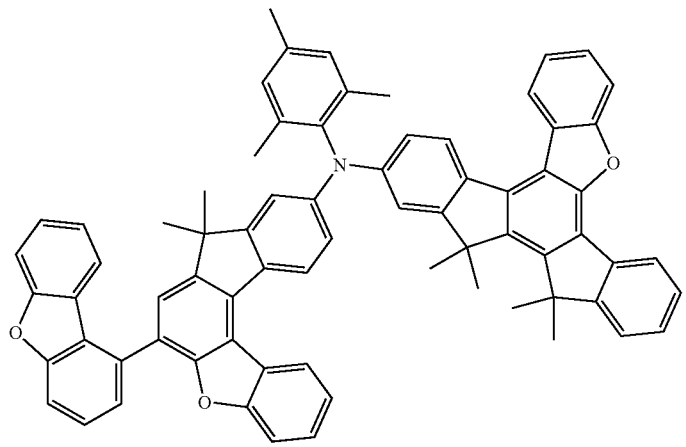 [SMILES: Cc1cc(C)c(N(c2ccc3c(c2)C(C)(C)c2cc(-c4cccc5oc6ccccc6c45)c4oc5ccccc5c4c2-3)c2ccc3c(c2)C(C)(C)c2c4c(c5oc6ccccc6c5c2-3)-c2ccccc2C4(C)C)c(C)c1]
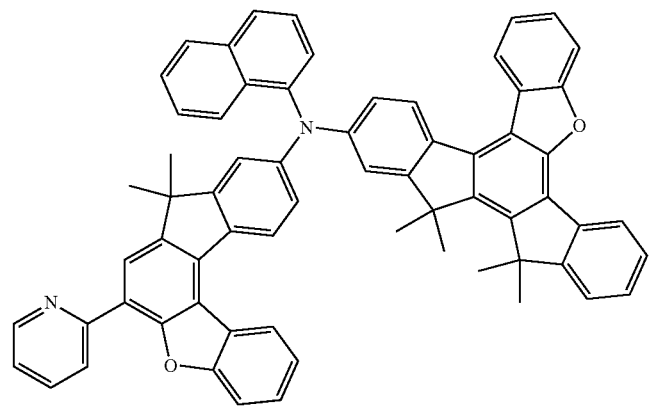 [SMILES: CC1(C)c2cc(N(c3ccc4c(c3)C(C)(C)c3c5c(c6oc7ccccc7c6c3-4)-c3ccccc3C5(C)C)c3cccc4ccccc34)ccc2-c2c1cc(-c1ccccn1)c1oc3ccccc3c21]
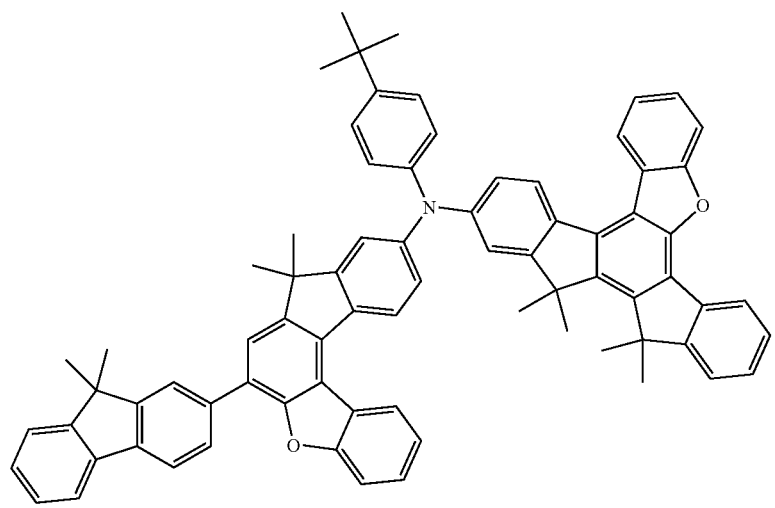 [SMILES: CC(C)(C)c1ccc(N(c2ccc3c(c2)C(C)(C)c2cc(-c4ccc5c(c4)C(C)(C)c4ccccc4-5)c4oc5ccccc5c4c2-3)c2ccc3c(c2)C(C)(C)c2c4c(c5oc6ccccc6c5c2-3)-c2ccccc2C4(C)C)cc1]

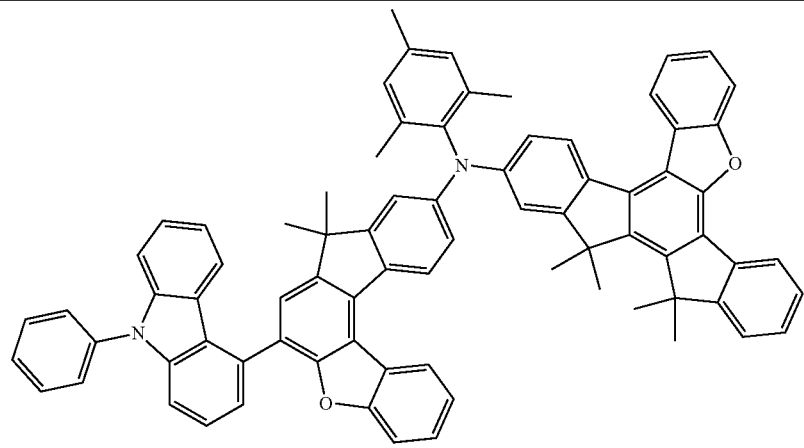
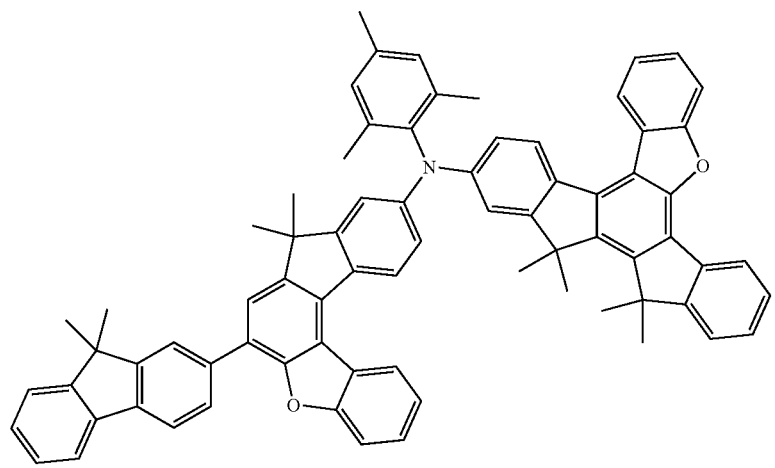 [SMILES: Cc1cc(C)c(N(c2ccc3c(c2)C(C)(C)c2cc(-c4ccc5c(c4)C(C)(C)c4ccccc4-5)c4oc5ccccc5c4c2-3)c2ccc3c(c2)C(C)(C)c2c4c(c5oc6ccccc6c5c2-3)-c2ccccc2C4(C)C)c(C)c1]
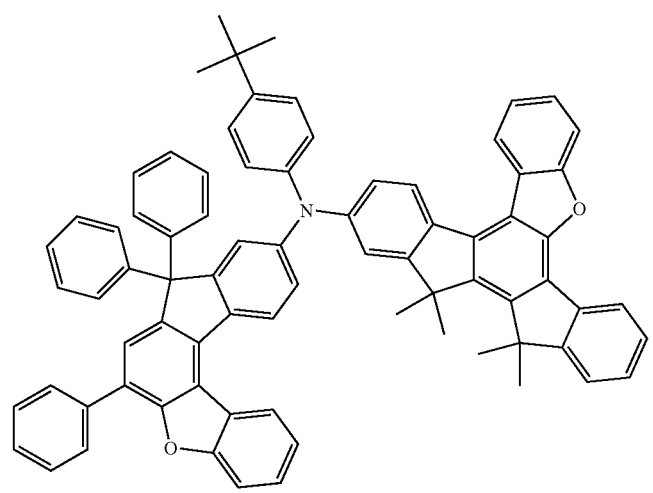 [SMILES: CC(C)(C)c1ccc(N(c2ccc3c(c2)C(C)(C)c2c4c(c5oc6ccccc6c5c2-3)-c2ccccc2C4(C)C)c2ccc3c(c2)C(c2ccccc2)(c2ccccc2)c2cc(-c4ccccc4)c4oc5ccccc5c4c2-3)cc1]

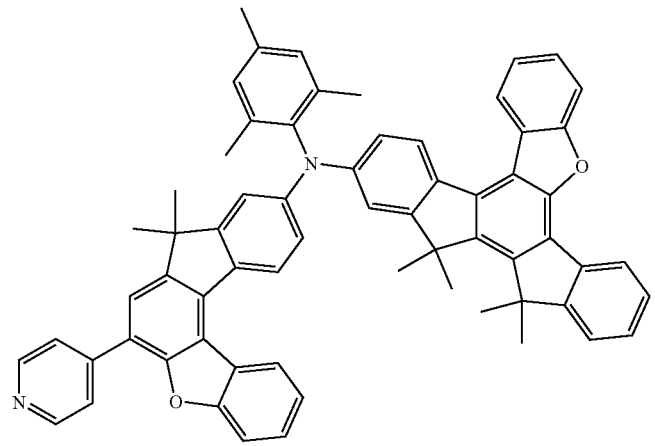 [SMILES: Cc1cc(C)c(N(c2ccc3c(c2)C(C)(C)c2cc(-c4ccncc4)c4oc5ccccc5c4c2-3)c2ccc3c(c2)C(C)(C)c2c4c(c5oc6ccccc6c5c2-3)-c2ccccc2C4(C)C)c(C)c1]
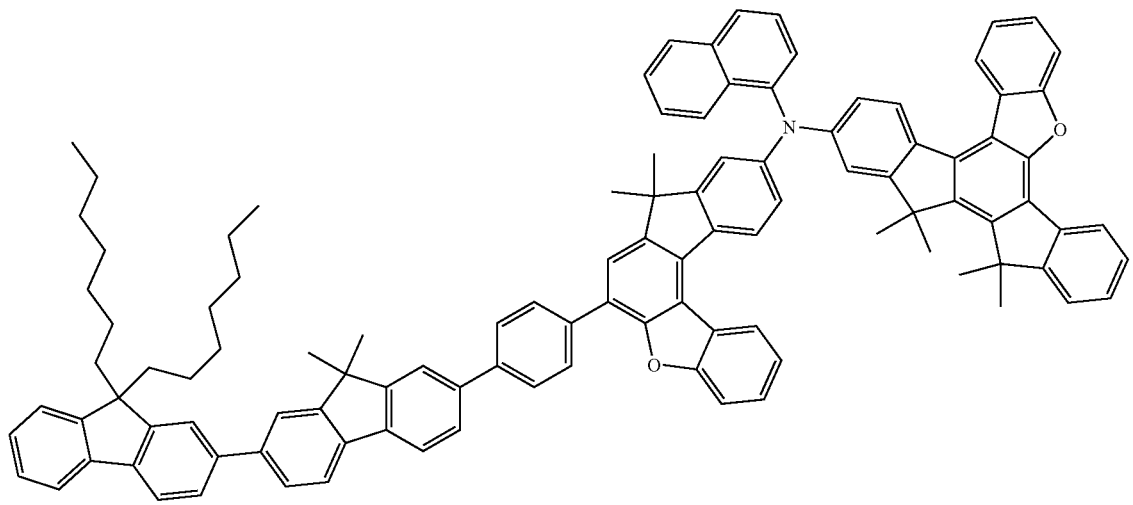 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8cccc9ccccc89)cc6C7(C)C)cc5)ccc3-4)cc21]
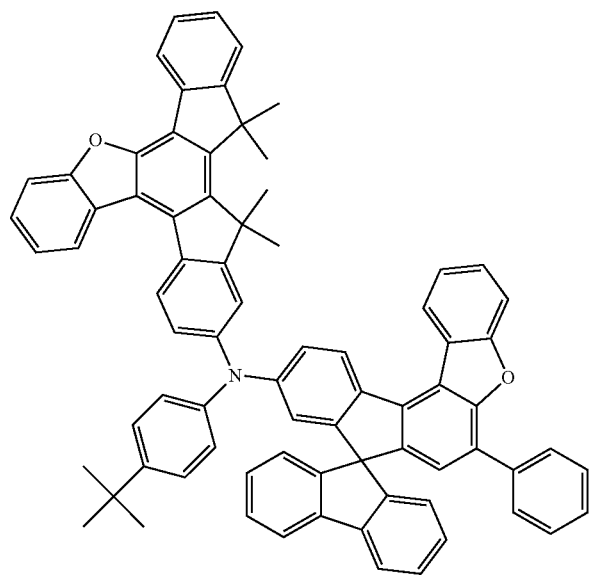 [SMILES: CC(C)(C)c1ccc(N(c2ccc3c(c2)C(C)(C)c2c4c(c5oc6ccccc6c5c2-3)-c2ccccc2C4(C)C)c2ccc3c(c2)C2(c4ccccc4-c4ccccc42)c2cc(-c4ccccc4)c4oc5ccccc5c4c2-3)cc1]

-continued
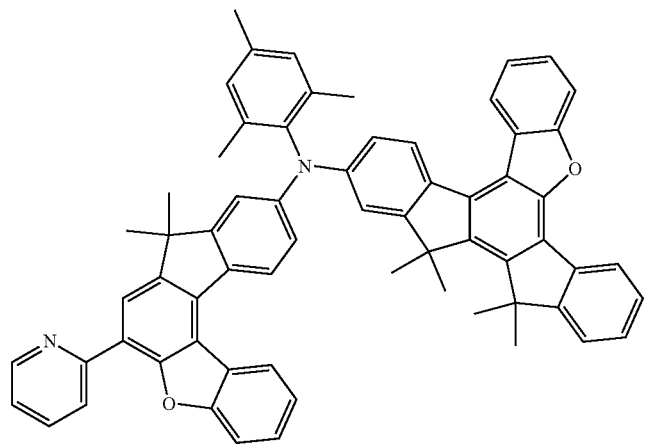 [SMILES: Cc1cc(C)c(N(c2ccc3c(c2)C(C)(C)c2cc(-c4ccccn4)c4oc5ccccc5c4c2-3)c2ccc3c(c2)C(C)(C)c2c4c(c5oc6ccccc6c5c2-3)-c2ccccc2C4(C)C)c(C)c1]
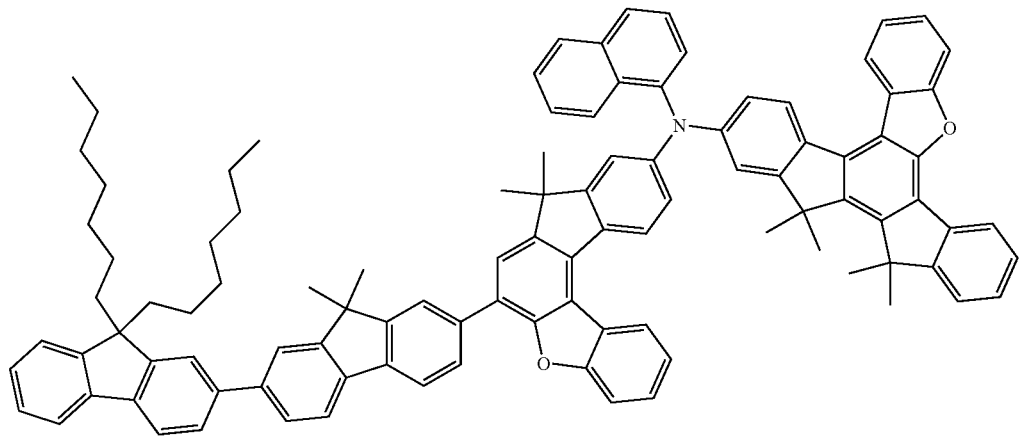 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7cccc8ccccc78)cc5C6(C)C)ccc3-4)cc21]
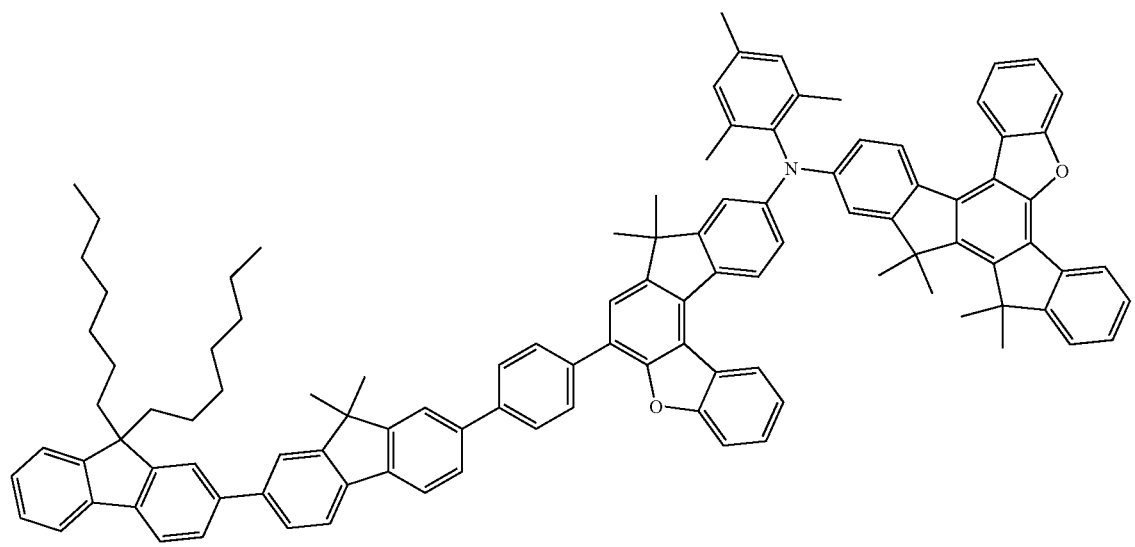 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8c(C)cc(C)cc8C)cc6C7(C)C)cc5)ccc3-4)cc21]

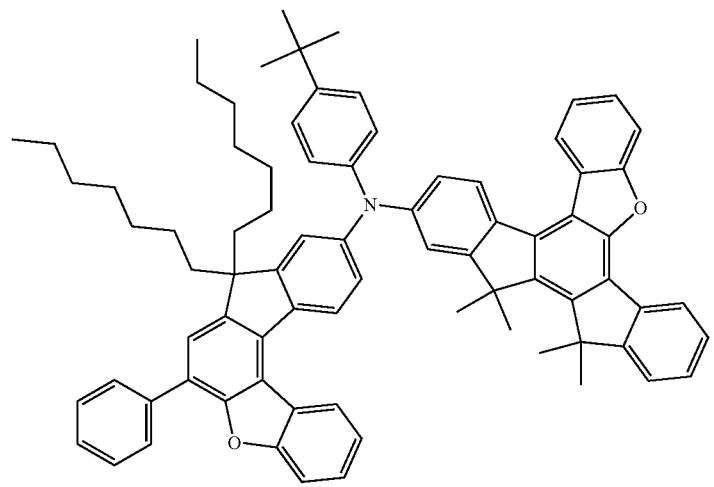 [SMILES: CCCCCCCC1(CCCCCCC)c2cc(N(c3ccc(C(C)(C)C)cc3)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]
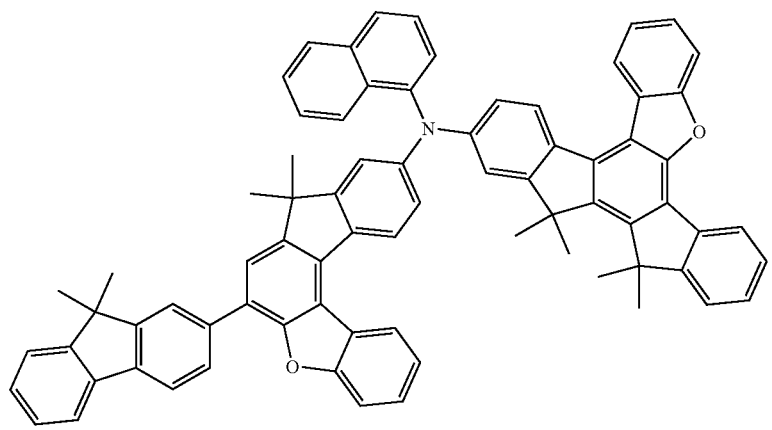 [SMILES: CC1(C)c2ccccc2-c2ccc(-c3cc4c(c5c3oc3ccccc35)-c3ccc(N(c5ccc6c(c5)C(C)(C)c5c7c(c8oc9ccccc9c8c5-6)-c5ccccc5C7(C)C)c5cccc6ccccc56)cc3C4(C)C)cc21]
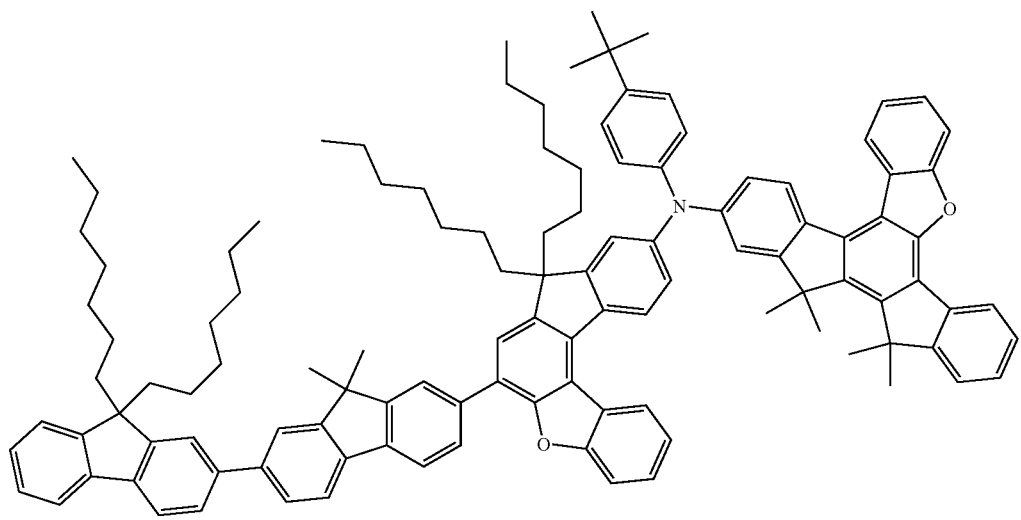 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc(C(C)(C)C)cc7)c7ccc8c(c7)C(C)(C)c7c9c(c%10oc%11ccccc%11c%10c7-8)-c7ccccc7C9(C)C)cc5C6(CCCCCCC)CCCCCCC)ccc3-4)cc21]

-continued
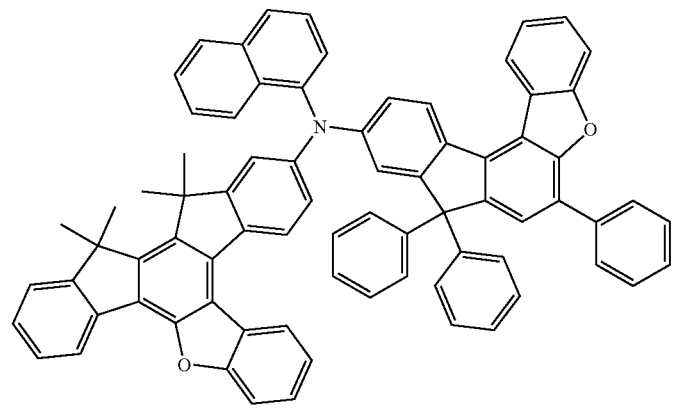 [SMILES: CC1(C)c2ccccc2-c2c1c1c(c3c2oc2ccccc23)-c2ccc(N(c3ccc4c(c3)C(c3ccccc3)(c3ccccc3)c3cc(-c5ccccc5)c5oc6ccccc6c5c3-4)c3cccc4ccccc34)cc2C1(C)C]
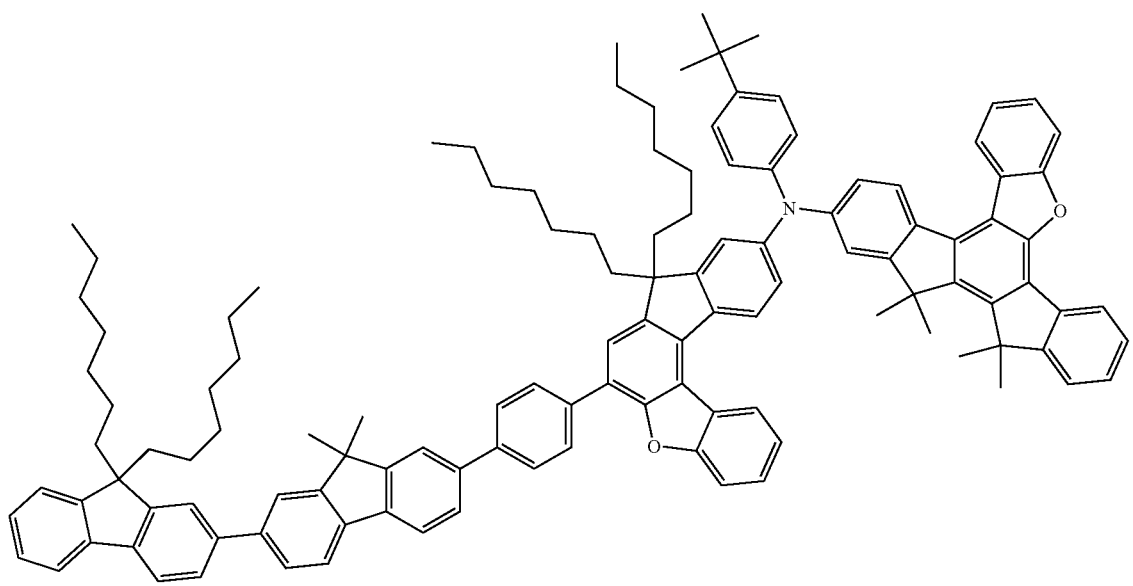 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc(C(C)(C)C)cc8)c8ccc9c(c8)C(C)(C)c8c%10c(c%11oc%12ccccc%12c%11c8-9)-c8ccccc8C%10(C)C)cc6C7(CCCCCCC)CCCCCCC)cc5)ccc3-4)cc21]
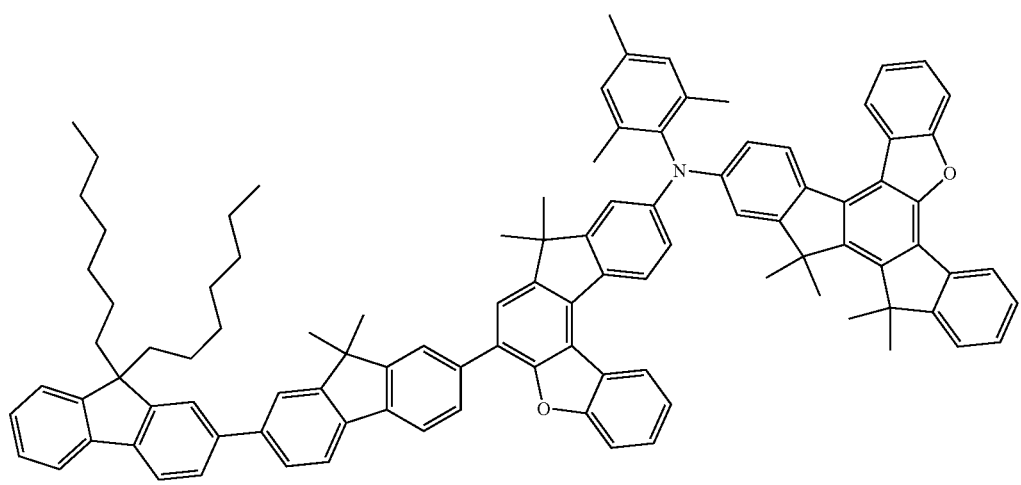 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7c(C)cc(C)cc7C)cc5C6(C)C)ccc3-4)cc21]

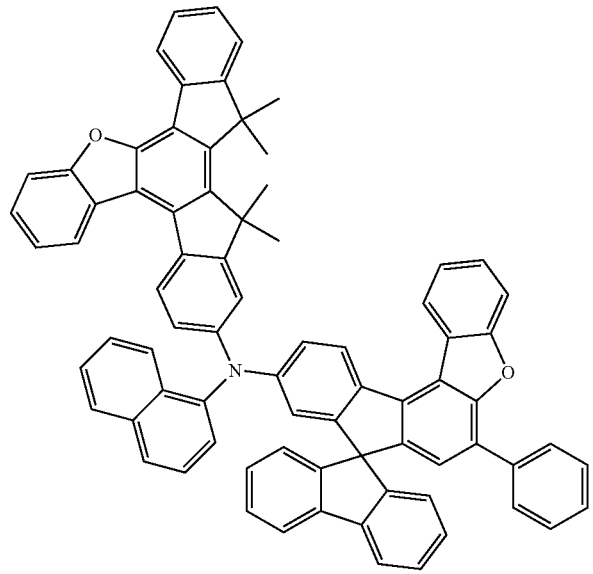 [SMILES: CC1(C)c2ccccc2-c2c1c1c(c3c2oc2ccccc23)-c2ccc(N(c3ccc4c(c3)C3(c5ccccc5-c5ccccc53)c3cc(-c5ccccc5)c5oc6ccccc6c5c3-4)c3cccc4ccccc34)cc2C1(C)C]
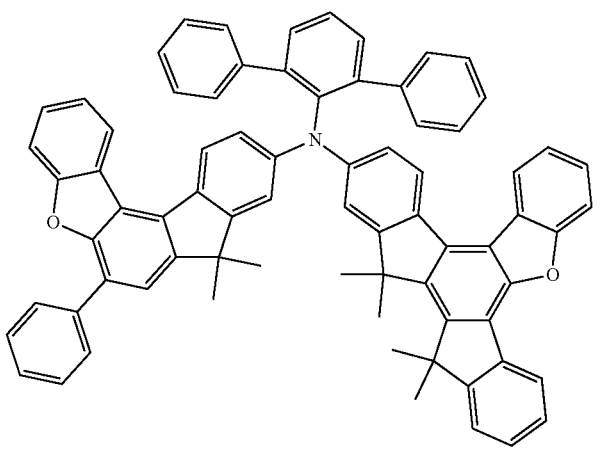 [SMILES: CC1(C)c2cc(N(c3ccc4c(c3)C(C)(C)c3c5c(c6oc7ccccc7c6c3-4)-c3ccccc3C5(C)C)c3c(-c4ccccc4)cccc3-c3ccccc3)ccc2-c2c1cc(-c1ccccc1)c1oc3ccccc3c21]
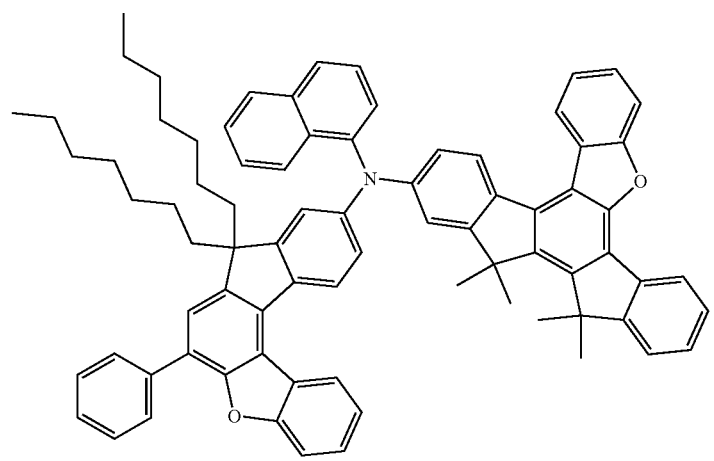 [SMILES: CCCCCCCC1(CCCCCCC)c2cc(N(c3ccc4c(c3)C(C)(C)c3c5c(c6oc7ccccc7c6c3-4)-c3ccccc3C5(C)C)c3cccc4ccccc34)ccc2-c2c1cc(-c1ccccc1)c1oc3ccccc3c21]

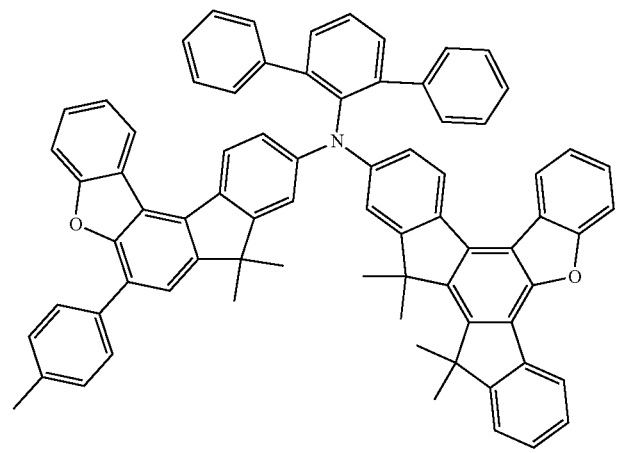 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4c(-c5ccccc5)cccc4-c4ccccc4)cc2C3(C)C)cc1]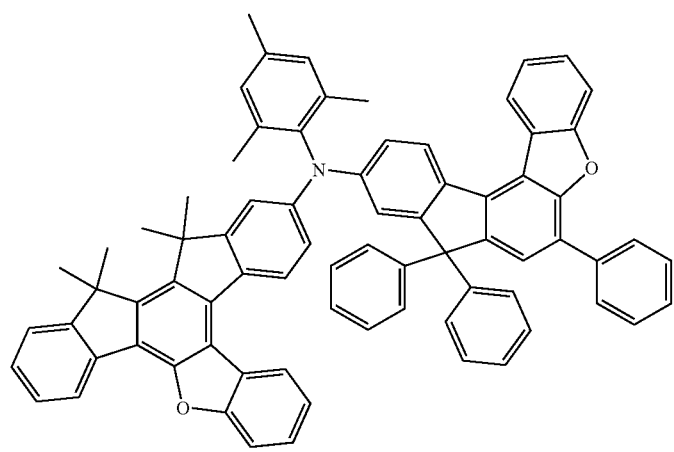 [SMILES: Cc1cc(C)c(N(c2ccc3c(c2)C(C)(C)c2c4c(c5oc6ccccc6c5c2-3)-c2ccccc2C4(C)C)c2ccc3c(c2)C(c2ccccc2)(c2ccccc2)c2cc(-c4ccccc4)c4oc5ccccc5c4c2-3)c(C)c1]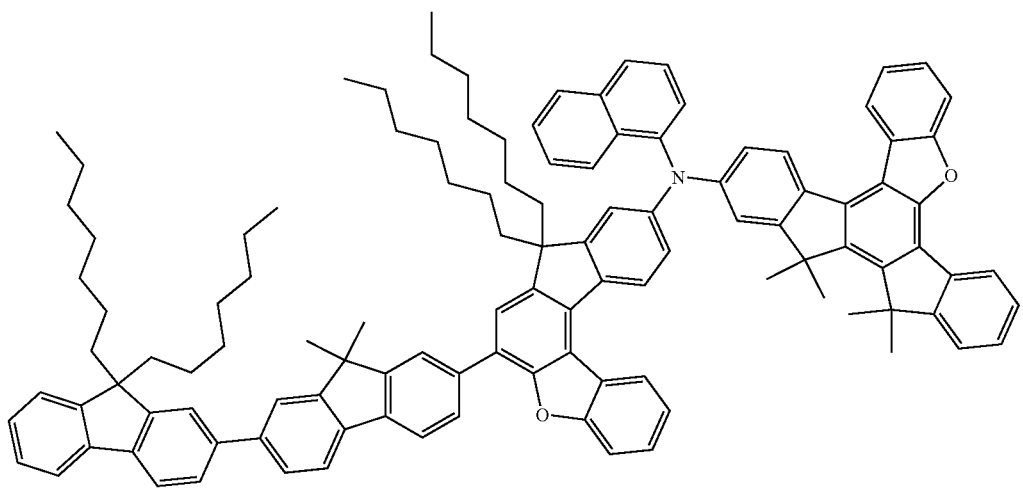 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7cccc8ccccc78)cc5C6(CCCCCCC)CCCCCCC)ccc3-4)cc21]

-continued
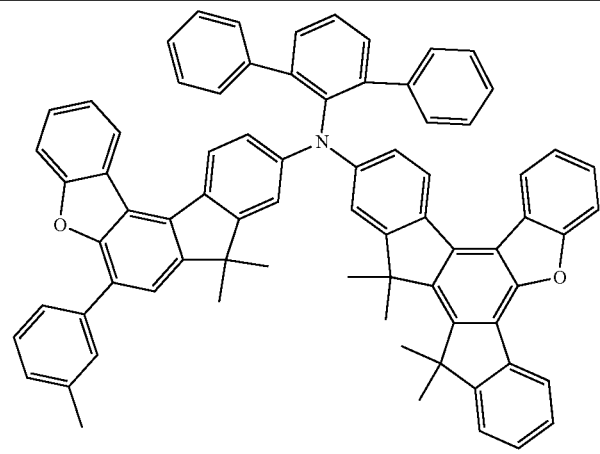
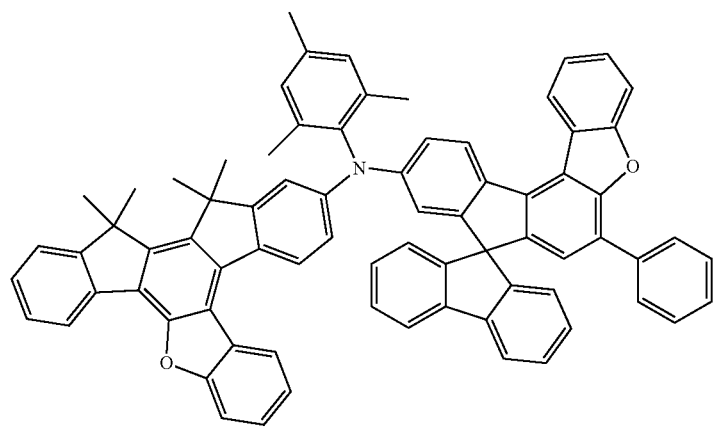 [SMILES: Cc1cc(C)c(N(c2ccc3c(c2)C(C)(C)c2c4c(c5oc6ccccc6c5c2-3)-c2ccccc2C4(C)C)c2ccc3c(c2)C2(c4ccccc4-c4ccccc42)c2cc(-c4ccccc4)c4oc5ccccc5c4c2-3)c(C)c1]
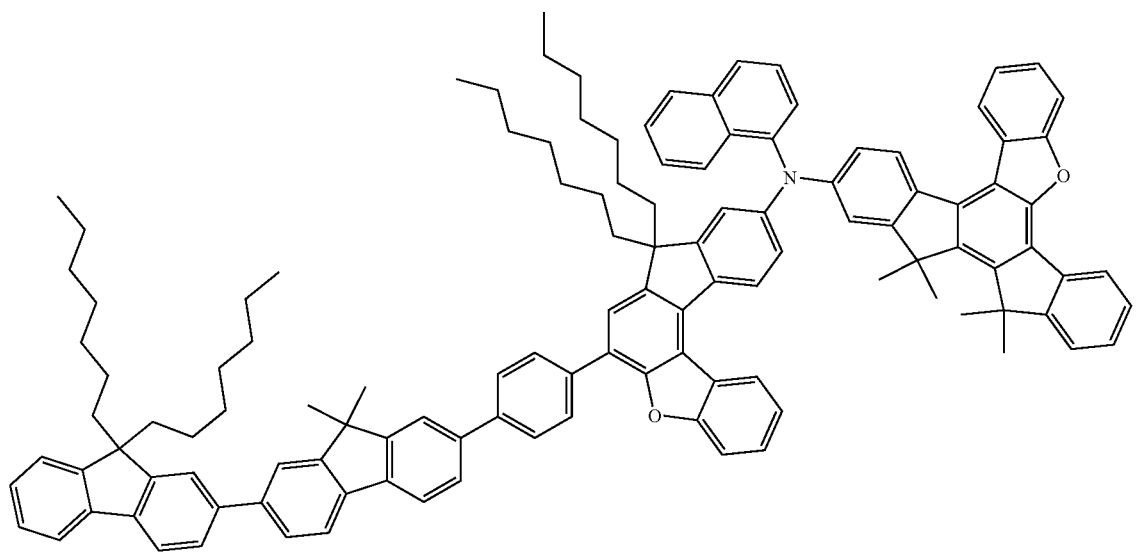 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8cccc9ccccc89)cc6C7(CCCCCCC)CCCCCCC)cc5)ccc3-4)cc21]

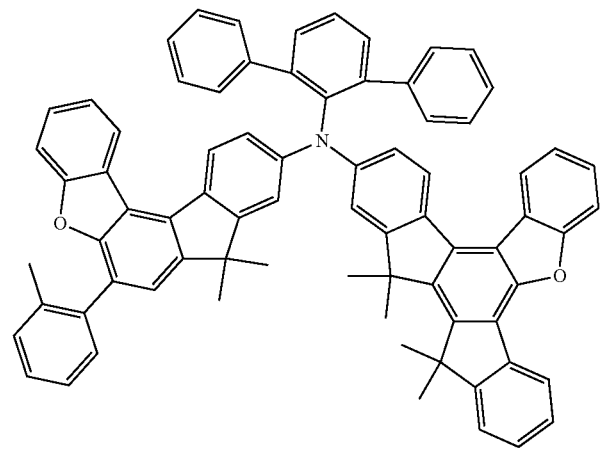 [SMILES: Cc1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3c(-c4ccccc4)cccc3-c3ccccc3)cc1C2(C)C]
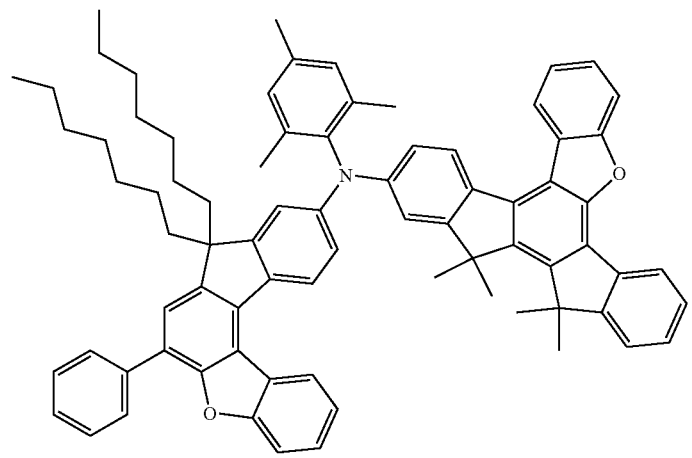 [SMILES: CCCCCCCC1(CCCCCCC)c2cc(N(c3ccc4c(c3)C(C)(C)c3c5c(c6oc7ccccc7c6c3-4)-c3ccccc3C5(C)C)c3c(C)cc(C)cc3C)ccc2-c2c1cc(-c1ccccc1)c1oc3ccccc3c21]
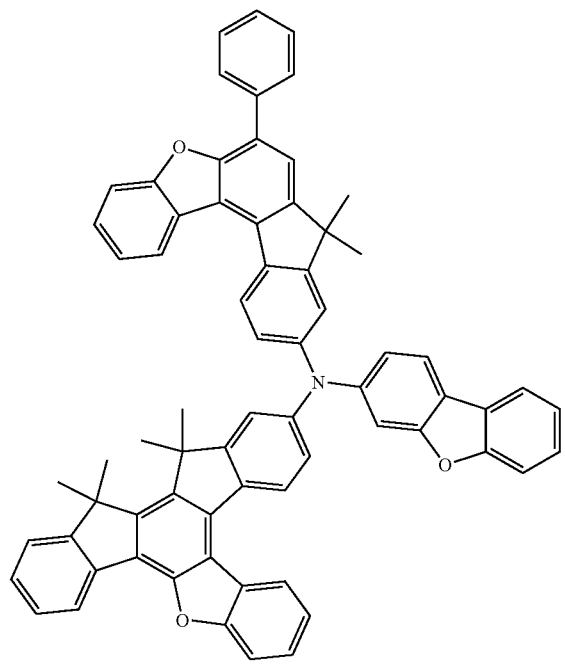 [SMILES: CC1(C)c2cc(N(c3ccc4c(c3)C(C)(C)c3c5c(c6oc7ccccc7c6c3-4)-c3ccccc3C5(C)C)c3ccc4c(c3)oc3ccccc34)ccc2-c2c1cc(-c1ccccc1)c1oc3ccccc3c21]

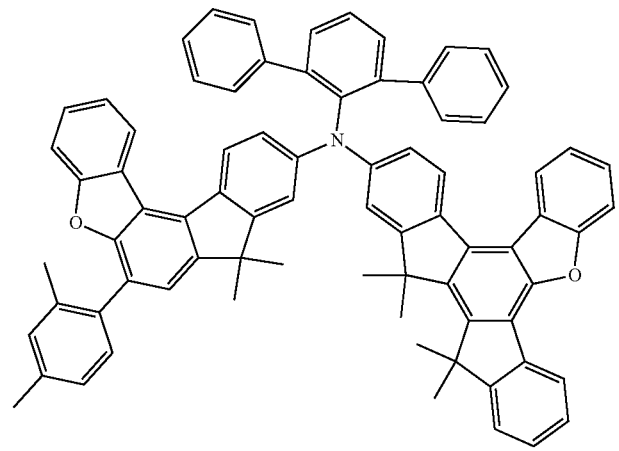 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4c(-c5ccccc5)cccc4-c4ccccc4)cc2C3(C)C)c(C)c1]
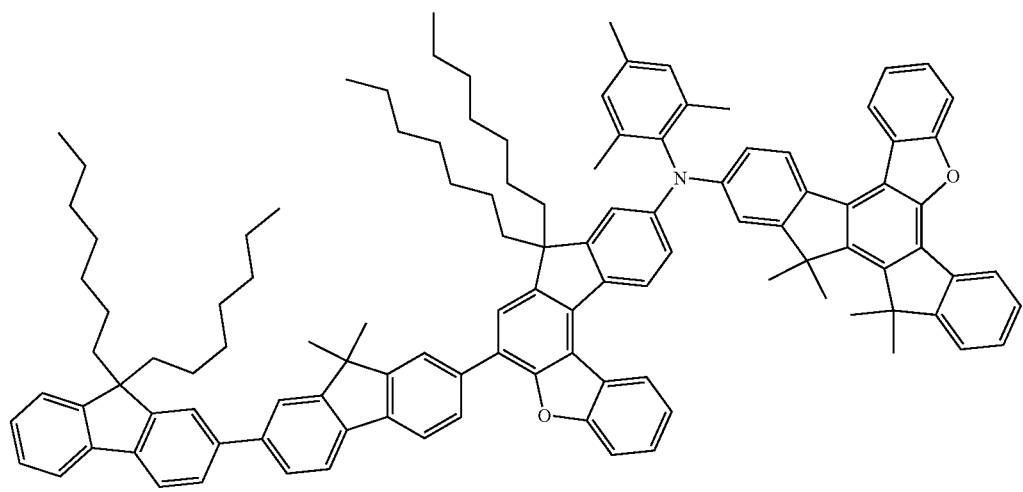 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7c(C)cc(C)cc7C)cc5C6(CCCCCCC)CCCCCCC)ccc3-4)cc21]
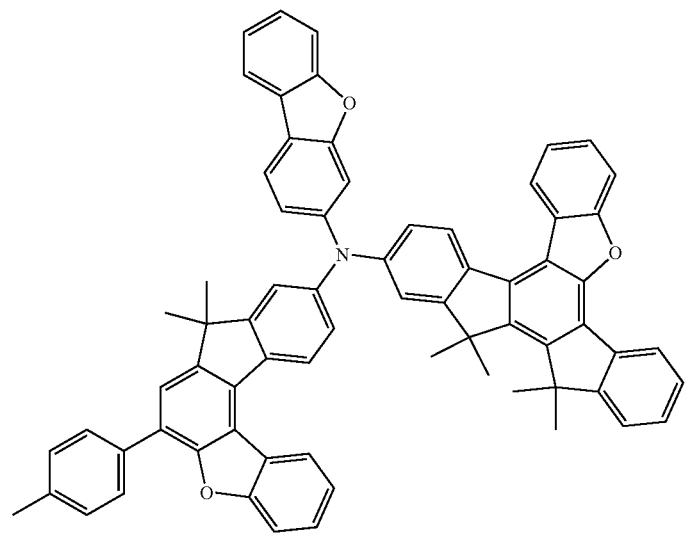 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccc5c(c4)oc4ccccc45)cc2C3(C)C)cc1]

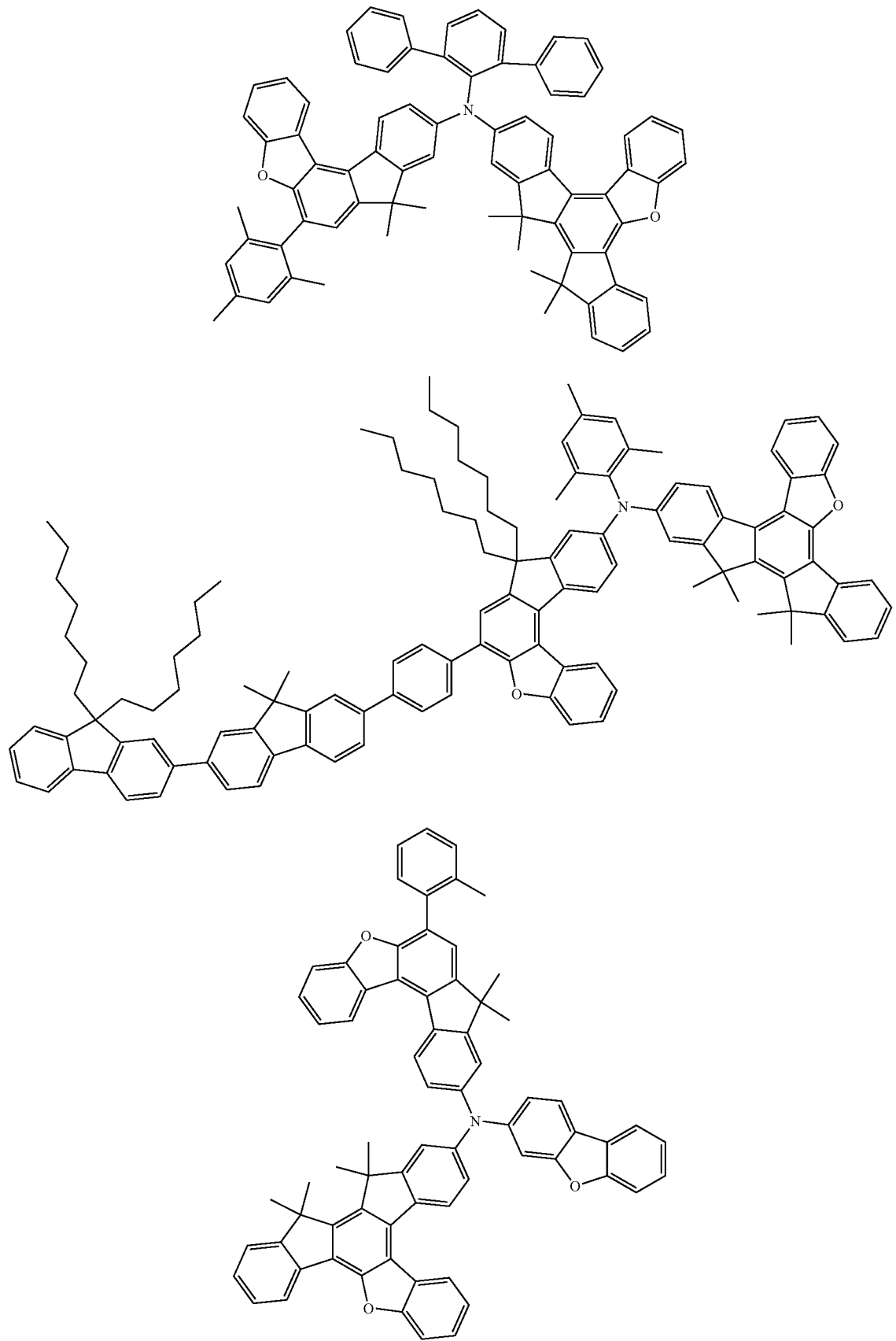

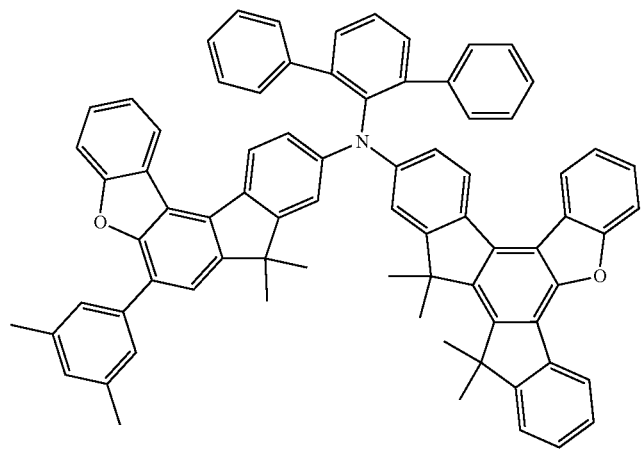 [SMILES: Cc1cc(C)cc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4c(-c5ccccc5)cccc4-c4ccccc4)cc2C3(C)C)c1]
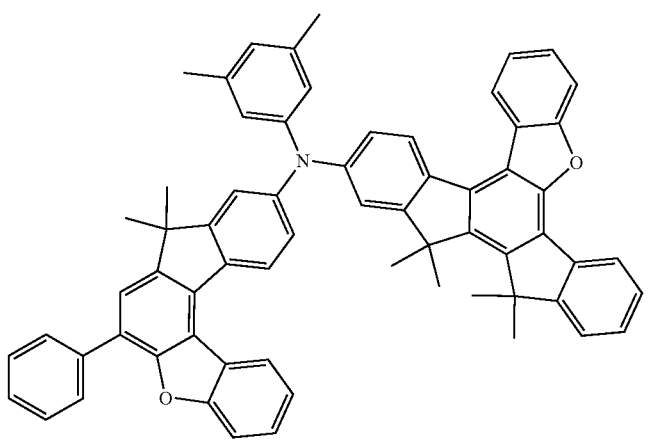 [SMILES: Cc1cc(C)cc(N(c2ccc3c(c2)C(C)(C)c2cc(-c4ccccc4)c4oc5ccccc5c4c2-3)c2ccc3c(c2)C(C)(C)c2c4c(c5oc6ccccc6c5c2-3)-c2ccccc2C4(C)C)c1]
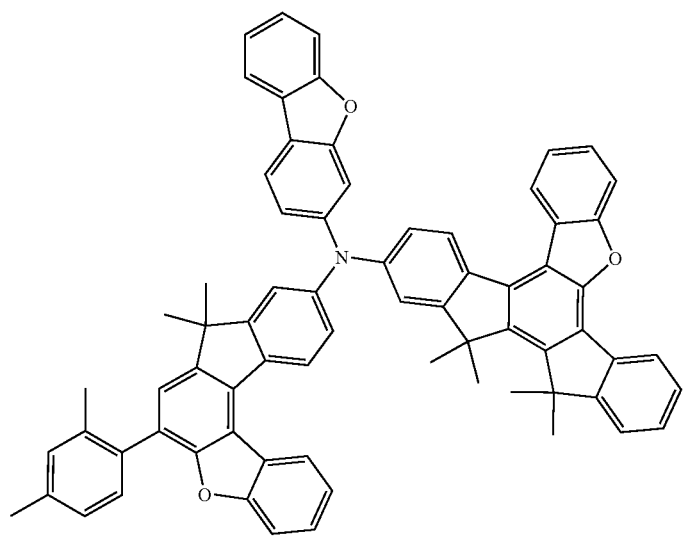 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccc5c(c4)oc4ccccc45)cc2C3(C)C)c(C)c1]

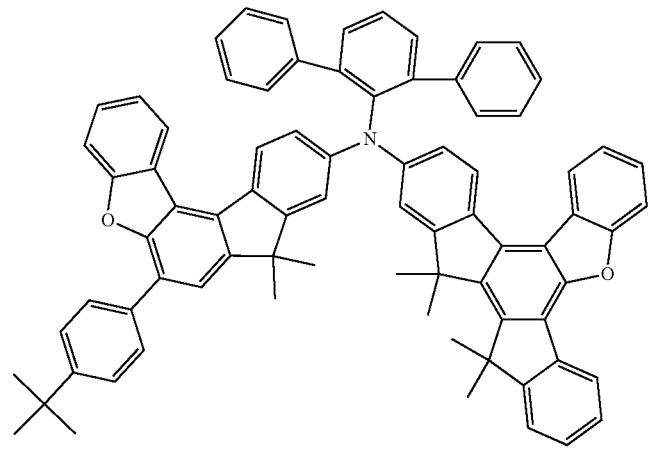 [SMILES: CC(C)(C)c1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4c(-c5ccccc5)cccc4-c4ccccc4)cc2C3(C)C)cc1]
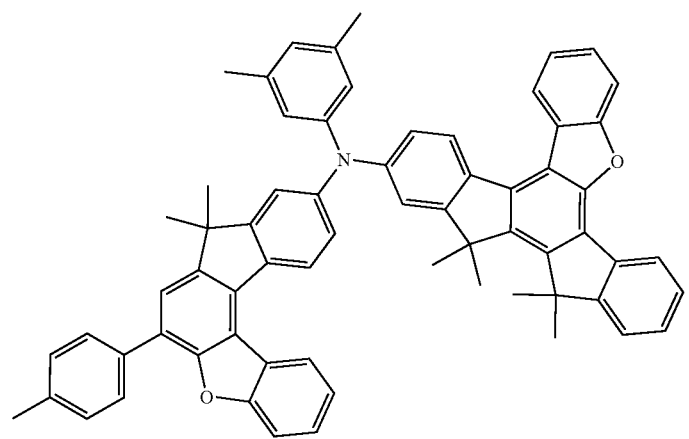 [SMILES: Cc1ccc(-c2cc3c(c4c2oc2ccccc24)-c2ccc(N(c4cc(C)cc(C)c4)c4ccc5c(c4)C(C)(C)c4c6c(c7oc8ccccc8c7c4-5)-c4ccccc4C6(C)C)cc2C3(C)C)cc1]
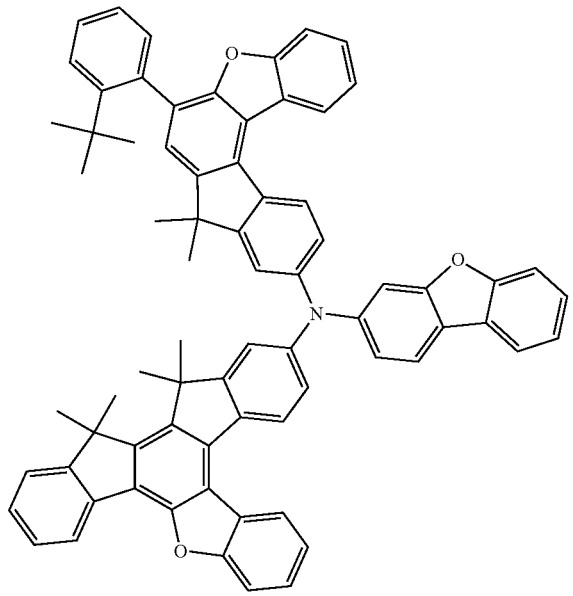 [SMILES: CC(C)(C)c1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3ccc4c(c3)oc3ccccc34)cc1C2(C)C]

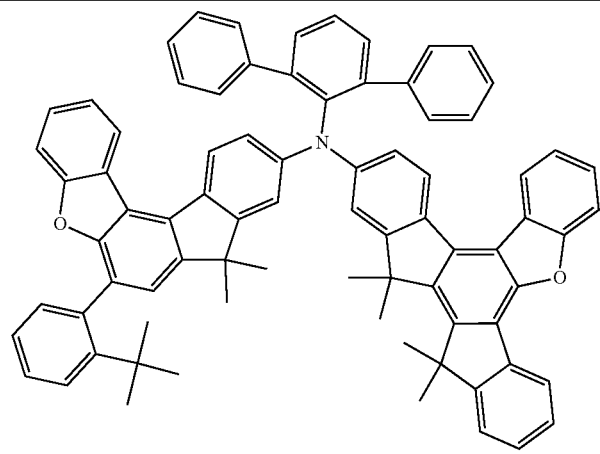
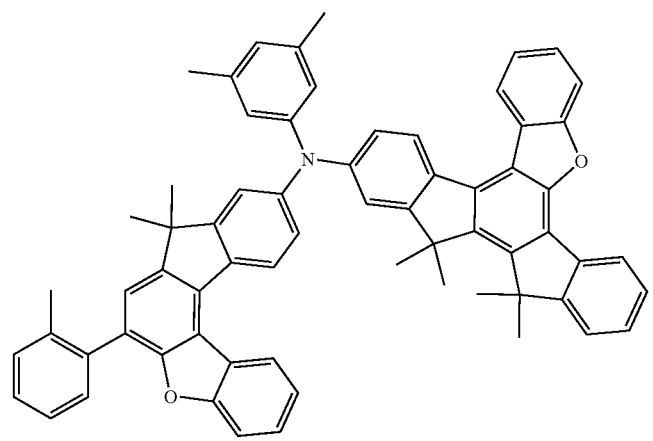 [SMILES: Cc1cc(C)cc(N(c2ccc3c(c2)C(C)(C)c2cc(-c4ccccc4C)c4oc5ccccc5c4c2-3)c2ccc3c(c2)C(C)(C)c2c4c(c5oc6ccccc6c5c2-3)-c2ccccc2C4(C)C)c1]
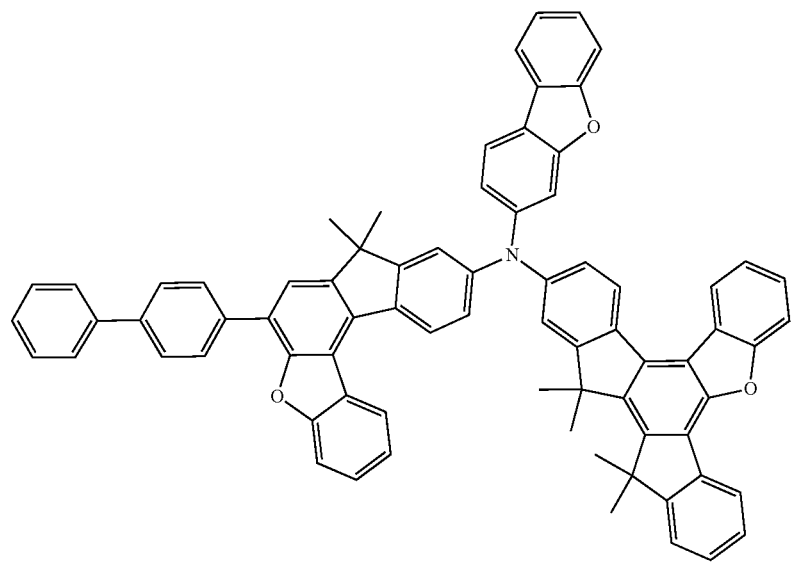 [SMILES: CC1(C)c2cc(N(c3ccc4c(c3)C(C)(C)c3c5c(c6oc7ccccc7c6c3-4)-c3ccccc3C5(C)C)c3ccc4c(c3)oc3ccccc34)ccc2-c2c1cc(-c1ccc(-c3ccccc3)cc1)c1oc3ccccc3c21]

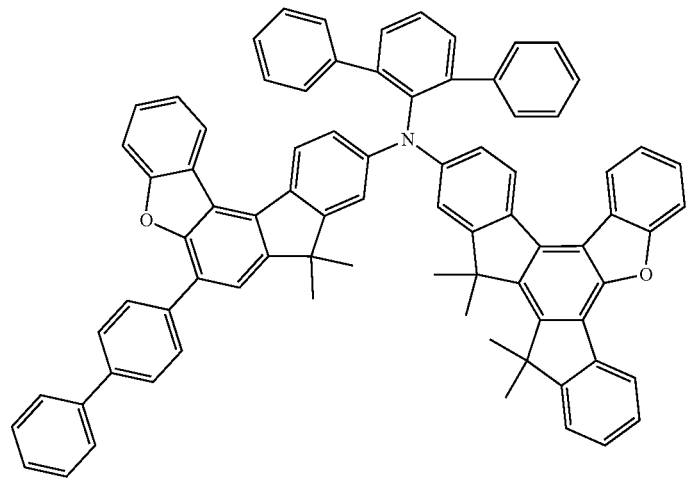 [SMILES: CC1(C)c2cc(N(c3ccc4c(c3)C(C)(C)c3c5c(c6oc7ccccc7c6c3-4)-c3ccccc3C5(C)C)c3c(-c4ccccc4)cccc3-c3ccccc3)ccc2-c2c1cc(-c1ccc(-c3ccccc3)cc1)c1oc3ccccc3c21]
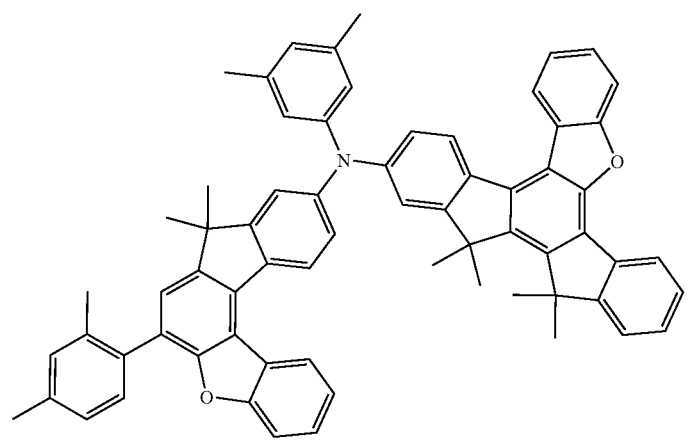 [SMILES: Cc1cc(C)cc(N(c2ccc3c(c2)C(C)(C)c2cc(-c4ccc(C)cc4C)c4oc5ccccc5c4c2-3)c2ccc3c(c2)C(C)(C)c2c4c(c5oc6ccccc6c5c2-3)-c2ccccc2C4(C)C)c1]
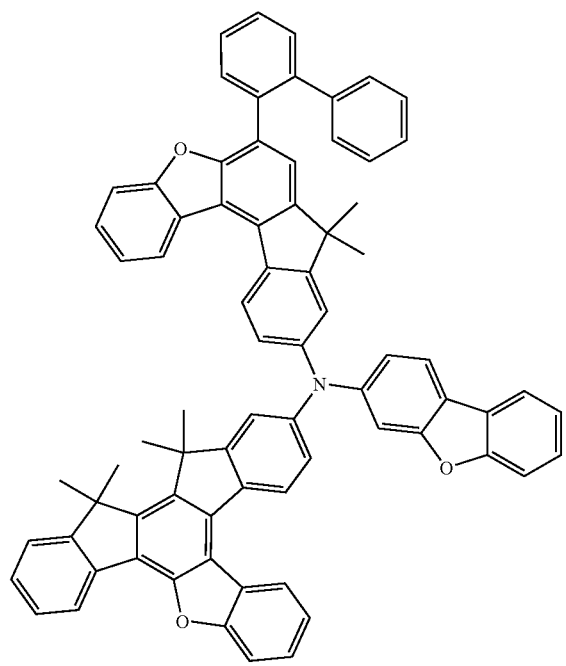 [SMILES: CC1(C)c2cc(N(c3ccc4c(c3)C(C)(C)c3c5c(c6oc7ccccc7c6c3-4)-c3ccccc3C5(C)C)c3ccc4c(c3)oc3ccccc34)ccc2-c2c1cc(-c1ccccc1-c1ccccc1)c1oc3ccccc3c21]

-continued
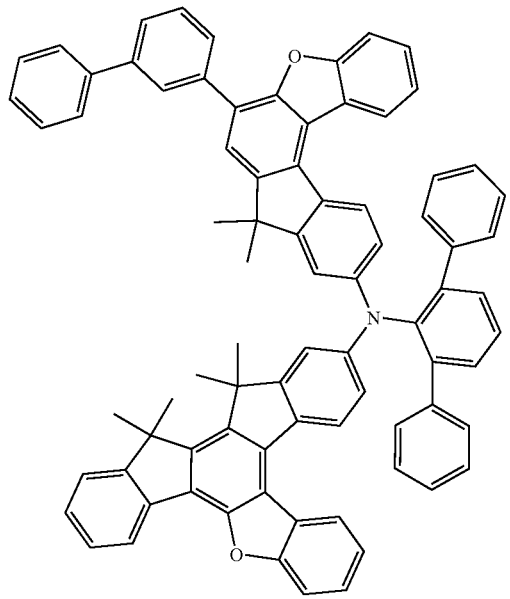 [SMILES: CC1(C)c2cc(N(c3ccc4c(c3)C(C)(C)c3c5c(c6oc7ccccc7c6c3-4)-c3ccccc3C5(C)C)c3c(-c4ccccc4)cccc3-c3ccccc3)ccc2-c2c1cc(-c1cccc(-c3ccccc3)c1)c1oc3ccccc3c21]
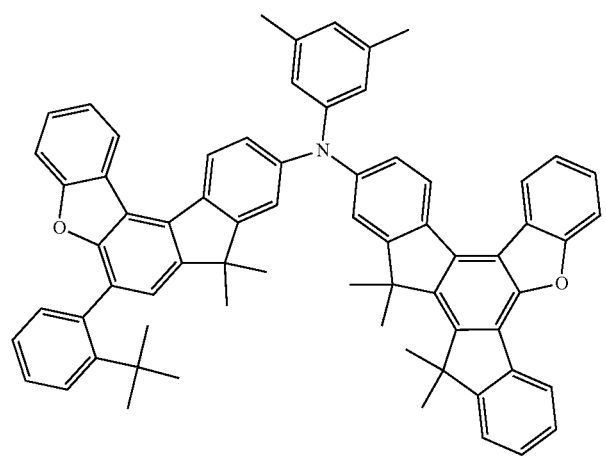 [SMILES: Cc1cc(C)cc(N(c2ccc3c(c2)C(C)(C)c2cc(-c4ccccc4C(C)(C)C)c4oc5ccccc5c4c2-3)c2ccc3c(c2)C(C)(C)c2c4c(c5oc6ccccc6c5c2-3)-c2ccccc2C4(C)C)c1]

-continued
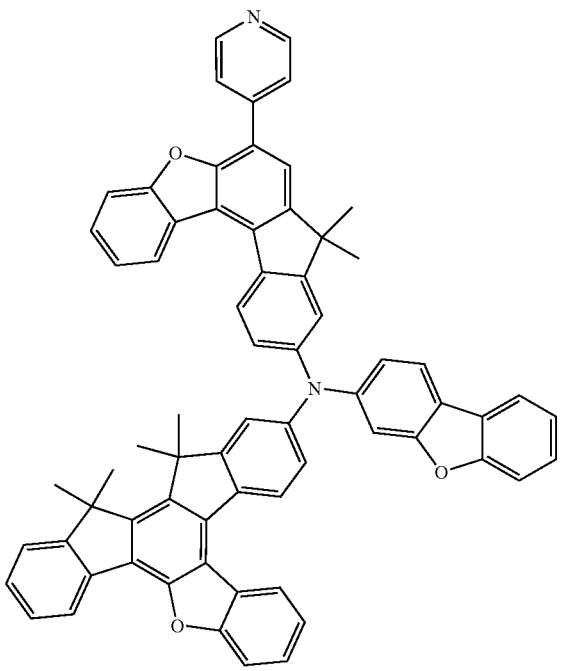 [SMILES: CC1(C)c2cc(N(c3ccc4c(c3)C(C)(C)c3c5c(c6oc7ccccc7c6c3-4)-c3ccccc3C5(C)C)c3ccc4c(c3)oc3ccccc34)ccc2-c2c1cc(-c1ccncc1)c1oc3ccccc3c21]
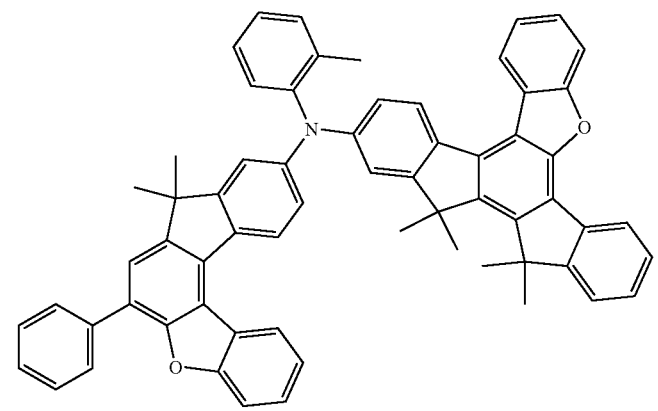 [SMILES: Cc1ccccc1N(c1ccc2c(c1)C(C)(C)c1cc(-c3ccccc3)c3oc4ccccc4c3c1-2)c1ccc2c(c1)C(C)(C)c1c3c(c4oc5ccccc5c4c1-2)-c1ccccc1C3(C)C]
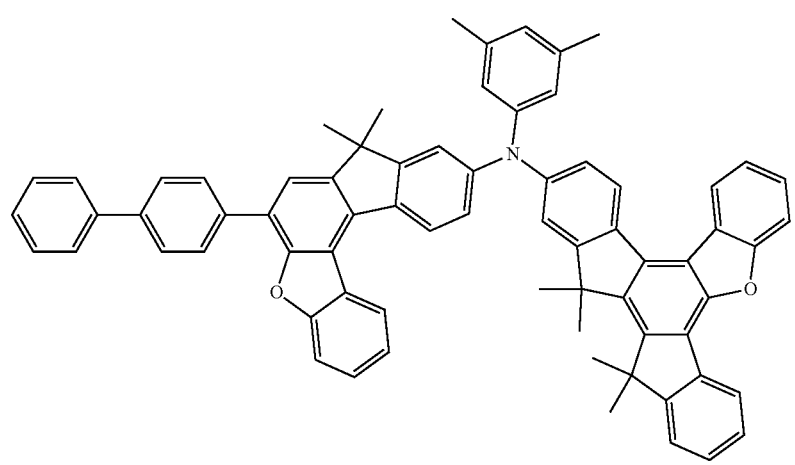 [SMILES: Cc1cc(C)cc(N(c2ccc3c(c2)C(C)(C)c2cc(-c4ccc(-c5ccccc5)cc4)c4oc5ccccc5c4c2-3)c2ccc3c(c2)C(C)(C)c2c4c(c5oc6ccccc6c5c2-3)-c2ccccc2C4(C)C)c1]

-continued
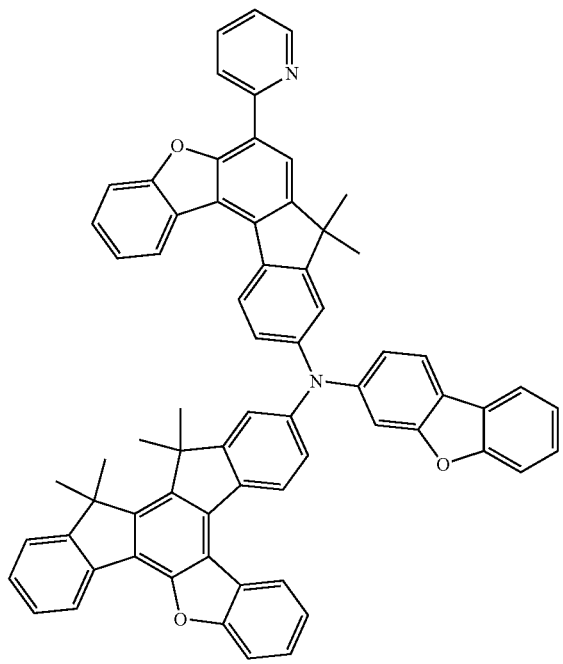 [SMILES: CC1(C)c2cc(N(c3ccc4c(c3)C(C)(C)c3c5c(c6oc7ccccc7c6c3-4)-c3ccccc3C5(C)C)c3ccc4c(c3)oc3ccccc34)ccc2-c2c1cc(-c1ccccn1)c1oc3ccccc3c21]

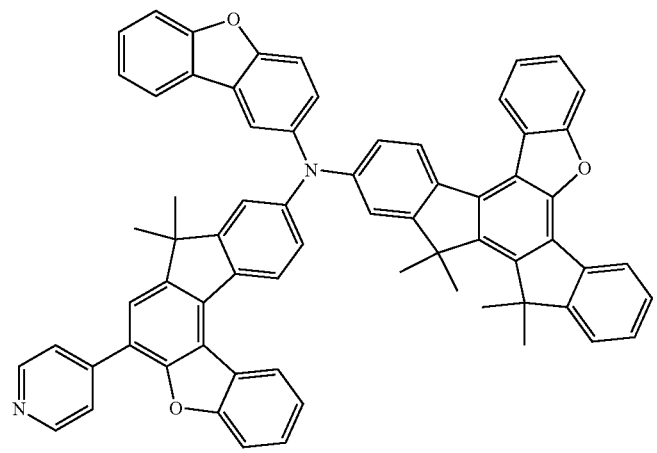 [SMILES: CC1(C)c2cc(N(c3ccc4c(c3)C(C)(C)c3c5c(c6oc7ccccc7c6c3-4)-c3ccccc3C5(C)C)c3ccc4oc5ccccc5c4c3)ccc2-c2c1cc(-c1ccncc1)c1oc3ccccc3c21]
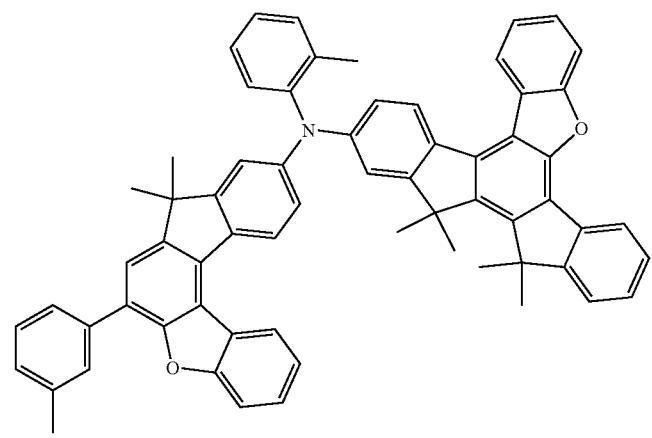 [SMILES: Cc1cccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccccc4C)cc2C3(C)C)c1]
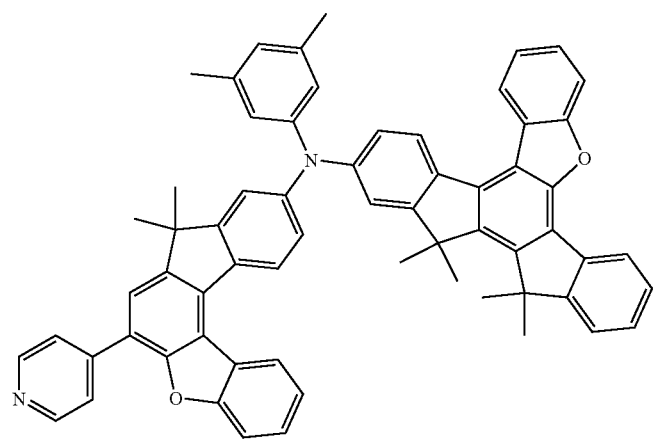 [SMILES: Cc1cc(C)cc(N(c2ccc3c(c2)C(C)(C)c2cc(-c4ccncc4)c4oc5ccccc5c4c2-3)c2ccc3c(c2)C(C)(C)c2c4c(c5oc6ccccc6c5c2-3)-c2ccccc2C4(C)C)c1]

-continued
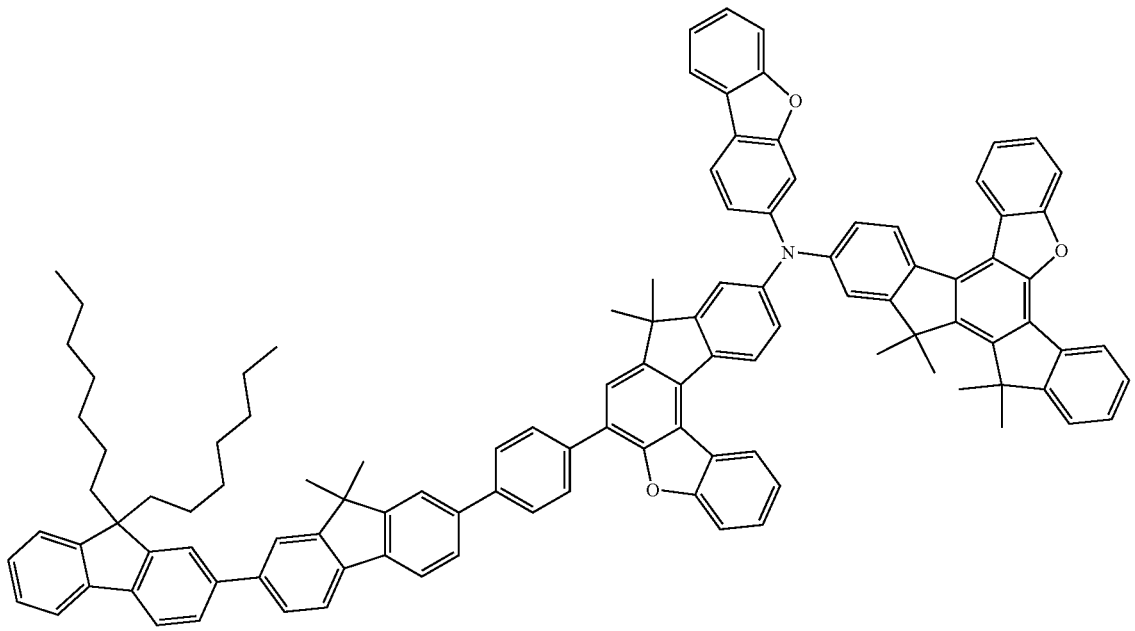 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8ccc9c(c8)oc8ccccc89)cc6C7(C)C)cc5)ccc3-4)cc21]
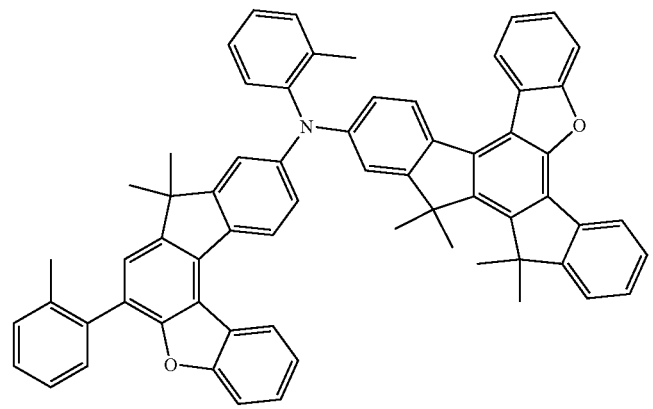 [SMILES: Cc1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3ccccc3C)cc1C2(C)C]
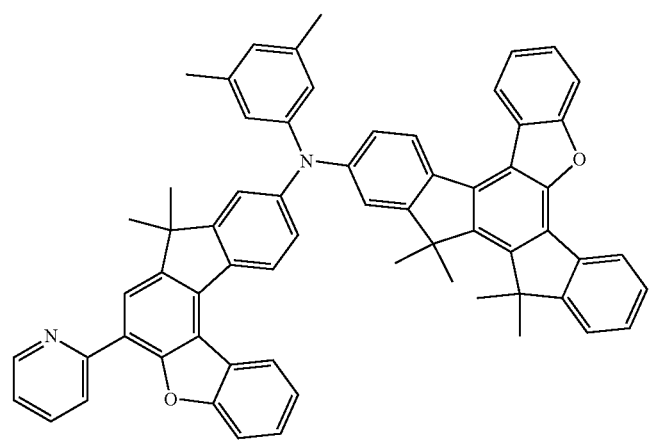 [SMILES: Cc1cc(C)cc(N(c2ccc3c(c2)C(C)(C)c2cc(-c4ccccn4)c4oc5ccccc5c4c2-3)c2ccc3c(c2)C(C)(C)c2c4c(c5oc6ccccc6c5c2-3)-c2ccccc2C4(C)C)c1]

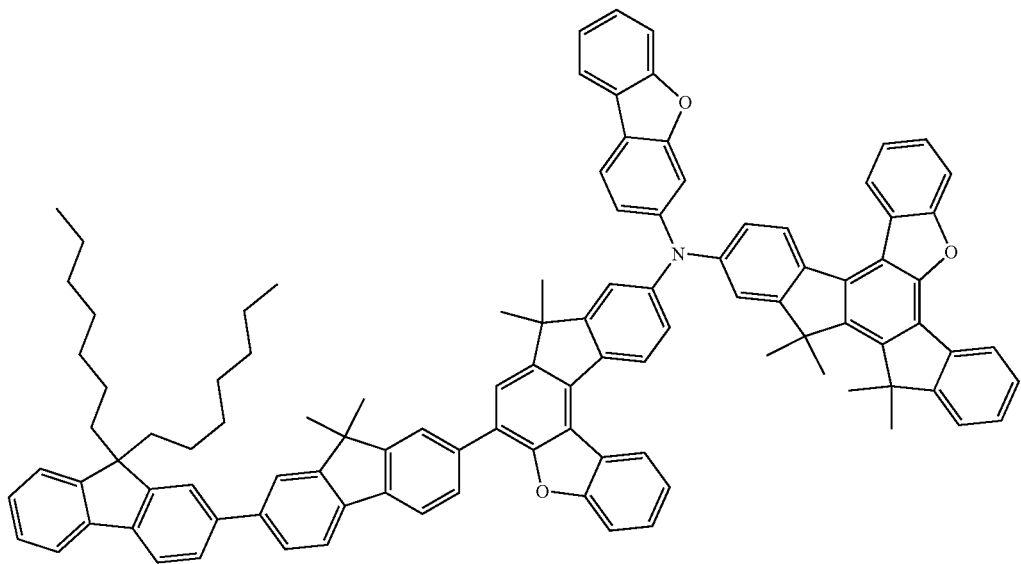 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7ccc8c(c7)oc7ccccc78)cc5C6(C)C)ccc3-4)cc21]

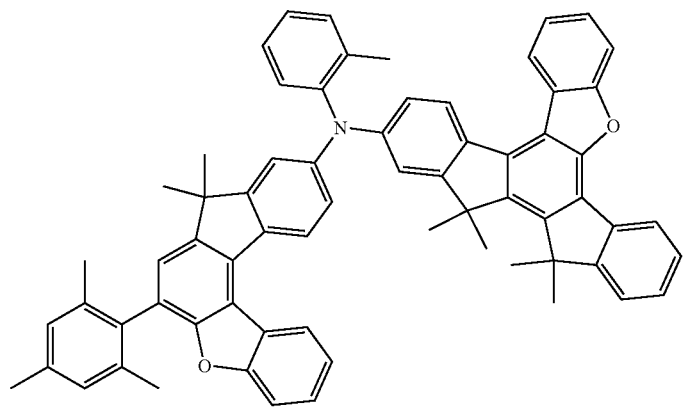 [SMILES: Cc1cc(C)c(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccccc4C)cc2C3(C)C)c(C)c1]
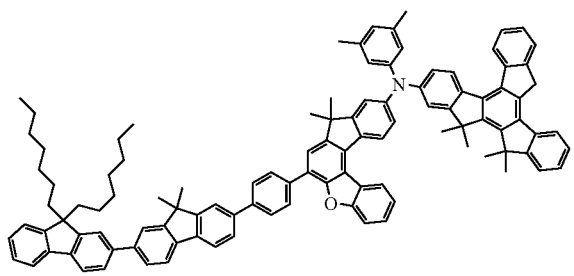 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8cc(C)cc(C)c8)c8ccc9c(c8)C(C)(C)c8c-9c9c(c%10c8C(C)(C)c8ccccc8-%10)Cc8ccccc8-9)cc6C7(C)C)cc5)ccc3-4)cc21]
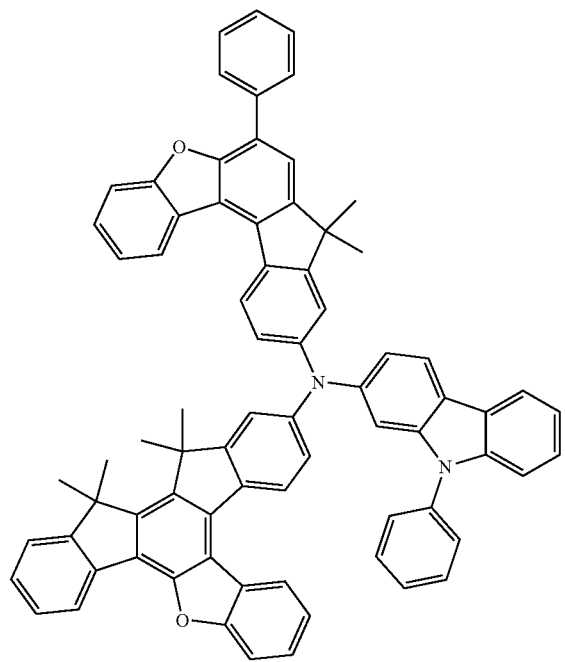 [SMILES: CC1(C)c2cc(N(c3ccc4c(c3)C(C)(C)c3c5c(c6oc7ccccc7c6c3-4)-c3ccccc3C5(C)C)c3ccc4c5ccccc5n(-c5ccccc5)c4c3)ccc2-c2c1cc(-c1ccccc1)c1oc3ccccc3c21]

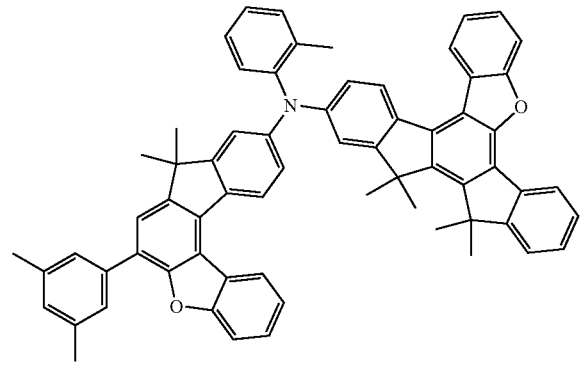 [SMILES: Cc1cc(C)cc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccccc4C)cc2C3(C)C)c1]
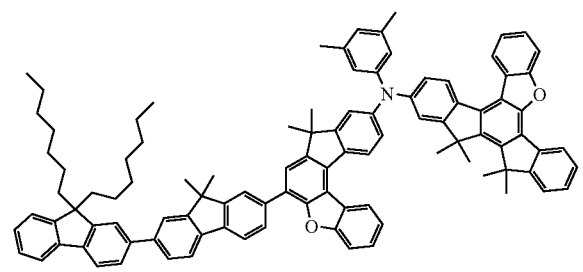 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7cc(C)cc(C)c7)c7ccc8c(c7)C(C)(C)c7c9c(c%10oc%11ccccc%11c%10c7-8)-c7ccccc7C9(C)C)cc5C6(C)C)ccc3-4)cc21]
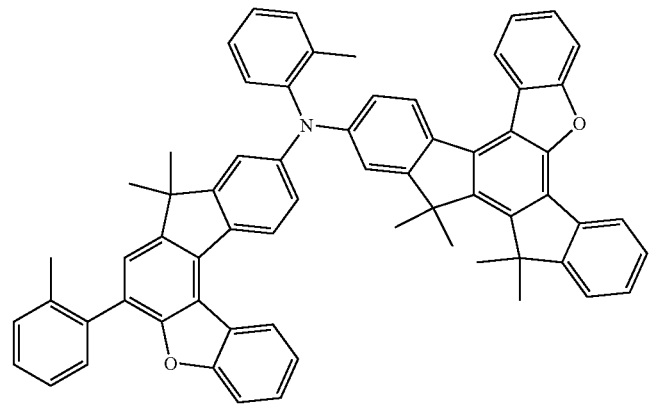 [SMILES: Cc1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3ccccc3C)cc1C2(C)C]
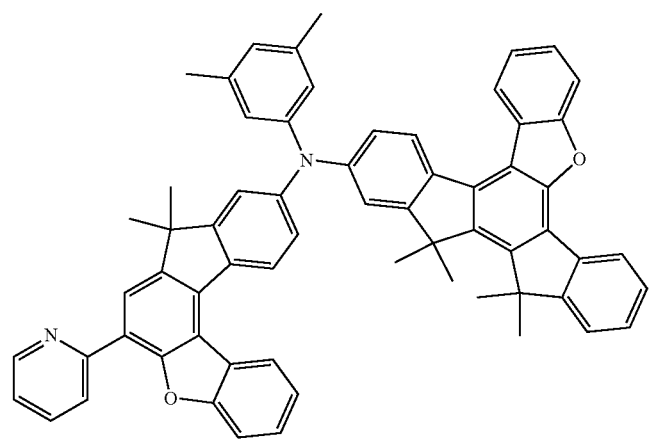 [SMILES: Cc1cc(C)cc(N(c2ccc3c(c2)C(C)(C)c2cc(-c4ccccn4)c4oc5ccccc5c4c2-3)c2ccc3c(c2)C(C)(C)c2c4c(c5oc6ccccc6c5c2-3)-c2ccccc2C4(C)C)c1]

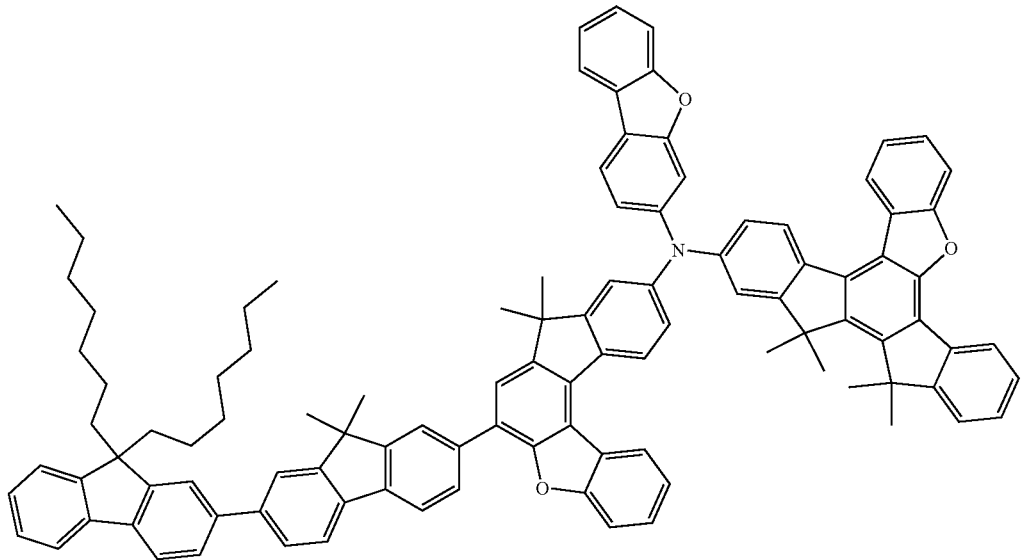 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7ccc8c(c7)oc7ccccc78)cc5C6(C)C)ccc3-4)cc21]
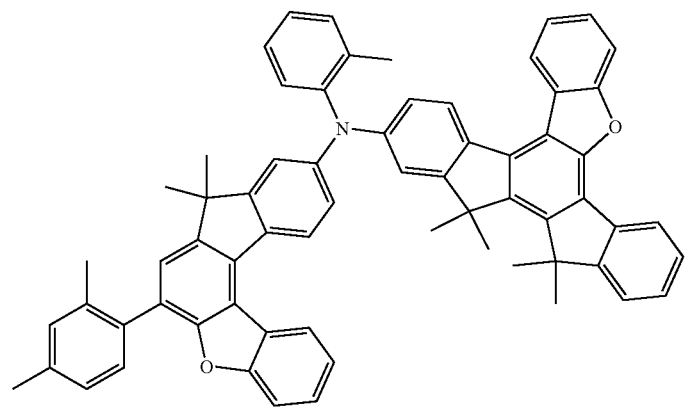 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccccc4C)cc2C3(C)C)c(C)c1]
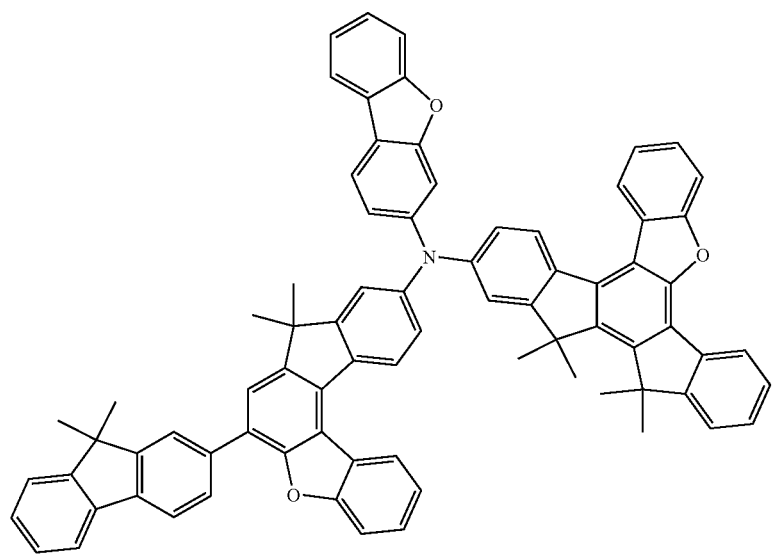 [SMILES: CC1(C)c2ccccc2-c2ccc(-c3cc4c(c5c3oc3ccccc35)-c3ccc(N(c5ccc6c(c5)C(C)(C)c5c7c(c8oc9ccccc9c8c5-6)-c5ccccc5C7(C)C)c5ccc6c(c5)oc5ccccc56)cc3C4(C)C)cc21]

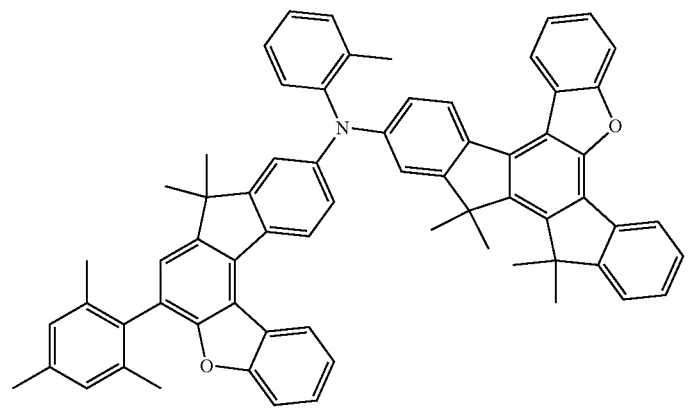 [SMILES: Cc1cc(C)c(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccccc4C)cc2C3(C)C)c(C)c1]
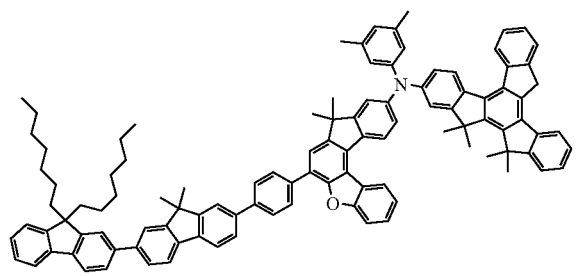 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8cc(C)cc(C)c8)c8ccc9c(c8)C(C)(C)c8c-9c9c(c%10c8C(C)(C)c8ccccc8-%10)Cc8ccccc8-9)cc6C7(C)C)cc5)ccc3-4)cc21]
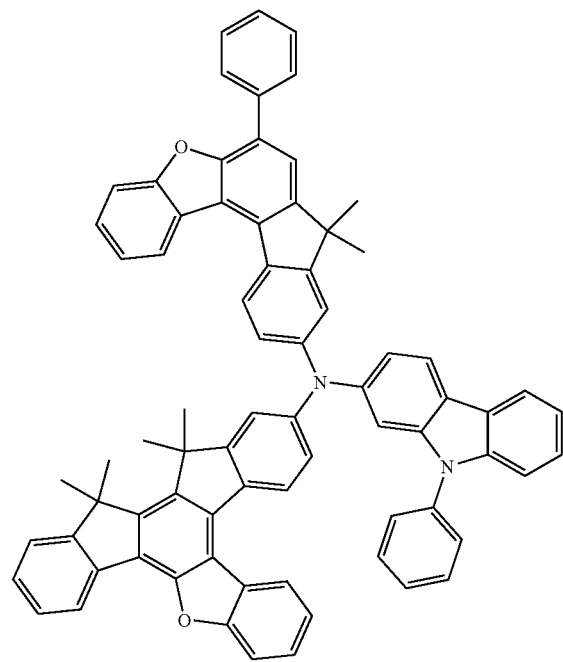 [SMILES: CC1(C)c2cc(N(c3ccc4c(c3)C(C)(C)c3c5c(c6oc7ccccc7c6c3-4)-c3ccccc3C5(C)C)c3ccc4c5ccccc5n(-c5ccccc5)c4c3)ccc2-c2c1cc(-c1ccccc1)c1oc3ccccc3c21]

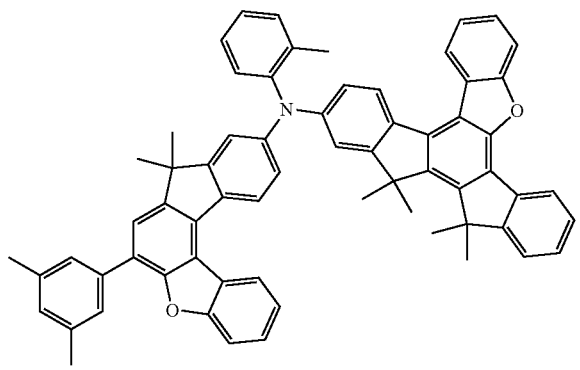 [SMILES: Cc1cc(C)cc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccccc4C)cc2C3(C)C)c1]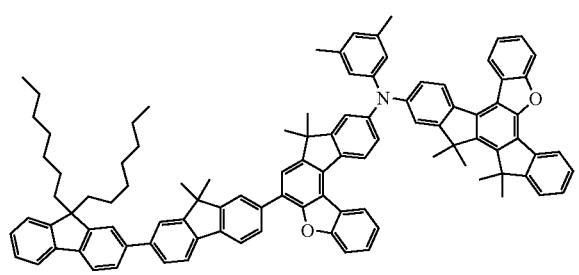 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7cc(C)cc(C)c7)c7ccc8c(c7)C(C)(C)c7c9c(c%10oc%11ccccc%11c%10c7-8)-c7ccccc7C9(C)C)cc5C6(C)C)ccc3-4)cc21]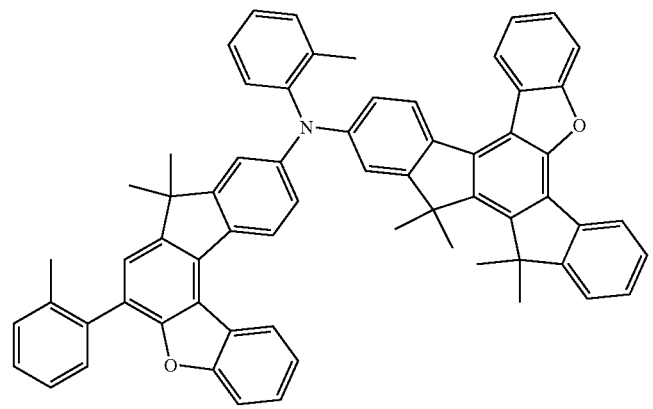 [SMILES: Cc1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3ccccc3C)cc1C2(C)C]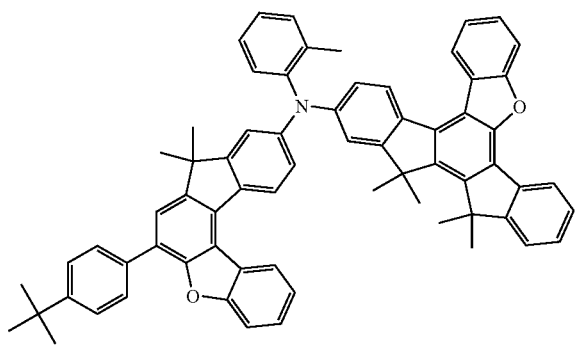 [SMILES: Cc1ccccc1N(c1ccc2c(c1)C(C)(C)c1cc(-c3ccc(C(C)(C)C)cc3)c3oc4ccccc4c3c1-2)c1ccc2c(c1)C(C)(C)c1c3c(c4oc5ccccc5c4c1-2)-c1ccccc1C3(C)C]

-continued
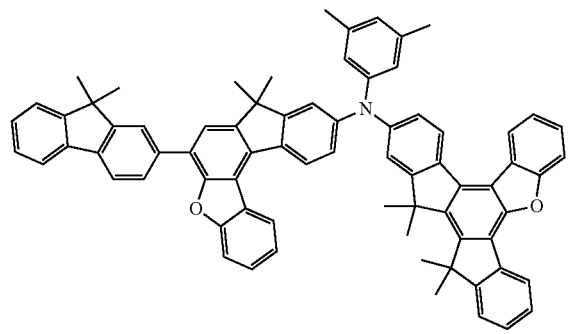 [SMILES: Cc1cc(C)cc(N(c2ccc3c(c2)C(C)(C)c2cc(-c4ccc5c(c4)C(C)(C)c4ccccc4-5)c4oc5ccccc5c4c2-3)c2ccc3c(c2)C(C)(C)c2c4c(c5oc6ccccc6c5c2-3)-c2ccccc2C4(C)C)c1]
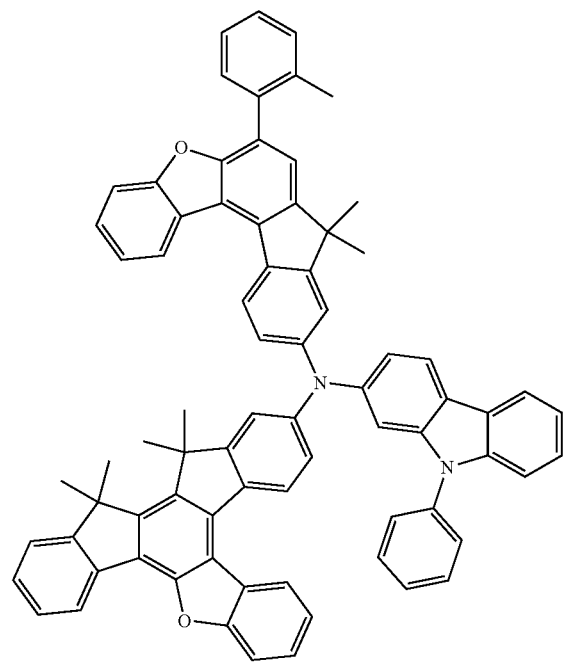 [SMILES: Cc1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3ccc4c5ccccc5n(-c5ccccc5)c4c3)cc1C2(C)C]
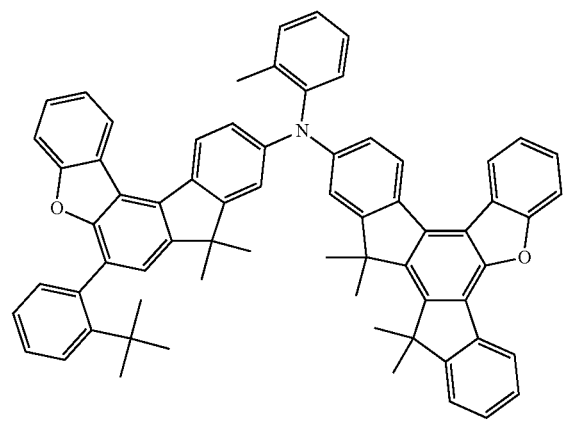 [SMILES: Cc1ccccc1N(c1ccc2c(c1)C(C)(C)c1cc(-c3ccccc3C(C)(C)C)c3oc4ccccc4c3c1-2)c1ccc2c(c1)C(C)(C)c1c3c(c4oc5ccccc5c4c1-2)-c1ccccc1C3(C)C]

-continued
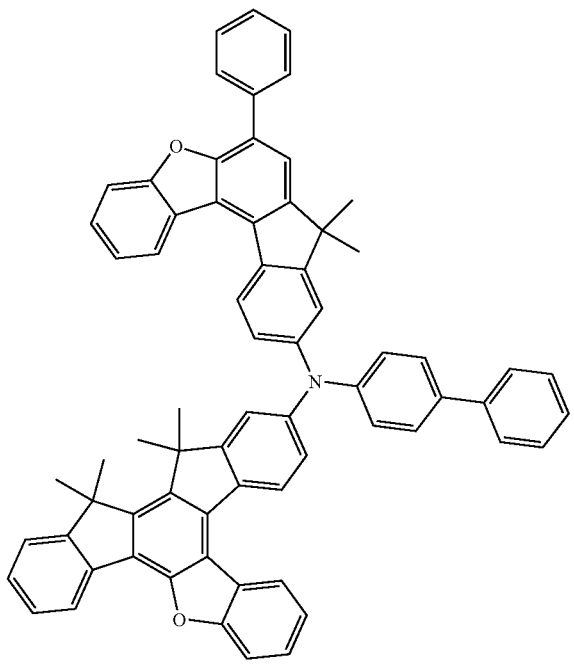 [SMILES: CC1(C)c2cc(N(c3ccc(-c4ccccc4)cc3)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]
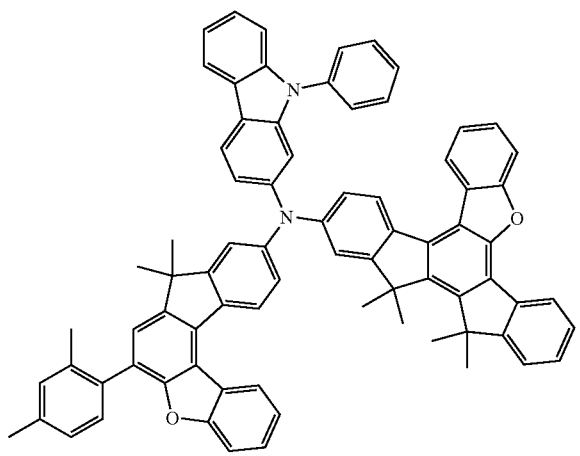 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccc5c6ccccc6n(-c6ccccc6)c5c4)cc2C3(C)C)c(C)c1]
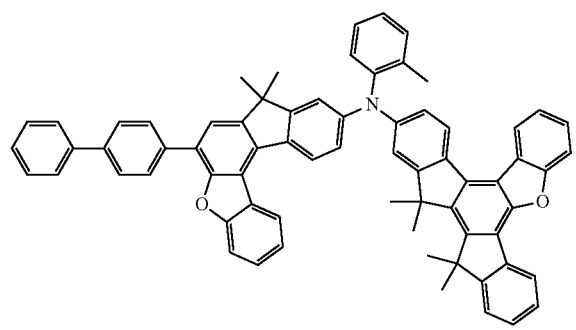 [SMILES: Cc1ccccc1N(c1ccc2c(c1)C(C)(C)c1cc(-c3ccc(-c4ccccc4)cc3)c3oc4ccccc4c3c1-2)c1ccc2c(c1)C(C)(C)c1c3c(c4oc5ccccc5c4c1-2)-c1ccccc1C3(C)C]

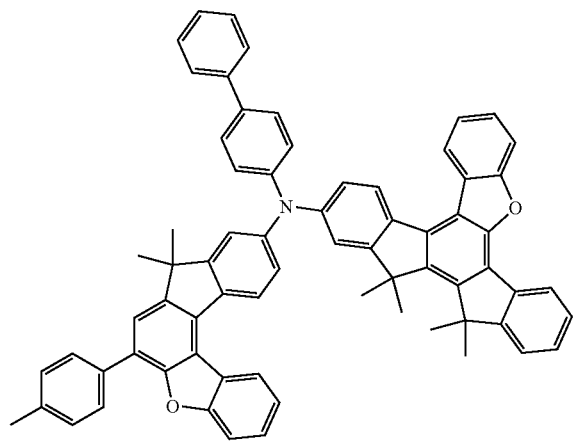 [SMILES: Cc1ccc(-c2cc3c(c4c2oc2ccccc24)-c2ccc(N(c4ccc(-c5ccccc5)cc4)c4ccc5c(c4)C(C)(C)c4c6c(c7oc8ccccc8c7c4-5)-c4ccccc4C6(C)C)cc2C3(C)C)cc1]
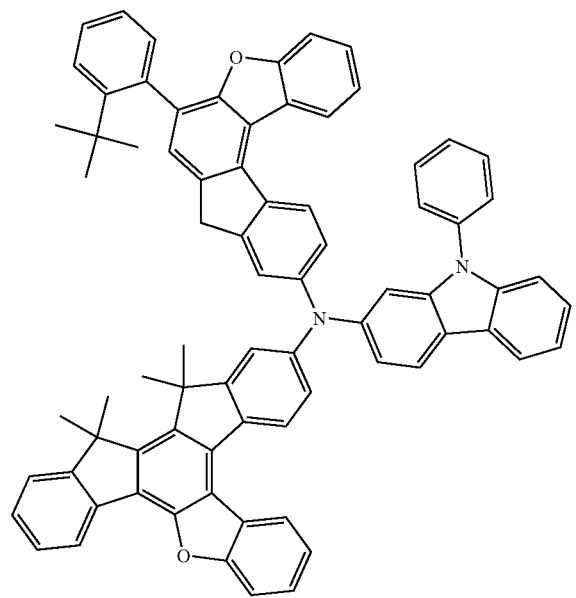 [SMILES: CC(C)(C)c1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3ccc4c5ccccc5n(-c5ccccc5)c4c3)cc1C2]
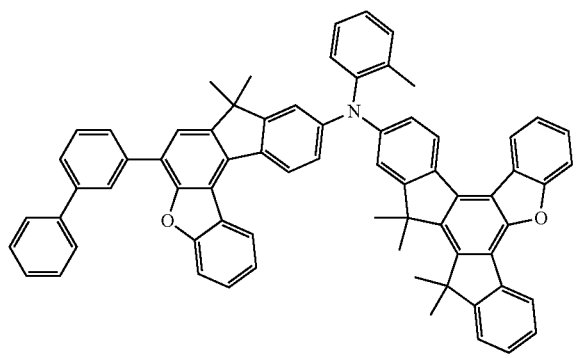 [SMILES: Cc1ccccc1N(c1ccc2c(c1)C(C)(C)c1cc(-c3cccc(-c4ccccc4)c3)c3oc4ccccc4c3c1-2)c1ccc2c(c1)C(C)(C)c1c3c(c4oc5ccccc5c4c1-2)-c1ccccc1C3(C)C]

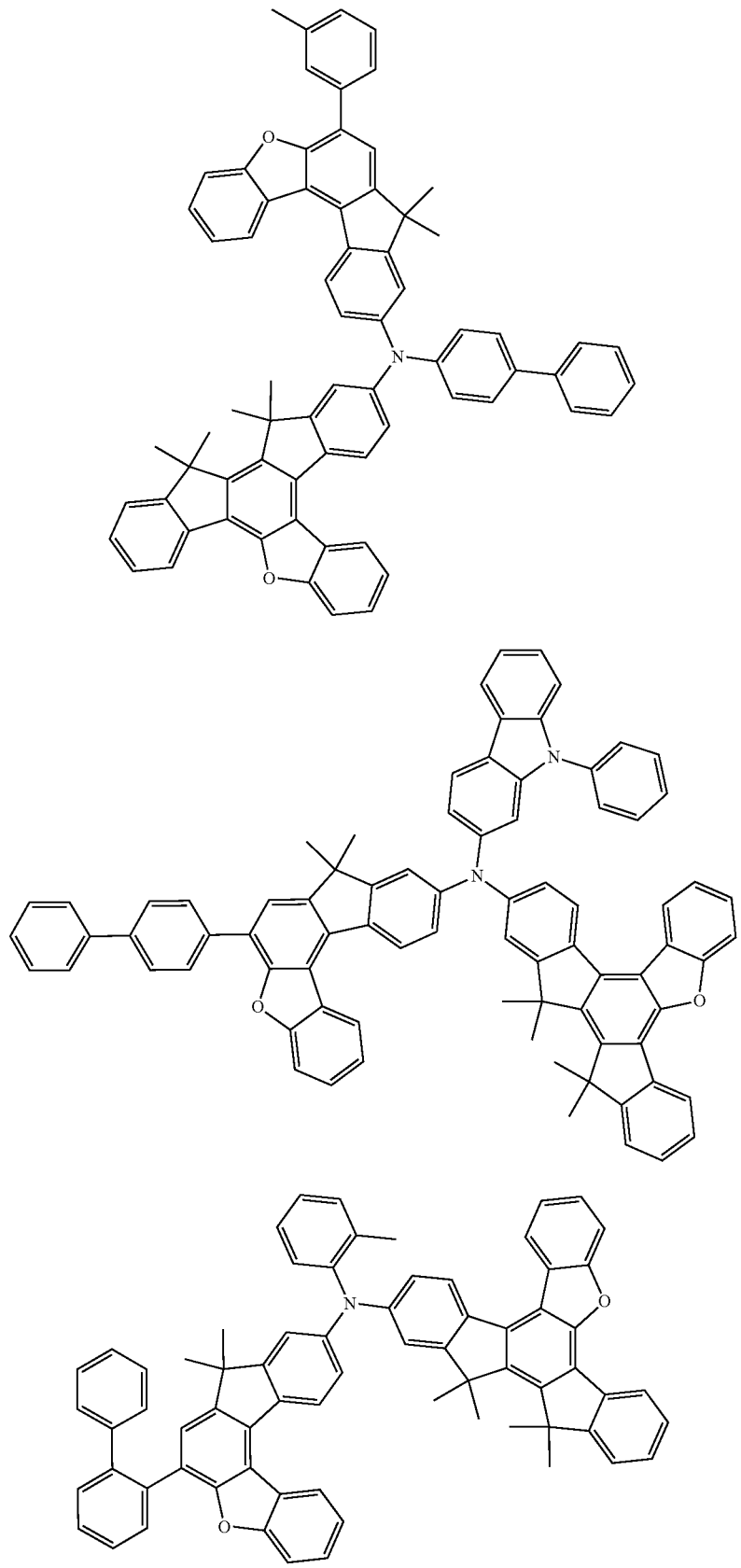

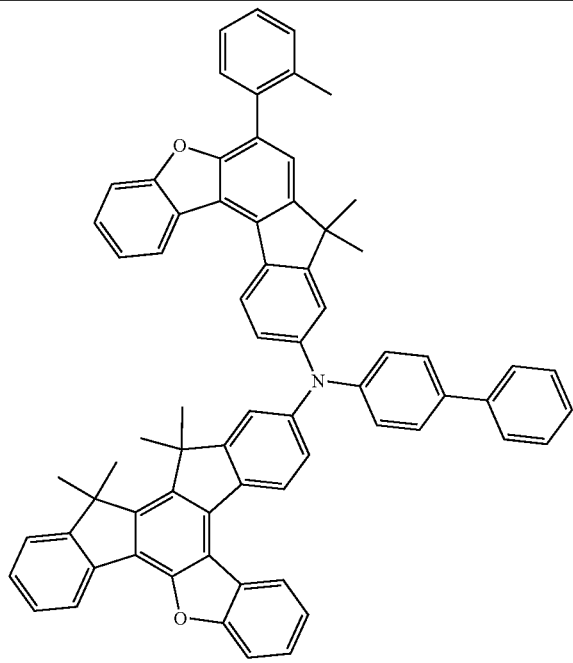
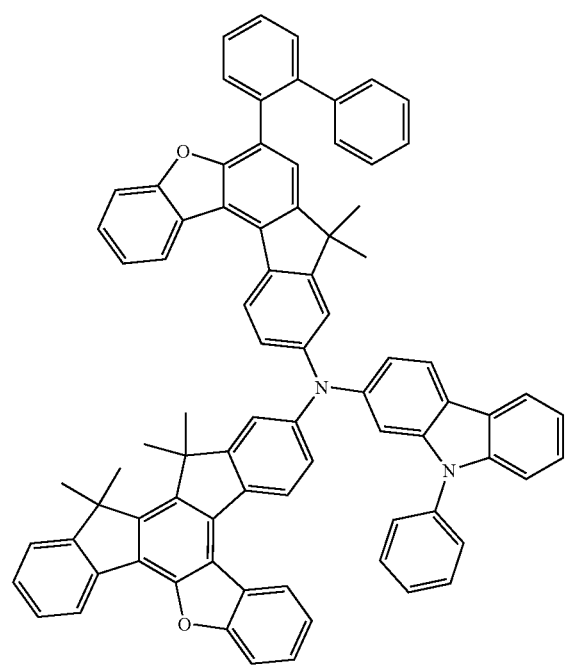 [SMILES: CC1(C)c2cc(N(c3ccc4c(c3)C(C)(C)c3c5c(c6oc7ccccc7c6c3-4)-c3ccccc3C5(C)C)c3ccc4c5ccccc5n(-c5ccccc5)c4c3)ccc2-c2c1cc(-c1ccccc1-c1ccccc1)c1oc3ccccc3c21]

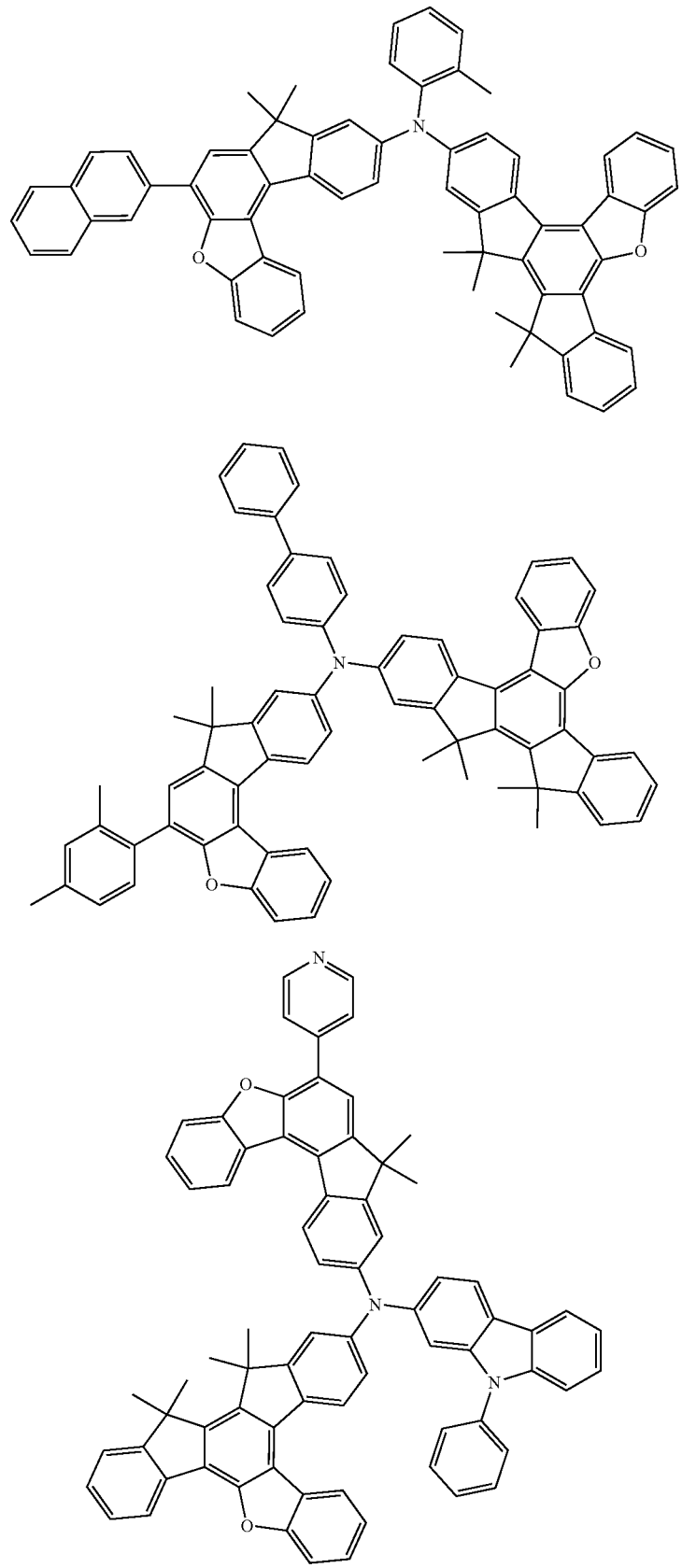

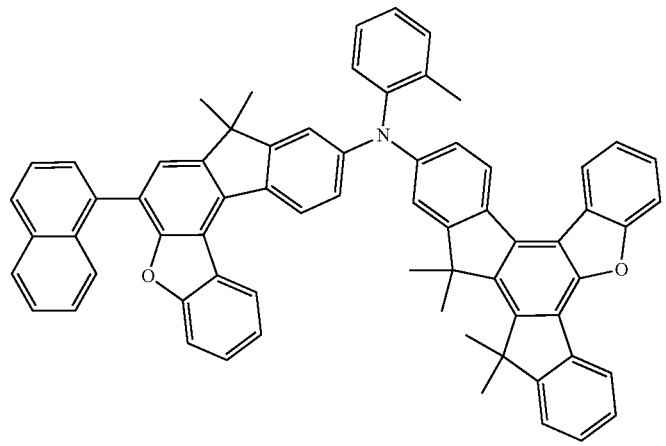 [SMILES: Cc1ccccc1N(c1ccc2c(c1)C(C)(C)c1cc(-c3cccc4ccccc34)c3oc4ccccc4c3c1-2)c1ccc2c(c1)C(C)(C)c1c3c(c4oc5ccccc5c4c1-2)-c1ccccc1C3(C)C]
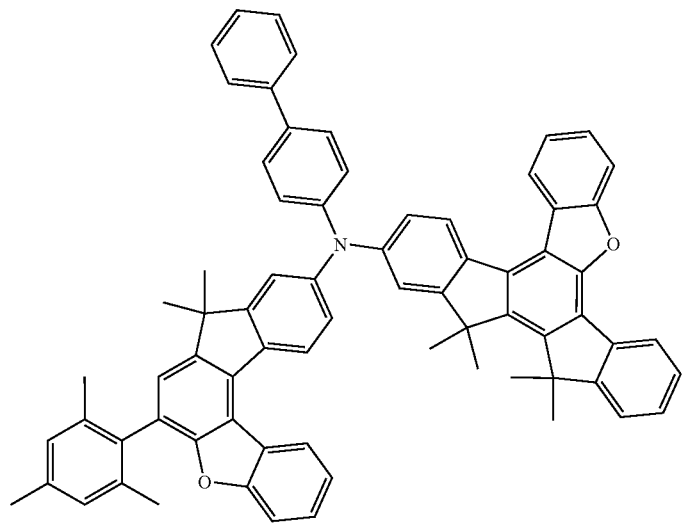 [SMILES: Cc1cc(C)c(-c2cc3c(c4c2oc2ccccc24)-c2ccc(N(c4ccc(-c5ccccc5)cc4)c4ccc5c(c4)C(C)(C)c4c6c(c7oc8ccccc8c7c4-5)-c4ccccc4C6(C)C)cc2C3(C)C)c(C)c1]
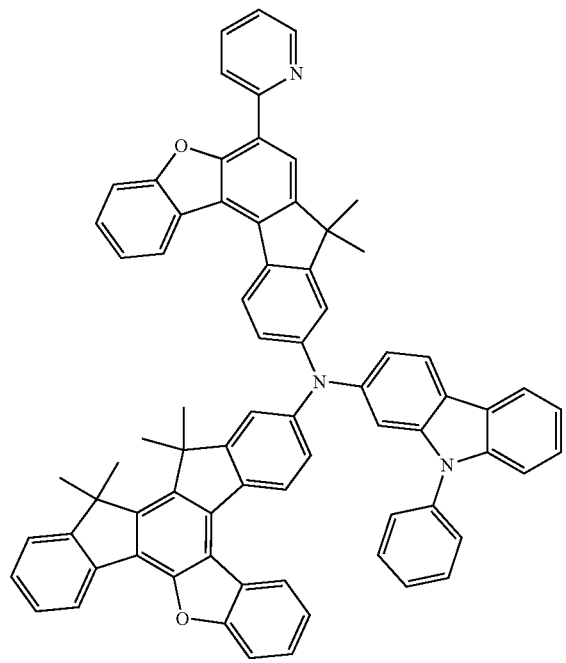 [SMILES: CC1(C)c2cc(N(c3ccc4c(c3)C(C)(C)c3c5c(c6oc7ccccc7c6c3-4)-c3ccccc3C5(C)C)c3ccc4c5ccccc5n(-c5ccccc5)c4c3)ccc2-c2c1cc(-c1ccccn1)c1oc3ccccc3c21]

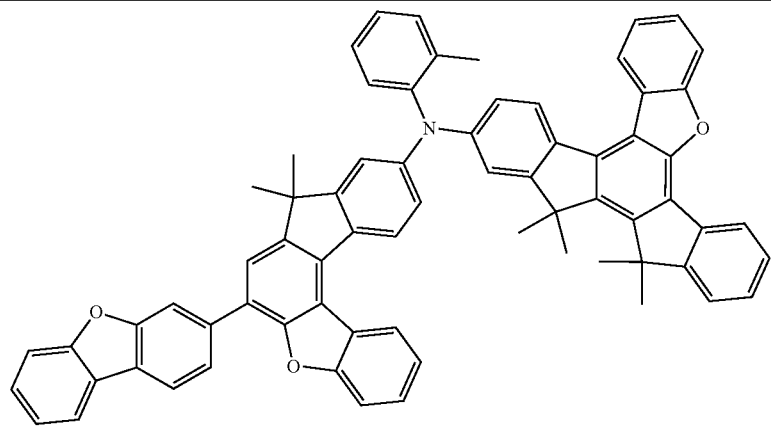
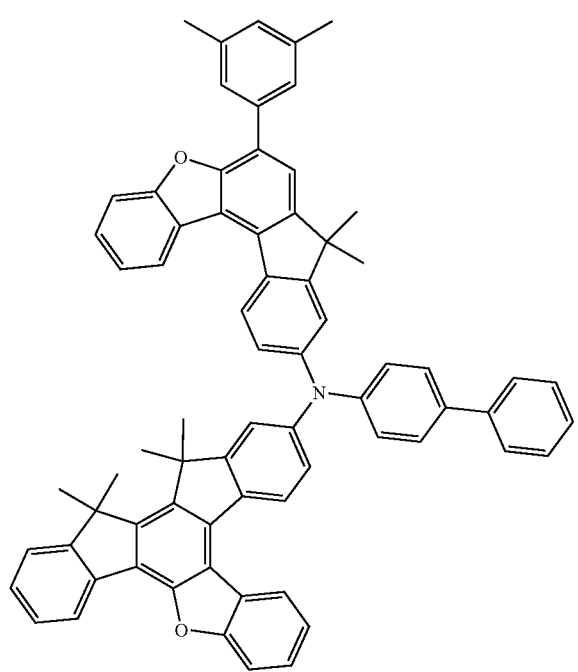 [SMILES: Cc1cc(C)cc(-c2cc3c(c4c2oc2ccccc24)-c2ccc(N(c4ccc(-c5ccccc5)cc4)c4ccc5c(c4)C(C)(C)c4c6c(c7oc8ccccc8c7c4-5)-c4ccccc4C6(C)C)cc2C3(C)C)c1]

-continued
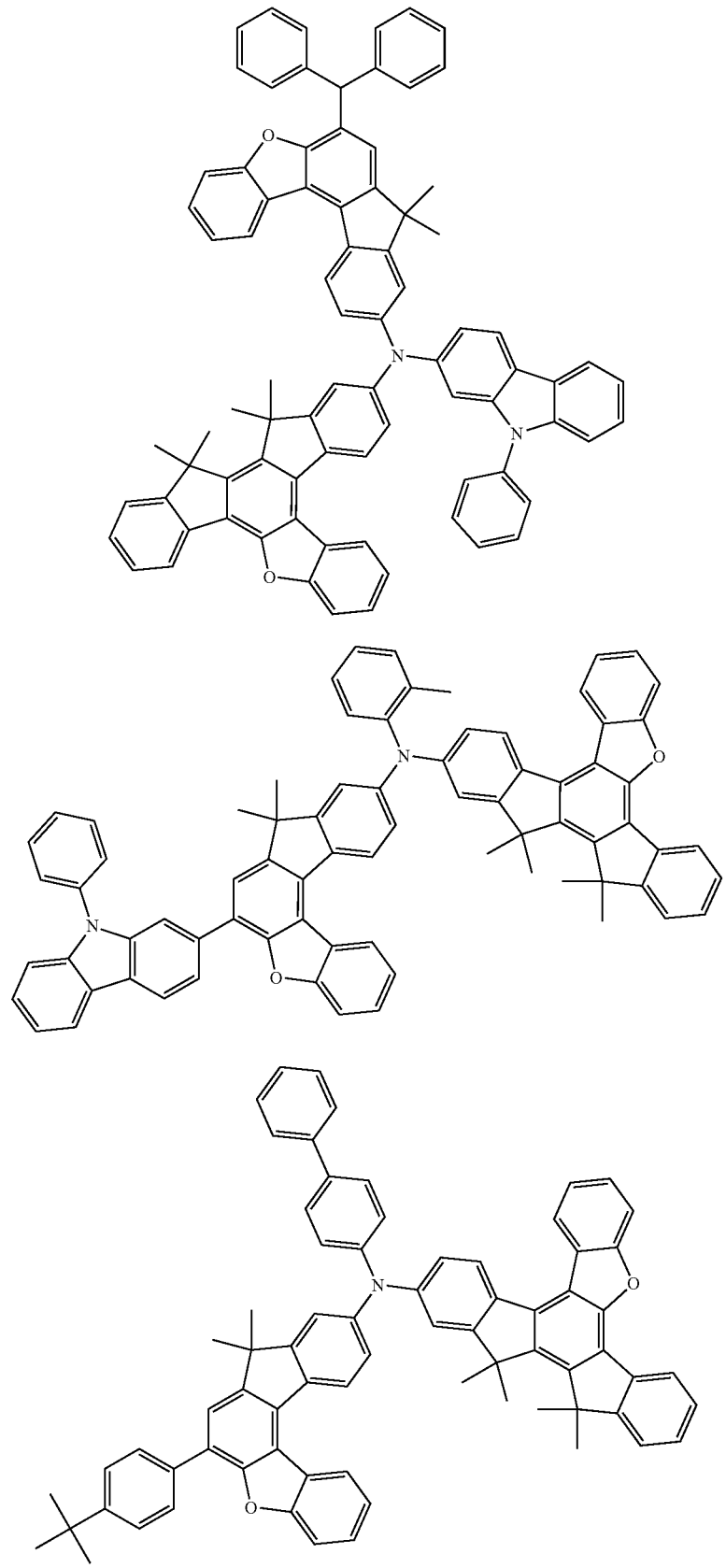

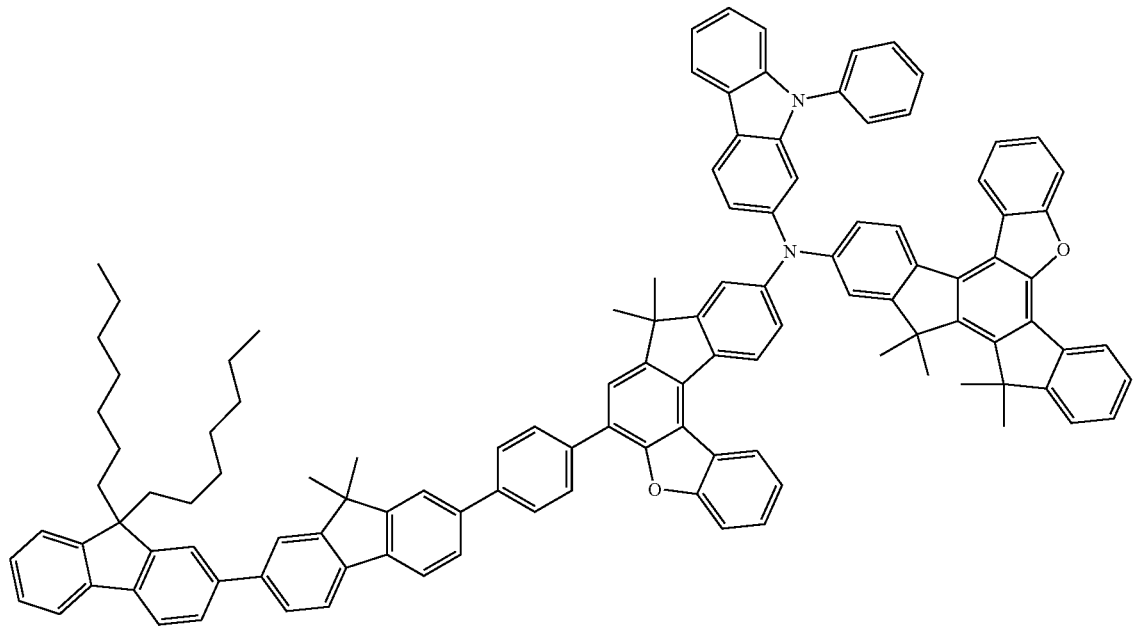 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8ccc9c%10ccccc%10n(-c%10ccccc%10)c9c8)cc6C7(C)C)cc5)ccc3-4)cc21]
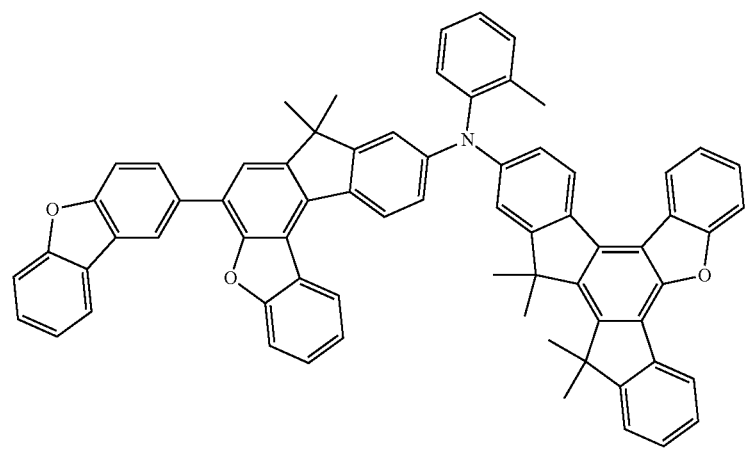 [SMILES: Cc1ccccc1N(c1ccc2c(c1)C(C)(C)c1cc(-c3ccc4oc5ccccc5c4c3)c3oc4ccccc4c3c1-2)c1ccc2c(c1)C(C)(C)c1c3c(c4oc5ccccc5c4c1-2)-c1ccccc1C3(C)C]

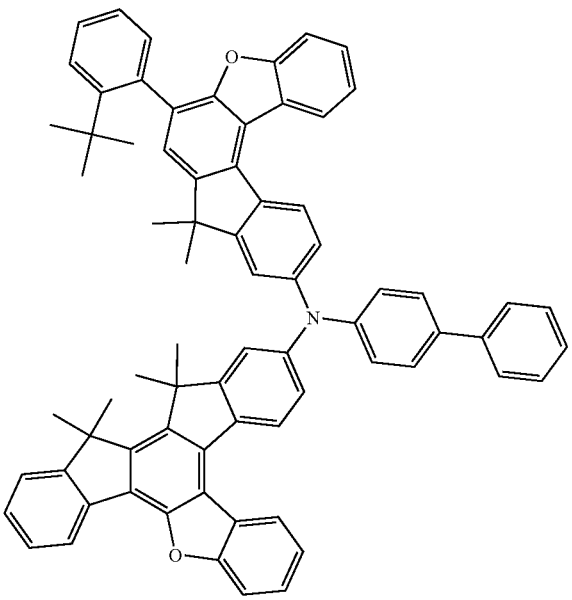 [SMILES: CC(C)(C)c1ccccc1-c1cc2c(c3c1oc1ccccc13)-c1ccc(N(c3ccc(-c4ccccc4)cc3)c3ccc4c(c3)C(C)(C)c3c5c(c6oc7ccccc7c6c3-4)-c3ccccc3C5(C)C)cc1C2(C)C]
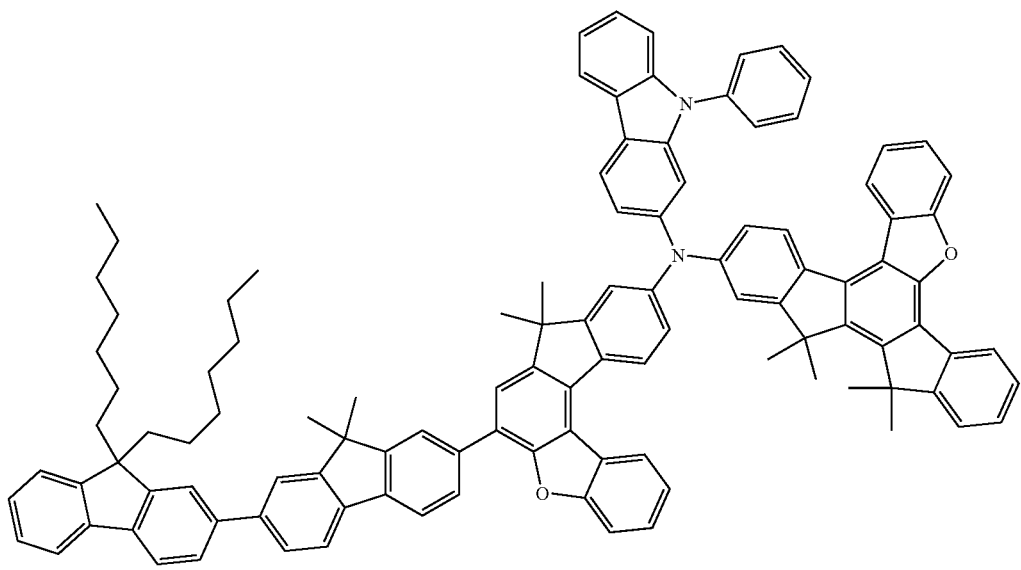 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7ccc8c9ccccc9n(-c9ccccc9)c8c7)cc5C6(C)C)ccc3-4)cc21]
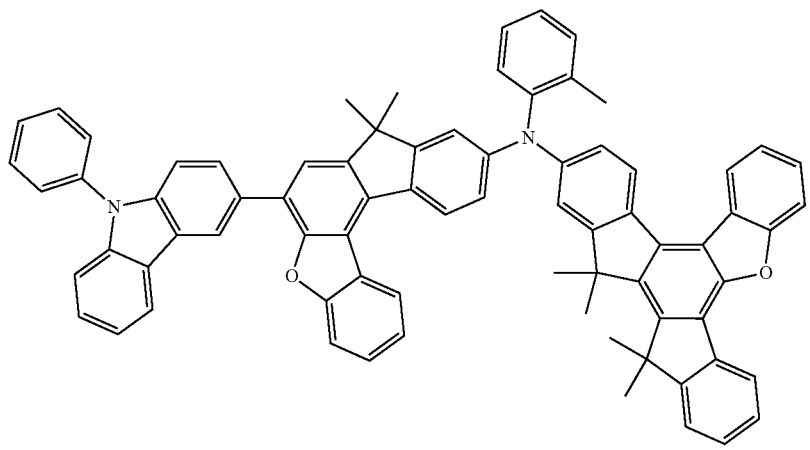 [SMILES: Cc1ccccc1N(c1ccc2c(c1)C(C)(C)c1cc(-c3ccc4c(c3)c3ccccc3n4-c3ccccc3)c3oc4ccccc4c3c1-2)c1ccc2c(c1)C(C)(C)c1c3c(c4oc5ccccc5c4c1-2)-c1ccccc1C3(C)C]

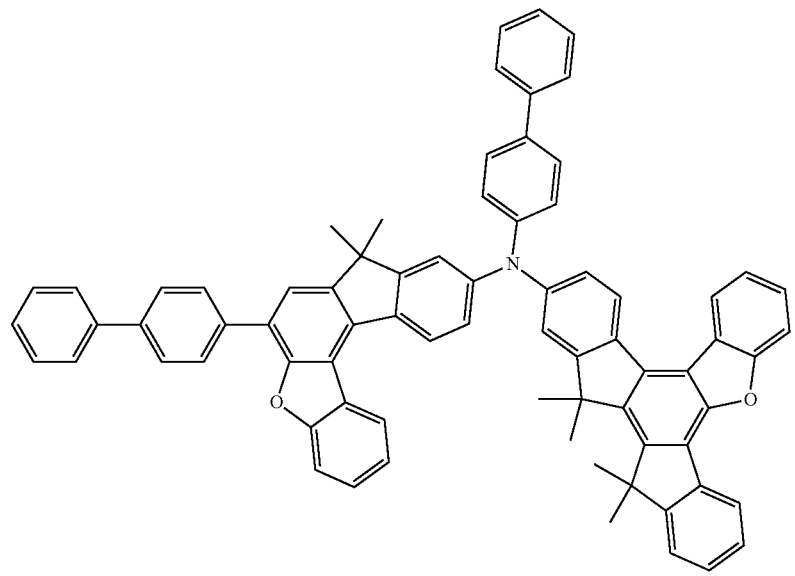 [SMILES: CC1(C)c2cc(N(c3ccc(-c4ccccc4)cc3)c3ccc4c(c3)C(C)(C)c3c5c(c6oc7ccccc7c6c3-4)-c3ccccc3C5(C)C)ccc2-c2c1cc(-c1ccc(-c3ccccc3)cc1)c1oc3ccccc3c21]
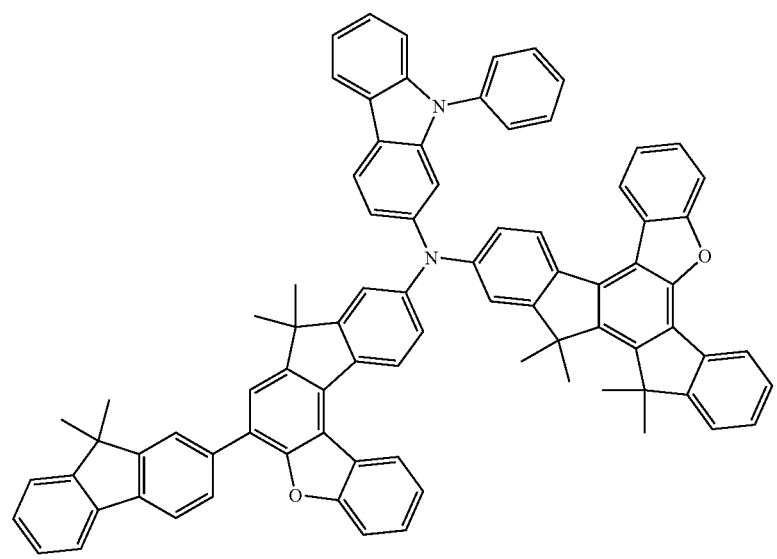 [SMILES: CC1(C)c2ccccc2-c2ccc(-c3cc4c(c5c3oc3ccccc35)-c3ccc(N(c5ccc6c(c5)C(C)(C)c5c7c(c8oc9ccccc9c8c5-6)-c5ccccc5C7(C)C)c5ccc6c7ccccc7n(-c7ccccc7)c6c5)cc3C4(C)C)cc21]
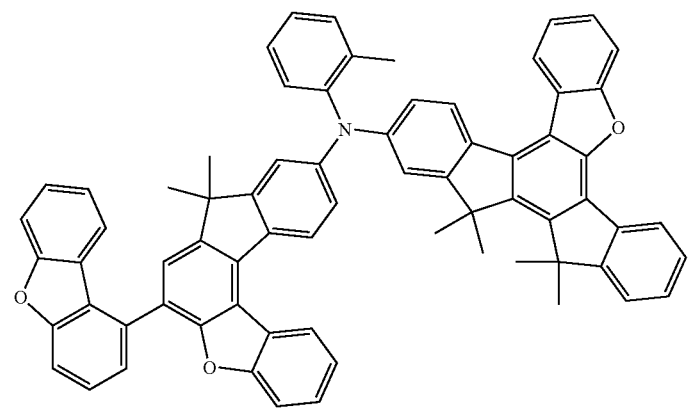 [SMILES: Cc1ccccc1N(c1ccc2c(c1)C(C)(C)c1cc(-c3cccc4oc5ccccc5c34)c3oc4ccccc4c3c1-2)c1ccc2c(c1)C(C)(C)c1c3c(c4oc5ccccc5c4c1-2)-c1ccccc1C3(C)C]

-continued
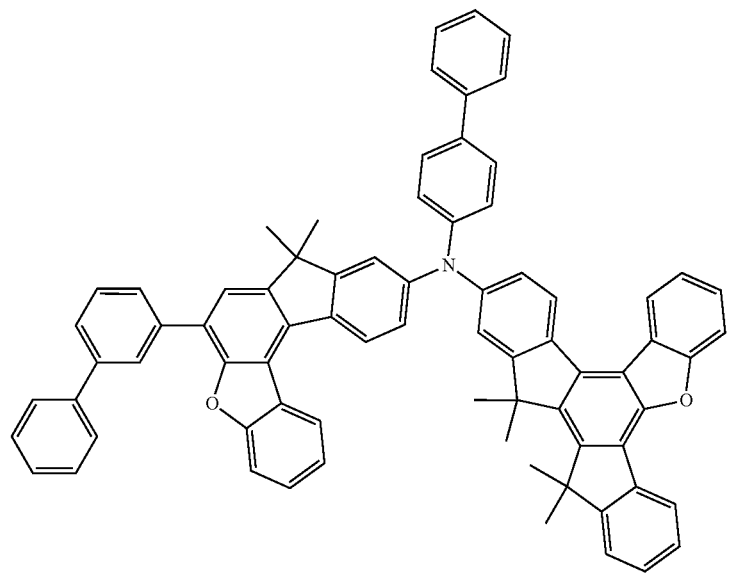 [SMILES: CC1(C)c2cc(N(c3ccc(-c4ccccc4)cc3)c3ccc4c(c3)C(C)(C)c3c5c(c6oc7ccccc7c6c3-4)-c3ccccc3C5(C)C)ccc2-c2c1cc(-c1cccc(-c3ccccc3)c1)c1oc3ccccc3c21]
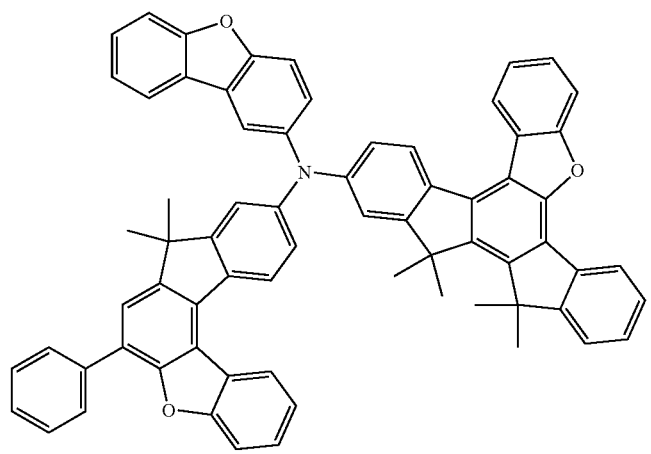 [SMILES: CC1(C)c2cc(N(c3ccc4c(c3)C(C)(C)c3c5c(c6oc7ccccc7c6c3-4)-c3ccccc3C5(C)C)c3ccc4oc5ccccc5c4c3)ccc2-c2c1cc(-c1ccccc1)c1oc3ccccc3c21]
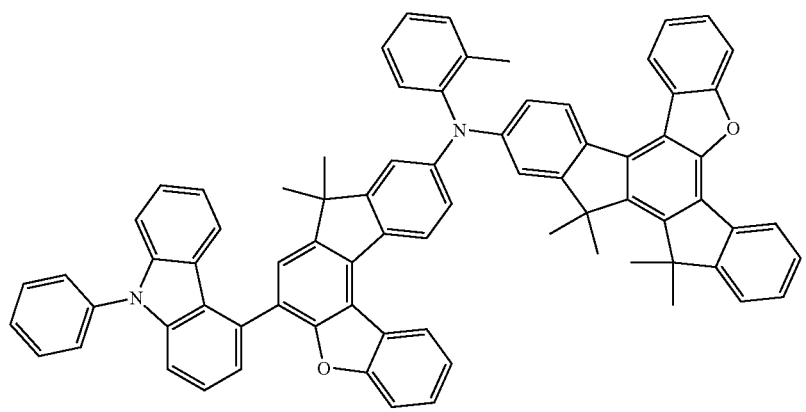 [SMILES: Cc1ccccc1N(c1ccc2c(c1)C(C)(C)c1cc(-c3cccc4c3c3ccccc3n4-c3ccccc3)c3oc4ccccc4c3c1-2)c1ccc2c(c1)C(C)(C)c1c3c(c4oc5ccccc5c4c1-2)-c1ccccc1C3(C)C]

-continued
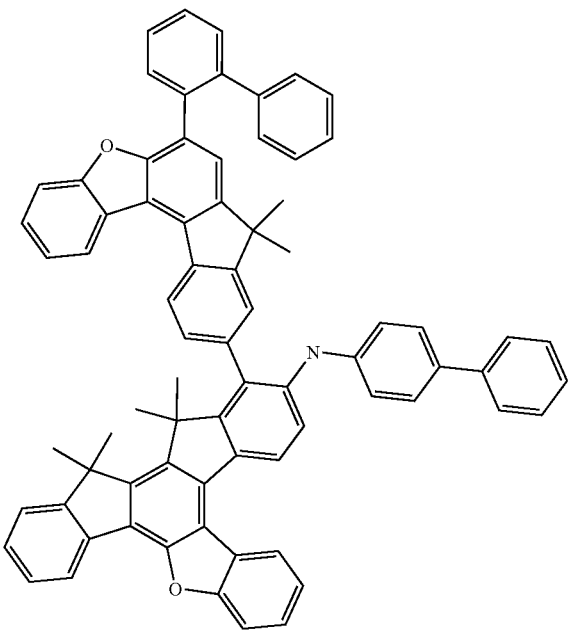 [SMILES: CC1(C)c2cc(-c3c(Nc4ccc(-c5ccccc5)cc4)ccc4c3C(C)(C)c3c5c(c6oc7ccccc7c6c3-4)-c3ccccc3C5(C)C)ccc2-c2c1cc(-c1ccccc1-c1ccccc1)c1oc3ccccc3c21]
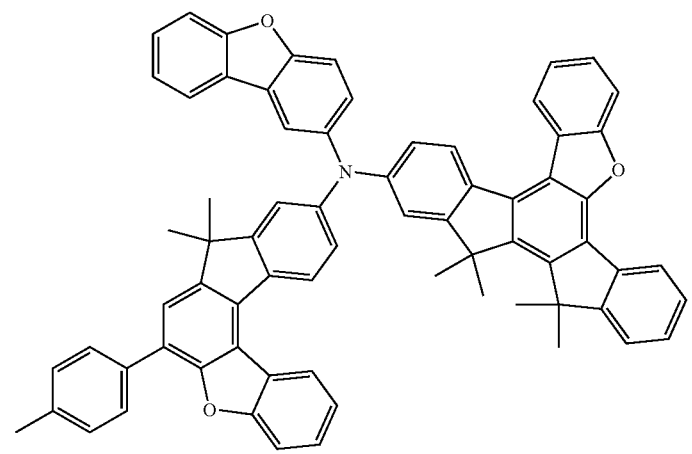 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccc5oc6ccccc6c5c4)cc2C3(C)C)cc1]
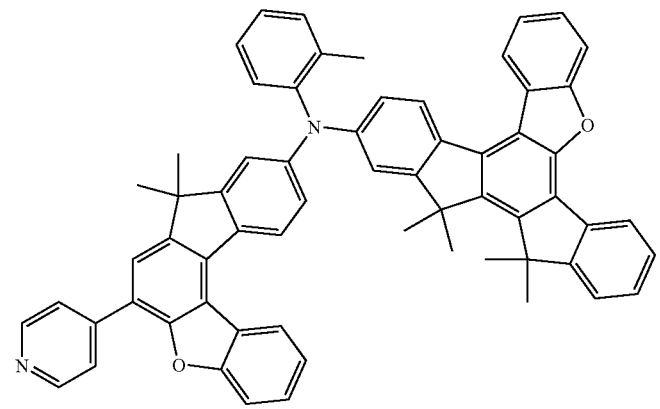 [SMILES: Cc1ccccc1N(c1ccc2c(c1)C(C)(C)c1cc(-c3ccncc3)c3oc4ccccc4c3c1-2)c1ccc2c(c1)C(C)(C)c1c3c(c4oc5ccccc5c4c1-2)-c1ccccc1C3(C)C]

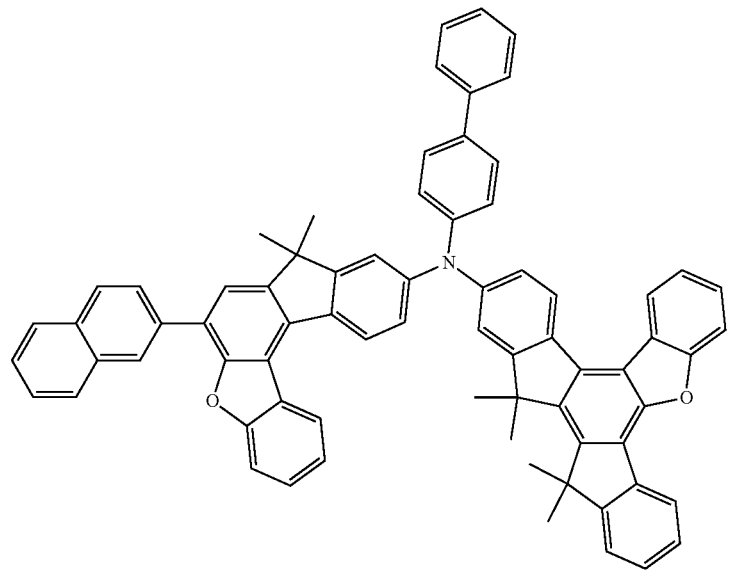 [SMILES: CC1(C)c2cc(N(c3ccc(-c4ccccc4)cc3)c3ccc4c(c3)C(C)(C)c3c5c(c6oc7ccccc7c6c3-4)-c3ccccc3C5(C)C)ccc2-c2c1cc(-c1ccc3ccccc3c1)c1oc3ccccc3c21]
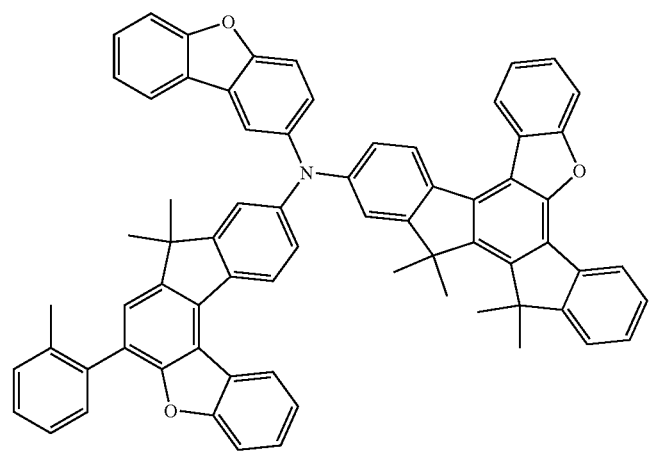 [SMILES: Cc1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3ccc4oc5ccccc5c4c3)cc1C2(C)C]
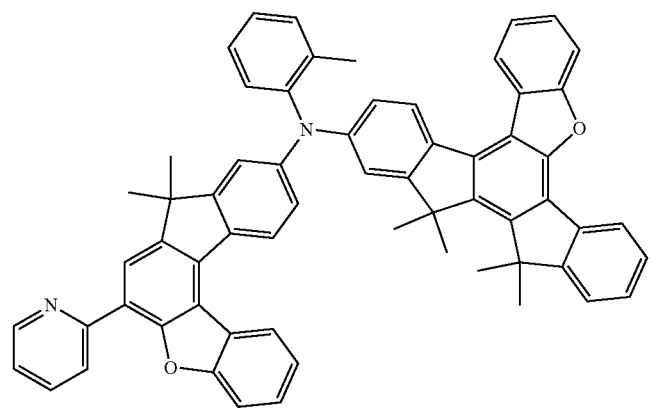 [SMILES: Cc1ccccc1N(c1ccc2c(c1)C(C)(C)c1cc(-c3ccccn3)c3oc4ccccc4c3c1-2)c1ccc2c(c1)C(C)(C)c1c3c(c4oc5ccccc5c4c1-2)-c1ccccc1C3(C)C]

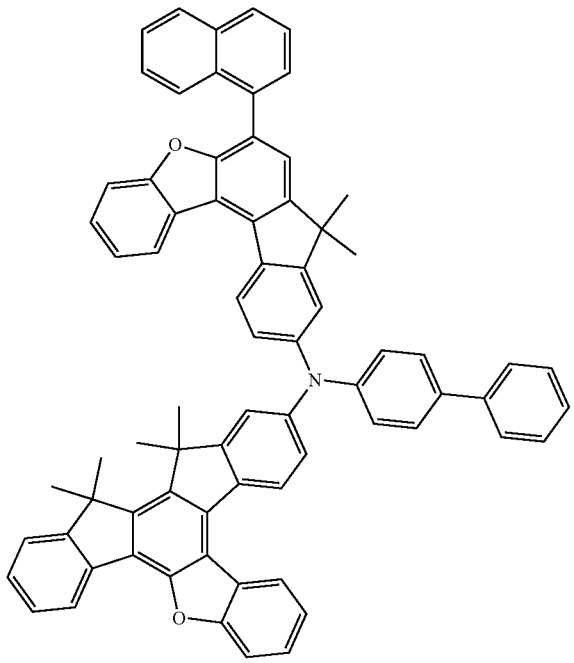 [SMILES: CC1(C)c2cc(N(c3ccc(-c4ccccc4)cc3)c3ccc4c(c3)C(C)(C)c3c5c(c6oc7ccccc7c6c3-4)-c3ccccc3C5(C)C)ccc2-c2c1cc(-c1cccc3ccccc13)c1oc3ccccc3c21]
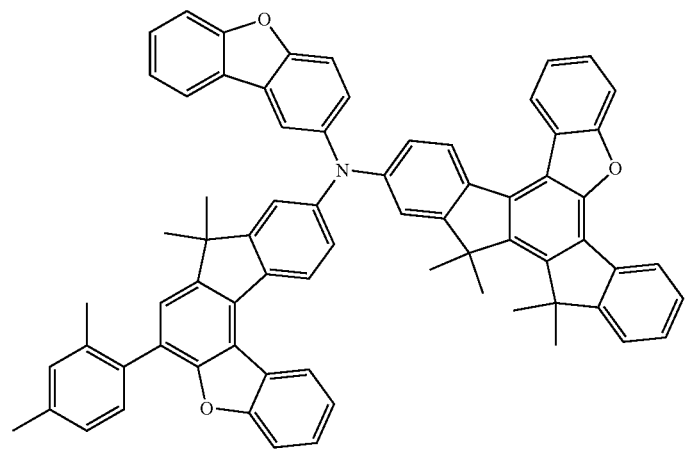 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccc5oc6ccccc6c5c4)cc2C3(C)C)c(C)c1]
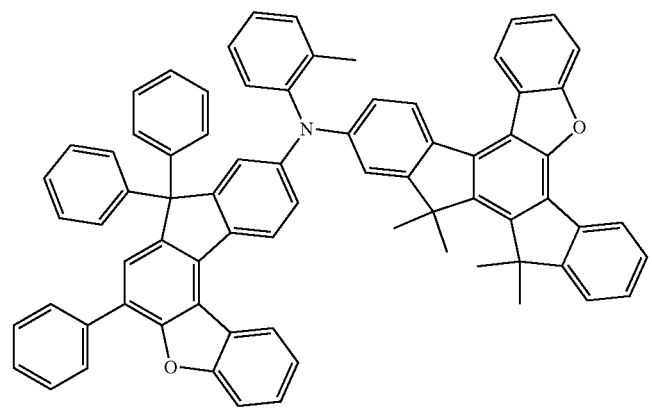 [SMILES: Cc1ccccc1N(c1ccc2c(c1)C(C)(C)c1c3c(c4oc5ccccc5c4c1-2)-c1ccccc1C3(C)C)c1ccc2c(c1)C(c1ccccc1)(c1ccccc1)c1cc(-c3ccccc3)c3oc4ccccc4c3c1-2]

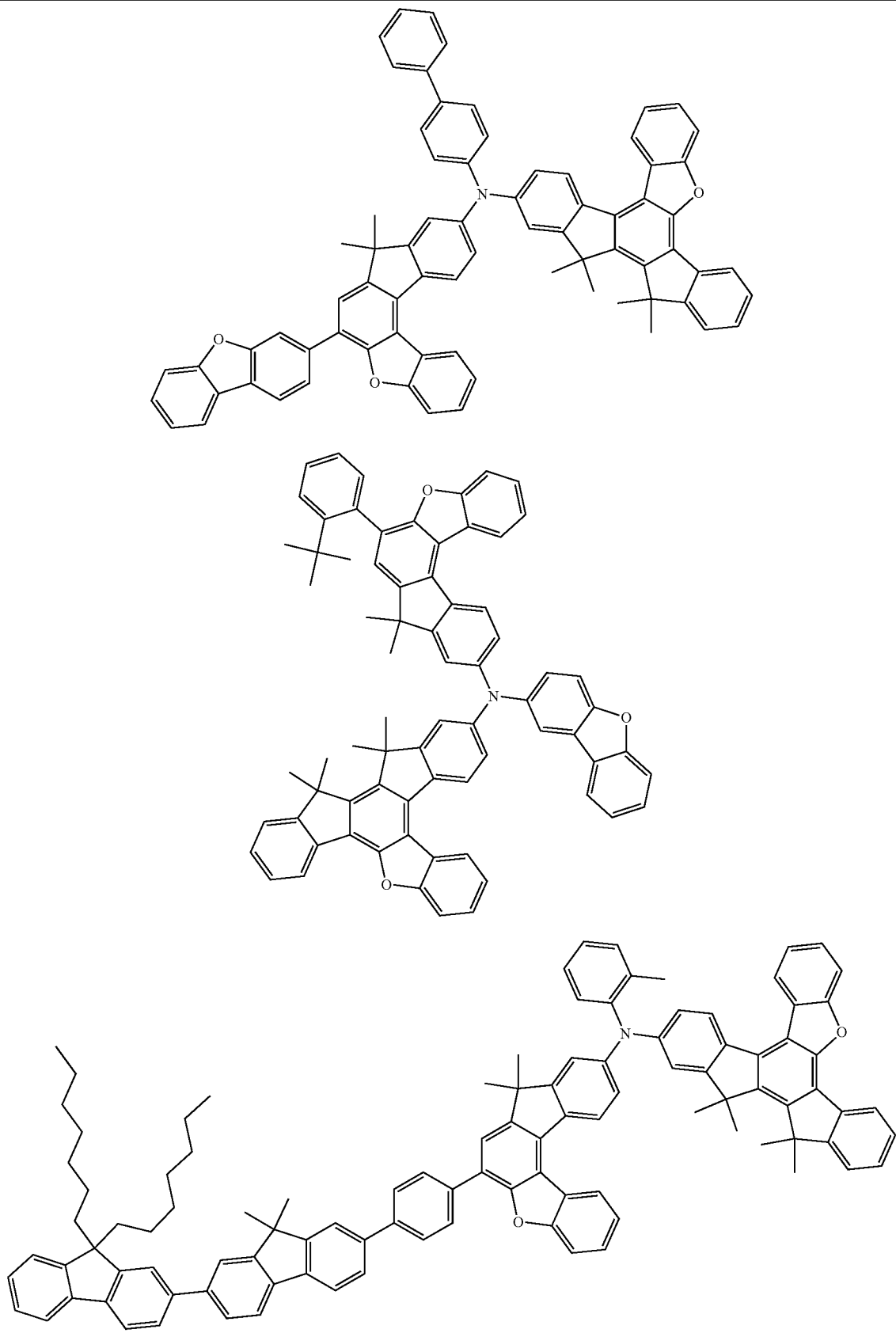

-continued
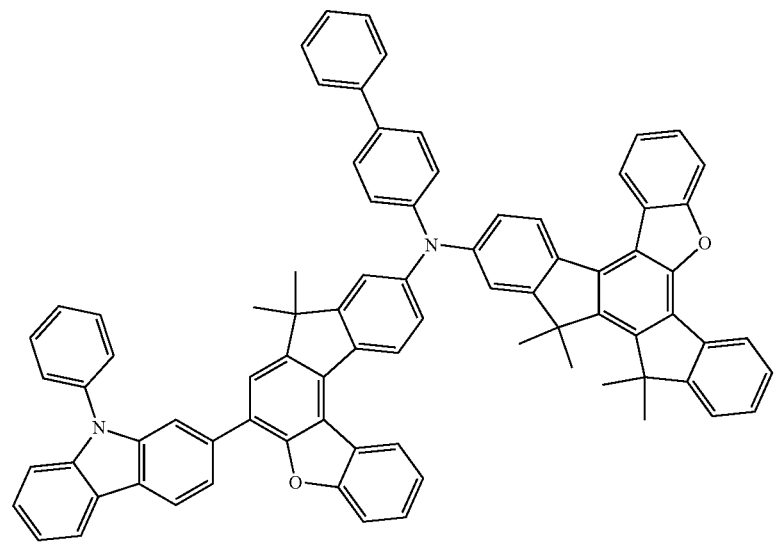 [SMILES: CC1(C)c2cc(N(c3ccc(-c4ccccc4)cc3)c3ccc4c(c3)C(C)(C)c3c5c(c6oc7ccccc7c6c3-4)-c3ccccc3C5(C)C)ccc2-c2c1cc(-c1ccc3c4ccccc4n(-c4ccccc4)c3c1)c1oc3ccccc3c21]
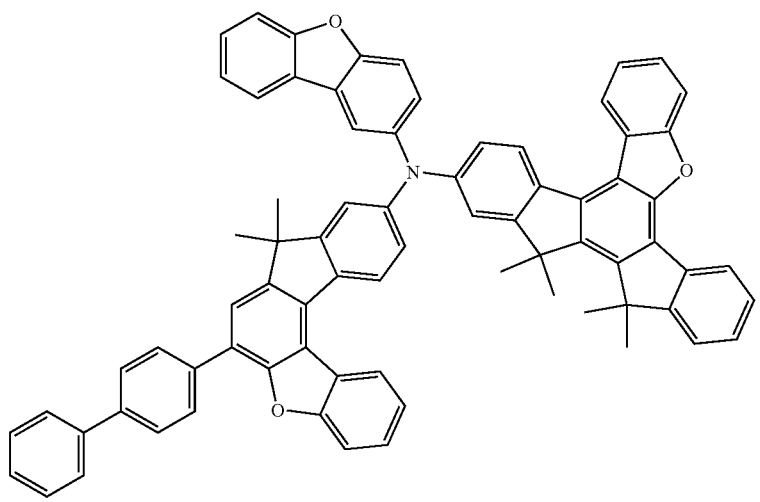 [SMILES: CC1(C)c2cc(N(c3ccc4c(c3)C(C)(C)c3c5c(c6oc7ccccc7c6c3-4)-c3ccccc3C5(C)C)c3ccc4oc5ccccc5c4c3)ccc2-c2c1cc(-c1ccc(-c3ccccc3)cc1)c1oc3ccccc3c21]
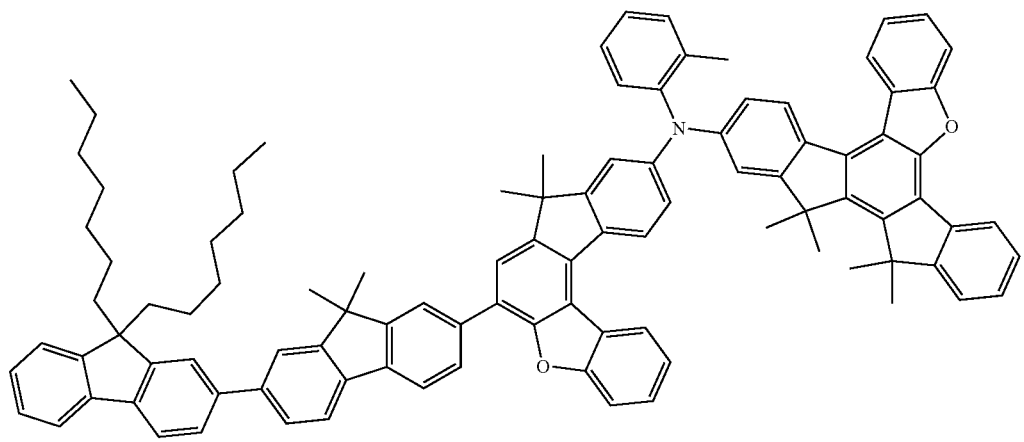 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7ccccc7C)cc5C6(C)C)ccc3-4)cc21]

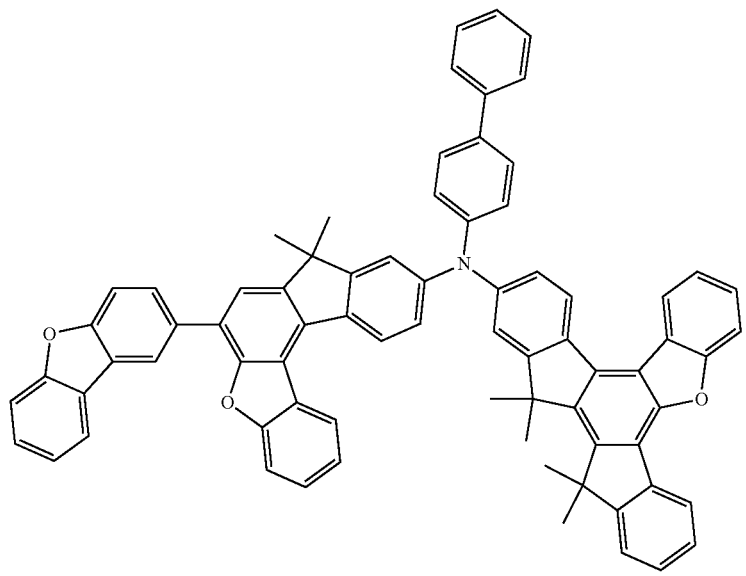 [SMILES: CC1(C)c2cc(N(c3ccc(-c4ccccc4)cc3)c3ccc4c(c3)C(C)(C)c3c5c(c6oc7ccccc7c6c3-4)-c3ccccc3C5(C)C)ccc2-c2c1cc(-c1ccc3oc4ccccc4c3c1)c1oc3ccccc3c21]
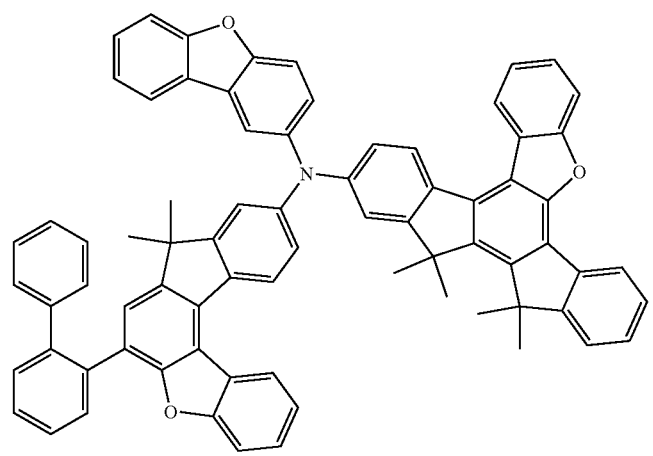 [SMILES: CC1(C)c2cc(N(c3ccc4c(c3)C(C)(C)c3c5c(c6oc7ccccc7c6c3-4)-c3ccccc3C5(C)C)c3ccc4oc5ccccc5c4c3)ccc2-c2c1cc(-c1ccccc1-c1ccccc1)c1oc3ccccc3c21]
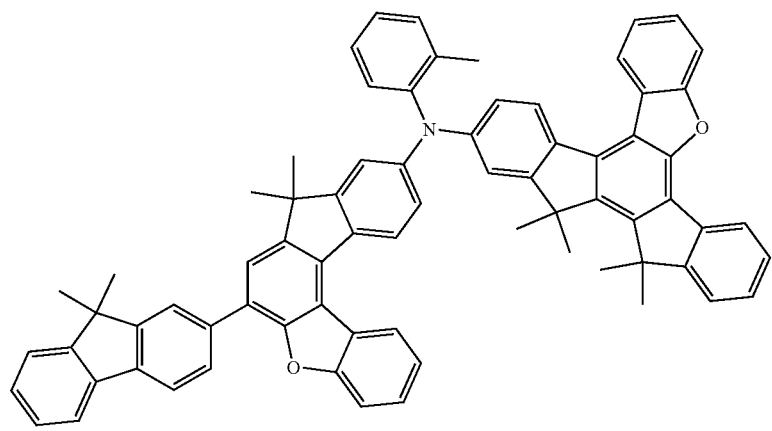 [SMILES: Cc1ccccc1N(c1ccc2c(c1)C(C)(C)c1cc(-c3ccc4c(c3)C(C)(C)c3ccccc3-4)c3oc4ccccc4c3c1-2)c1ccc2c(c1)C(C)(C)c1c3c(c4oc5ccccc5c4c1-2)-c1ccccc1C3(C)C]

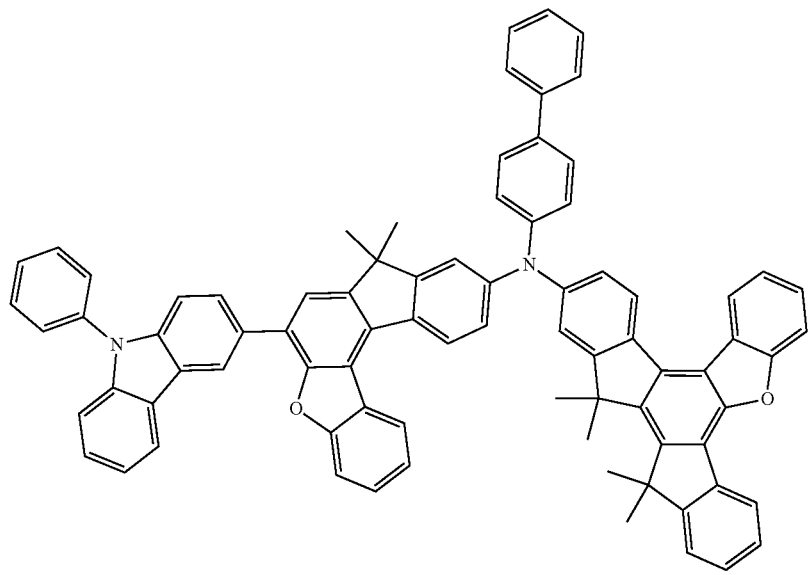 [SMILES: CC1(C)c2cc(N(c3ccc(-c4ccccc4)cc3)c3ccc4c(c3)C(C)(C)c3c5c(c6oc7ccccc7c6c3-4)-c3ccccc3C5(C)C)ccc2-c2c1cc(-c1ccc3c(c1)c1ccccc1n3-c1ccccc1)c1oc3ccccc3c21]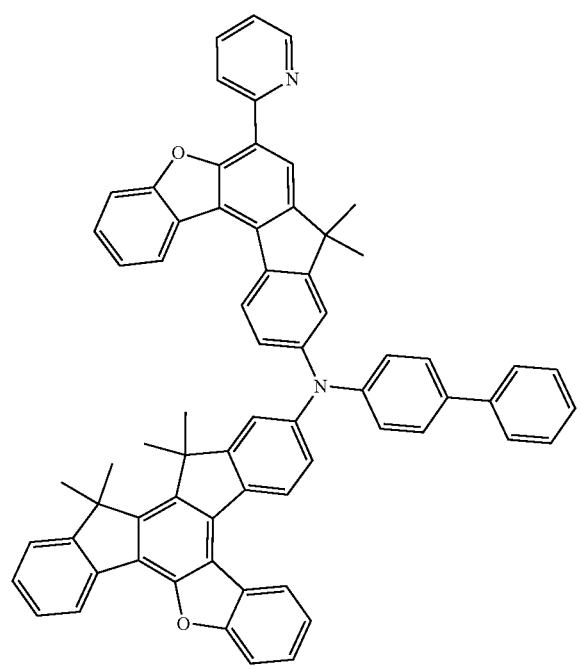 [SMILES: CC1(C)c2cc(N(c3ccc(-c4ccccc4)cc3)c3ccc4c(c3)C(C)(C)c3c5c(c6oc7ccccc7c6c3-4)-c3ccccc3C5(C)C)ccc2-c2c1cc(-c1ccccn1)c1oc3ccccc3c21]

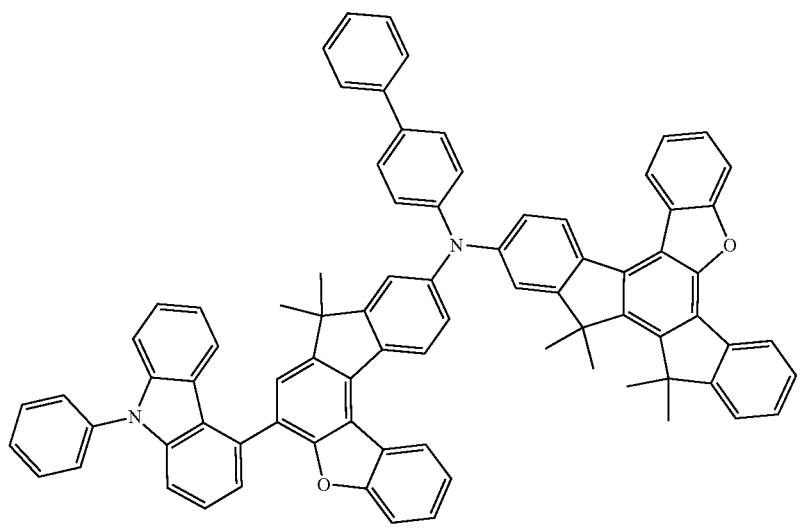 [SMILES: CC1(C)c2cc(N(c3ccc(-c4ccccc4)cc3)c3ccc4c(c3)C(C)(C)c3c5c(c6oc7ccccc7c6c3-4)-c3ccccc3C5(C)C)ccc2-c2c1cc(-c1cccc3c1c1ccccc1n3-c1ccccc1)c1oc3ccccc3c21]
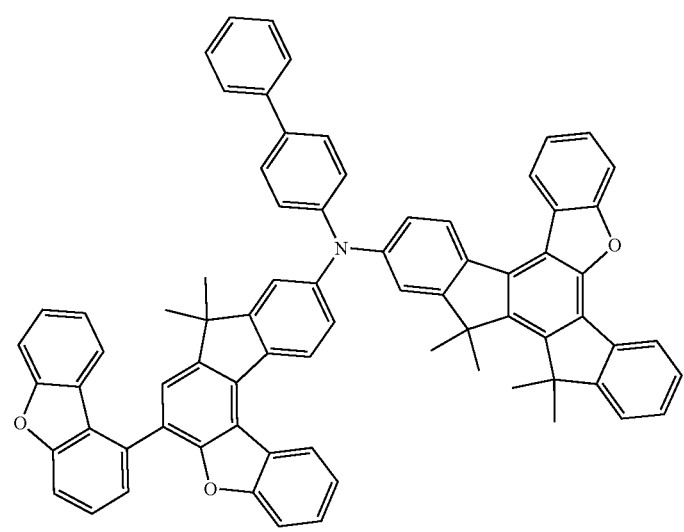 [SMILES: CC1(C)c2cc(N(c3ccc(-c4ccccc4)cc3)c3ccc4c(c3)C(C)(C)c3c5c(c6oc7ccccc7c6c3-4)-c3ccccc3C5(C)C)ccc2-c2c1cc(-c1cccc3oc4ccccc4c13)c1oc3ccccc3c21]

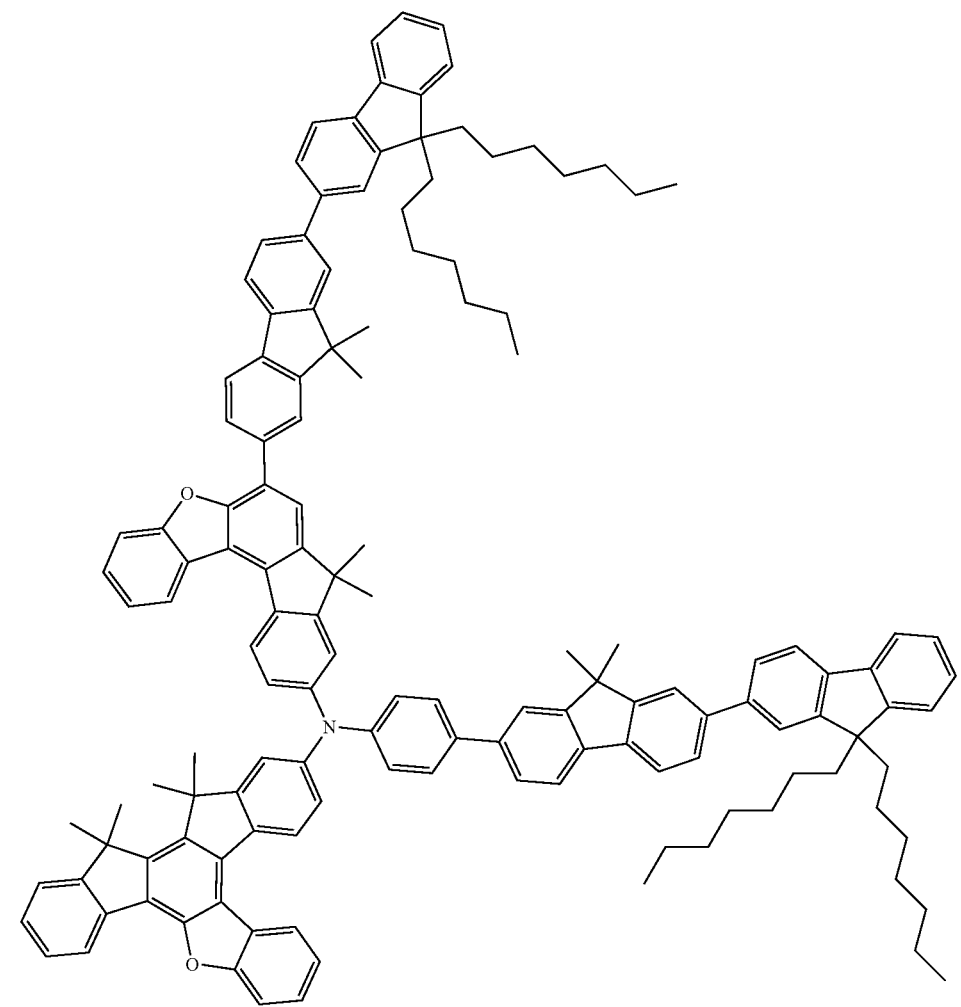 [SMILES: CCCCCCCC1(CCCCCCC)c2ccccc2-c2ccc(-c3ccc4c(c3)C(C)(C)c3cc(-c5ccc(N(c6ccc7c(c6)C(C)(C)c6cc(-c8ccc9c(c8)C(C)(C)c8cc(-c%10ccc%11c(c%10)C(CCCCCCC)(CCCCCCC)c%10ccccc%10-%11)ccc8-9)c8oc9ccccc9c8c6-7)c6ccc7c(c6)C(C)(C)c6c8c(c9oc%10ccccc%10c9c6-7)-c6ccccc6C8(C)C)cc5)ccc3-4)cc21]
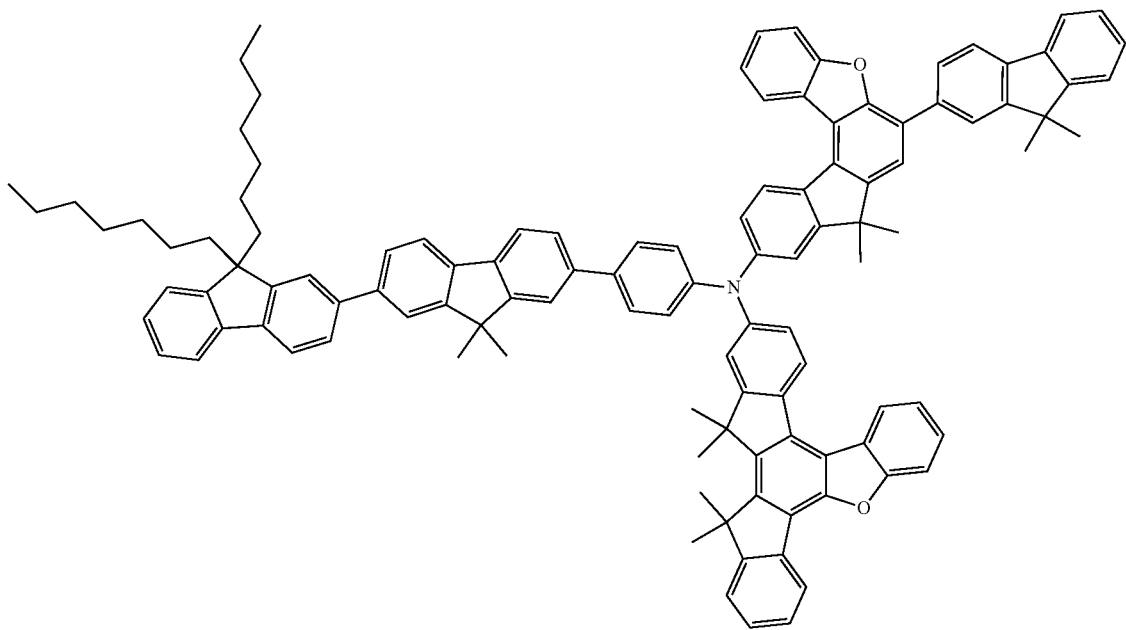 [SMILES: CCCCCCCC1(CCCCCCC)c2ccccc2-c2ccc(-c3ccc4c(c3)C(C)(C)c3cc(-c5ccc(N(c6ccc7c(c6)C(C)(C)c6cc(-c8ccc9c(c8)C(C)(C)c8ccccc8-9)c8oc9ccccc9c8c6-7)c6ccc7c(c6)C(C)(C)c6c8c(c9oc%10ccccc%10c9c6-7)-c6ccccc6C8(C)C)cc5)ccc3-4)cc21]

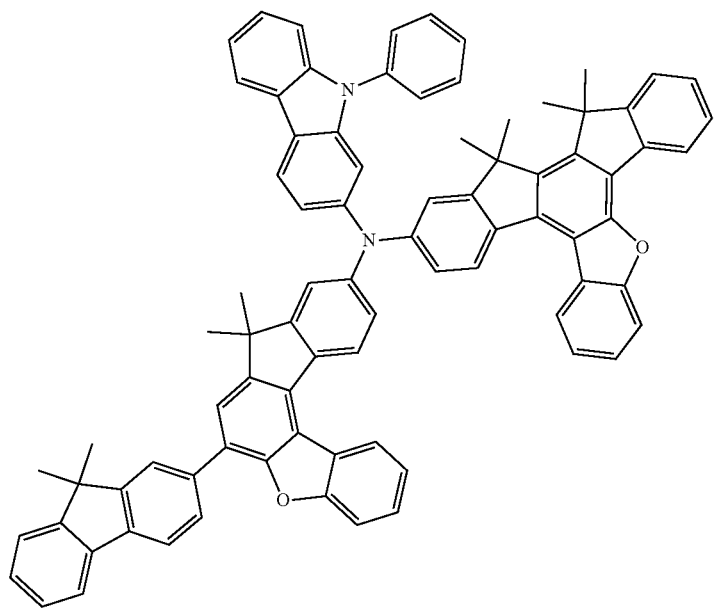 [SMILES: CC1(C)c2ccccc2-c2ccc(-c3cc4c(c5c3oc3ccccc35)-c3ccc(N(c5ccc6c(c5)C(C)(C)c5c7c(c8oc9ccccc9c8c5-6)-c5ccccc5C7(C)C)c5ccc6c7ccccc7n(-c7ccccc7)c6c5)cc3C4(C)C)cc21]
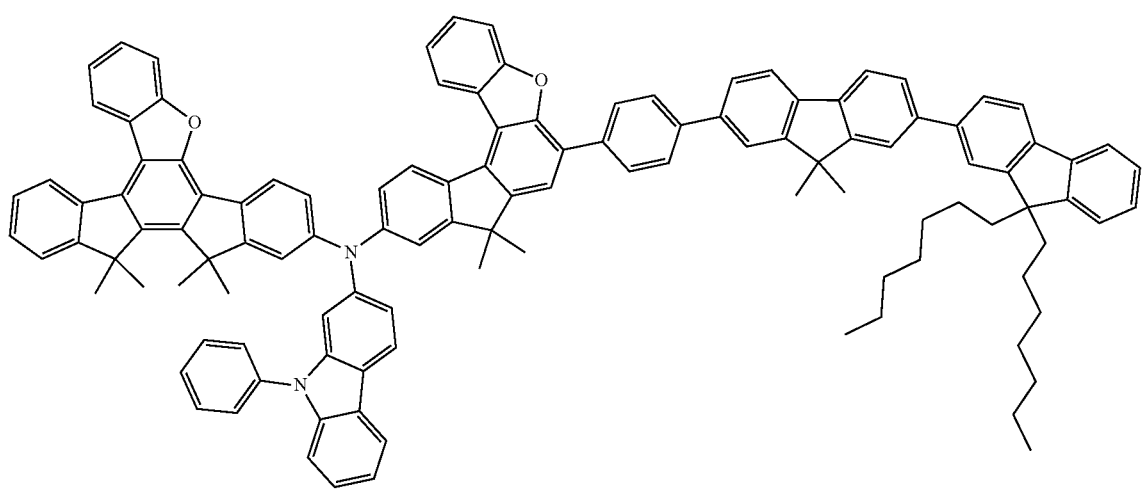 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11c(oc%12ccccc%12%11)c8-9)-c8ccccc8C%10(C)C)c8ccc9c%10ccccc%10n(-c%10ccccc%10)c9c8)cc6C7(C)C)cc5)ccc3-4)cc21]

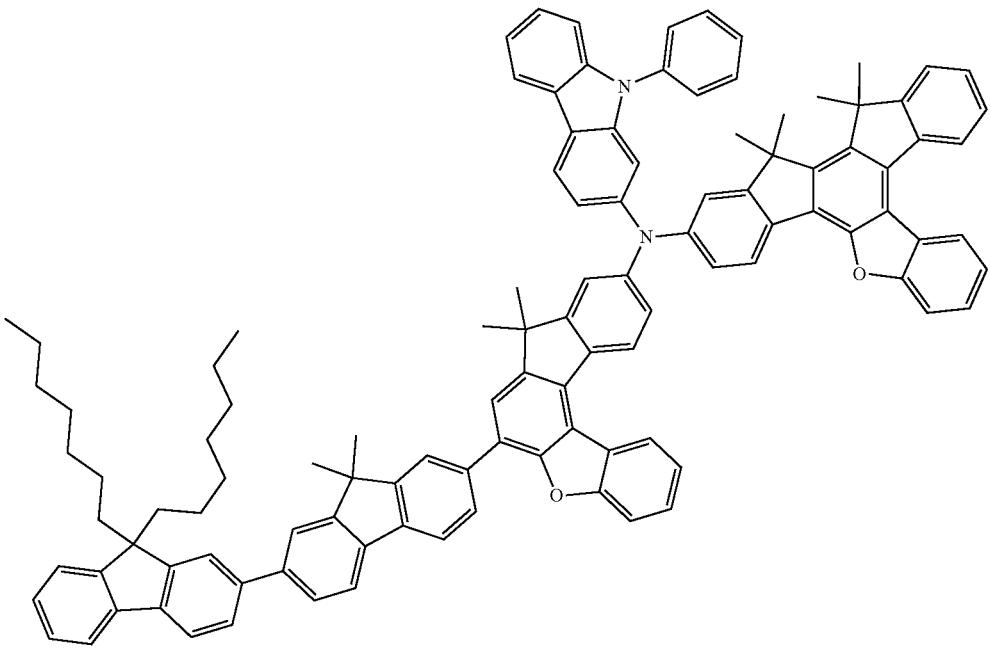 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10c(oc%11ccccc%11%10)c7-8)-c7ccccc7C9(C)C)c7ccc8c9ccccc9n(-c9ccccc9)c8c7)cc5C6(C)C)ccc3-4)cc21]
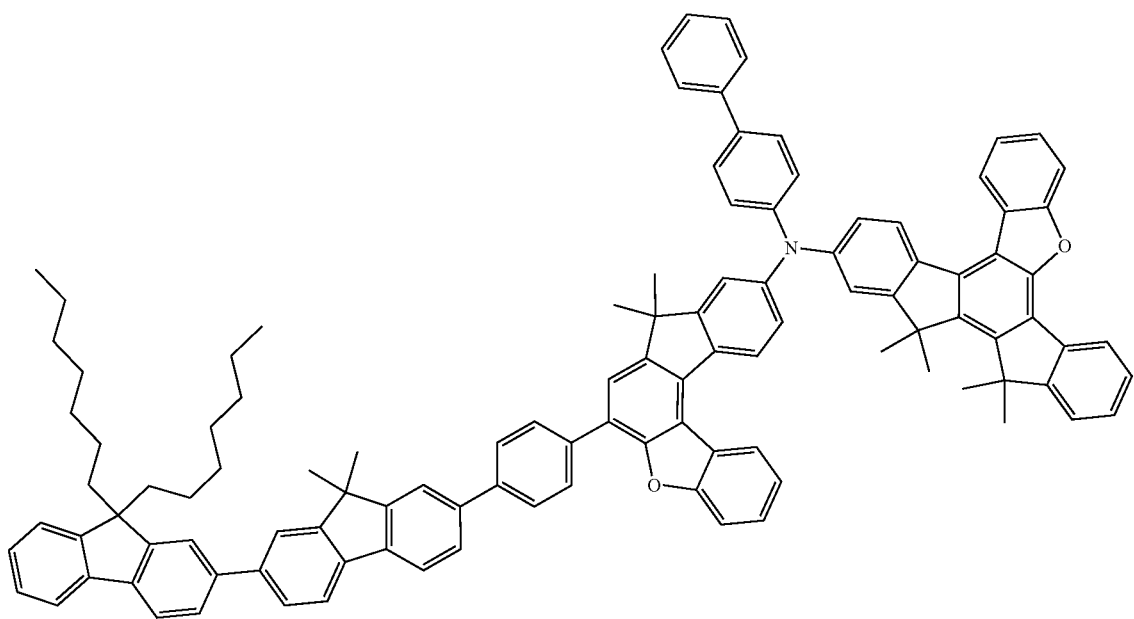 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc(-c9ccccc9)cc8)c8ccc9c(c8)C(C)(C)c8c%10c(c%11oc%12ccccc%12c%11c8-9)-c8ccccc8C%10(C)C)cc6C7(C)C)cc5)ccc3-4)cc21]

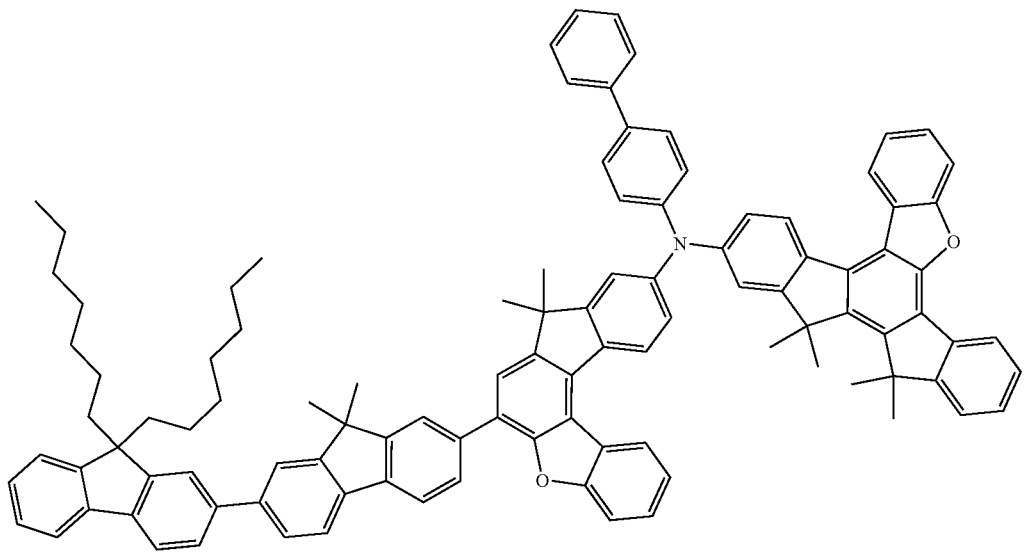 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc(-c8ccccc8)cc7)c7ccc8c(c7)C(C)(C)c7c9c(c%10oc%11ccccc%11c%10c7-8)-c7ccccc7C9(C)C)cc5C6(C)C)ccc3-4)cc21]
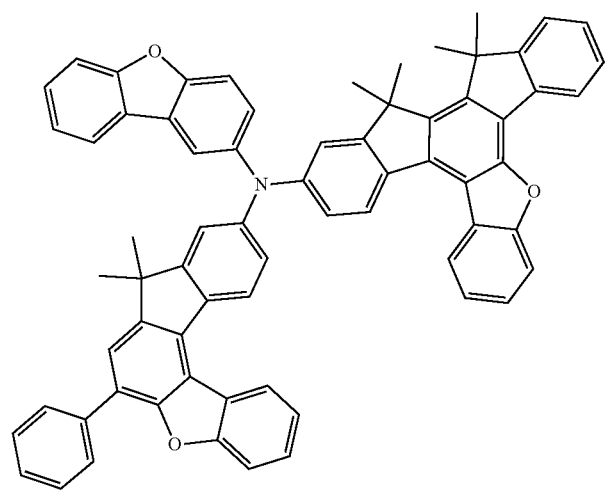 [SMILES: CC1(C)c2cc(N(c3ccc4c(c3)C(C)(C)c3c5c(c6oc7ccccc7c6c3-4)-c3ccccc3C5(C)C)c3ccc4oc5ccccc5c4c3)ccc2-c2c1cc(-c1ccccc1)c1oc3ccccc3c21]

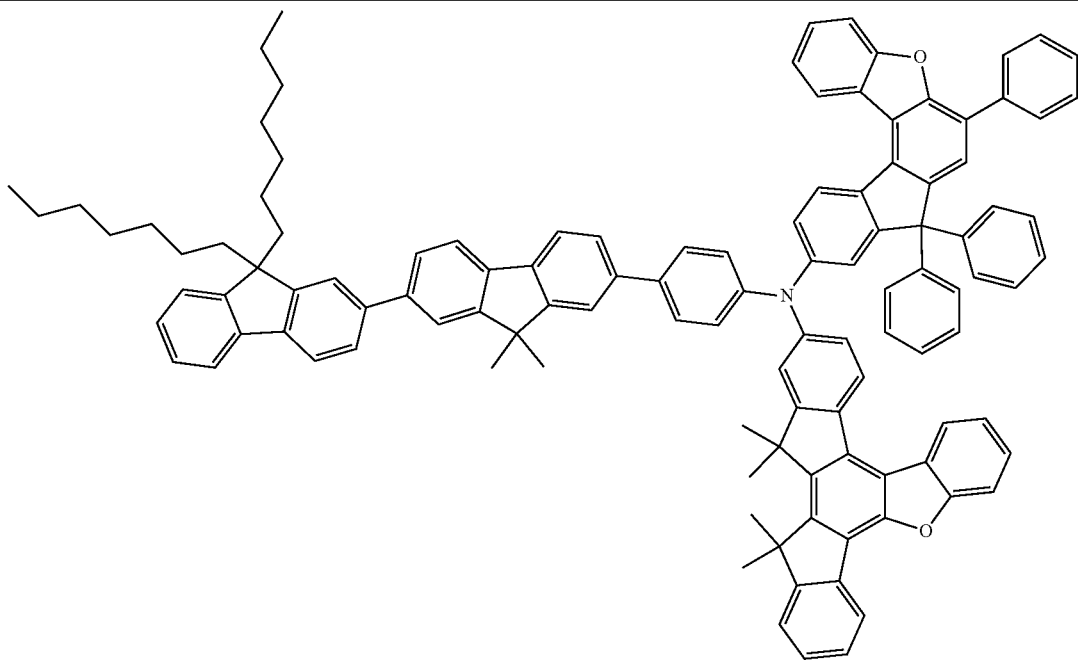
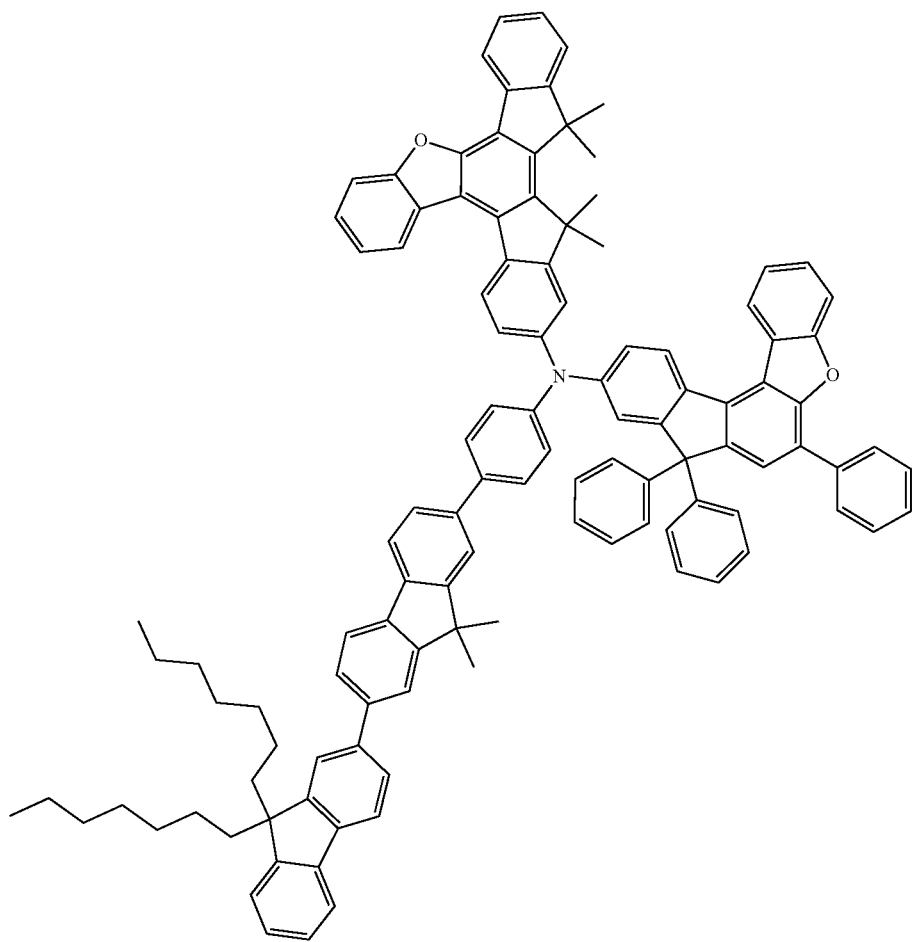 [SMILES: CCCCCCCC1(CCCCCCC)c2ccccc2-c2ccc(-c3ccc4c(c3)C(C)(C)c3cc(-c5ccc(N(c6ccc7c(c6)C(C)(C)c6c8c(c9oc%10ccccc%10c9c6-7)-c6ccccc6C8(C)C)c6ccc7c(c6)C(c6ccccc6)(c6ccccc6)c6cc(-c8ccccc8)c8oc9ccccc9c8c6-7)cc5)ccc3-4)cc21]

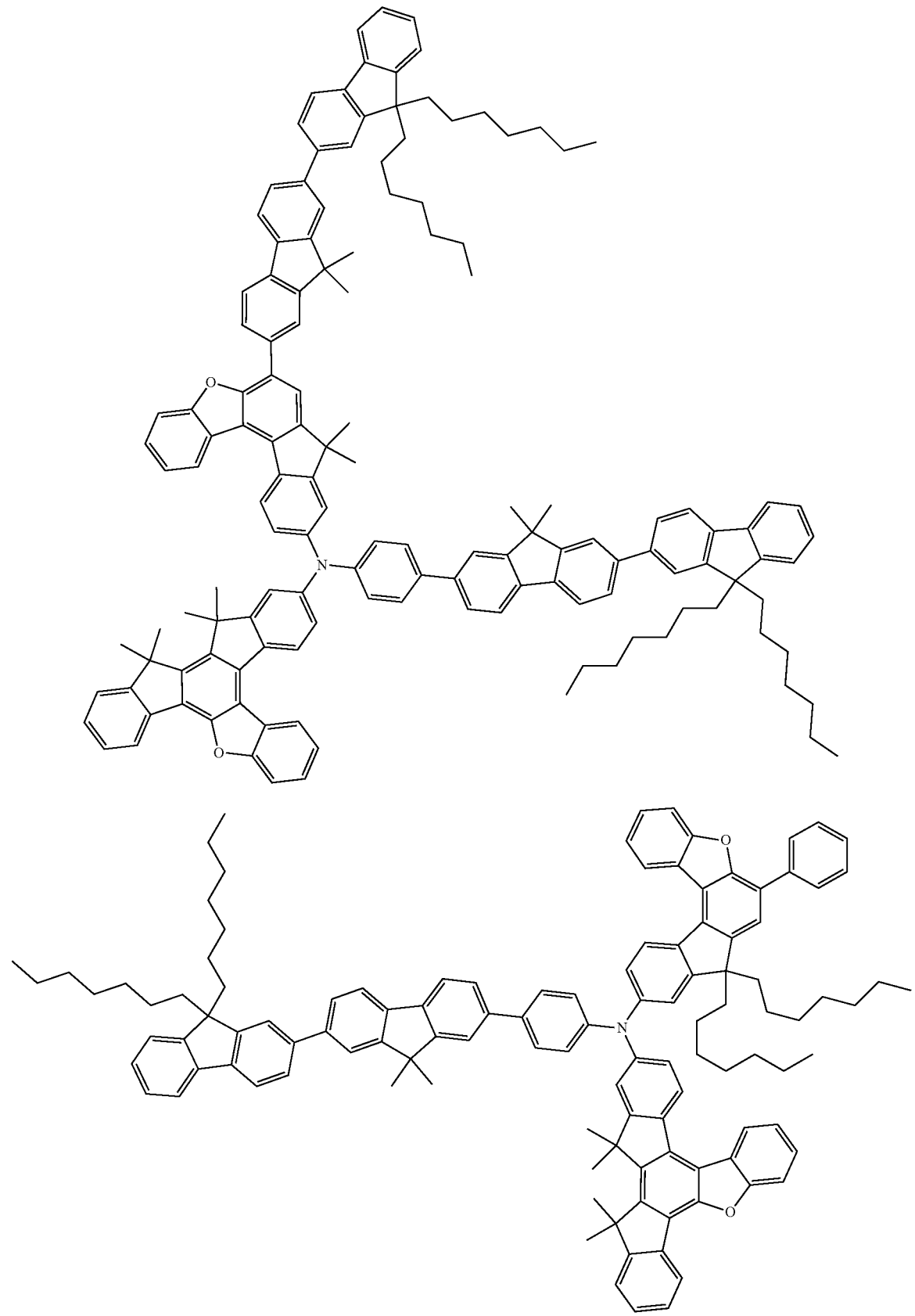

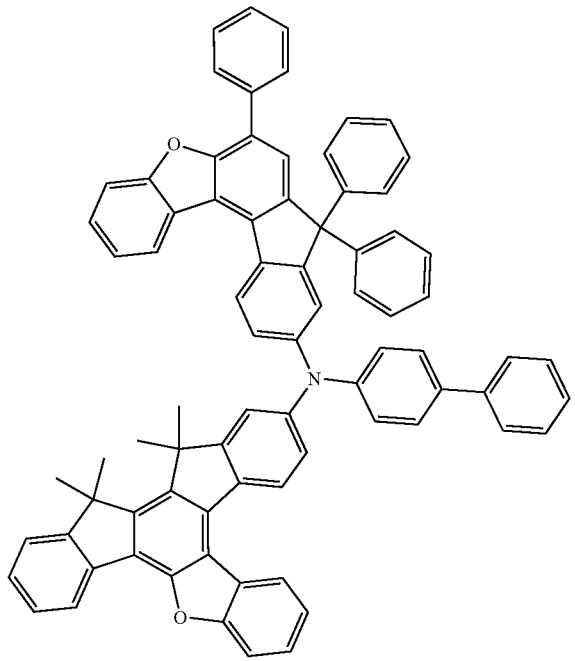 [SMILES: CC1(C)c2ccccc2-c2c1c1c(c3c2oc2ccccc23)-c2ccc(N(c3ccc(-c4ccccc4)cc3)c3ccc4c(c3)C(c3ccccc3)(c3ccccc3)c3cc(-c5ccccc5)c5oc6ccccc6c5c3-4)cc2C1(C)C]
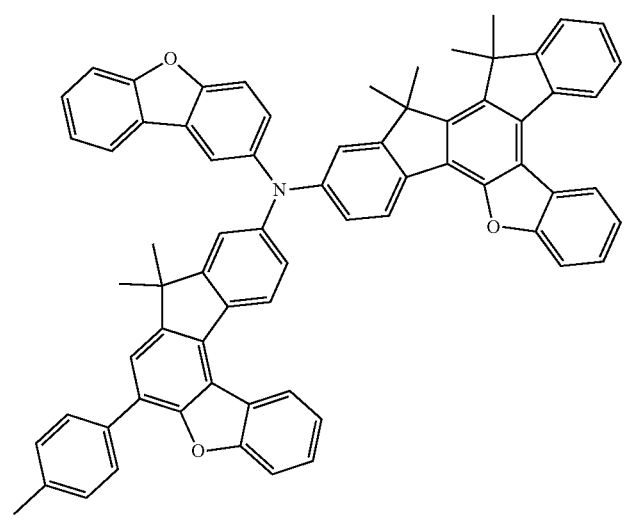 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccc5oc6ccccc6c5c4)cc2C3(C)C)cc1]

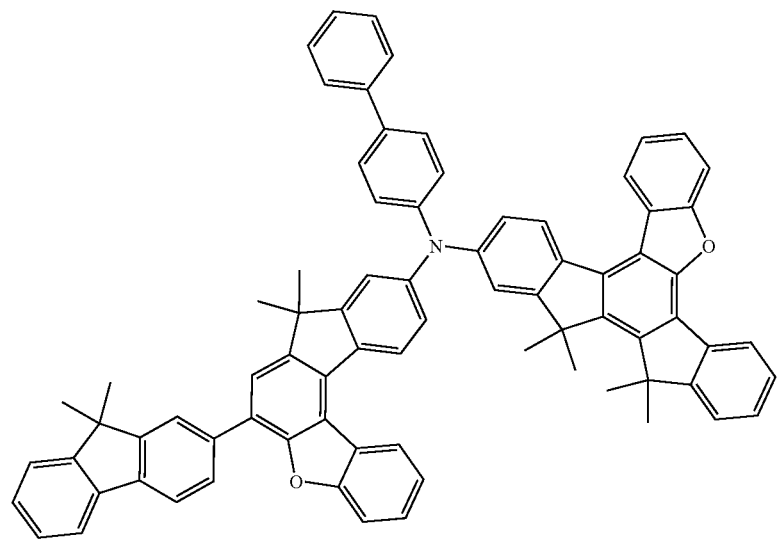 [SMILES: CC1(C)c2ccccc2-c2ccc(-c3cc4c(c5c3oc3ccccc35)-c3ccc(N(c5ccc(-c6ccccc6)cc5)c5ccc6c(c5)C(C)(C)c5c7c(c8oc9ccccc9c8c5-6)-c5ccccc5C7(C)C)cc3C4(C)C)cc21]
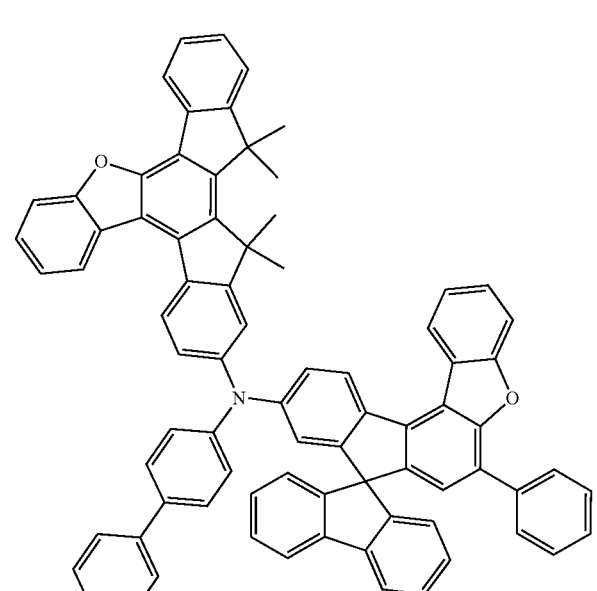

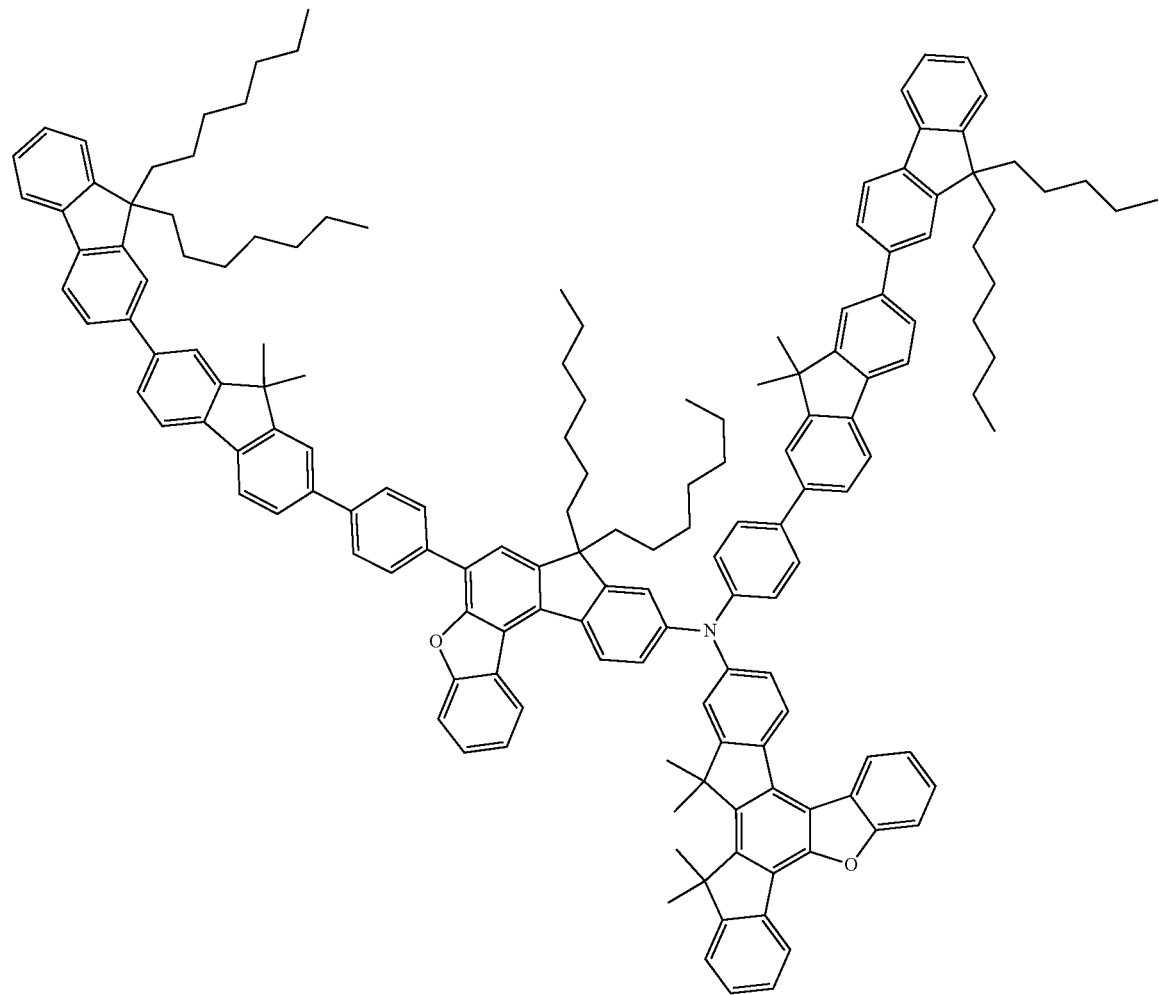 [SMILES: CCCCCCCC1(CCCCC)c2ccccc2-c2ccc(-c3ccc4c(c3)C(C)(C)c3cc(-c5ccc(N(c6ccc7c(c6)C(C)(C)c6c8c(c9oc%10ccccc%10c9c6-7)-c6ccccc6C8(C)C)c6ccc7c(c6)C(CCCCCCC)(CCCCCCC)c6cc(-c8ccc(-c9ccc%10c(c9)C(C)(C)c9cc(-c%11ccc%12c(c%11)C(CCCCCCC)(CCCCCCC)c%11ccccc%11-%12)ccc9-%10)cc8)c8oc9ccccc9c8c6-7)cc5)ccc3-4)cc21]
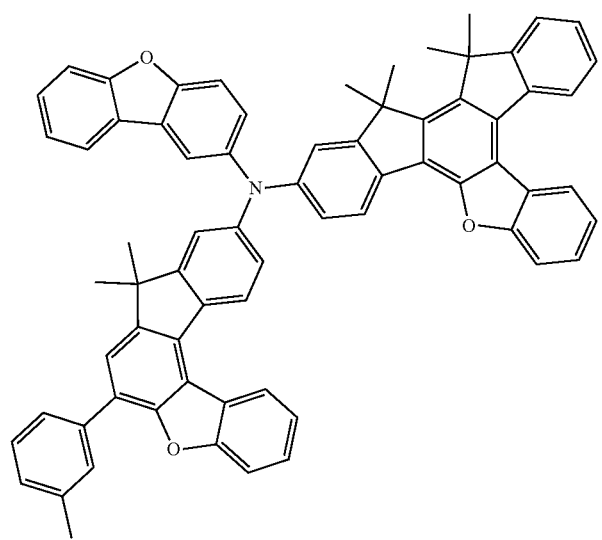 [SMILES: Cc1cccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccc5oc6ccccc6c5c4)cc2C3(C)C)c1]

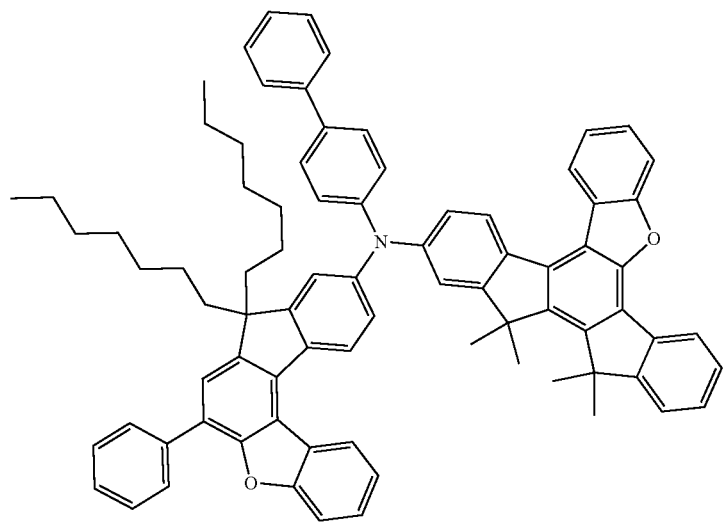 [SMILES: CCCCCCCC1(CCCCCCC)c2cc(N(c3ccc(-c4ccccc4)cc3)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]
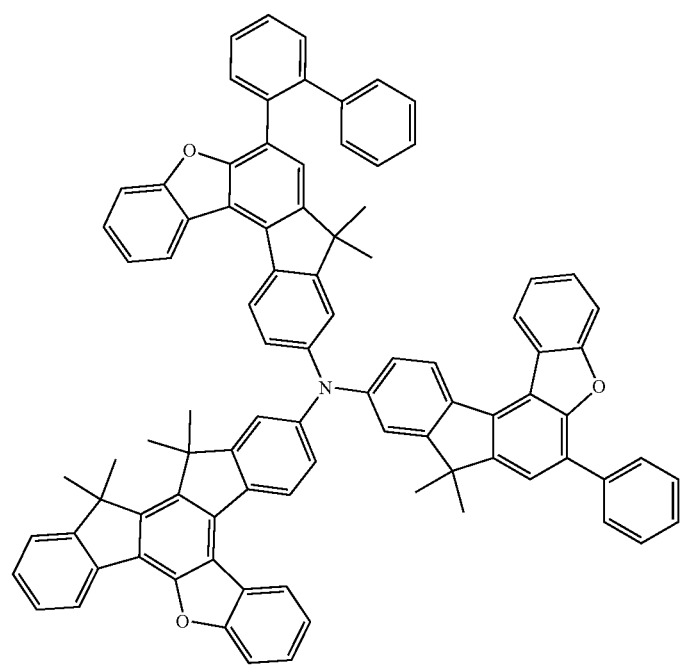 [SMILES: CC1(C)c2cc(N(c3ccc4c(c3)C(C)(C)c3cc(-c5ccccc5-c5ccccc5)c5oc6ccccc6c5c3-4)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]

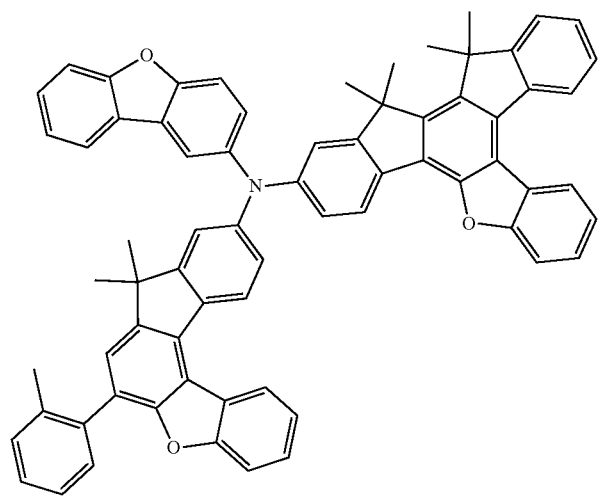 [SMILES: Cc1ccccc1-c1cc2c(c3c1oc1ccccc13)-c1ccc(N(c3ccc4c(c3)C(C)(C)c3c5c(c6c(oc7ccccc76)c3-4)-c3ccccc3C5(C)C)c3ccc4oc5ccccc5c4c3)cc1C2(C)C]
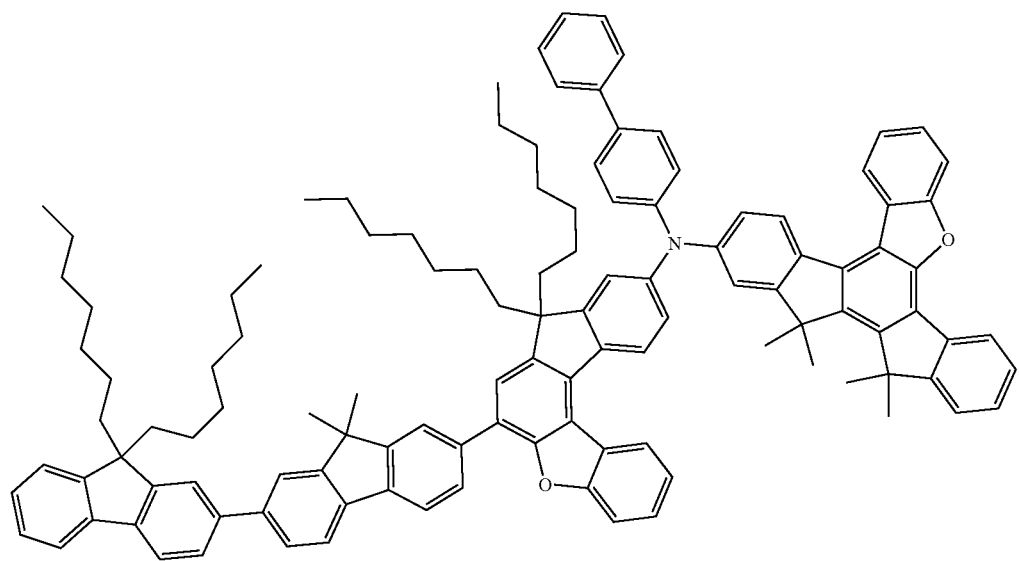 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc(-c8ccccc8)cc7)c7ccc8c(c7)C(C)(C)c7c9c(c%10oc%11ccccc%11c%10c7-8)-c7ccccc7C9(C)C)cc5C6(CCCCCCC)CCCCCCC)ccc3-4)cc21]

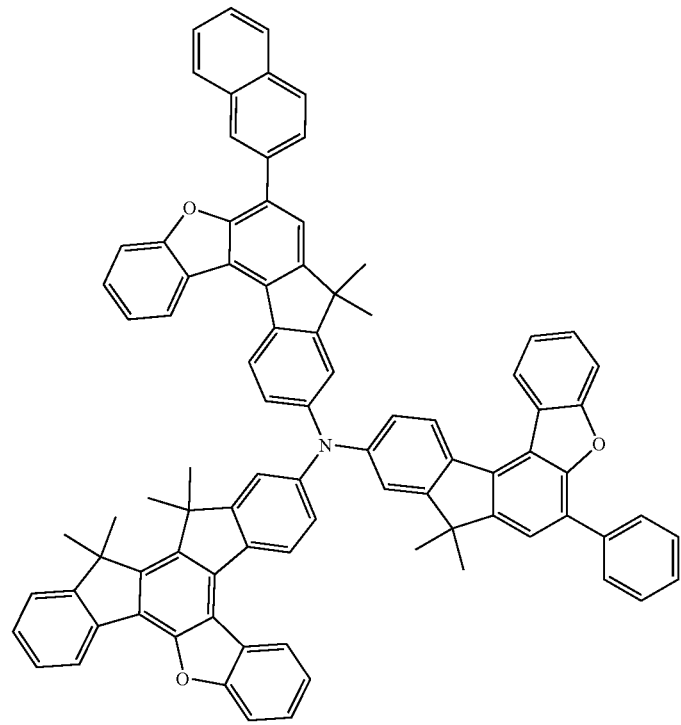 [SMILES: CC1(C)c2cc(N(c3ccc4c(c3)C(C)(C)c3cc(-c5ccc6ccccc6c5)c5oc6ccccc6c5c3-4)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]
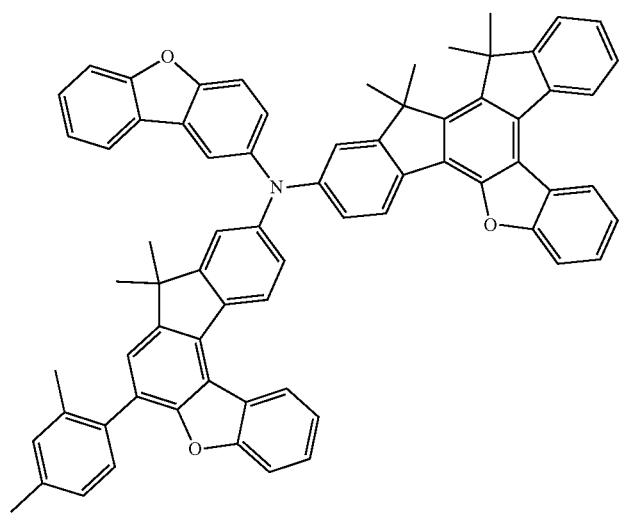 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccc5oc6ccccc6c5c4)cc2C3(C)C)c(C)c1]

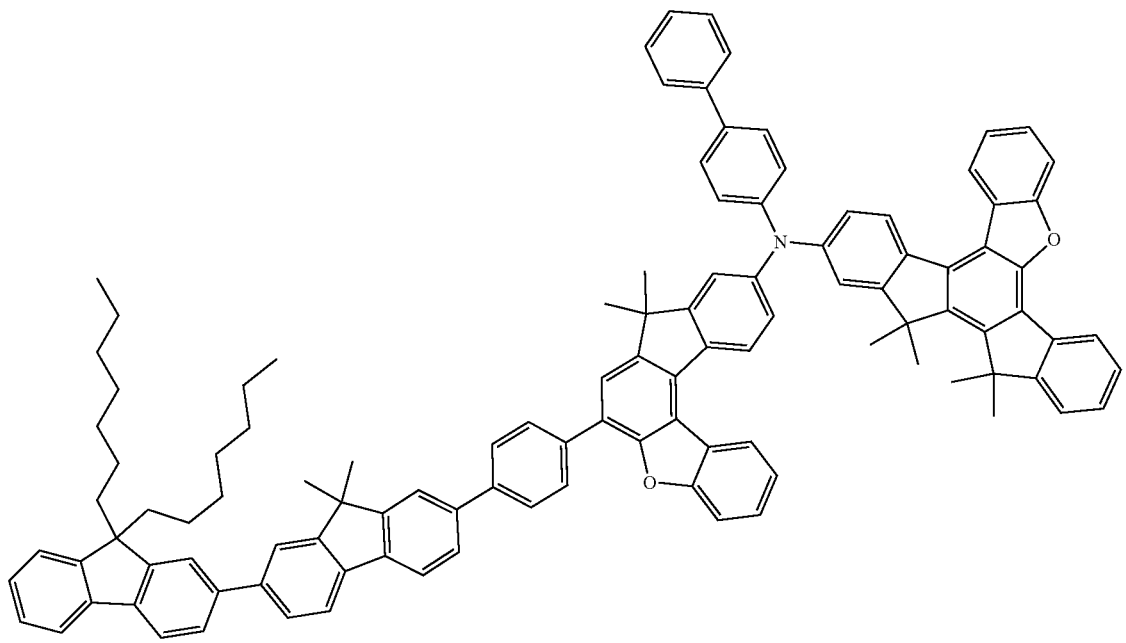 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc(-c9ccccc9)cc8)c8ccc9c(c8)C(C)(C)c8c%10c(c%11oc%12ccccc%12c%11c8-9)-c8ccccc8C%10(C)C)cc6C7(C)C)cc5)ccc3-4)cc21]
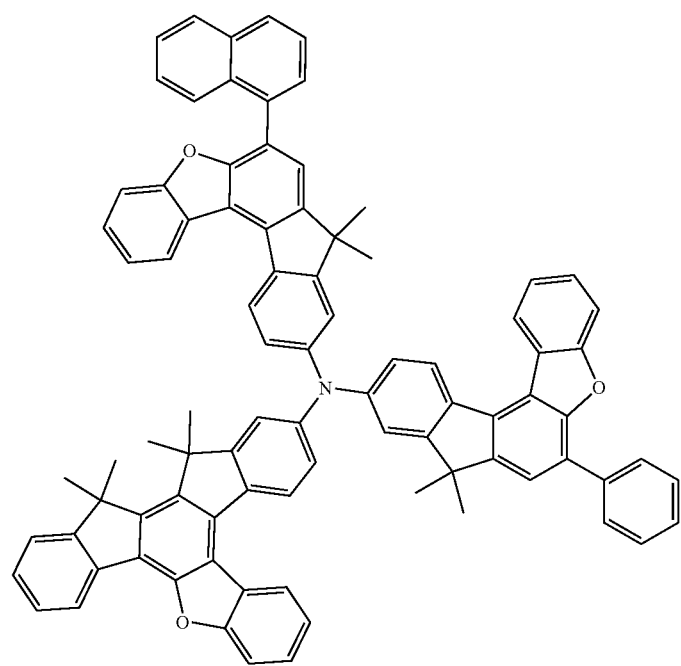 [SMILES: CC1(C)c2cc(N(c3ccc4c(c3)C(C)(C)c3cc(-c5cccc6ccccc56)c5oc6ccccc6c5c3-4)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]

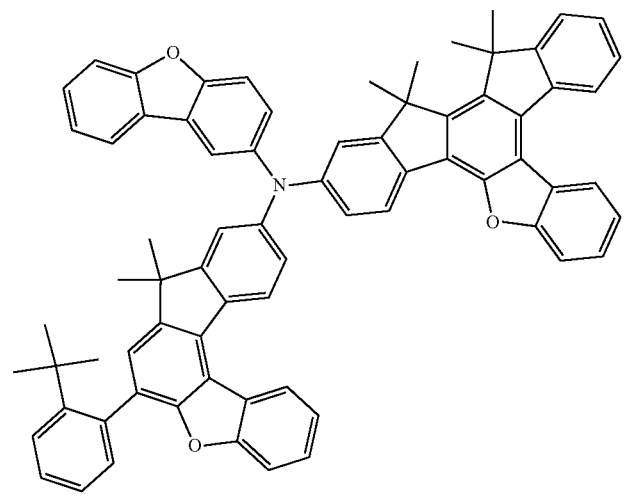 [SMILES: CC(C)(C)c1ccccc1-c1cc2c(c3c1oc1ccccc13)-c1ccc(N(c3ccc4c(c3)C(C)(C)c3c5c(c6c(oc7ccccc76)c3-4)-c3ccccc3C5(C)C)c3ccc4oc5ccccc5c4c3)cc1C2(C)C]
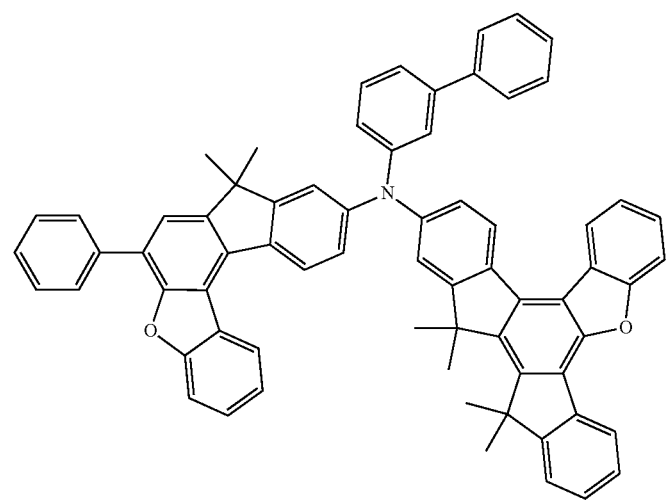 [SMILES: CC1(C)c2cc(N(c3cccc(-c4ccccc4)c3)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]

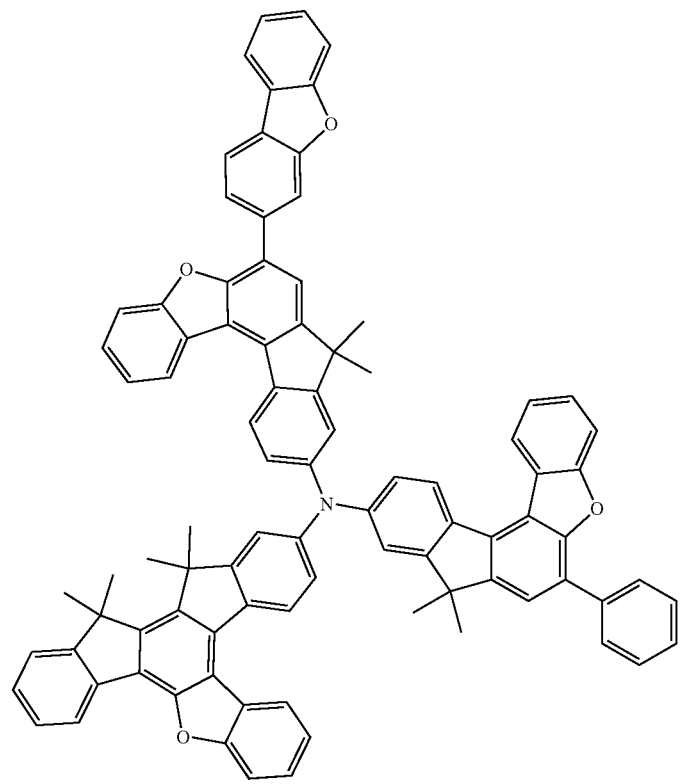 [SMILES: CC1(C)c2cc(N(c3ccc4c(c3)C(C)(C)c3cc(-c5ccc6c(c5)oc5ccccc56)c5oc6ccccc6c5c3-4)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]
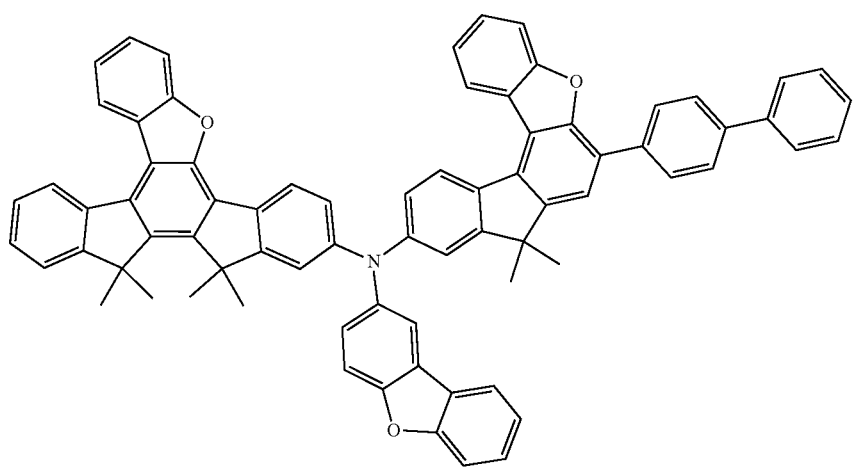 [SMILES: CC1(C)c2cc(N(c3ccc4c(c3)C(C)(C)c3c5c(c6c(oc7ccccc76)c3-4)-c3ccccc3C5(C)C)c3ccc4oc5ccccc5c4c3)ccc2-c2c1cc(-c1ccc(-c3ccccc3)cc1)c1oc3ccccc3c21]

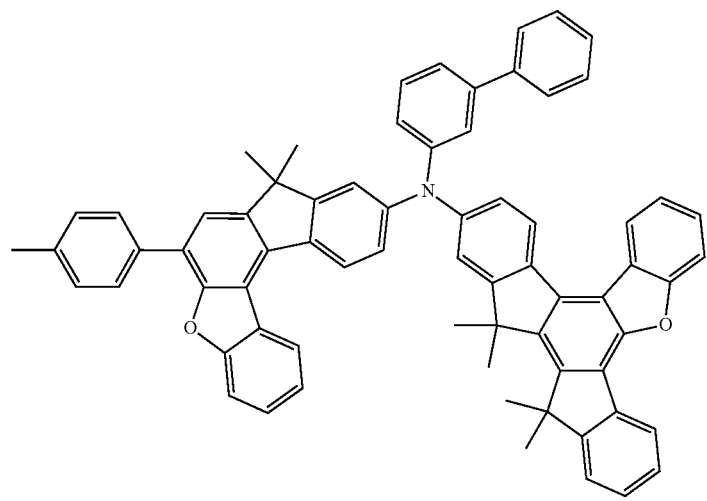 [SMILES: Cc1ccc(-c2cc3c(c4c2oc2ccccc24)-c2ccc(N(c4cccc(-c5ccccc5)c4)c4ccc5c(c4)C(C)(C)c4c6c(c7oc8ccccc8c7c4-5)-c4ccccc4C6(C)C)cc2C3(C)C)cc1]
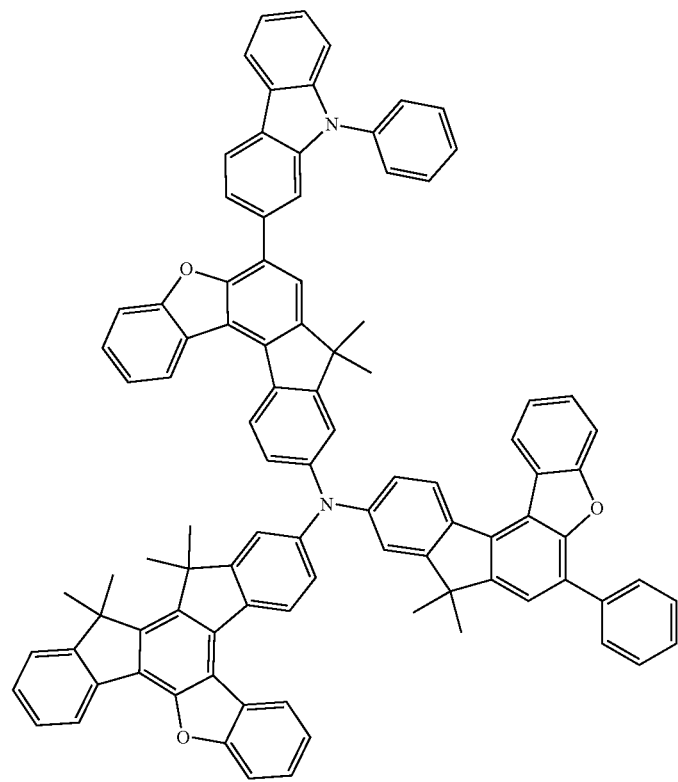 [SMILES: CC1(C)c2cc(N(c3ccc4c(c3)C(C)(C)c3cc(-c5ccc6c7ccccc7n(-c7ccccc7)c6c5)c5oc6ccccc6c5c3-4)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]

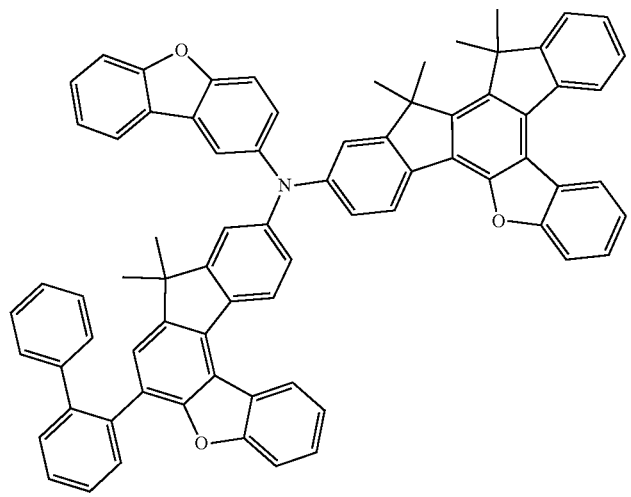 [SMILES: CC1(C)c2cc(N(c3ccc4c(c3)C(C)(C)c3c5c(c6c(oc7ccccc76)c3-4)-c3ccccc3C5(C)C)c3ccc4oc5ccccc5c4c3)ccc2-c2c1cc(-c1ccccc1-c1ccccc1)c1oc3ccccc3c21]
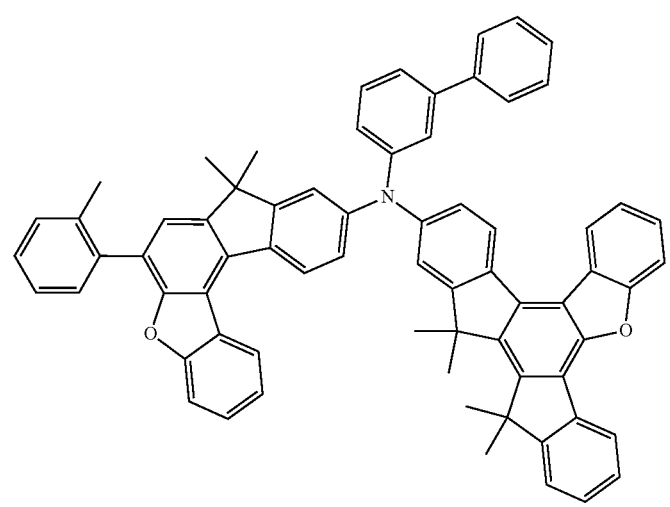 [SMILES: Cc1ccccc1-c1cc2c(c3c1oc1ccccc13)-c1ccc(N(c3cccc(-c4ccccc4)c3)c3ccc4c(c3)C(C)(C)c3c5c(c6oc7ccccc7c6c3-4)-c3ccccc3C5(C)C)cc1C2(C)C]

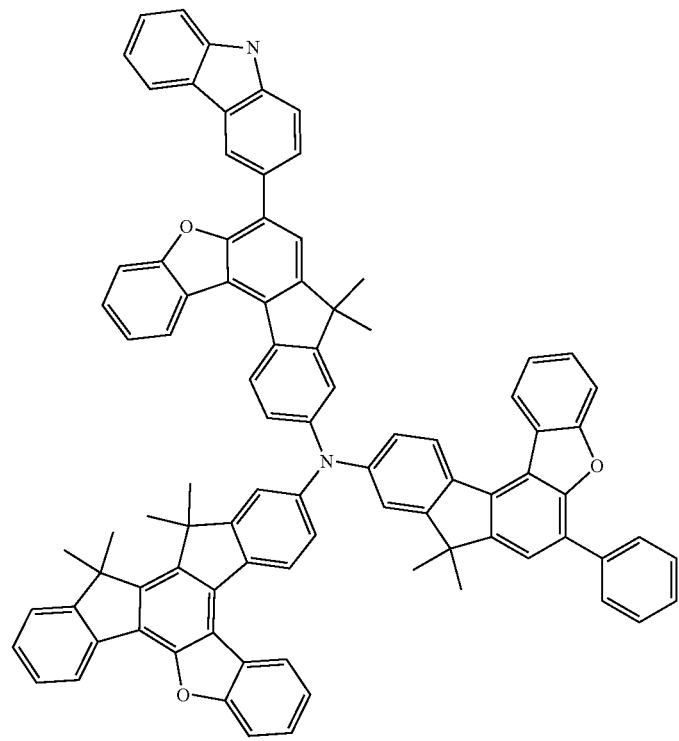 [SMILES: CC1(C)c2cc(N(c3ccc4c(c3)C(C)(C)c3cc(-c5ccc6[nH]c7ccccc7c6c5)c5oc6ccccc6c5c3-4)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]
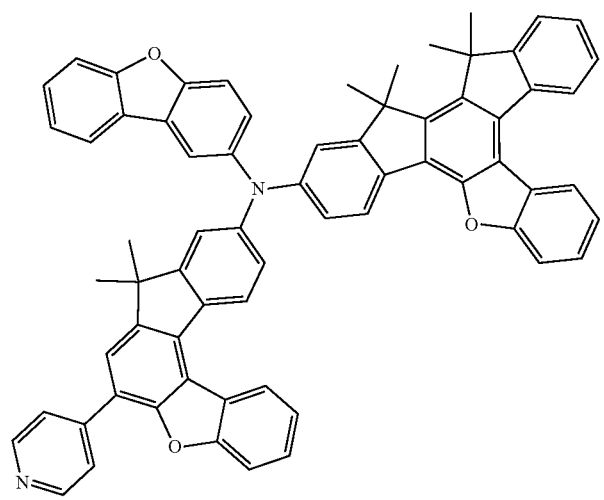 [SMILES: CC1(C)c2cc(N(c3ccc4c(c3)C(C)(C)c3c5c(c6c(oc7ccccc76)c3-4)-c3ccccc3C5(C)C)c3ccc4oc5ccccc5c4c3)ccc2-c2c1cc(-c1ccncc1)c1oc3ccccc3c21]

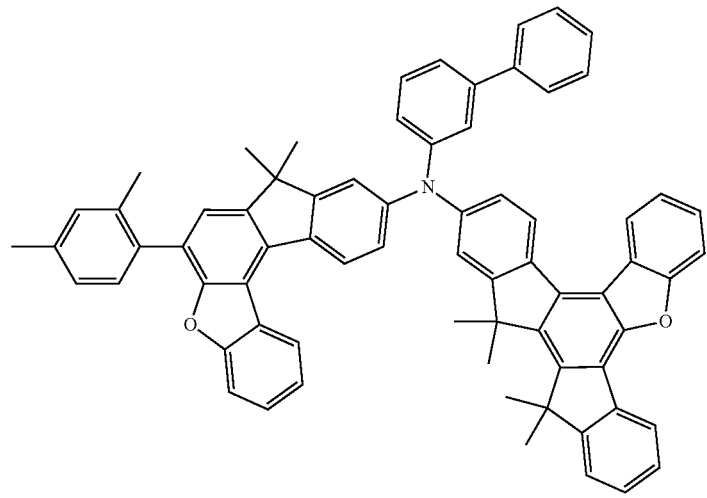 [SMILES: Cc1ccc(-c2cc3c(c4c2oc2ccccc24)-c2ccc(N(c4cccc(-c5ccccc5)c4)c4ccc5c(c4)C(C)(C)c4c6c(c7oc8ccccc8c7c4-5)-c4ccccc4C6(C)C)cc2C3(C)C)c(C)c1]
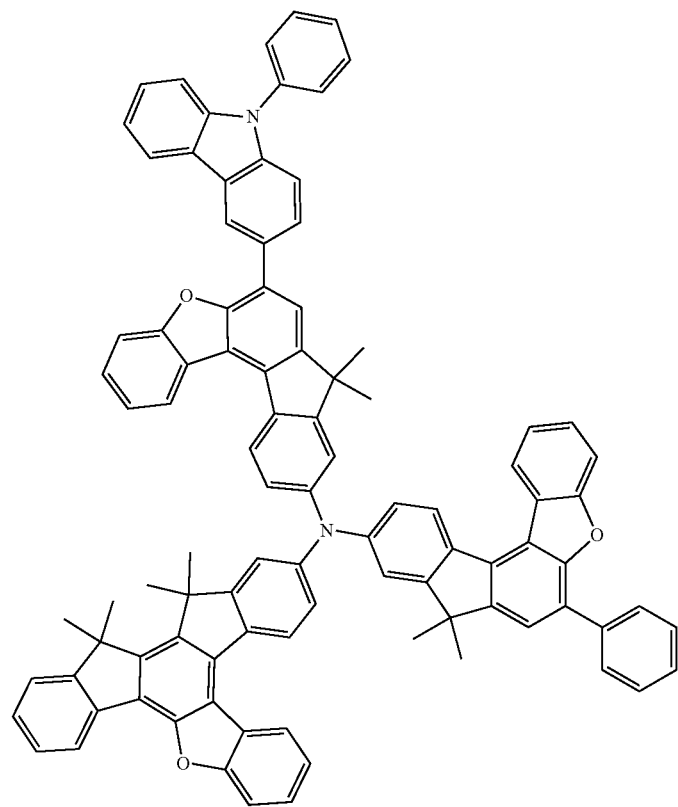 [SMILES: CC1(C)c2cc(N(c3ccc4c(c3)C(C)(C)c3cc(-c5ccc6c(c5)c5ccccc5n6-c5ccccc5)c5oc6ccccc6c5c3-4)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]

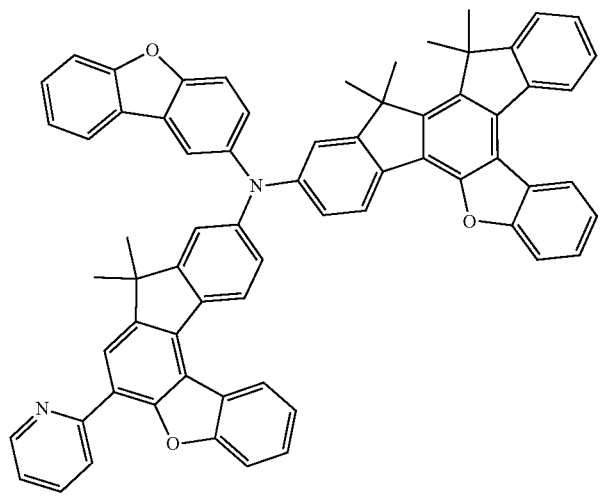
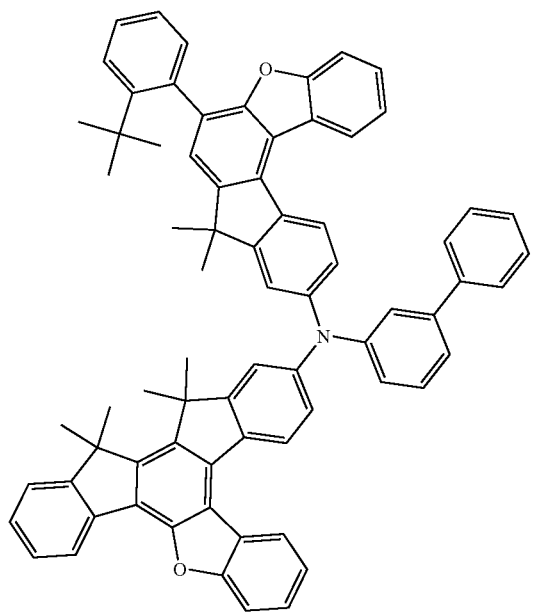 [SMILES: CC(C)(C)c1ccccc1-c1cc2c(c3c1oc1ccccc13)-c1ccc(N(c3cccc(-c4ccccc4)c3)c3ccc4c(c3)C(C)(C)c3c5c(c6oc7ccccc7c6c3-4)-c3ccccc3C5(C)C)cc1C2(C)C]

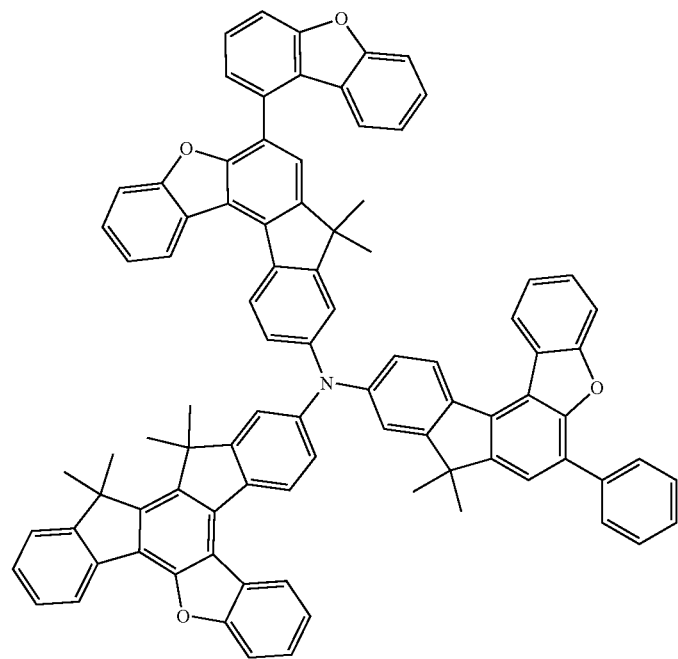 [SMILES: CC1(C)c2cc(N(c3ccc4c(c3)C(C)(C)c3cc(-c5cccc6oc7ccccc7c56)c5oc6ccccc6c5c3-4)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]
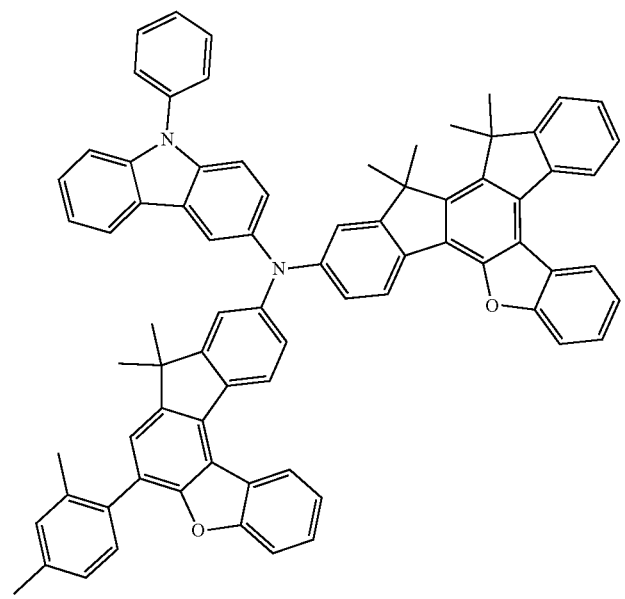 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccc5c(c4)c4ccccc4n5-c4ccccc4)cc2C3(C)C)c(C)c1]

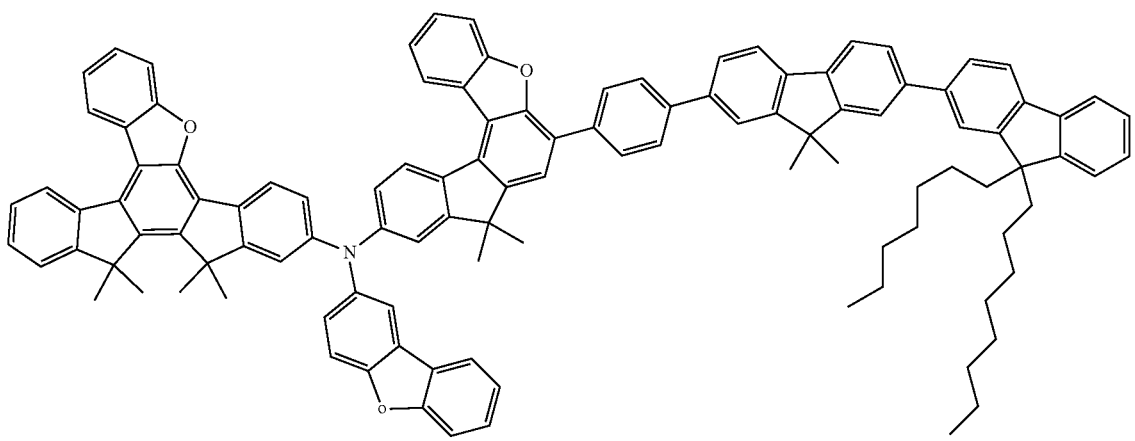
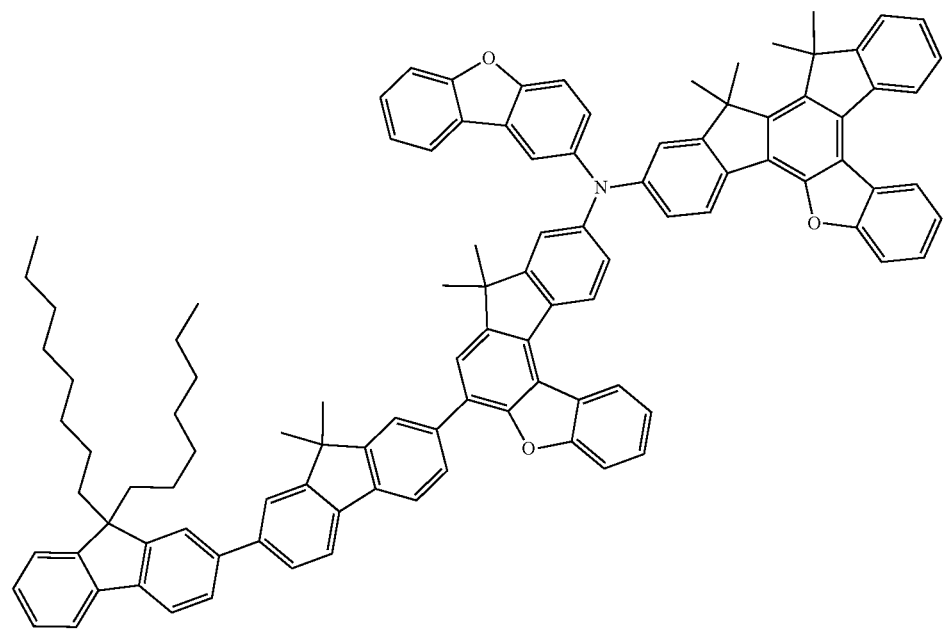 [SMILES: CCCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10c(oc%11ccccc%11%10)c7-8)-c7ccccc7C9(C)C)c7ccc8oc9ccccc9c8c7)cc5C6(C)C)ccc3-4)cc21]

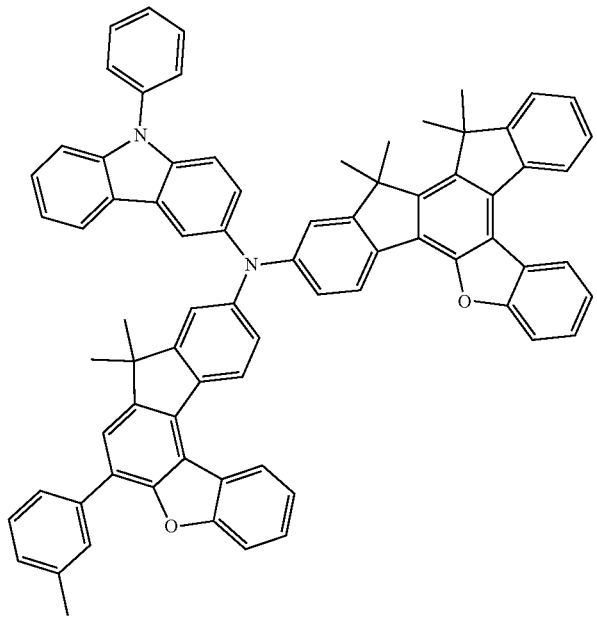 [SMILES: Cc1cccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccc5c(c4)c4ccccc4n5-c4ccccc4)cc2C3(C)C)c1]
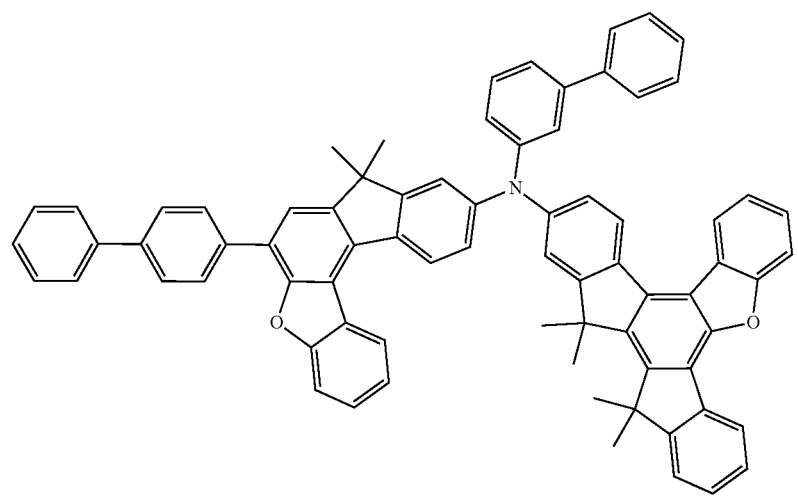 [SMILES: CC1(C)c2cc(N(c3cccc(-c4ccccc4)c3)c3ccc4c(c3)C(C)(C)c3c5c(c6oc7ccccc7c6c3-4)-c3ccccc3C5(C)C)ccc2-c2c1cc(-c1ccc(-c3ccccc3)cc1)c1oc3ccccc3c21]

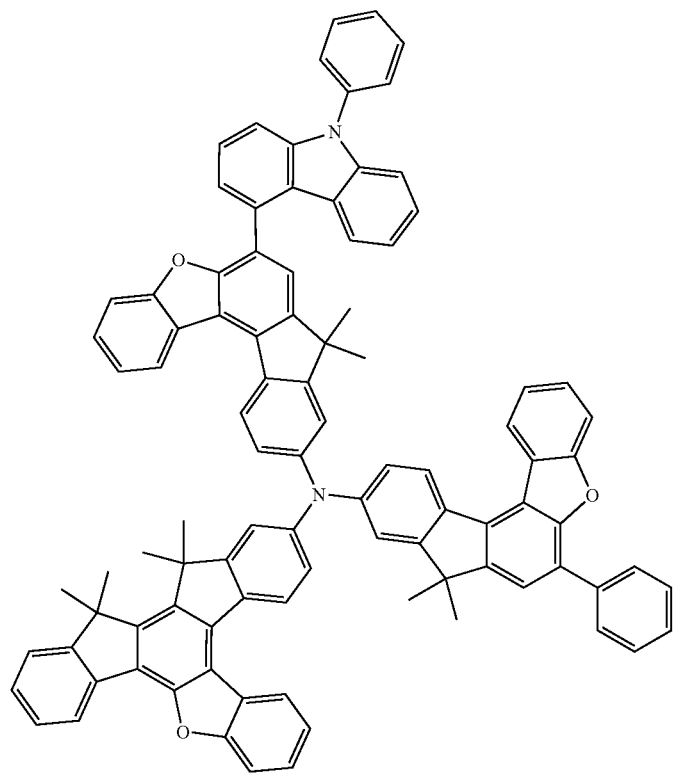 [SMILES: CC1(C)c2cc(N(c3ccc4c(c3)C(C)(C)c3cc(-c5cccc6c5c5ccccc5n6-c5ccccc5)c5oc6ccccc6c5c3-4)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]
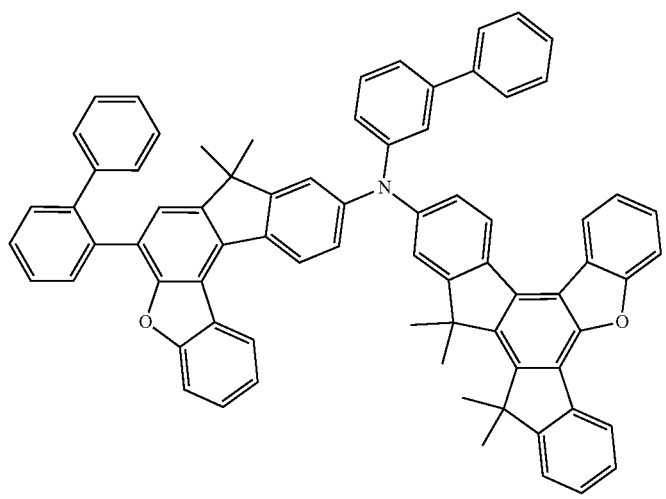 [SMILES: CC1(C)c2cc(N(c3cccc(-c4ccccc4)c3)c3ccc4c(c3)C(C)(C)c3c5c(c6oc7ccccc7c6c3-4)-c3ccccc3C5(C)C)ccc2-c2c1cc(-c1ccccc1-c1ccccc1)c1oc3ccccc3c21]

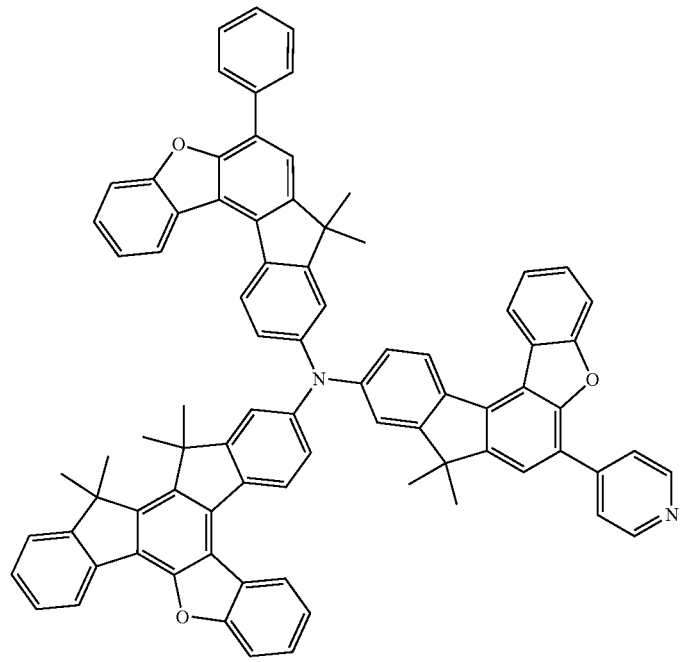 [SMILES: CC1(C)c2cc(N(c3ccc4c(c3)C(C)(C)c3cc(-c5ccncc5)c5oc6ccccc6c5c3-4)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]
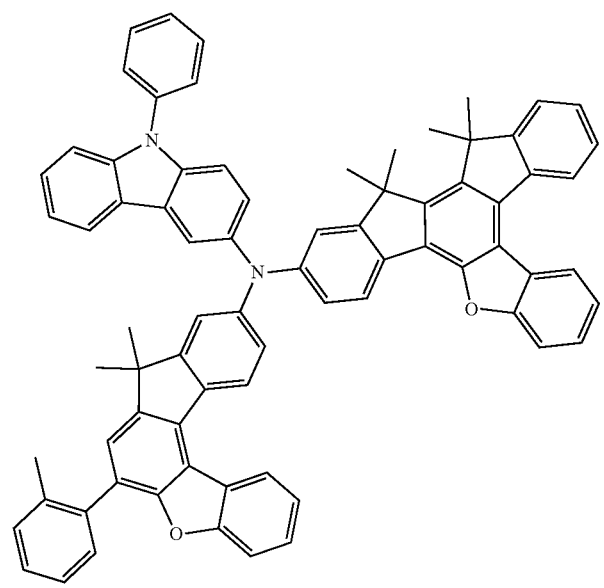 [SMILES: Cc1ccccc1-c1cc2c(c3c1oc1ccccc13)-c1ccc(N(c3ccc4c(c3)C(C)(C)c3c5c(c6c(oc7ccccc76)c3-4)-c3ccccc3C5(C)C)c3ccc4c(c3)c3ccccc3n4-c3ccccc3)cc1C2(C)C]

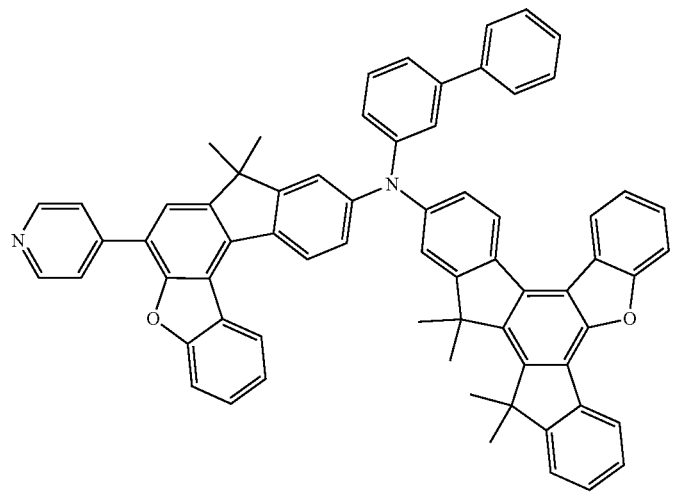 [SMILES: CC1(C)c2cc(N(c3cccc(-c4ccccc4)c3)c3ccc4c(c3)C(C)(C)c3c5c(c6oc7ccccc7c6c3-4)-c3ccccc3C5(C)C)ccc2-c2c1cc(-c1ccncc1)c1oc3ccccc3c21]
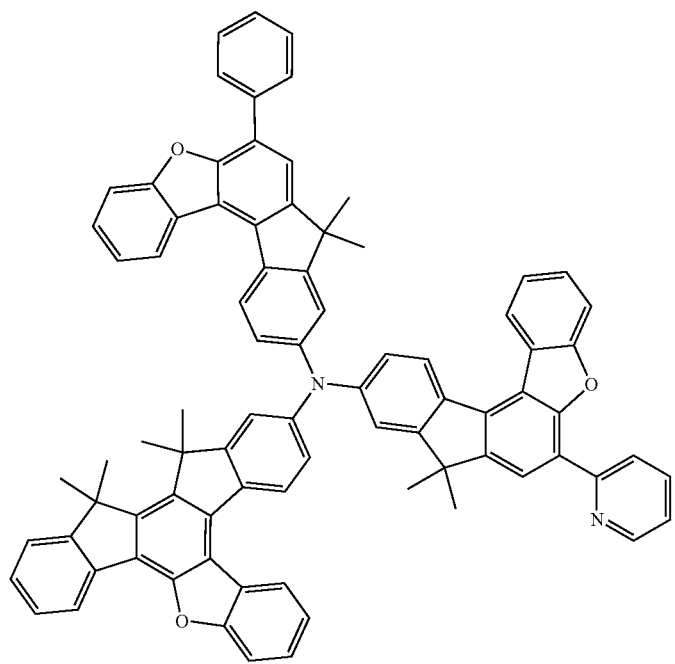 [SMILES: CC1(C)c2cc(N(c3ccc4c(c3)C(C)(C)c3cc(-c5ccccn5)c5oc6ccccc6c5c3-4)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]

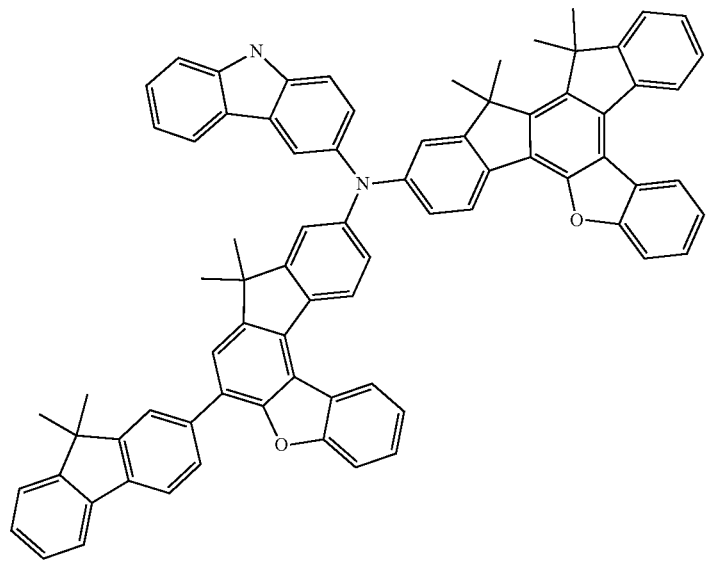 [SMILES: CC1(C)c2ccccc2-c2ccc(-c3cc4c(c5c3oc3ccccc35)-c3ccc(N(c5ccc6c(c5)C(C)(C)c5c7c(c8c(oc9ccccc98)c5-6)-c5ccccc5C7(C)C)c5ccc6[nH]c7ccccc7c6c5)cc3C4(C)C)cc21]
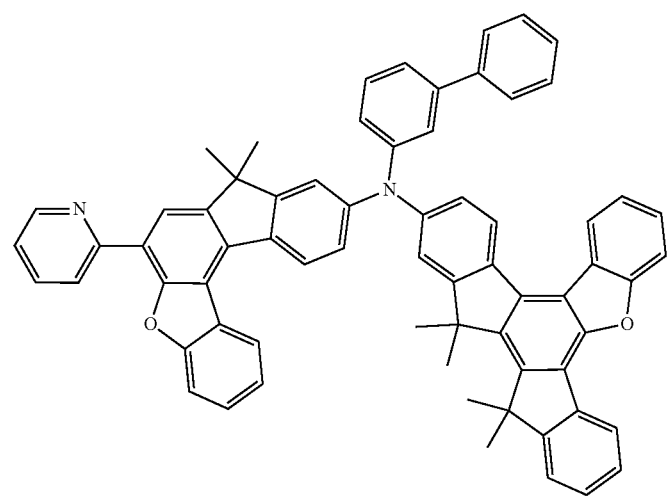 [SMILES: CC1(C)c2cc(N(c3cccc(-c4ccccc4)c3)c3ccc4c(c3)C(C)(C)c3c5c(c6oc7ccccc7c6c3-4)-c3ccccc3C5(C)C)ccc2-c2c1cc(-c1ccccn1)c1oc3ccccc3c21]

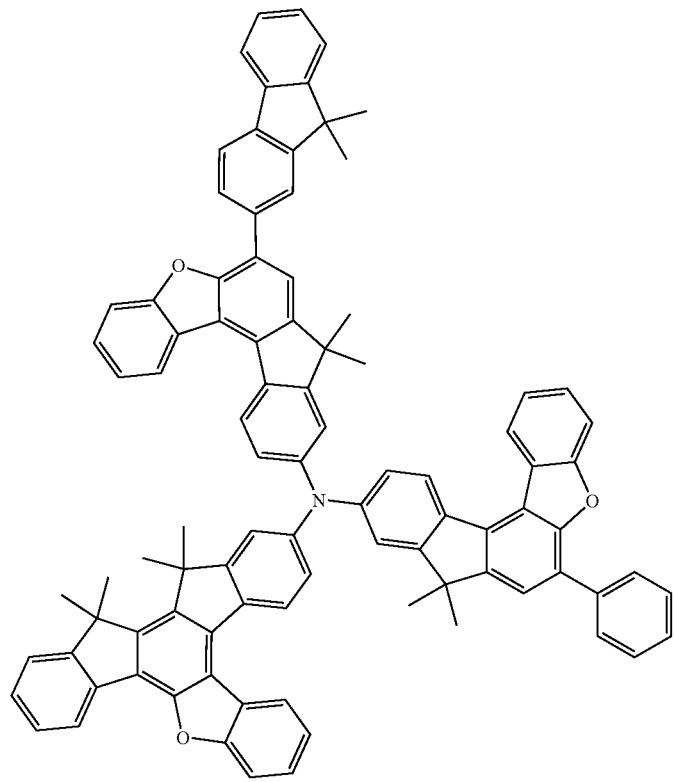 [SMILES: CC1(C)c2ccccc2-c2ccc(-c3cc4c(c5c3oc3ccccc35)-c3ccc(N(c5ccc6c(c5)C(C)(C)c5cc(-c7ccccc7)c7oc8ccccc8c7c5-6)c5ccc6c(c5)C(C)(C)c5c7c(c8oc9ccccc9c8c5-6)-c5ccccc5C7(C)C)cc3C4(C)C)cc21]
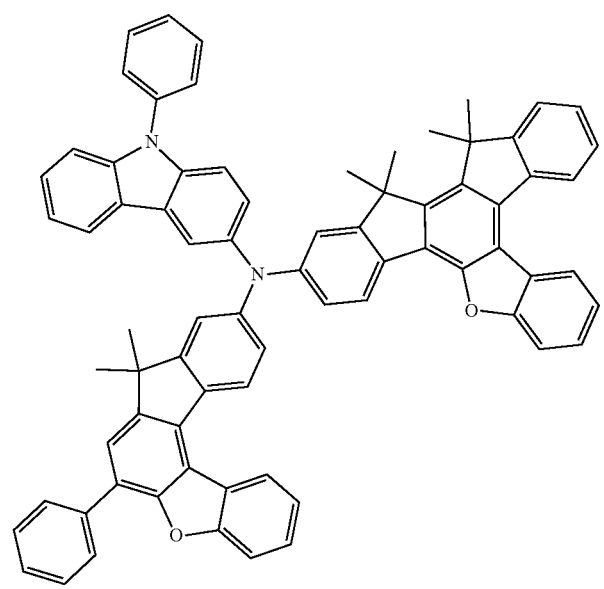 [SMILES: CC1(C)c2cc(N(c3ccc4c(c3)C(C)(C)c3c5c(c6c(oc7ccccc76)c3-4)-c3ccccc3C5(C)C)c3ccc4c(c3)c3ccccc3n4-c3ccccc3)ccc2-c2c1cc(-c1ccccc1)c1oc3ccccc3c21]

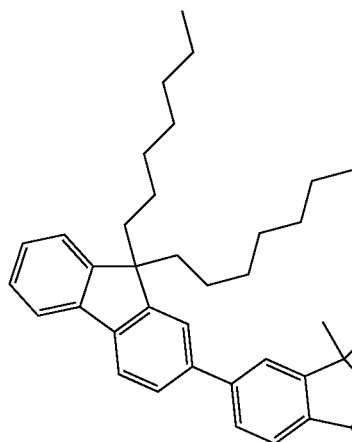
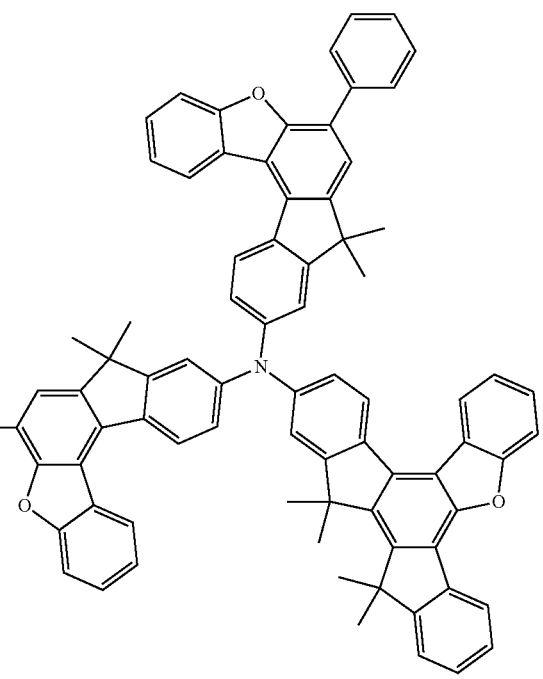
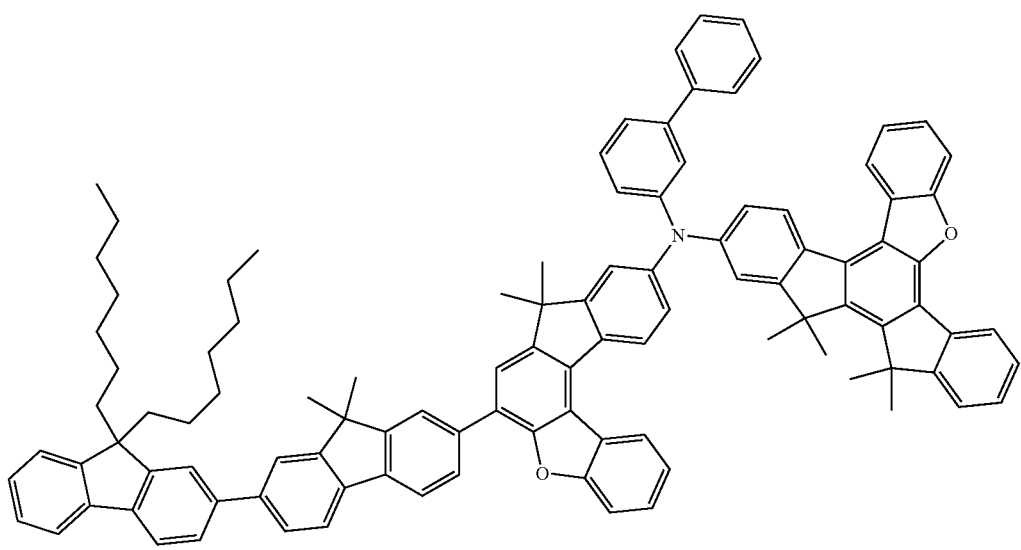 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7cccc(-c8ccccc8)c7)c7ccc8c(c7)C(C)(C)c7c9c(c%10oc%11ccccc%11c%10c7-8)-c7ccccc7C9(C)C)cc5C6(C)C)ccc3-4)cc21]

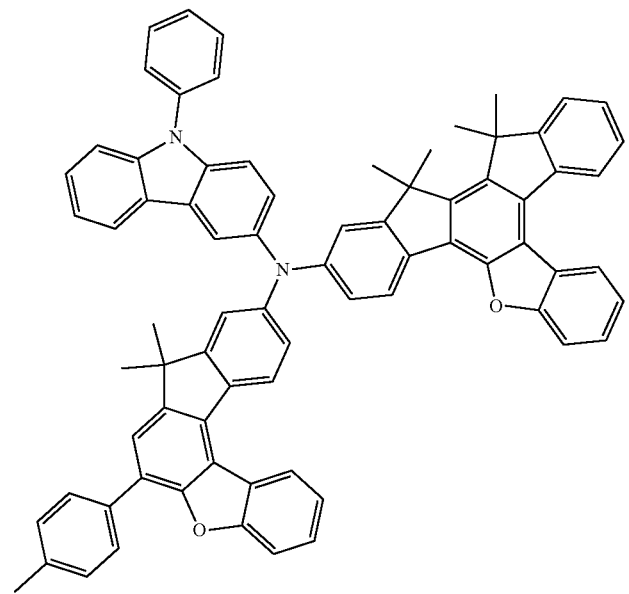 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccc5c(c4)c4ccccc4n5-c4ccccc4)cc2C3(C)C)cc1]
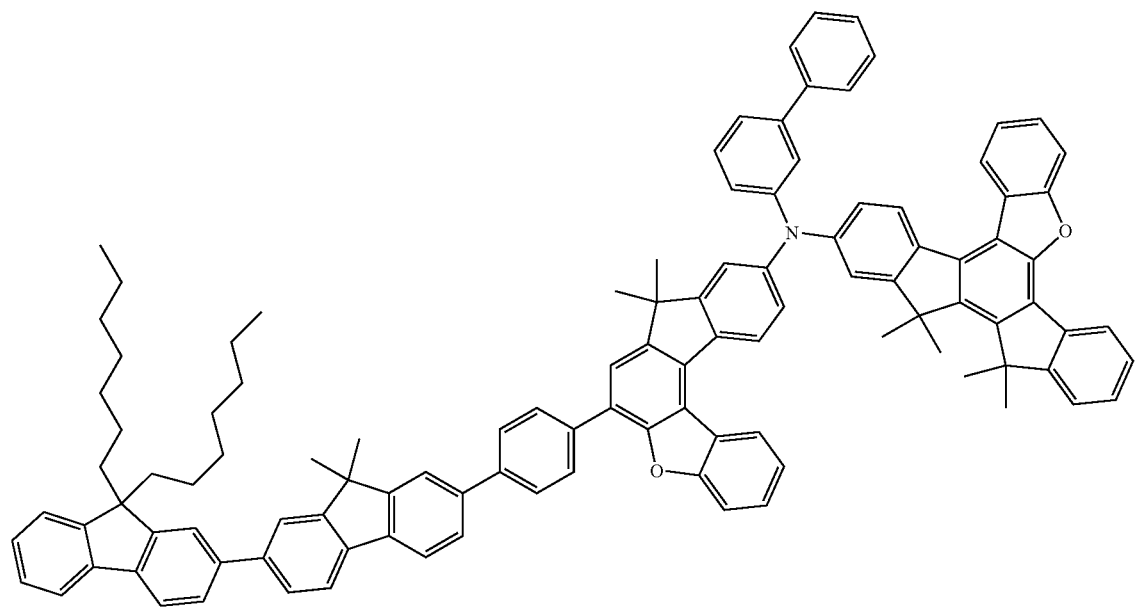 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8cccc(-c9ccccc9)c8)c8ccc9c(c8)C(C)(C)c8c%10c(c%11oc%12ccccc%12c%11c8-9)-c8ccccc8C%10(C)C)cc6C7(C)C)cc5)ccc3-4)cc21]

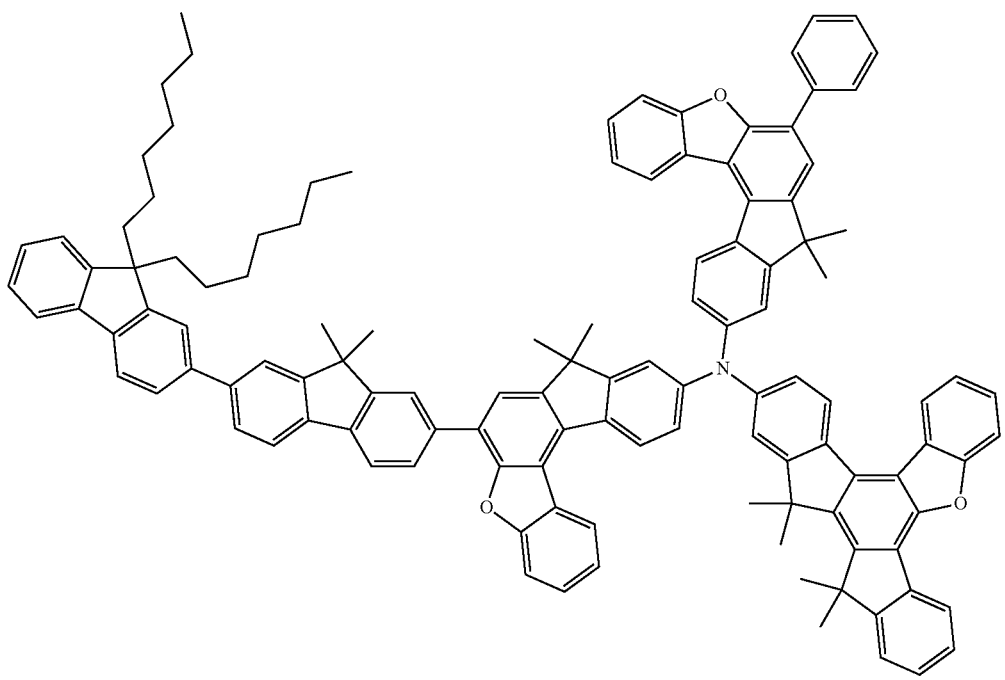 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7cc(-c9ccccc9)c9oc%10ccccc%10c9c7-8)c7ccc8c(c7)C(C)(C)c7c9c(c%10oc%11ccccc%11c%10c7-8)-c7ccccc7C9(C)C)cc5C6(C)C)ccc3-4)cc21]
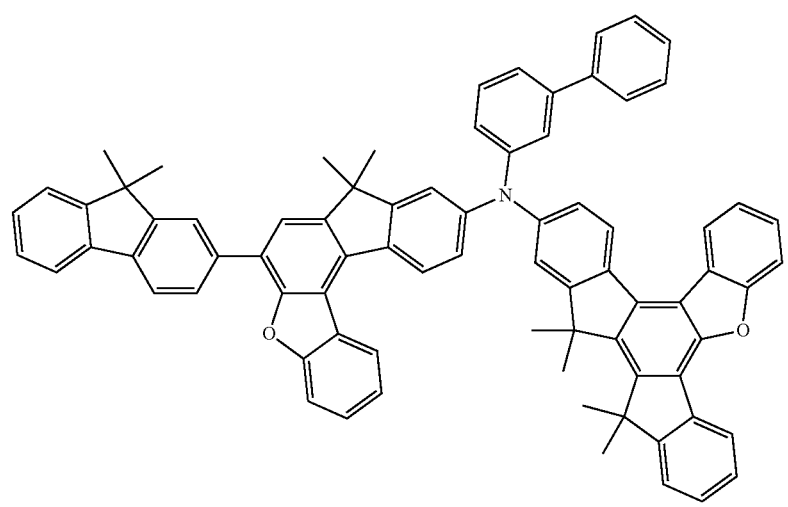 [SMILES: CC1(C)c2ccccc2-c2ccc(-c3cc4c(c5c3oc3ccccc35)-c3ccc(N(c5cccc(-c6ccccc6)c5)c5ccc6c(c5)C(C)(C)c5c7c(c8oc9ccccc9c8c5-6)-c5ccccc5C7(C)C)cc3C4(C)C)cc21]

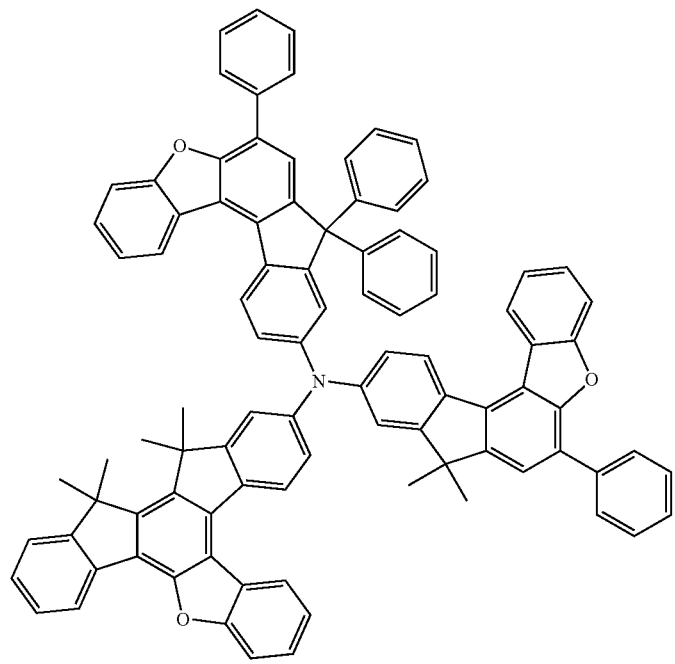 [SMILES: CC1(C)c2cc(N(c3ccc4c(c3)C(C)(C)c3c5c(c6oc7ccccc7c6c3-4)-c3ccccc3C5(C)C)c3ccc4c(c3)C(c3ccccc3)(c3ccccc3)c3cc(-c5ccccc5)c5oc6ccccc6c5c3-4)ccc2-c2c1cc(-c1ccccc1)c1oc3ccccc3c21]
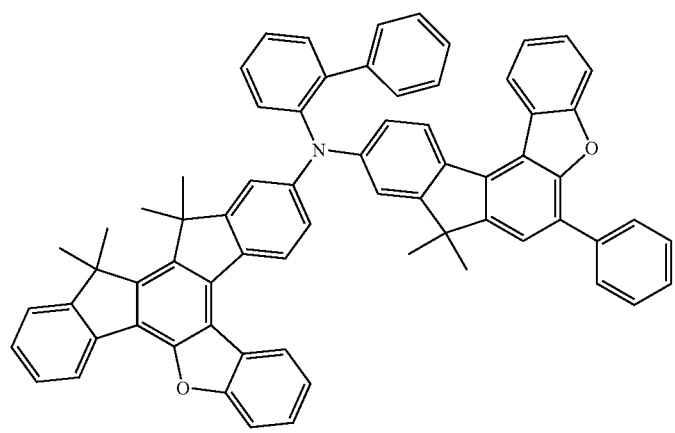 [SMILES: CC1(C)c2cc(N(c3ccc4c(c3)C(C)(C)c3c5c(c6oc7ccccc7c6c3-4)-c3ccccc3C5(C)C)c3ccccc3-c3ccccc3)ccc2-c2c1cc(-c1ccccc1)c1oc3ccccc3c21]

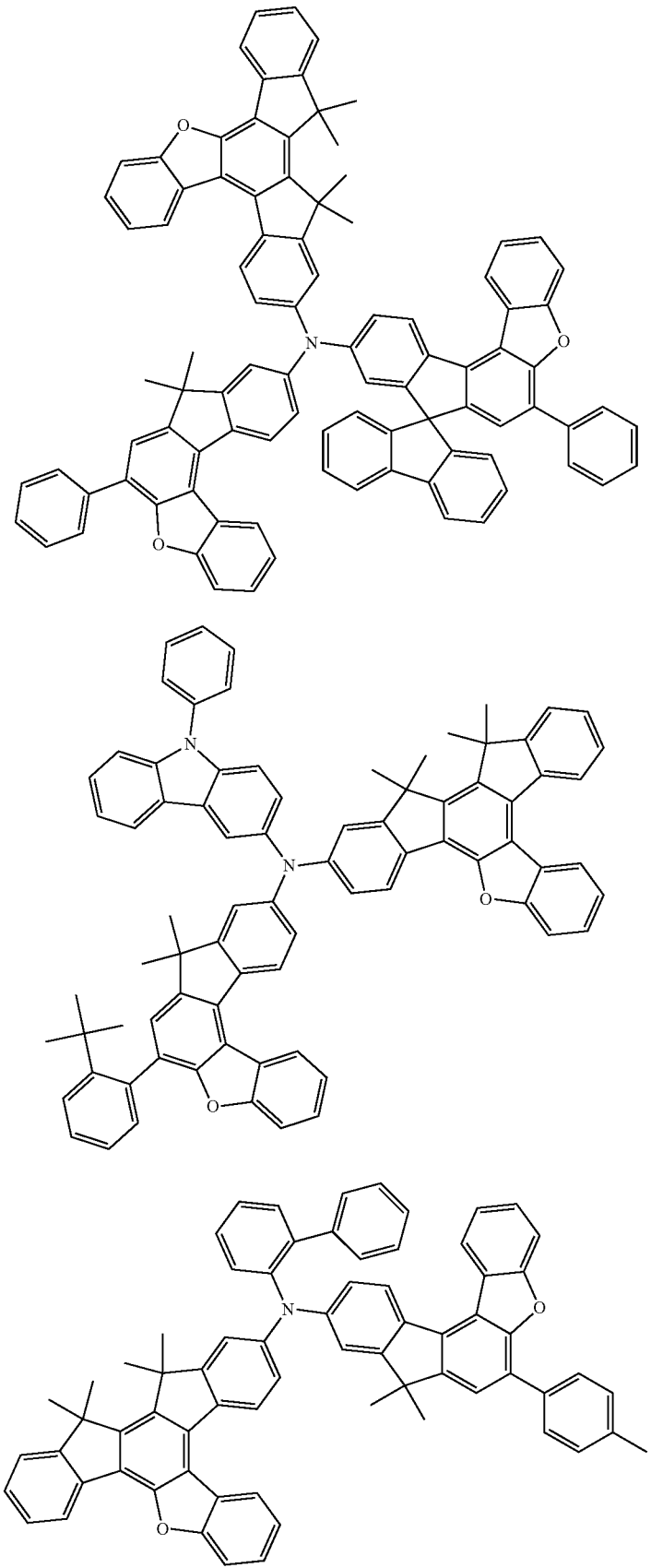

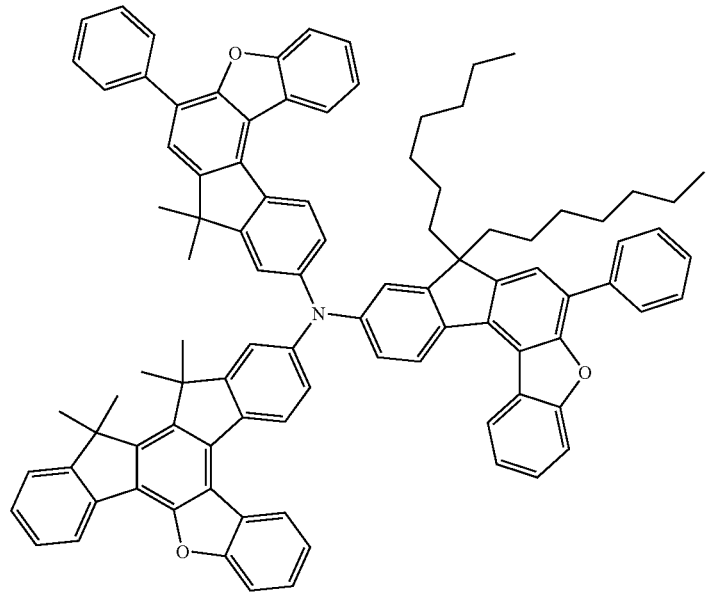 [SMILES: CCCCCCCC1(CCCCCCC)c2cc(N(c3ccc4c(c3)C(C)(C)c3cc(-c5ccccc5)c5oc6ccccc6c5c3-4)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]
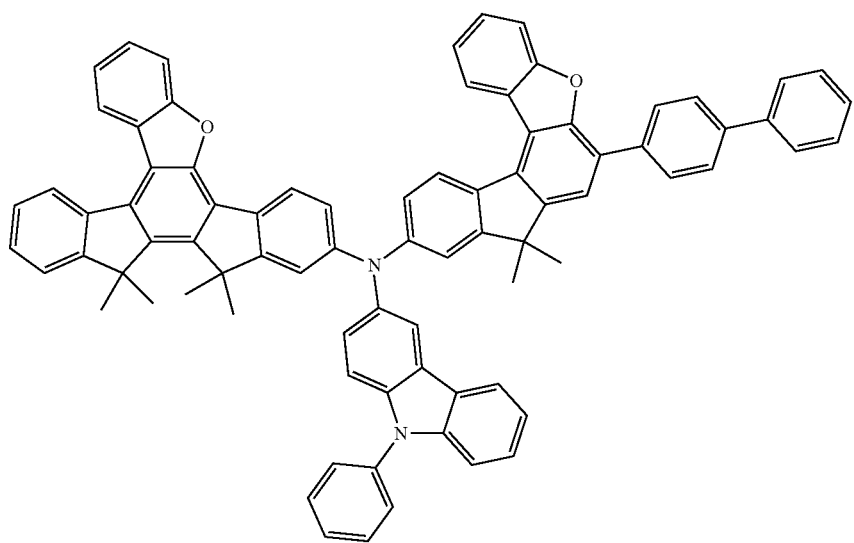 [SMILES: CC1(C)c2cc(N(c3ccc4c(c3)C(C)(C)c3c5c(c6c(oc7ccccc76)c3-4)-c3ccccc3C5(C)C)c3ccc4c(c3)c3ccccc3n4-c3ccccc3)ccc2-c2c1cc(-c1ccc(-c3ccccc3)cc1)c1oc3ccccc3c21]

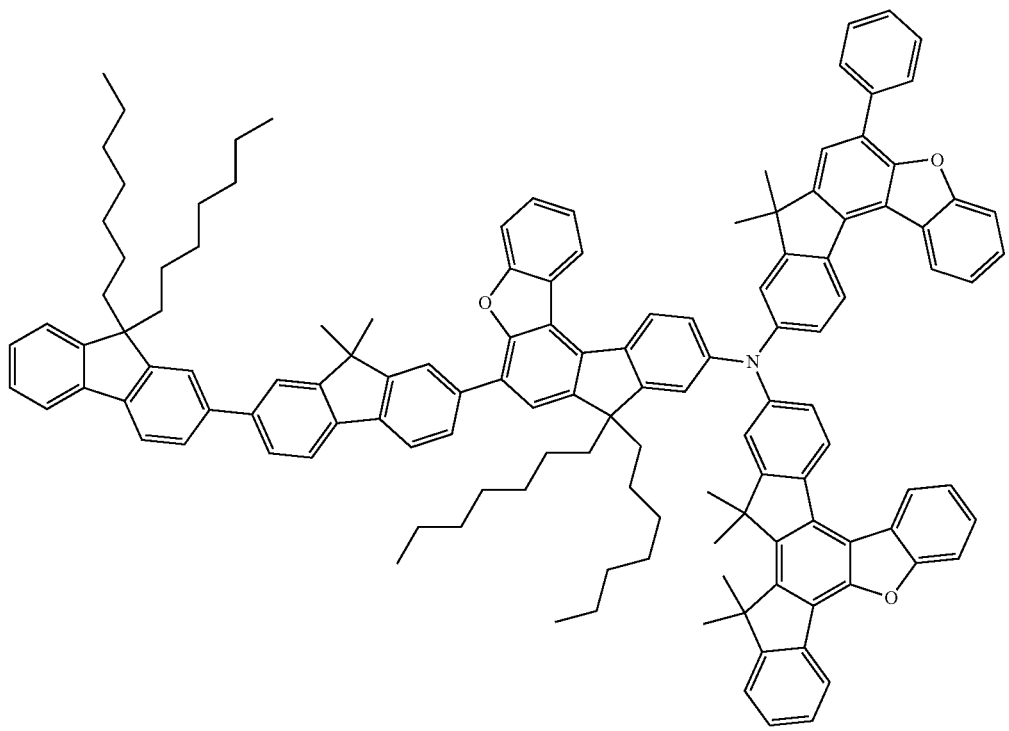 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7cc(-c9ccccc9)c9oc%10ccccc%10c9c7-8)c7ccc8c(c7)C(C)(C)c7c9c(c%10oc%11ccccc%11c%10c7-8)-c7ccccc7C9(C)C)cc5C6(CCCCCCC)CCCCCCC)ccc3-4)cc21]
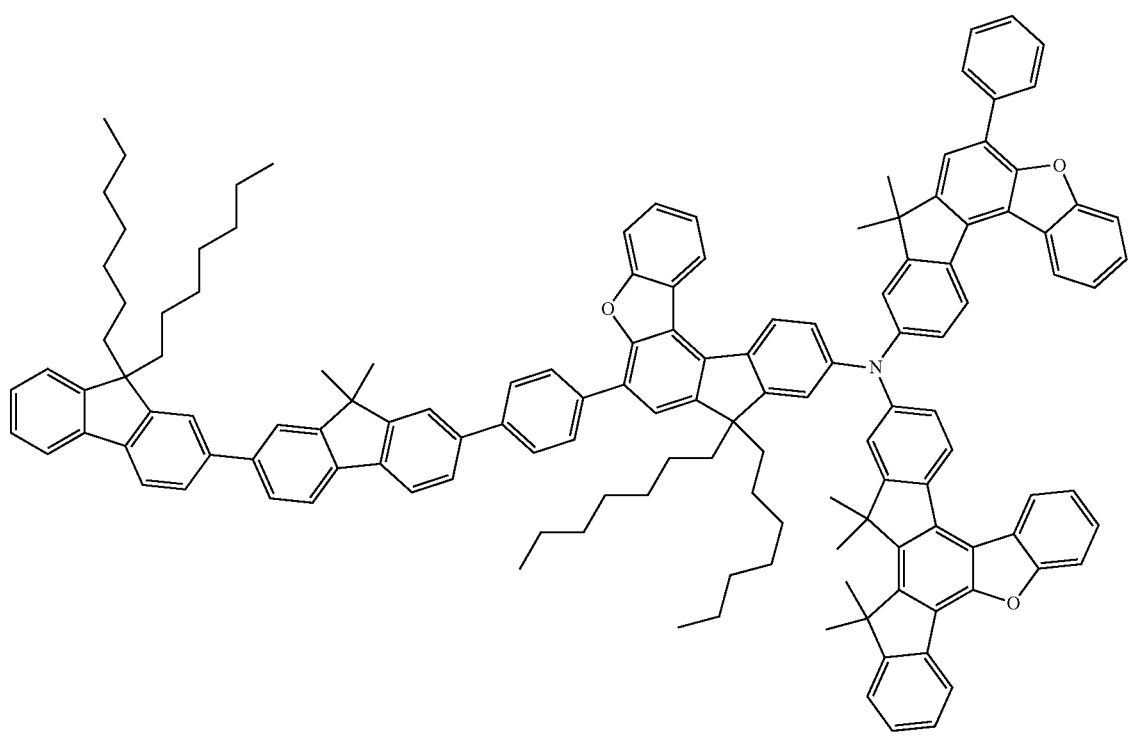 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8cc(-c%10ccccc%10)c%10oc%11ccccc%11c%10c8-9)c8ccc9c(c8)C(C)(C)c8c%10c(c%11oc%12ccccc%12c%11c8-9)-c8ccccc8C%10(C)C)cc6C7(CCCCCCC)CCCCCCC)cc5)ccc3-4)cc21]

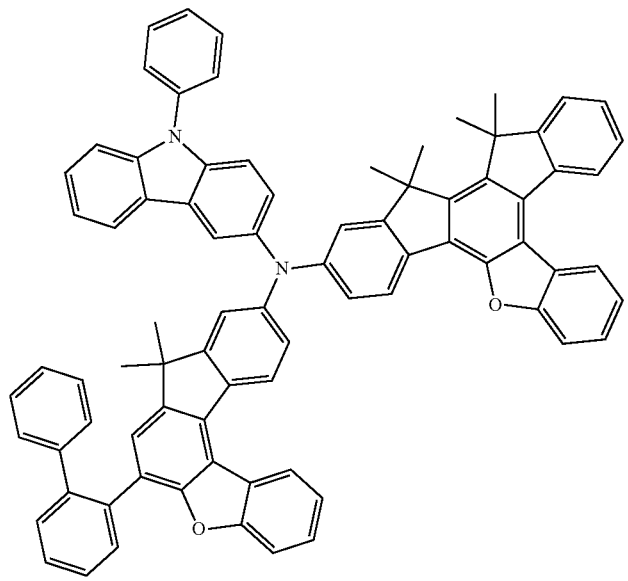 [SMILES: CC1(C)c2cc(N(c3ccc4c(c3)C(C)(C)c3c5c(c6c(oc7ccccc76)c3-4)-c3ccccc3C5(C)C)c3ccc4c(c3)c3ccccc3n4-c3ccccc3)ccc2-c2c1cc(-c1ccccc1-c1ccccc1)c1oc3ccccc3c21]
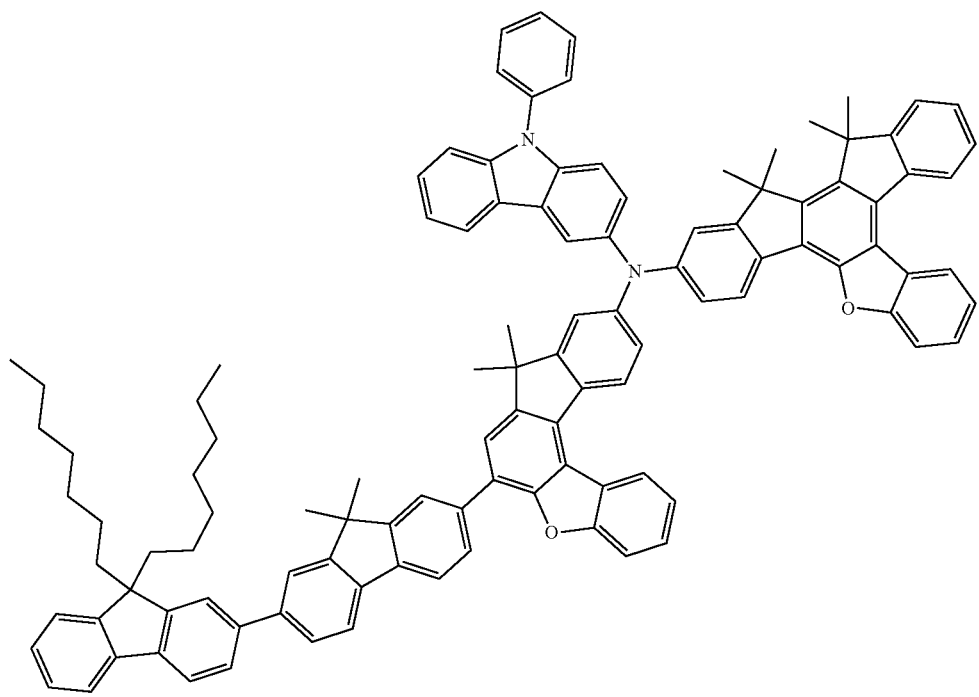 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10c(oc%11ccccc%11%10)c7-8)-c7ccccc7C9(C)C)c7ccc8c(c7)c7ccccc7n8-c7ccccc7)cc5C6(C)C)ccc3-4)cc21]

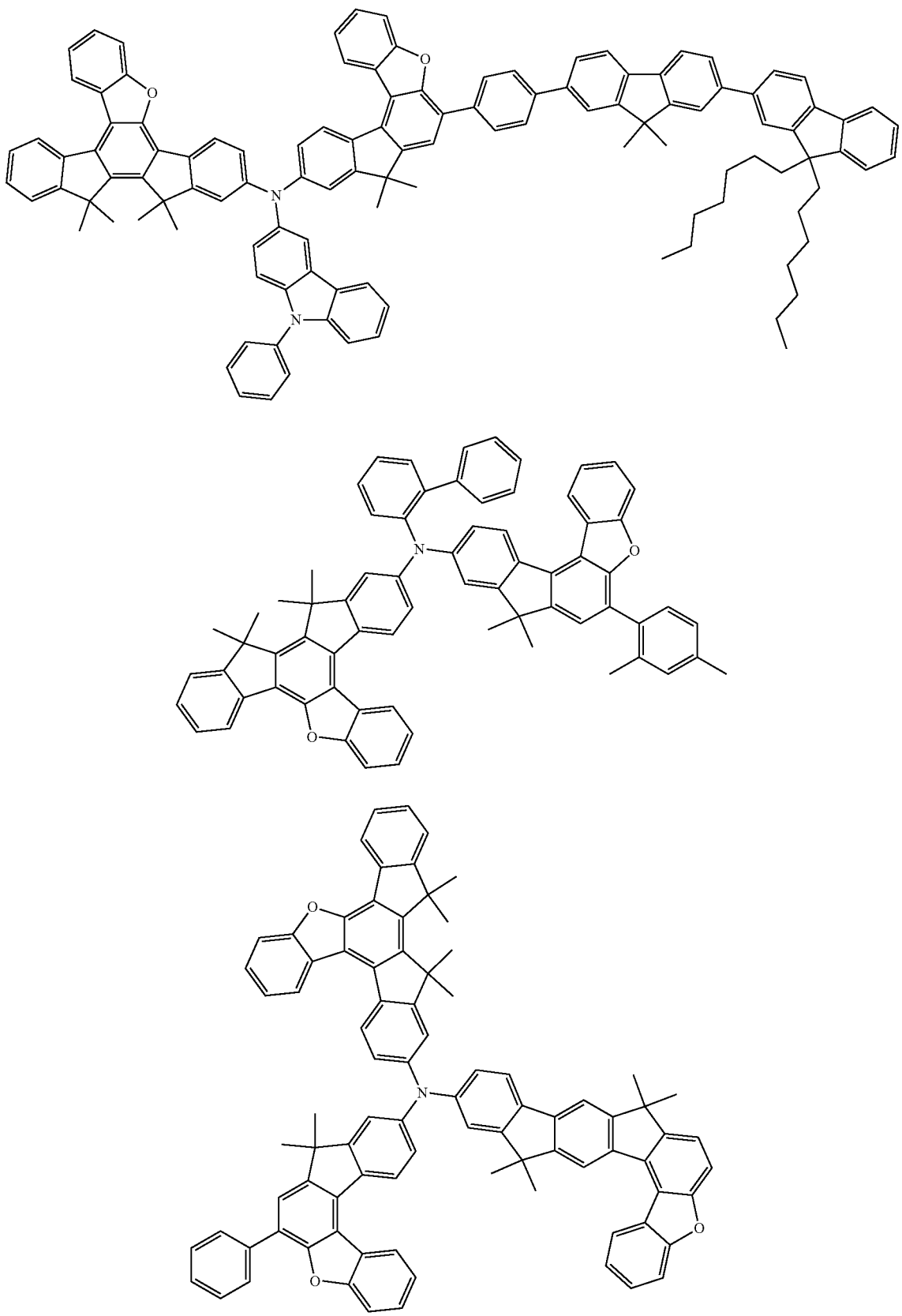

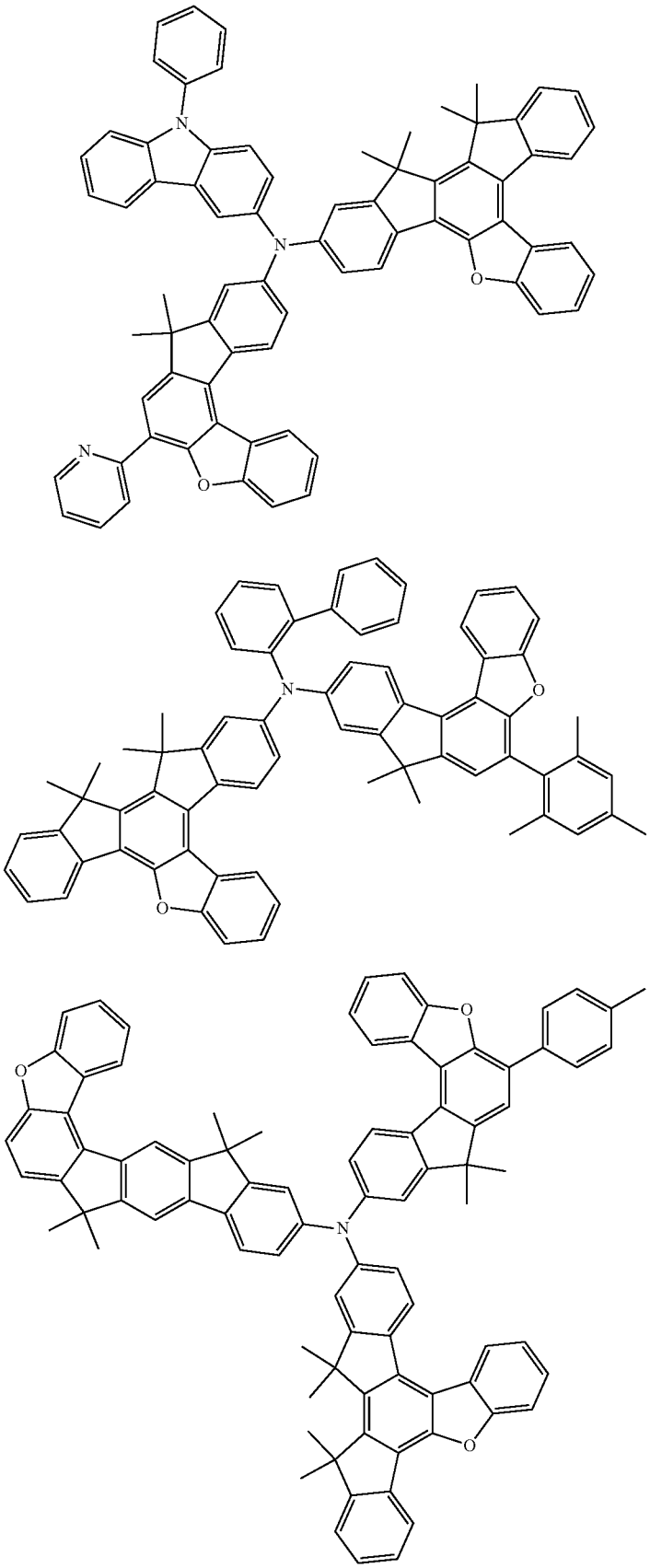

-continued
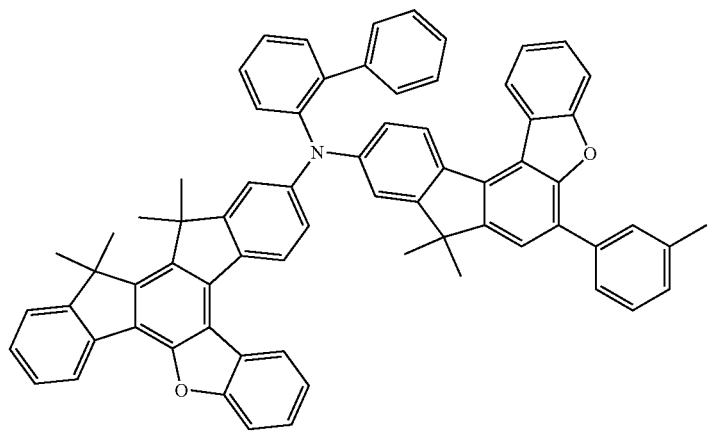 [SMILES: Cc1cccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccccc4-c4ccccc4)cc2C3(C)C)c1]
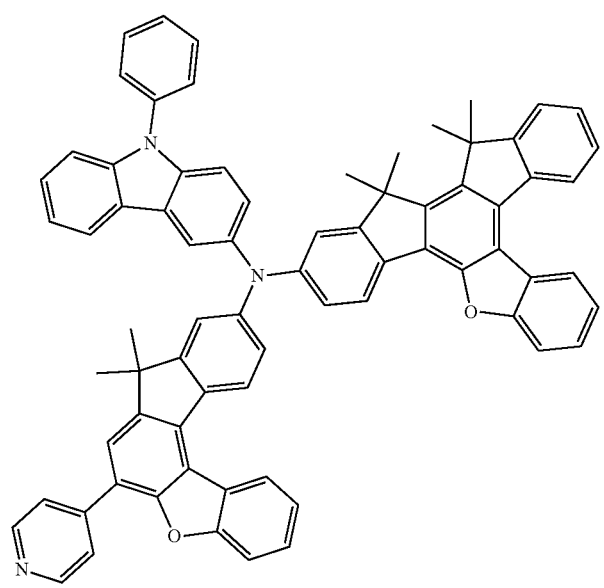 [SMILES: CC1(C)c2cc(N(c3ccc4c(c3)C(C)(C)c3c5c(c6c(oc7ccccc76)c3-4)-c3ccccc3C5(C)C)c3ccc4c(c3)c3ccccc3n4-c3ccccc3)ccc2-c2c1cc(-c1ccncc1)c1oc3ccccc3c21]
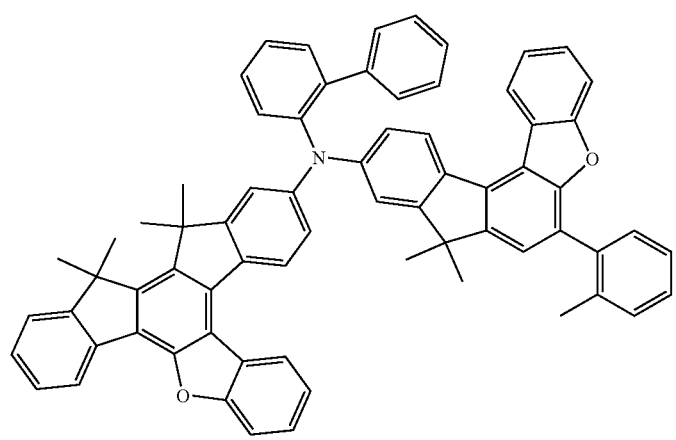 [SMILES: Cc1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3ccccc3-c3ccccc3)cc1C2(C)C]

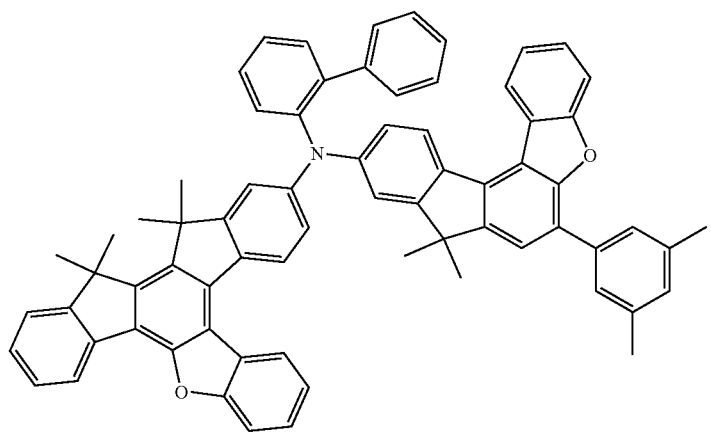 [SMILES: Cc1cc(C)cc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccccc4-c4ccccc4)cc2C3(C)C)c1]
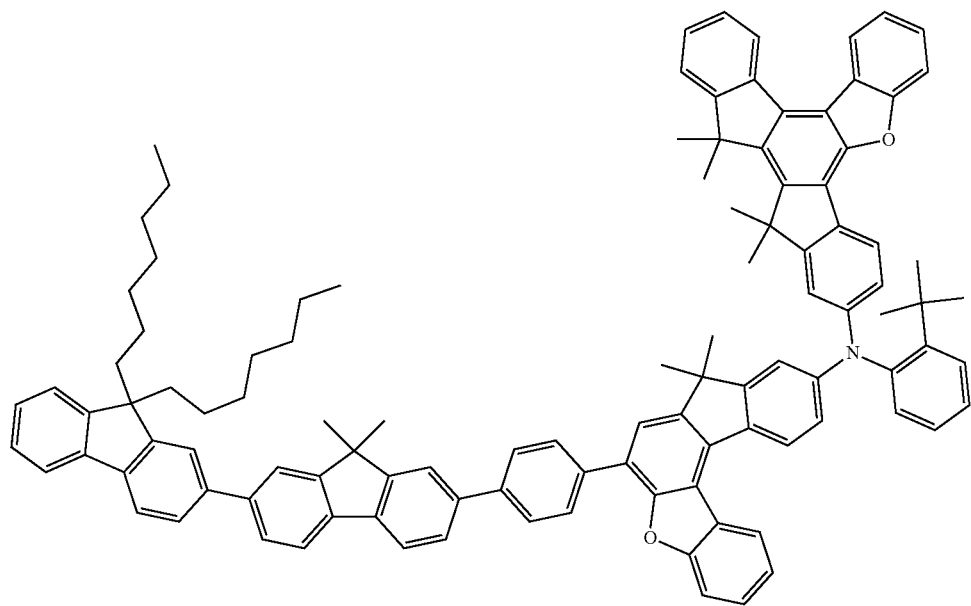 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11c(oc%12ccccc%12%11)c8-9)-c8ccccc8C%10(C)C)c8ccccc8C(C)(C)C)cc6C7(C)C)cc5)ccc3-4)cc21]

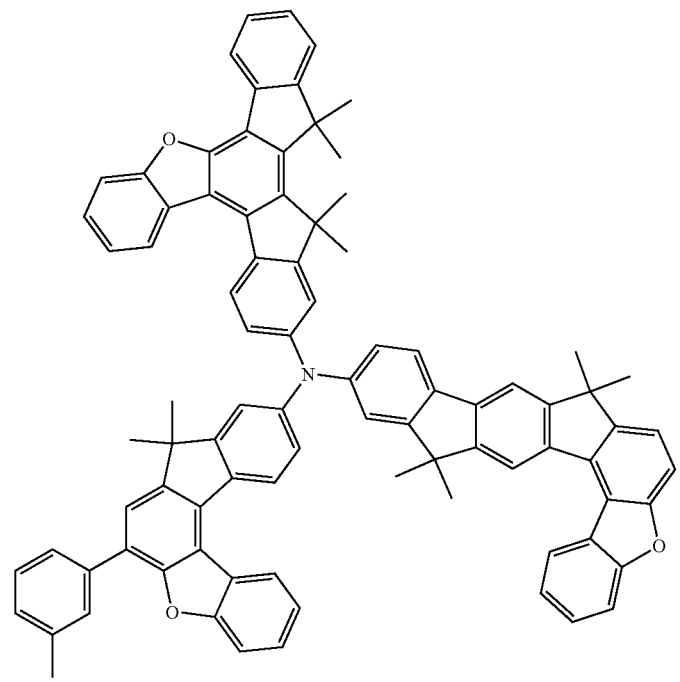 [SMILES: Cc1cccc(-c2cc3c(c4c2oc2ccccc24)-c2ccc(N(c4ccc5c(c4)C(C)(C)c4cc6c(cc4-5)C(C)(C)c4ccc5oc7ccccc7c5c4-6)c4ccc5c(c4)C(C)(C)c4c6c(c7oc8ccccc8c7c4-5)-c4ccccc4C6(C)C)cc2C3(C)C)c1]
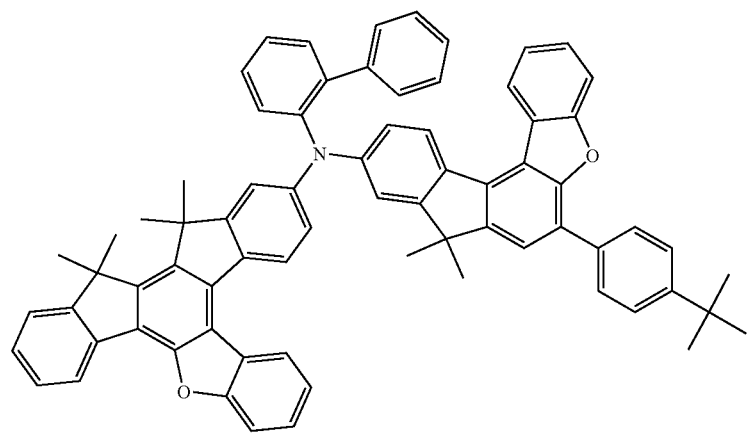 [SMILES: CC(C)(C)c1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccccc4-c4ccccc4)cc2C3(C)C)cc1]

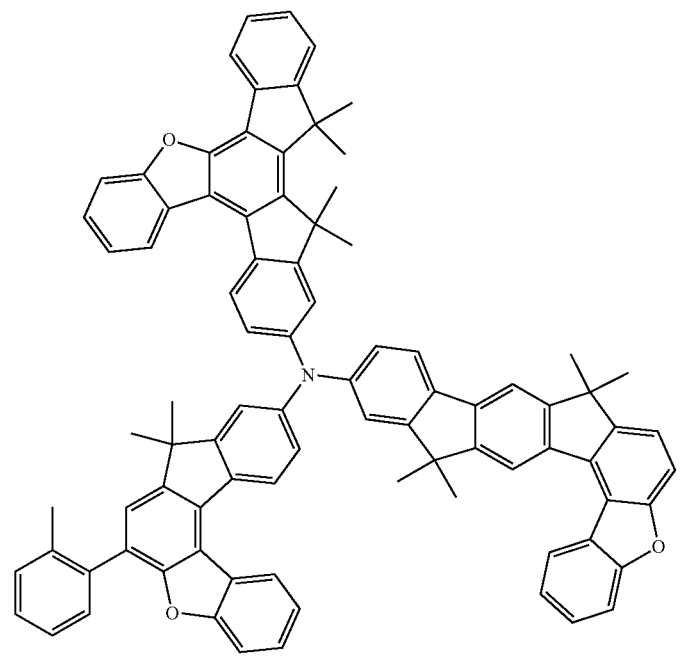 [SMILES: Cc1ccccc1-c1cc2c(c3c1oc1ccccc13)-c1ccc(N(c3ccc4c(c3)C(C)(C)c3cc5c(cc3-4)C(C)(C)c3ccc4oc6ccccc6c4c3-5)c3ccc4c(c3)C(C)(C)c3c5c(c6oc7ccccc7c6c3-4)-c3ccccc3C5(C)C)cc1C2(C)C]
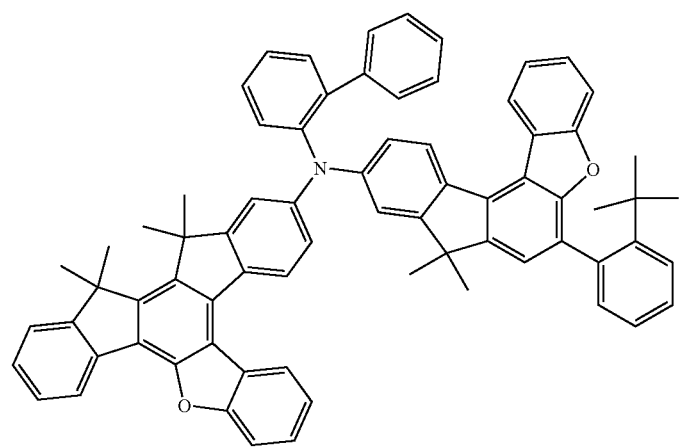 [SMILES: CC(C)(C)c1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3ccccc3-c3ccccc3)cc1C2(C)C]

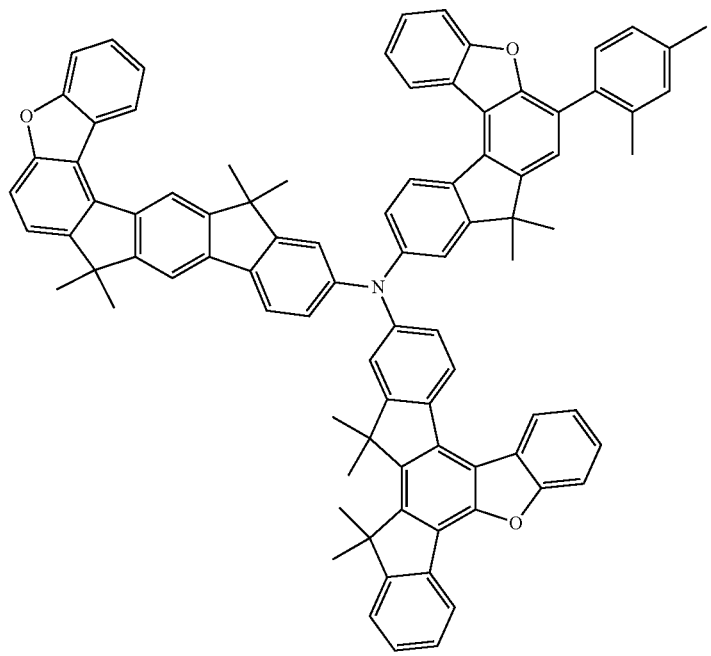 [SMILES: Cc1ccc(-c2cc3c(c4c2oc2ccccc24)-c2ccc(N(c4ccc5c(c4)C(C)(C)c4cc6c(cc4-5)C(C)(C)c4ccc5oc7ccccc7c5c4-6)c4ccc5c(c4)C(C)(C)c4c6c(c7oc8ccccc8c7c4-5)-c4ccccc4C6(C)C)cc2C3(C)C)c(C)c1]
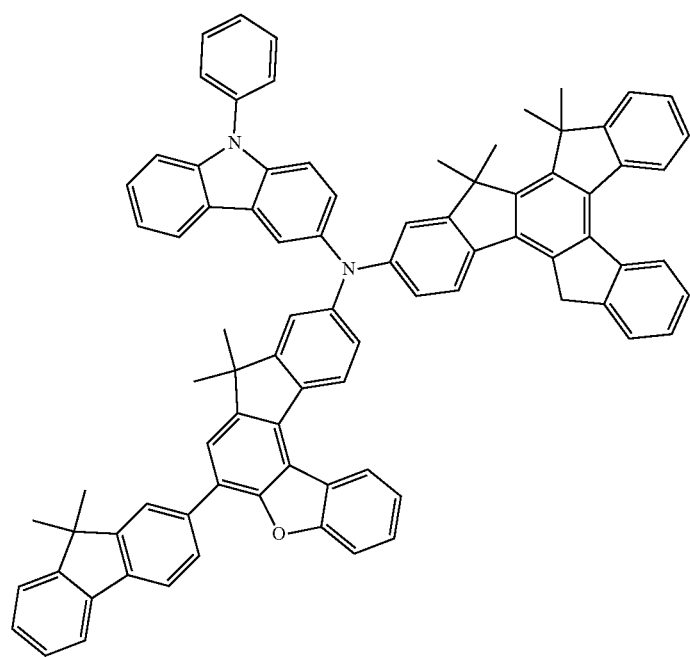 [SMILES: CC1(C)c2ccccc2-c2ccc(-c3cc4c(c5c3oc3ccccc35)-c3ccc(N(c5ccc6c(c5)C(C)(C)c5c-6c6c(c7c5C(C)(C)c5ccccc5-7)-c5ccccc5C6)c5ccc6c(c5)c5ccccc5n6-c5ccccc5)cc3C4(C)C)cc21]

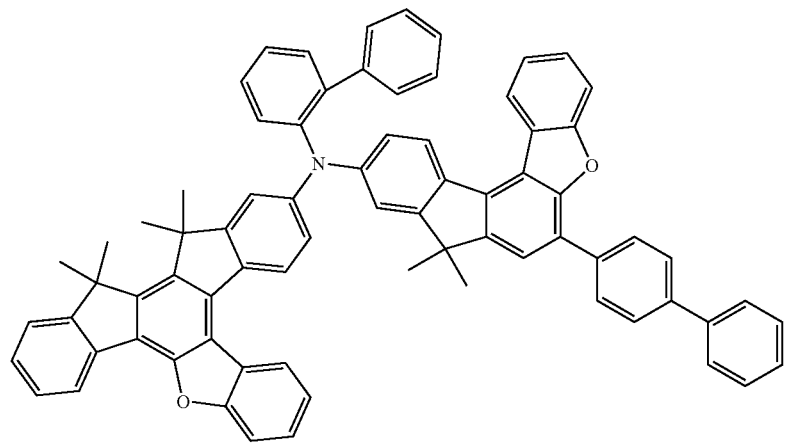 [SMILES: CC1(C)c2cc(N(c3ccc4c(c3)C(C)(C)c3c5c(c6oc7ccccc7c6c3-4)-c3ccccc3C5(C)C)c3ccccc3-c3ccccc3)ccc2-c2c1cc(-c1ccc(-c3ccccc3)cc1)c1oc3ccccc3c21]
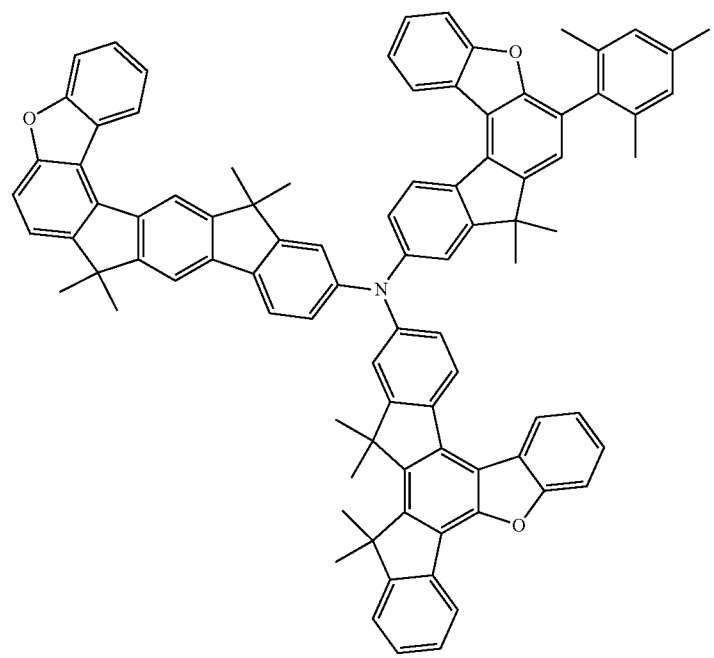 [SMILES: Cc1cc(C)c(-c2cc3c(c4c2oc2ccccc24)-c2ccc(N(c4ccc5c(c4)C(C)(C)c4cc6c(cc4-5)C(C)(C)c4ccc5oc7ccccc7c5c4-6)c4ccc5c(c4)C(C)(C)c4c6c(c7oc8ccccc8c7c4-5)-c4ccccc4C6(C)C)cc2C3(C)C)c(C)c1]
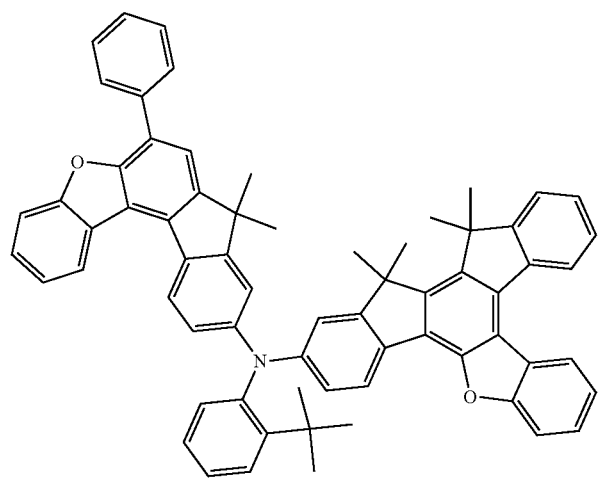 [SMILES: CC(C)(C)c1ccccc1N(c1ccc2c(c1)C(C)(C)c1cc(-c3ccccc3)c3oc4ccccc4c3c1-2)c1ccc2c(c1)C(C)(C)c1c3c(c4c(oc5ccccc54)c1-2)-c1ccccc1C3(C)C]

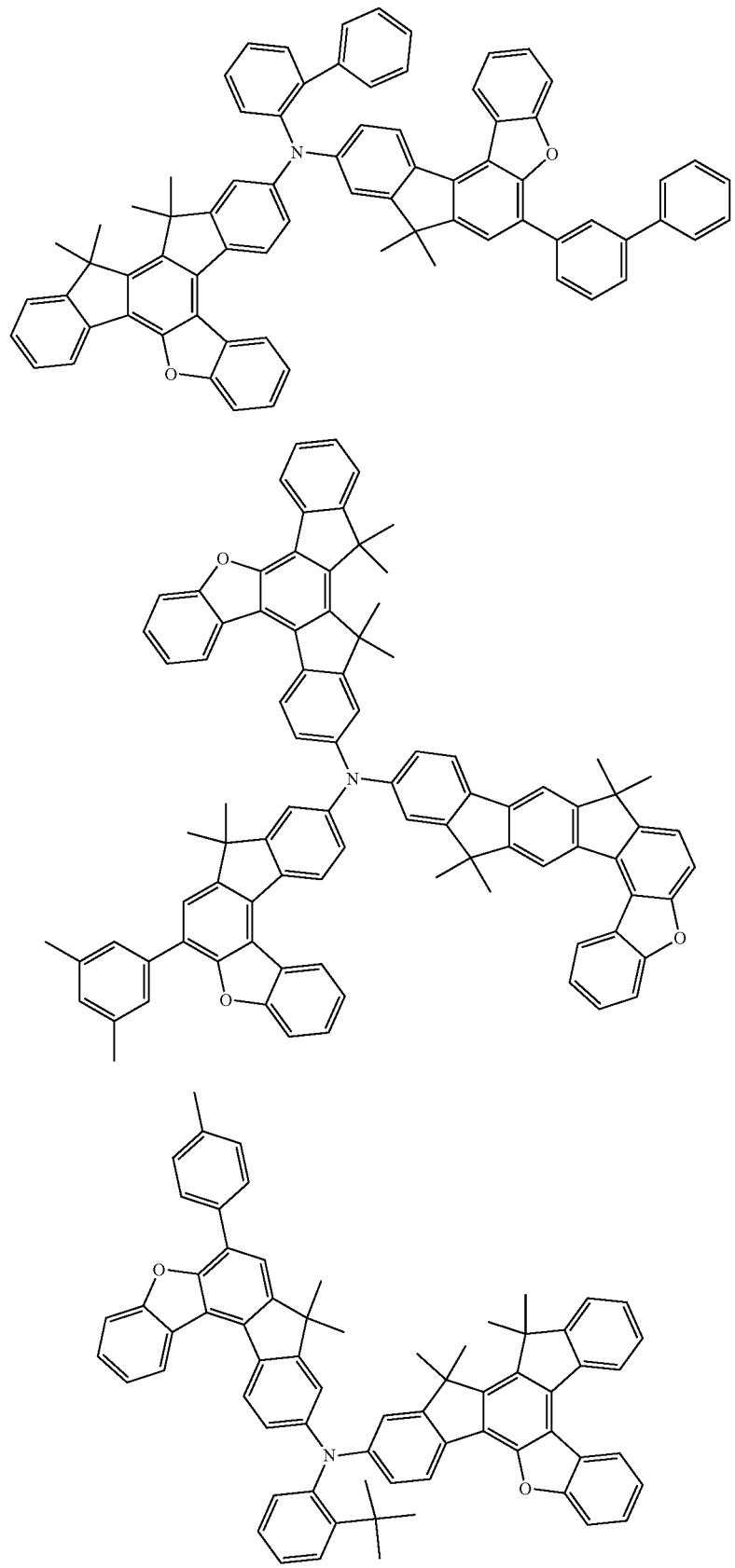

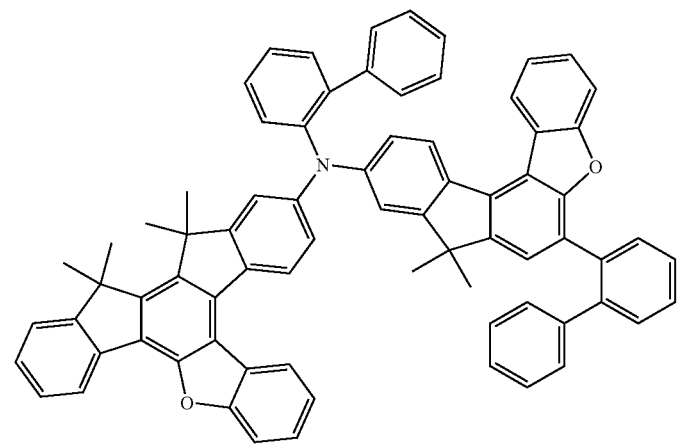 [SMILES: CC1(C)c2cc(N(c3ccc4c(c3)C(C)(C)c3c5c(c6oc7ccccc7c6c3-4)-c3ccccc3C5(C)C)c3ccccc3-c3ccccc3)ccc2-c2c1cc(-c1ccccc1-c1ccccc1)c1oc3ccccc3c21]
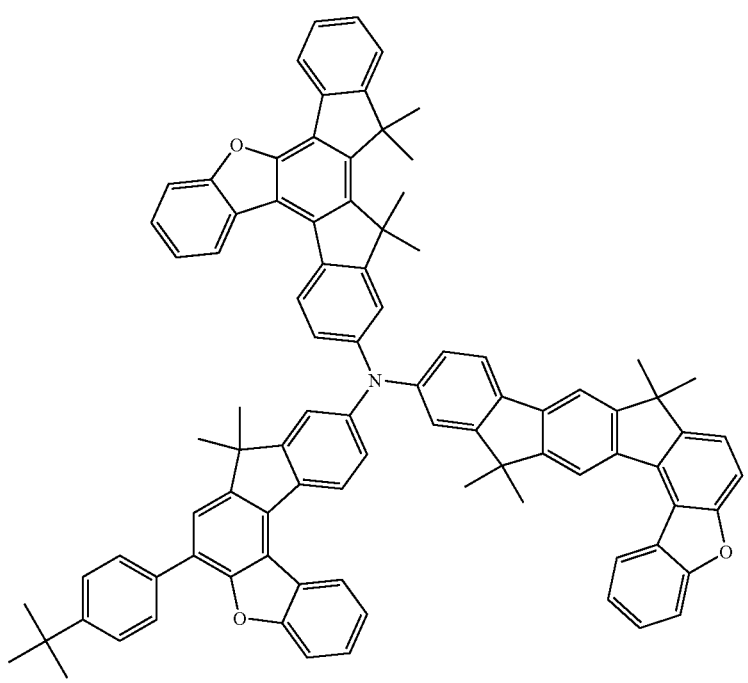 [SMILES: CC(C)(C)c1ccc(-c2cc3c(c4c2oc2ccccc24)-c2ccc(N(c4ccc5c(c4)C(C)(C)c4cc6c(cc4-5)C(C)(C)c4ccc5oc7ccccc7c5c4-6)c4ccc5c(c4)C(C)(C)c4c6c(c7oc8ccccc8c7c4-5)-c4ccccc4C6(C)C)cc2C3(C)C)cc1]
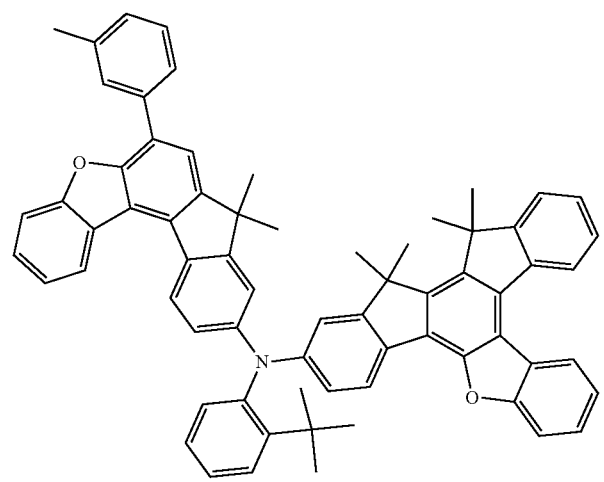 [SMILES: Cc1cccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccccc4C(C)(C)C)cc2C3(C)C)c1]

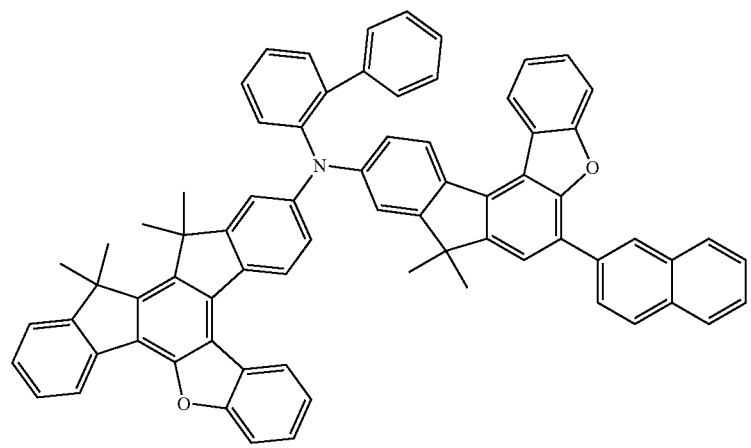 [SMILES: CC1(C)c2cc(N(c3ccc4c(c3)C(C)(C)c3c5c(c6oc7ccccc7c6c3-4)-c3ccccc3C5(C)C)c3ccccc3-c3ccccc3)ccc2-c2c1cc(-c1ccc3ccccc3c1)c1oc3ccccc3c21]
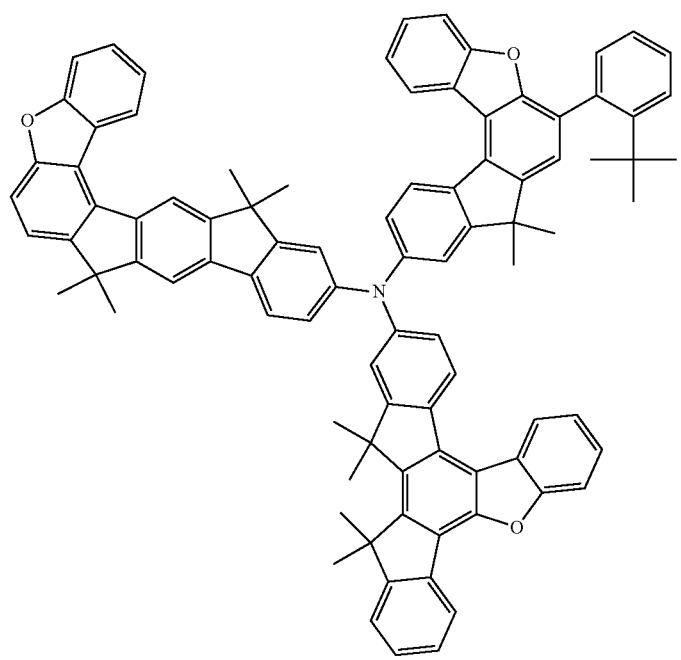 [SMILES: CC(C)(C)c1ccccc1-c1cc2c(c3c1oc1ccccc13)-c1ccc(N(c3ccc4c(c3)C(C)(C)c3cc5c(cc3-4)C(C)(C)c3ccc4oc6ccccc6c4c3-5)c3ccc4c(c3)C(C)(C)c3c5c(c6oc7ccccc7c6c3-4)-c3ccccc3C5(C)C)cc1C2(C)C]
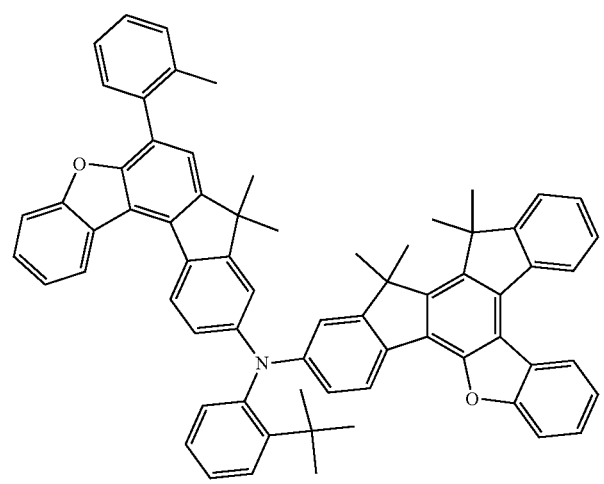 [SMILES: Cc1ccccc1-c1cc2c(c3c1oc1ccccc13)-c1ccc(N(c3ccc4c(c3)C(C)(C)c3c5c(c6c(oc7ccccc76)c3-4)-c3ccccc3C5(C)C)c3ccccc3C(C)(C)C)cc1C2(C)C]

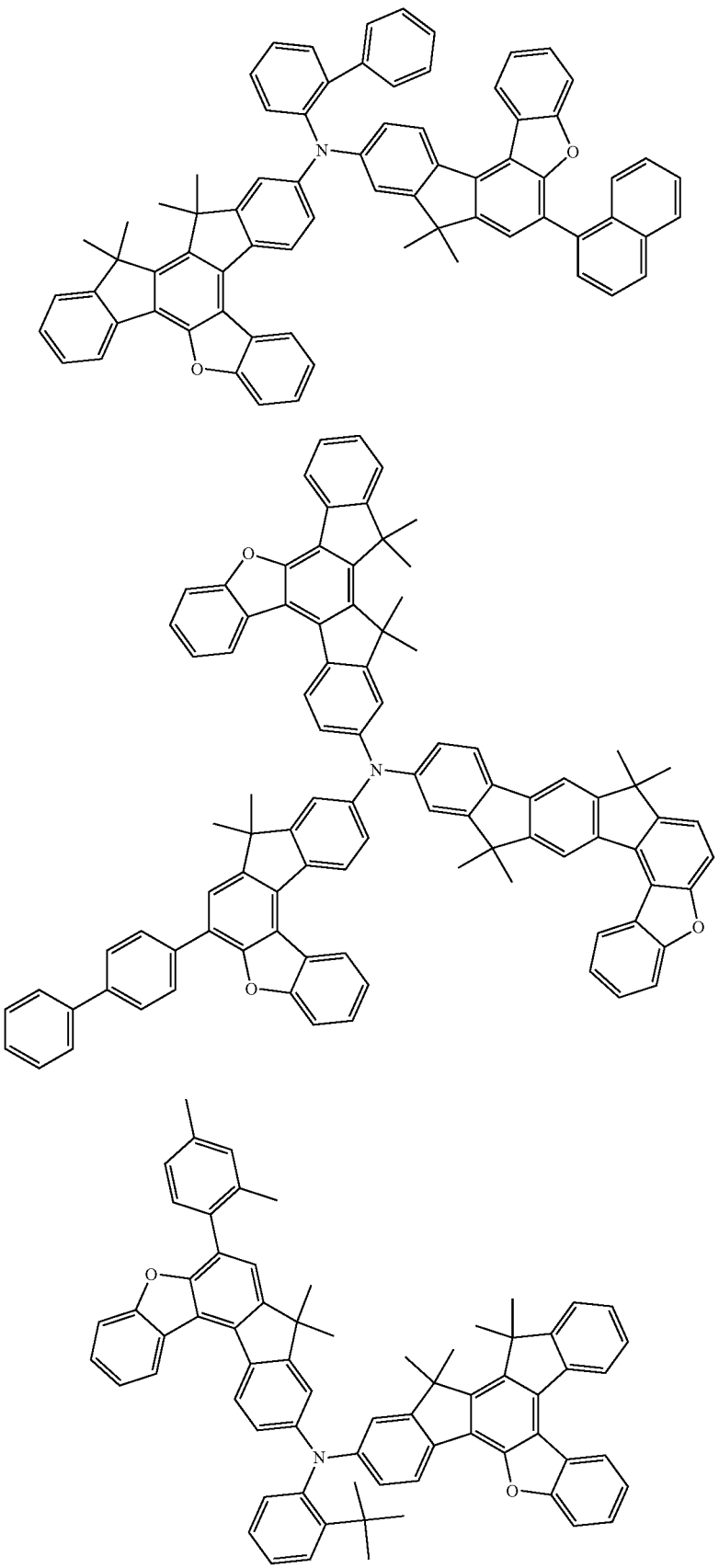

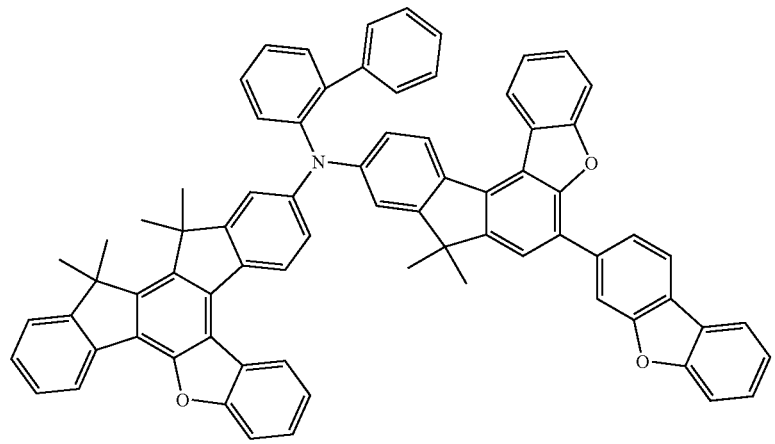 [SMILES: CC1(C)c2cc(N(c3ccc4c(c3)C(C)(C)c3c5c(c6oc7ccccc7c6c3-4)-c3ccccc3C5(C)C)c3ccccc3-c3ccccc3)ccc2-c2c1cc(-c1ccc3c(c1)oc1ccccc13)c1oc3ccccc3c21]
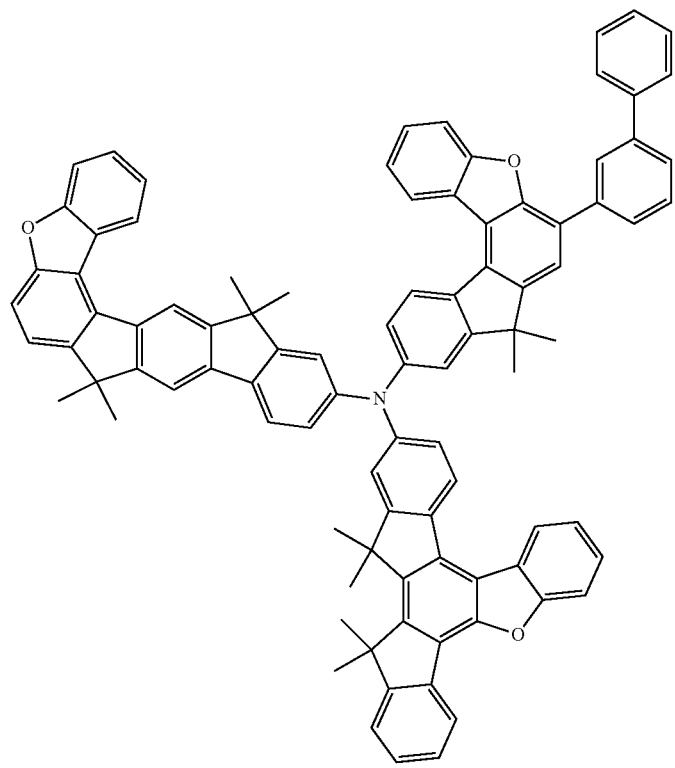 [SMILES: CC1(C)c2cc(N(c3ccc4c(c3)C(C)(C)c3cc(-c5cccc(-c6ccccc6)c5)c5oc6ccccc6c5c3-4)c3ccc4c(c3)C(C)(C)c3c5c(c6oc7ccccc7c6c3-4)-c3ccccc3C5(C)C)ccc2-c2cc3c(cc21)-c1c(ccc2oc4ccccc4c12)C3(C)C]

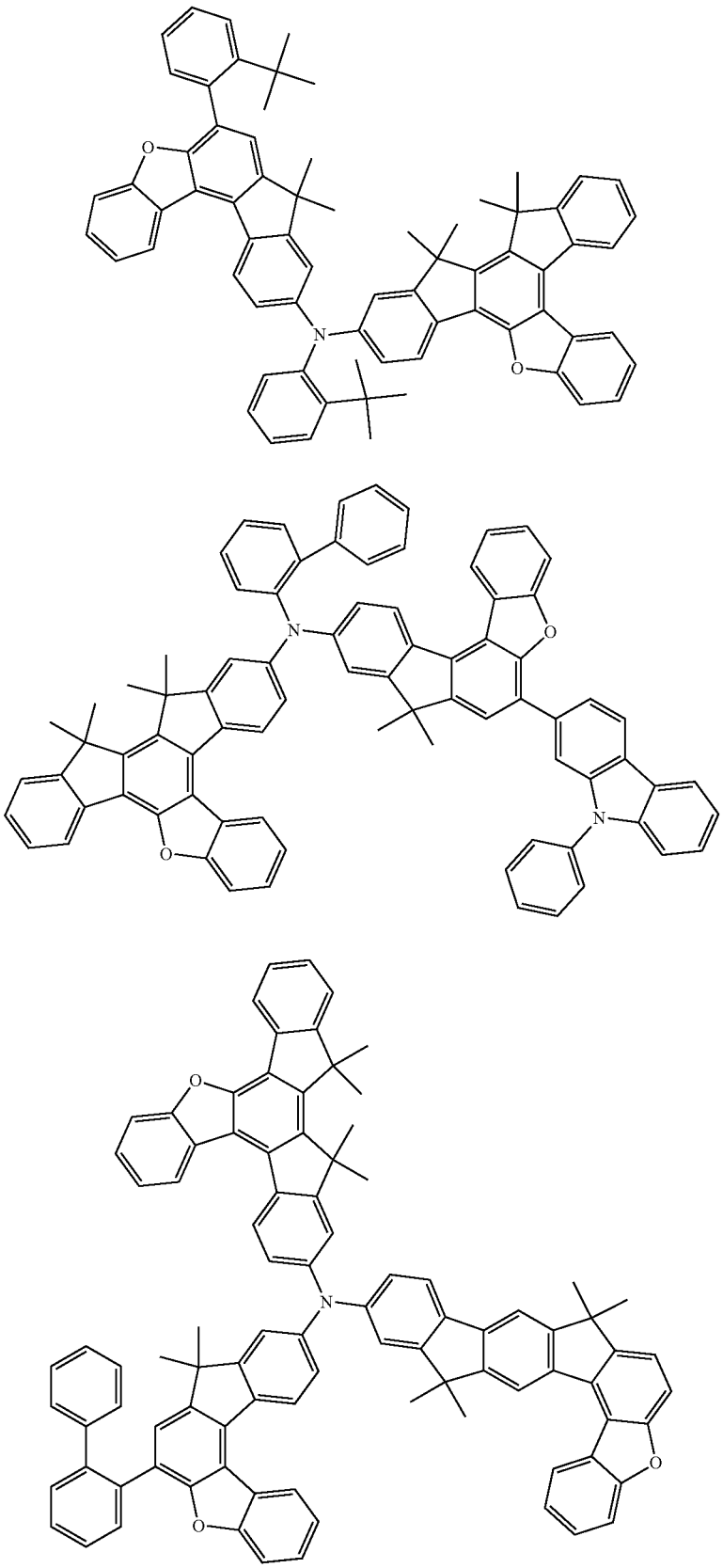

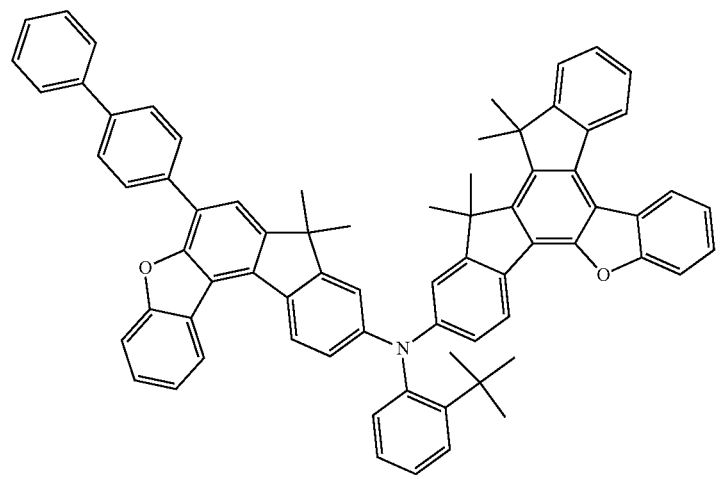 [SMILES: CC(C)(C)c1ccccc1N(c1ccc2c(c1)C(C)(C)c1cc(-c3ccc(-c4ccccc4)cc3)c3oc4ccccc4c3c1-2)c1ccc2c(c1)C(C)(C)c1c3c(c4c(oc5ccccc54)c1-2)-c1ccccc1C3(C)C]
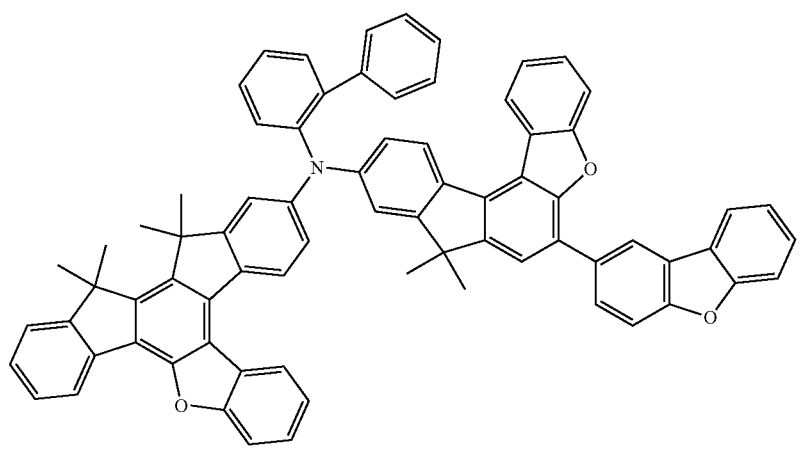 [SMILES: CC1(C)c2cc(N(c3ccc4c(c3)C(C)(C)c3c5c(c6oc7ccccc7c6c3-4)-c3ccccc3C5(C)C)c3ccccc3-c3ccccc3)ccc2-c2c1cc(-c1ccc3oc4ccccc4c3c1)c1oc3ccccc3c21]
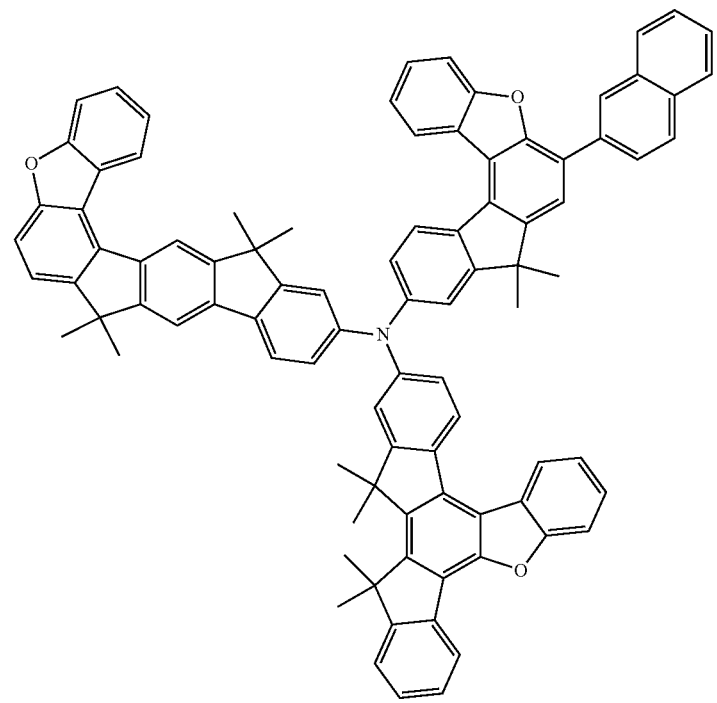 [SMILES: CC1(C)c2cc(N(c3ccc4c(c3)C(C)(C)c3cc(-c5ccc6ccccc6c5)c5oc6ccccc6c5c3-4)c3ccc4c(c3)C(C)(C)c3c5c(c6oc7ccccc7c6c3-4)-c3ccccc3C5(C)C)ccc2-c2cc3c(cc21)-c1c(ccc2oc4ccccc4c12)C3(C)C]

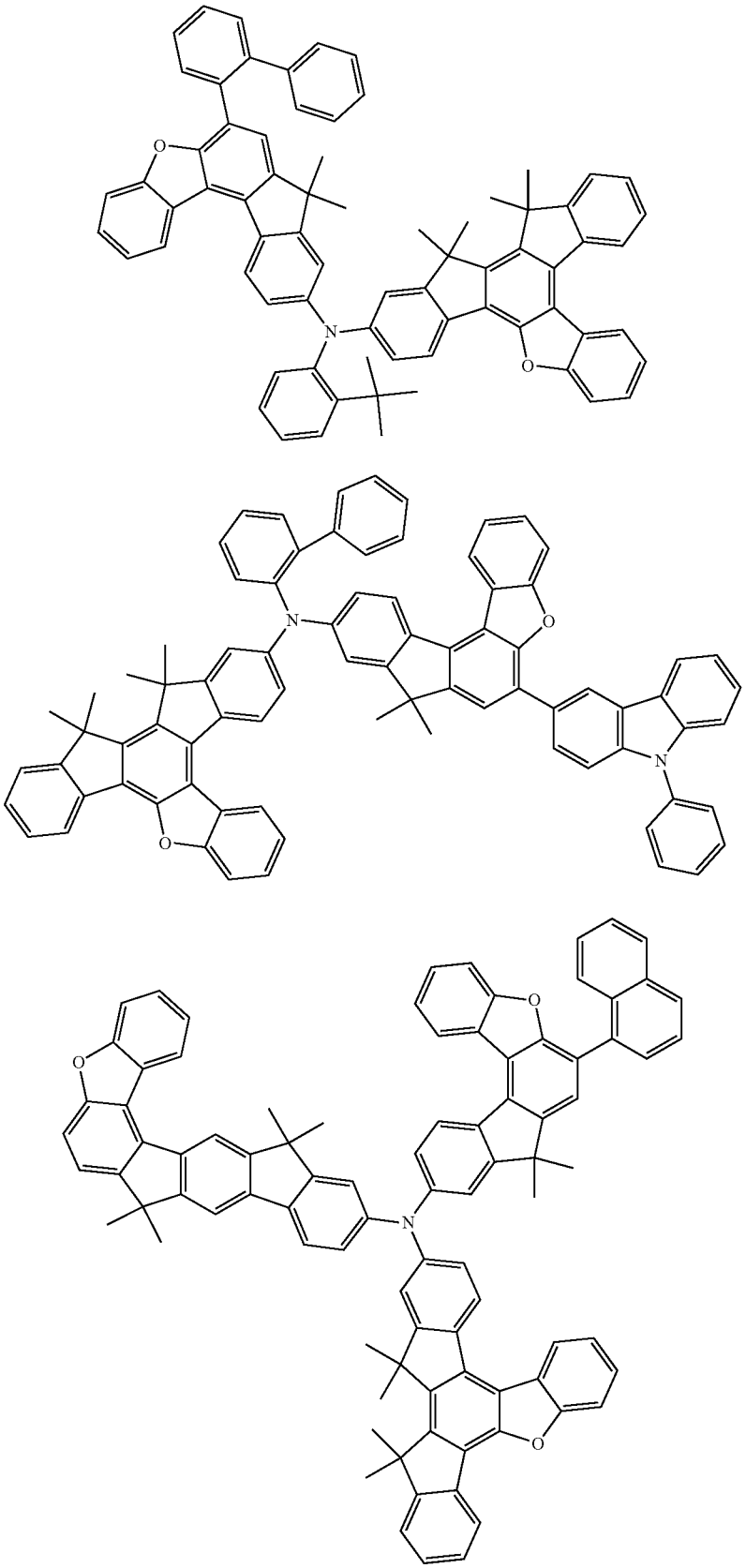

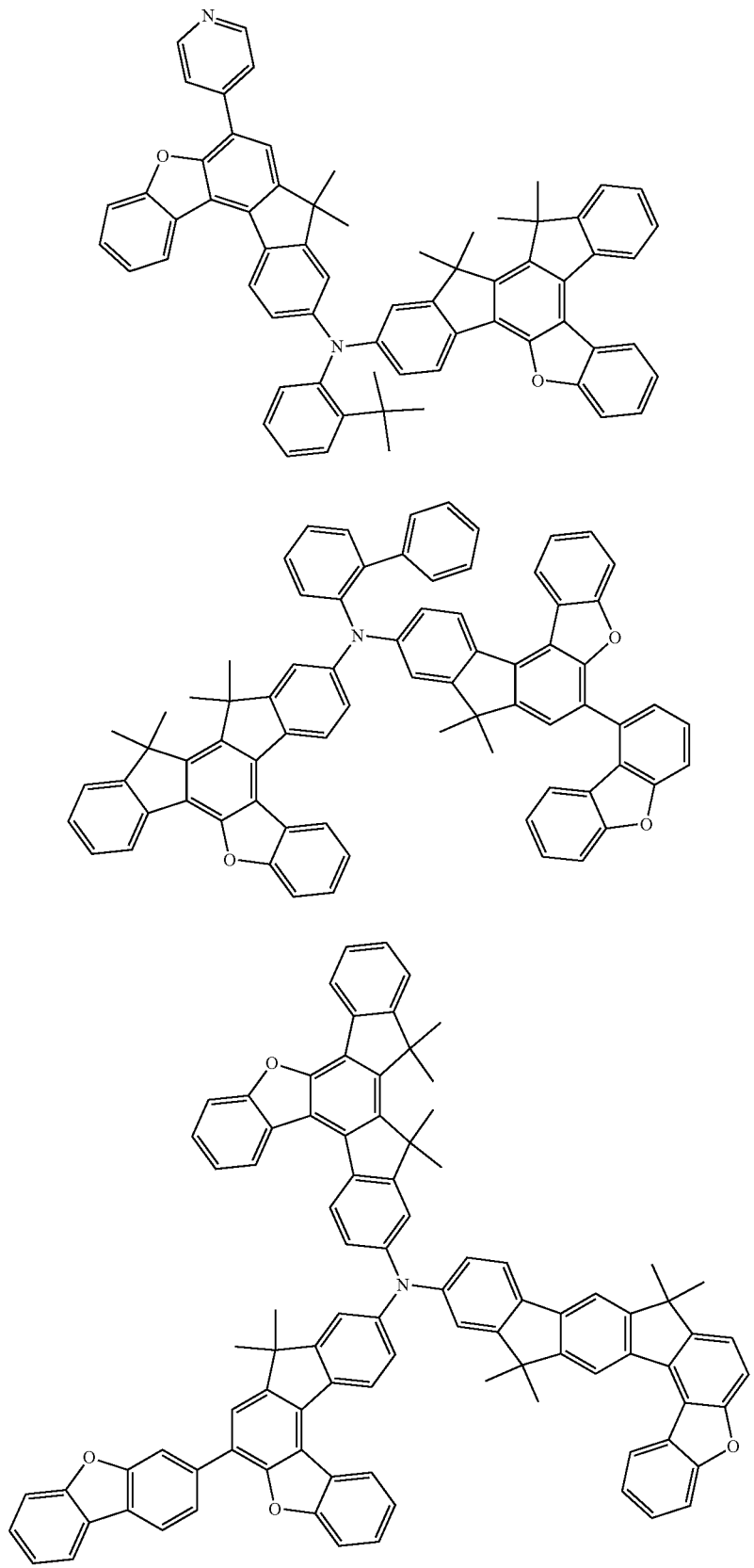

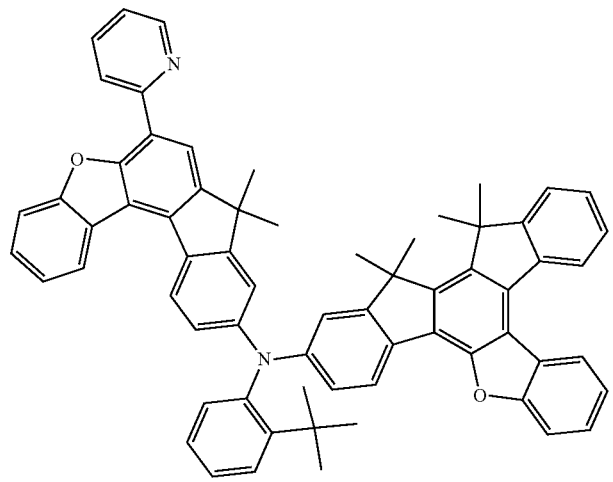 [SMILES: CC(C)(C)c1ccccc1N(c1ccc2c(c1)C(C)(C)c1cc(-c3ccccn3)c3oc4ccccc4c3c1-2)c1ccc2c(c1)C(C)(C)c1c3c(c4c(oc5ccccc54)c1-2)-c1ccccc1C3(C)C]
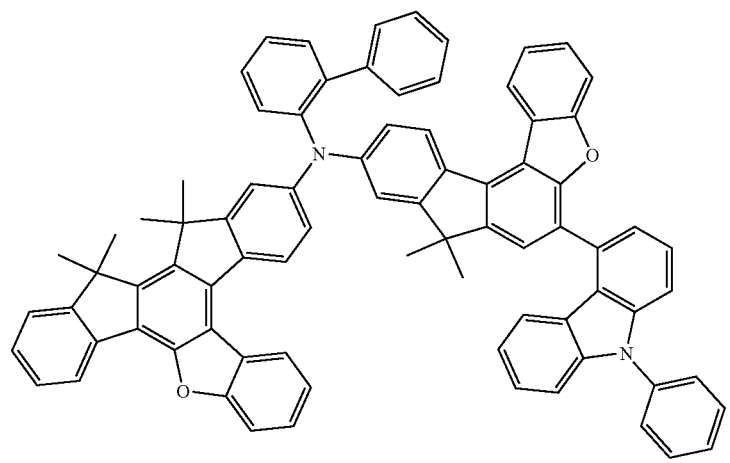 [SMILES: CC1(C)c2cc(N(c3ccc4c(c3)C(C)(C)c3c5c(c6oc7ccccc7c6c3-4)-c3ccccc3C5(C)C)c3ccccc3-c3ccccc3)ccc2-c2c1cc(-c1cccc3c1c1ccccc1n3-c1ccccc1)c1oc3ccccc3c21]
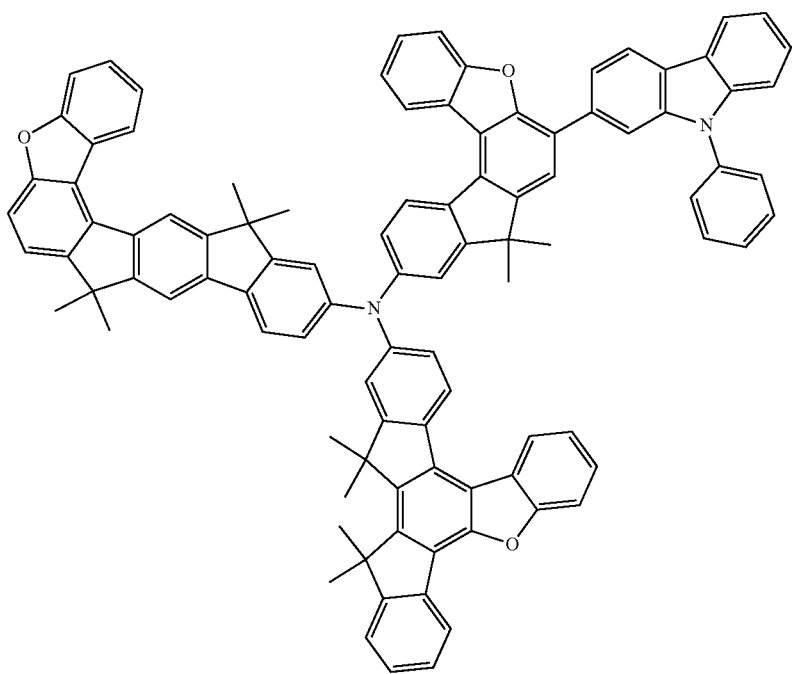 [SMILES: CC1(C)c2cc(N(c3ccc4c(c3)C(C)(C)c3cc(-c5ccc6c7ccccc7n(-c7ccccc7)c6c5)c5oc6ccccc6c5c3-4)c3ccc4c(c3)C(C)(C)c3c5c(c6oc7ccccc7c6c3-4)-c3ccccc3C5(C)C)ccc2-c2cc3c(cc21)-c1c(ccc2oc4ccccc4c12)C3(C)C]

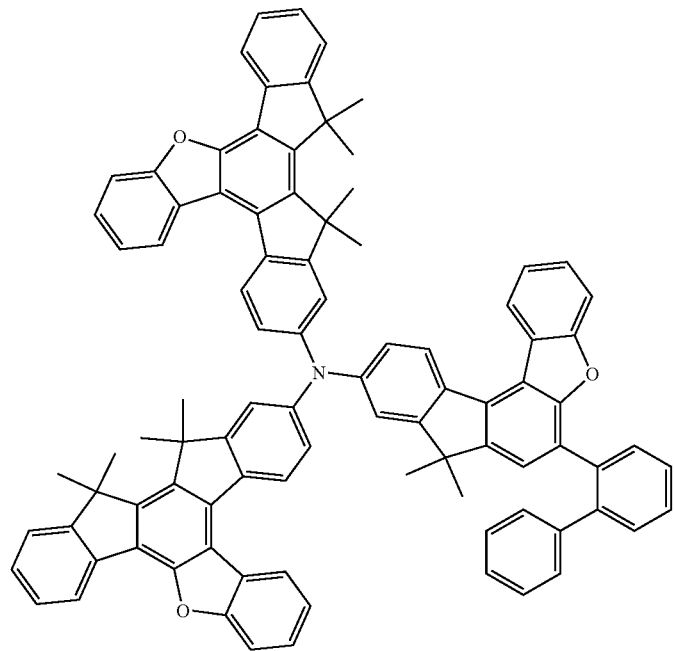 [SMILES: CC1(C)c2cc(N(c3ccc4c(c3)C(C)(C)c3c5c(c6oc7ccccc7c6c3-4)-c3ccccc3C5(C)C)c3ccc4c(c3)C(C)(C)c3c5c(c6oc7ccccc7c6c3-4)-c3ccccc3C5(C)C)ccc2-c2c1cc(-c1ccccc1-c1ccccc1)c1oc3ccccc3c21]
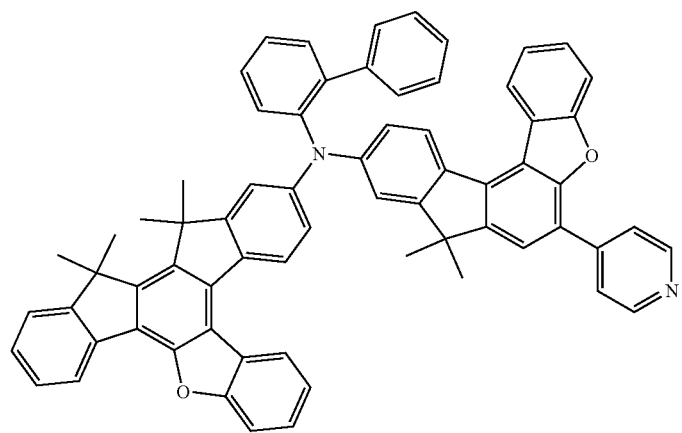 [SMILES: CC1(C)c2cc(N(c3ccc4c(c3)C(C)(C)c3c5c(c6oc7ccccc7c6c3-4)-c3ccccc3C5(C)C)c3ccccc3-c3ccccc3)ccc2-c2c1cc(-c1ccncc1)c1oc3ccccc3c21]

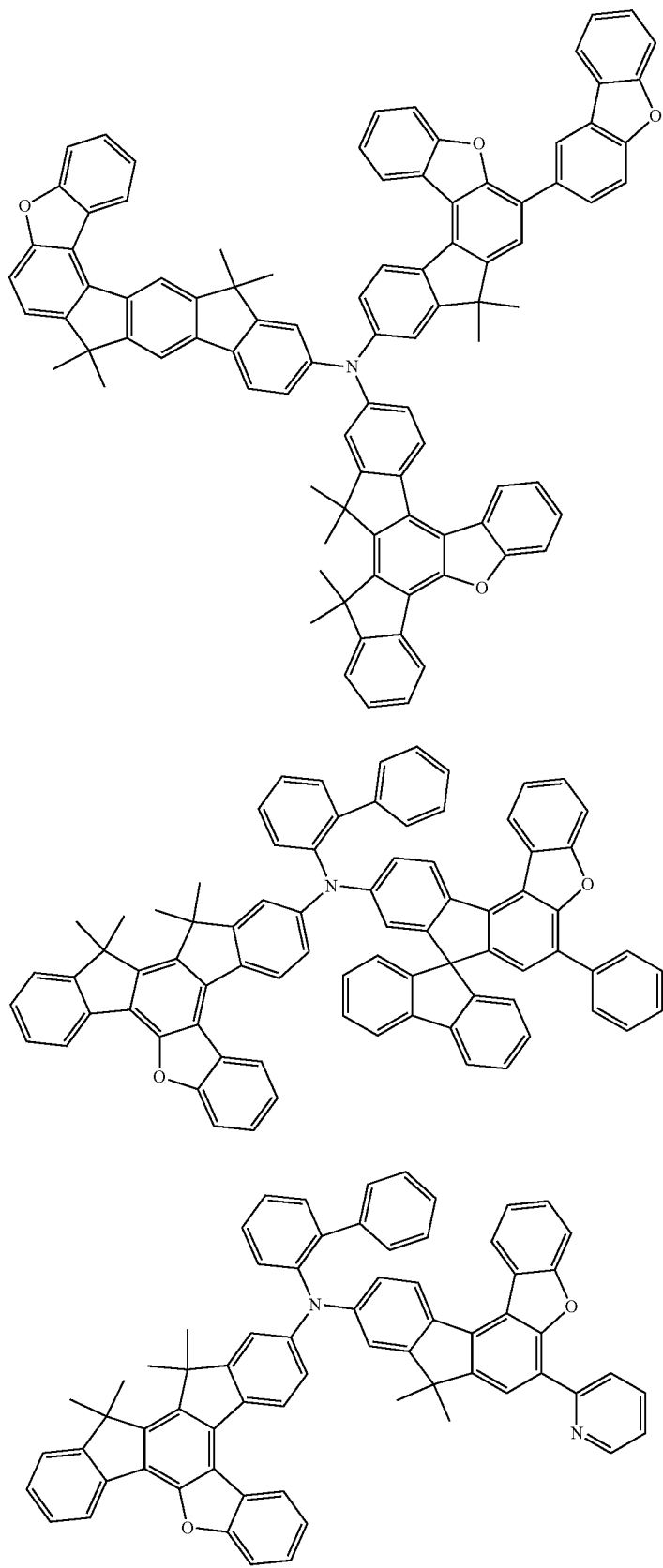

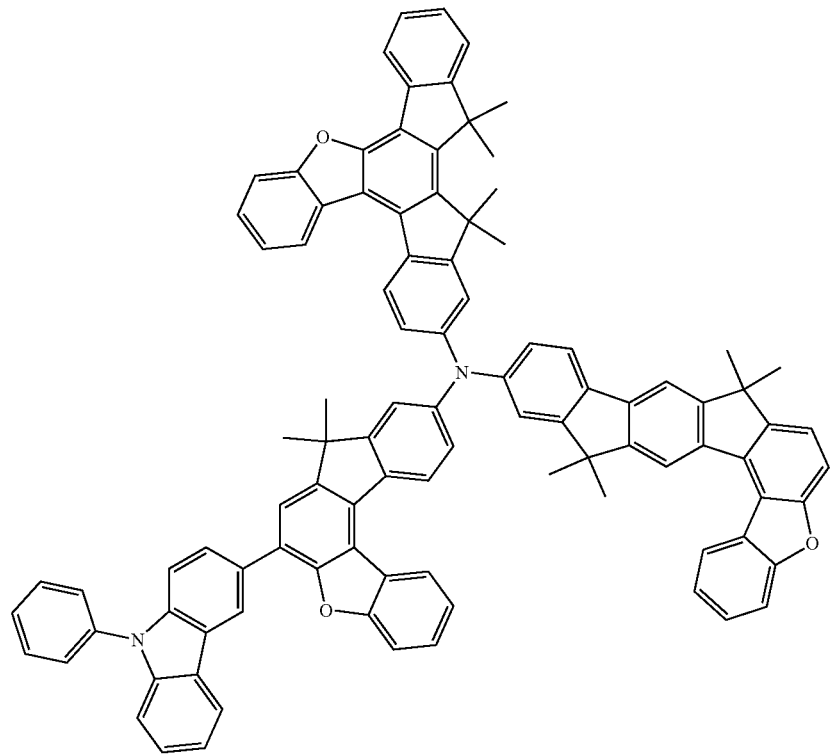 [SMILES: CC1(C)c2cc(N(c3ccc4c(c3)C(C)(C)c3cc(-c5ccc6c(c5)c5ccccc5n6-c5ccccc5)c5oc6ccccc6c5c3-4)c3ccc4c(c3)C(C)(C)c3c5c(c6oc7ccccc7c6c3-4)-c3ccccc3C5(C)C)ccc2-c2cc3c(cc21)-c1c(ccc2oc4ccccc4c12)C3(C)C]
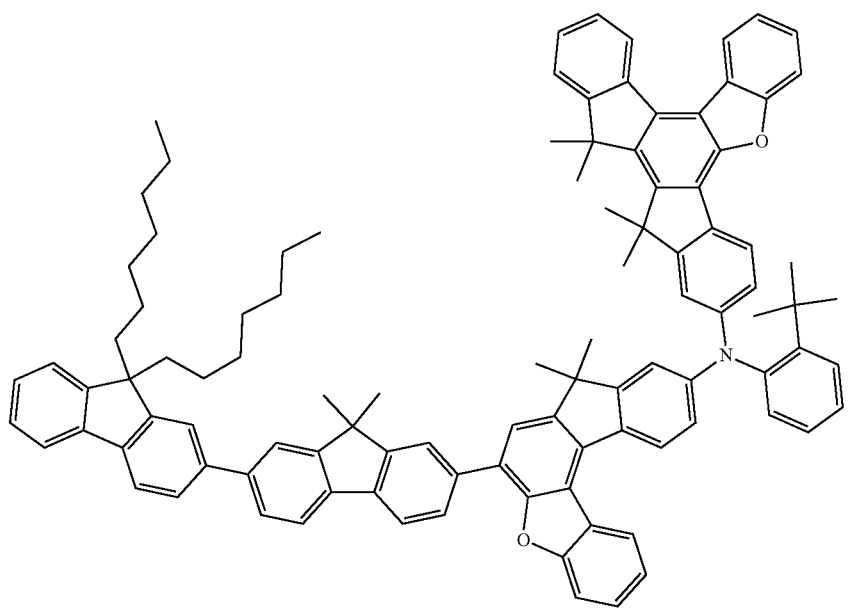 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10c(oc%11ccccc%11%10)c7-8)-c7ccccc7C9(C)C)c7ccccc7C(C)(C)C)cc5C6(C)C)ccc3-4)cc21]

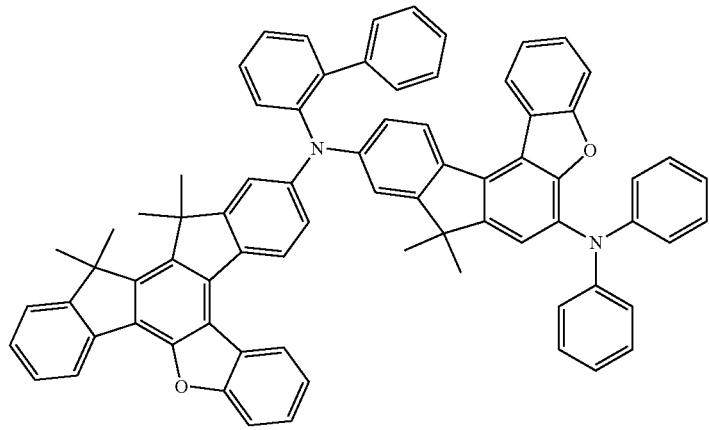 [SMILES: CC1(C)c2cc(N(c3ccc4c(c3)C(C)(C)c3c5c(c6oc7ccccc7c6c3-4)-c3ccccc3C5(C)C)c3ccccc3-c3ccccc3)ccc2-c2c1cc(N(c1ccccc1)c1ccccc1)c1oc3ccccc3c21]
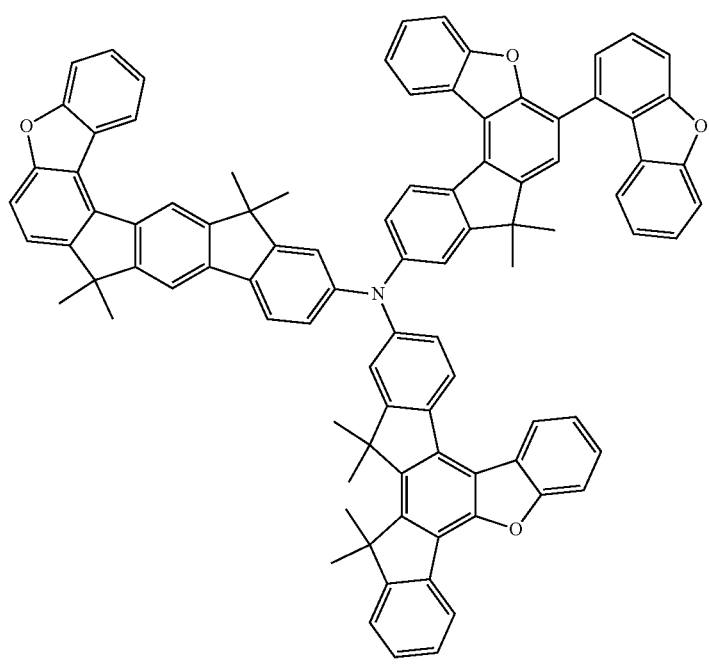 [SMILES: CC1(C)c2cc(N(c3ccc4c(c3)C(C)(C)c3cc(-c5cccc6oc7ccccc7c56)c5oc6ccccc6c5c3-4)c3ccc4c(c3)C(C)(C)c3c5c(c6oc7ccccc7c6c3-4)-c3ccccc3C5(C)C)ccc2-c2cc3c(cc21)-c1c(ccc2oc4ccccc4c12)C3(C)C]

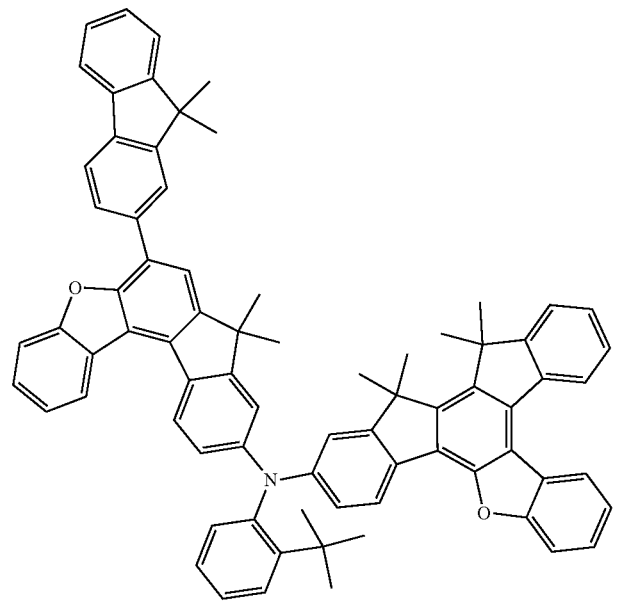 [SMILES: CC(C)(C)c1ccccc1N(c1ccc2c(c1)C(C)(C)c1cc(-c3ccc4c(c3)C(C)(C)c3ccccc3-4)c3oc4ccccc4c3c1-2)c1ccc2c(c1)C(C)(C)c1c3c(c4c(oc5ccccc54)c1-2)-c1ccccc1C3(C)C]
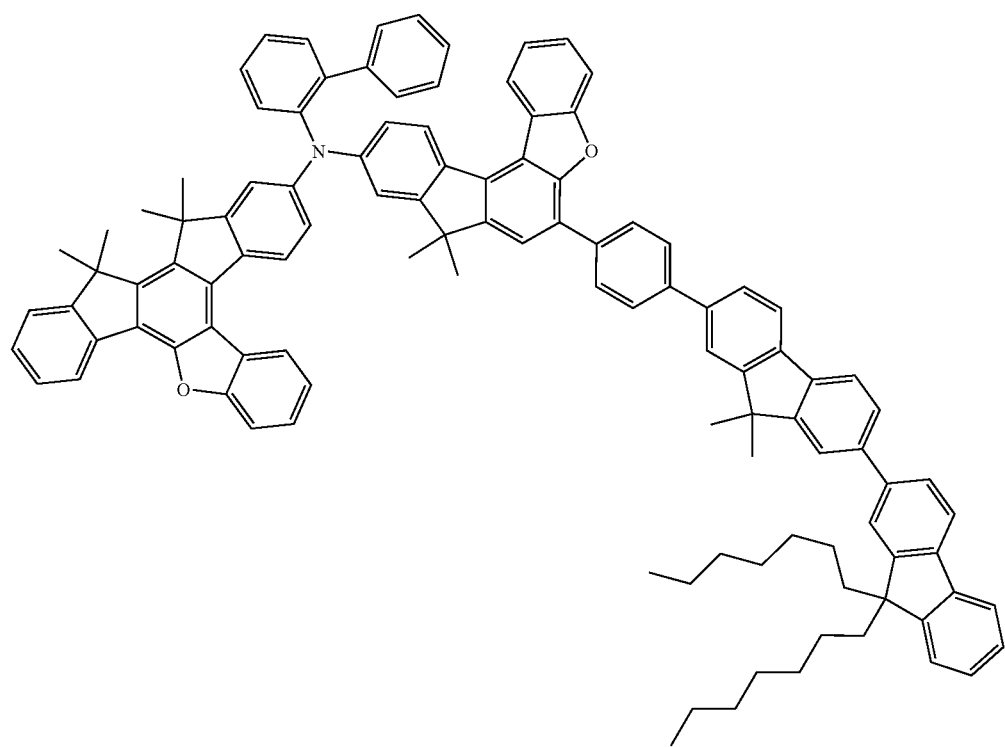 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8ccccc8-c8ccccc8)cc6C7(C)C)cc5)ccc3-4)cc21]

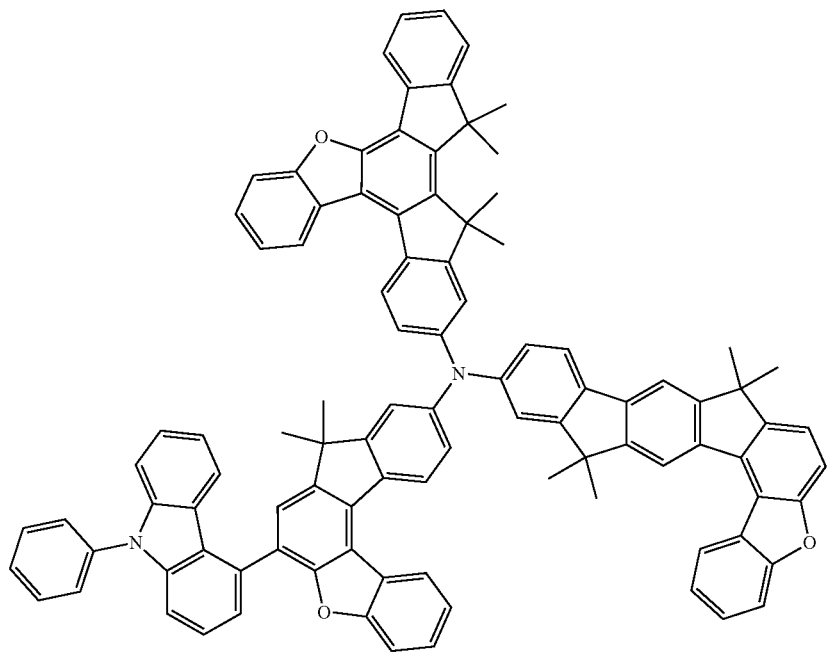 [SMILES: CC1(C)c2cc(N(c3ccc4c(c3)C(C)(C)c3cc(-c5cccc6c5c5ccccc5n6-c5ccccc5)c5oc6ccccc6c5c3-4)c3ccc4c(c3)C(C)(C)c3c5c(c6oc7ccccc7c6c3-4)-c3ccccc3C5(C)C)ccc2-c2cc3c(cc21)-c1c(ccc2oc4ccccc4c12)C3(C)C]
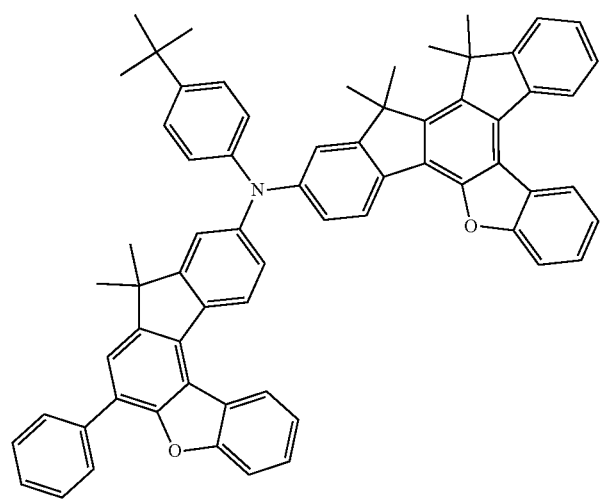 [SMILES: CC(C)(C)c1ccc(N(c2ccc3c(c2)C(C)(C)c2cc(-c4ccccc4)c4oc5ccccc5c4c2-3)c2ccc3c(c2)C(C)(C)c2c4c(c5c(oc6ccccc65)c2-3)-c2ccccc2C4(C)C)cc1]

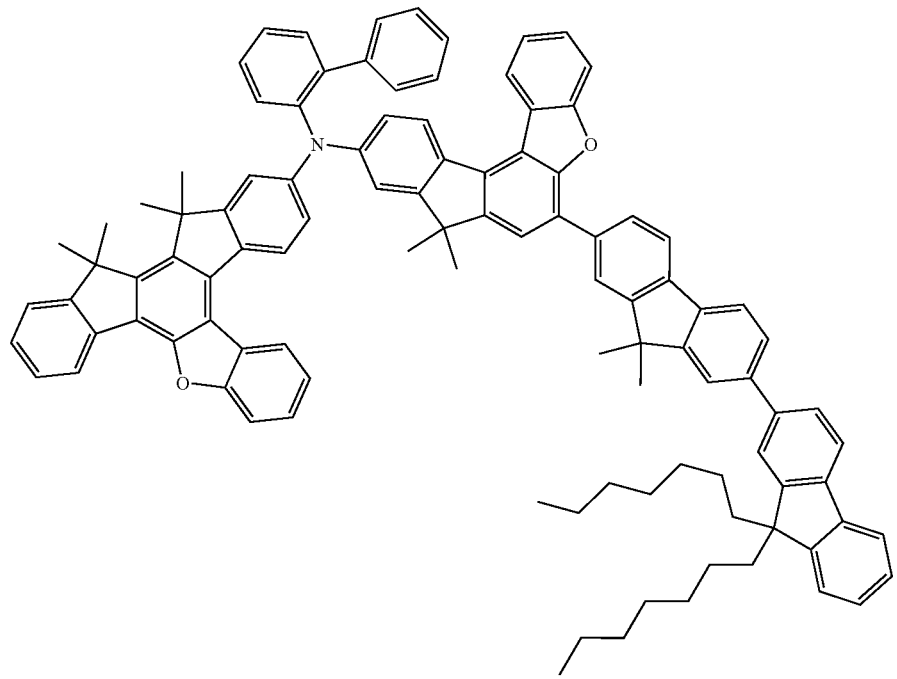 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7ccccc7-c7ccccc7)cc5C6(C)C)ccc3-4)cc21]
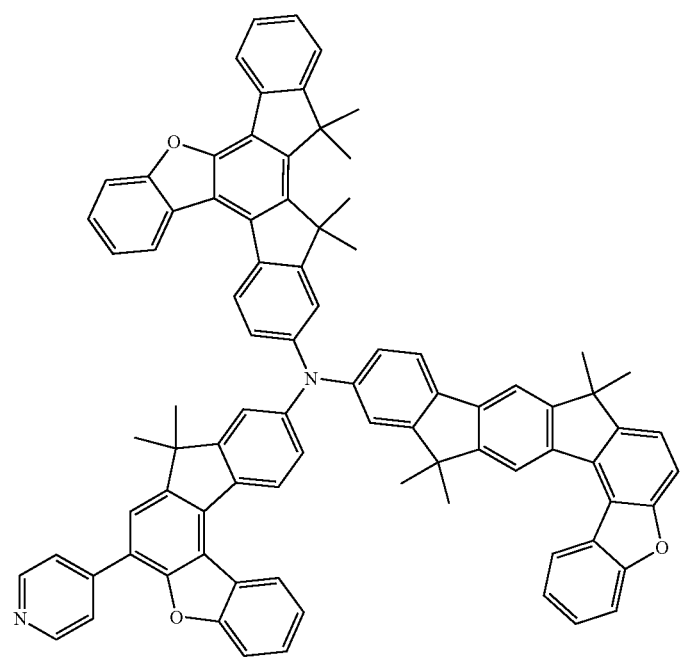 [SMILES: CC1(C)c2cc(N(c3ccc4c(c3)C(C)(C)c3cc(-c5ccncc5)c5oc6ccccc6c5c3-4)c3ccc4c(c3)C(C)(C)c3c5c(c6oc7ccccc7c6c3-4)-c3ccccc3C5(C)C)ccc2-c2cc3c(cc21)-c1c(ccc2oc4ccccc4c12)C3(C)C]

-continued
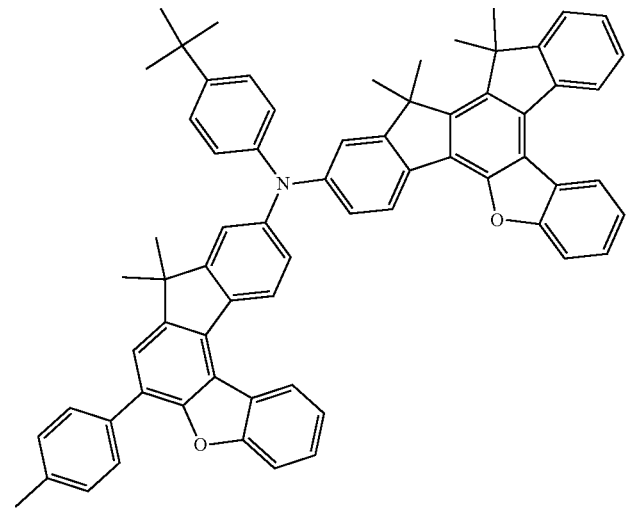 [SMILES: Cc1ccc(-c2cc3c(c4c2oc2ccccc24)-c2ccc(N(c4ccc(C(C)(C)C)cc4)c4ccc5c(c4)C(C)(C)c4c6c(c7c(oc8ccccc87)c4-5)-c4ccccc4C6(C)C)cc2C3(C)C)cc1]
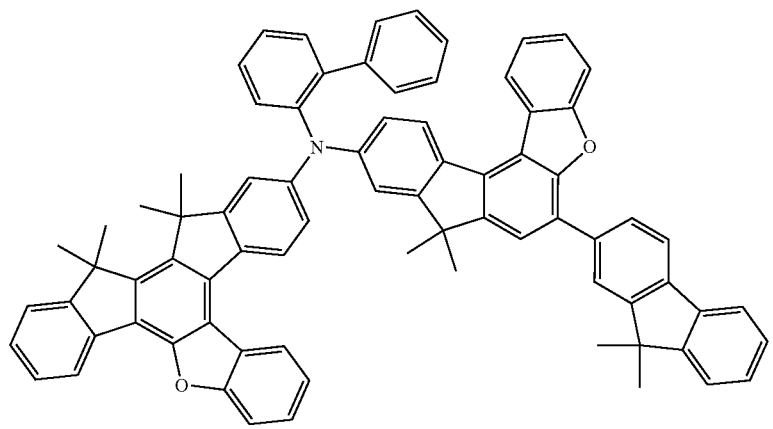 [SMILES: CC1(C)c2ccccc2-c2ccc(-c3cc4c(c5c3oc3ccccc35)-c3ccc(N(c5ccc6c(c5)C(C)(C)c5c7c(c8oc9ccccc9c8c5-6)-c5ccccc5C7(C)C)c5ccccc5-c5ccccc5)cc3C4(C)C)cc21]
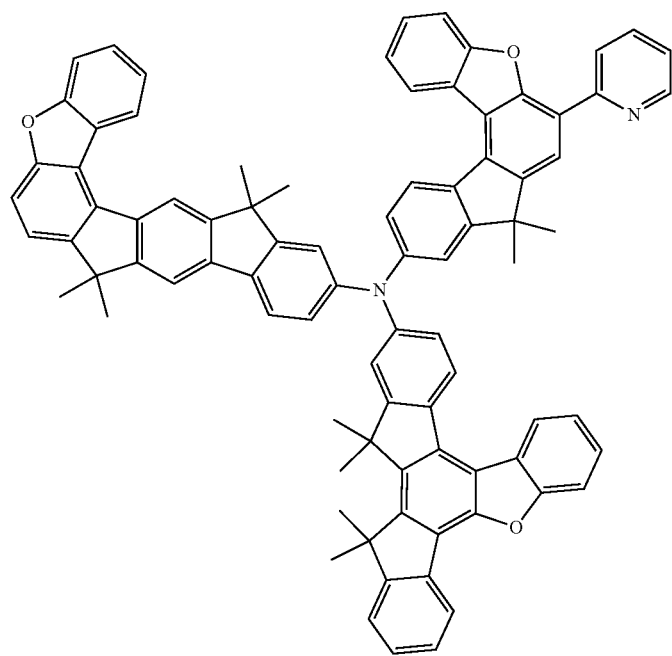 [SMILES: CC1(C)c2cc(N(c3ccc4c(c3)C(C)(C)c3cc(-c5ccccn5)c5oc6ccccc6c5c3-4)c3ccc4c(c3)C(C)(C)c3c5c(c6oc7ccccc7c6c3-4)-c3ccccc3C5(C)C)ccc2-c2cc3c(cc21)-c1c(ccc2oc4ccccc4c12)C3(C)C]

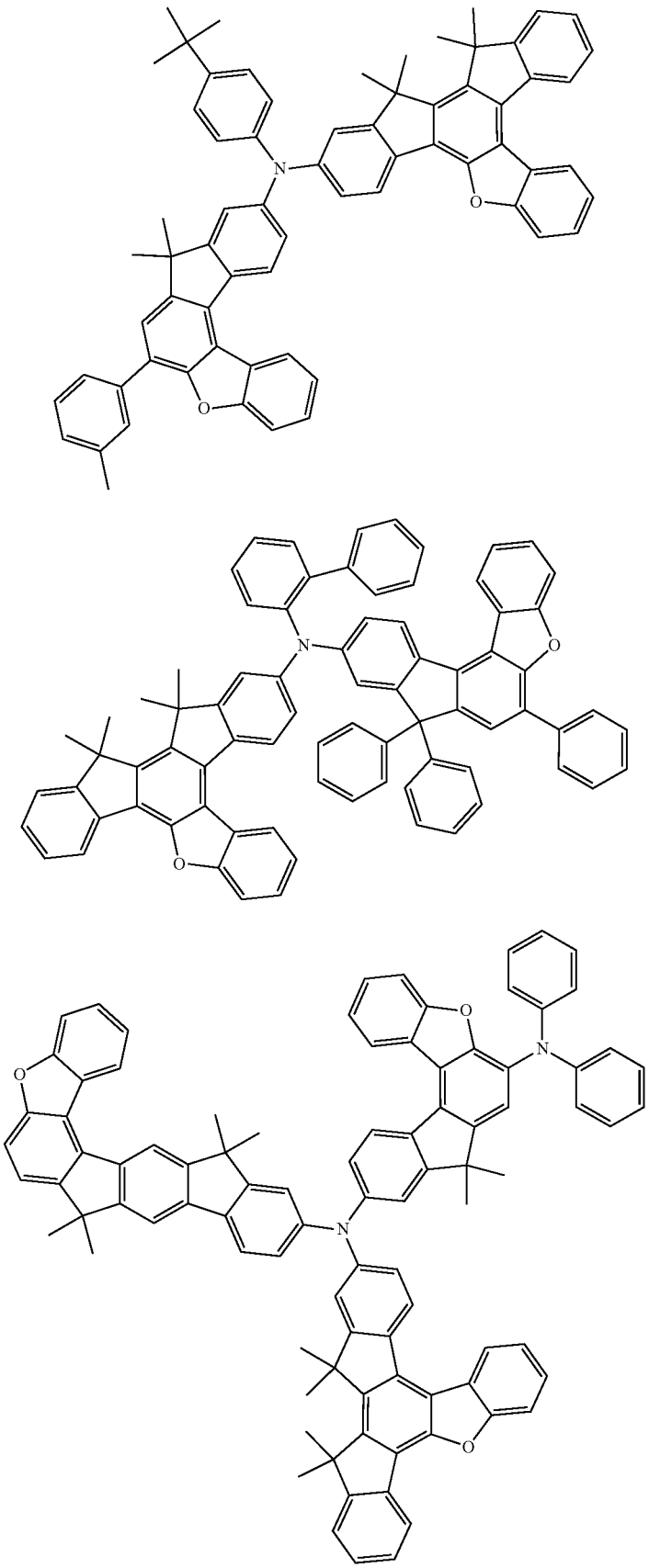

-continued
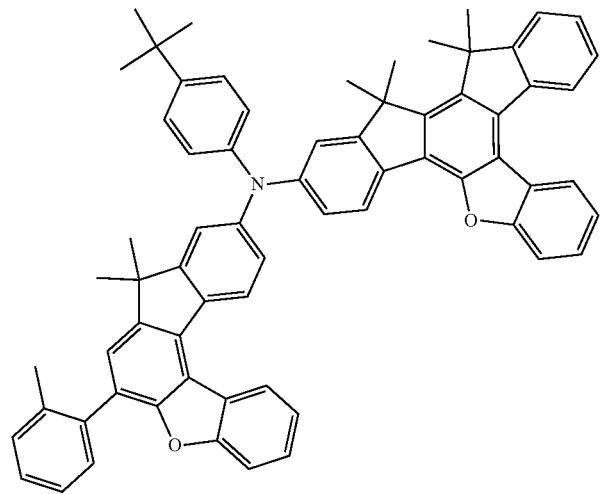 [SMILES: Cc1ccccc1-c1cc2c(c3c1oc1ccccc13)-c1ccc(N(c3ccc(C(C)(C)C)cc3)c3ccc4c(c3)C(C)(C)c3c5c(c6c(oc7ccccc76)c3-4)-c3ccccc3C5(C)C)cc1C2(C)C]
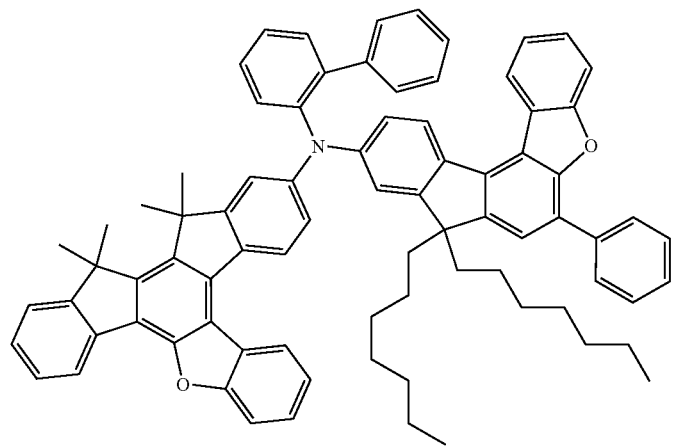 [SMILES: CCCCCCCC1(CCCCCCC)c2cc(N(c3ccc4c(c3)C(C)(C)c3c5c(c6oc7ccccc7c6c3-4)-c3ccccc3C5(C)C)c3ccccc3-c3ccccc3)ccc2-c2c1cc(-c1ccccc1)c1oc3ccccc3c21]
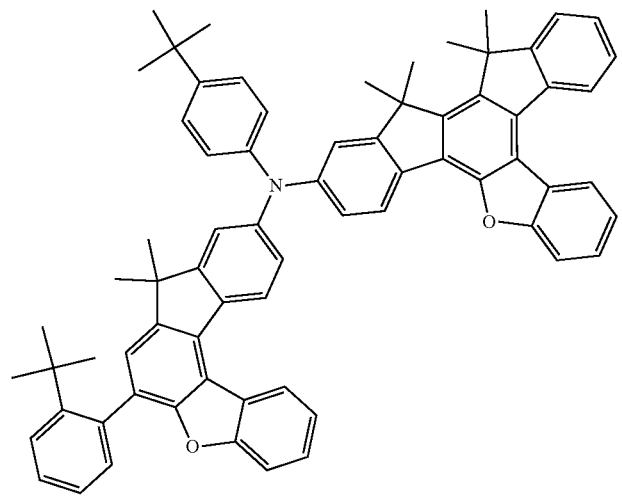 [SMILES: CC(C)(C)c1ccc(N(c2ccc3c(c2)C(C)(C)c2cc(-c4ccccc4C(C)(C)C)c4oc5ccccc5c4c2-3)c2ccc3c(c2)C(C)(C)c2c4c(c5c(oc6ccccc65)c2-3)-c2ccccc2C4(C)C)cc1]

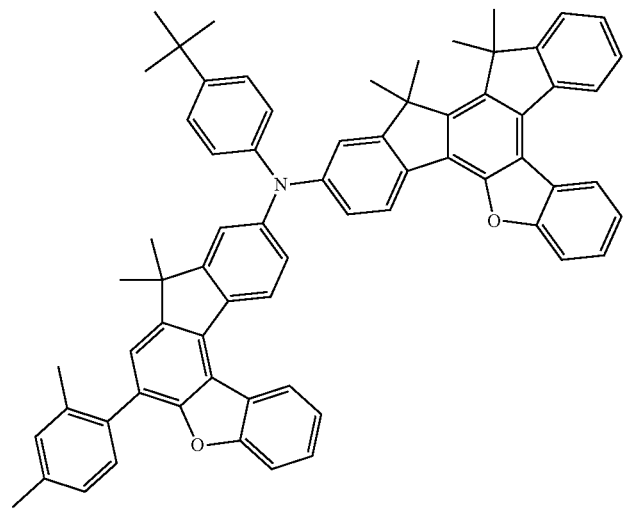 [SMILES: Cc1ccc(-c2cc3c(c4c2oc2ccccc24)-c2ccc(N(c4ccc(C(C)(C)C)cc4)c4ccc5c(c4)C(C)(C)c4c6c(c7c(oc8ccccc87)c4-5)-c4ccccc4C6(C)C)cc2C3(C)C)c(C)c1]
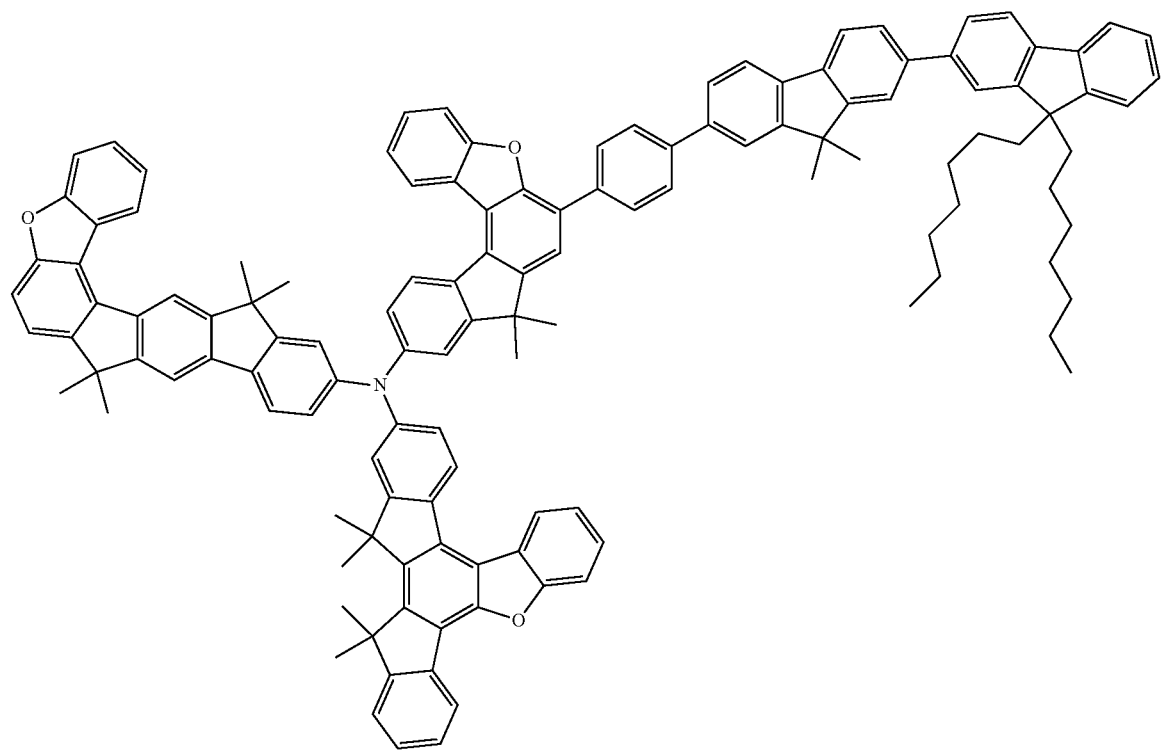 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8cc%10c(cc8-9)C(C)(C)c8ccc9oc%11ccccc%11c9c8-%10)c8ccc9c(c8)C(C)(C)c8c%10c(c%11oc%12ccccc%12c%11c8-9)-c8ccccc8C%10(C)C)cc6C7(C)C)cc5)ccc3-4)cc21]

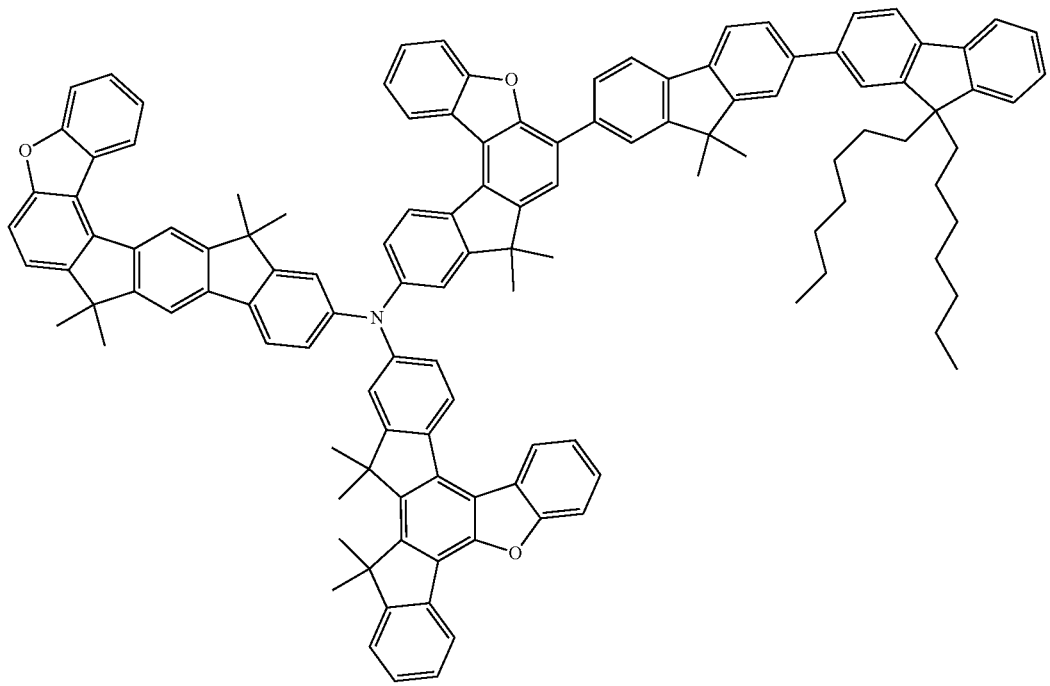 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7cc9c(cc7-8)C(C)(C)c7ccc8oc%10ccccc%10c8c7-9)c7ccc8c(c7)C(C)(C)c7c9c(c%10oc%11ccccc%11c%10c7-8)-c7ccccc7C9(C)C)cc5C6(C)C)ccc3-4)cc21]
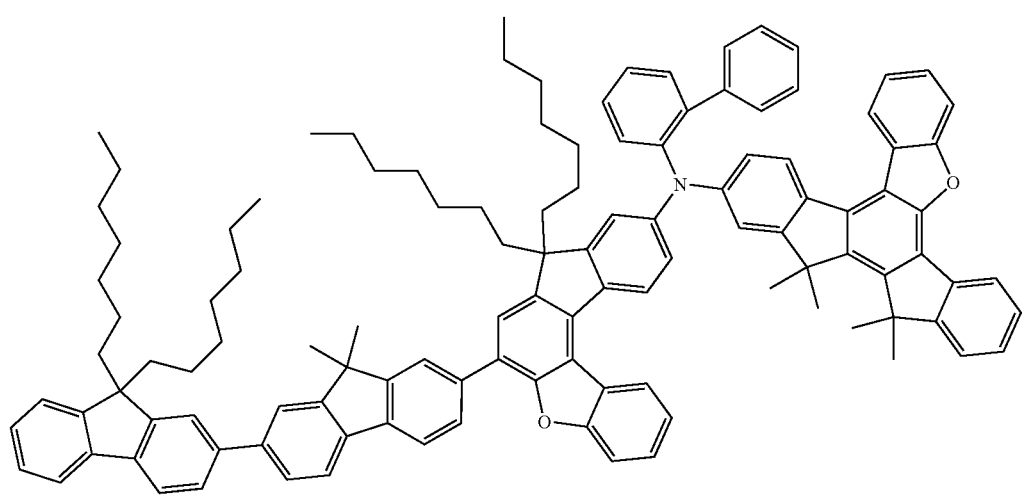 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7ccccc7-c7ccccc7)cc5C6(CCCCCCC)CCCCCCC)ccc3-4)cc21]

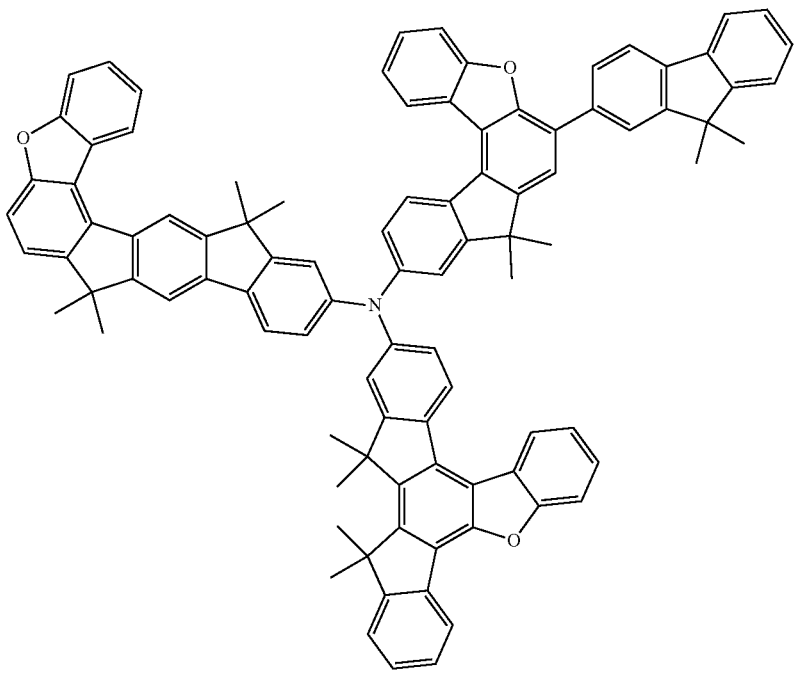 [SMILES: CC1(C)c2ccccc2-c2ccc(-c3cc4c(c5c3oc3ccccc35)-c3ccc(N(c5ccc6c(c5)C(C)(C)c5cc7c(cc5-6)C(C)(C)c5ccc6oc8ccccc8c6c5-7)c5ccc6c(c5)C(C)(C)c5c7c(c8oc9ccccc9c8c5-6)-c5ccccc5C7(C)C)cc3C4(C)C)cc21]
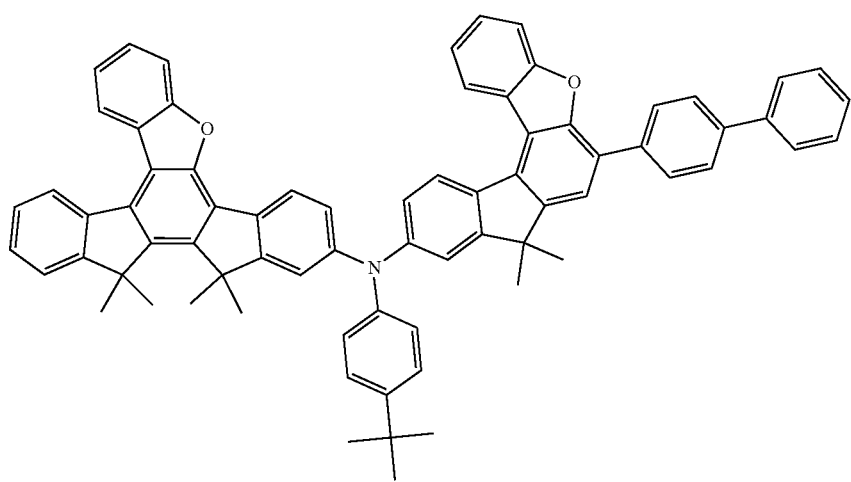 [SMILES: CC(C)(C)c1ccc(N(c2ccc3c(c2)C(C)(C)c2cc(-c4ccc(-c5ccccc5)cc4)c4oc5ccccc5c4c2-3)c2ccc3c(c2)C(C)(C)c2c4c(c5c(oc6ccccc65)c2-3)-c2ccccc2C4(C)C)cc1]

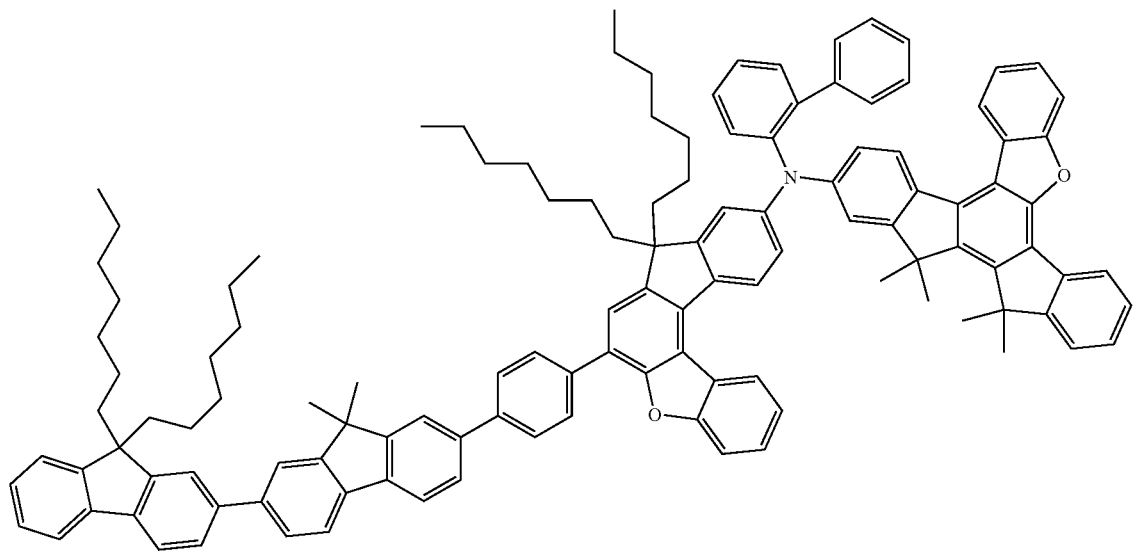 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8ccccc8-c8ccccc8)cc6C7(CCCCCCC)CCCCCCC)cc5)ccc3-4)cc21]
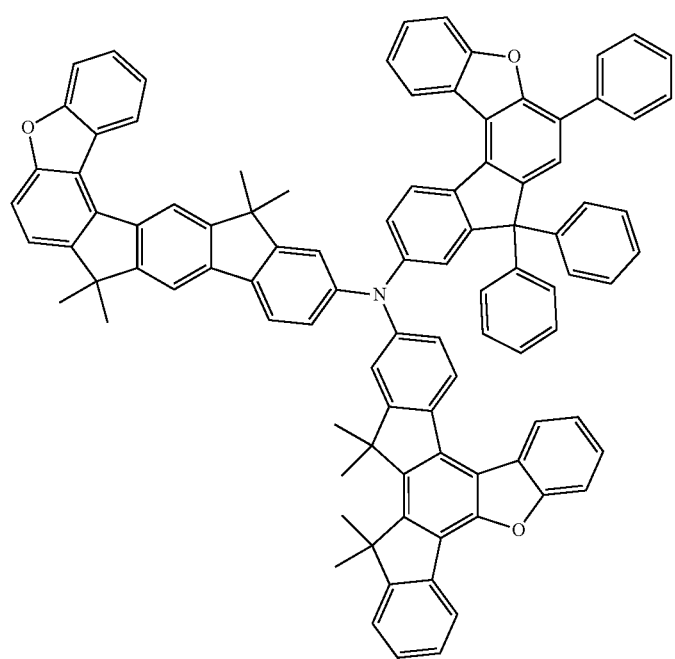 [SMILES: CC1(C)c2cc(N(c3ccc4c(c3)C(C)(C)c3c5c(c6oc7ccccc7c6c3-4)-c3ccccc3C5(C)C)c3ccc4c(c3)C(c3ccccc3)(c3ccccc3)c3cc(-c5ccccc5)c5oc6ccccc6c5c3-4)ccc2-c2cc3c(cc21)-c1c(ccc2oc4ccccc4c12)C3(C)C]

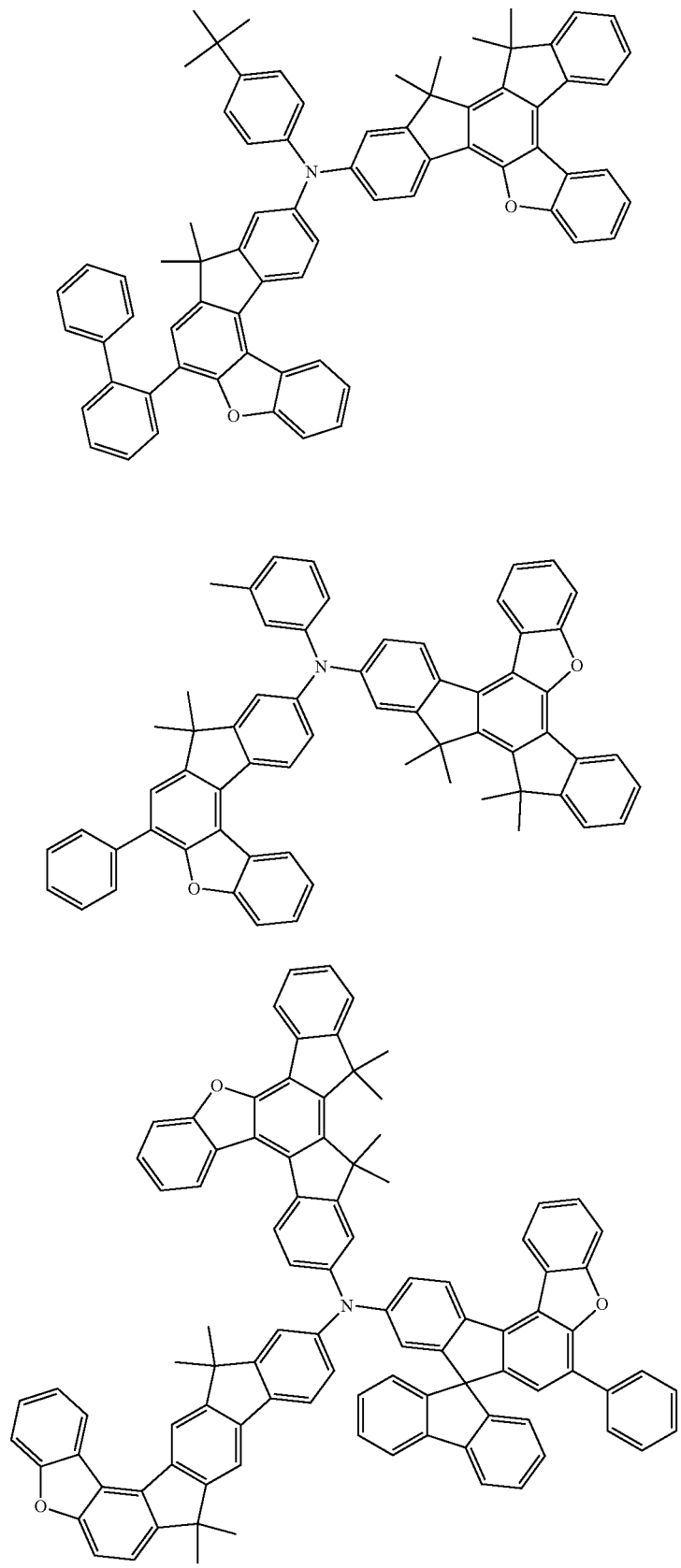

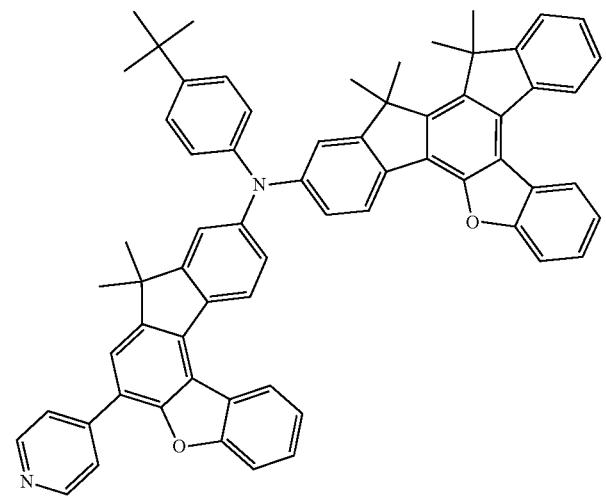 [SMILES: CC(C)(C)c1ccc(N(c2ccc3c(c2)C(C)(C)c2cc(-c4ccncc4)c4oc5ccccc5c4c2-3)c2ccc3c(c2)C(C)(C)c2c4c(c5c(oc6ccccc65)c2-3)-c2ccccc2C4(C)C)cc1]
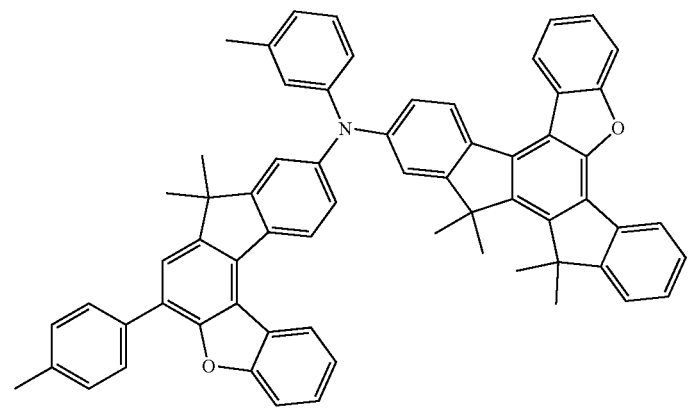 [SMILES: Cc1ccc(-c2cc3c(c4c2oc2ccccc24)-c2ccc(N(c4cccc(C)c4)c4ccc5c(c4)C(C)(C)c4c6c(c7oc8ccccc8c7c4-5)-c4ccccc4C6(C)C)cc2C3(C)C)cc1]
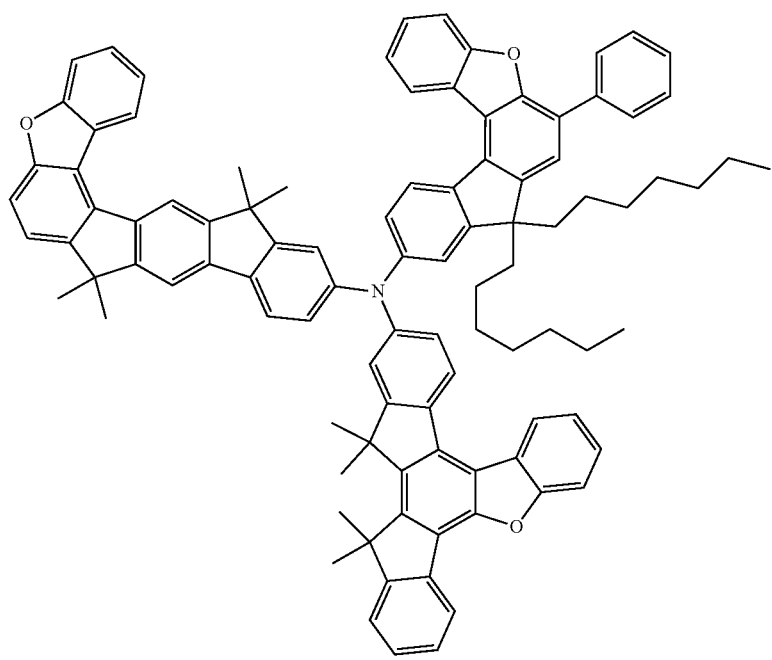 [SMILES: CCCCCCCC1(CCCCCCC)c2cc(N(c3ccc4c(c3)C(C)(C)c3cc5c(cc3-4)C(C)(C)c3ccc4oc6ccccc6c4c3-5)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]

-continued
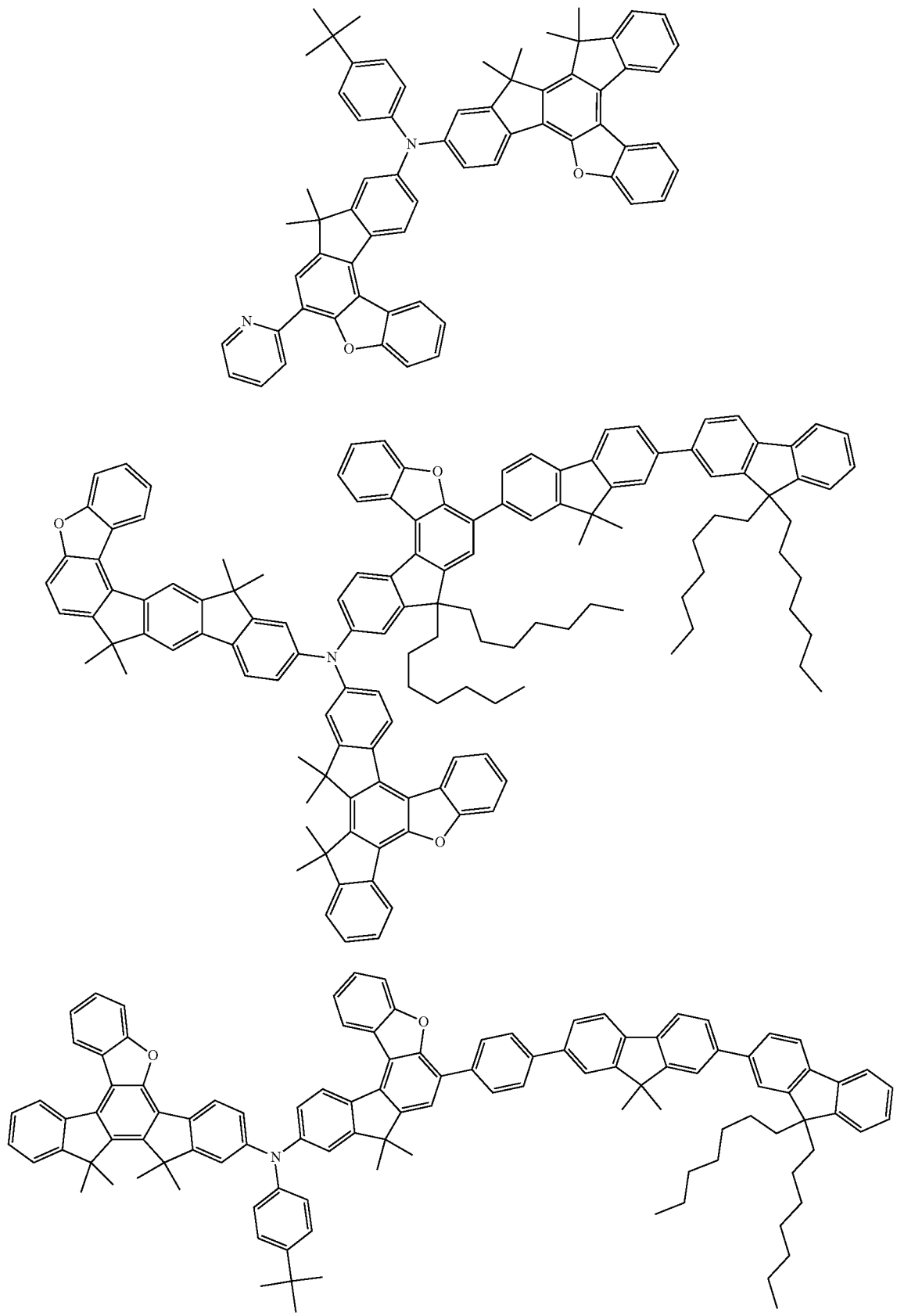

-continued
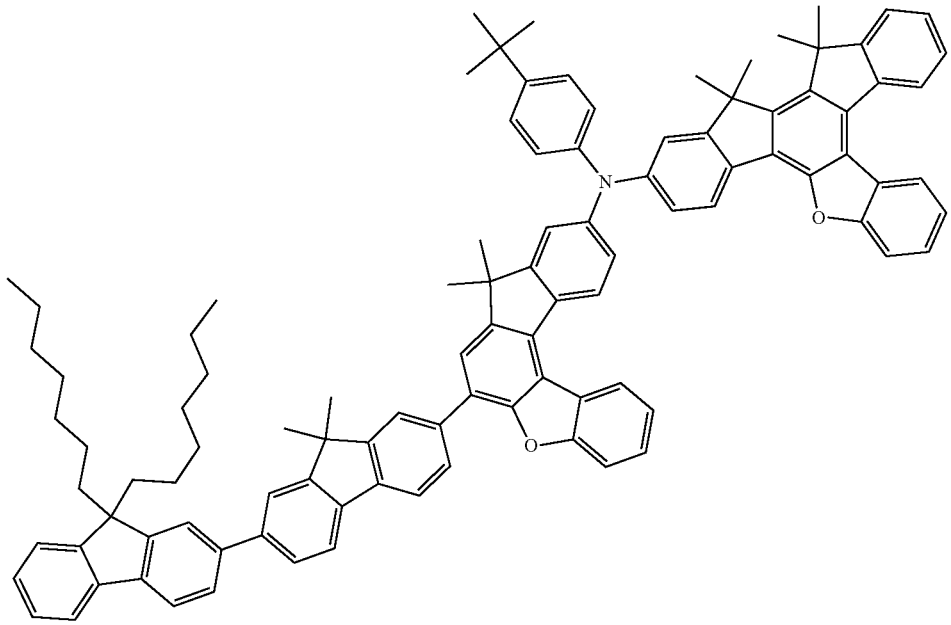 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc(C(C)(C)C)cc7)c7ccc8c(c7)C(C)(C)c7c9c(c%10c(oc%11ccccc%11%10)c7-8)-c7ccccc7C9(C)C)cc5C6(C)C)ccc3-4)cc21]
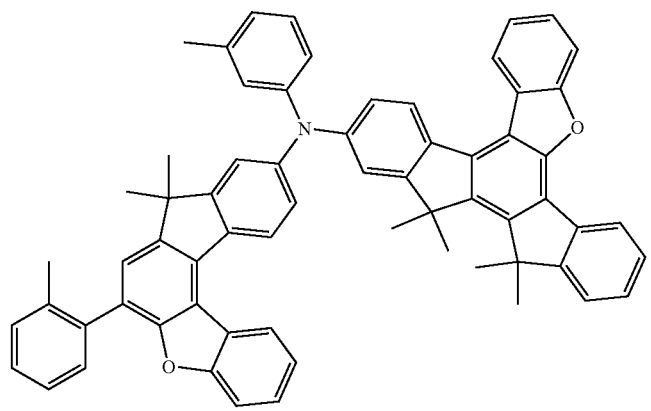 [SMILES: Cc1cccc(N(c2ccc3c(c2)C(C)(C)c2cc(-c4ccccc4C)c4oc5ccccc5c4c2-3)c2ccc3c(c2)C(C)(C)c2c4c(c5oc6ccccc6c5c2-3)-c2ccccc2C4(C)C)c1]
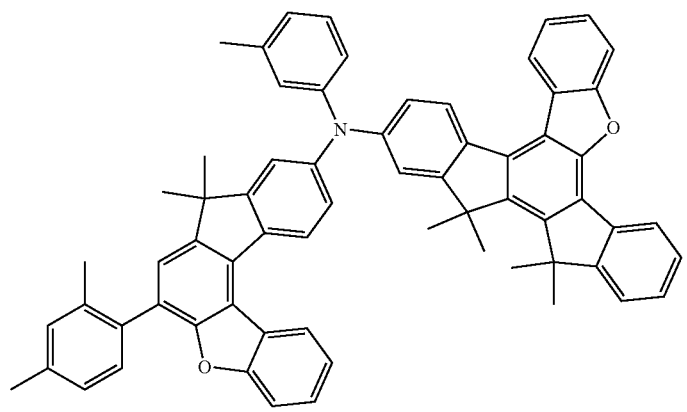 [SMILES: Cc1cccc(N(c2ccc3c(c2)C(C)(C)c2cc(-c4ccc(C)cc4C)c4oc5ccccc5c4c2-3)c2ccc3c(c2)C(C)(C)c2c4c(c5oc6ccccc6c5c2-3)-c2ccccc2C4(C)C)c1]

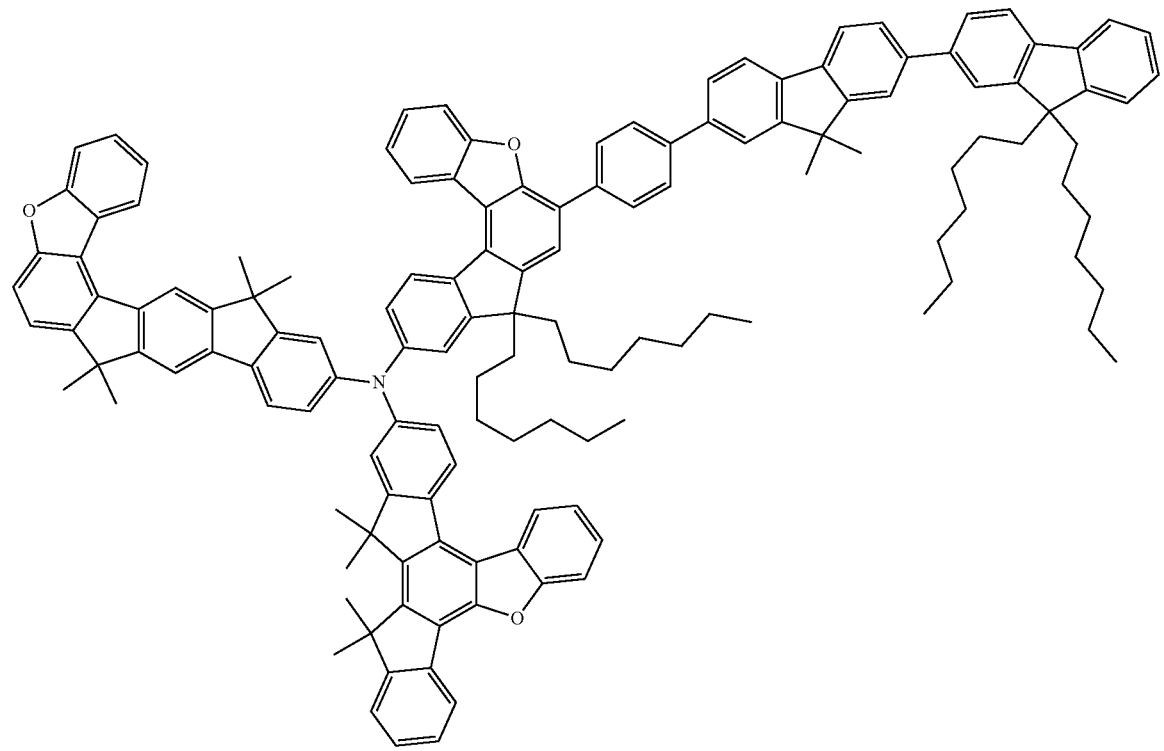 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8cc%10c(cc8-9)C(C)(C)c8ccc9oc%11ccccc%11c9c8-%10)c8ccc9c(c8)C(C)(C)c8c%10c(c%11oc%12ccccc%12c%11c8-9)-c8ccccc8C%10(C)C)cc6C7(CCCCCCC)CCCCCCC)cc5)ccc3-4)cc21]
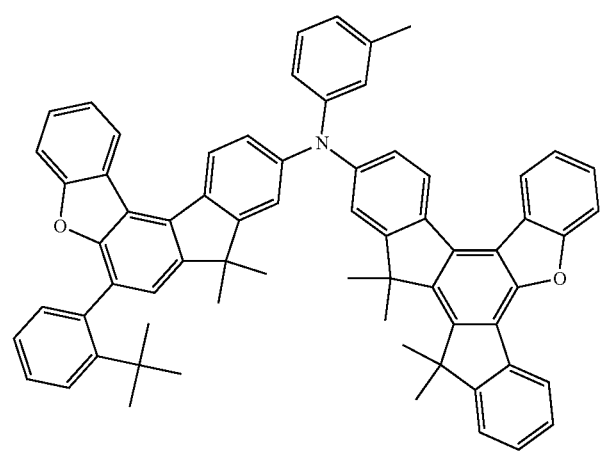 [SMILES: Cc1cccc(N(c2ccc3c(c2)C(C)(C)c2cc(-c4ccccc4C(C)(C)C)c4oc5ccccc5c4c2-3)c2ccc3c(c2)C(C)(C)c2c4c(c5oc6ccccc6c5c2-3)-c2ccccc2C4(C)C)c1]

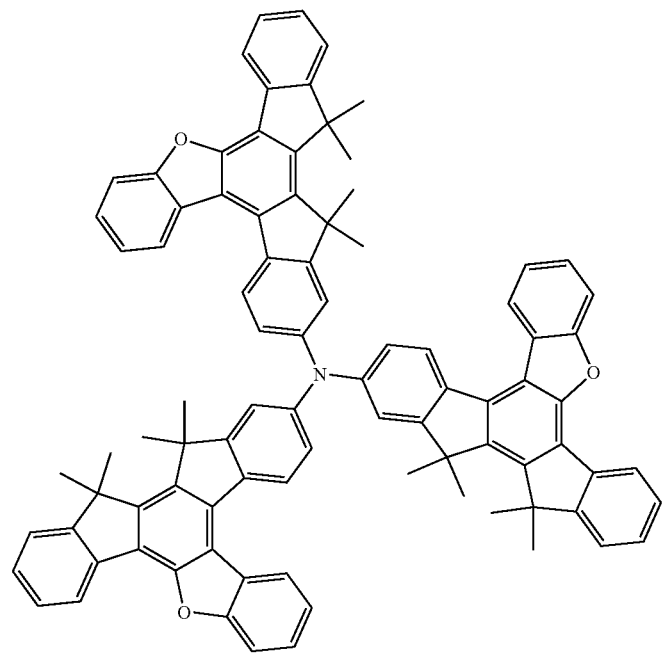 [SMILES: CC1(C)c2ccccc2-c2c1c1c(c3c2oc2ccccc23)-c2ccc(N(c3ccc4c(c3)C(C)(C)c3c5c(c6oc7ccccc7c6c3-4)-c3ccccc3C5(C)C)c3ccc4c(c3)C(C)(C)c3c5c(c6oc7ccccc7c6c3-4)-c3ccccc3C5(C)C)cc2C1(C)C]
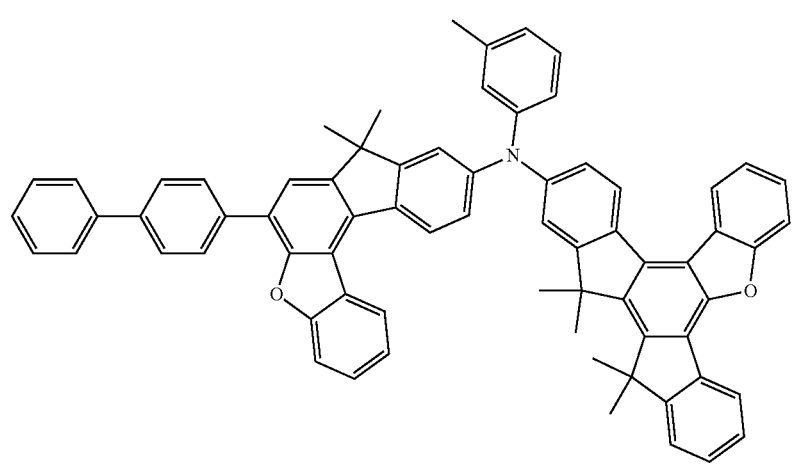 [SMILES: Cc1cccc(N(c2ccc3c(c2)C(C)(C)c2cc(-c4ccc(-c5ccccc5)cc4)c4oc5ccccc5c4c2-3)c2ccc3c(c2)C(C)(C)c2c4c(c5oc6ccccc6c5c2-3)-c2ccccc2C4(C)C)c1]

-continued
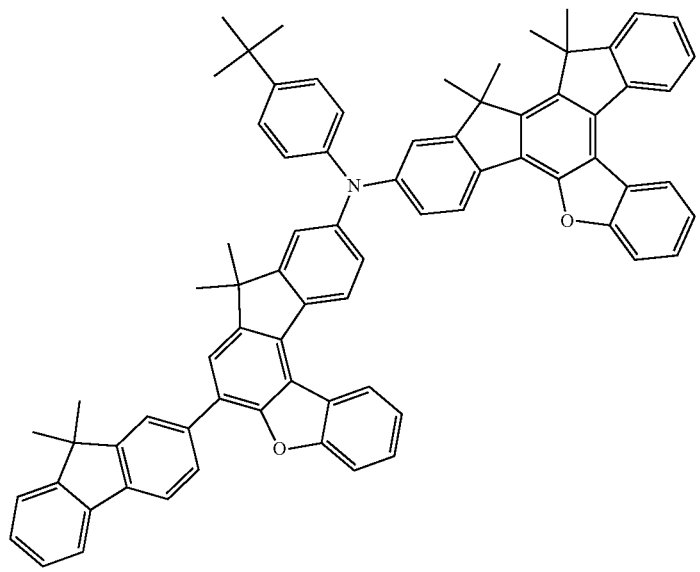 [SMILES: CC(C)(C)c1ccc(N(c2ccc3c(c2)C(C)(C)c2cc(-c4ccc5c(c4)C(C)(C)c4ccccc4-5)c4oc5ccccc5c4c2-3)c2ccc3c(c2)C(C)(C)c2c4c(c5c(oc6ccccc65)c2-3)-c2ccccc2C4(C)C)cc1]
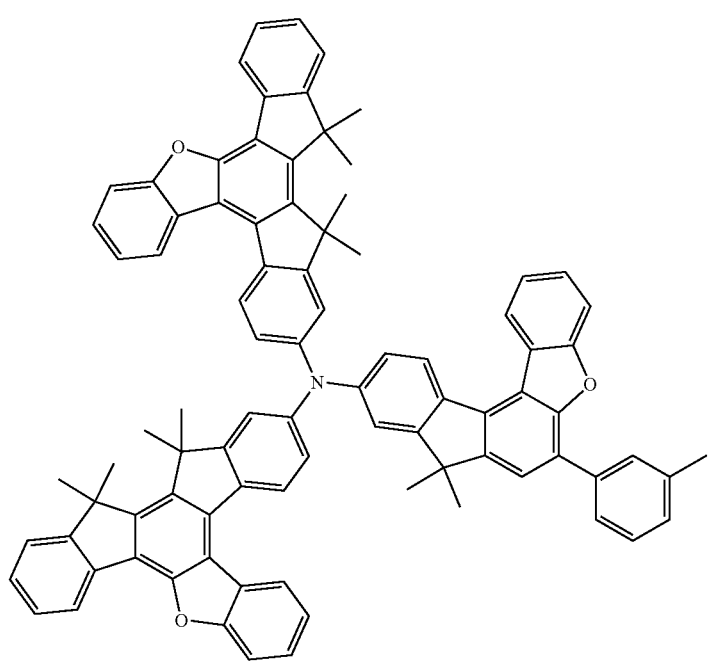 [SMILES: Cc1cccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccc5c(c4)C(C)(C)c4c6c(c7oc8ccccc8c7c4-5)-c4ccccc4C6(C)C)cc2C3(C)C)c1]

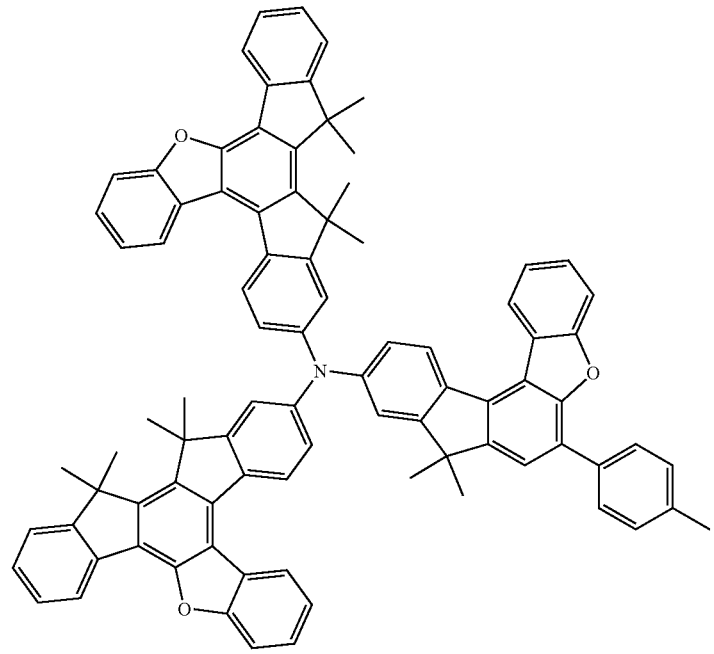 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccc5c(c4)C(C)(C)c4c6c(c7oc8ccccc8c7c4-5)-c4ccccc4C6(C)C)cc2C3(C)C)cc1]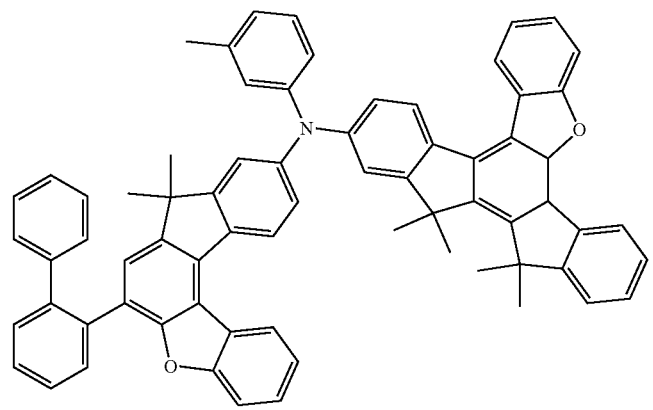 [SMILES: Cc1cccc(N(c2ccc3c(c2)C(C)(C)C2=C4C(c5ccccc5C4(C)C)C4Oc5ccccc5C4=C23)c2ccc3c(c2)C(C)(C)c2cc(-c4ccccc4-c4ccccc4)c4oc5ccccc5c4c2-3)c1]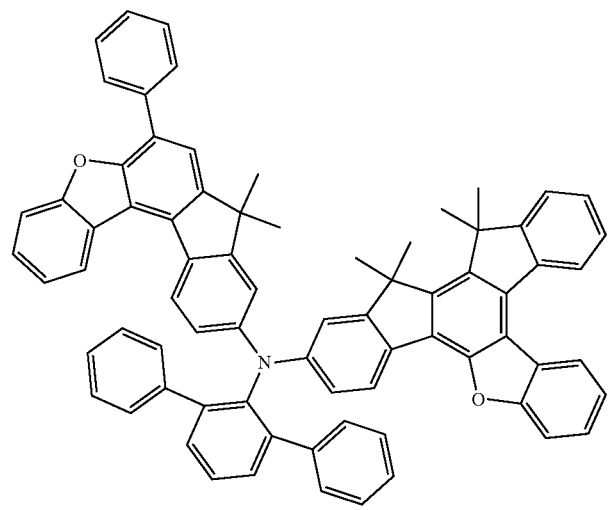 [SMILES: CC1(C)c2cc(N(c3ccc4c(c3)C(C)(C)c3c5c(c6c(oc7ccccc76)c3-4)-c3ccccc3C5(C)C)c3c(-c4ccccc4)cccc3-c3ccccc3)ccc2-c2c1cc(-c1ccccc1)c1oc3ccccc3c21]

-continued
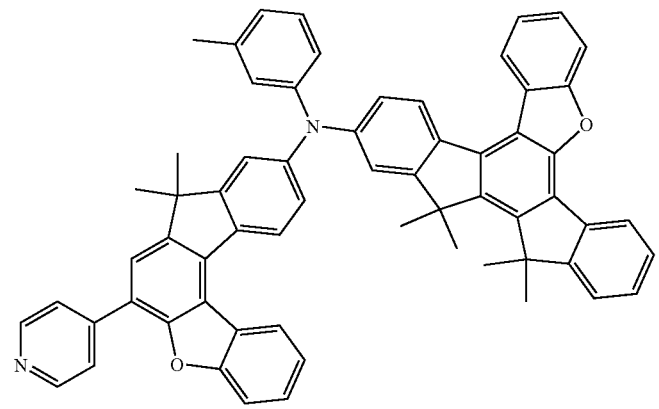 [SMILES: Cc1cccc(N(c2ccc3c(c2)C(C)(C)c2cc(-c4ccncc4)c4oc5ccccc5c4c2-3)c2ccc3c(c2)C(C)(C)c2c4c(c5oc6ccccc6c5c2-3)-c2ccccc2C4(C)C)c1]
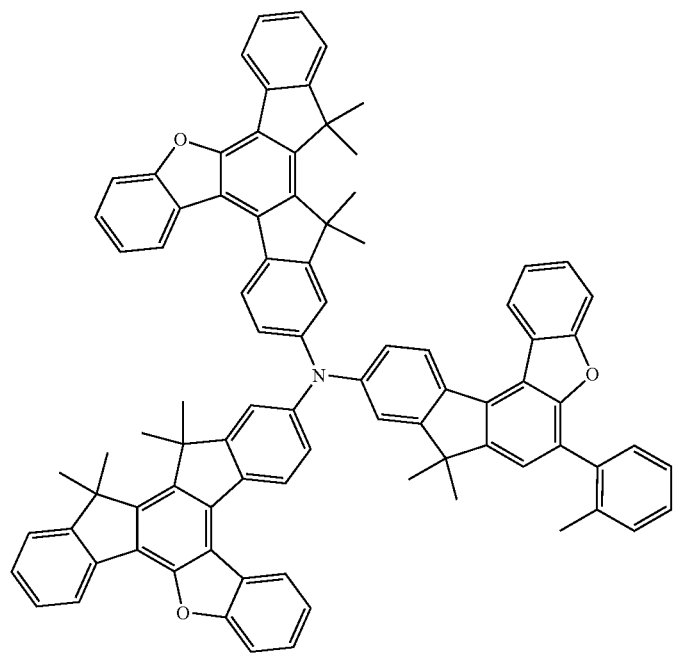 [SMILES: Cc1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3ccc4c(c3)C(C)(C)c3c5c(c6oc7ccccc7c6c3-4)-c3ccccc3C5(C)C)cc1C2(C)C]
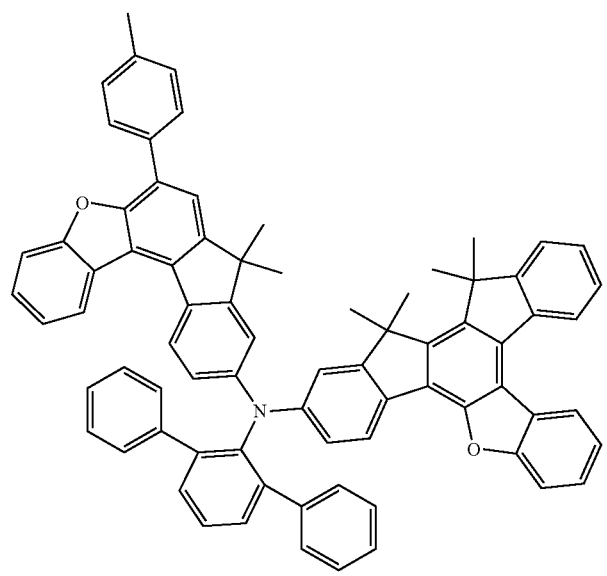 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4c(-c5ccccc5)cccc4-c4ccccc4)cc2C3(C)C)cc1]

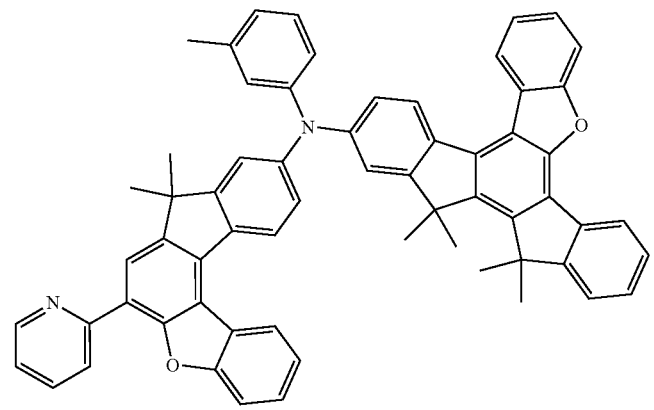 [SMILES: Cc1cccc(N(c2ccc3c(c2)C(C)(C)c2cc(-c4ccccn4)c4oc5ccccc5c4c2-3)c2ccc3c(c2)C(C)(C)c2c4c(c5oc6ccccc6c5c2-3)-c2ccccc2C4(C)C)c1]
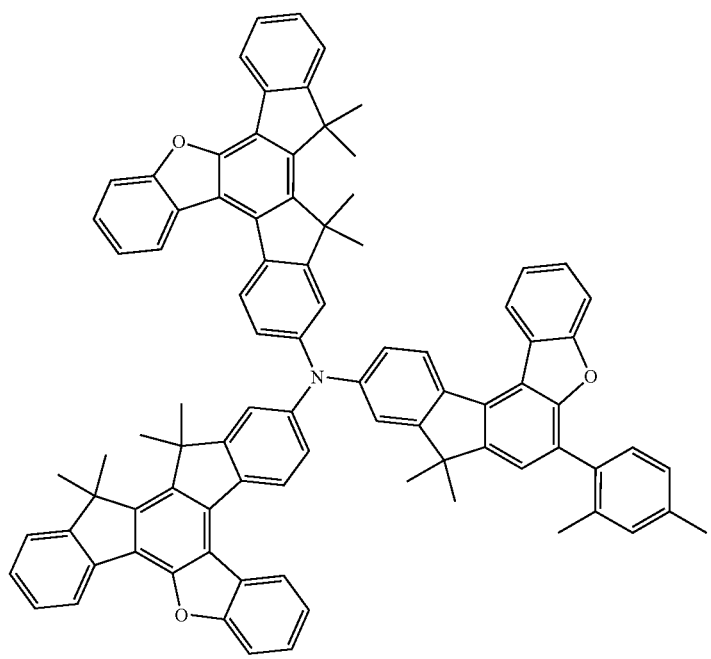 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccc5c(c4)C(C)(C)c4c6c(c7oc8ccccc8c7c4-5)-c4ccccc4C6(C)C)cc2C3(C)C)c(C)c1]
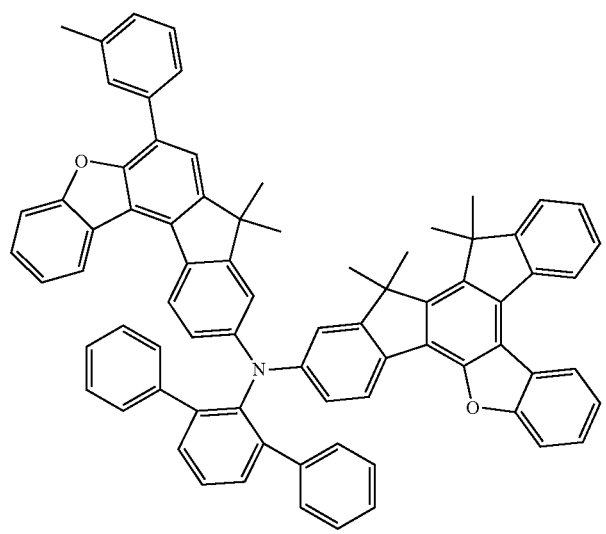 [SMILES: Cc1cccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4c(-c5ccccc5)cccc4-c4ccccc4)cc2C3(C)C)c1]

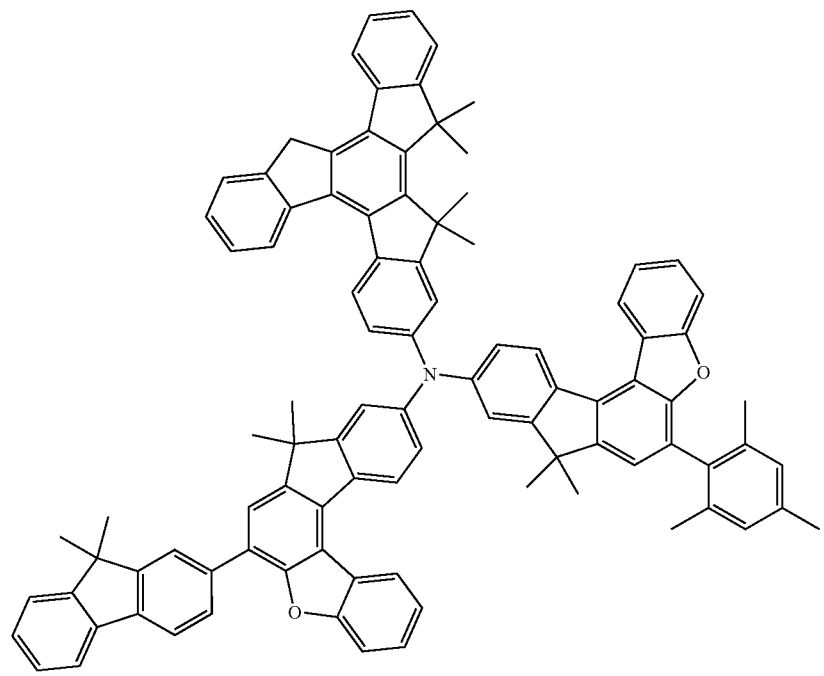 [SMILES: Cc1cc(C)c(-c2cc3c(c4c2oc2ccccc24)-c2ccc(N(c4ccc5c(c4)C(C)(C)c4cc(-c6ccc7c(c6)C(C)(C)c6ccccc6-7)c6oc7ccccc7c6c4-5)c4ccc5c(c4)C(C)(C)c4c-5c5c(c6c4C(C)(C)c4ccccc4-6)Cc4ccccc4-5)cc2C3(C)C)c(C)c1]
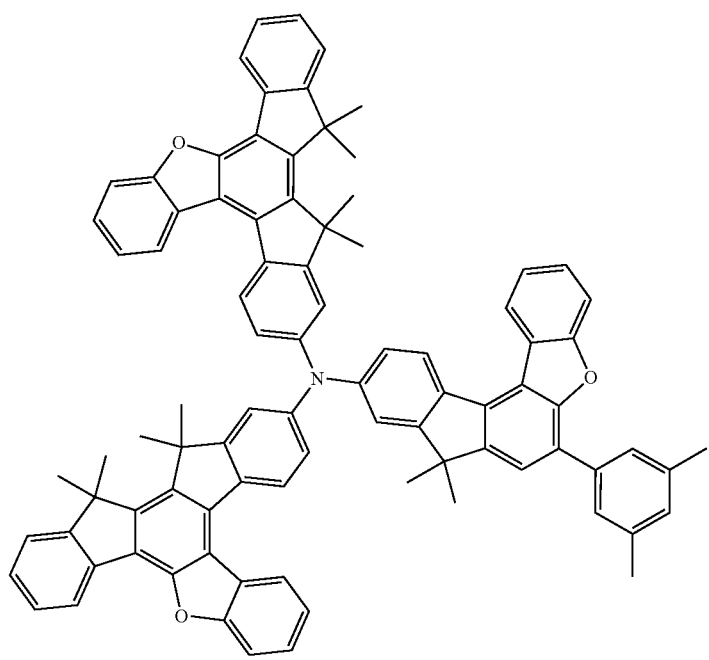 [SMILES: Cc1cc(C)cc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ccc5c(c4)C(C)(C)c4c6c(c7oc8ccccc8c7c4-5)-c4ccccc4C6(C)C)cc2C3(C)C)c1]

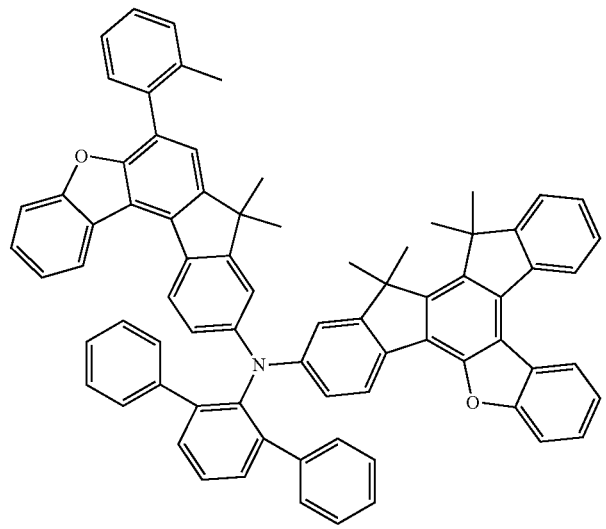 [SMILES: Cc1ccccc1-c1cc2c(c3c1oc1ccccc13)-c1ccc(N(c3ccc4c(c3)C(C)(C)c3c5c(c6c(oc7ccccc76)c3-4)-c3ccccc3C5(C)C)c3c(-c4ccccc4)cccc3-c3ccccc3)cc1C2(C)C]
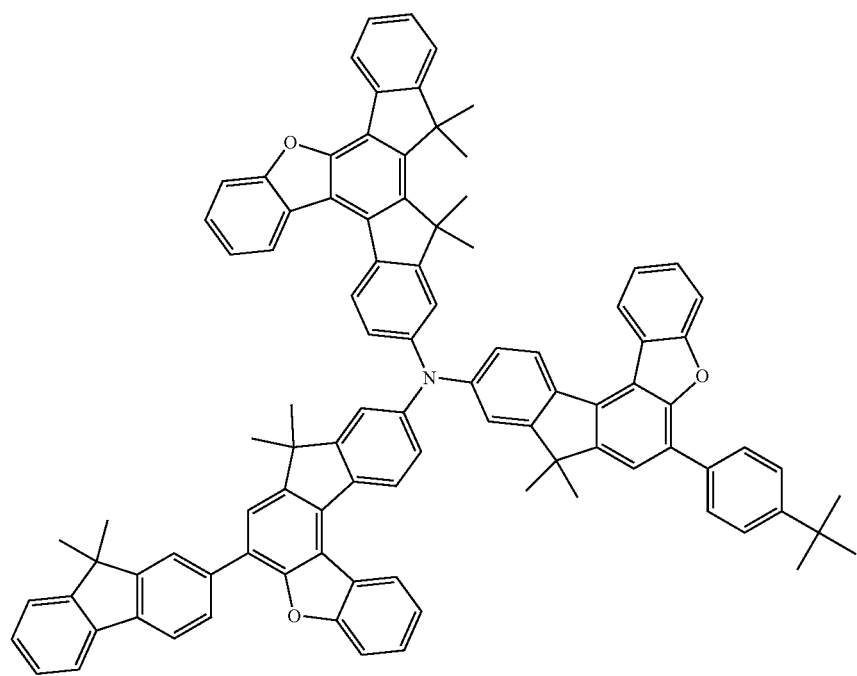 [SMILES: CC(C)(C)c1ccc(-c2cc3c(c4c2oc2ccccc24)-c2ccc(N(c4ccc5c(c4)C(C)(C)c4cc(-c6ccc7c(c6)C(C)(C)c6ccccc6-7)c6oc7ccccc7c6c4-5)c4ccc5c(c4)C(C)(C)c4c6c(c7oc8ccccc8c7c4-5)-c4ccccc4C6(C)C)cc2C3(C)C)cc1]

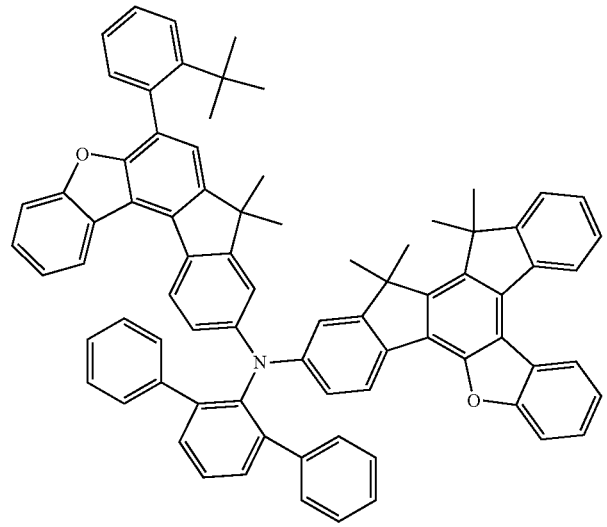 [SMILES: CC(C)(C)c1ccccc1-c1cc2c(c3c1oc1ccccc13)-c1ccc(N(c3ccc4c(c3)C(C)(C)c3c5c(c6c(oc7ccccc76)c3-4)-c3ccccc3C5(C)C)c3c(-c4ccccc4)cccc3-c3ccccc3)cc1C2(C)C]
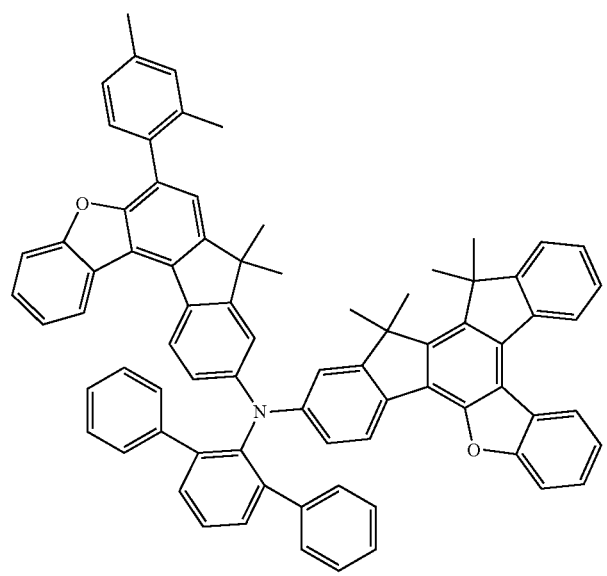 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4c(-c5ccccc5)cccc4-c4ccccc4)cc2C3(C)C)c(C)c1]
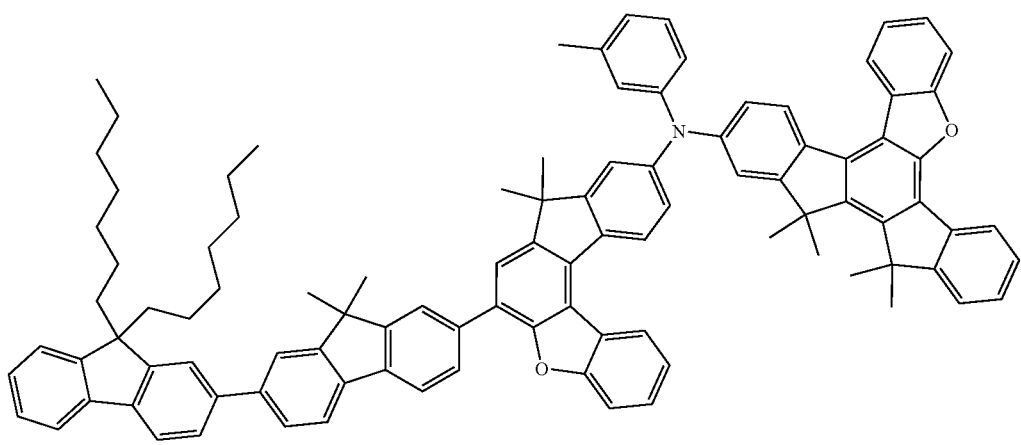 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7cccc(C)c7)c7ccc8c(c7)C(C)(C)c7c9c(c%10oc%11ccccc%11c%10c7-8)-c7ccccc7C9(C)C)cc5C6(C)C)ccc3-4)cc21]

-continued
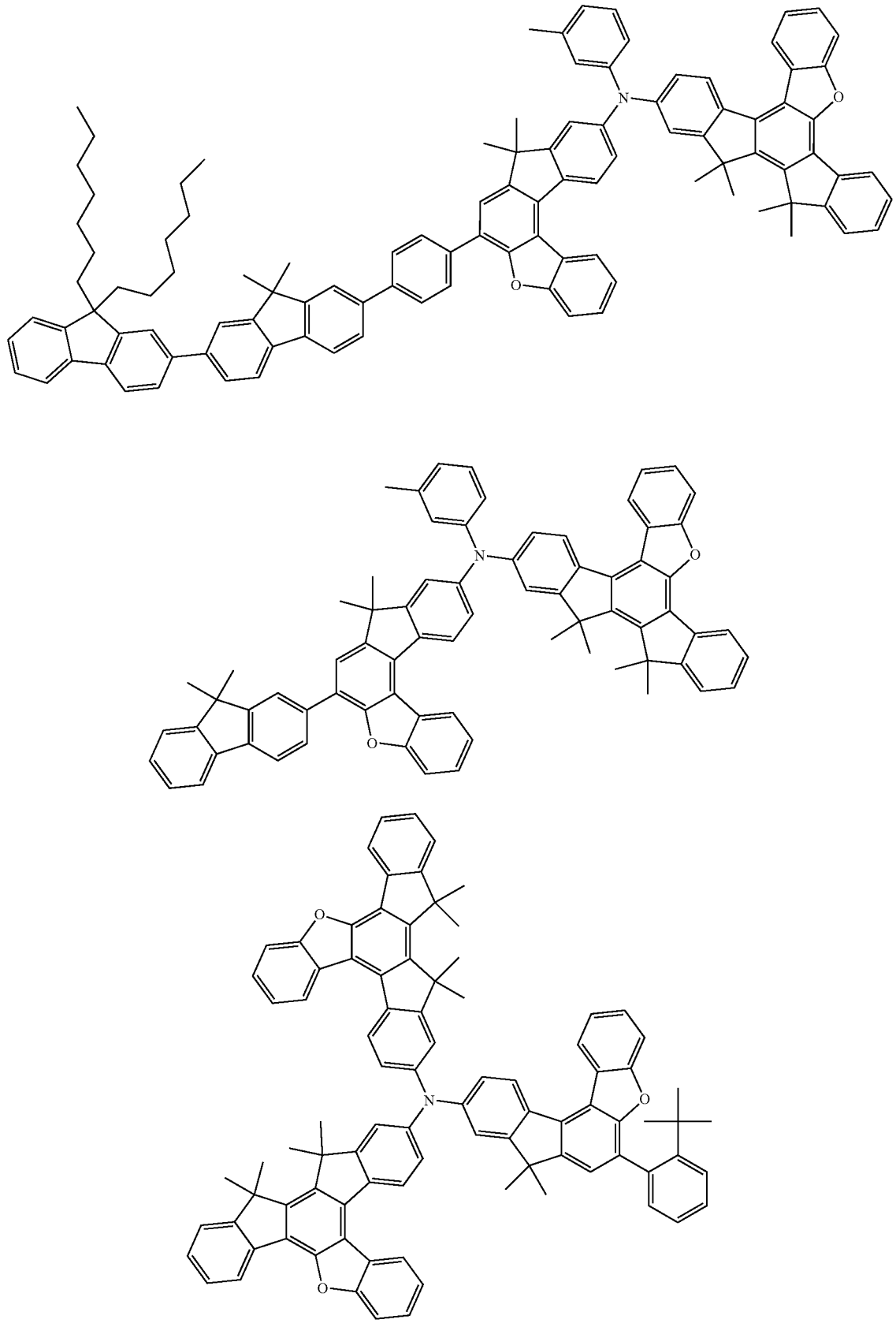

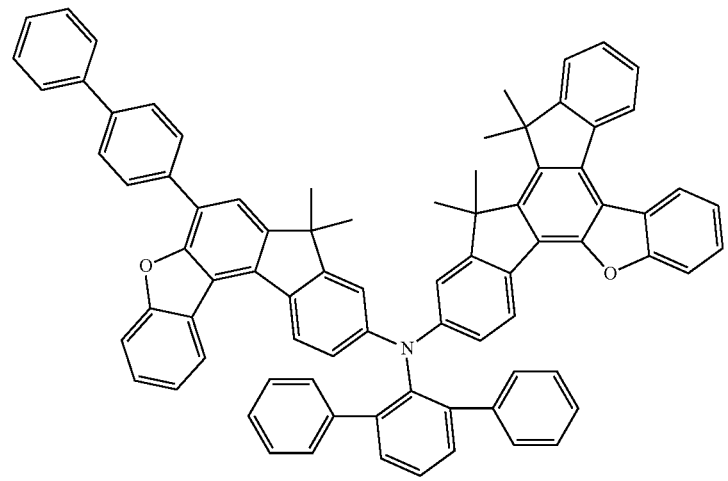 [SMILES: CC1(C)c2cc(N(c3ccc4c(c3)C(C)(C)c3c5c(c6c(oc7ccccc76)c3-4)-c3ccccc3C5(C)C)c3c(-c4ccccc4)cccc3-c3ccccc3)ccc2-c2c1cc(-c1ccc(-c3ccccc3)cc1)c1oc3ccccc3c21]
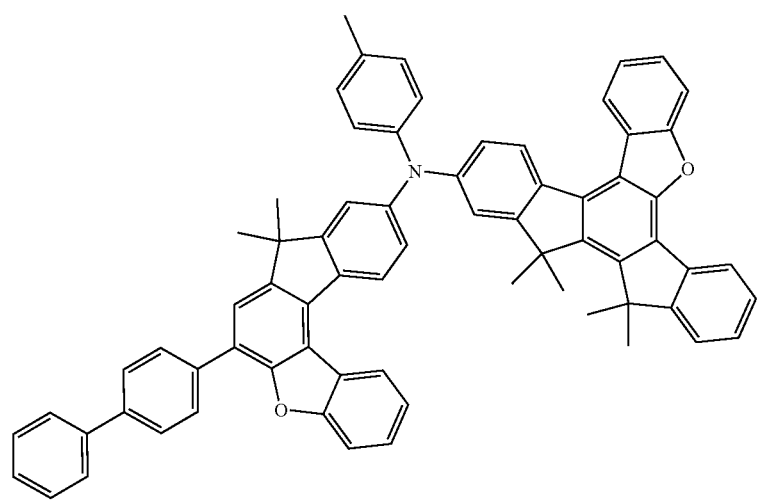 [SMILES: Cc1ccc(N(c2ccc3c(c2)C(C)(C)c2cc(-c4ccc(-c5ccccc5)cc4)c4oc5ccccc5c4c2-3)c2ccc3c(c2)C(C)(C)c2c4c(c5oc6ccccc6c5c2-3)-c2ccccc2C4(C)C)cc1]
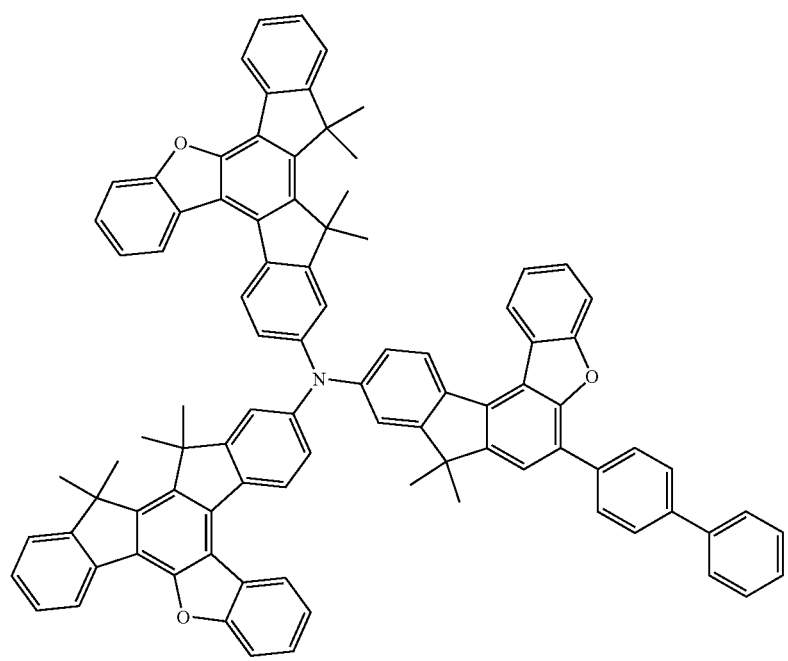 [SMILES: CC1(C)c2cc(N(c3ccc4c(c3)C(C)(C)c3c5c(c6oc7ccccc7c6c3-4)-c3ccccc3C5(C)C)c3ccc4c(c3)C(C)(C)c3c5c(c6oc7ccccc7c6c3-4)-c3ccccc3C5(C)C)ccc2-c2c1cc(-c1ccc(-c3ccccc3)cc1)c1oc3ccccc3c21]

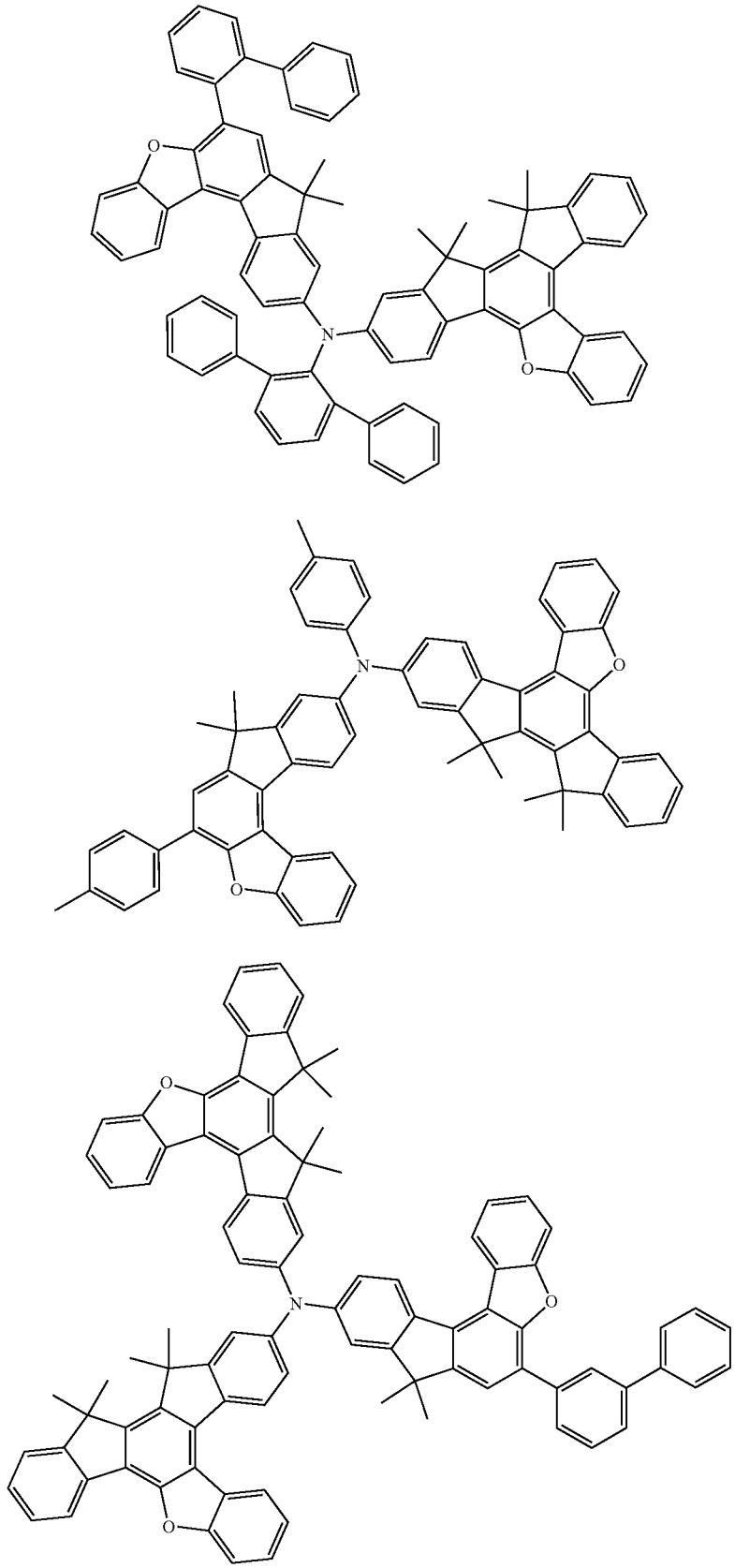

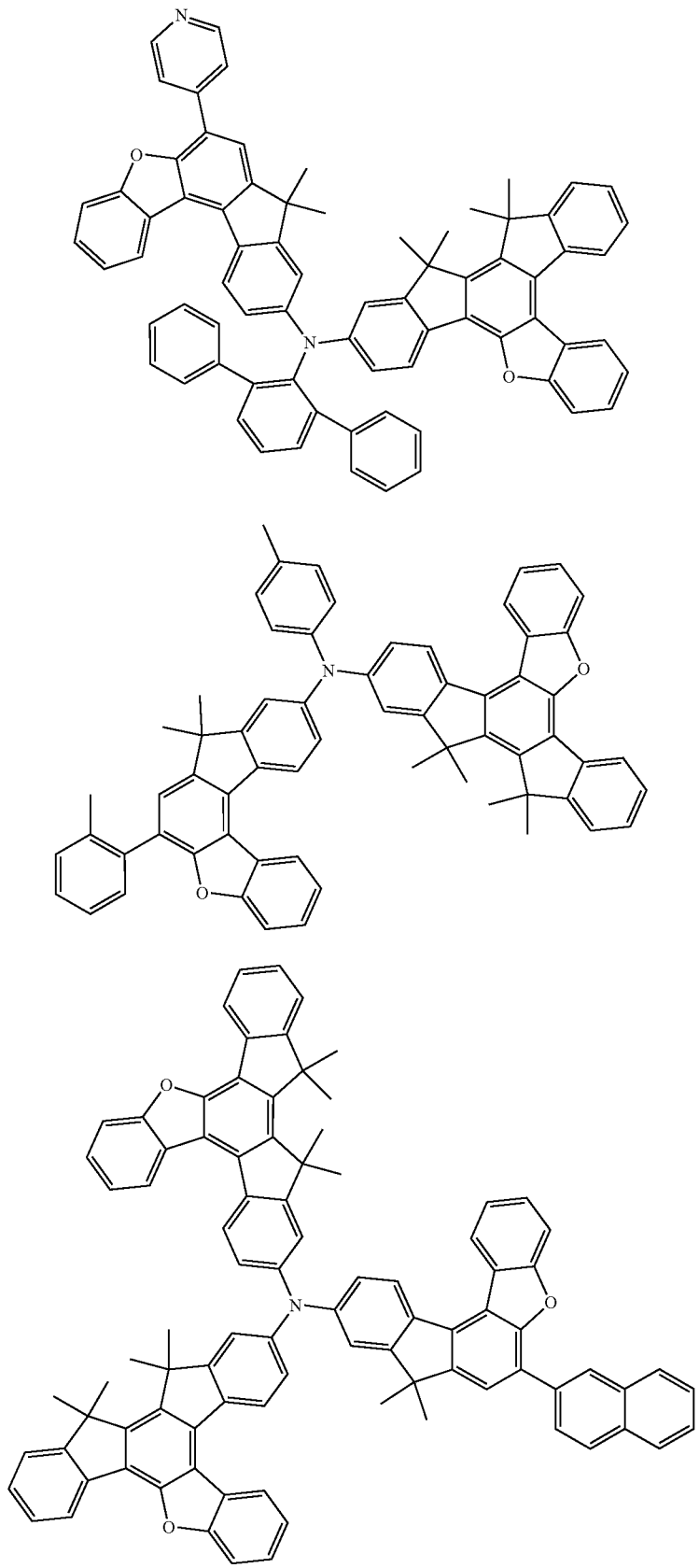

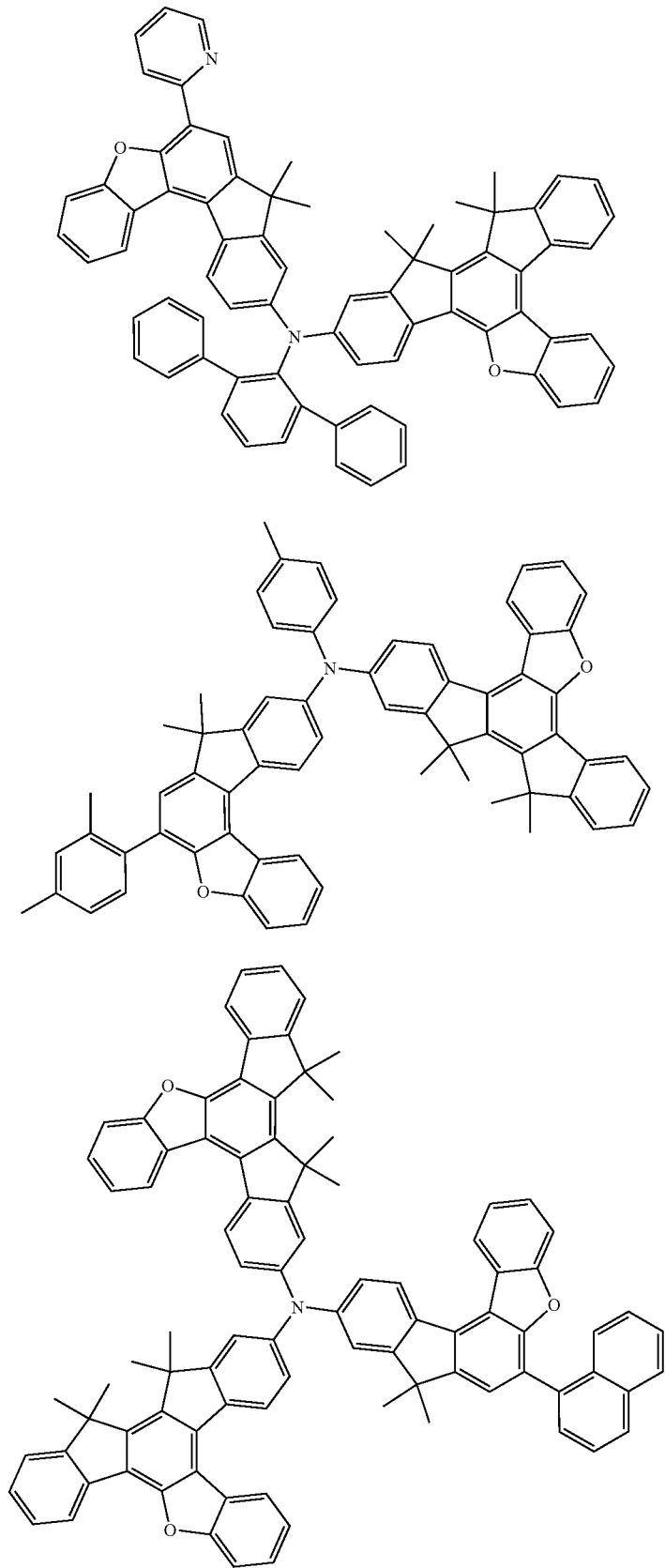

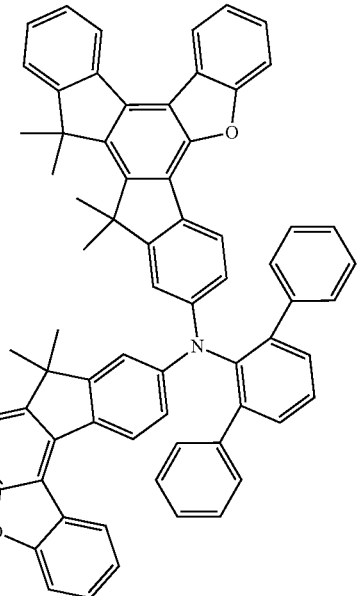
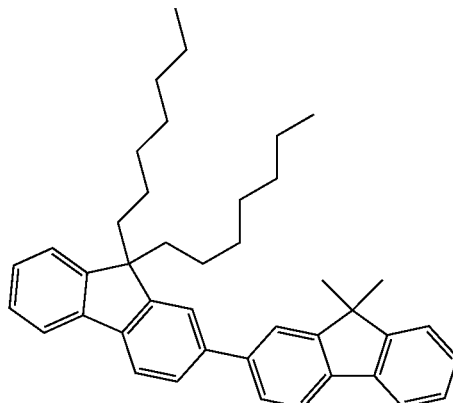
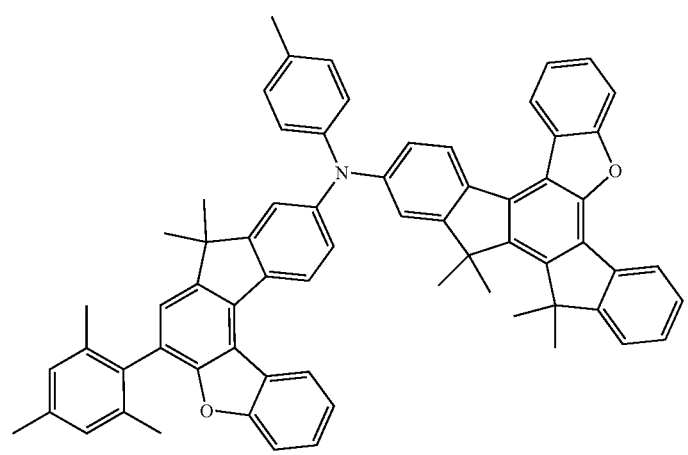 [SMILES: Cc1ccc(N(c2ccc3c(c2)C(C)(C)c2cc(-c4c(C)cc(C)cc4C)c4oc5ccccc5c4c2-3)c2ccc3c(c2)C(C)(C)c2c4c(c5oc6ccccc6c5c2-3)-c2ccccc2C4(C)C)cc1]

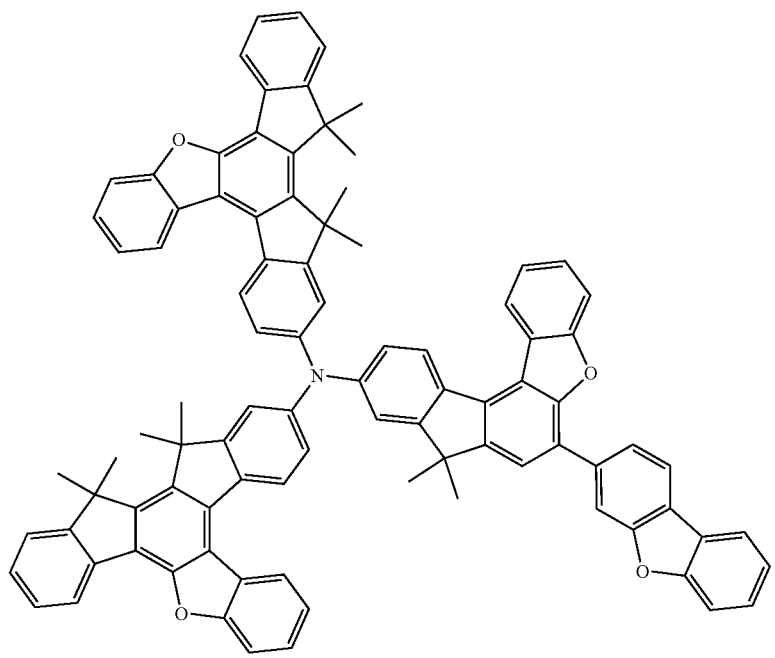 [SMILES: CC1(C)c2cc(N(c3ccc4c(c3)C(C)(C)c3c5c(c6oc7ccccc7c6c3-4)-c3ccccc3C5(C)C)c3ccc4c(c3)C(C)(C)c3c5c(c6oc7ccccc7c6c3-4)-c3ccccc3C5(C)C)ccc2-c2c1cc(-c1ccc3c(c1)oc1ccccc13)c1oc3ccccc3c21]
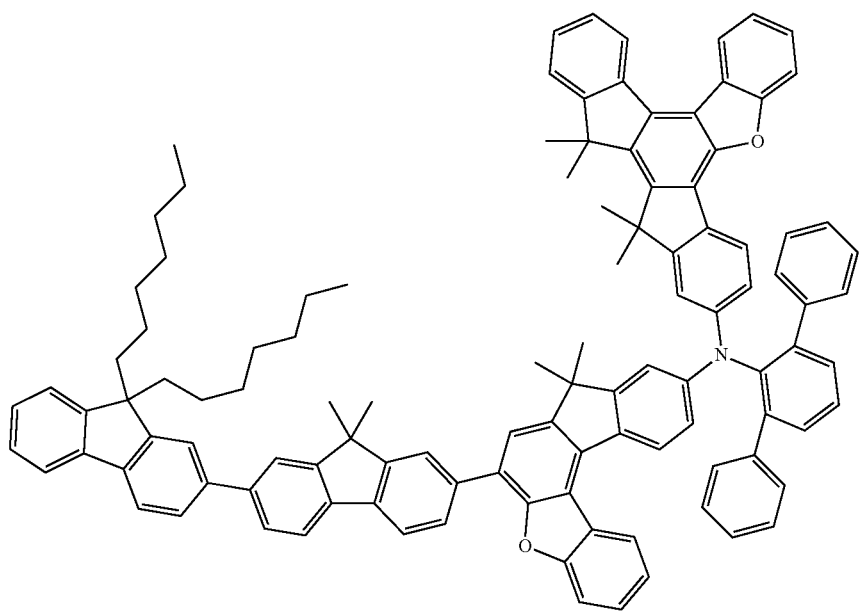 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10c(oc%11ccccc%11%10)c7-8)-c7ccccc7C9(C)C)c7c(-c8ccccc8)cccc7-c7ccccc7)cc5C6(C)C)ccc3-4)cc21]

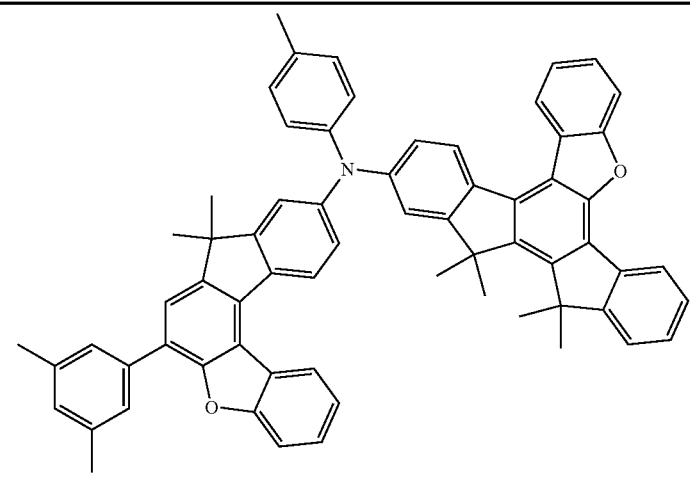
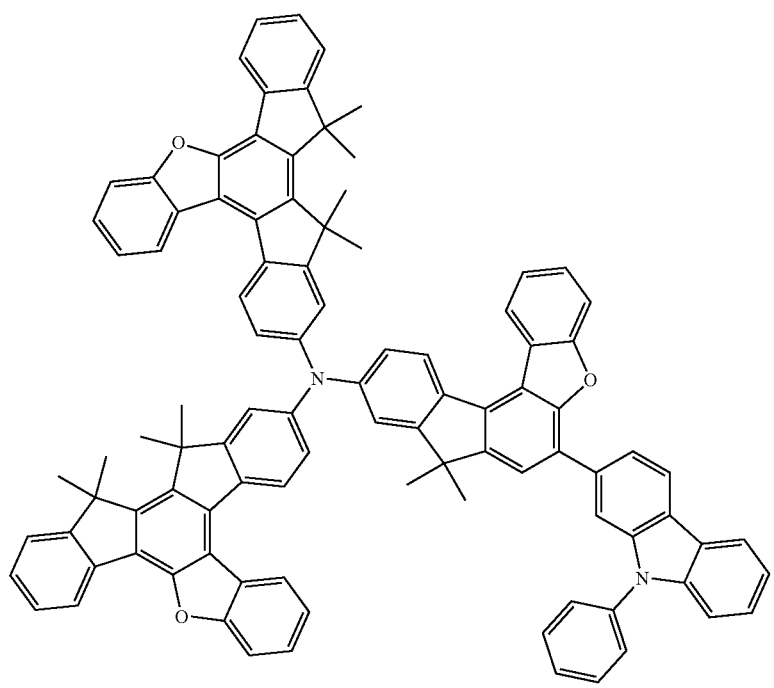 [SMILES: CC1(C)c2cc(N(c3ccc4c(c3)C(C)(C)c3c5c(c6oc7ccccc7c6c3-4)-c3ccccc3C5(C)C)c3ccc4c(c3)C(C)(C)c3c5c(c6oc7ccccc7c6c3-4)-c3ccccc3C5(C)C)ccc2-c2c1cc(-c1ccc3c4ccccc4n(-c4ccccc4)c3c1)c1oc3ccccc3c21]
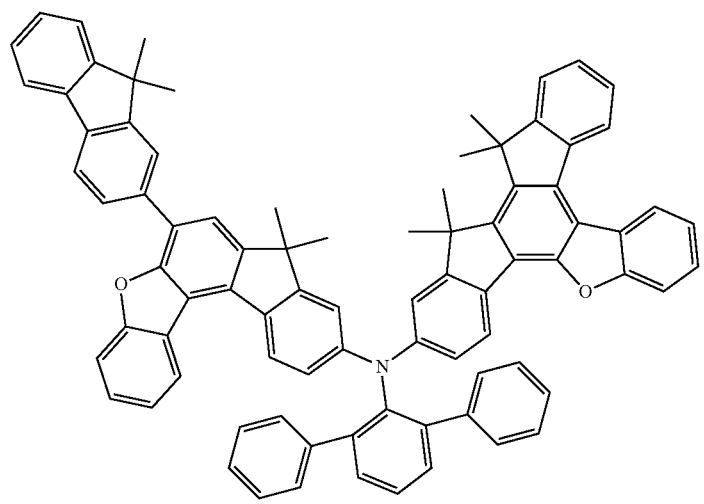 [SMILES: CC1(C)c2ccccc2-c2ccc(-c3cc4c(c5c3oc3ccccc35)-c3ccc(N(c5ccc6c(c5)C(C)(C)c5c7c(c8c(oc9ccccc98)c5-6)-c5ccccc5C7(C)C)c5c(-c6ccccc6)cccc5-c5ccccc5)cc3C4(C)C)cc21]

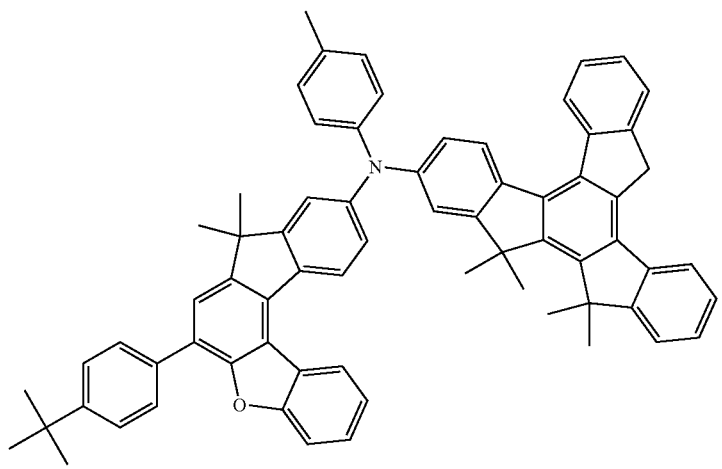 [SMILES: Cc1ccc(N(c2ccc3c(c2)C(C)(C)c2cc(-c4ccc(C(C)(C)C)cc4)c4oc5ccccc5c4c2-3)c2ccc3c(c2)C(C)(C)c2c-3c3c(c4c2C(C)(C)c2ccccc2-4)Cc2ccccc2-3)cc1]
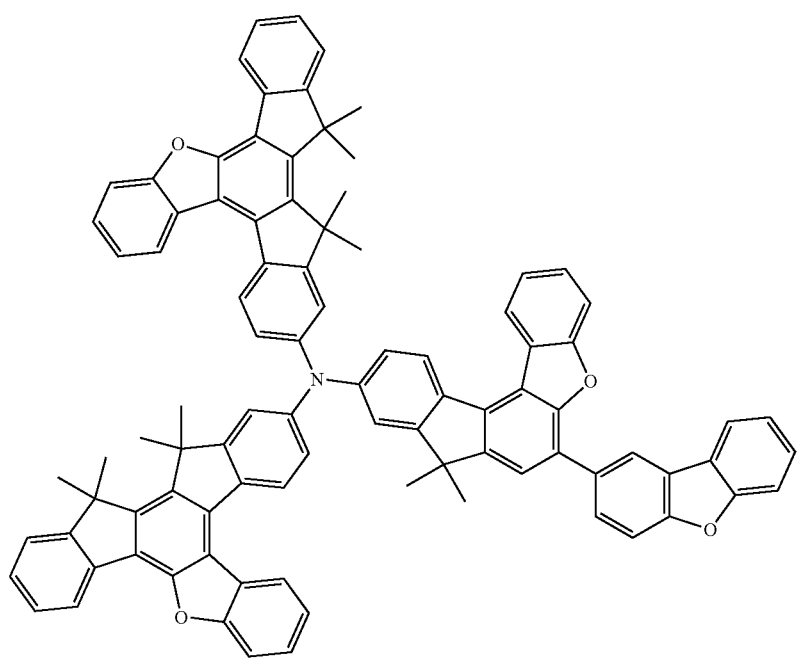 [SMILES: CC1(C)c2cc(N(c3ccc4c(c3)C(C)(C)c3c5c(c6oc7ccccc7c6c3-4)-c3ccccc3C5(C)C)c3ccc4c(c3)C(C)(C)c3c5c(c6oc7ccccc7c6c3-4)-c3ccccc3C5(C)C)ccc2-c2c1cc(-c1ccc3oc4ccccc4c3c1)c1oc3ccccc3c21]
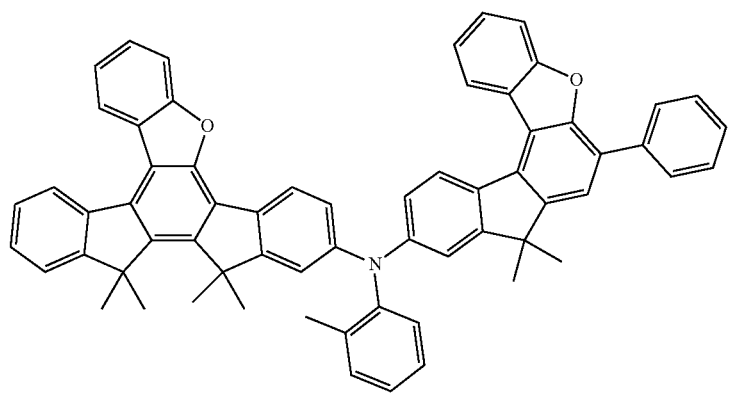 [SMILES: Cc1ccccc1N(c1ccc2c(c1)C(C)(C)c1cc(-c3ccccc3)c3oc4ccccc4c3c1-2)c1ccc2c(c1)C(C)(C)c1c3c(c4c(oc5ccccc54)c1-2)-c1ccccc1C3(C)C]

-continued
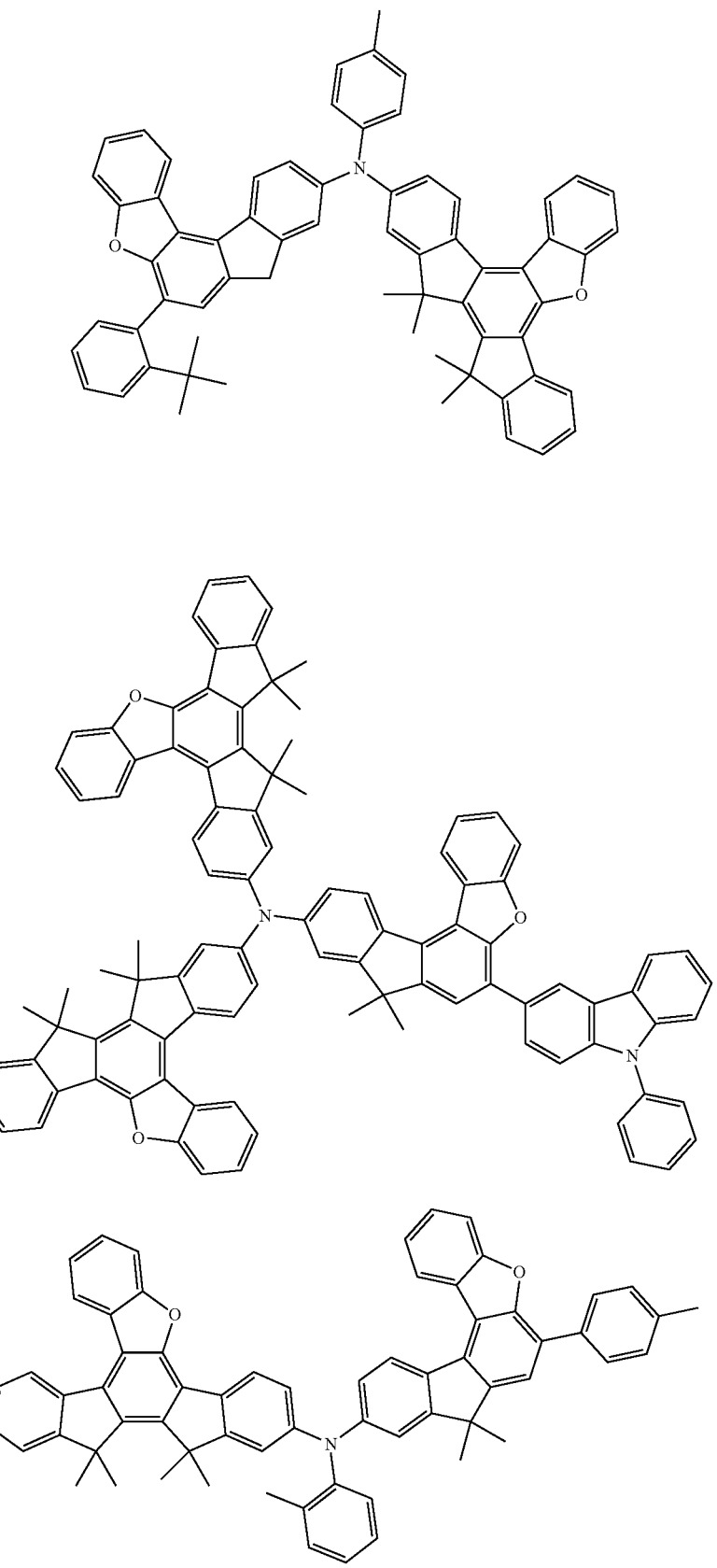

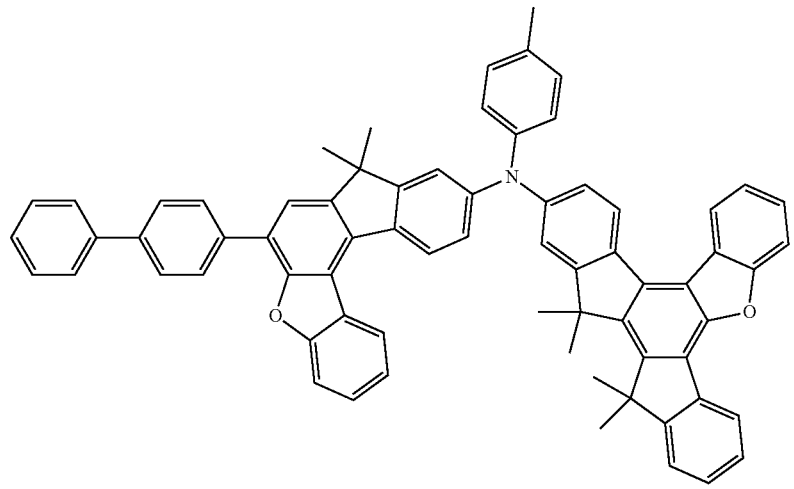 [SMILES: Cc1ccc(N(c2ccc3c(c2)C(C)(C)c2cc(-c4ccc(-c5ccccc5)cc4)c4oc5ccccc5c4c2-3)c2ccc3c(c2)C(C)(C)c2c4c(c5oc6ccccc6c5c2-3)-c2ccccc2C4(C)C)cc1]
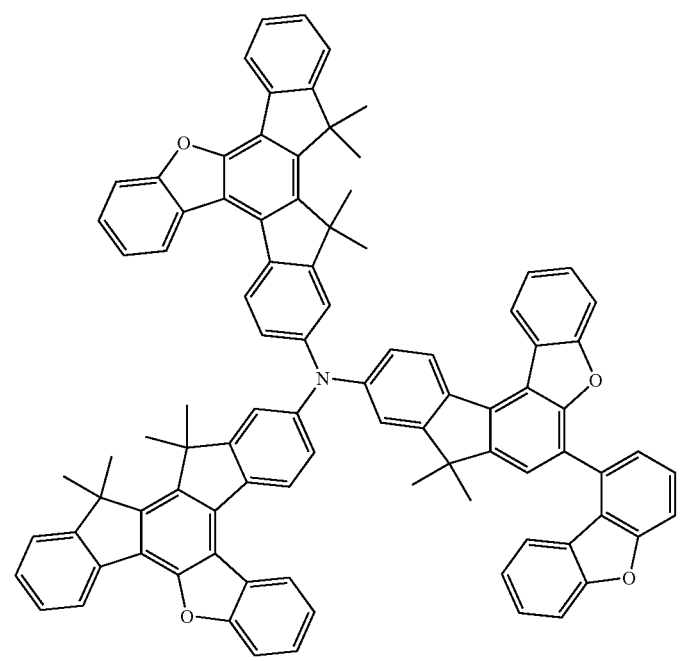 [SMILES: CC1(C)c2cc(N(c3ccc4c(c3)C(C)(C)c3c5c(c6oc7ccccc7c6c3-4)-c3ccccc3C5(C)C)c3ccc4c(c3)C(C)(C)c3c5c(c6oc7ccccc7c6c3-4)-c3ccccc3C5(C)C)ccc2-c2c1cc(-c1cccc3oc4ccccc4c13)c1oc3ccccc3c21]
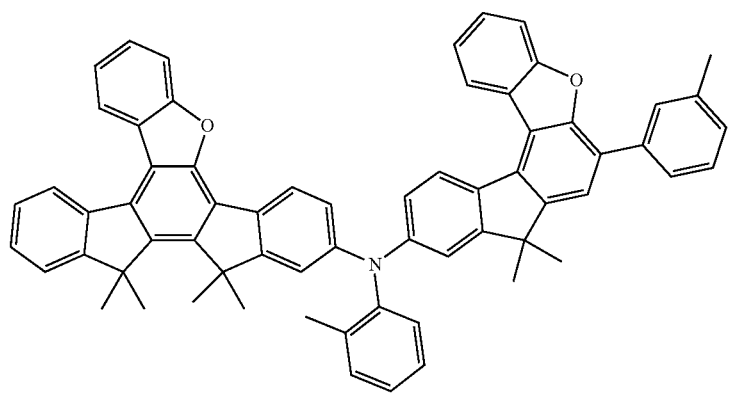 [SMILES: Cc1cccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccccc4C)cc2C3(C)C)c1]

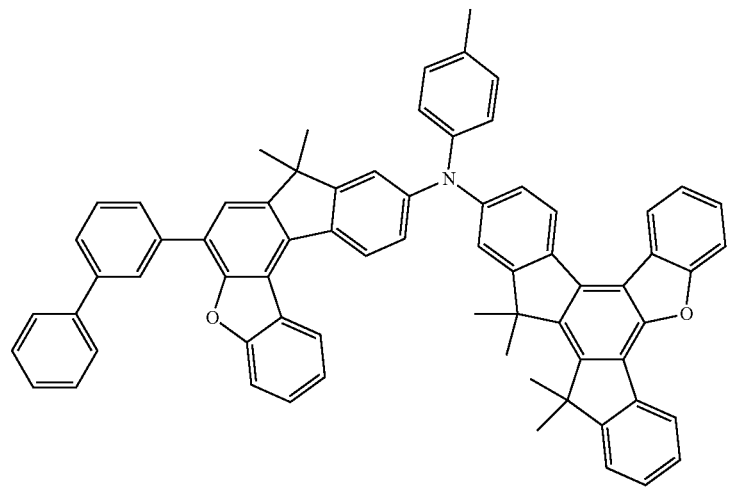 [SMILES: Cc1ccc(N(c2ccc3c(c2)C(C)(C)c2cc(-c4cccc(-c5ccccc5)c4)c4oc5ccccc5c4c2-3)c2ccc3c(c2)C(C)(C)c2c4c(c5oc6ccccc6c5c2-3)-c2ccccc2C4(C)C)cc1]
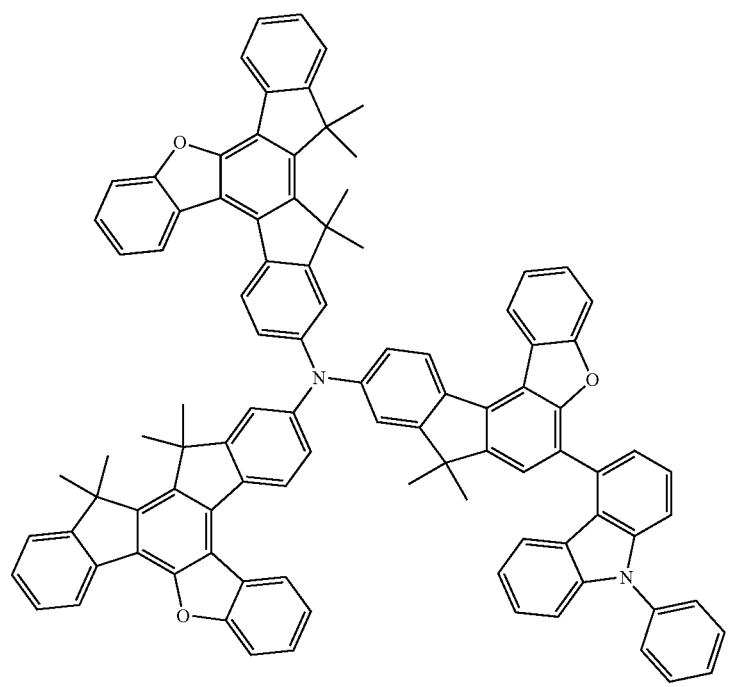 [SMILES: CC1(C)c2cc(N(c3ccc4c(c3)C(C)(C)c3c5c(c6oc7ccccc7c6c3-4)-c3ccccc3C5(C)C)c3ccc4c(c3)C(C)(C)c3c5c(c6oc7ccccc7c6c3-4)-c3ccccc3C5(C)C)ccc2-c2c1cc(-c1cccc3c1c1ccccc1n3-c1ccccc1)c1oc3ccccc3c21]
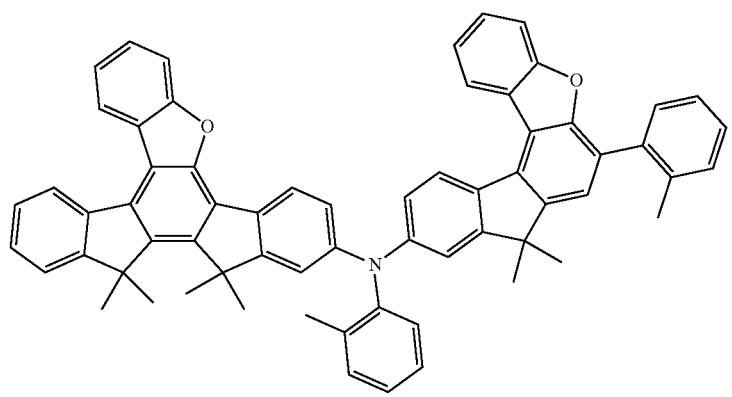 [SMILES: Cc1ccccc1-c1cc2c(c3c1oc1ccccc13)-c1ccc(N(c3ccc4c(c3)C(C)(C)c3c5c(c6c(oc7ccccc76)c3-4)-c3ccccc3C5(C)C)c3ccccc3C)cc1C2(C)C]

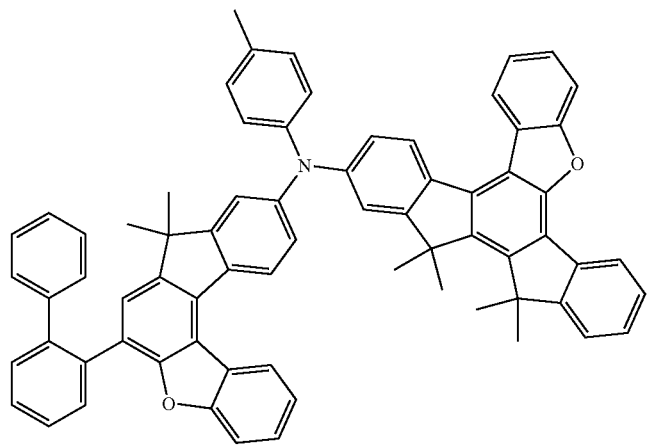 [SMILES: Cc1ccc(N(c2ccc3c(c2)C(C)(C)c2cc(-c4ccccc4-c4ccccc4)c4oc5ccccc5c4c2-3)c2ccc3c(c2)C(C)(C)c2c4c(c5oc6ccccc6c5c2-3)-c2ccccc2C4(C)C)cc1]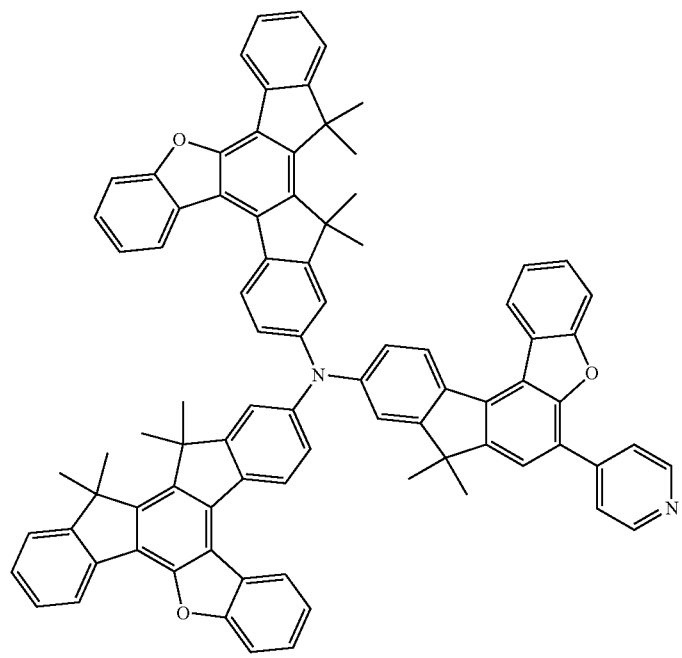 [SMILES: CC1(C)c2cc(N(c3ccc4c(c3)C(C)(C)c3c5c(c6oc7ccccc7c6c3-4)-c3ccccc3C5(C)C)c3ccc4c(c3)C(C)(C)c3c5c(c6oc7ccccc7c6c3-4)-c3ccccc3C5(C)C)ccc2-c2c1cc(-c1ccncc1)c1oc3ccccc3c21]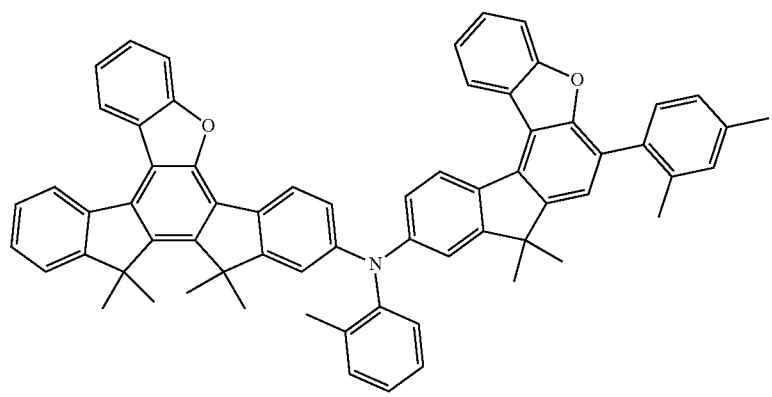 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccccc4C)cc2C3(C)C)c(C)c1]

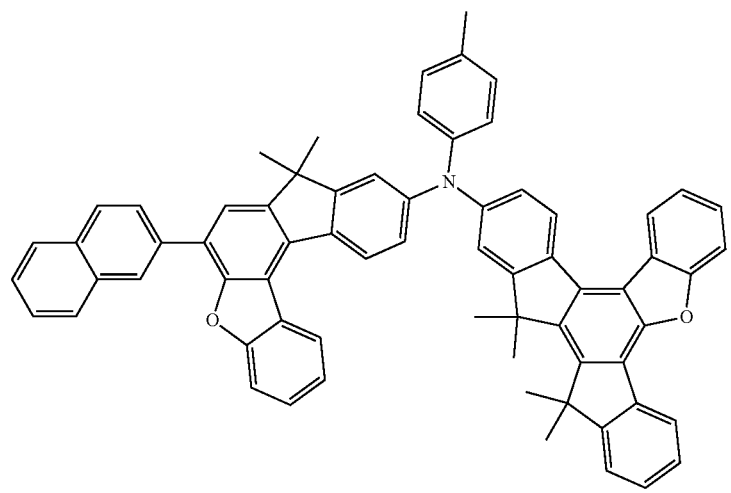 [SMILES: Cc1ccc(N(c2ccc3c(c2)C(C)(C)c2cc(-c4ccc5ccccc5c4)c4oc5ccccc5c4c2-3)c2ccc3c(c2)C(C)(C)c2c4c(c5oc6ccccc6c5c2-3)-c2ccccc2C4(C)C)cc1]
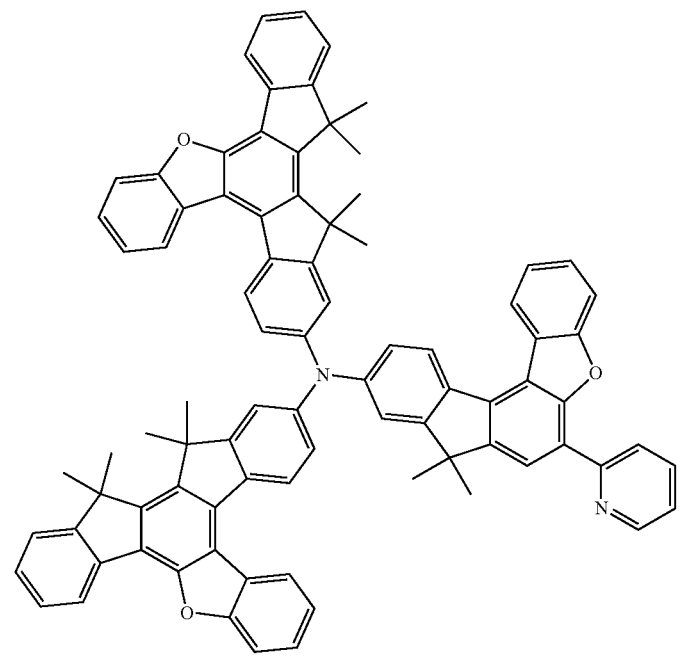 [SMILES: CC1(C)c2cc(N(c3ccc4c(c3)C(C)(C)c3c5c(c6oc7ccccc7c6c3-4)-c3ccccc3C5(C)C)c3ccc4c(c3)C(C)(C)c3c5c(c6oc7ccccc7c6c3-4)-c3ccccc3C5(C)C)ccc2-c2c1cc(-c1ccccn1)c1oc3ccccc3c21]
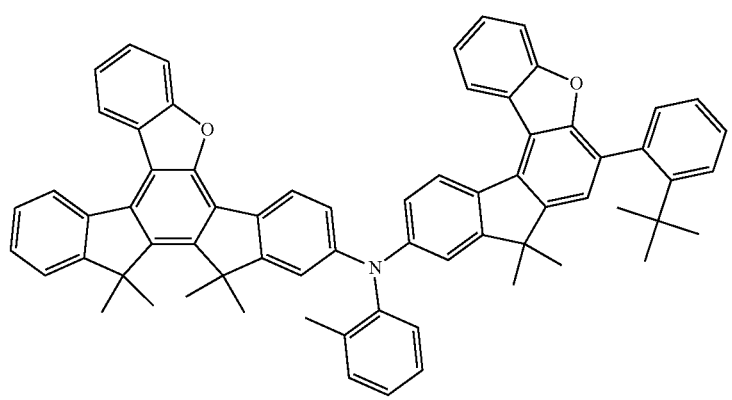 [SMILES: Cc1ccccc1N(c1ccc2c(c1)C(C)(C)c1cc(-c3ccccc3C(C)(C)C)c3oc4ccccc4c3c1-2)c1ccc2c(c1)C(C)(C)c1c3c(c4c(oc5ccccc54)c1-2)-c1ccccc1C3(C)C]

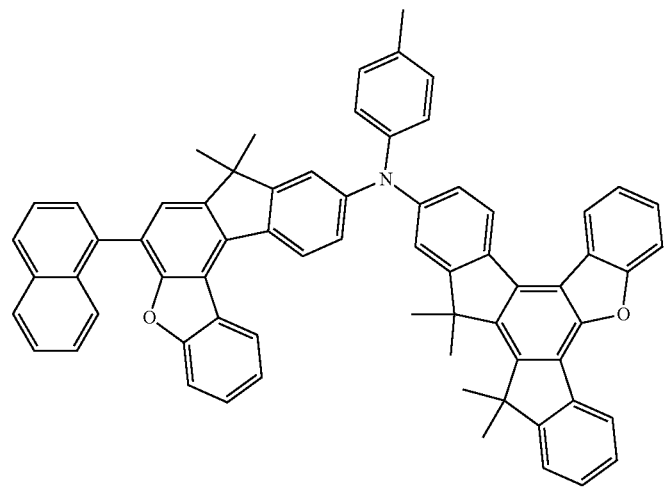 [SMILES: Cc1ccc(N(c2ccc3c(c2)C(C)(C)c2cc(-c4cccc5ccccc45)c4oc5ccccc5c4c2-3)c2ccc3c(c2)C(C)(C)c2c4c(c5oc6ccccc6c5c2-3)-c2ccccc2C4(C)C)cc1]
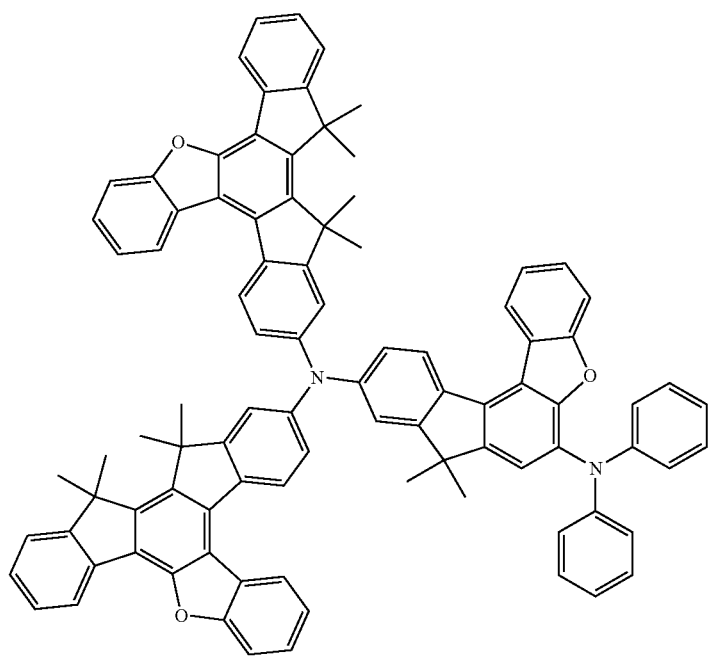 [SMILES: CC1(C)c2cc(N(c3ccc4c(c3)C(C)(C)c3c5c(c6oc7ccccc7c6c3-4)-c3ccccc3C5(C)C)c3ccc4c(c3)C(C)(C)c3c5c(c6oc7ccccc7c6c3-4)-c3ccccc3C5(C)C)ccc2-c2c1cc(N(c1ccccc1)c1ccccc1)c1oc3ccccc3c21]
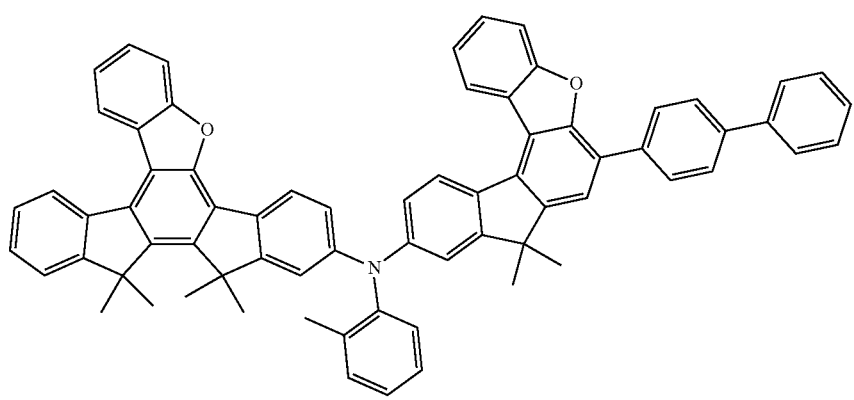 [SMILES: Cc1ccccc1N(c1ccc2c(c1)C(C)(C)c1cc(-c3ccc(-c4ccccc4)cc3)c3oc4ccccc4c3c1-2)c1ccc2c(c1)C(C)(C)c1c3c(c4c(oc5ccccc54)c1-2)-c1ccccc1C3(C)C]

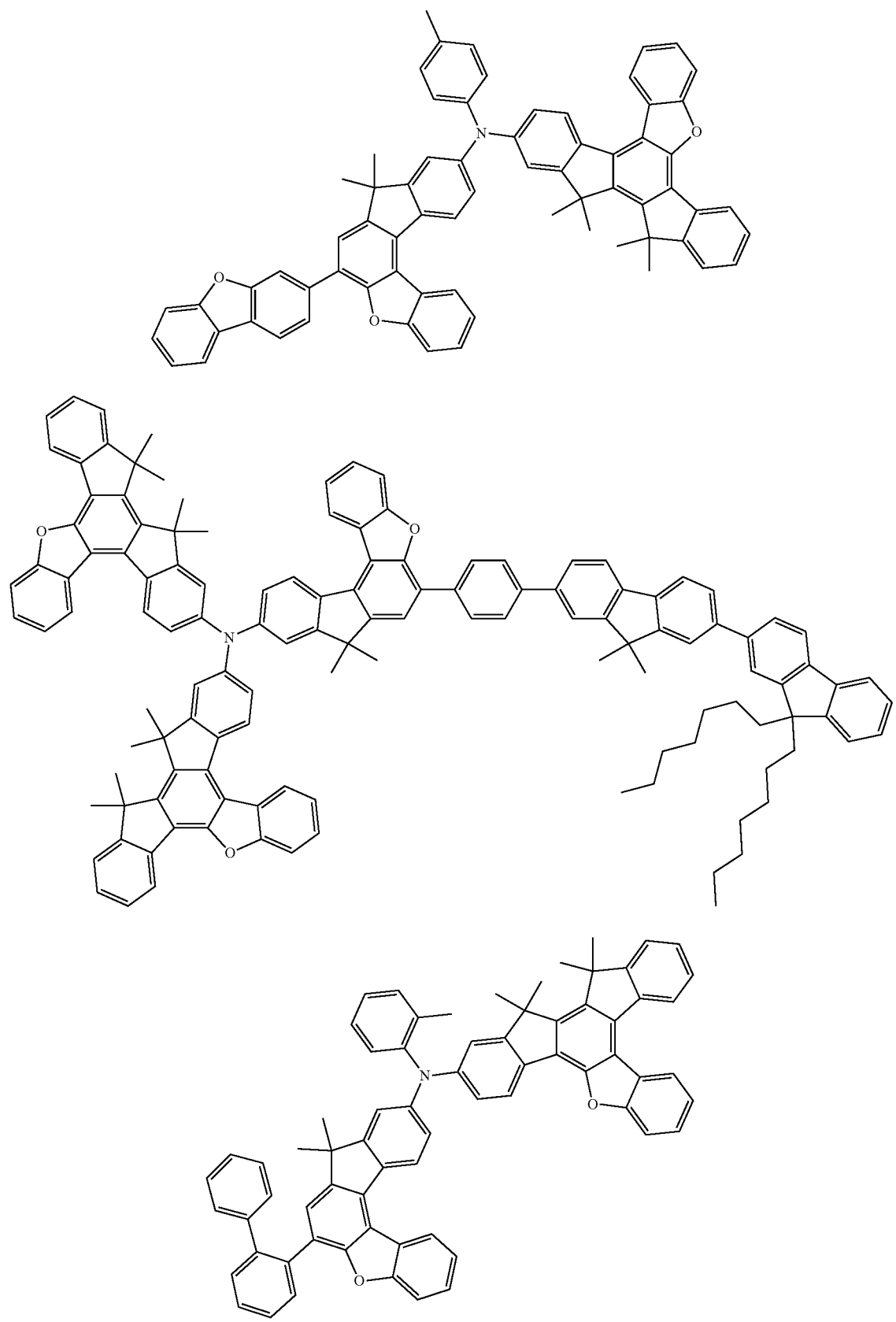

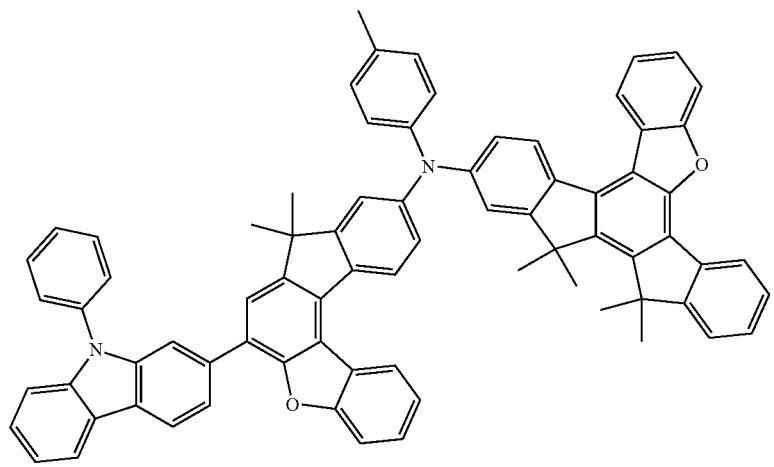 [SMILES: Cc1ccc(N(c2ccc3c(c2)C(C)(C)c2cc(-c4ccc5c6ccccc6n(-c6ccccc6)c5c4)c4oc5ccccc5c4c2-3)c2ccc3c(c2)C(C)(C)c2c4c(c5oc6ccccc6c5c2-3)-c2ccccc2C4(C)C)cc1]
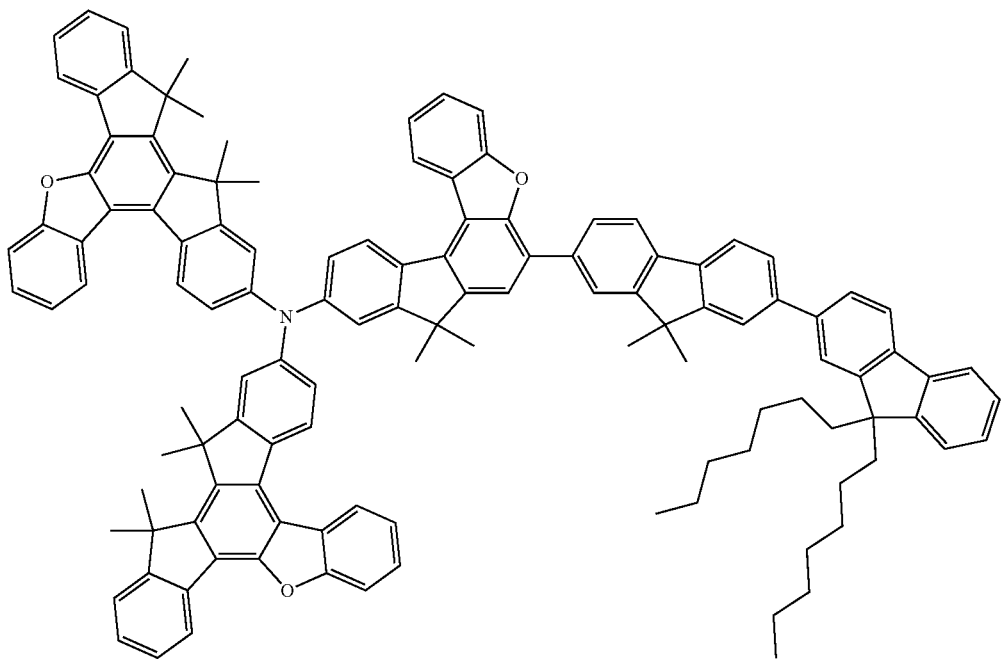 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7ccc8c(c7)C(C)(C)c7c9c(c%10oc%11ccccc%11c%10c7-8)-c7ccccc7C9(C)C)cc5C6(C)C)ccc3-4)cc21]
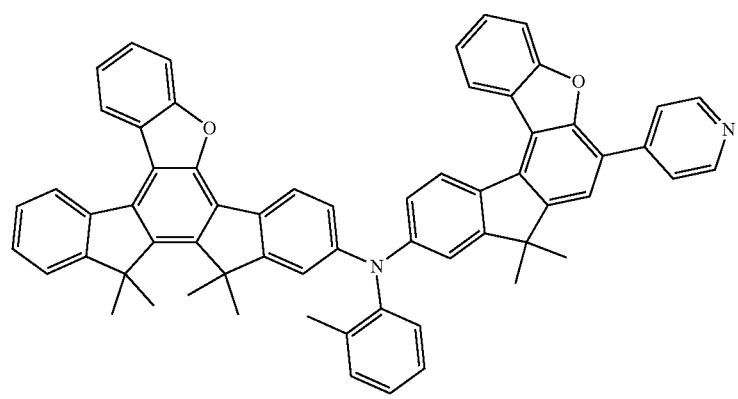 [SMILES: Cc1ccccc1N(c1ccc2c(c1)C(C)(C)c1cc(-c3ccncc3)c3oc4ccccc4c3c1-2)c1ccc2c(c1)C(C)(C)c1c3c(c4c(oc5ccccc54)c1-2)-c1ccccc1C3(C)C]

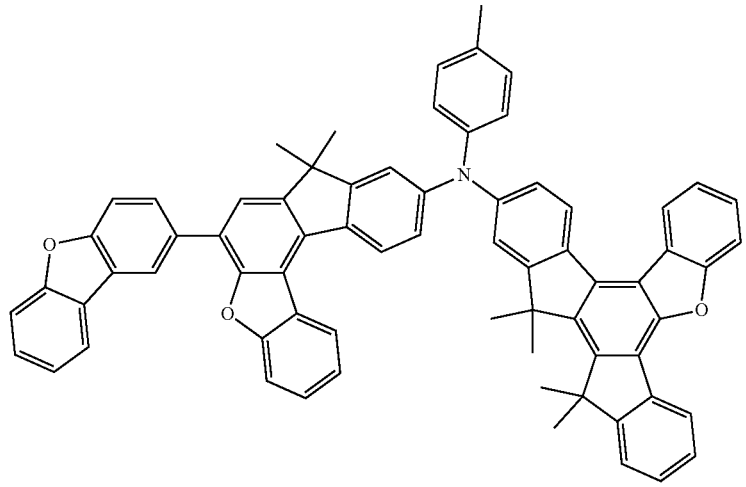 [SMILES: Cc1ccc(N(c2ccc3c(c2)C(C)(C)c2cc(-c4ccc5oc6ccccc6c5c4)c4oc5ccccc5c4c2-3)c2ccc3c(c2)C(C)(C)c2c4c(c5oc6ccccc6c5c2-3)-c2ccccc2C4(C)C)cc1]
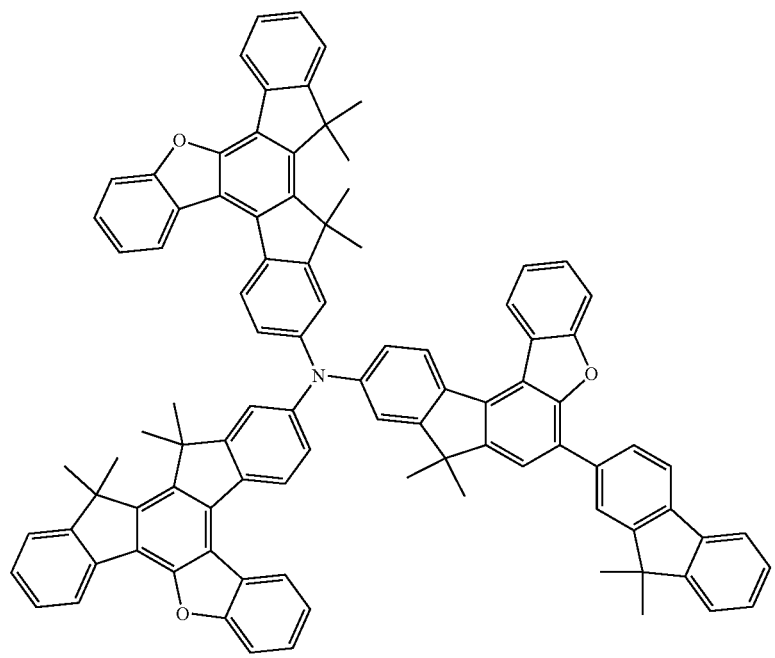 [SMILES: CC1(C)c2ccccc2-c2ccc(-c3cc4c(c5c3oc3ccccc35)-c3ccc(N(c5ccc6c(c5)C(C)(C)c5c7c(c8oc9ccccc9c8c5-6)-c5ccccc5C7(C)C)c5ccc6c(c5)C(C)(C)c5c7c(c8oc9ccccc9c8c5-6)-c5ccccc5C7(C)C)cc3C4(C)C)cc21]
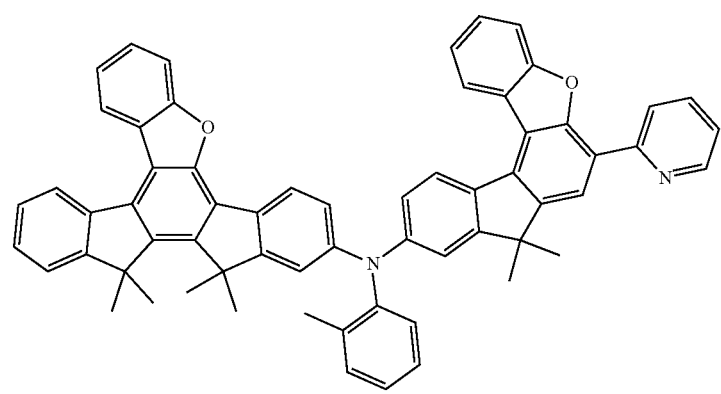 [SMILES: Cc1ccccc1N(c1ccc2c(c1)C(C)(C)c1cc(-c3ccccn3)c3oc4ccccc4c3c1-2)c1ccc2c(c1)C(C)(C)c1c3c(c4c(oc5ccccc54)c1-2)-c1ccccc1C3(C)C]

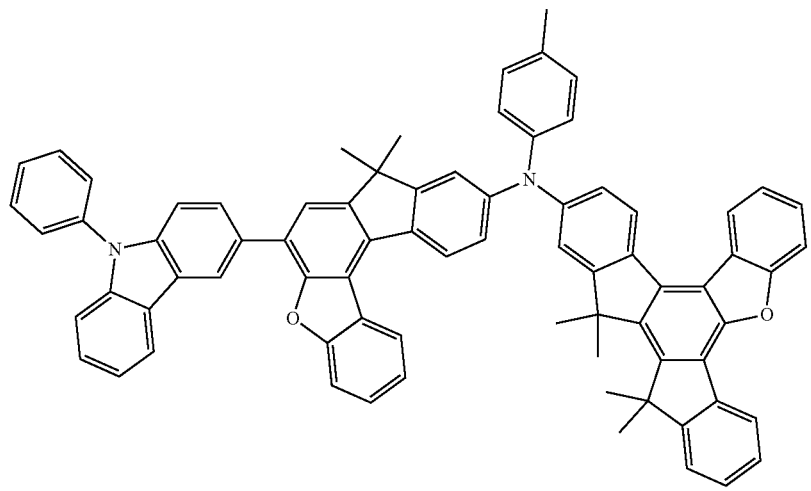 [SMILES: Cc1ccc(N(c2ccc3c(c2)C(C)(C)c2cc(-c4ccc5c(c4)c4ccccc4n5-c4ccccc4)c4oc5ccccc5c4c2-3)c2ccc3c(c2)C(C)(C)c2c4c(c5oc6ccccc6c5c2-3)-c2ccccc2C4(C)C)cc1]
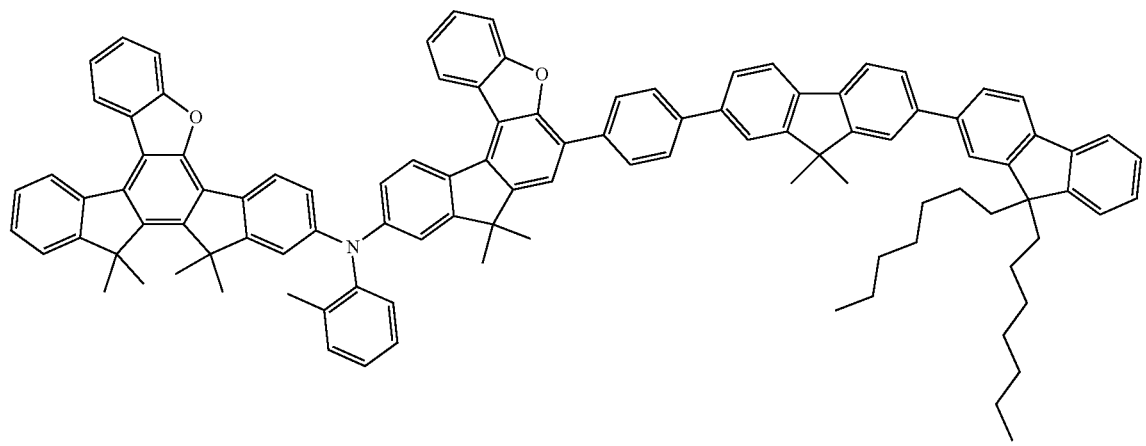 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11c(oc%12ccccc%12%11)c8-9)-c8ccccc8C%10(C)C)c8ccccc8C)cc6C7(C)C)cc5)ccc3-4)cc21]
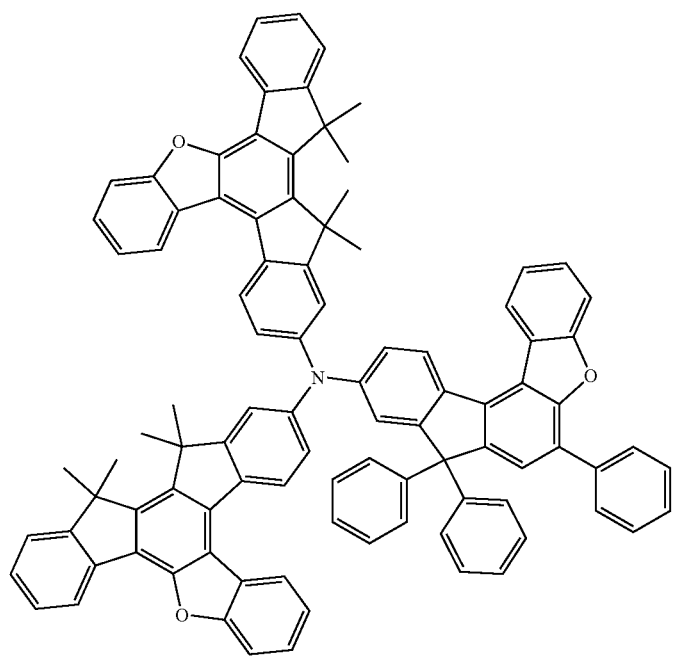 [SMILES: CC1(C)c2ccccc2-c2c1c1c(c3c2oc2ccccc23)-c2ccc(N(c3ccc4c(c3)C(C)(C)c3c5c(c6oc7ccccc7c6c3-4)-c3ccccc3C5(C)C)c3ccc4c(c3)C(c3ccccc3)(c3ccccc3)c3cc(-c5ccccc5)c5oc6ccccc6c5c3-4)cc2C1(C)C]

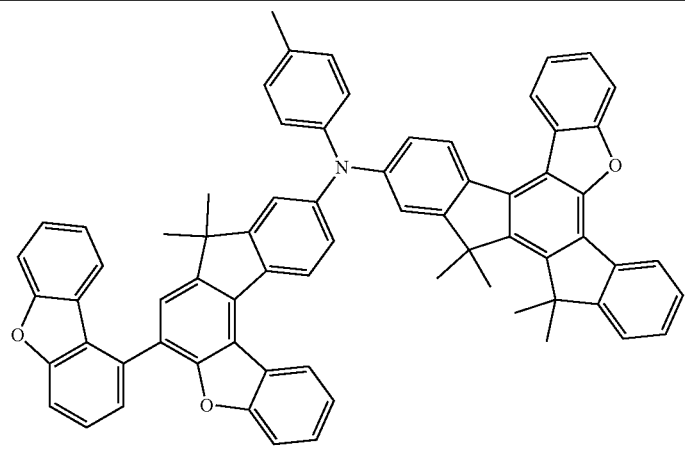
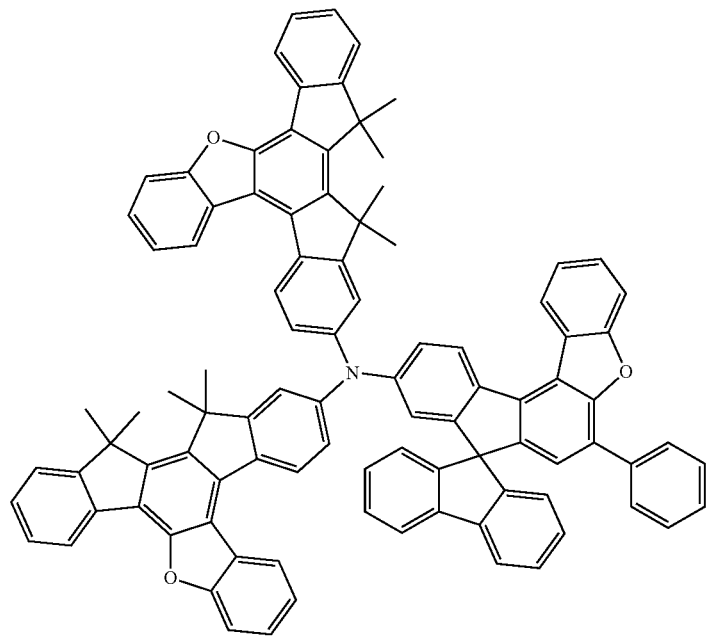 [SMILES: CC1(C)c2ccccc2-c2c1c1c(c3c2oc2ccccc23)-c2ccc(N(c3ccc4c(c3)C(C)(C)c3c5c(c6oc7ccccc7c6c3-4)-c3ccccc3C5(C)C)c3ccc4c(c3)C3(c5ccccc5-c5ccccc53)c3cc(-c5ccccc5)c5oc6ccccc6c5c3-4)cc2C1(C)C]
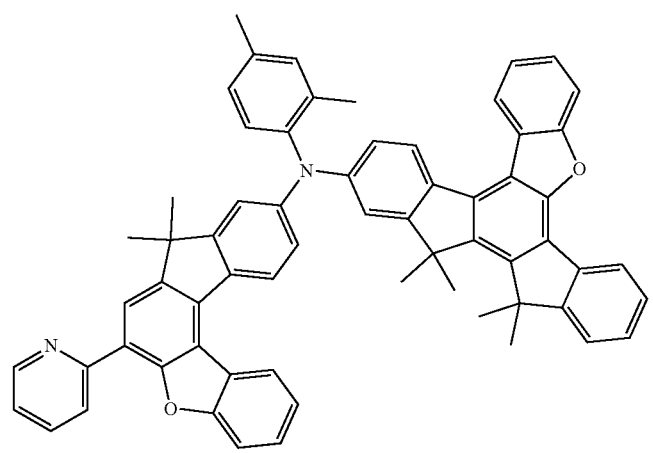 [SMILES: Cc1ccc(N(c2ccc3c(c2)C(C)(C)c2cc(-c4ccccn4)c4oc5ccccc5c4c2-3)c2ccc3c(c2)C(C)(C)c2c4c(c5oc6ccccc6c5c2-3)-c2ccccc2C4(C)C)c(C)c1]

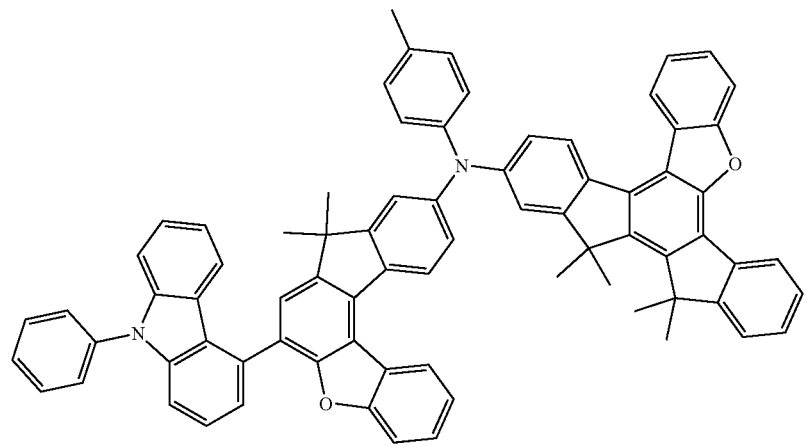 [SMILES: Cc1ccc(N(c2ccc3c(c2)C(C)(C)c2cc(-c4cccc5c4c4ccccc4n5-c4ccccc4)c4oc5ccccc5c4c2-3)c2ccc3c(c2)C(C)(C)c2c4c(c5oc6ccccc6c5c2-3)-c2ccccc2C4(C)C)cc1]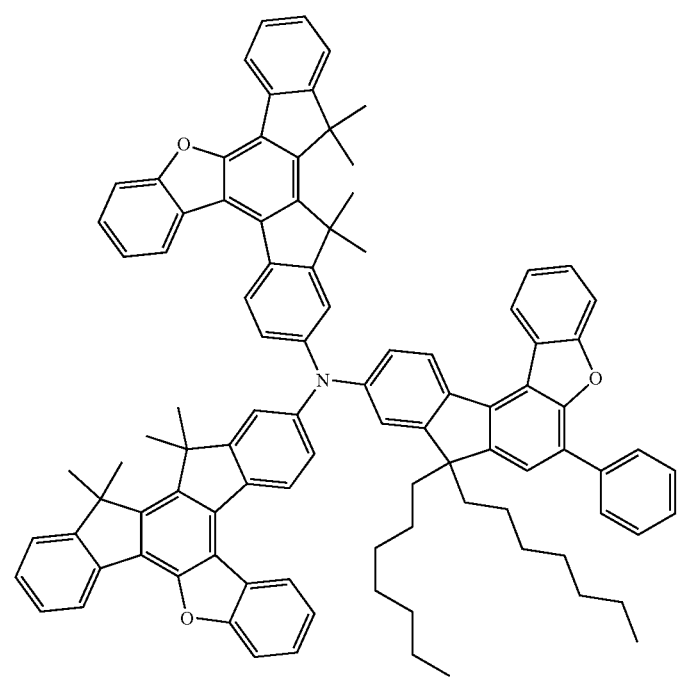 [SMILES: CCCCCCCC1(CCCCCCC)c2cc(N(c3ccc4c(c3)C(C)(C)c3c5c(c6oc7ccccc7c6c3-4)-c3ccccc3C5(C)C)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]

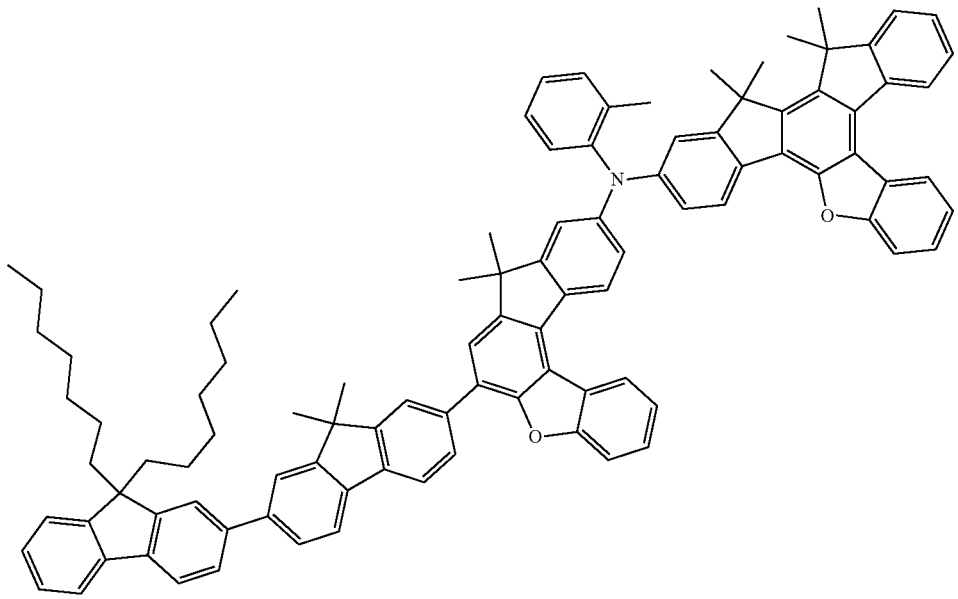 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10c(oc%11ccccc%11%10)c7-8)-c7ccccc7C9(C)C)c7ccccc7C)cc5C6(C)C)ccc3-4)cc21]
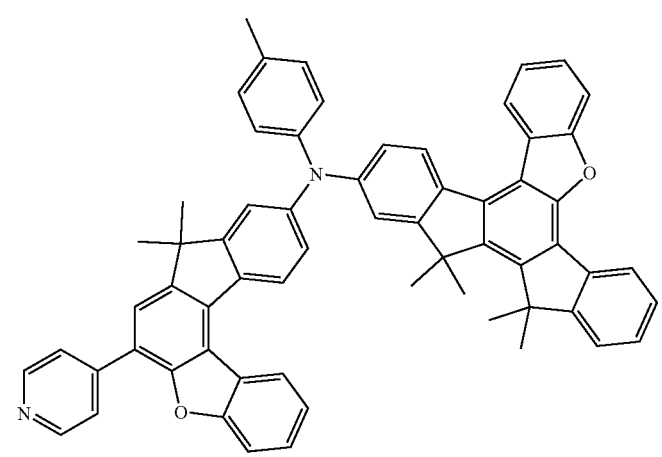 [SMILES: Cc1ccc(N(c2ccc3c(c2)C(C)(C)c2cc(-c4ccncc4)c4oc5ccccc5c4c2-3)c2ccc3c(c2)C(C)(C)c2c4c(c5oc6ccccc6c5c2-3)-c2ccccc2C4(C)C)cc1]

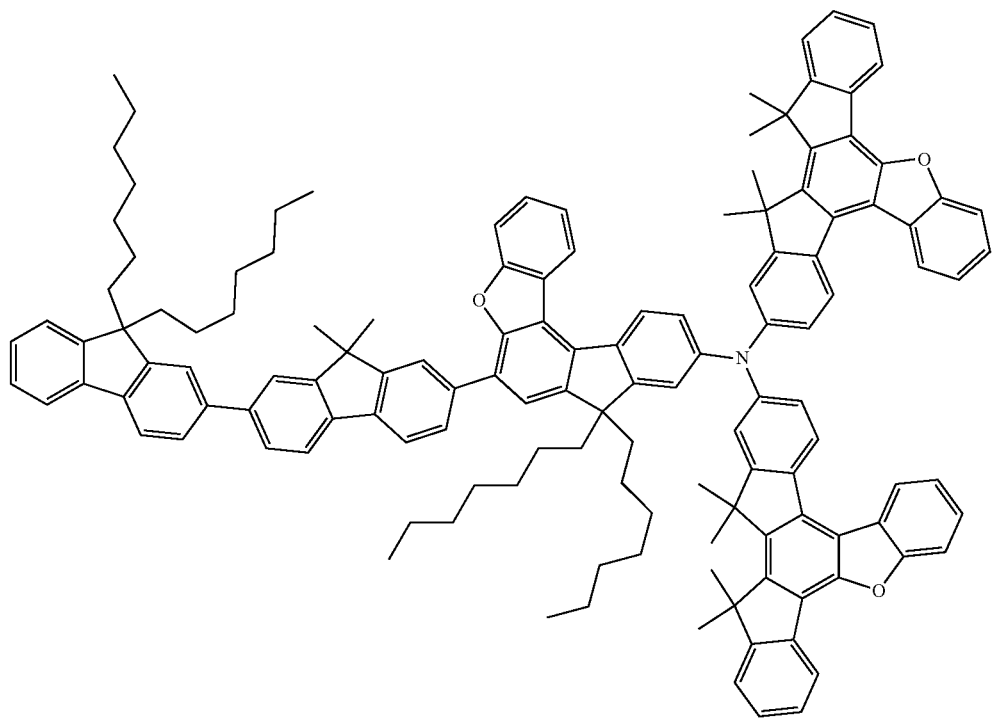 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7ccc8c(c7)C(C)(C)c7c9c(c%10oc%11ccccc%11c%10c7-8)-c7ccccc7C9(C)C)cc5C6(CCCCCCC)CCCCCCC)ccc3-4)cc21]
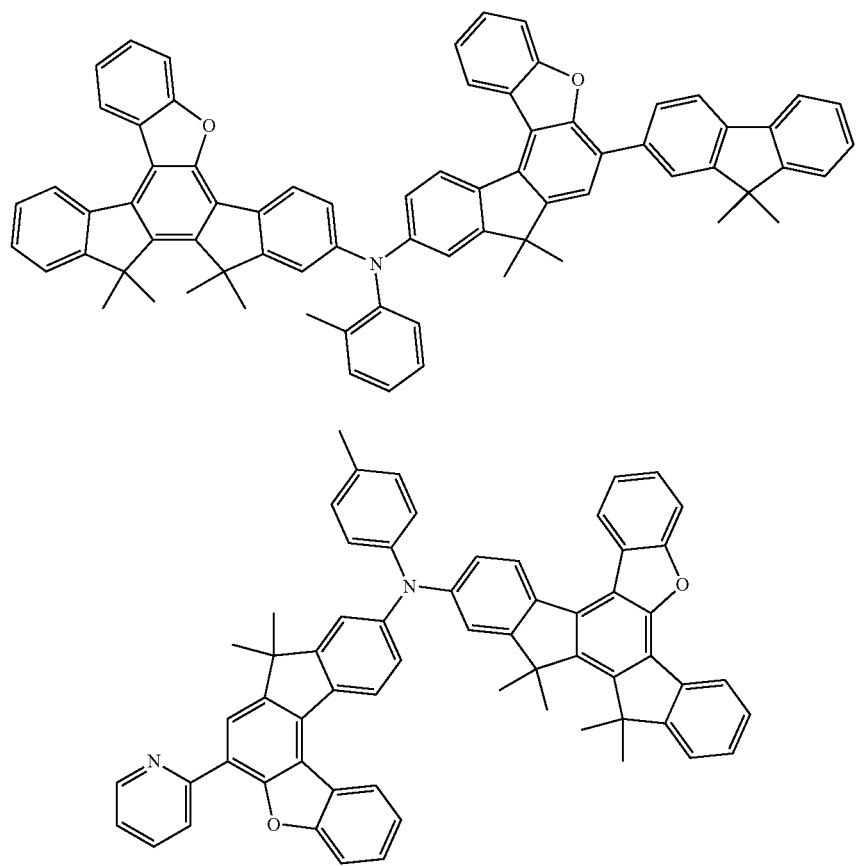

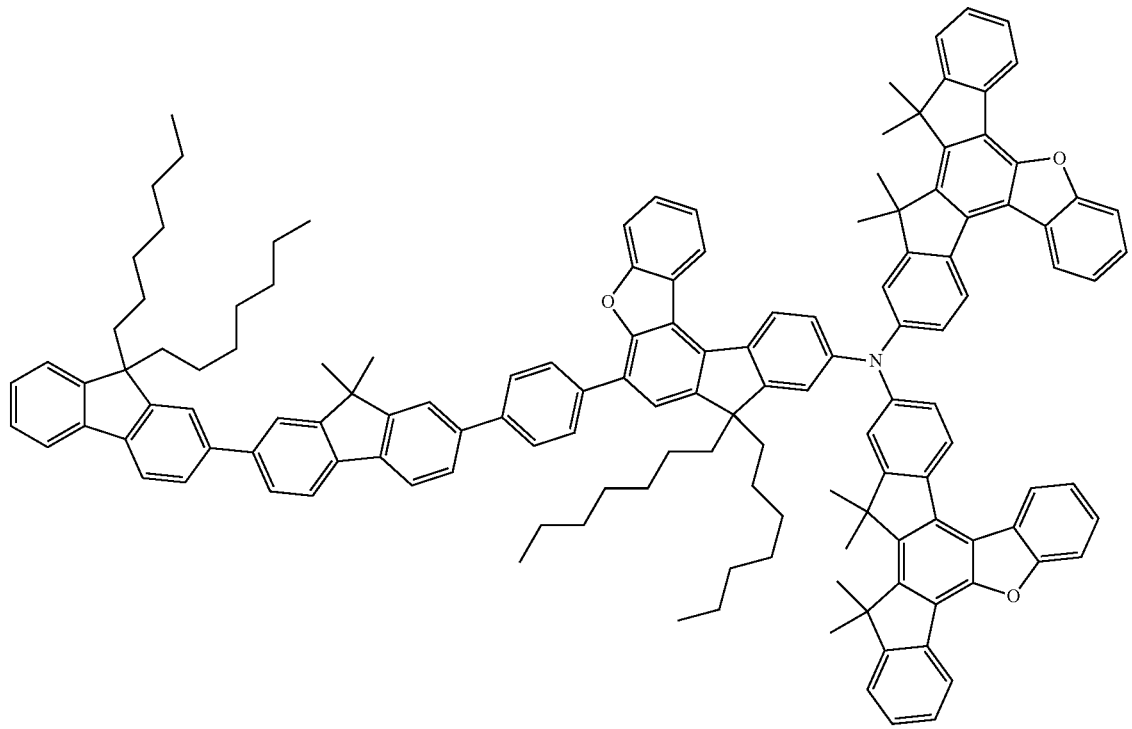 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8ccc9c(c8)C(C)(C)c8c%10c(c%11oc%12ccccc%12c%11c8-9)-c8ccccc8C%10(C)C)cc6C7(CCCCCCC)CCCCCCC)cc5)ccc3-4)cc21]
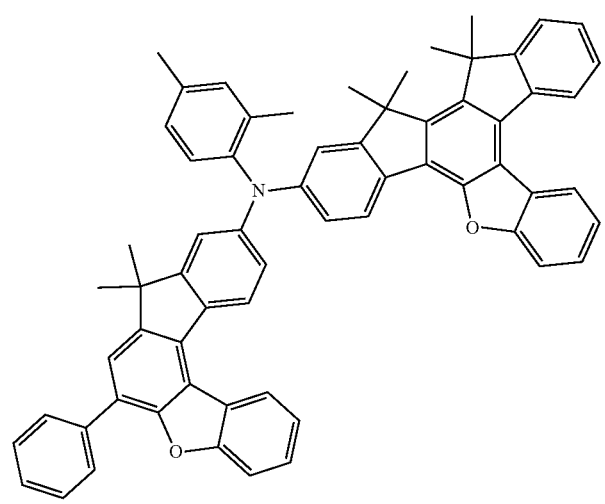 [SMILES: Cc1ccc(N(c2ccc3c(c2)C(C)(C)c2cc(-c4ccccc4)c4oc5ccccc5c4c2-3)c2ccc3c(c2)C(C)(C)c2c4c(c5c(oc6ccccc65)c2-3)-c2ccccc2C4(C)C)c(C)c1]

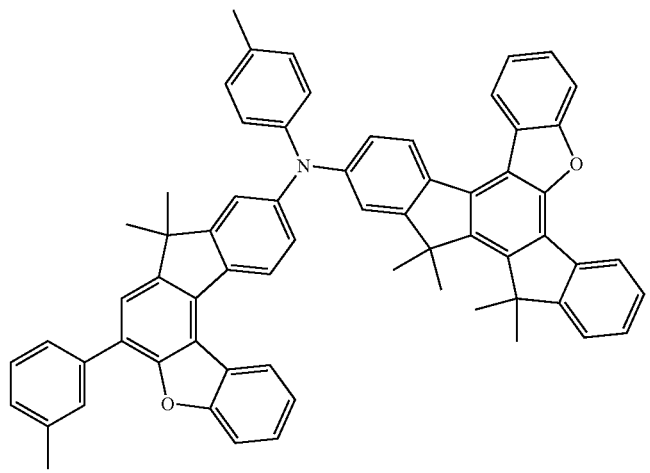 [SMILES: Cc1ccc(N(c2ccc3c(c2)C(C)(C)c2cc(-c4cccc(C)c4)c4oc5ccccc5c4c2-3)c2ccc3c(c2)C(C)(C)c2c4c(c5oc6ccccc6c5c2-3)-c2ccccc2C4(C)C)cc1]
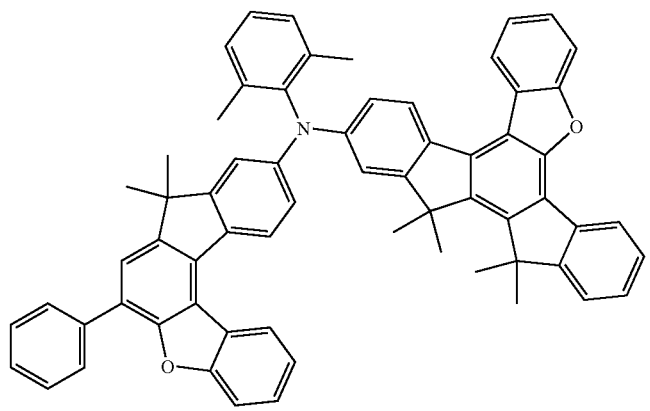 [SMILES: Cc1cccc(C)c1N(c1ccc2c(c1)C(C)(C)c1cc(-c3ccccc3)c3oc4ccccc4c3c1-2)c1ccc2c(c1)C(C)(C)c1c3c(c4oc5ccccc5c4c1-2)-c1ccccc1C3(C)C]
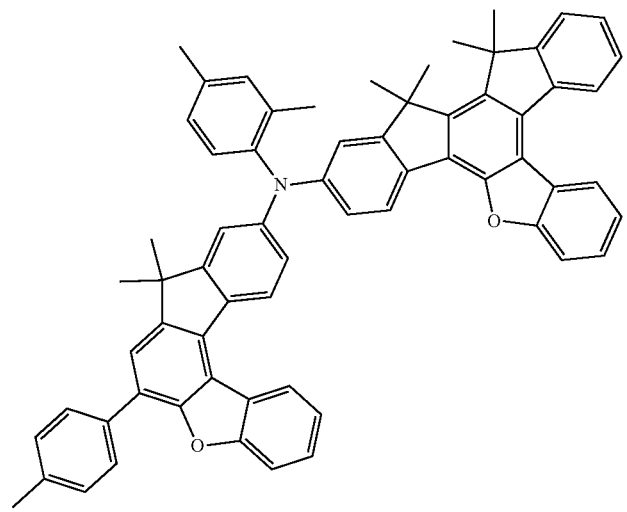 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccc(C)cc4C)cc2C3(C)C)cc1]

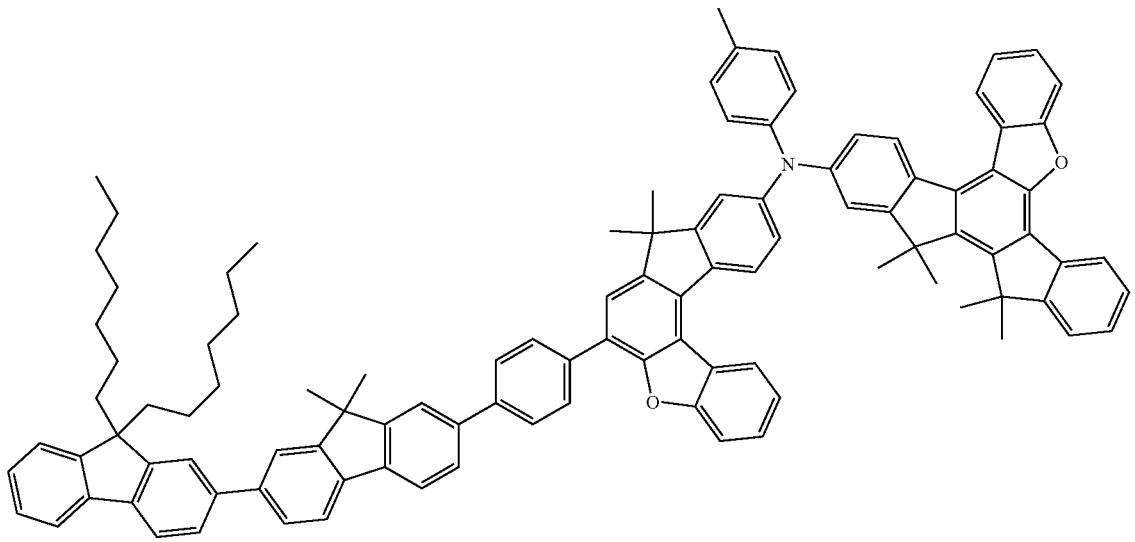 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc(C)cc8)c8ccc9c(c8)C(C)(C)c8c%10c(c%11oc%12ccccc%12c%11c8-9)-c8ccccc8C%10(C)C)cc6C7(C)C)cc5)ccc3-4)cc21]
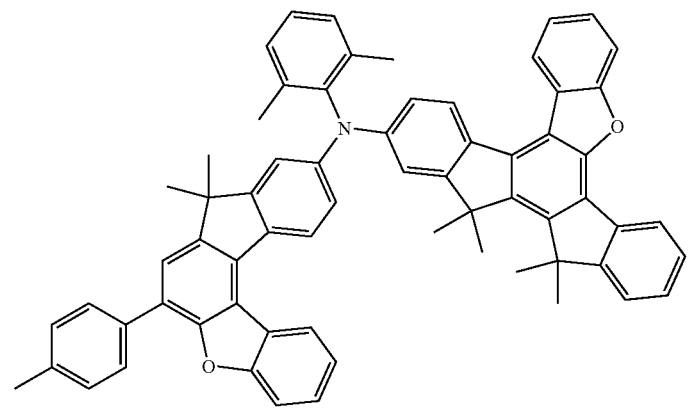 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4c(C)cccc4C)cc2C3(C)C)cc1]
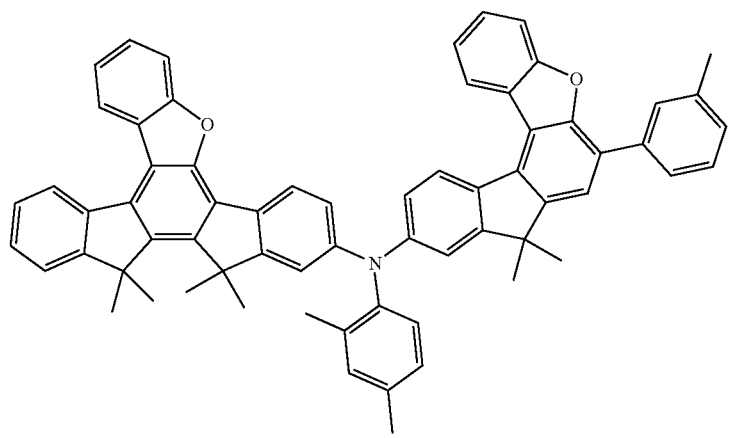 [SMILES: Cc1cccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccc(C)cc4C)cc2C3(C)C)c1]

-continued
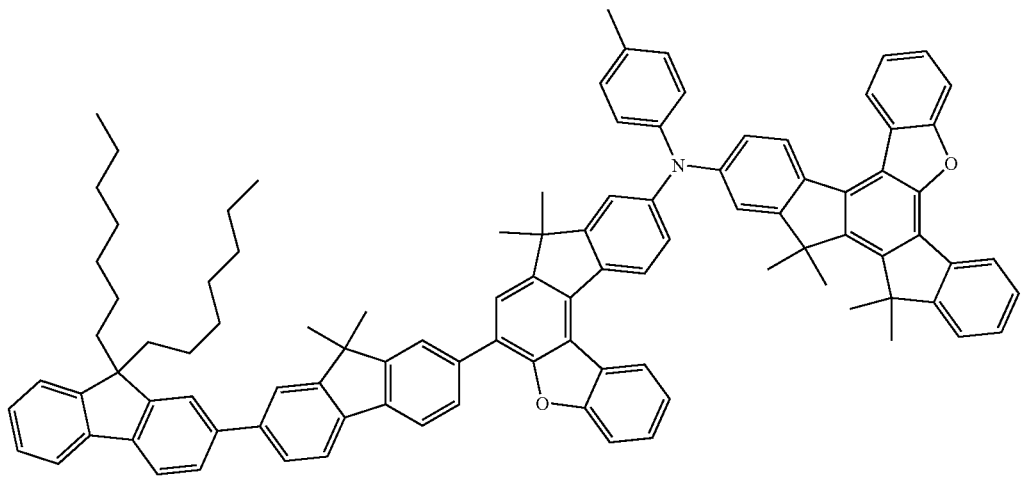 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc(C)cc7)c7ccc8c(c7)C(C)(C)c7c9c(c%10oc%11ccccc%11c%10c7-8)-c7ccccc7C9(C)C)cc5C6(C)C)ccc3-4)cc21]
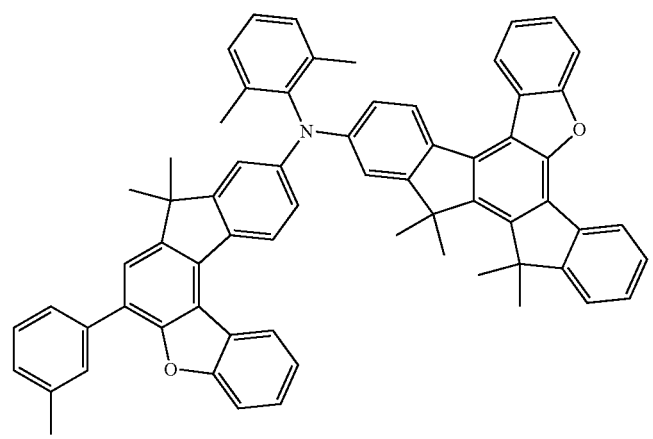 [SMILES: Cc1cccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4c(C)cccc4C)cc2C3(C)C)c1]
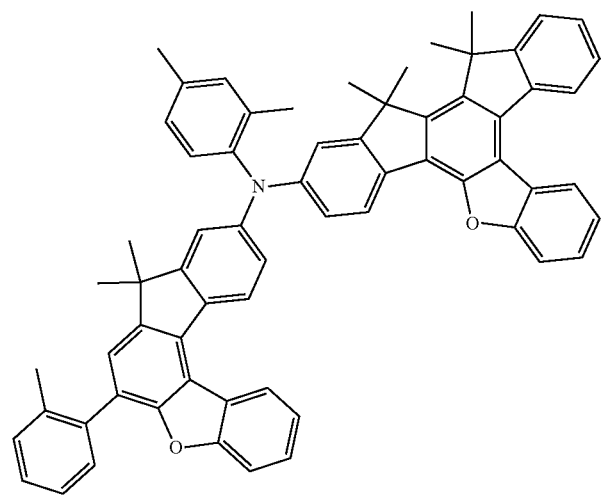 [SMILES: Cc1ccc(N(c2ccc3c(c2)C(C)(C)c2cc(-c4ccccc4C)c4oc5ccccc5c4c2-3)c2ccc3c(c2)C(C)(C)c2c4c(c5c(oc6ccccc65)c2-3)-c2ccccc2C4(C)C)c(C)c1]

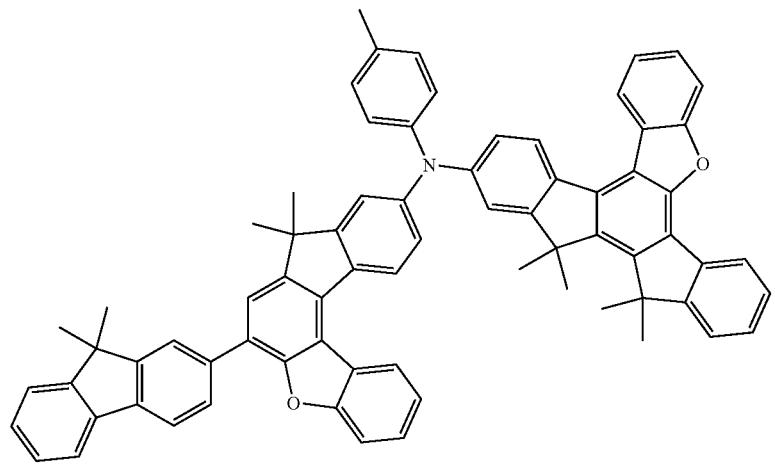 [SMILES: Cc1ccc(N(c2ccc3c(c2)C(C)(C)c2cc(-c4ccc5c(c4)C(C)(C)c4ccccc4-5)c4oc5ccccc5c4c2-3)c2ccc3c(c2)C(C)(C)c2c4c(c5oc6ccccc6c5c2-3)-c2ccccc2C4(C)C)cc1]
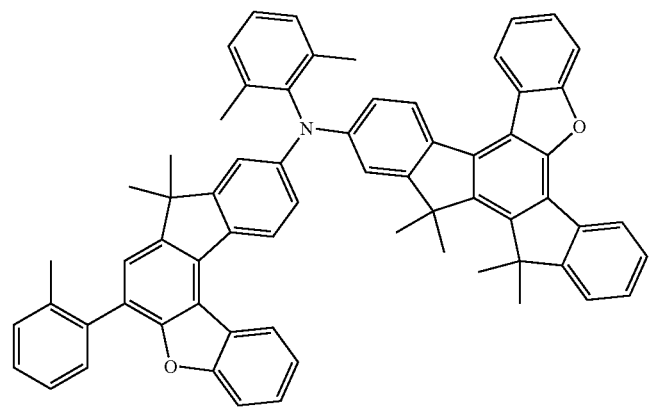 [SMILES: Cc1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3c(C)cccc3C)cc1C2(C)C]
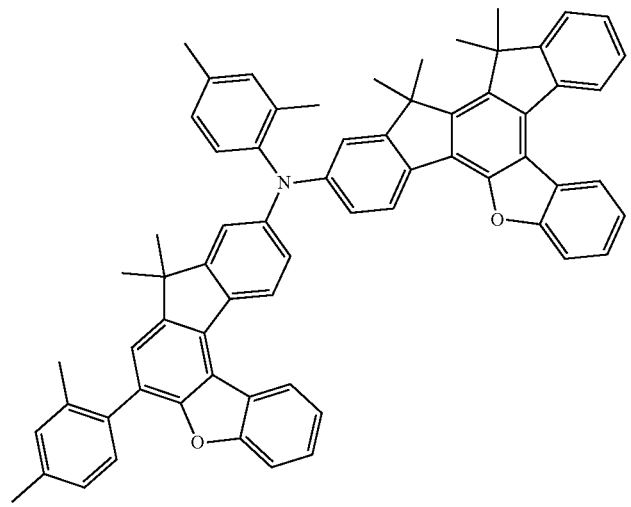 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccc(C)cc4C)cc2C3(C)C)c(C)c1]

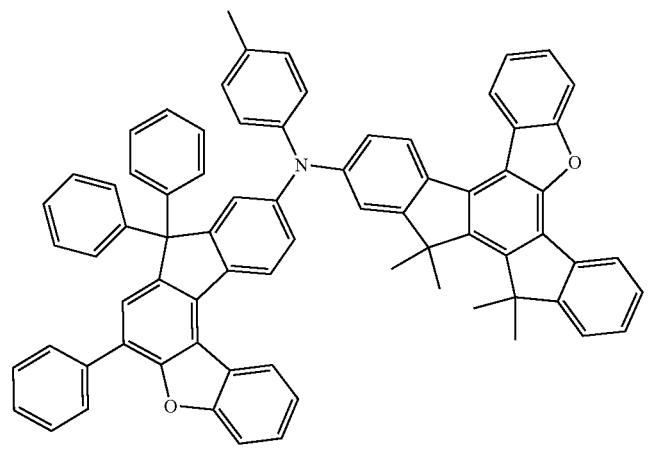 [SMILES: Cc1ccc(N(c2ccc3c(c2)C(C)(C)c2c4c(c5oc6ccccc6c5c2-3)-c2ccccc2C4(C)C)c2ccc3c(c2)C(c2ccccc2)(c2ccccc2)c2cc(-c4ccccc4)c4oc5ccccc5c4c2-3)cc1]
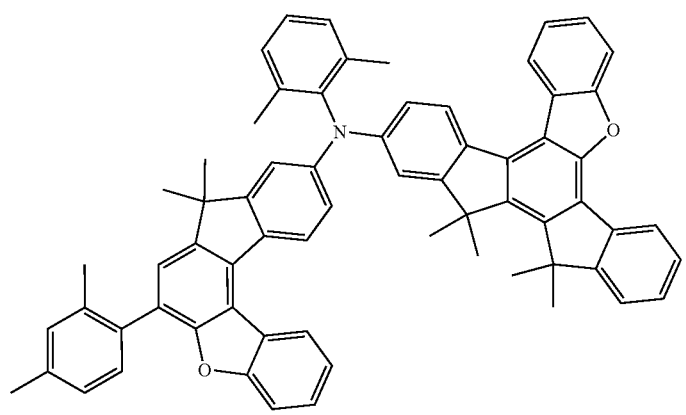 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4c(C)cccc4C)cc2C3(C)C)c(C)c1]
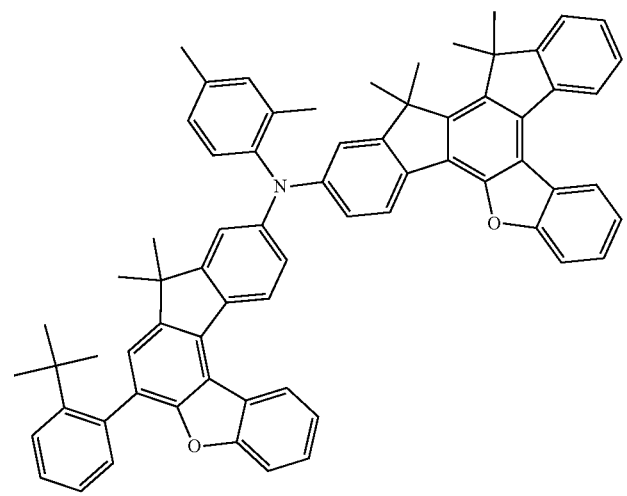 [SMILES: Cc1ccc(N(c2ccc3c(c2)C(C)(C)c2cc(-c4ccccc4C(C)(C)C)c4oc5ccccc5c4c2-3)c2ccc3c(c2)C(C)(C)c2c4c(c5c(oc6ccccc65)c2-3)-c2ccccc2C4(C)C)c(C)c1]

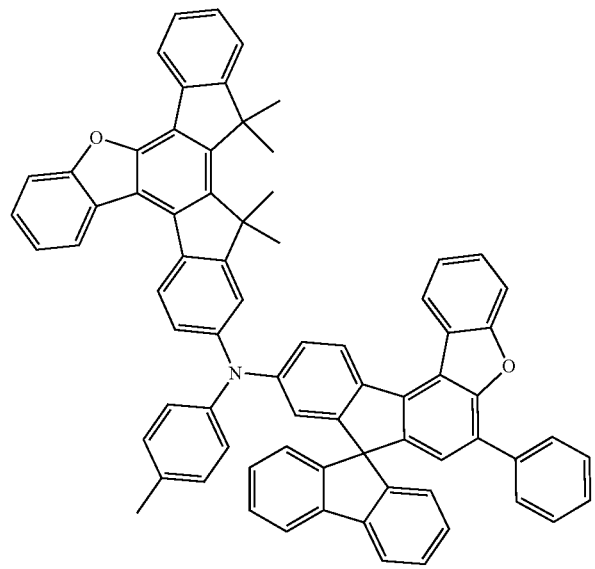 [SMILES: Cc1ccc(N(c2ccc3c(c2)C(C)(C)c2c4c(c5oc6ccccc6c5c2-3)-c2ccccc2C4(C)C)c2ccc3c(c2)C2(c4ccccc4-c4ccccc42)c2cc(-c4ccccc4)c4oc5ccccc5c4c2-3)cc1]
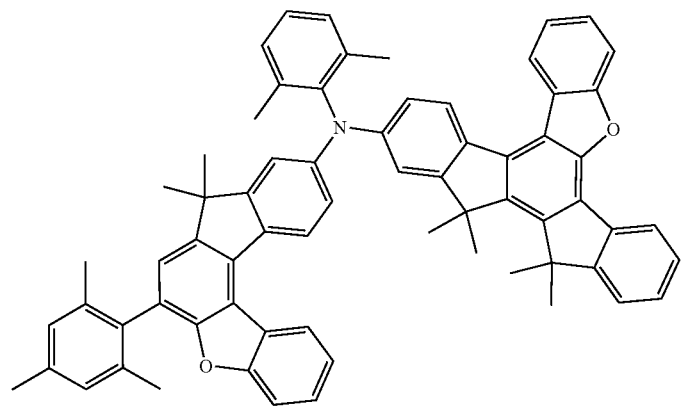 [SMILES: Cc1cc(C)c(-c2cc3c(c4c2oc2ccccc24)-c2ccc(N(c4ccc5c(c4)C(C)(C)c4c6c(c7oc8ccccc8c7c4-5)-c4ccccc4C6(C)C)c4c(C)cccc4C)cc2C3(C)C)c(C)c1]
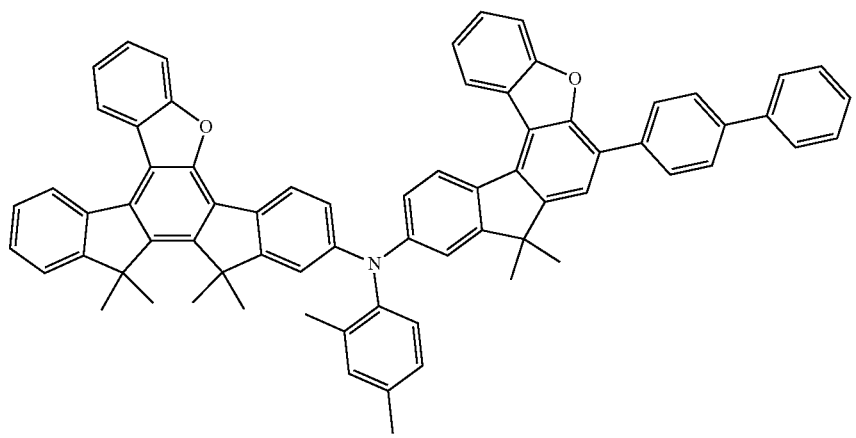 [SMILES: Cc1ccc(N(c2ccc3c(c2)C(C)(C)c2cc(-c4ccc(-c5ccccc5)cc4)c4oc5ccccc5c4c2-3)c2ccc3c(c2)C(C)(C)c2c4c(c5c(oc6ccccc65)c2-3)-c2ccccc2C4(C)C)c(C)c1]

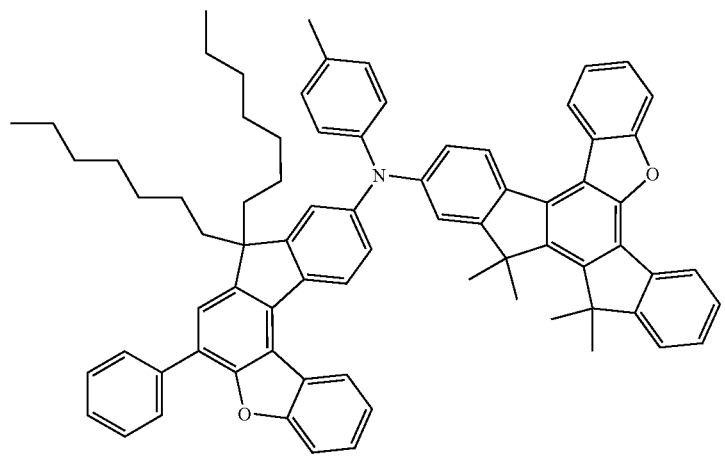 [SMILES: CCCCCCCC1(CCCCCCC)c2cc(N(c3ccc(C)cc3)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]
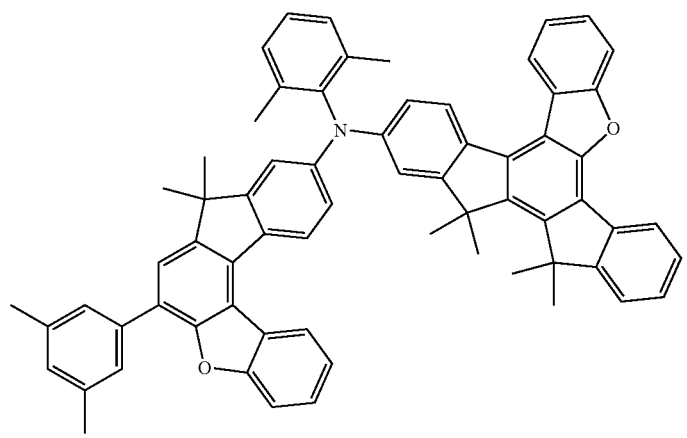 [SMILES: Cc1cc(C)cc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4c(C)cccc4C)cc2C3(C)C)c1]
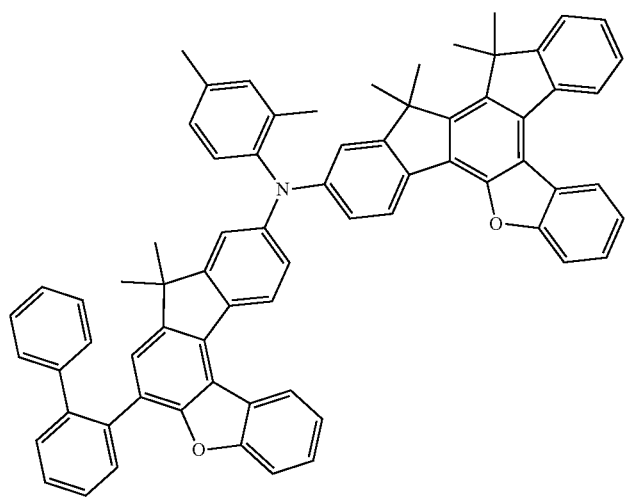 [SMILES: Cc1ccc(N(c2ccc3c(c2)C(C)(C)c2cc(-c4ccccc4-c4ccccc4)c4oc5ccccc5c4c2-3)c2ccc3c(c2)C(C)(C)c2c4c(c5c(oc6ccccc65)c2-3)-c2ccccc2C4(C)C)c(C)c1]

-continued
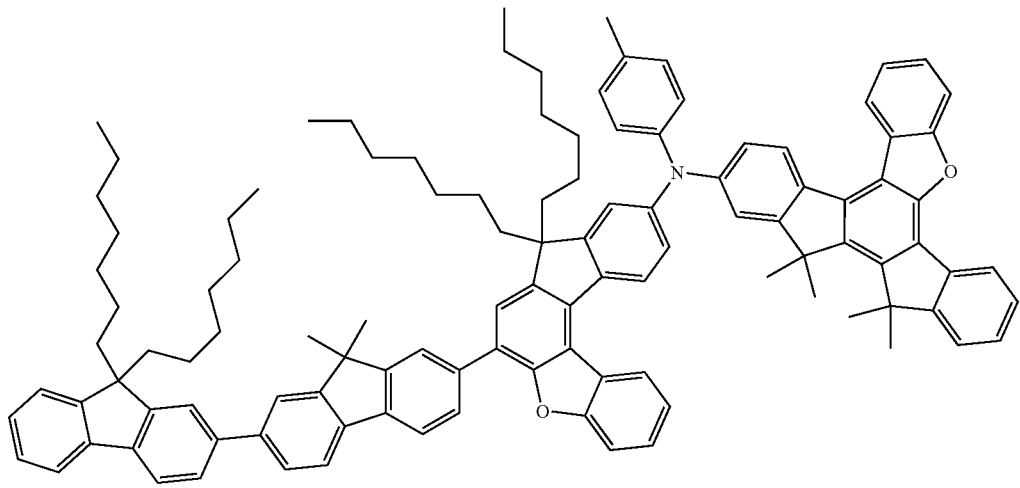 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc(C)cc7)c7ccc8c(c7)C(C)(C)c7c9c(c%10oc%11ccccc%11c%10c7-8)-c7ccccc7C9(C)C)cc5C6(CCCCCCC)CCCCCCC)ccc3-4)cc21]

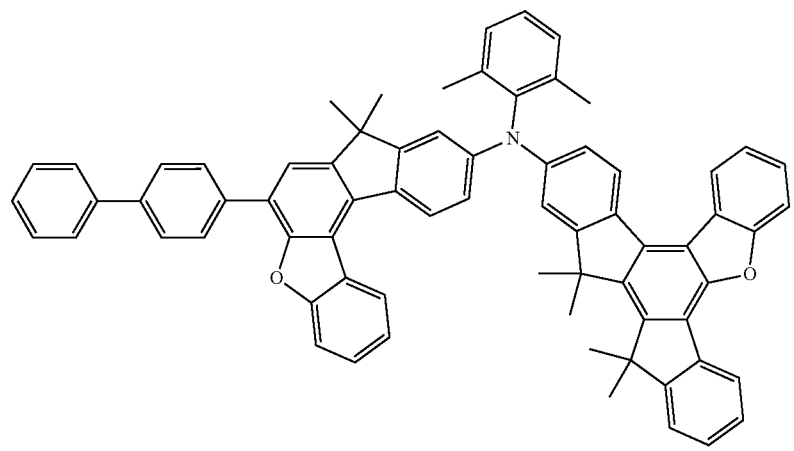 [SMILES: Cc1cccc(C)c1N(c1ccc2c(c1)C(C)(C)c1cc(-c3ccc(-c4ccccc4)cc3)c3oc4ccccc4c3c1-2)c1ccc2c(c1)C(C)(C)c1c3c(c4oc5ccccc5c4c1-2)-c1ccccc1C3(C)C]
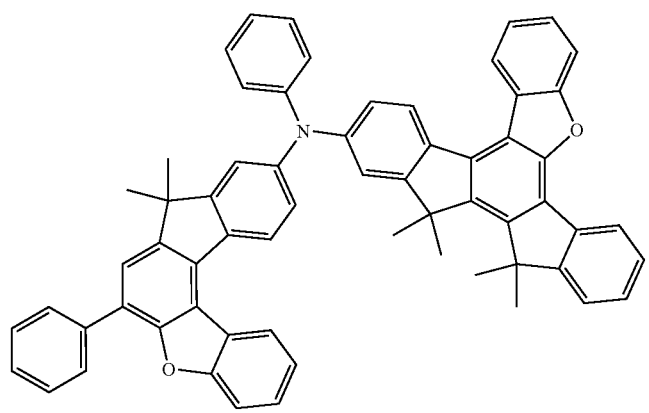 [SMILES: CC1(C)c2cc(N(c3ccccc3)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]
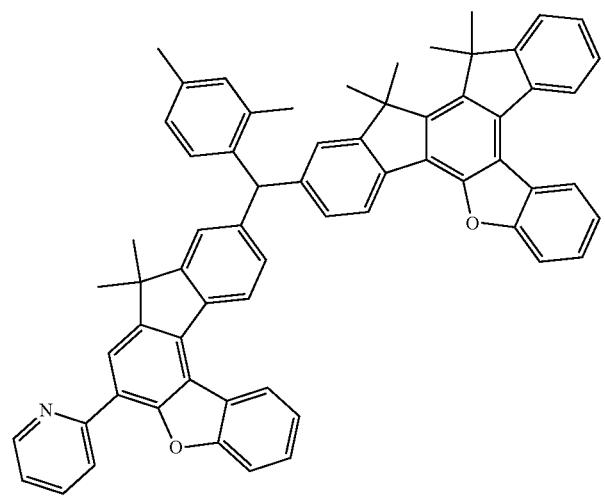 [SMILES: Cc1ccc(C(c2ccc3c(c2)C(C)(C)c2cc(-c4ccccn4)c4oc5ccccc5c4c2-3)c2ccc3c(c2)C(C)(C)c2c4c(c5c(oc6ccccc65)c2-3)-c2ccccc2C4(C)C)c(C)c1]

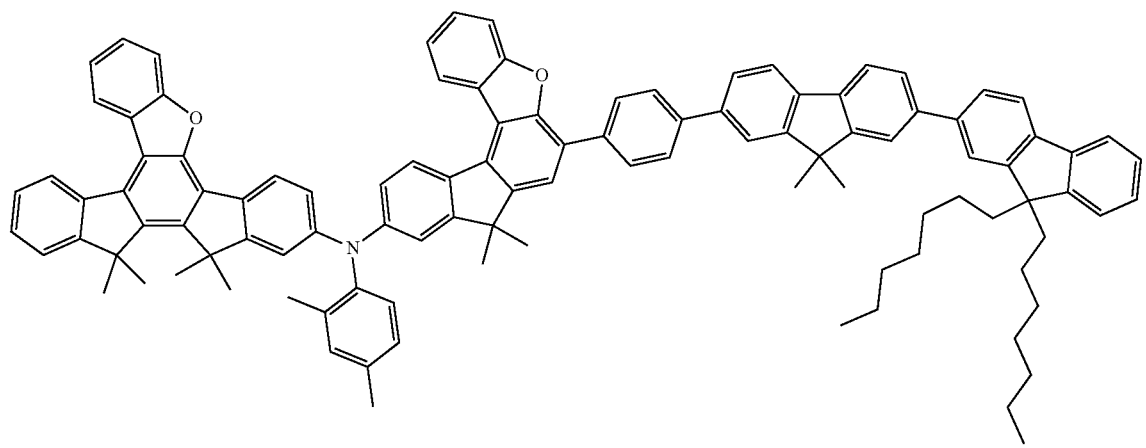 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11c(oc%12ccccc%12%11)c8-9)-c8ccccc8C%10(C)C)c8ccc(C)cc8C)cc6C7(C)C)cc5)ccc3-4)cc21]
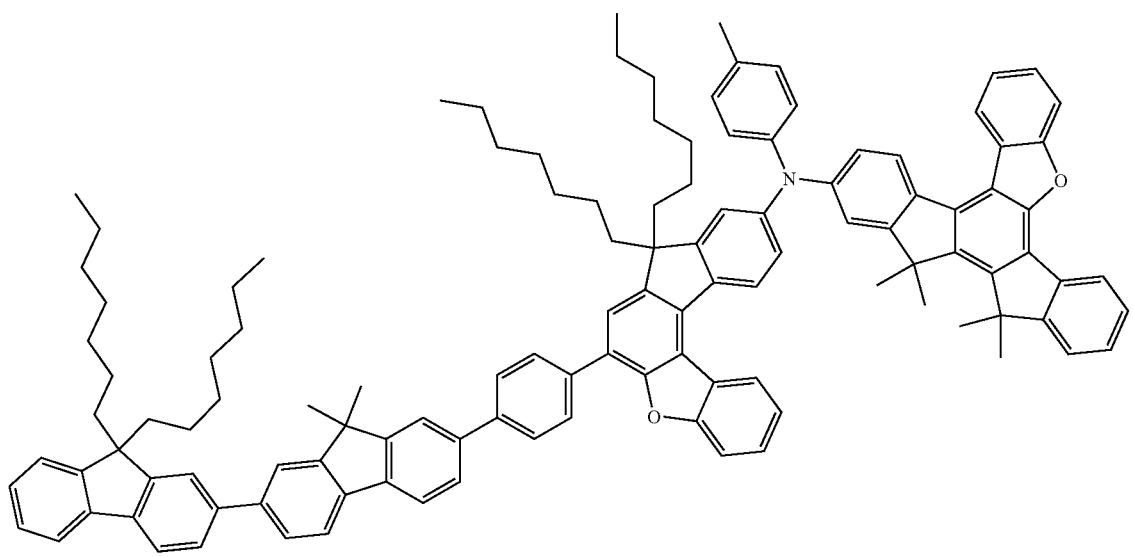 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc(C)cc8)c8ccc9c(c8)C(C)(C)c8c%10c(c%11oc%12ccccc%12c%11c8-9)-c8ccccc8C%10(C)C)cc6C7(CCCCCCC)CCCCCCC)cc5)ccc3-4)cc21]
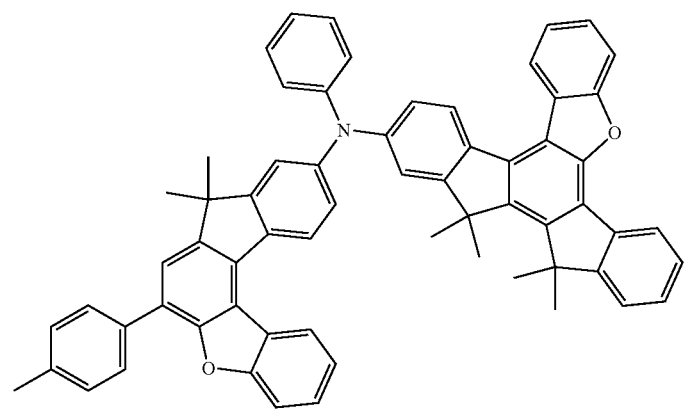 [SMILES: Cc1ccc(-c2cc3c(c4c2oc2ccccc24)-c2ccc(N(c4ccccc4)c4ccc5c(c4)C(C)(C)c4c6c(c7oc8ccccc8c7c4-5)-c4ccccc4C6(C)C)cc2C3(C)C)cc1]

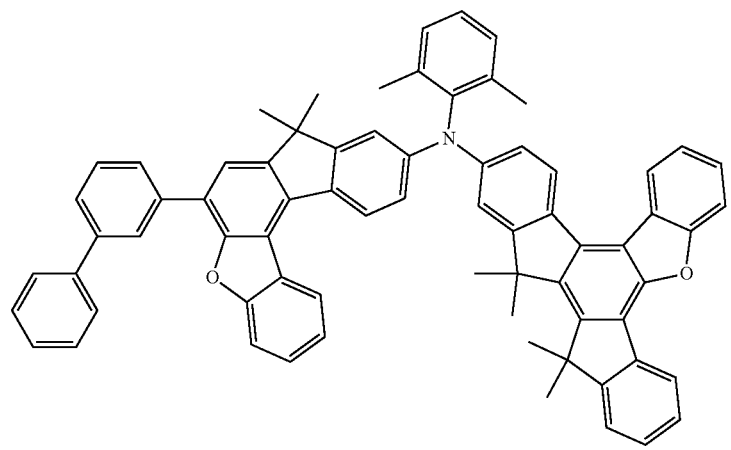 [SMILES: Cc1cccc(C)c1N(c1ccc2c(c1)C(C)(C)c1cc(-c3cccc(-c4ccccc4)c3)c3oc4ccccc4c3c1-2)c1ccc2c(c1)C(C)(C)c1c3c(c4oc5ccccc5c4c1-2)-c1ccccc1C3(C)C]
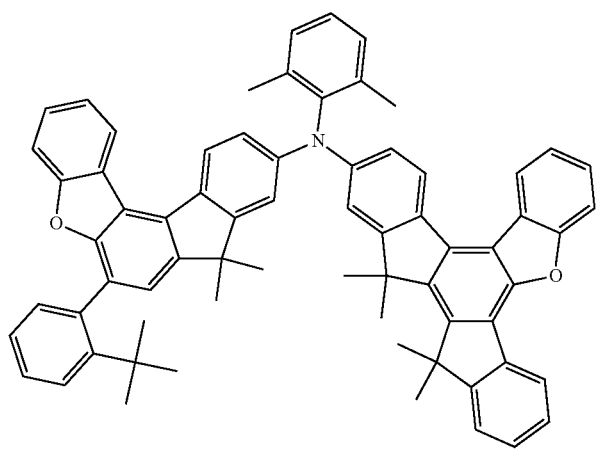 [SMILES: Cc1cccc(C)c1N(c1ccc2c(c1)C(C)(C)c1cc(-c3ccccc3C(C)(C)C)c3oc4ccccc4c3c1-2)c1ccc2c(c1)C(C)(C)c1c3c(c4oc5ccccc5c4c1-2)-c1ccccc1C3(C)C]
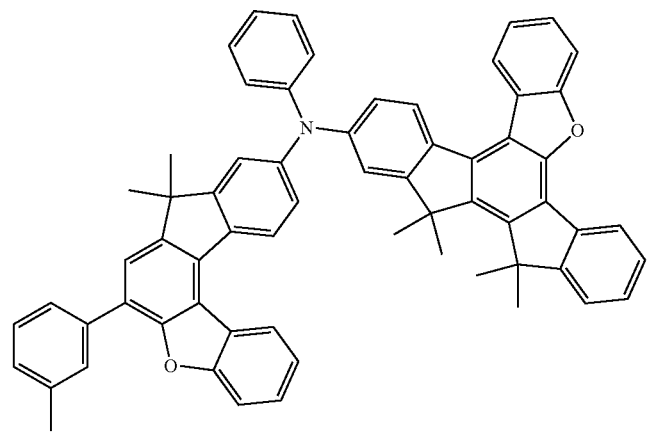 [SMILES: Cc1cccc(-c2cc3c(c4c2oc2ccccc24)-c2ccc(N(c4ccccc4)c4ccc5c(c4)C(C)(C)c4c6c(c7oc8ccccc8c7c4-5)-c4ccccc4C6(C)C)cc2C3(C)C)c1]

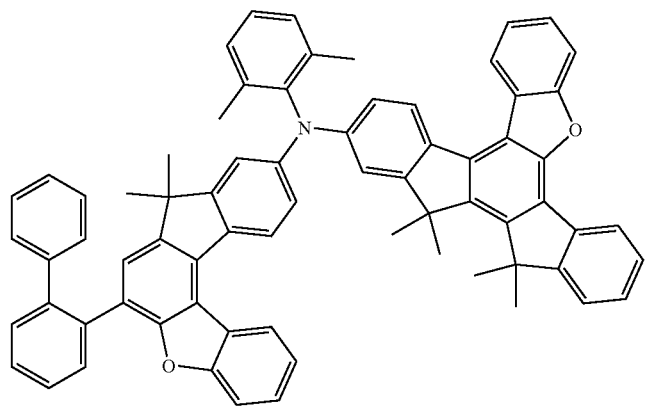 [SMILES: Cc1cccc(C)c1N(c1ccc2c(c1)C(C)(C)c1cc(-c3ccccc3-c3ccccc3)c3oc4ccccc4c3c1-2)c1ccc2c(c1)C(C)(C)c1c3c(c4oc5ccccc5c4c1-2)-c1ccccc1C3(C)C]
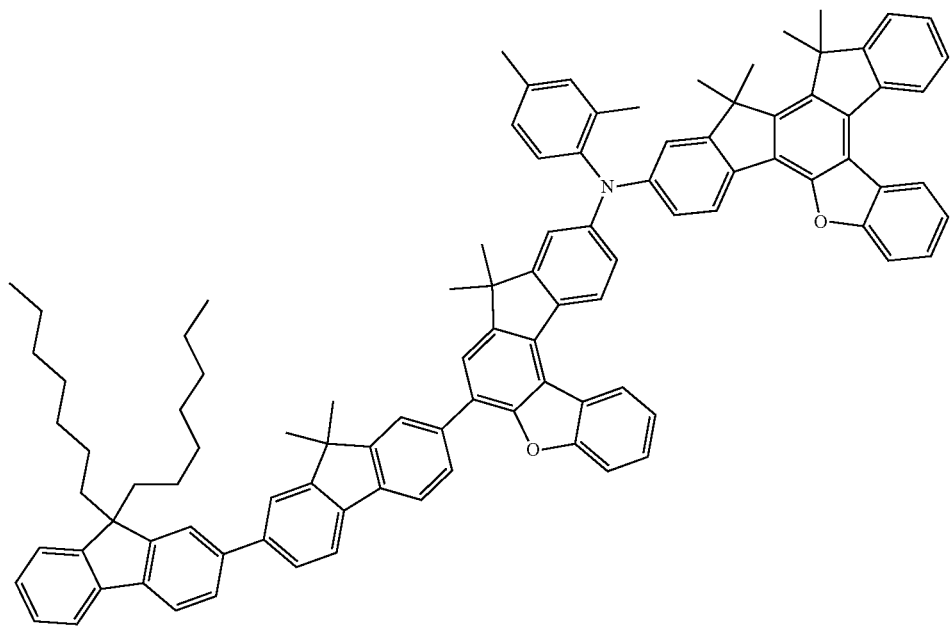 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10c(oc%11ccccc%11%10)c7-8)-c7ccccc7C9(C)C)c7ccc(C)cc7C)cc5C6(C)C)ccc3-4)cc21]
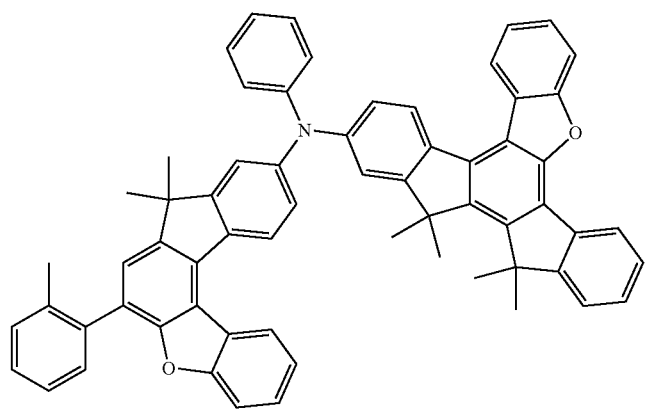 [SMILES: Cc1ccccc1-c1cc2c(c3c1oc1ccccc13)-c1ccc(N(c3ccccc3)c3ccc4c(c3)C(C)(C)c3c5c(c6oc7ccccc7c6c3-4)-c3ccccc3C5(C)C)cc1C2(C)C]

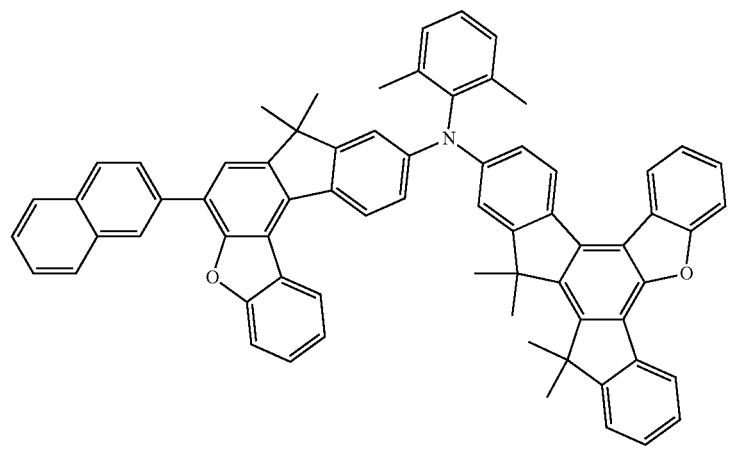 [SMILES: Cc1cccc(C)c1N(c1ccc2c(c1)C(C)(C)c1cc(-c3ccc4ccccc4c3)c3oc4ccccc4c3c1-2)c1ccc2c(c1)C(C)(C)c1c3c(c4oc5ccccc5c4c1-2)-c1ccccc1C3(C)C]
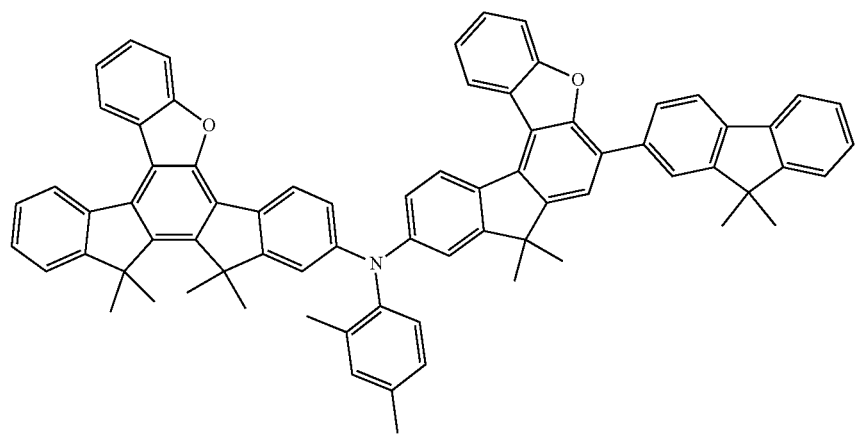 [SMILES: Cc1ccc(N(c2ccc3c(c2)C(C)(C)c2cc(-c4ccc5c(c4)C(C)(C)c4ccccc4-5)c4oc5ccccc5c4c2-3)c2ccc3c(c2)C(C)(C)c2c4c(c5c(oc6ccccc65)c2-3)-c2ccccc2C4(C)C)c(C)c1]
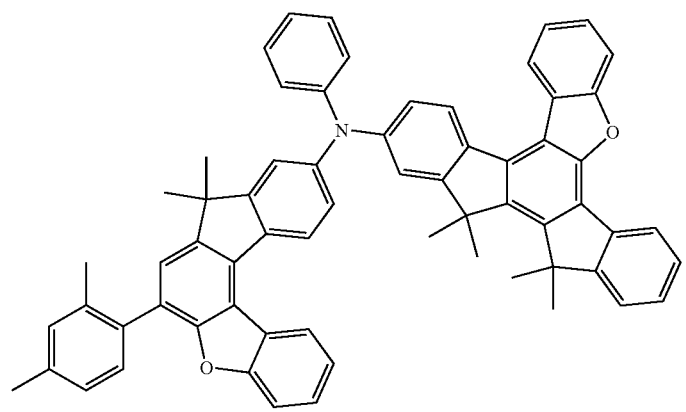 [SMILES: Cc1ccc(-c2cc3c(c4c2oc2ccccc24)-c2ccc(N(c4ccccc4)c4ccc5c(c4)C(C)(C)c4c6c(c7oc8ccccc8c7c4-5)-c4ccccc4C6(C)C)cc2C3(C)C)c(C)c1]

-continued
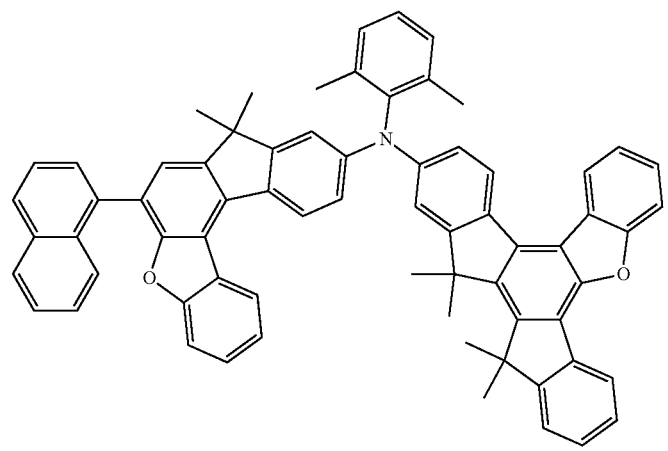 [SMILES: Cc1cccc(C)c1N(c1ccc2c(c1)C(C)(C)c1cc(-c3cccc4ccccc34)c3oc4ccccc4c3c1-2)c1ccc2c(c1)C(C)(C)c1c3c(c4oc5ccccc5c4c1-2)-c1ccccc1C3(C)C]
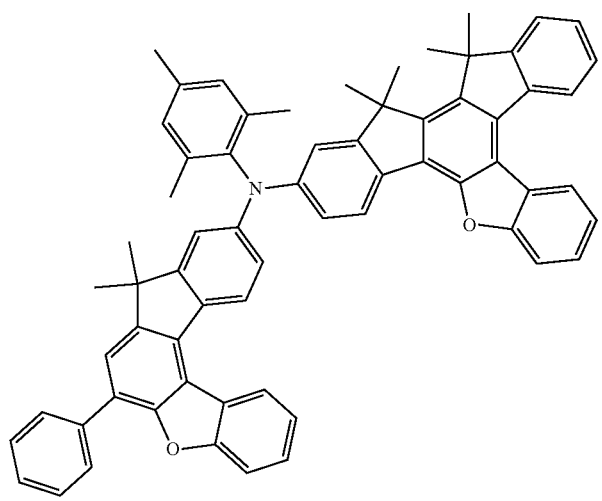 [SMILES: Cc1cc(C)c(N(c2ccc3c(c2)C(C)(C)c2cc(-c4ccccc4)c4oc5ccccc5c4c2-3)c2ccc3c(c2)C(C)(C)c2c4c(c5c(oc6ccccc65)c2-3)-c2ccccc2C4(C)C)c(C)c1]
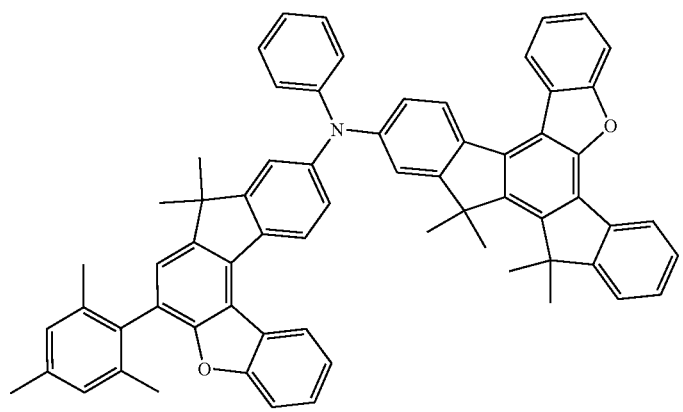 [SMILES: Cc1cc(C)c(-c2cc3c(c4c2oc2ccccc24)-c2ccc(N(c4ccccc4)c4ccc5c(c4)C(C)(C)c4c6c(c7oc8ccccc8c7c4-5)-c4ccccc4C6(C)C)cc2C3(C)C)c(C)c1]

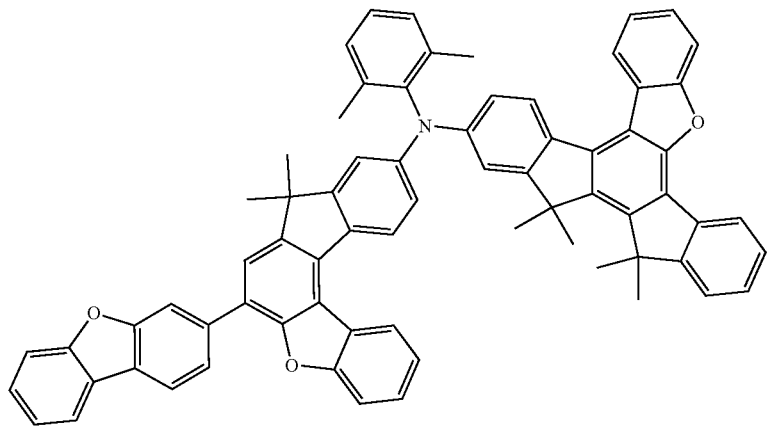 [SMILES: Cc1cccc(C)c1N(c1ccc2c(c1)C(C)(C)c1cc(-c3ccc4c(c3)oc3ccccc34)c3oc4ccccc4c3c1-2)c1ccc2c(c1)C(C)(C)c1c3c(c4oc5ccccc5c4c1-2)-c1ccccc1C3(C)C]
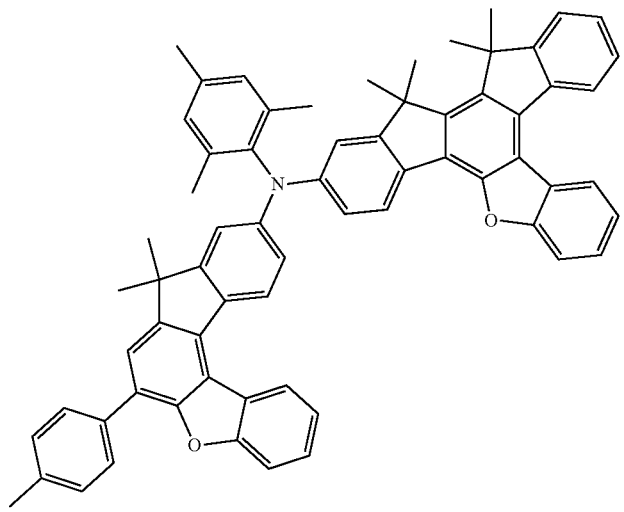 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4c(C)cc(C)cc4C)cc2C3(C)C)cc1]
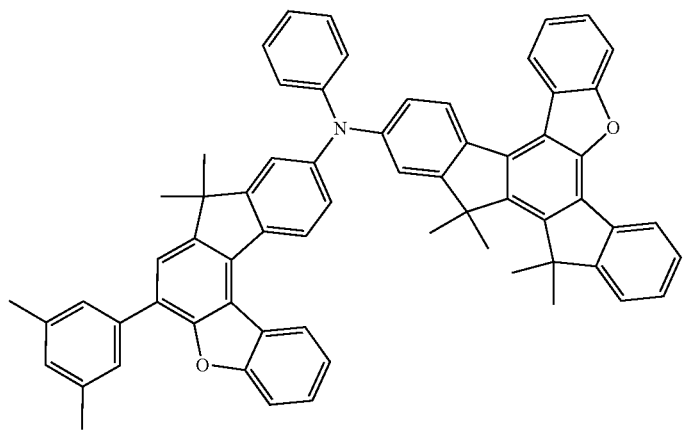 [SMILES: Cc1cc(C)cc(-c2cc3c(c4c2oc2ccccc24)-c2ccc(N(c4ccccc4)c4ccc5c(c4)C(C)(C)c4c6c(c7oc8ccccc8c7c4-5)-c4ccccc4C6(C)C)cc2C3(C)C)c1]

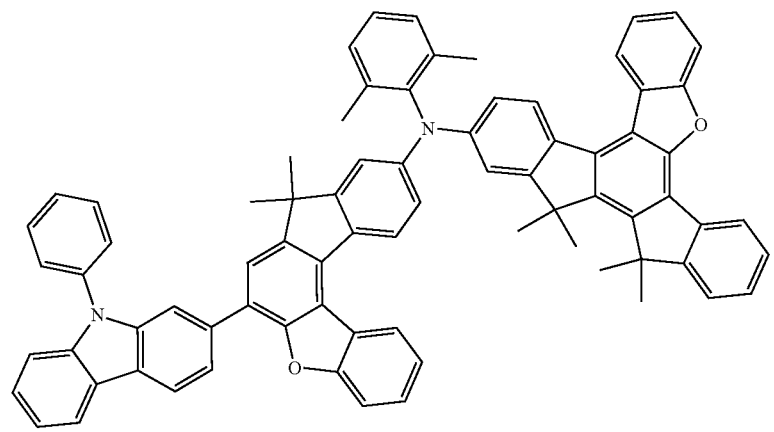 [SMILES: Cc1cccc(C)c1N(c1ccc2c(c1)C(C)(C)c1cc(-c3ccc4c5ccccc5n(-c5ccccc5)c4c3)c3oc4ccccc4c3c1-2)c1ccc2c(c1)C(C)(C)c1c3c(c4oc5ccccc5c4c1-2)-c1ccccc1C3(C)C]
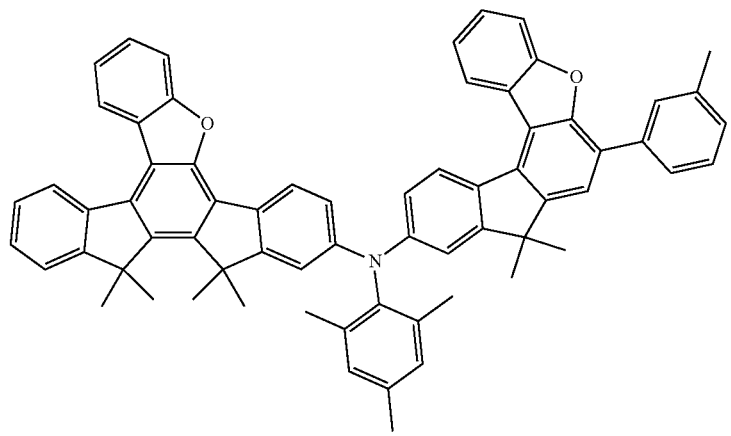 [SMILES: Cc1cccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4c(C)cc(C)cc4C)cc2C3(C)C)c1]
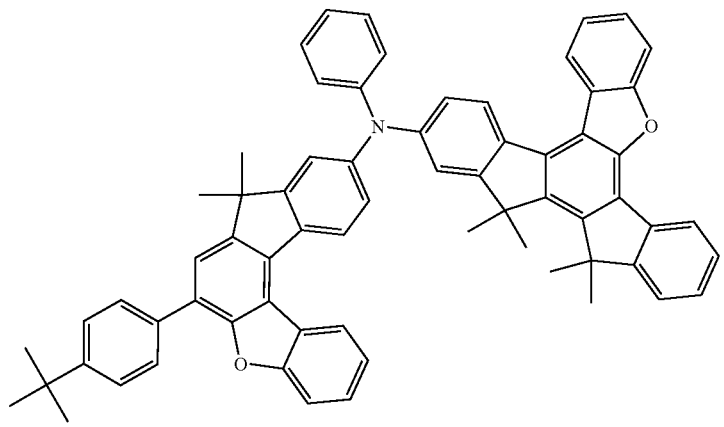 [SMILES: CC(C)(C)c1ccc(-c2cc3c(c4c2oc2ccccc24)-c2ccc(N(c4ccccc4)c4ccc5c(c4)C(C)(C)c4c6c(c7oc8ccccc8c7c4-5)-c4ccccc4C6(C)C)cc2C3(C)C)cc1]

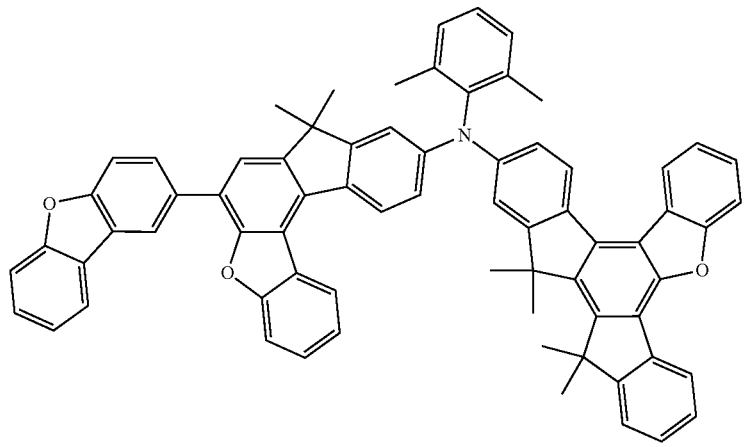 [SMILES: Cc1cccc(C)c1N(c1ccc2c(c1)C(C)(C)c1cc(-c3ccc4oc5ccccc5c4c3)c3oc4ccccc4c3c1-2)c1ccc2c(c1)C(C)(C)c1c3c(c4oc5ccccc5c4c1-2)-c1ccccc1C3(C)C]
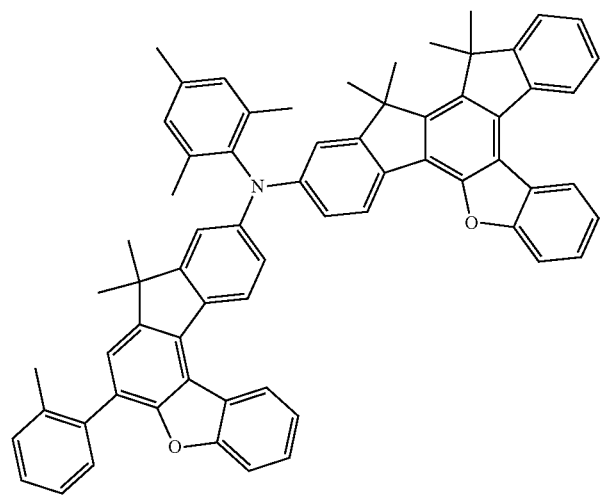 [SMILES: Cc1cc(C)c(N(c2ccc3c(c2)C(C)(C)c2cc(-c4ccccc4C)c4oc5ccccc5c4c2-3)c2ccc3c(c2)C(C)(C)c2c4c(c5c(oc6ccccc65)c2-3)-c2ccccc2C4(C)C)c(C)c1]
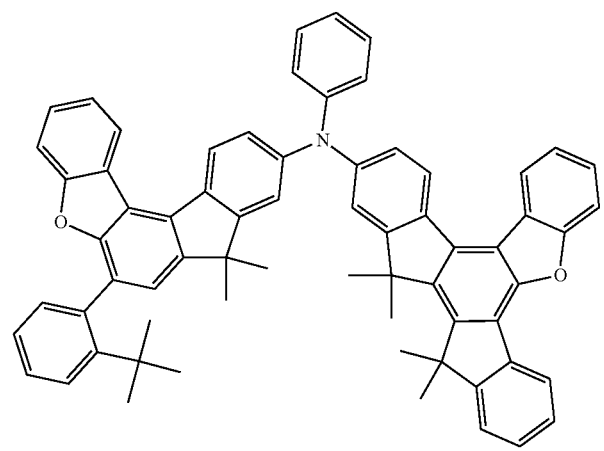 [SMILES: CC(C)(C)c1ccccc1-c1cc2c(c3c1oc1ccccc13)-c1ccc(N(c3ccccc3)c3ccc4c(c3)C(C)(C)c3c5c(c6oc7ccccc7c6c3-4)-c3ccccc3C5(C)C)cc1C2(C)C]

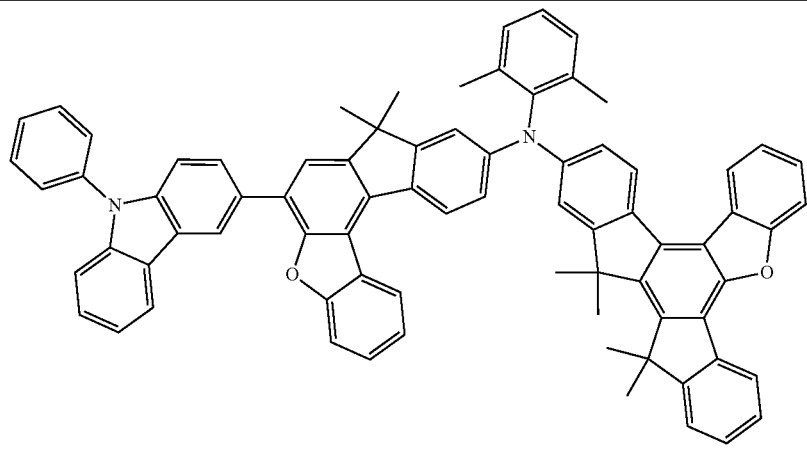
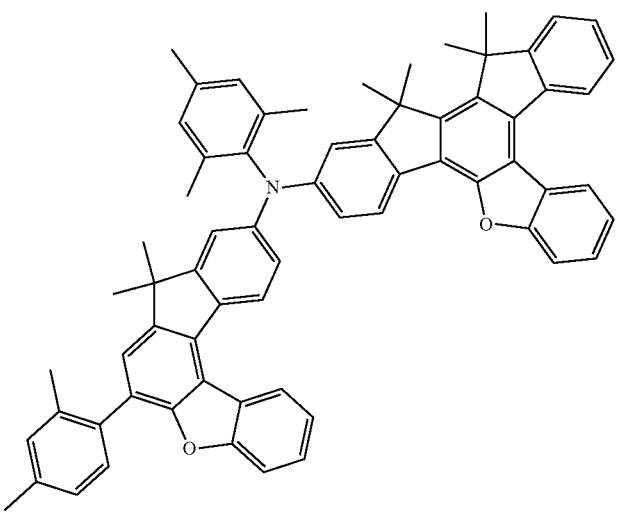 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4c(C)cc(C)cc4C)cc2C3(C)C)c(C)c1]
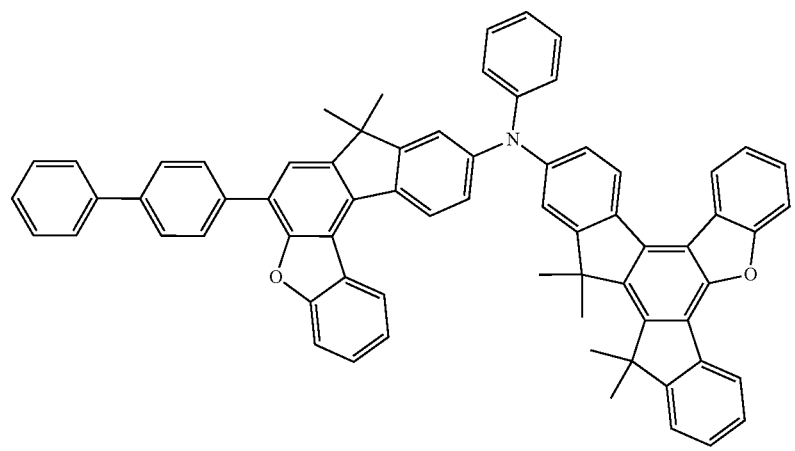 [SMILES: CC1(C)c2cc(N(c3ccccc3)c3ccc4c(c3)C(C)(C)c3c5c(c6oc7ccccc7c6c3-4)-c3ccccc3C5(C)C)ccc2-c2c1cc(-c1ccc(-c3ccccc3)cc1)c1oc3ccccc3c21]

-continued
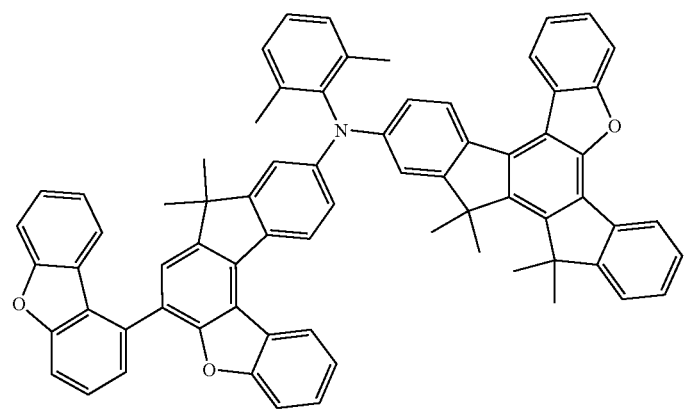 [SMILES: Cc1cccc(C)c1N(c1ccc2c(c1)C(C)(C)c1cc(-c3cccc4oc5ccccc5c34)c3oc4ccccc4c3c1-2)c1ccc2c(c1)C(C)(C)c1c3c(c4oc5ccccc5c4c1-2)-c1ccccc1C3(C)C]
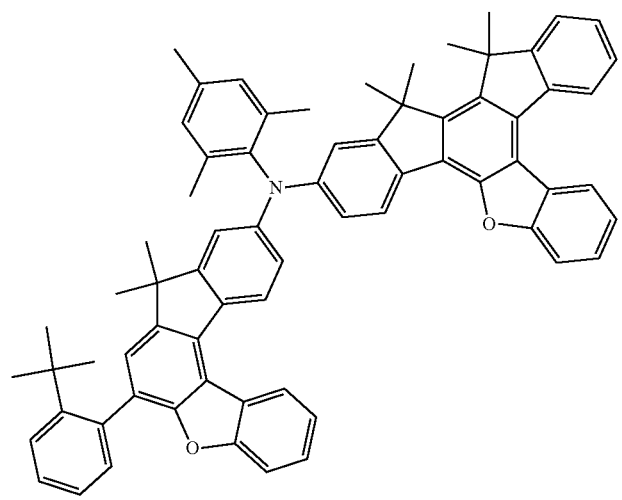 [SMILES: Cc1cc(C)c(N(c2ccc3c(c2)C(C)(C)c2cc(-c4ccccc4C(C)(C)C)c4oc5ccccc5c4c2-3)c2ccc3c(c2)C(C)(C)c2c4c(c5c(oc6ccccc65)c2-3)-c2ccccc2C4(C)C)c(C)c1]
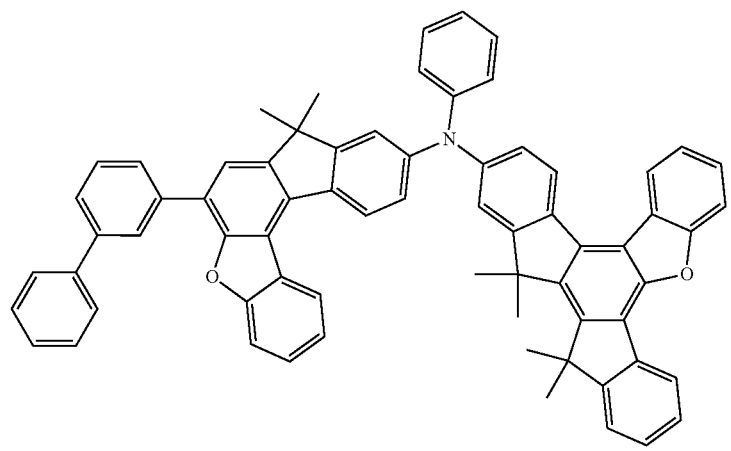 [SMILES: CC1(C)c2cc(N(c3ccccc3)c3ccc4c(c3)C(C)(C)c3c5c(c6oc7ccccc7c6c3-4)-c3ccccc3C5(C)C)ccc2-c2c1cc(-c1cccc(-c3ccccc3)c1)c1oc3ccccc3c21]

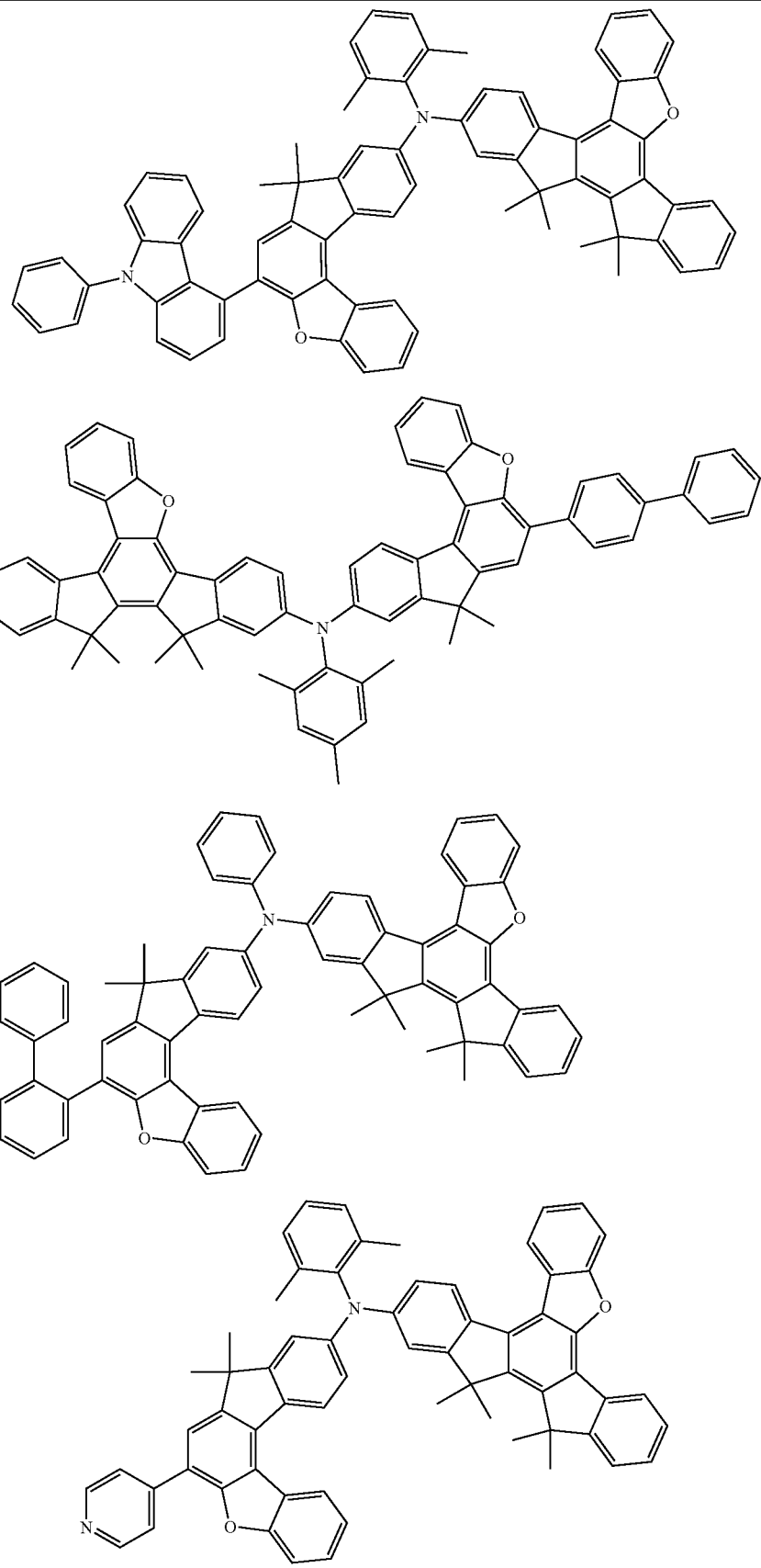

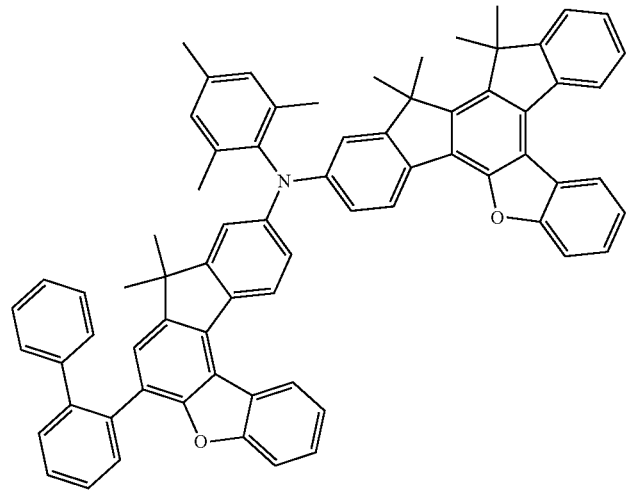 [SMILES: Cc1cc(C)c(N(c2ccc3c(c2)C(C)(C)c2cc(-c4ccccc4-c4ccccc4)c4oc5ccccc5c4c2-3)c2ccc3c(c2)C(C)(C)c2c4c(c5c(oc6ccccc65)c2-3)-c2ccccc2C4(C)C)c(C)c1]

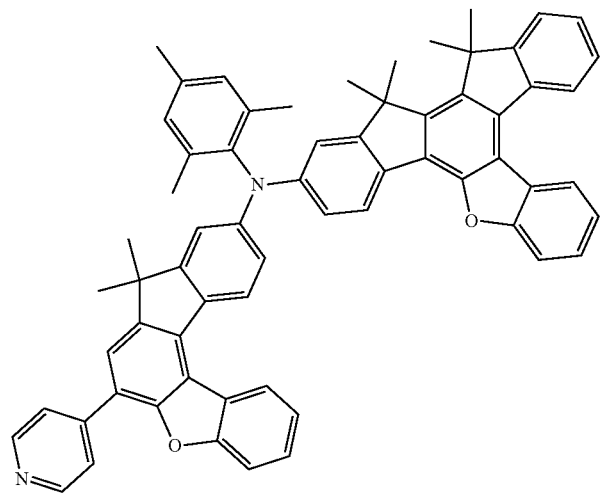 [SMILES: Cc1cc(C)c(N(c2ccc3c(c2)C(C)(C)c2cc(-c4ccncc4)c4oc5ccccc5c4c2-3)c2ccc3c(c2)C(C)(C)c2c4c(c5c(oc6ccccc65)c2-3)-c2ccccc2C4(C)C)c(C)c1]
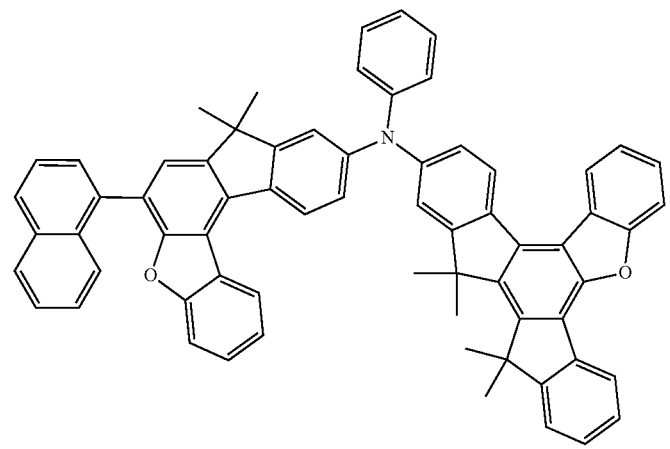 [SMILES: CC1(C)c2cc(N(c3ccccc3)c3ccc4c(c3)C(C)(C)c3c5c(c6oc7ccccc7c6c3-4)-c3ccccc3C5(C)C)ccc2-c2c1cc(-c1cccc3ccccc13)c1oc3ccccc3c21]
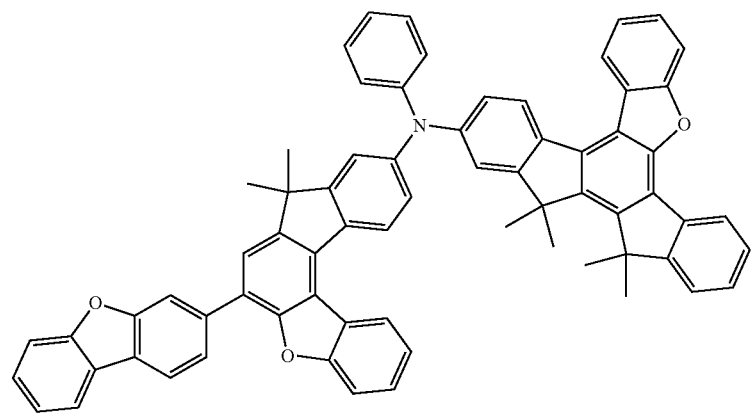 [SMILES: CC1(C)c2cc(N(c3ccccc3)c3ccc4c(c3)C(C)(C)c3c5c(c6oc7ccccc7c6c3-4)-c3ccccc3C5(C)C)ccc2-c2c1cc(-c1ccc3c(c1)oc1ccccc13)c1oc3ccccc3c21]

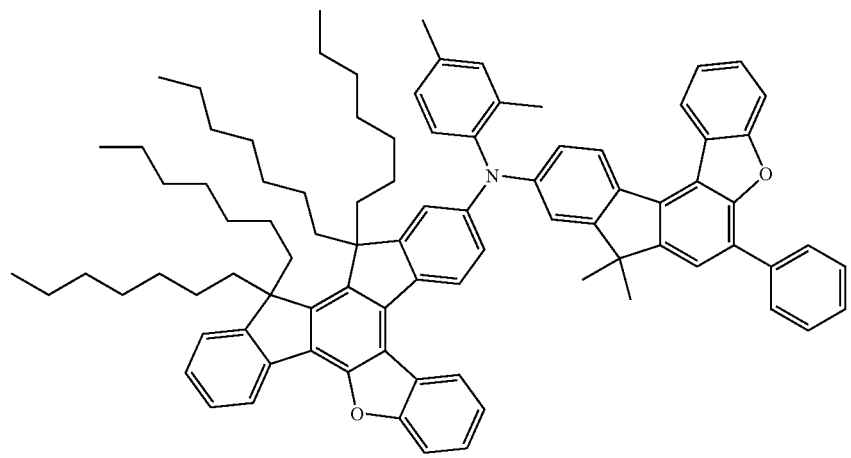 [SMILES: CCCCCCCC1(CCCCCCC)c2ccccc2-c2c1c1c(c3c2oc2ccccc23)-c2ccc(N(c3ccc4c(c3)C(C)(C)c3cc(-c5ccccc5)c5oc6ccccc6c5c3-4)c3ccc(C)cc3C)cc2C1(CCCCCCC)CCCCCCC]
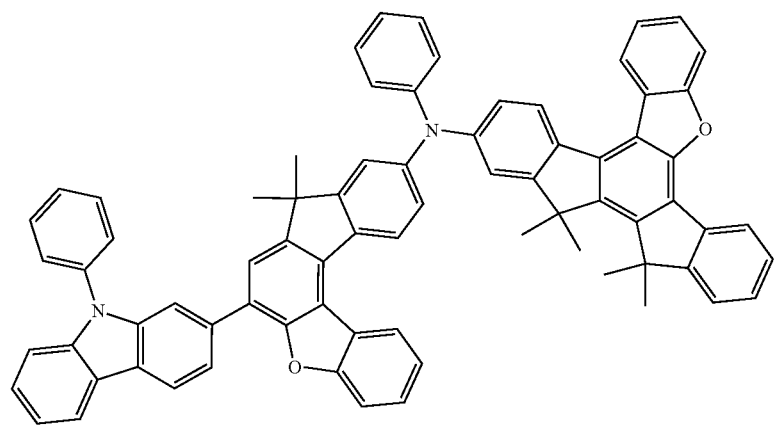 [SMILES: CC1(C)c2cc(N(c3ccccc3)c3ccc4c(c3)C(C)(C)c3c5c(c6oc7ccccc7c6c3-4)-c3ccccc3C5(C)C)ccc2-c2c1cc(-c1ccc3c4ccccc4n(-c4ccccc4)c3c1)c1oc3ccccc3c21]
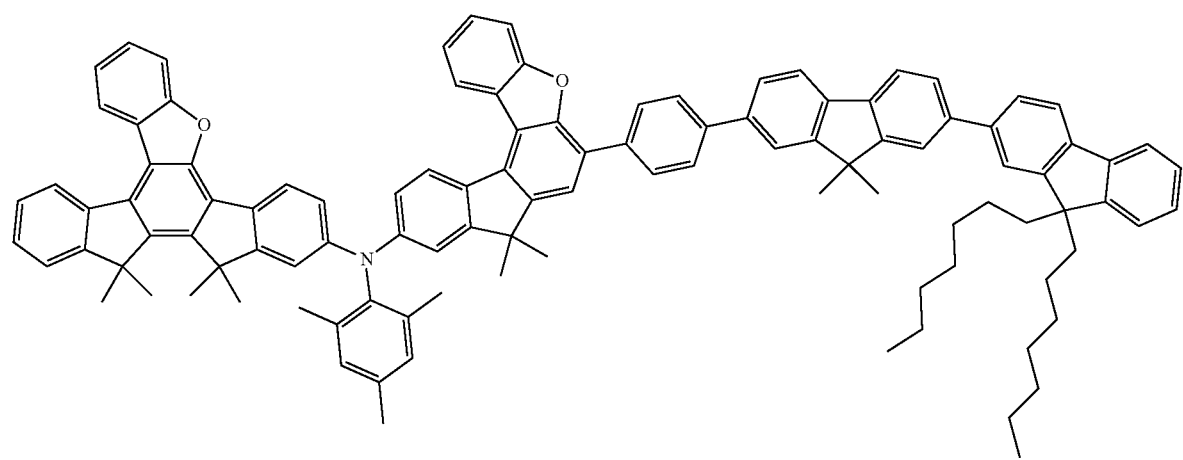 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11c(oc%12ccccc%12%11)c8-9)-c8ccccc8C%10(C)C)c8c(C)cc(C)cc8C)cc6C7(C)C)cc5)ccc3-4)cc21]

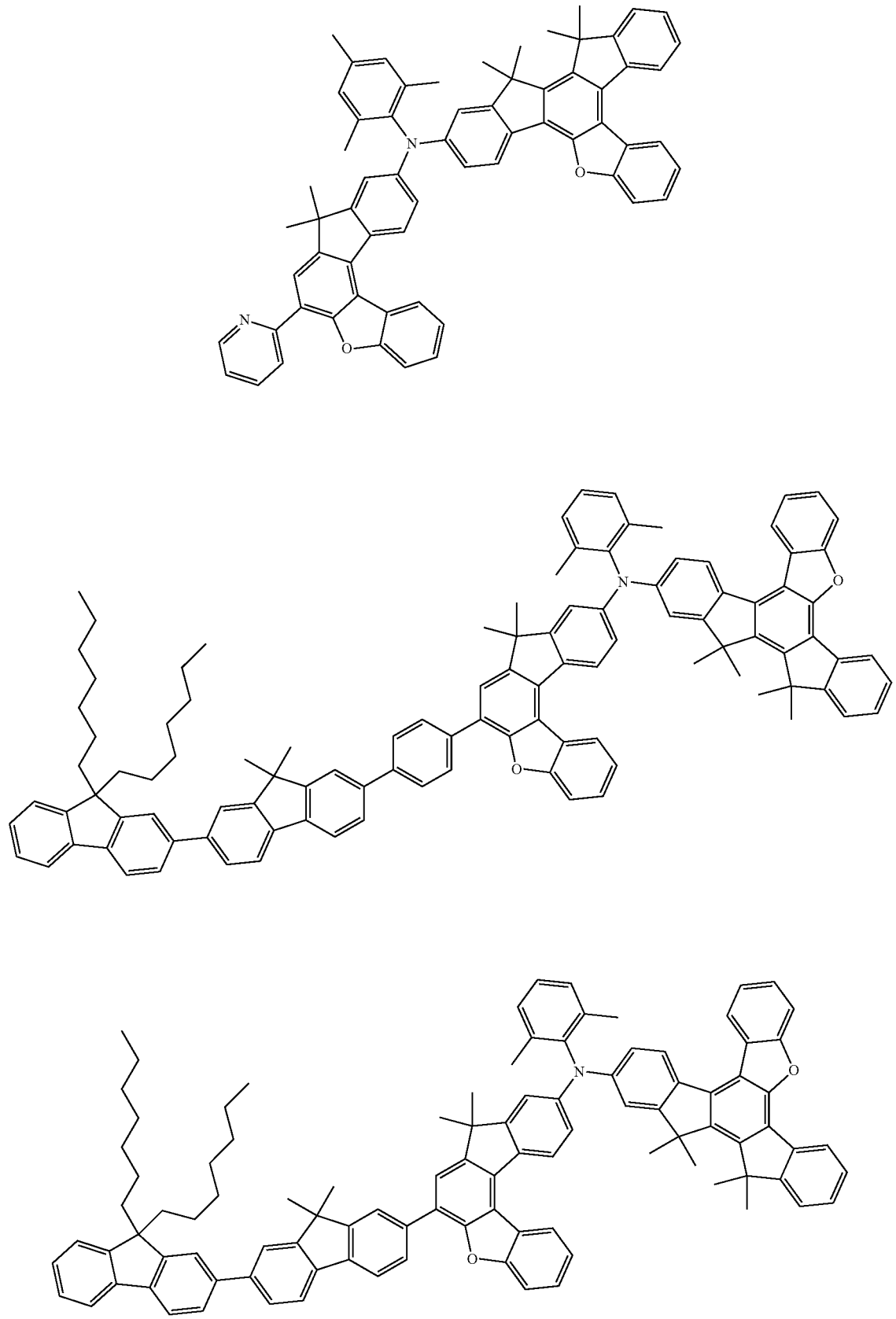

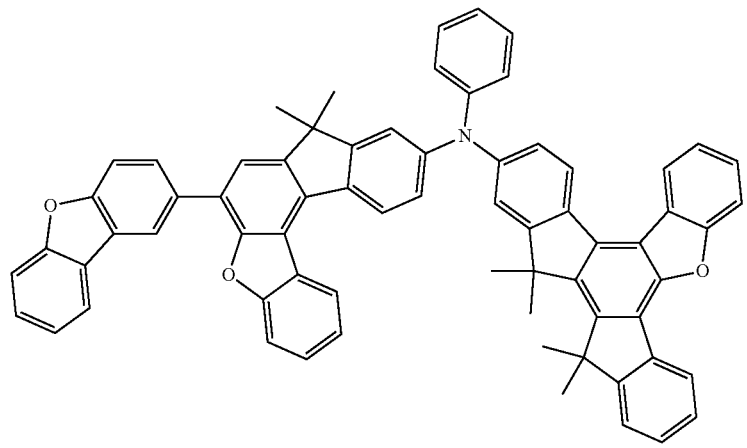 [SMILES: CC1(C)c2cc(N(c3ccccc3)c3ccc4c(c3)C(C)(C)c3c5c(c6oc7ccccc7c6c3-4)-c3ccccc3C5(C)C)ccc2-c2c1cc(-c1ccc3oc4ccccc4c3c1)c1oc3ccccc3c21]
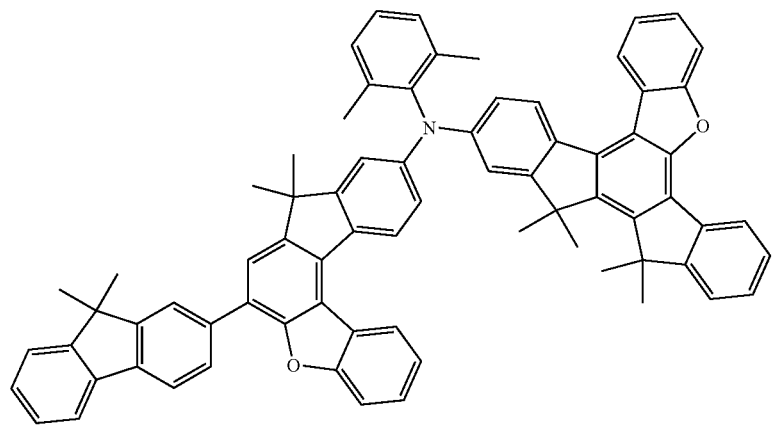 [SMILES: Cc1cccc(C)c1N(c1ccc2c(c1)C(C)(C)c1cc(-c3ccc4c(c3)C(C)(C)c3ccccc3-4)c3oc4ccccc4c3c1-2)c1ccc2c(c1)C(C)(C)c1c3c(c4oc5ccccc5c4c1-2)-c1ccccc1C3(C)C]
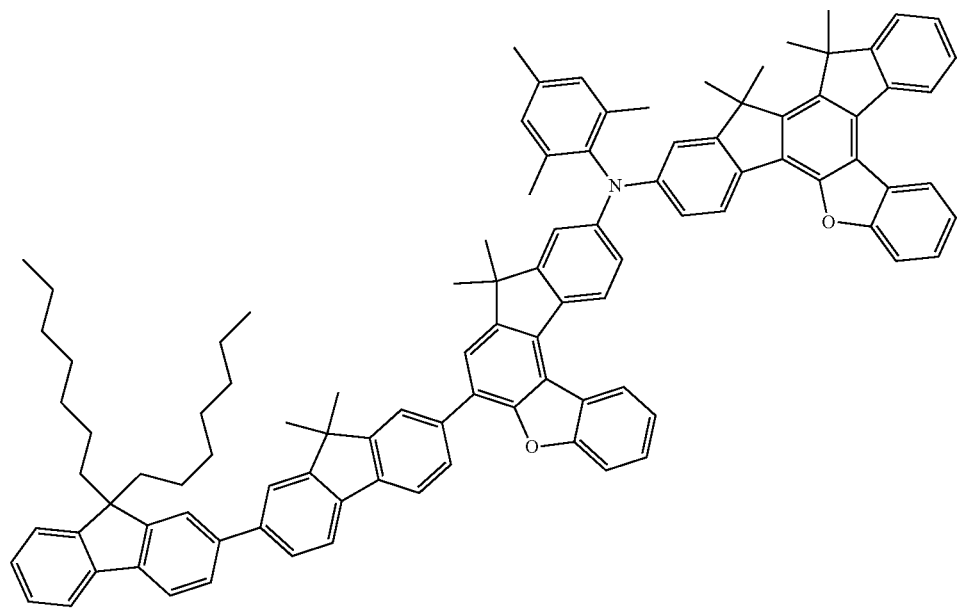 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10c(oc%11ccccc%11%10)c7-8)-c7ccccc7C9(C)C)c7c(C)cc(C)cc7C)cc5C6(C)C)ccc3-4)cc21]

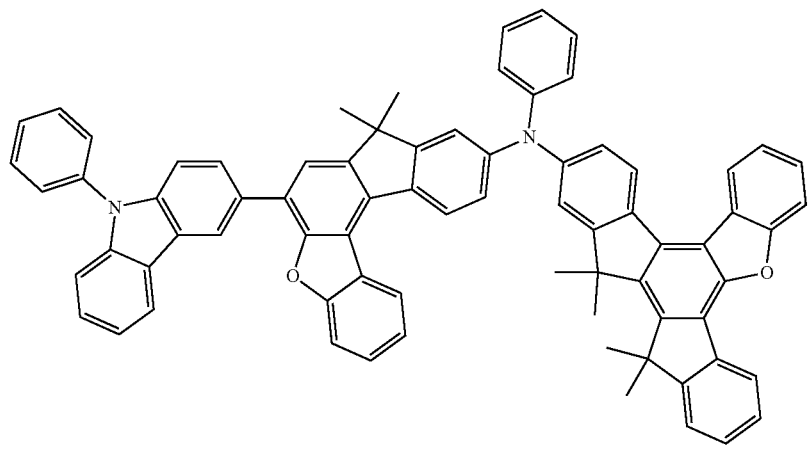 [SMILES: CC1(C)c2cc(N(c3ccccc3)c3ccc4c(c3)C(C)(C)c3c5c(c6oc7ccccc7c6c3-4)-c3ccccc3C5(C)C)ccc2-c2c1cc(-c1ccc3c(c1)c1ccccc1n3-c1ccccc1)c1oc3ccccc3c21]
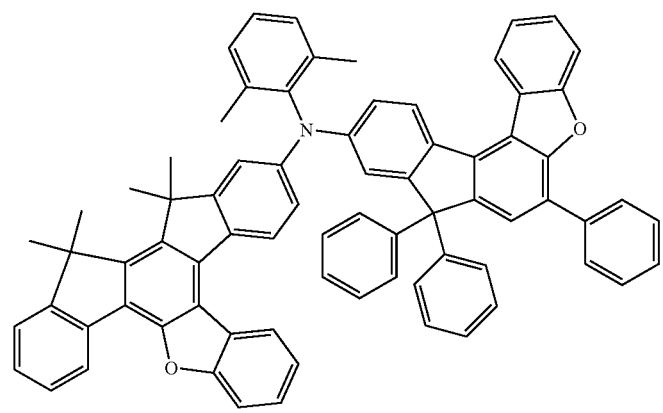 [SMILES: Cc1cccc(C)c1N(c1ccc2c(c1)C(C)(C)c1c3c(c4oc5ccccc5c4c1-2)-c1ccccc1C3(C)C)c1ccc2c(c1)C(c1ccccc1)(c1ccccc1)c1cc(-c3ccccc3)c3oc4ccccc4c3c1-2]
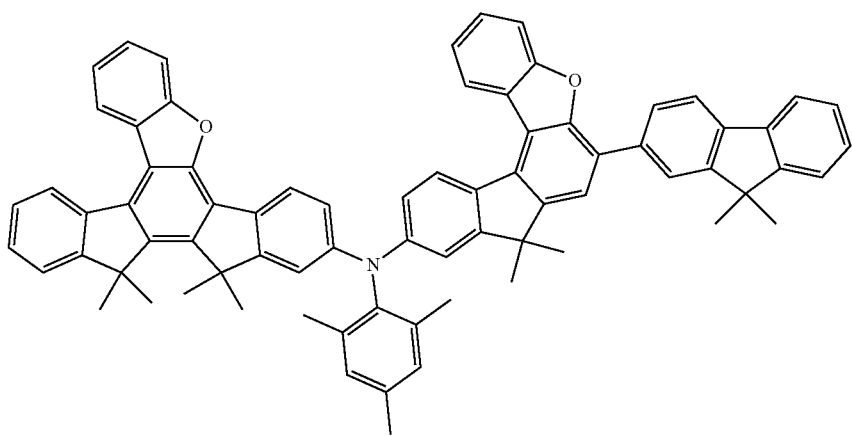 [SMILES: Cc1cc(C)c(N(c2ccc3c(c2)C(C)(C)c2cc(-c4ccc5c(c4)C(C)(C)c4ccccc4-5)c4oc5ccccc5c4c2-3)c2ccc3c(c2)C(C)(C)c2c4c(c5c(oc6ccccc65)c2-3)-c2ccccc2C4(C)C)c(C)c1]

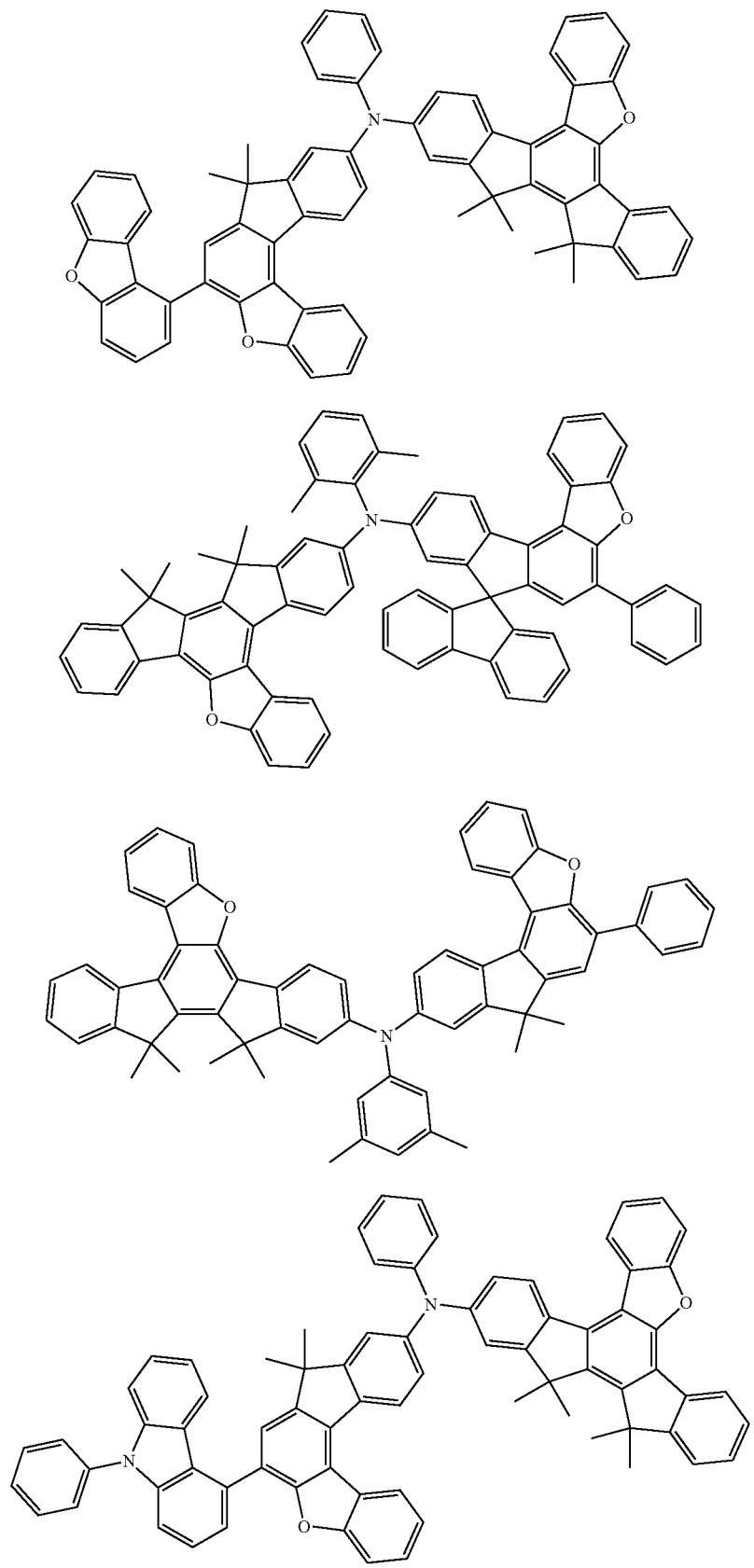

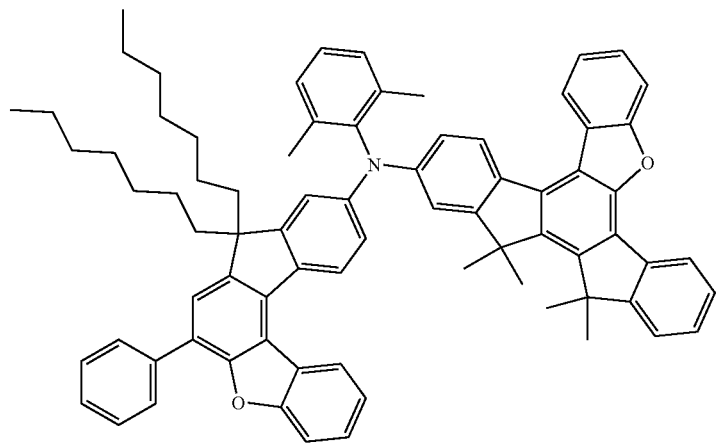 [SMILES: CCCCCCCC1(CCCCCCC)c2cc(N(c3ccc4c(c3)C(C)(C)c3c5c(c6oc7ccccc7c6c3-4)-c3ccccc3C5(C)C)c3c(C)cccc3C)ccc2-c2c1cc(-c1ccccc1)c1oc3ccccc3c21]
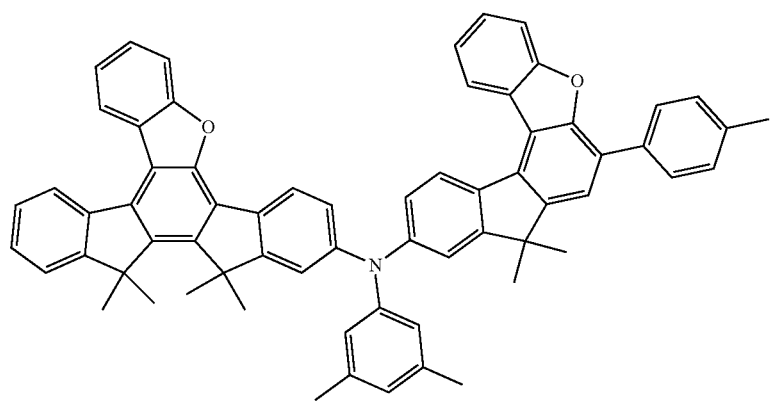 [SMILES: Cc1ccc(-c2cc3c(c4c2oc2ccccc24)-c2ccc(N(c4cc(C)cc(C)c4)c4ccc5c(c4)C(C)(C)c4c6c(c7c(oc8ccccc87)c4-5)-c4ccccc4C6(C)C)cc2C3(C)C)cc1]
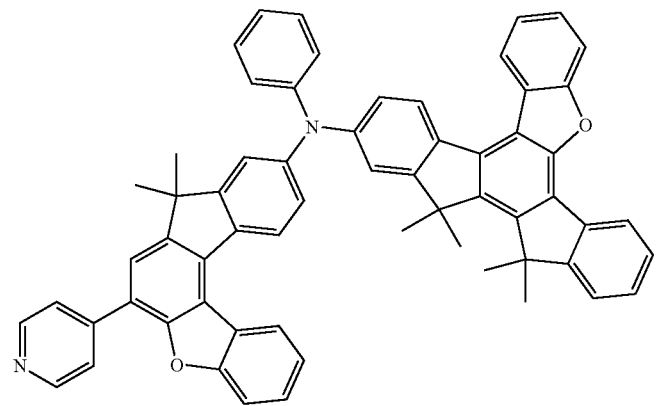 [SMILES: CC1(C)c2cc(N(c3ccccc3)c3ccc4c(c3)C(C)(C)c3c5c(c6oc7ccccc7c6c3-4)-c3ccccc3C5(C)C)ccc2-c2c1cc(-c1ccncc1)c1oc3ccccc3c21]

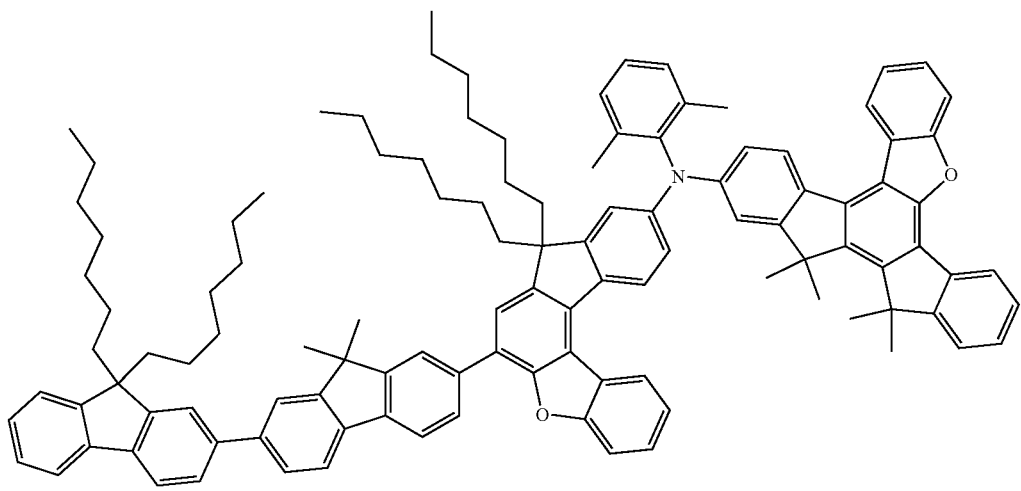 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7c(C)cccc7C)cc5C6(CCCCCCC)CCCCCCC)ccc3-4)cc21]
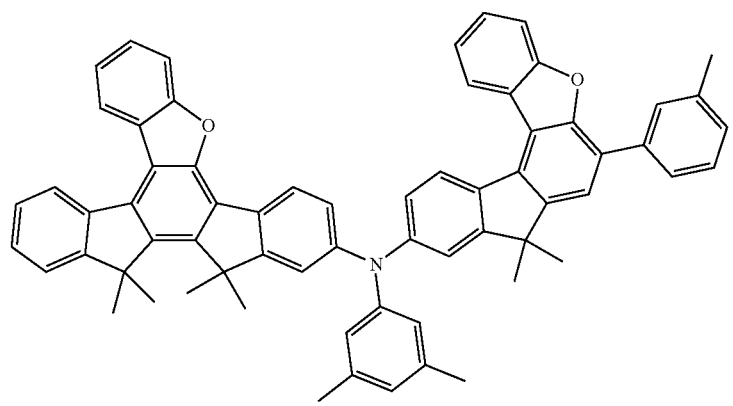 [SMILES: Cc1cccc(-c2cc3c(c4c2oc2ccccc24)-c2ccc(N(c4cc(C)cc(C)c4)c4ccc5c(c4)C(C)(C)c4c6c(c7c(oc8ccccc87)c4-5)-c4ccccc4C6(C)C)cc2C3(C)C)c1]
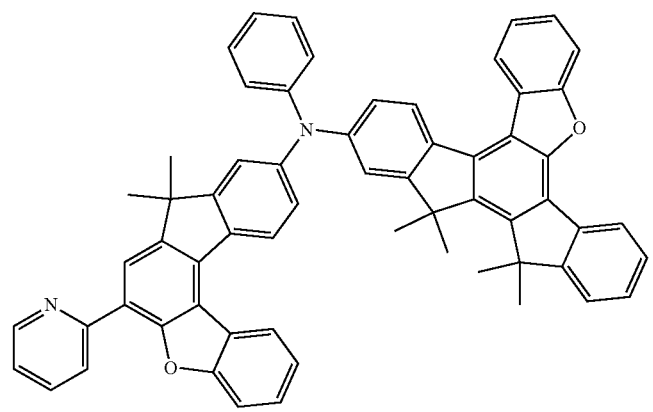 [SMILES: CC1(C)c2cc(N(c3ccccc3)c3ccc4c(c3)C(C)(C)c3c5c(c6oc7ccccc7c6c3-4)-c3ccccc3C5(C)C)ccc2-c2c1cc(-c1ccccn1)c1oc3ccccc3c21]

-continued
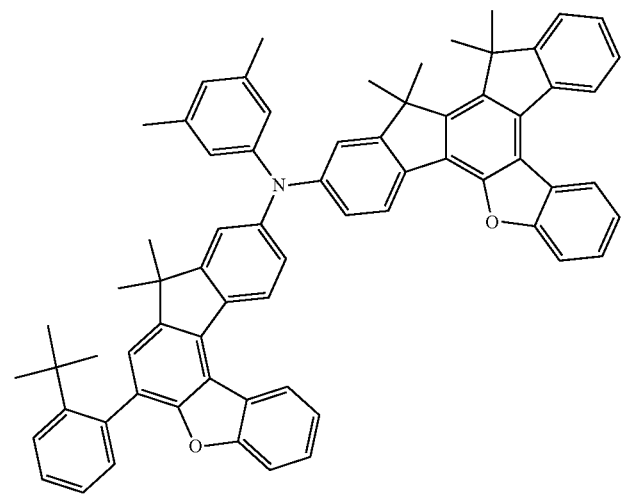 [SMILES: Cc1cc(C)cc(N(c2ccc3c(c2)C(C)(C)c2cc(-c4ccccc4C(C)(C)C)c4oc5ccccc5c4c2-3)c2ccc3c(c2)C(C)(C)c2c4c(c5c(oc6ccccc65)c2-3)-c2ccccc2C4(C)C)c1]
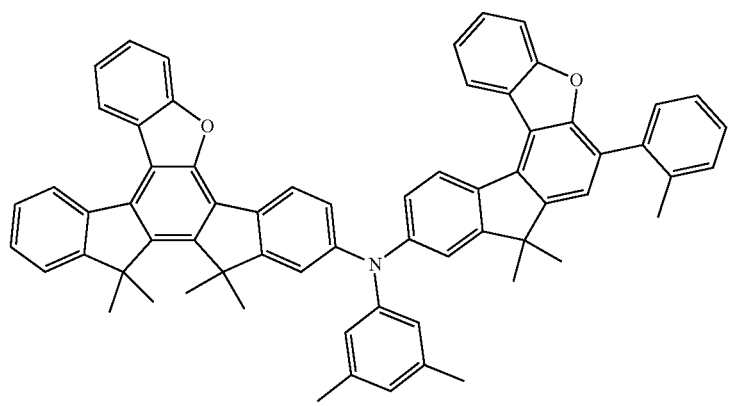 [SMILES: Cc1cc(C)cc(N(c2ccc3c(c2)C(C)(C)c2cc(-c4ccccc4C)c4oc5ccccc5c4c2-3)c2ccc3c(c2)C(C)(C)c2c4c(c5c(oc6ccccc65)c2-3)-c2ccccc2C4(C)C)c1]
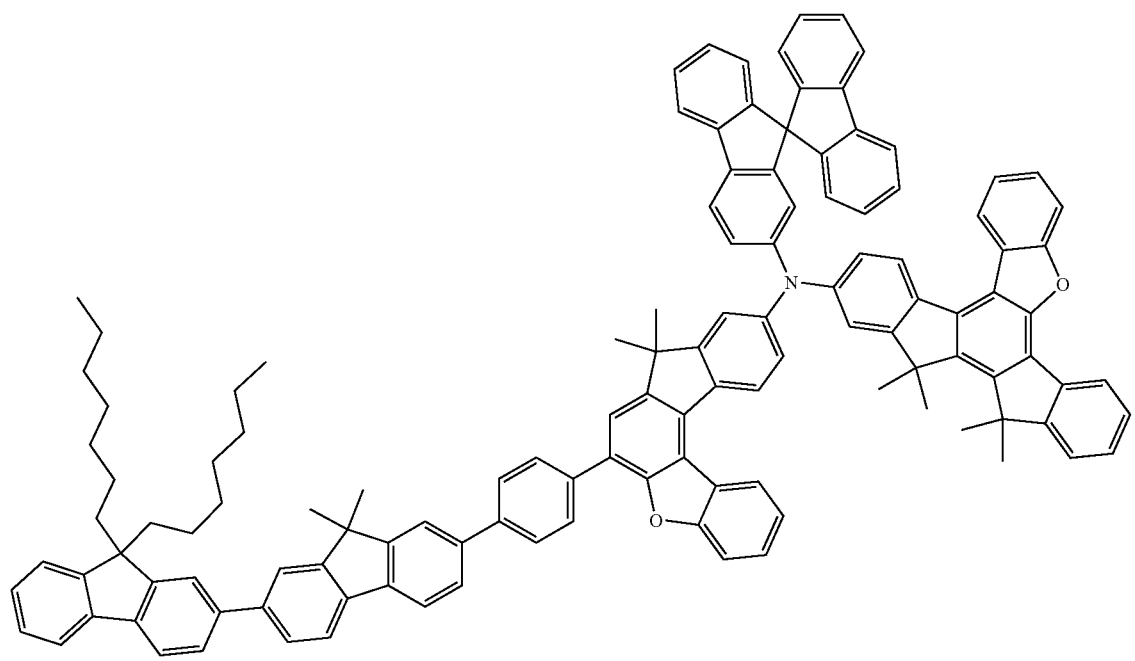 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8ccc9c(c8)C8(c%10ccccc%10-c%10ccccc%108)c8ccccc8-9)cc6C7(C)C)cc5)ccc3-4)cc21]

-continued
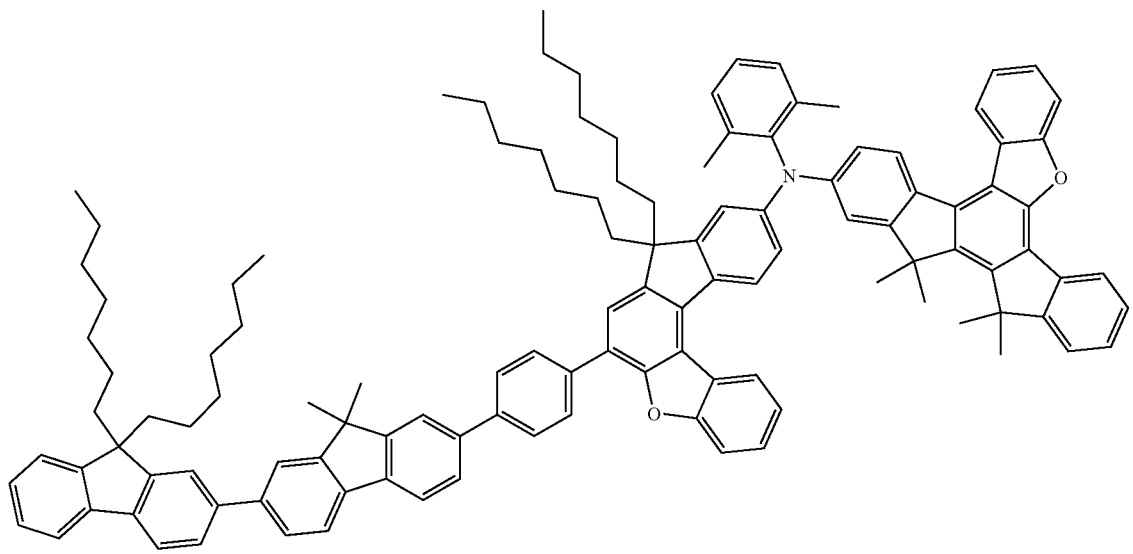 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8c(C)cccc8C)cc6C7(CCCCCCC)CCCCCCC)cc5)ccc3-4)cc21]
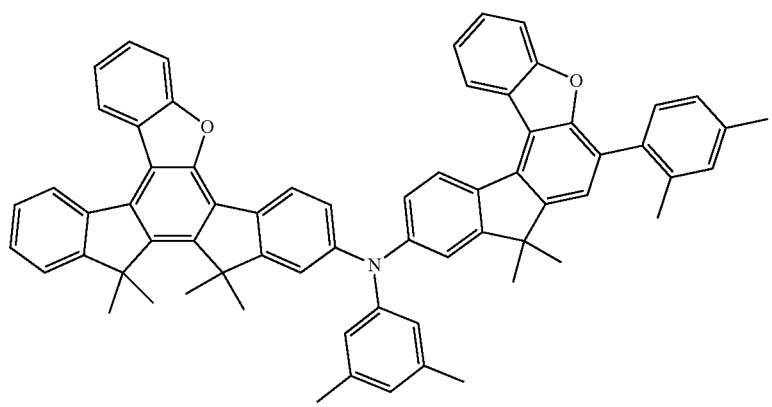 [SMILES: Cc1cc(C)cc(N(c2ccc3c(c2)C(C)(C)c2cc(-c4ccc(C)cc4C)c4oc5ccccc5c4c2-3)c2ccc3c(c2)C(C)(C)c2c4c(c5c(oc6ccccc65)c2-3)-c2ccccc2C4(C)C)c1]
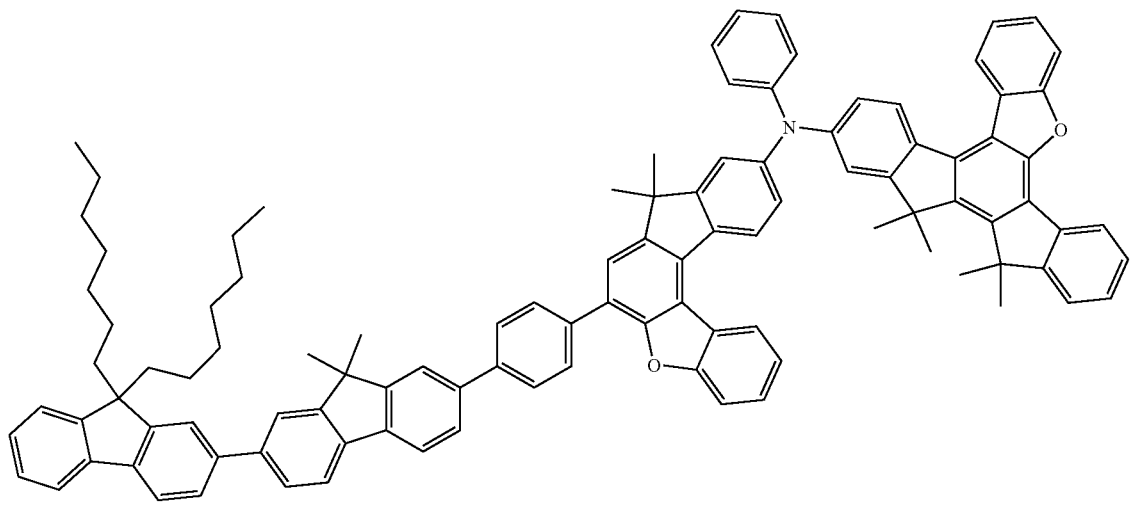 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccccc8)c8ccc9c(c8)C(C)(C)c8c%10c(c%11oc%12ccccc%12c%11c8-9)-c8ccccc8C%10(C)C)cc6C7(C)C)cc5)ccc3-4)cc21]

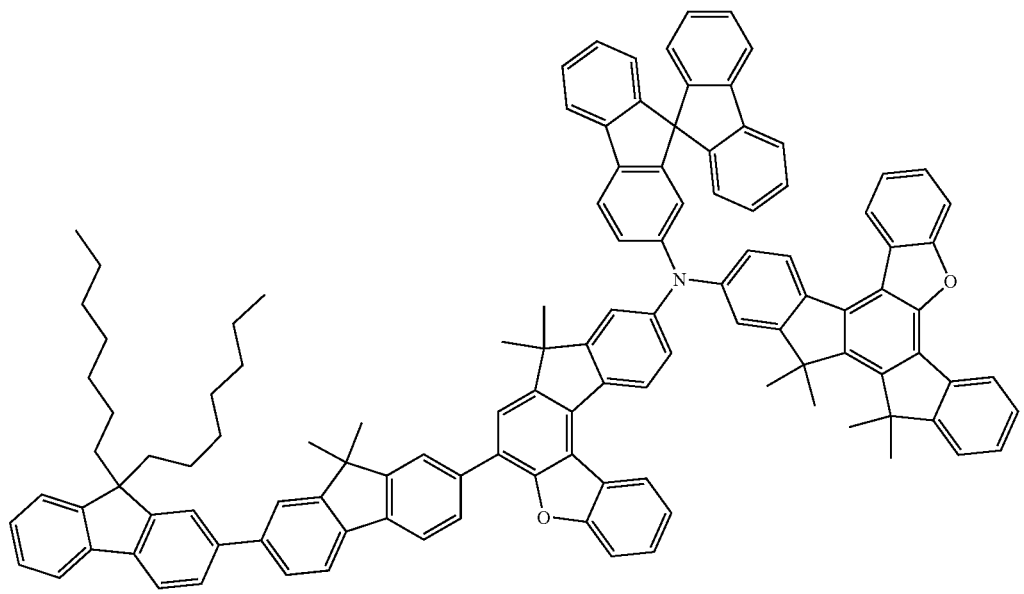 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7ccc8c(c7)C7(c9ccccc9-c9ccccc97)c7ccccc7-8)cc5C6(C)C)ccc3-4)cc21]
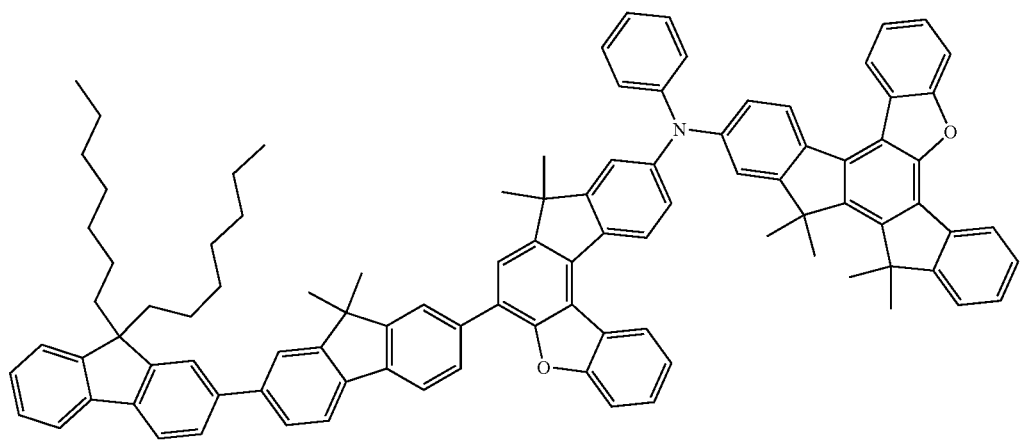 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccccc7)c7ccc8c(c7)C(C)(C)c7c9c(c%10oc%11ccccc%11c%10c7-8)-c7ccccc7C9(C)C)cc5C6(C)C)ccc3-4)cc21]
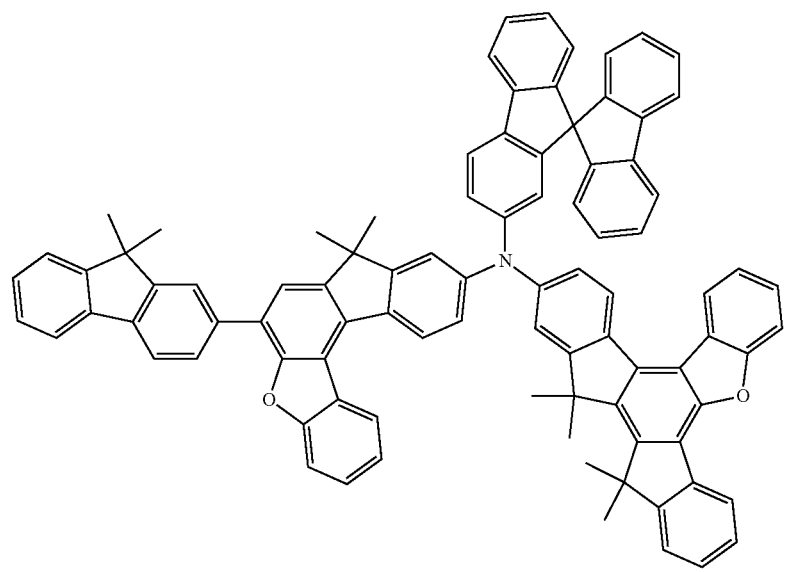 [SMILES: CC1(C)c2ccccc2-c2ccc(-c3cc4c(c5c3oc3ccccc35)-c3ccc(N(c5ccc6c(c5)C(C)(C)c5c7c(c8oc9ccccc9c8c5-6)-c5ccccc5C7(C)C)c5ccc6c(c5)C5(c7ccccc7-c7ccccc75)c5ccccc5-6)cc3C4(C)C)cc21]

-continued
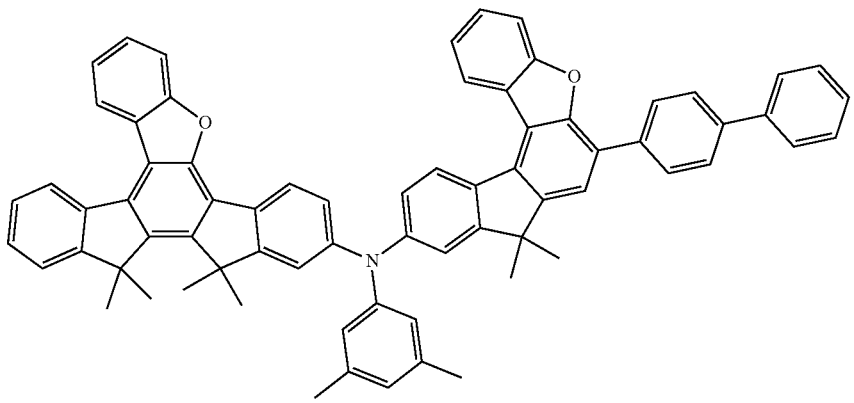 [SMILES: Cc1cc(C)cc(N(c2ccc3c(c2)C(C)(C)c2cc(-c4ccc(-c5ccccc5)cc4)c4oc5ccccc5c4c2-3)c2ccc3c(c2)C(C)(C)c2c4c(c5c(oc6ccccc65)c2-3)-c2ccccc2C4(C)C)c1]
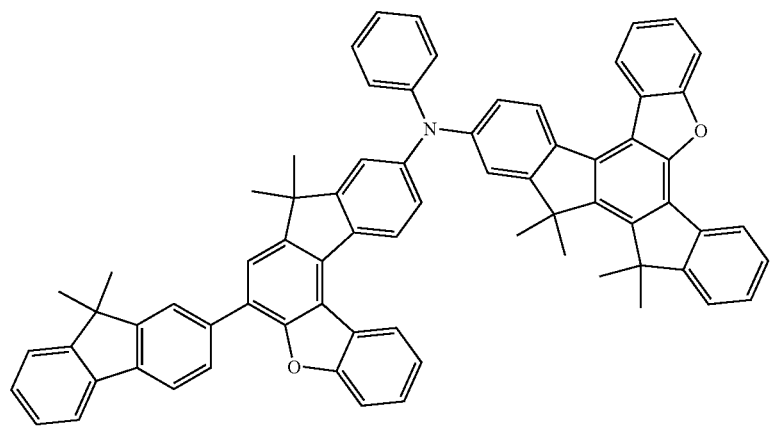 [SMILES: CC1(C)c2ccccc2-c2ccc(-c3cc4c(c5c3oc3ccccc35)-c3ccc(N(c5ccccc5)c5ccc6c(c5)C(C)(C)c5c7c(c8oc9ccccc9c8c5-6)-c5ccccc5C7(C)C)cc3C4(C)C)cc21]
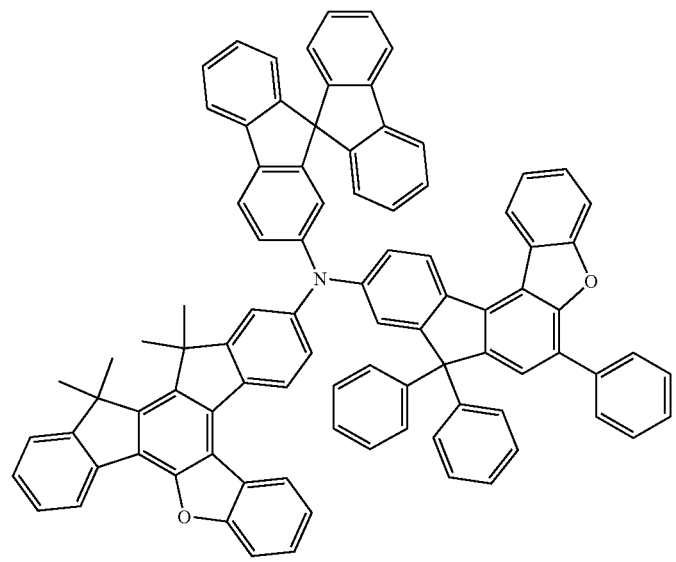 [SMILES: CC1(C)c2ccccc2-c2c1c1c(c3c2oc2ccccc23)-c2ccc(N(c3ccc4c(c3)C(c3ccccc3)(c3ccccc3)c3cc(-c5ccccc5)c5oc6ccccc6c5c3-4)c3ccc4c(c3)C3(c5ccccc5-c5ccccc53)c3ccccc3-4)cc2C1(C)C]

-continued
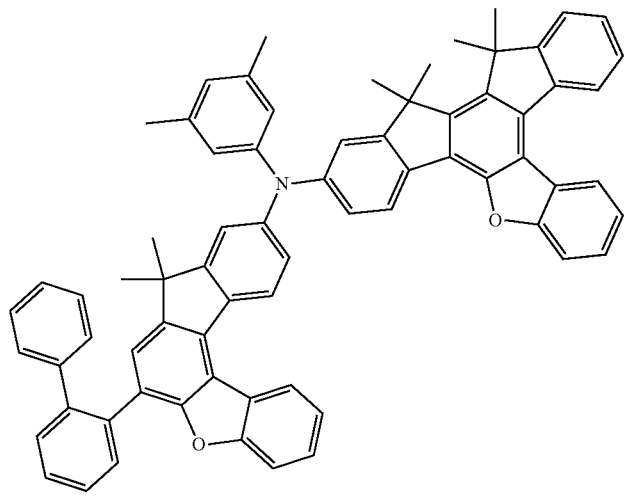 [SMILES: Cc1cc(C)cc(N(c2ccc3c(c2)C(C)(C)c2cc(-c4ccccc4-c4ccccc4)c4oc5ccccc5c4c2-3)c2ccc3c(c2)C(C)(C)c2c4c(c5c(oc6ccccc65)c2-3)-c2ccccc2C4(C)C)c1]
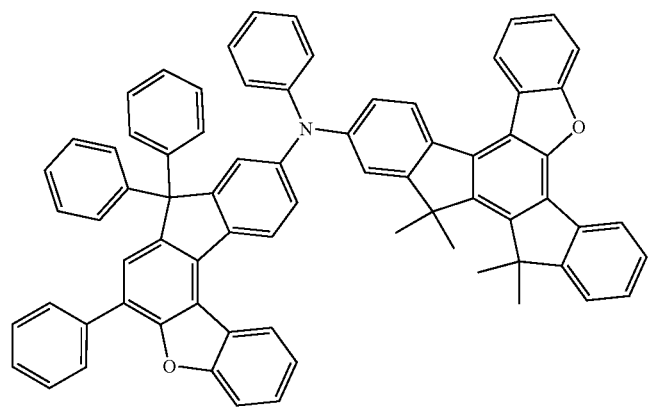 [SMILES: CC1(C)c2ccccc2-c2c1c1c(c3c2oc2ccccc23)-c2ccc(N(c3ccccc3)c3ccc4c(c3)C(c3ccccc3)(c3ccccc3)c3cc(-c5ccccc5)c5oc6ccccc6c5c3-4)cc2C1(C)C]
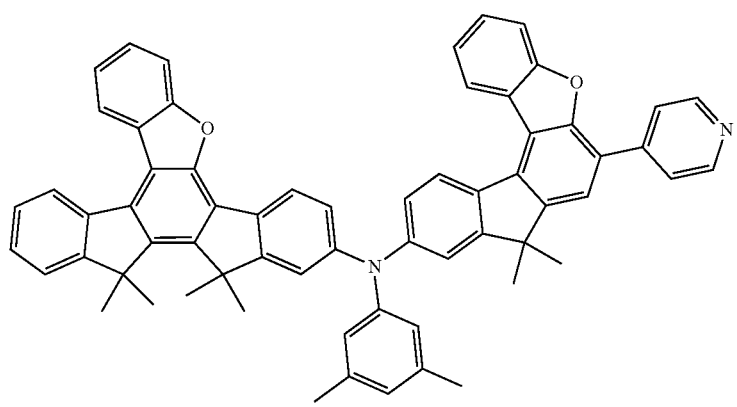 [SMILES: Cc1cc(C)cc(N(c2ccc3c(c2)C(C)(C)c2cc(-c4ccncc4)c4oc5ccccc5c4c2-3)c2ccc3c(c2)C(C)(C)c2c4c(c5c(oc6ccccc65)c2-3)-c2ccccc2C4(C)C)c1]

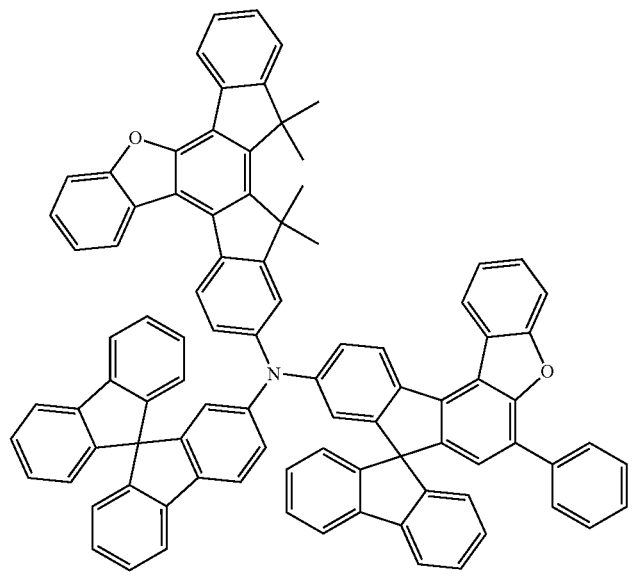 [SMILES: CC1(C)c2ccccc2-c2c1c1c(c3c2oc2ccccc23)-c2ccc(N(c3ccc4c(c3)C3(c5ccccc5-c5ccccc53)c3ccccc3-4)c3ccc4c(c3)C3(c5ccccc5-c5ccccc53)c3cc(-c5ccccc5)c5oc6ccccc6c5c3-4)cc2C1(C)C]
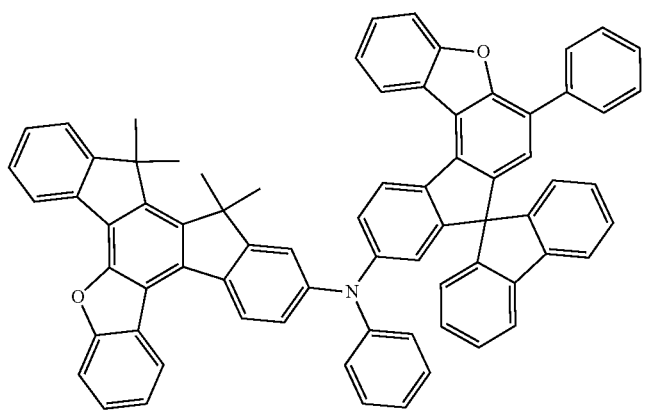 [SMILES: CC1(C)c2ccccc2-c2c1c1c(c3c2oc2ccccc23)-c2ccc(N(c3ccccc3)c3ccc4c(c3)C3(c5ccccc5-c5ccccc53)c3cc(-c5ccccc5)c5oc6ccccc6c5c3-4)cc2C1(C)C]
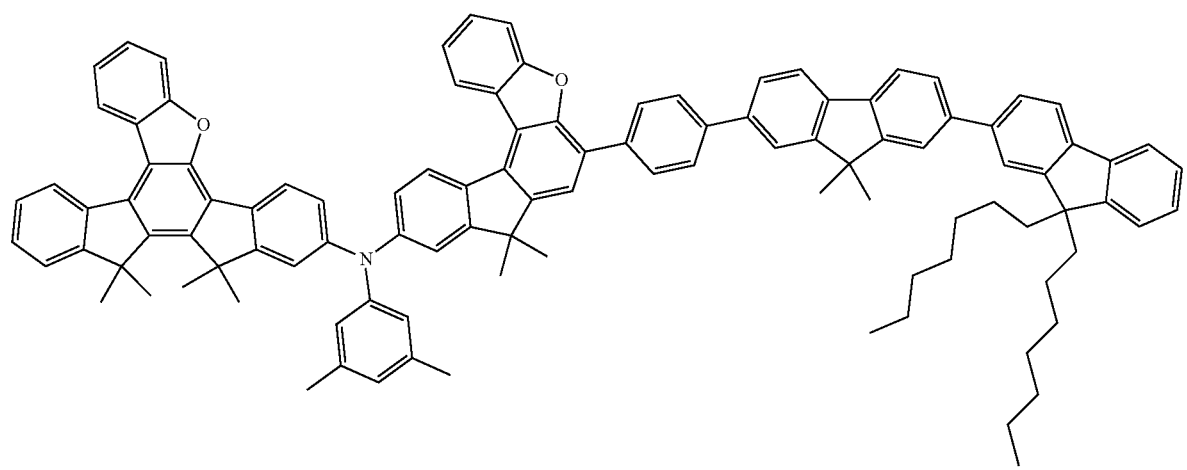 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8cc(C)cc(C)c8)c8ccc9c(c8)C(C)(C)c8c%10c(c%11c(oc%12ccccc%12%11)c8-9)-c8ccccc8C%10(C)C)cc6C7(C)C)cc5)ccc3-4)cc21]

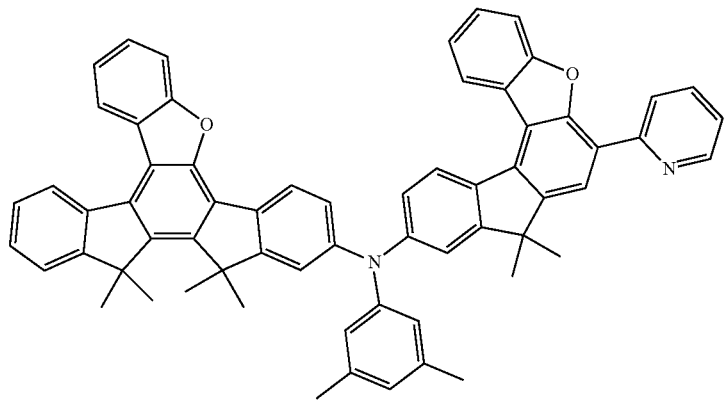 [SMILES: Cc1cc(C)cc(N(c2ccc3c(c2)C(C)(C)c2cc(-c4ccccn4)c4oc5ccccc5c4c2-3)c2ccc3c(c2)C(C)(C)c2c4c(c5c(oc6ccccc65)c2-3)-c2ccccc2C4(C)C)c1]
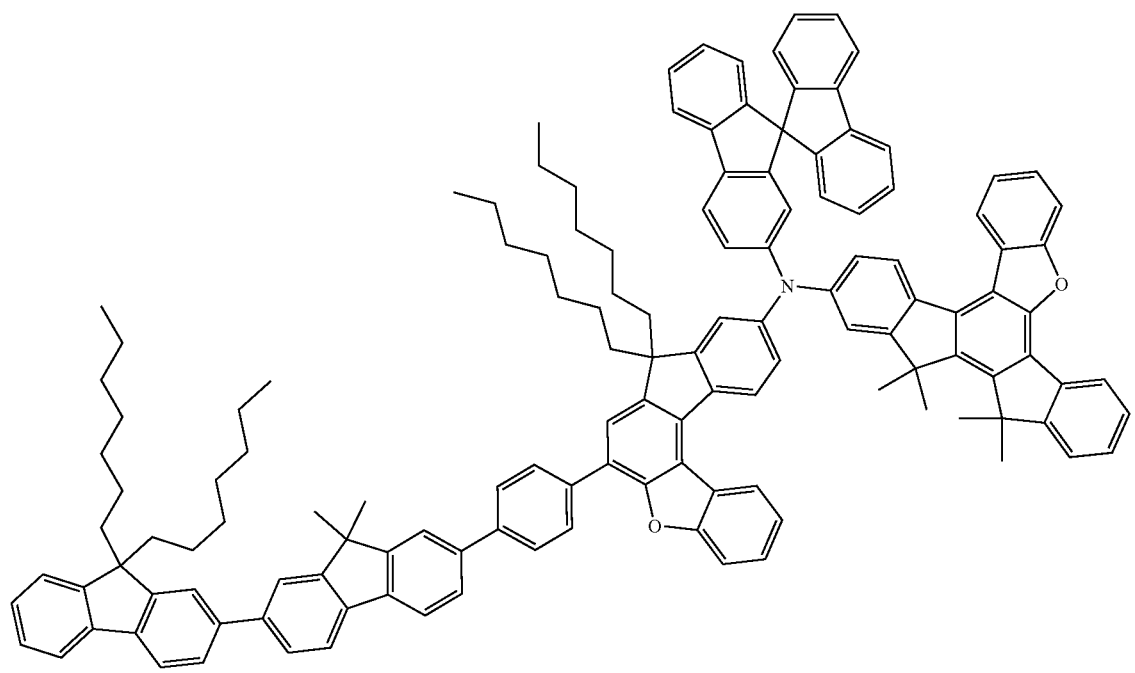 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8ccc9c(c8)C8(c%10ccccc%10-c%10ccccc%108)c8ccccc8-9)cc6C7(CCCCCCC)CCCCCCC)cc5)ccc3-4)cc21]
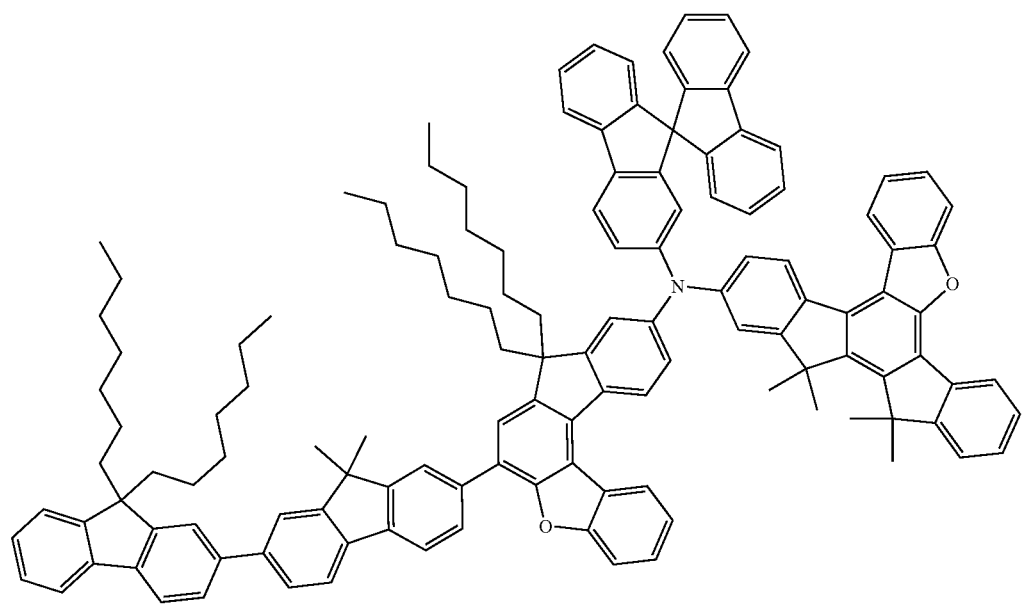 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7ccc8c(c7)C7(c9ccccc9-c9ccccc97)c7ccccc7-8)cc5C6(CCCCCCC)CCCCCCC)ccc3-4)cc21]

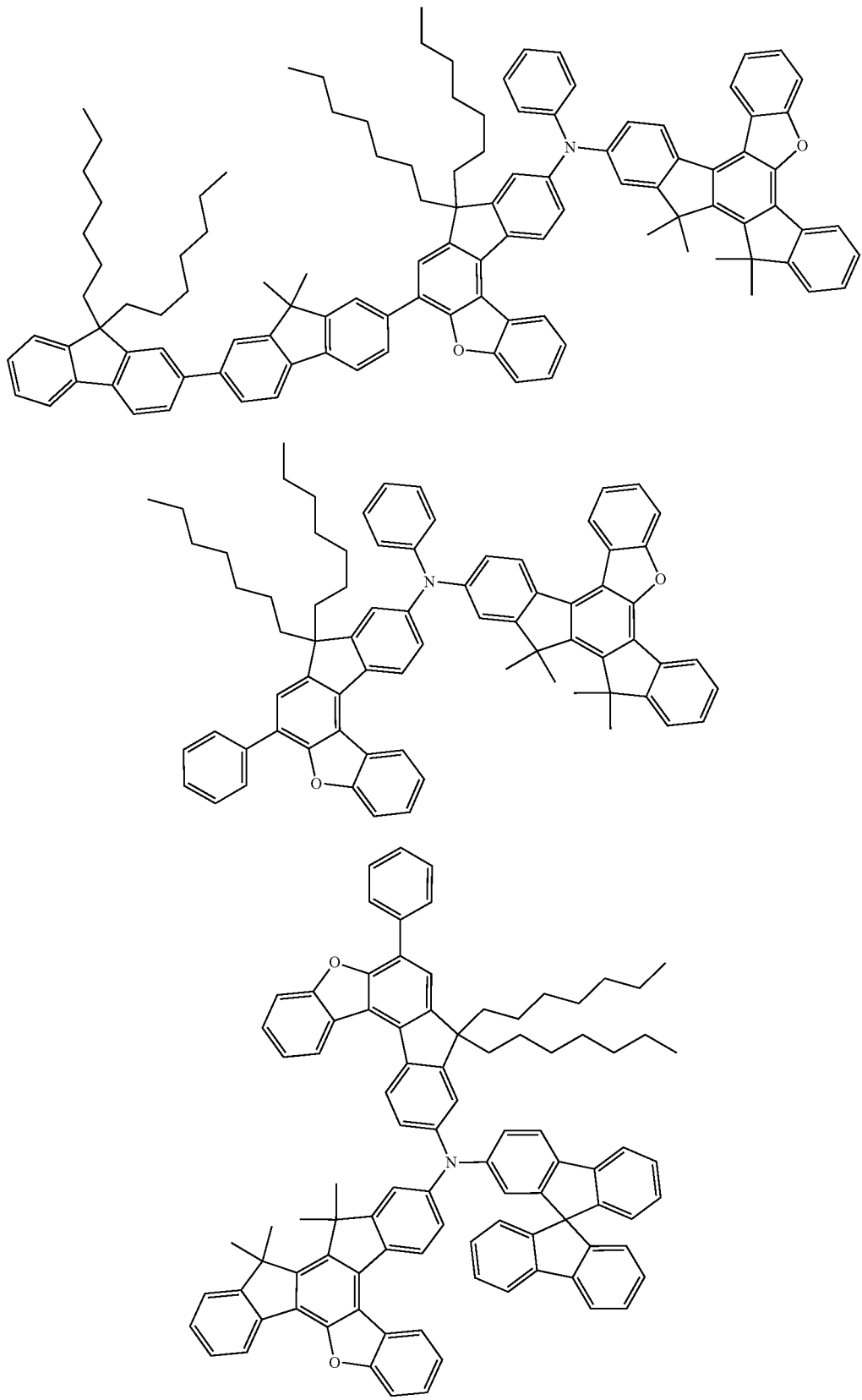

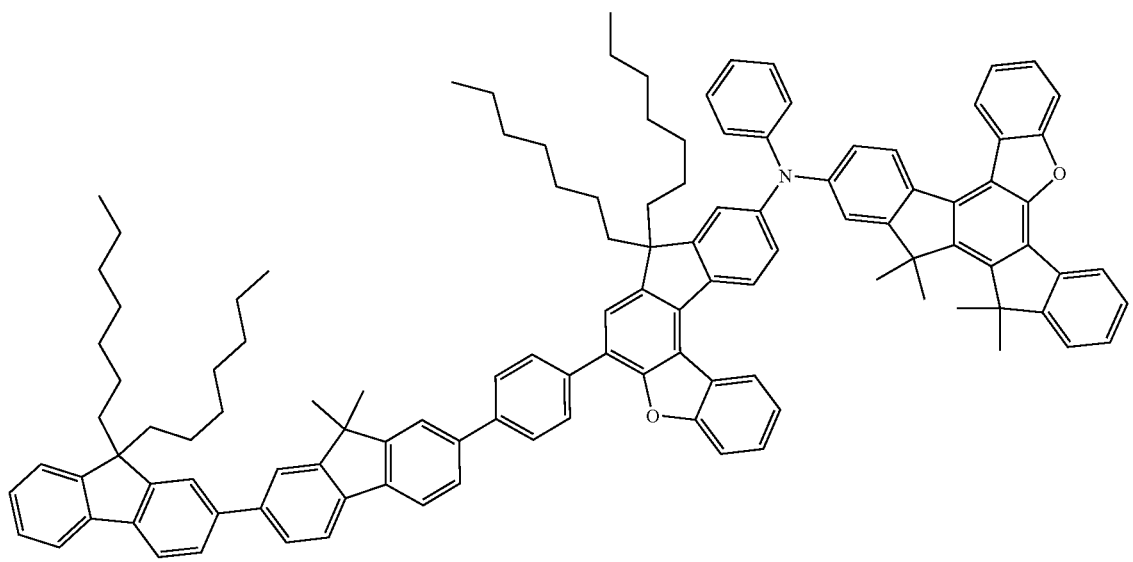 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccccc8)c8ccc9c(c8)C(C)(C)c8c%10c(c%11oc%12ccccc%12c%11c8-9)-c8ccccc8C%10(C)C)cc6C7(CCCCCCC)CCCCCCC)cc5)ccc3-4)cc21]
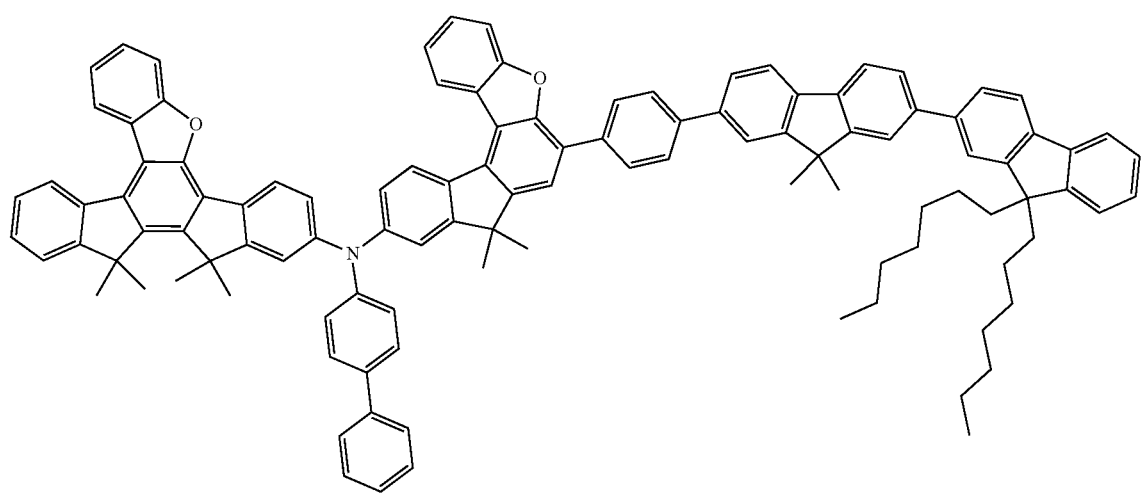 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc(-c9ccccc9)cc8)c8ccc9c(c8)C(C)(C)c8c%10c(c%11c(oc%12ccccc%12%11)c8-9)-c8ccccc8C%10(C)C)cc6C7(C)C)cc5)ccc3-4)cc21]

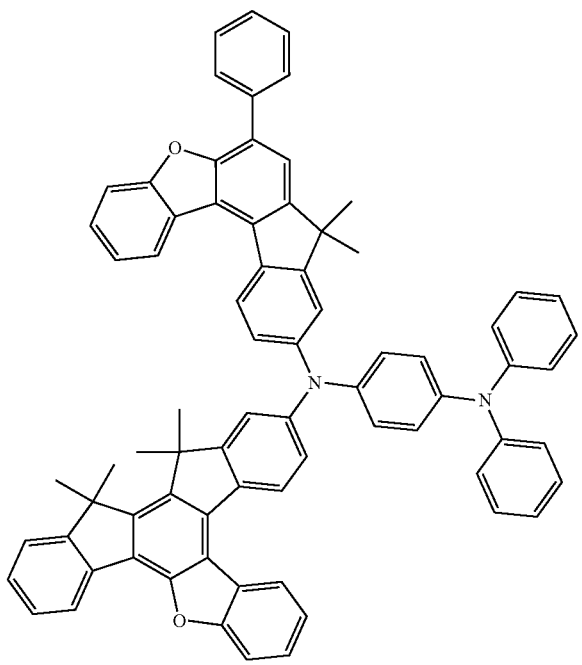 [SMILES: CC1(C)c2cc(N(c3ccc(N(c4ccccc4)c4ccccc4)cc3)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]
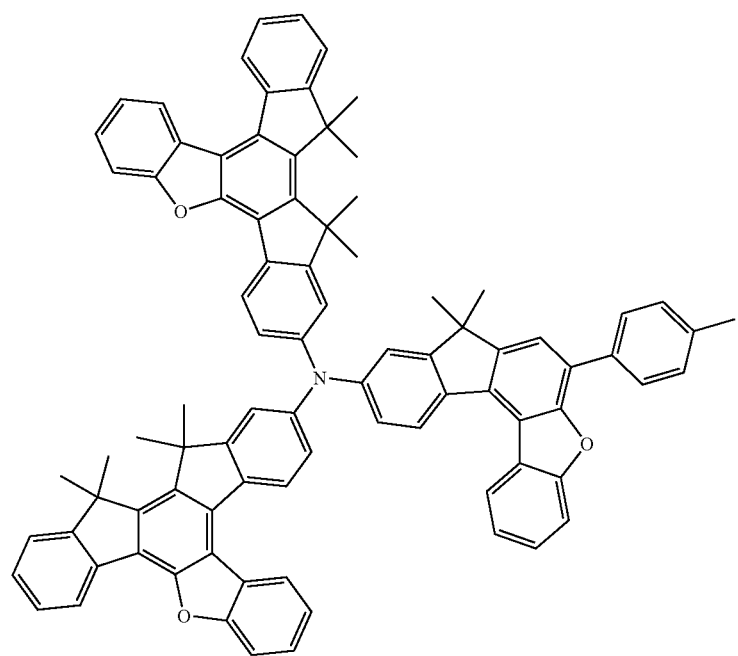 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccc5c(c4)C(C)(C)c4c6c(c7oc8ccccc8c7c4-5)-c4ccccc4C6(C)C)cc2C3(C)C)cc1]

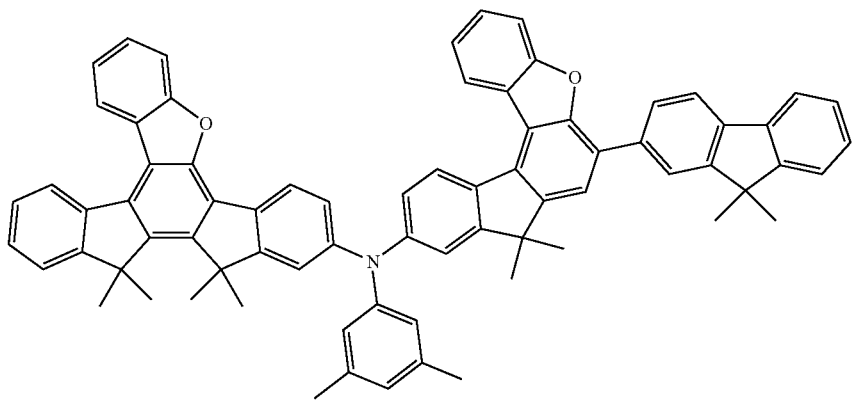 [SMILES: Cc1cc(C)cc(N(c2ccc3c(c2)C(C)(C)c2cc(-c4ccc5c(c4)C(C)(C)c4ccccc4-5)c4oc5ccccc5c4c2-3)c2ccc3c(c2)C(C)(C)c2c4c(c5c(oc6ccccc65)c2-3)-c2ccccc2C4(C)C)c1]
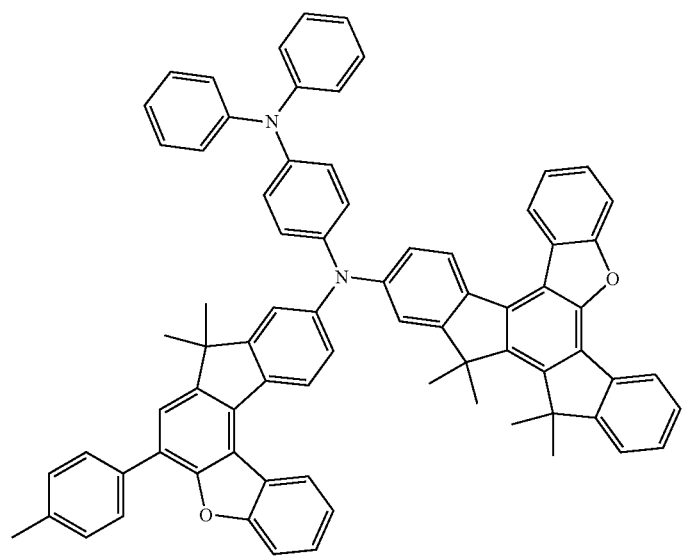 [SMILES: Cc1ccc(-c2cc3c(c4c2oc2ccccc24)-c2ccc(N(c4ccc(N(c5ccccc5)c5ccccc5)cc4)c4ccc5c(c4)C(C)(C)c4c6c(c7oc8ccccc8c7c4-5)-c4ccccc4C6(C)C)cc2C3(C)C)cc1]
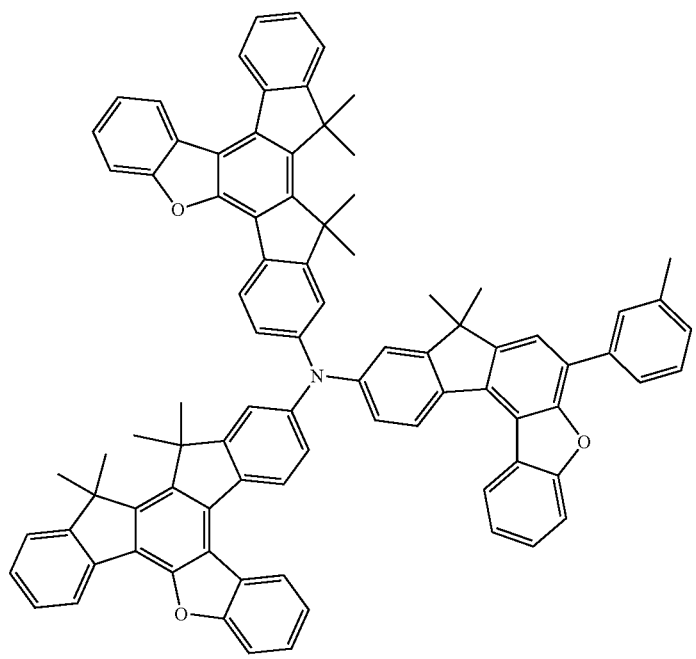 [SMILES: Cc1cccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccc5c(c4)C(C)(C)c4c6c(c7oc8ccccc8c7c4-5)-c4ccccc4C6(C)C)cc2C3(C)C)c1]

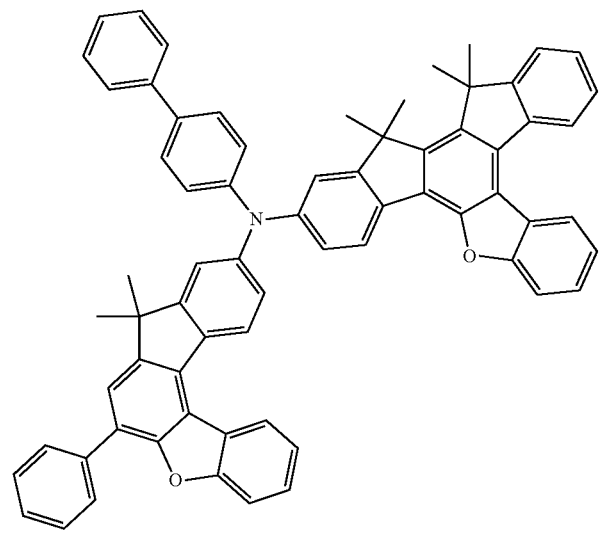 [SMILES: CC1(C)c2cc(N(c3ccc(-c4ccccc4)cc3)c3ccc4c(c3)C(C)(C)c3c5c(c6c(oc7ccccc76)c3-4)-c3ccccc3C5(C)C)ccc2-c2c1cc(-c1ccccc1)c1oc3ccccc3c21]
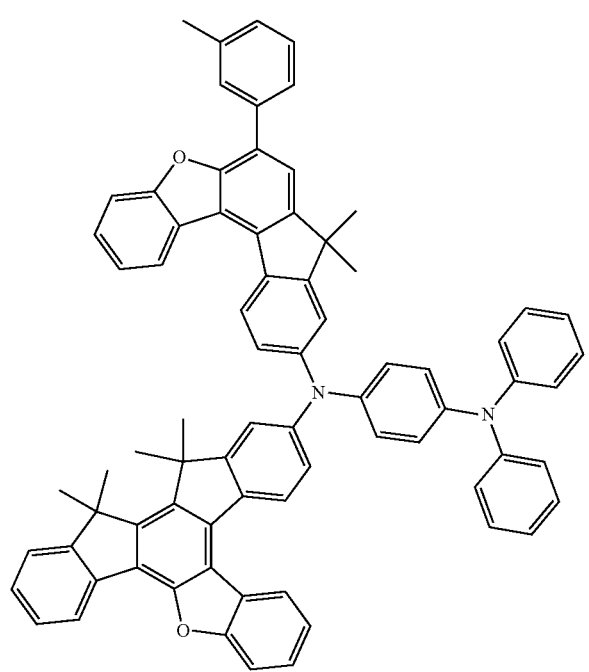 [SMILES: Cc1cccc(-c2cc3c(c4c2oc2ccccc24)-c2ccc(N(c4ccc(N(c5ccccc5)c5ccccc5)cc4)c4ccc5c(c4)C(C)(C)c4c6c(c7oc8ccccc8c7c4-5)-c4ccccc4C6(C)C)cc2C3(C)C)c1]

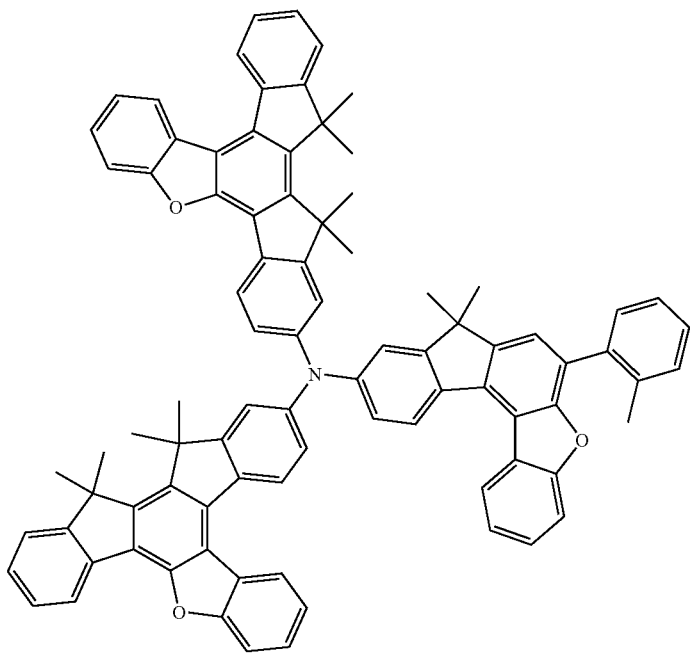 [SMILES: Cc1ccccc1-c1cc2c(c3c1oc1ccccc13)-c1ccc(N(c3ccc4c(c3)C(C)(C)c3c5c(c6c(oc7ccccc76)c3-4)-c3ccccc3C5(C)C)c3ccc4c(c3)C(C)(C)c3c5c(c6oc7ccccc7c6c3-4)-c3ccccc3C5(C)C)cc1C2(C)C]
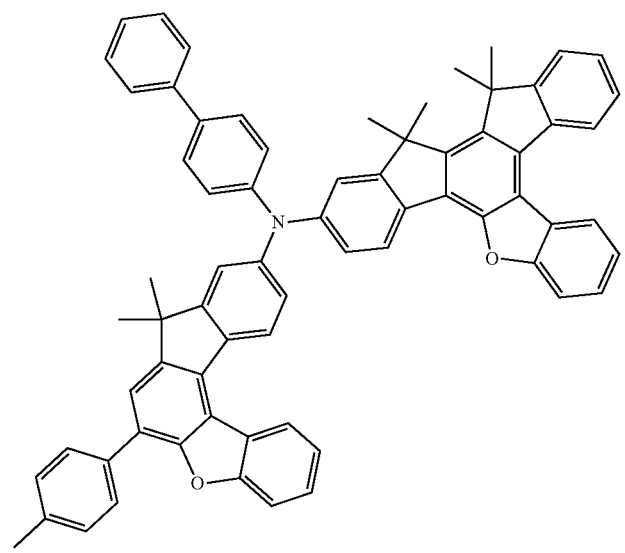 [SMILES: Cc1ccc(-c2cc3c(c4c2oc2ccccc24)-c2ccc(N(c4ccc(-c5ccccc5)cc4)c4ccc5c(c4)C(C)(C)c4c6c(c7c(oc8ccccc87)c4-5)-c4ccccc4C6(C)C)cc2C3(C)C)cc1]

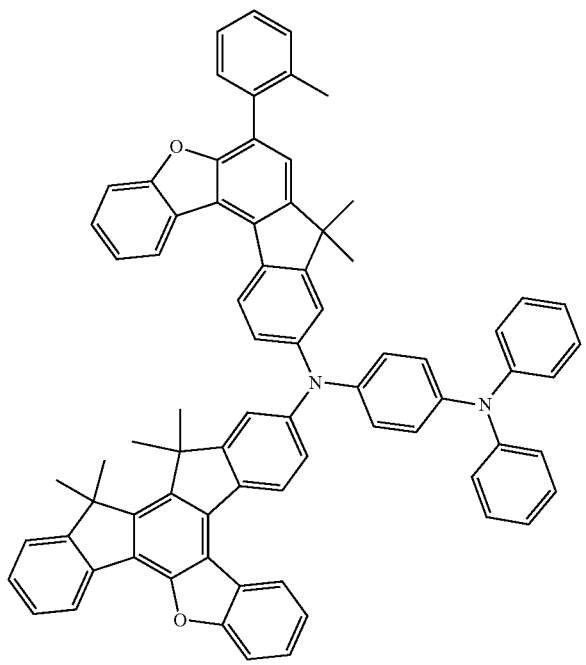 [SMILES: Cc1ccccc1-c1cc2c(c3c1oc1ccccc13)-c1ccc(N(c3ccc(N(c4ccccc4)c4ccccc4)cc3)c3ccc4c(c3)C(C)(C)c3c5c(c6oc7ccccc7c6c3-4)-c3ccccc3C5(C)C)cc1C2(C)C]
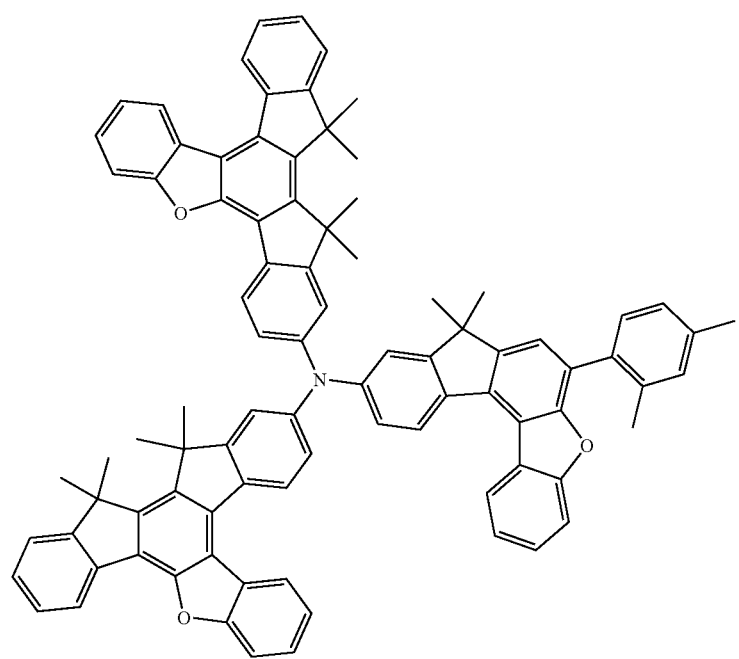 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccc5c(c4)C(C)(C)c4c6c(c7oc8ccccc8c7c4-5)-c4ccccc4C6(C)C)cc2C3(C)C)c(C)c1]

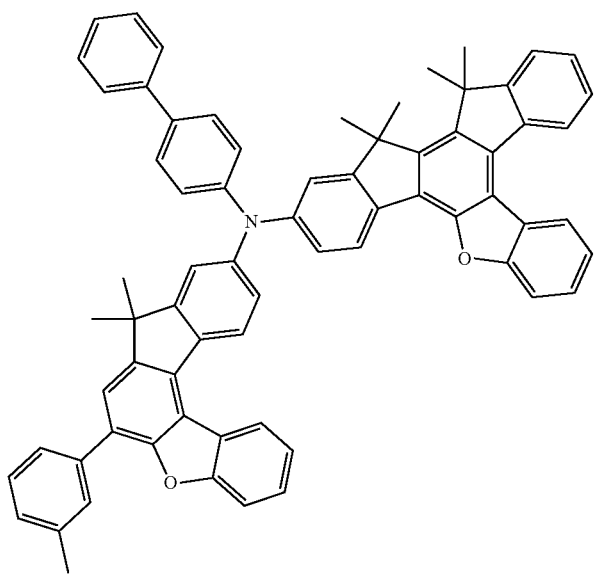 [SMILES: Cc1cccc(-c2cc3c(c4c2oc2ccccc24)-c2ccc(N(c4ccc(-c5ccccc5)cc4)c4ccc5c(c4)C(C)(C)c4c6c(c7c(oc8ccccc87)c4-5)-c4ccccc4C6(C)C)cc2C3(C)C)c1]
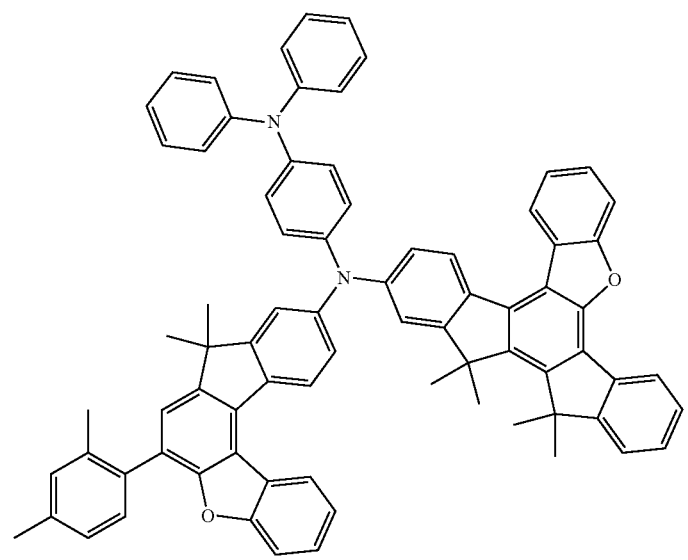 [SMILES: Cc1ccc(-c2cc3c(c4c2oc2ccccc24)-c2ccc(N(c4ccc(N(c5ccccc5)c5ccccc5)cc4)c4ccc5c(c4)C(C)(C)c4c6c(c7oc8ccccc8c7c4-5)-c4ccccc4C6(C)C)cc2C3(C)C)c(C)c1]

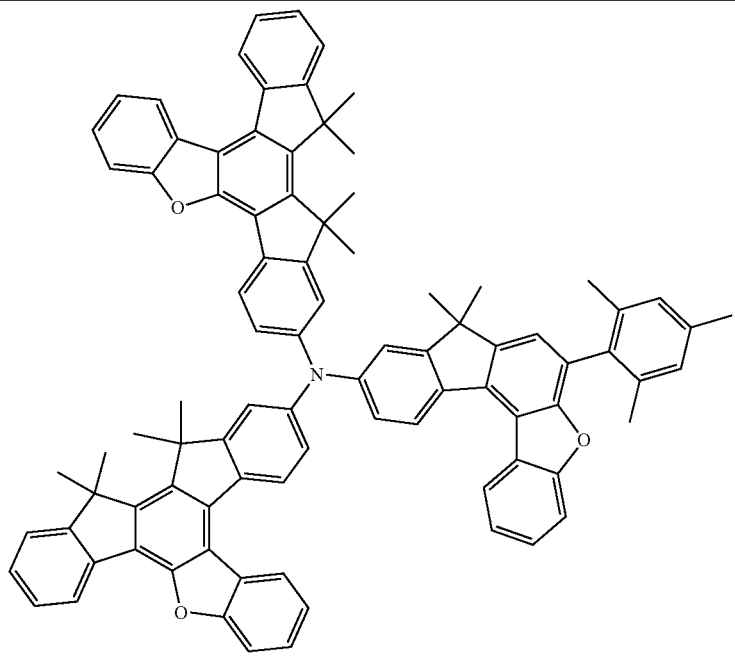
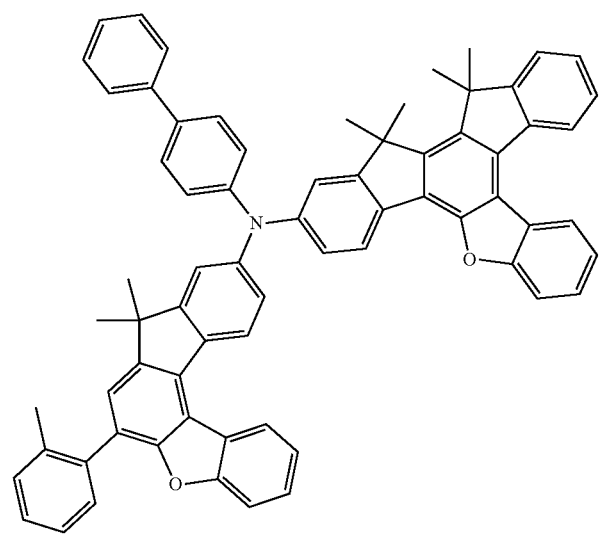 [SMILES: Cc1ccccc1-c1cc2c(c3c1oc1ccccc13)-c1ccc(N(c3ccc(-c4ccccc4)cc3)c3ccc4c(c3)C(C)(C)c3c5c(c6c(oc7ccccc76)c3-4)-c3ccccc3C5(C)C)cc1C2(C)C]

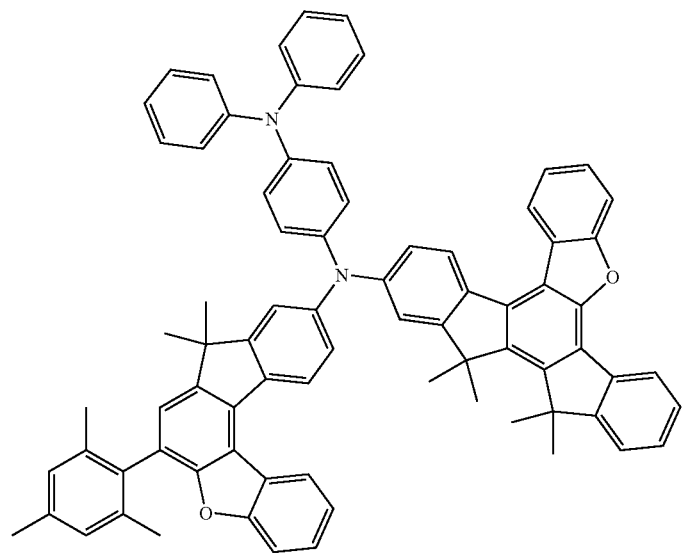 [SMILES: Cc1cc(C)c(-c2cc3c(c4c2oc2ccccc24)-c2ccc(N(c4ccc(N(c5ccccc5)c5ccccc5)cc4)c4ccc5c(c4)C(C)(C)c4c6c(c7oc8ccccc8c7c4-5)-c4ccccc4C6(C)C)cc2C3(C)C)c(C)c1]
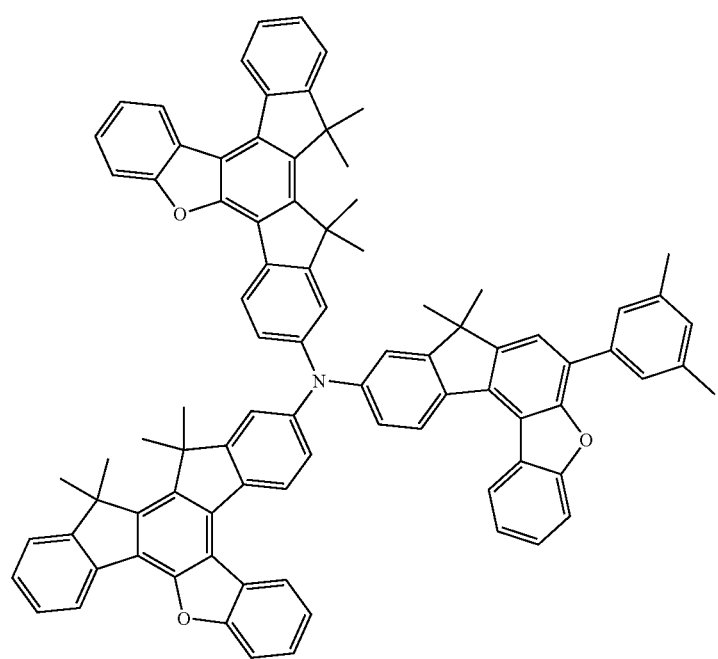 [SMILES: Cc1cc(C)cc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccc5c(c4)C(C)(C)c4c6c(c7oc8ccccc8c7c4-5)-c4ccccc4C6(C)C)cc2C3(C)C)c1]

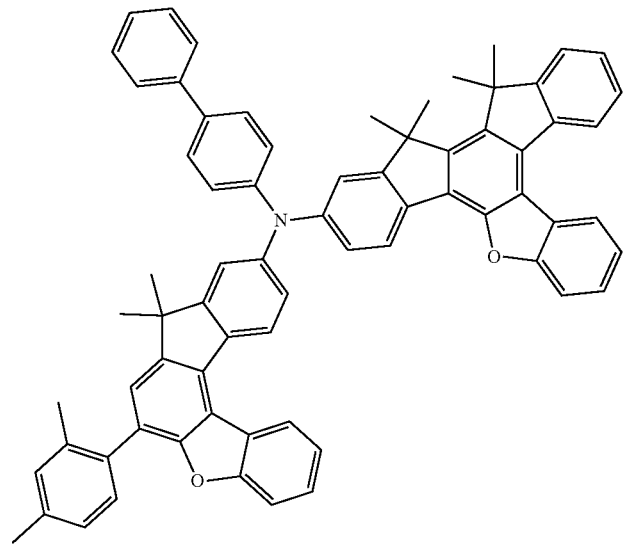 [SMILES: Cc1ccc(-c2cc3c(c4c2oc2ccccc24)-c2ccc(N(c4ccc(-c5ccccc5)cc4)c4ccc5c(c4)C(C)(C)c4c6c(c7c(oc8ccccc87)c4-5)-c4ccccc4C6(C)C)cc2C3(C)C)c(C)c1]
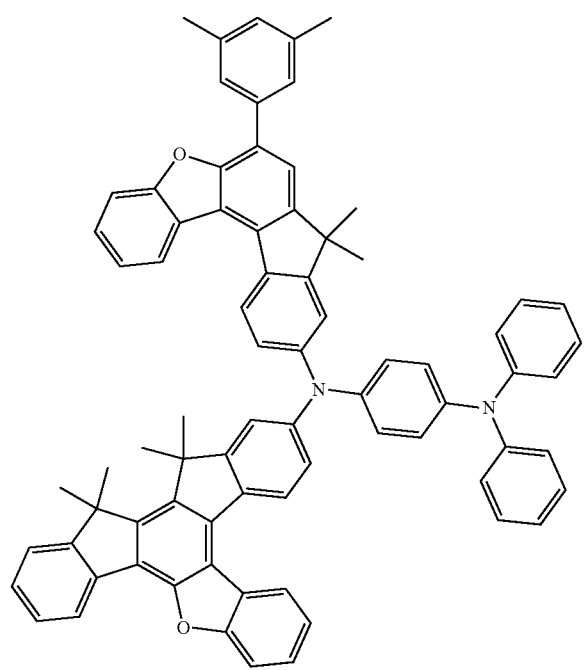 [SMILES: Cc1cc(C)cc(-c2cc3c(c4c2oc2ccccc24)-c2ccc(N(c4ccc(N(c5ccccc5)c5ccccc5)cc4)c4ccc5c(c4)C(C)(C)c4c6c(c7oc8ccccc8c7c4-5)-c4ccccc4C6(C)C)cc2C3(C)C)c1]

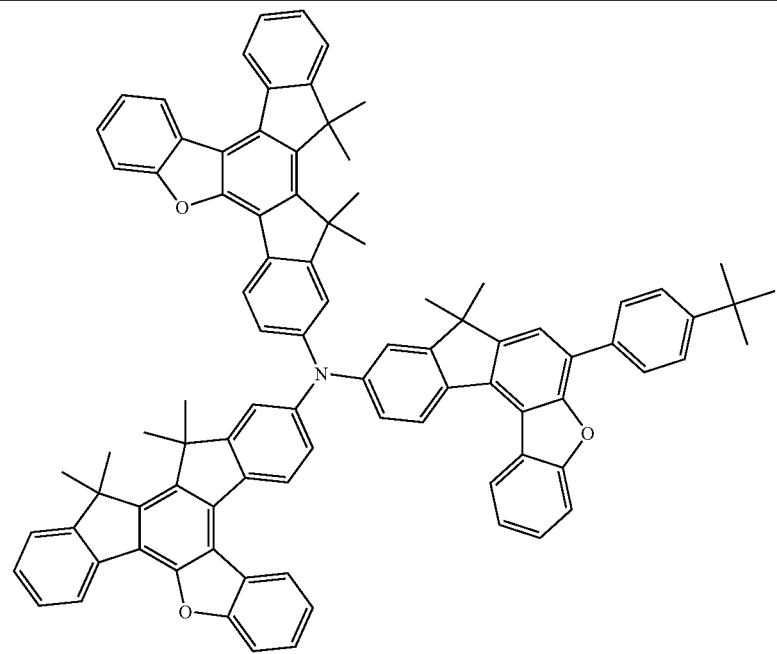
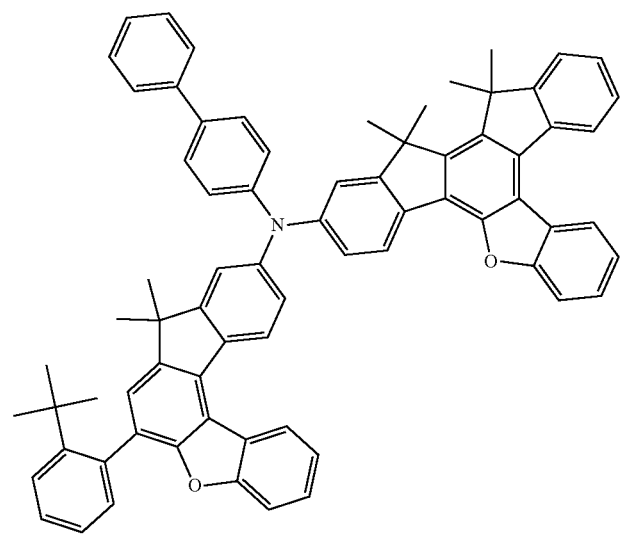 [SMILES: CC(C)(C)c1ccccc1-c1cc2c(c3c1oc1ccccc13)-c1ccc(N(c3ccc(-c4ccccc4)cc3)c3ccc4c(c3)C(C)(C)c3c5c(c6c(oc7ccccc76)c3-4)-c3ccccc3C5(C)C)cc1C2(C)C]

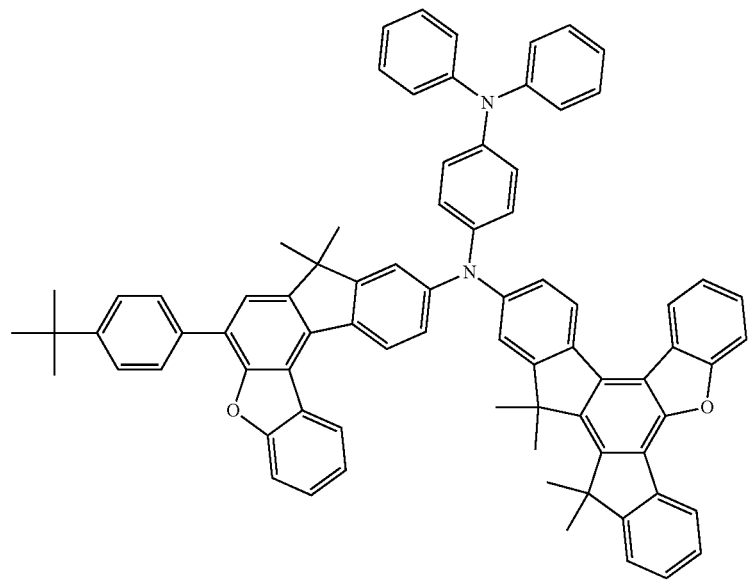 [SMILES: CC(C)(C)c1ccc(-c2cc3c(c4c2oc2ccccc24)-c2ccc(N(c4ccc(N(c5ccccc5)c5ccccc5)cc4)c4ccc5c(c4)C(C)(C)c4c6c(c7oc8ccccc8c7c4-5)-c4ccccc4C6(C)C)cc2C3(C)C)cc1]
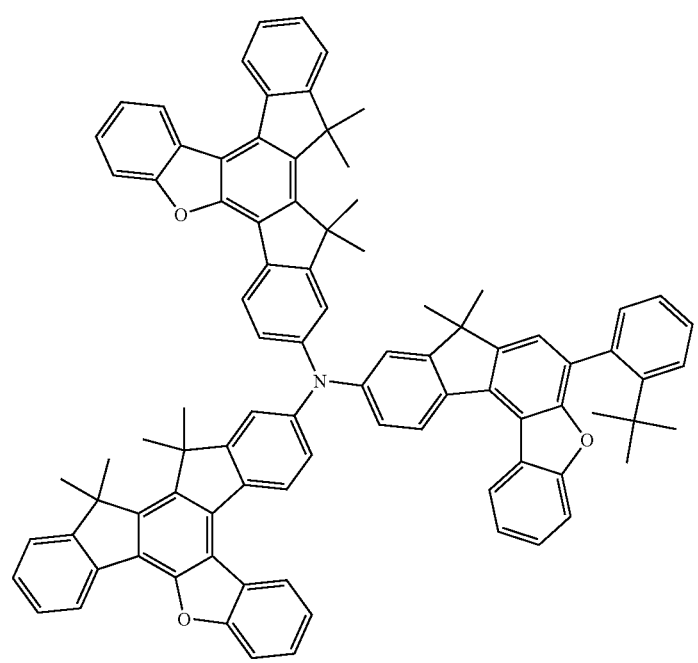 [SMILES: CC(C)(C)c1ccccc1-c1cc2c(c3c1oc1ccccc13)-c1ccc(N(c3ccc4c(c3)C(C)(C)c3c5c(c6c(oc7ccccc76)c3-4)-c3ccccc3C5(C)C)c3ccc4c(c3)C(C)(C)c3c5c(c6oc7ccccc7c6c3-4)-c3ccccc3C5(C)C)cc1C2(C)C]

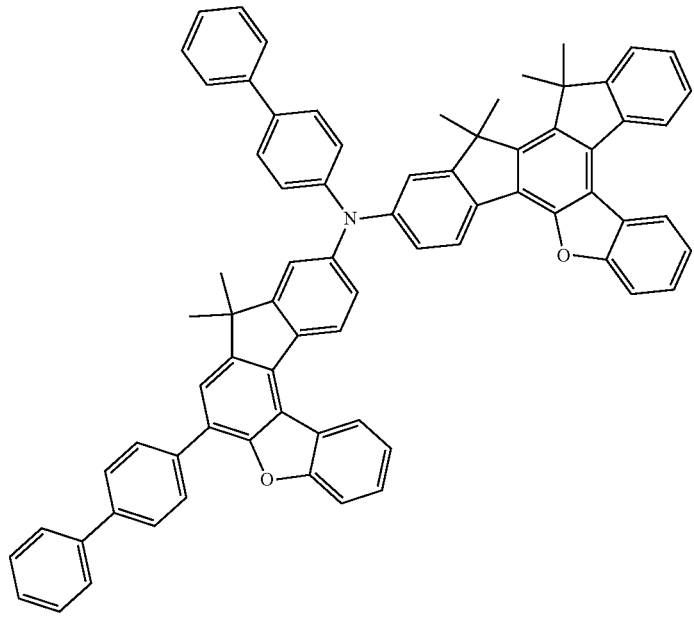 [SMILES: CC1(C)c2cc(N(c3ccc(-c4ccccc4)cc3)c3ccc4c(c3)C(C)(C)c3c5c(c6c(oc7ccccc76)c3-4)-c3ccccc3C5(C)C)ccc2-c2c1cc(-c1ccc(-c3ccccc3)cc1)c1oc3ccccc3c21]
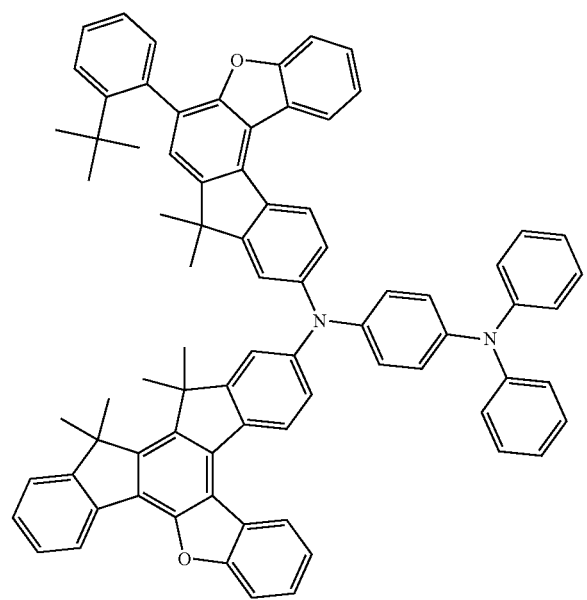 [SMILES: CC(C)(C)c1ccccc1-c1cc2c(c3c1oc1ccccc13)-c1ccc(N(c3ccc(N(c4ccccc4)c4ccccc4)cc3)c3ccc4c(c3)C(C)(C)c3c5c(c6oc7ccccc7c6c3-4)-c3ccccc3C5(C)C)cc1C2(C)C]

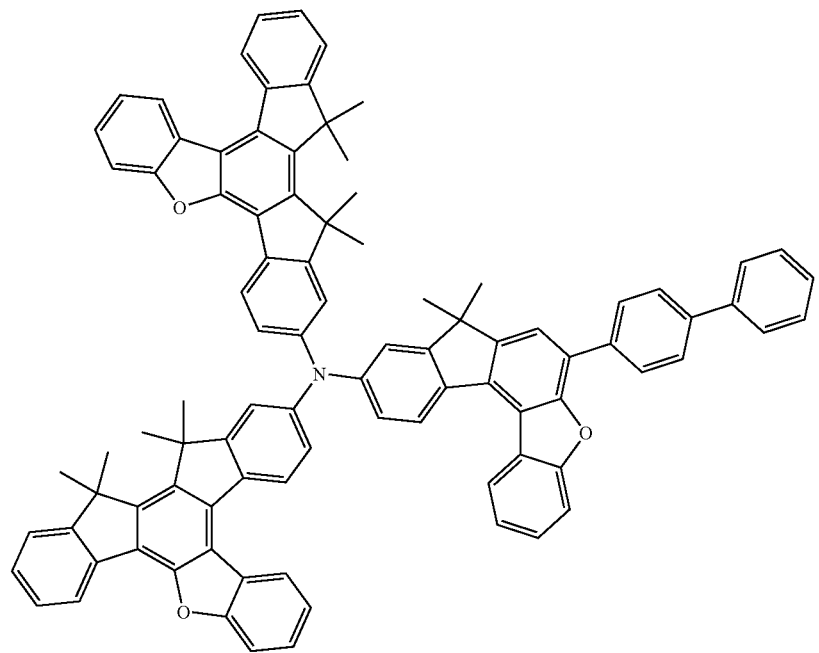 [SMILES: CC1(C)c2cc(N(c3ccc4c(c3)C(C)(C)c3c5c(c6c(oc7ccccc76)c3-4)-c3ccccc3C5(C)C)c3ccc4c(c3)C(C)(C)c3c5c(c6oc7ccccc7c6c3-4)-c3ccccc3C5(C)C)ccc2-c2c1cc(-c1ccc(-c3ccccc3)cc1)c1oc3ccccc3c21]
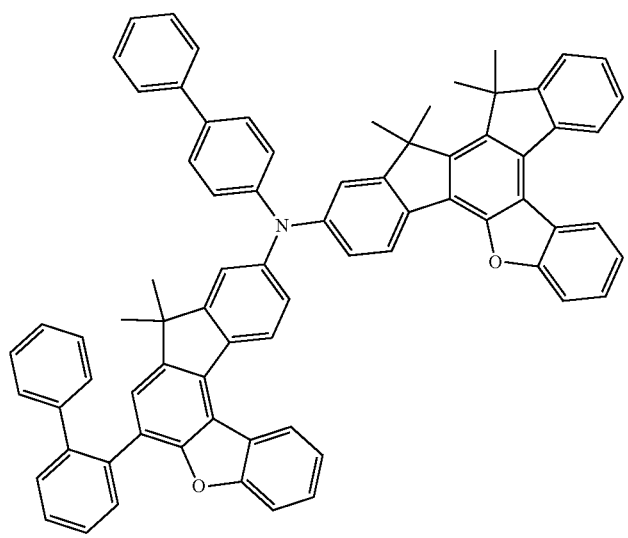 [SMILES: CC1(C)c2cc(N(c3ccc(-c4ccccc4)cc3)c3ccc4c(c3)C(C)(C)c3c5c(c6c(oc7ccccc76)c3-4)-c3ccccc3C5(C)C)ccc2-c2c1cc(-c1ccccc1-c1ccccc1)c1oc3ccccc3c21]

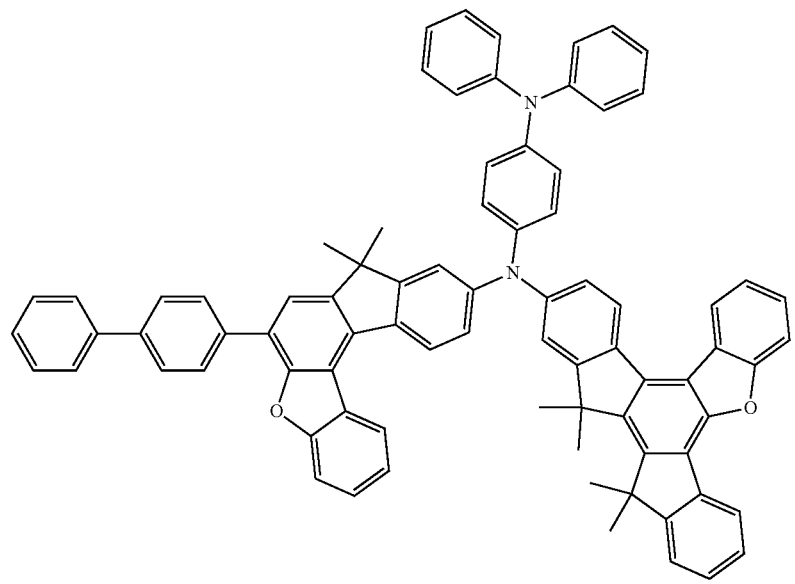 [SMILES: CC1(C)c2cc(N(c3ccc(N(c4ccccc4)c4ccccc4)cc3)c3ccc4c(c3)C(C)(C)c3c5c(c6oc7ccccc7c6c3-4)-c3ccccc3C5(C)C)ccc2-c2c1cc(-c1ccc(-c3ccccc3)cc1)c1oc3ccccc3c21]
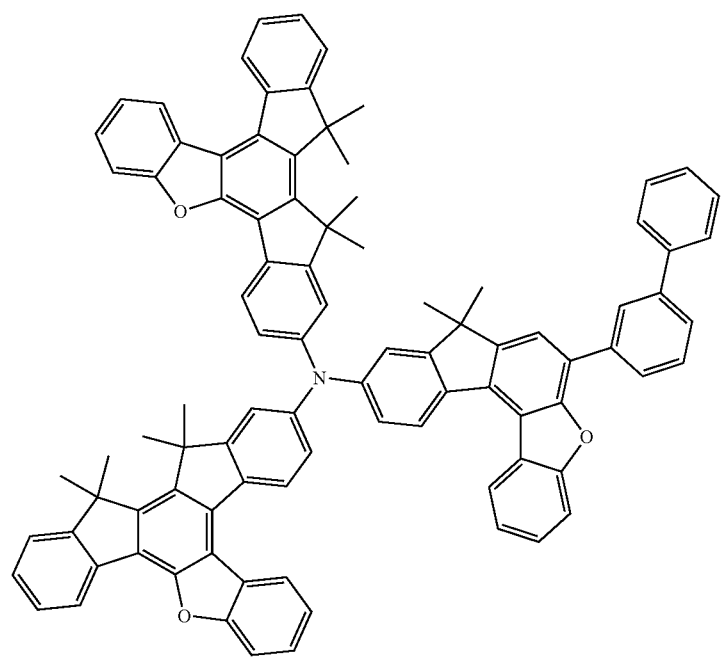 [SMILES: CC1(C)c2cc(N(c3ccc4c(c3)C(C)(C)c3c5c(c6c(oc7ccccc76)c3-4)-c3ccccc3C5(C)C)c3ccc4c(c3)C(C)(C)c3c5c(c6oc7ccccc7c6c3-4)-c3ccccc3C5(C)C)ccc2-c2c1cc(-c1cccc(-c3ccccc3)c1)c1oc3ccccc3c21]

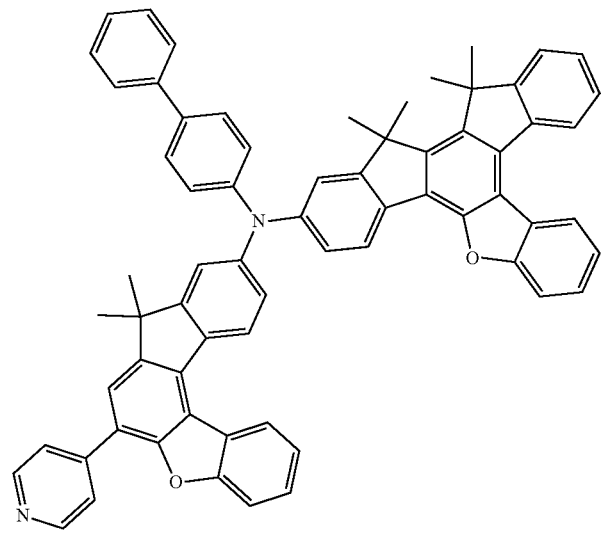 [SMILES: CC1(C)c2cc(N(c3ccc(-c4ccccc4)cc3)c3ccc4c(c3)C(C)(C)c3c5c(c6c(oc7ccccc76)c3-4)-c3ccccc3C5(C)C)ccc2-c2c1cc(-c1ccncc1)c1oc3ccccc3c21]
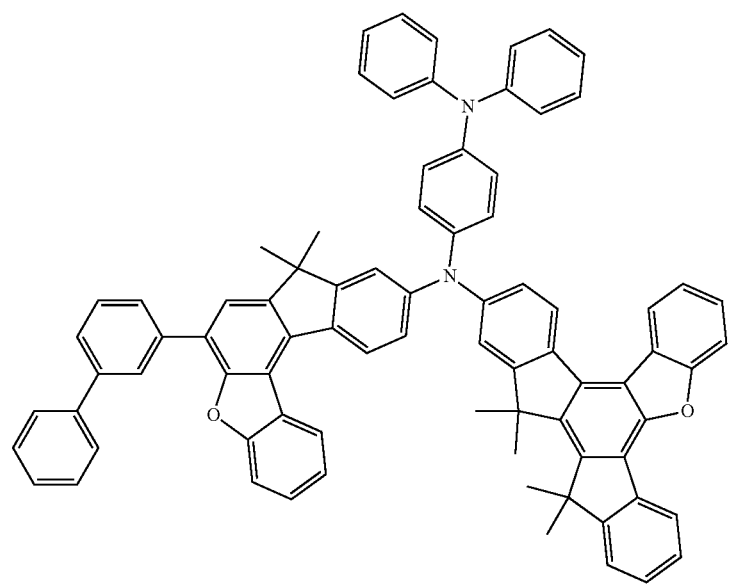 [SMILES: CC1(C)c2cc(N(c3ccc(N(c4ccccc4)c4ccccc4)cc3)c3ccc4c(c3)C(C)(C)c3c5c(c6oc7ccccc7c6c3-4)-c3ccccc3C5(C)C)ccc2-c2c1cc(-c1cccc(-c3ccccc3)c1)c1oc3ccccc3c21]

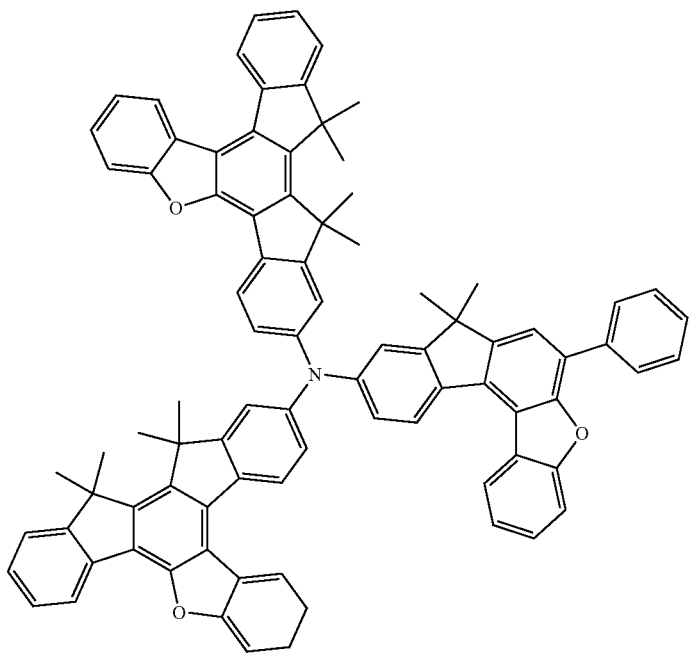 [SMILES: CC1(C)c2cc(N(c3ccc4c(c3)C(C)(C)c3c5c(c6c(oc7ccccc76)c3-4)-c3ccccc3C5(C)C)c3ccc4c(c3)C(C)(C)c3c5c(c6oc7c(c6c3-4)=CCCC=7)-c3ccccc3C5(C)C)ccc2-c2c1cc(-c1ccccc1)c1oc3ccccc3c21]
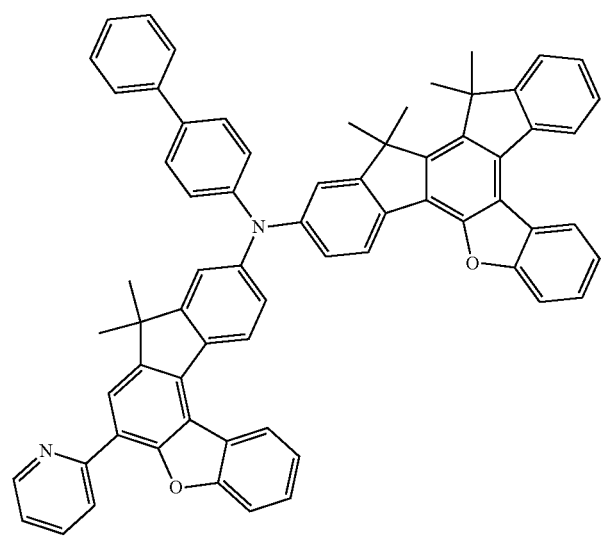 [SMILES: CC1(C)c2cc(N(c3ccc(-c4ccccc4)cc3)c3ccc4c(c3)C(C)(C)c3c5c(c6c(oc7ccccc76)c3-4)-c3ccccc3C5(C)C)ccc2-c2c1cc(-c1ccccn1)c1oc3ccccc3c21]

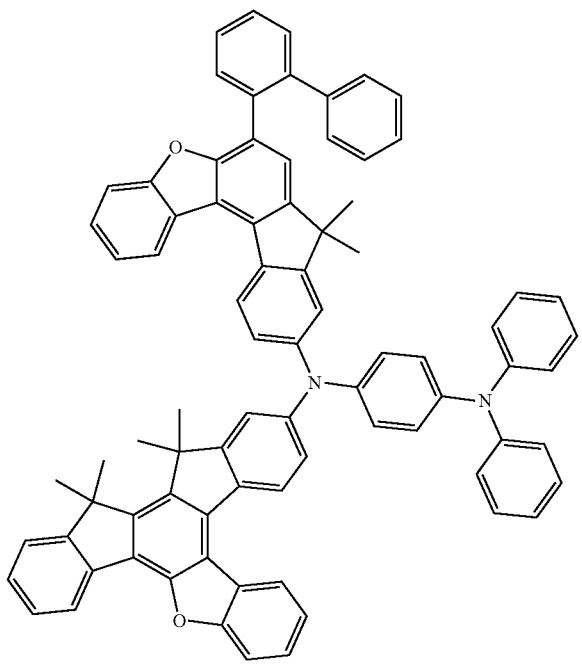 [SMILES: CC1(C)c2cc(N(c3ccc(N(c4ccccc4)c4ccccc4)cc3)c3ccc4c(c3)C(C)(C)c3c5c(c6oc7ccccc7c6c3-4)-c3ccccc3C5(C)C)ccc2-c2c1cc(-c1ccccc1-c1ccccc1)c1oc3ccccc3c21]
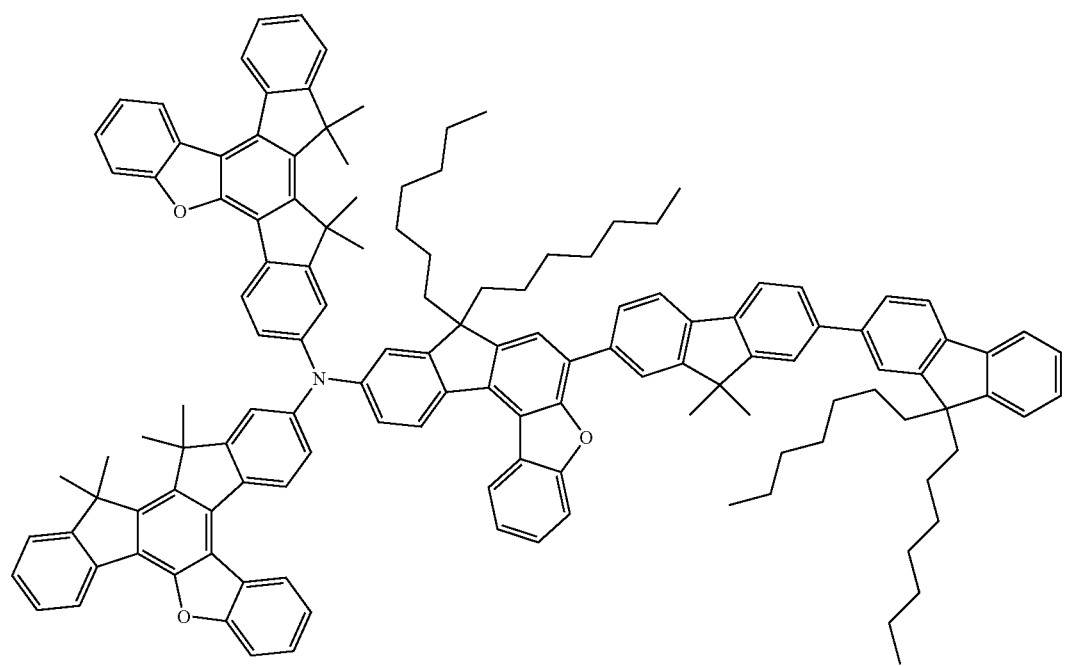 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10c(oc%11ccccc%11%10)c7-8)-c7ccccc7C9(C)C)c7ccc8c(c7)C(C)(C)c7c9c(c%10oc%11ccccc%11c%10c7-8)-c7ccccc7C9(C)C)cc5C6(CCCCCCC)CCCCCCC)ccc3-4)cc21]

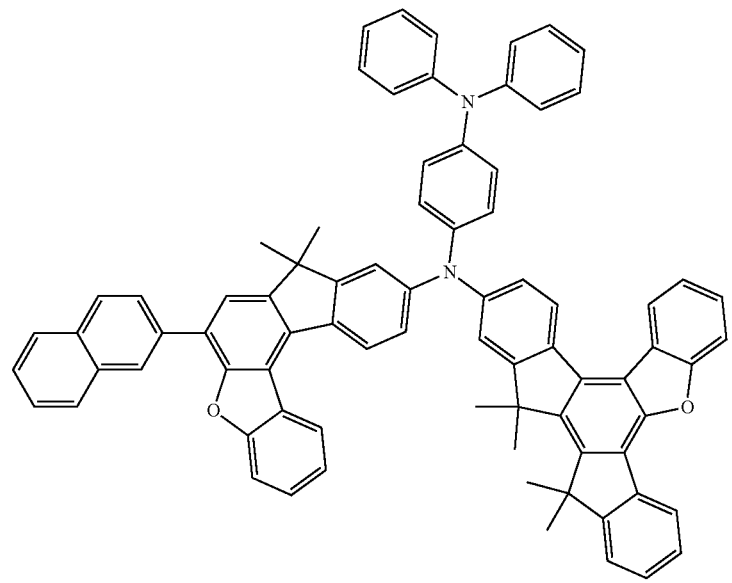 [SMILES: CC1(C)c2cc(N(c3ccc(N(c4ccccc4)c4ccccc4)cc3)c3ccc4c(c3)C(C)(C)c3c5c(c6oc7ccccc7c6c3-4)-c3ccccc3C5(C)C)ccc2-c2c1cc(-c1ccc3ccccc3c1)c1oc3ccccc3c21]
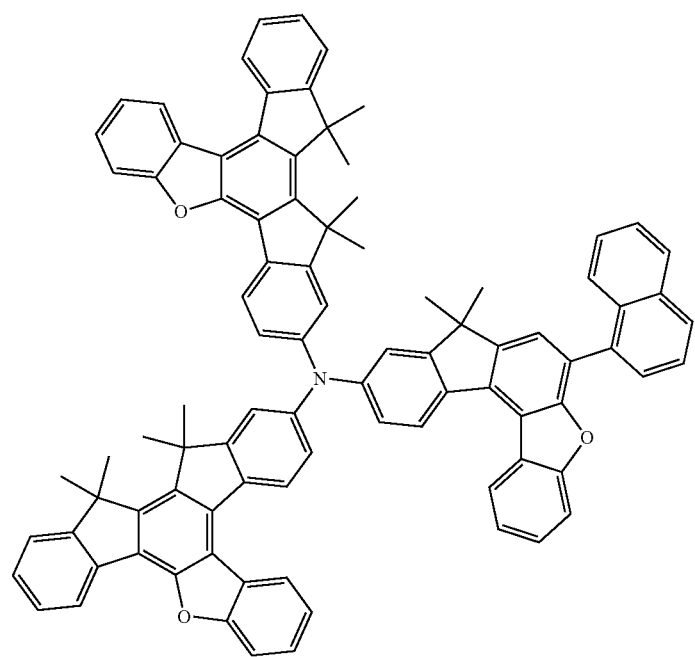 [SMILES: CC1(C)c2cc(N(c3ccc4c(c3)C(C)(C)c3c5c(c6c(oc7ccccc76)c3-4)-c3ccccc3C5(C)C)c3ccc4c(c3)C(C)(C)c3c5c(c6oc7ccccc7c6c3-4)-c3ccccc3C5(C)C)ccc2-c2c1cc(-c1cccc3ccccc13)c1oc3ccccc3c21]

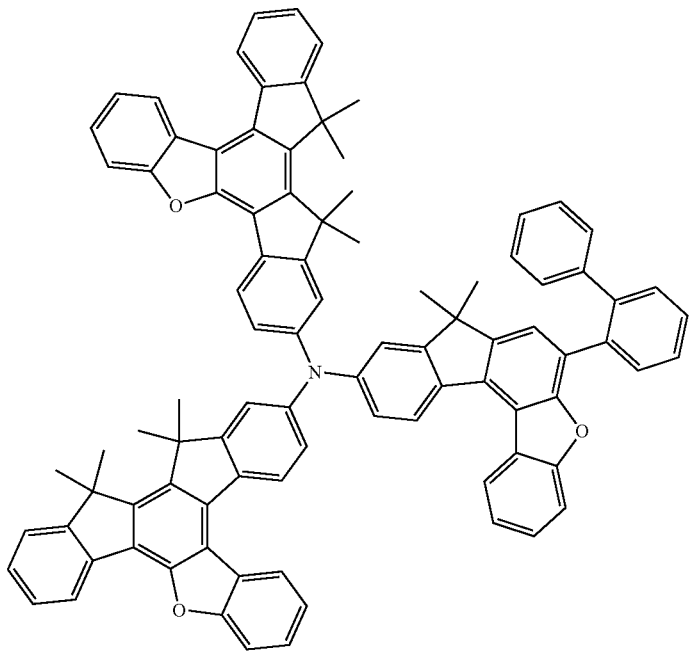 [SMILES: CC1(C)c2cc(N(c3ccc4c(c3)C(C)(C)c3c5c(c6c(oc7ccccc76)c3-4)-c3ccccc3C5(C)C)c3ccc4c(c3)C(C)(C)c3c5c(c6oc7ccccc7c6c3-4)-c3ccccc3C5(C)C)ccc2-c2c1cc(-c1ccccc1-c1ccccc1)c1oc3ccccc3c21]
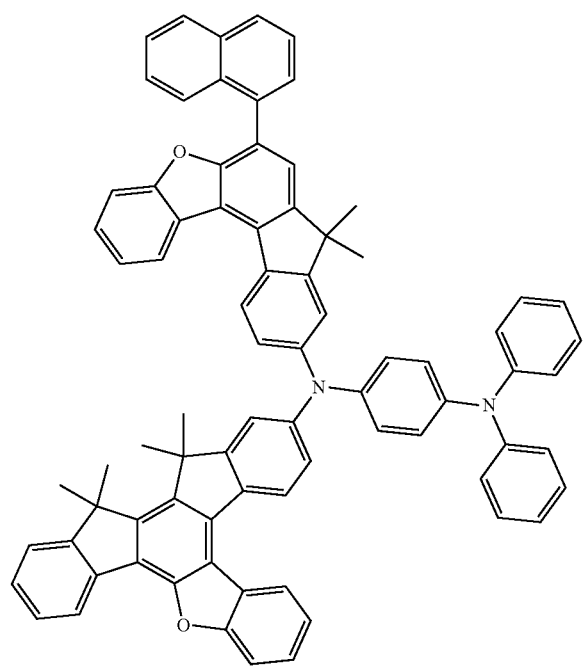 [SMILES: CC1(C)c2cc(N(c3ccc(N(c4ccccc4)c4ccccc4)cc3)c3ccc4c(c3)C(C)(C)c3c5c(c6oc7ccccc7c6c3-4)-c3ccccc3C5(C)C)ccc2-c2c1cc(-c1cccc3ccccc13)c1oc3ccccc3c21]

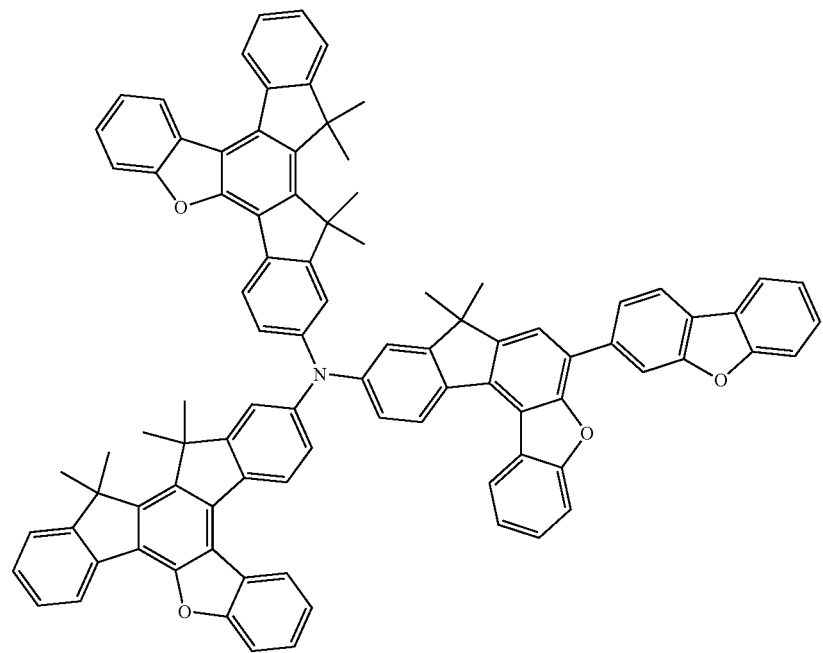 [SMILES: CC1(C)c2cc(N(c3ccc4c(c3)C(C)(C)c3c5c(c6c(oc7ccccc76)c3-4)-c3ccccc3C5(C)C)c3ccc4c(c3)C(C)(C)c3c5c(c6oc7ccccc7c6c3-4)-c3ccccc3C5(C)C)ccc2-c2c1cc(-c1ccc3c(c1)oc1ccccc13)c1oc3ccccc3c21]
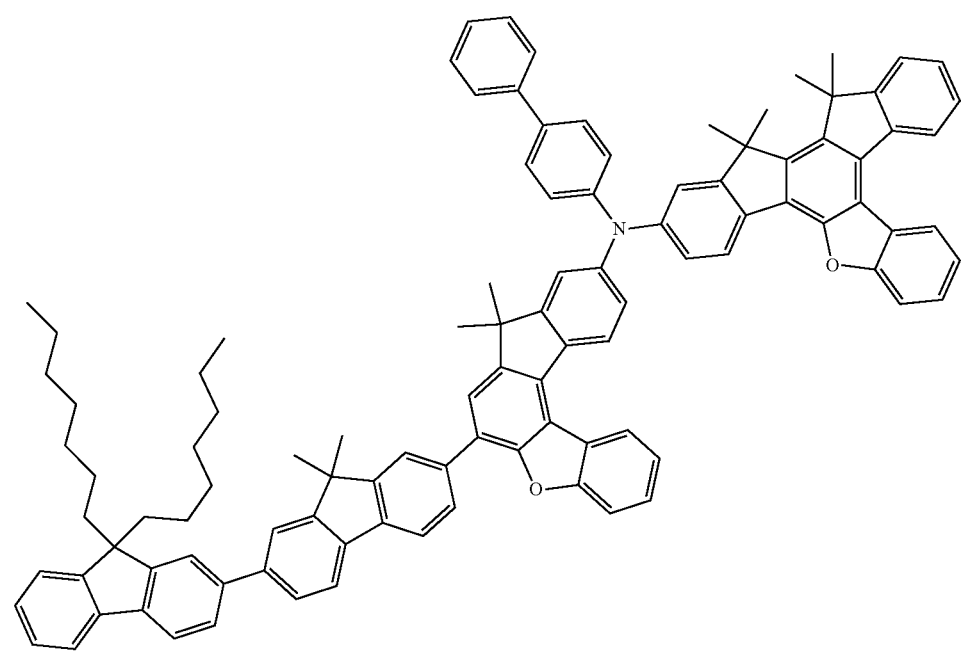 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc(-c8ccccc8)cc7)c7ccc8c(c7)C(C)(C)c7c9c(c%10c(oc%11ccccc%11%10)c7-8)-c7ccccc7C9(C)C)cc5C6(C)C)ccc3-4)cc21]

-continued
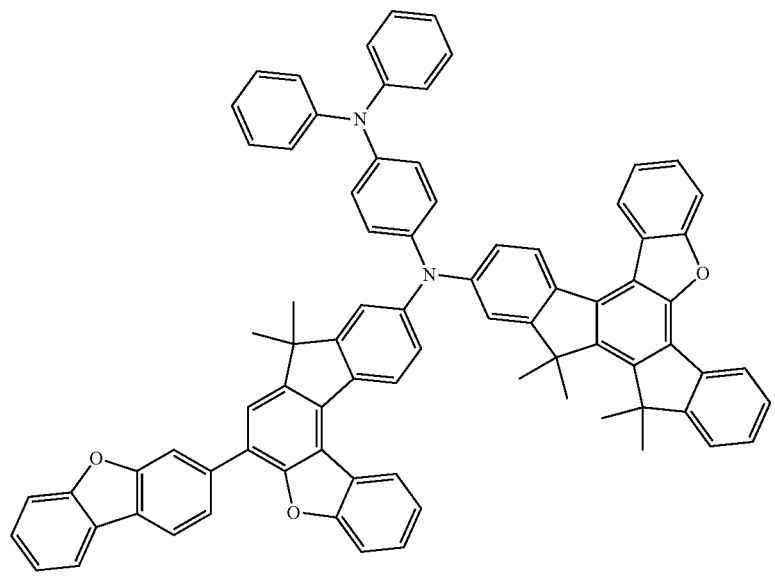 [SMILES: CC1(C)c2cc(N(c3ccc(N(c4ccccc4)c4ccccc4)cc3)c3ccc4c(c3)C(C)(C)c3c5c(c6oc7ccccc7c6c3-4)-c3ccccc3C5(C)C)ccc2-c2c1cc(-c1ccc3c(c1)oc1ccccc13)c1oc3ccccc3c21]
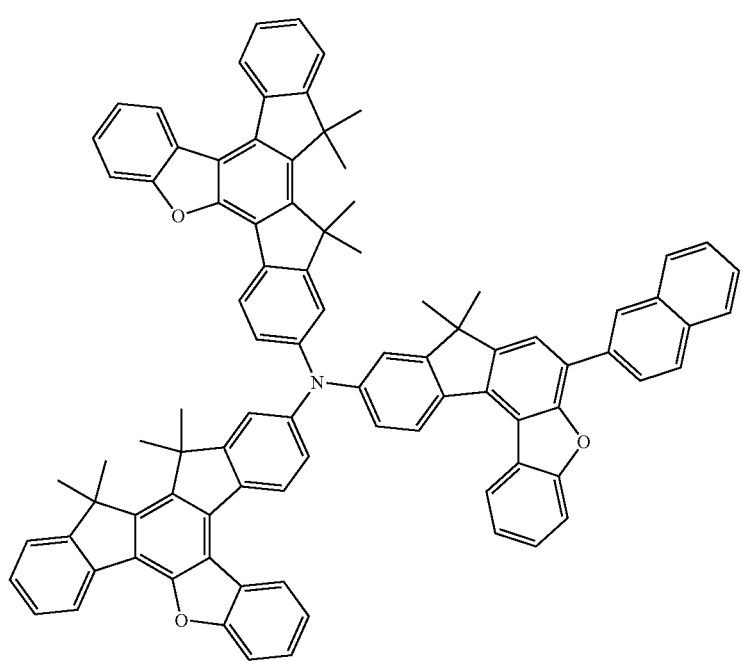 [SMILES: CC1(C)c2cc(N(c3ccc4c(c3)C(C)(C)c3c5c(c6c(oc7ccccc76)c3-4)-c3ccccc3C5(C)C)c3ccc4c(c3)C(C)(C)c3c5c(c6oc7ccccc7c6c3-4)-c3ccccc3C5(C)C)ccc2-c2c1cc(-c1ccc3ccccc3c1)c1oc3ccccc3c21]

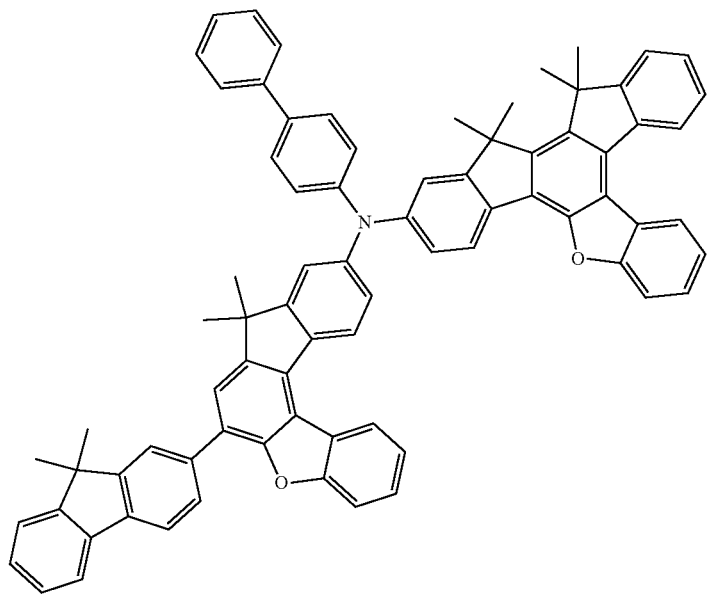 [SMILES: CC1(C)c2ccccc2-c2ccc(-c3cc4c(c5c3oc3ccccc35)-c3ccc(N(c5ccc(-c6ccccc6)cc5)c5ccc6c(c5)C(C)(C)c5c7c(c8c(oc9ccccc98)c5-6)-c5ccccc5C7(C)C)cc3C4(C)C)cc21]
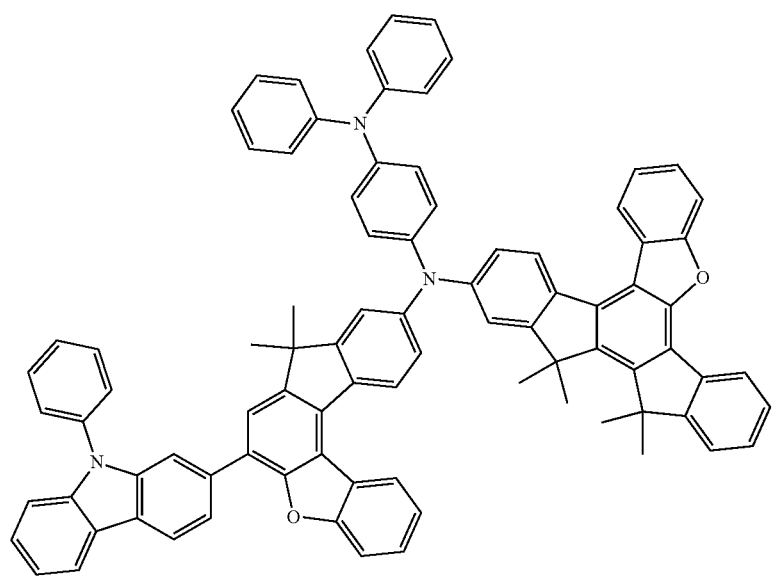 [SMILES: CC1(C)c2cc(N(c3ccc(N(c4ccccc4)c4ccccc4)cc3)c3ccc4c(c3)C(C)(C)c3c5c(c6oc7ccccc7c6c3-4)-c3ccccc3C5(C)C)ccc2-c2c1cc(-c1ccc3c4ccccc4n(-c4ccccc4)c3c1)c1oc3ccccc3c21]

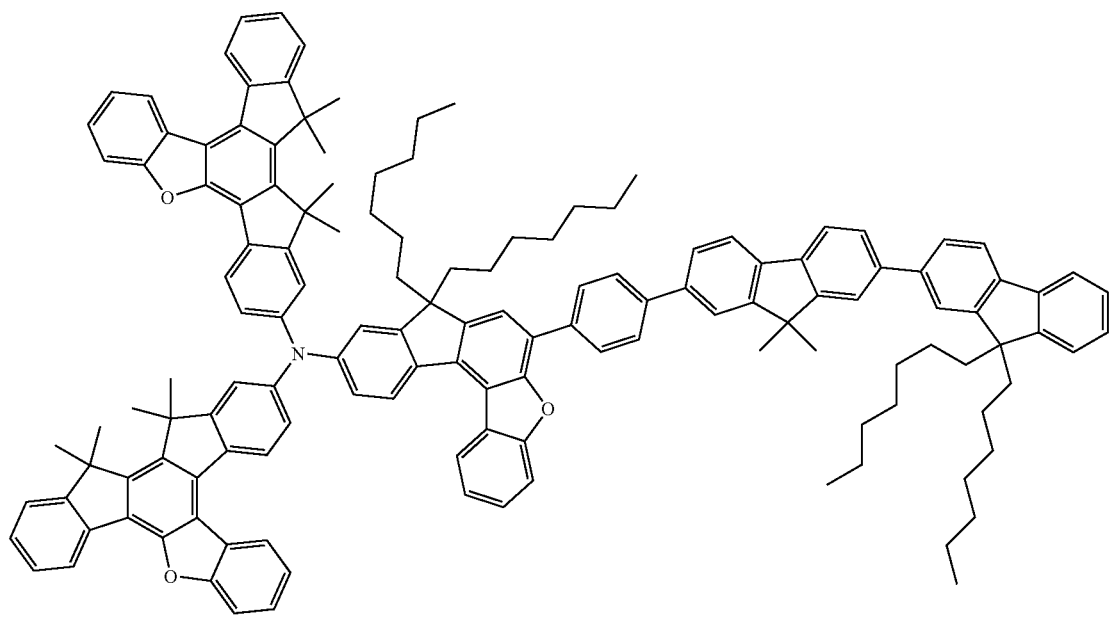 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11c(oc%12ccccc%12%11)c8-9)-c8ccccc8C%10(C)C)c8ccc9c(c8)C(C)(C)c8c%10c(c%11oc%12ccccc%12c%11c8-9)-c8ccccc8C%10(C)C)cc6C7(CCCCCCC)CCCCCCC)cc5)ccc3-4)cc21]
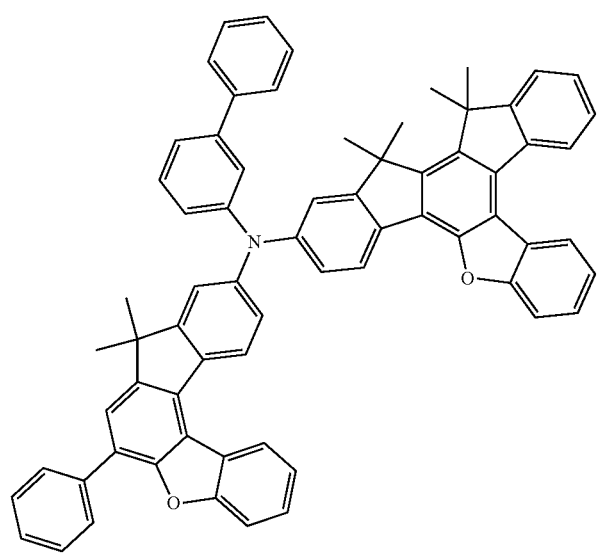 [SMILES: CC1(C)c2cc(N(c3cccc(-c4ccccc4)c3)c3ccc4c(c3)C(C)(C)c3c5c(c6c(oc7ccccc76)c3-4)-c3ccccc3C5(C)C)ccc2-c2c1cc(-c1ccccc1)c1oc3ccccc3c21]

-continued
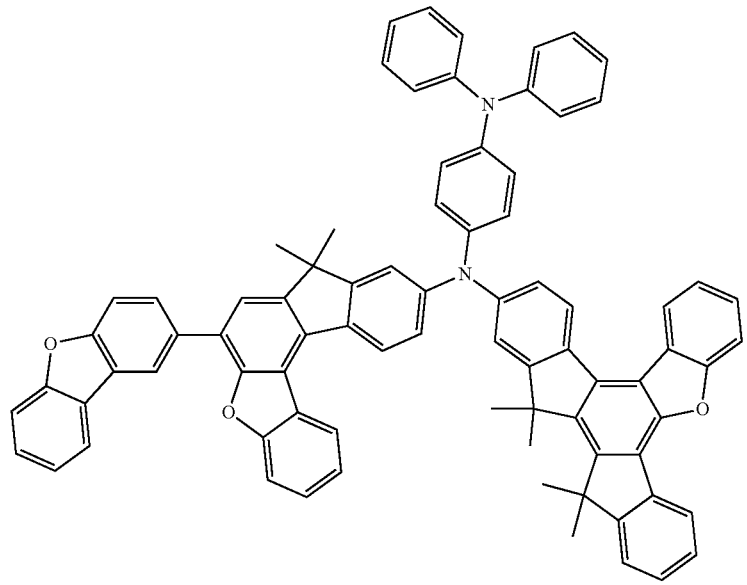 [SMILES: CC1(C)c2cc(N(c3ccc(N(c4ccccc4)c4ccccc4)cc3)c3ccc4c(c3)C(C)(C)c3c5c(c6oc7ccccc7c6c3-4)-c3ccccc3C5(C)C)ccc2-c2c1cc(-c1ccc3oc4ccccc4c3c1)c1oc3ccccc3c21]
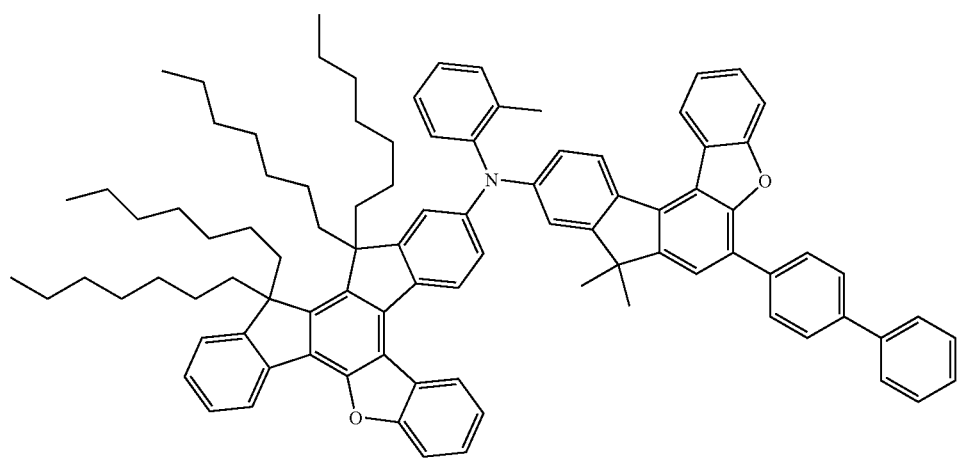 [SMILES: CCCCCCCC1(CCCCCCC)c2ccccc2-c2c1c1c(c3c2oc2ccccc23)-c2ccc(N(c3ccc4c(c3)C(C)(C)c3cc(-c5ccc(-c6ccccc6)cc5)c5oc6ccccc6c5c3-4)c3ccccc3C)cc2C1(CCCCCCC)CCCCCCC]
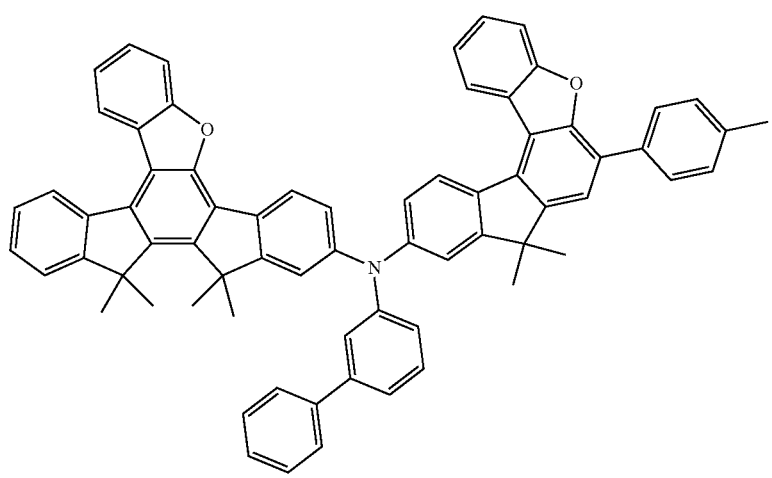 [SMILES: Cc1ccc(-c2cc3c(c4c2oc2ccccc24)-c2ccc(N(c4cccc(-c5ccccc5)c4)c4ccc5c(c4)C(C)(C)c4c6c(c7c(oc8ccccc87)c4-5)-c4ccccc4C6(C)C)cc2C3(C)C)cc1]

-continued
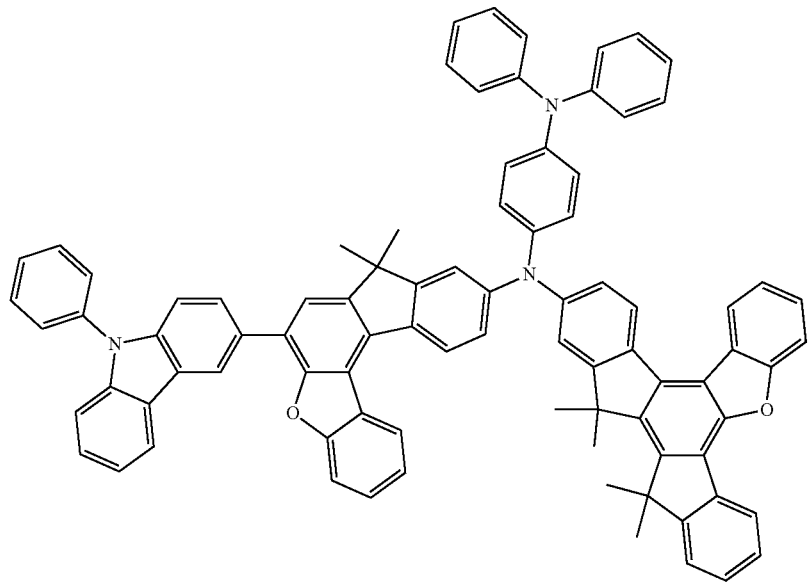 [SMILES: CC1(C)c2cc(N(c3ccc(N(c4ccccc4)c4ccccc4)cc3)c3ccc4c(c3)C(C)(C)c3c5c(c6oc7ccccc7c6c3-4)-c3ccccc3C5(C)C)ccc2-c2c1cc(-c1ccc3c(c1)c1ccccc1n3-c1ccccc1)c1oc3ccccc3c21]
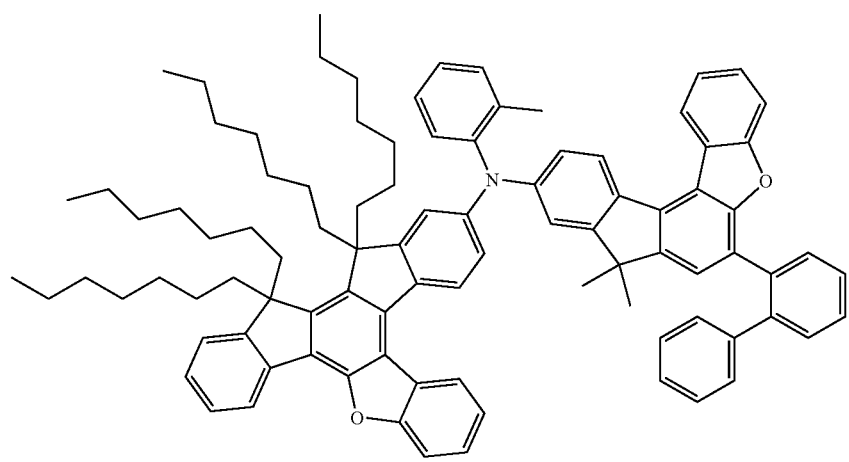 [SMILES: CCCCCCCC1(CCCCCCC)c2ccccc2-c2c1c1c(c3c2oc2ccccc23)-c2ccc(N(c3ccc4c(c3)C(C)(C)c3cc(-c5ccccc5-c5ccccc5)c5oc6ccccc6c5c3-4)c3ccccc3C)cc2C1(CCCCCCC)CCCCCCC]
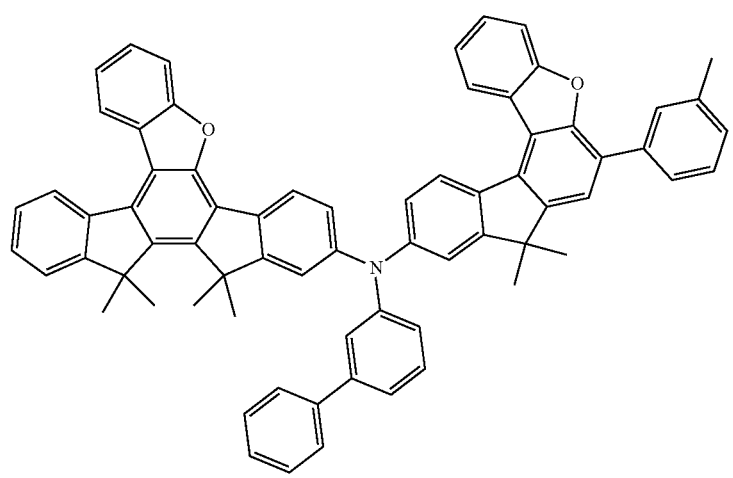 [SMILES: Cc1cccc(-c2cc3c(c4c2oc2ccccc24)-c2ccc(N(c4cccc(-c5ccccc5)c4)c4ccc5c(c4)C(C)(C)c4c6c(c7c(oc8ccccc87)c4-5)-c4ccccc4C6(C)C)cc2C3(C)C)c1]

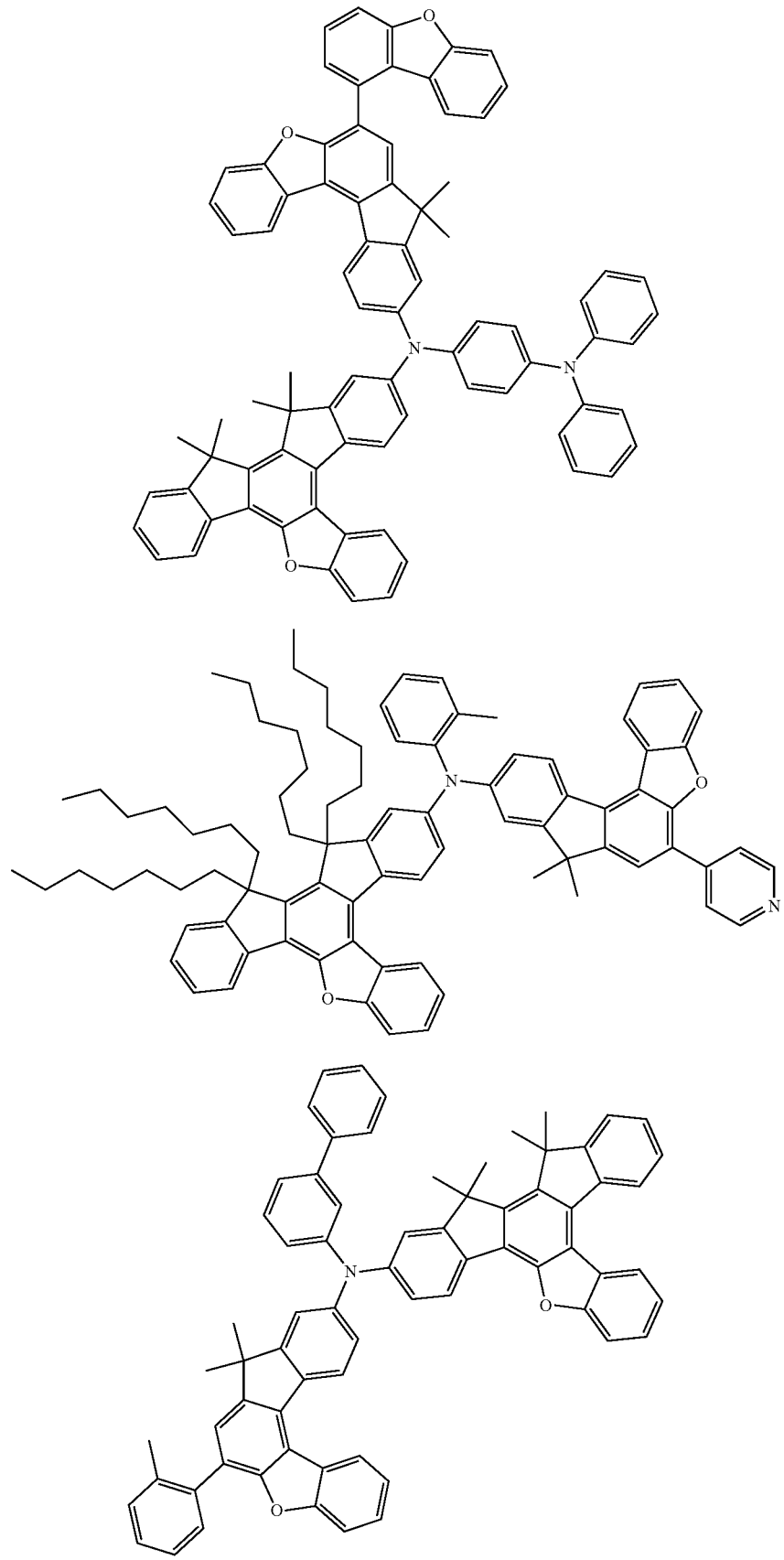

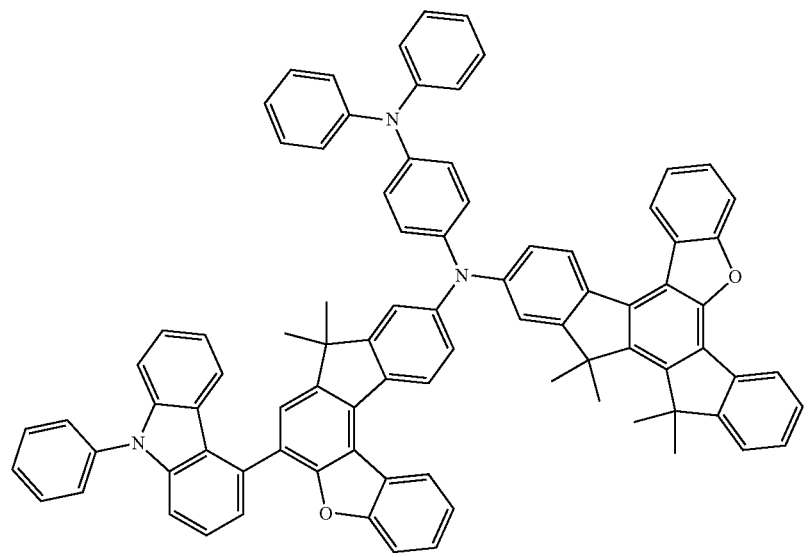 [SMILES: CC1(C)c2cc(N(c3ccc(N(c4ccccc4)c4ccccc4)cc3)c3ccc4c(c3)C(C)(C)c3c5c(c6oc7ccccc7c6c3-4)-c3ccccc3C5(C)C)ccc2-c2c1cc(-c1cccc3c1c1ccccc1n3-c1ccccc1)c1oc3ccccc3c21]
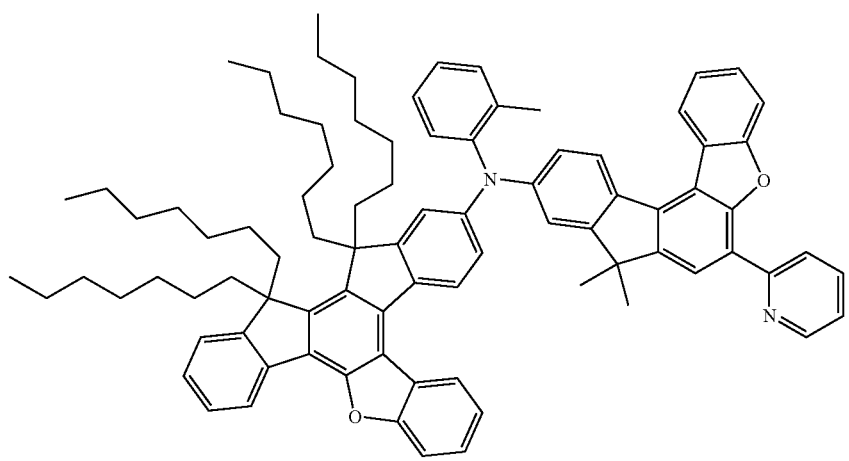 [SMILES: CCCCCCCC1(CCCCCCC)c2ccccc2-c2c1c1c(c3c2oc2ccccc23)-c2ccc(N(c3ccc4c(c3)C(C)(C)c3cc(-c5ccccn5)c5oc6ccccc6c5c3-4)c3ccccc3C)cc2C1(CCCCCCC)CCCCCCC]
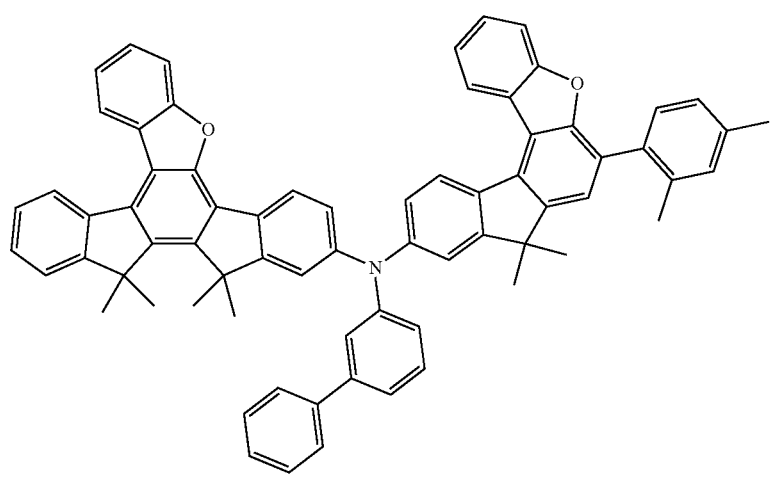 [SMILES: Cc1ccc(-c2cc3c(c4c2oc2ccccc24)-c2ccc(N(c4cccc(-c5ccccc5)c4)c4ccc5c(c4)C(C)(C)c4c6c(c7c(oc8ccccc87)c4-5)-c4ccccc4C6(C)C)cc2C3(C)C)c(C)c1]

-continued
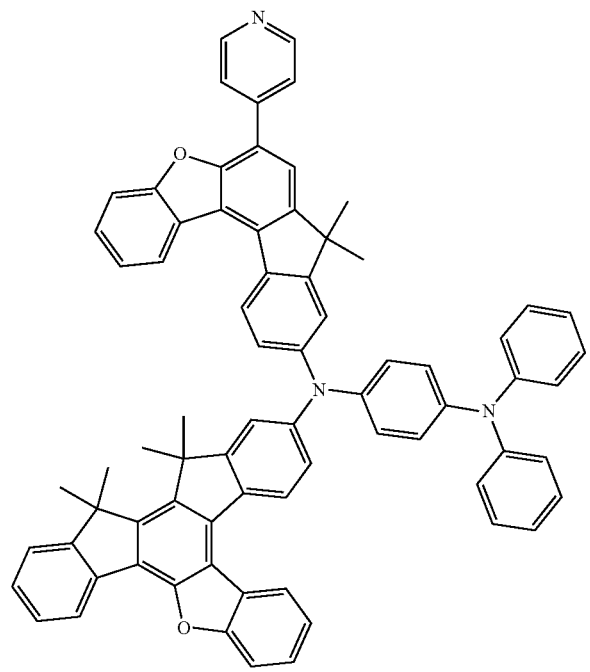 [SMILES: CC1(C)c2cc(N(c3ccc(N(c4ccccc4)c4ccccc4)cc3)c3ccc4c(c3)C(C)(C)c3c5c(c6oc7ccccc7c6c3-4)-c3ccccc3C5(C)C)ccc2-c2c1cc(-c1ccncc1)c1oc3ccccc3c21]
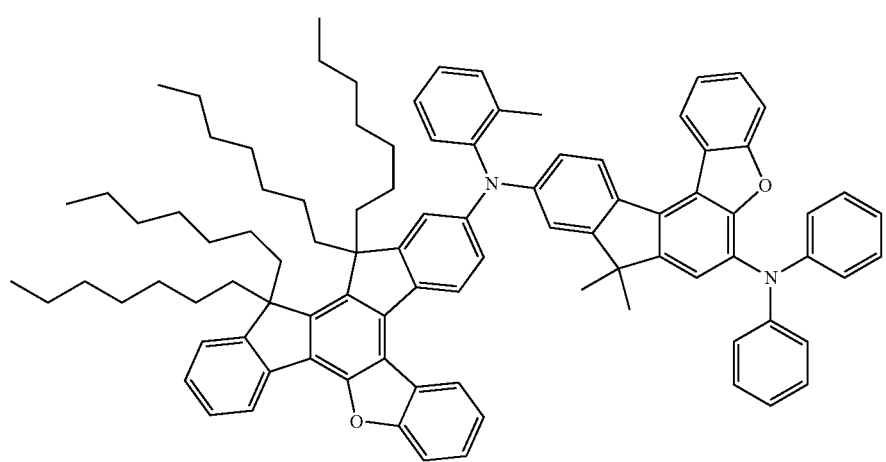 [SMILES: CCCCCCCC1(CCCCCCC)c2ccccc2-c2c1c1c(c3c2oc2ccccc23)-c2ccc(N(c3ccc4c(c3)C(C)(C)c3cc(N(c5ccccc5)c5ccccc5)c5oc6ccccc6c5c3-4)c3ccccc3C)cc2C1(CCCCCCC)CCCCCCC]

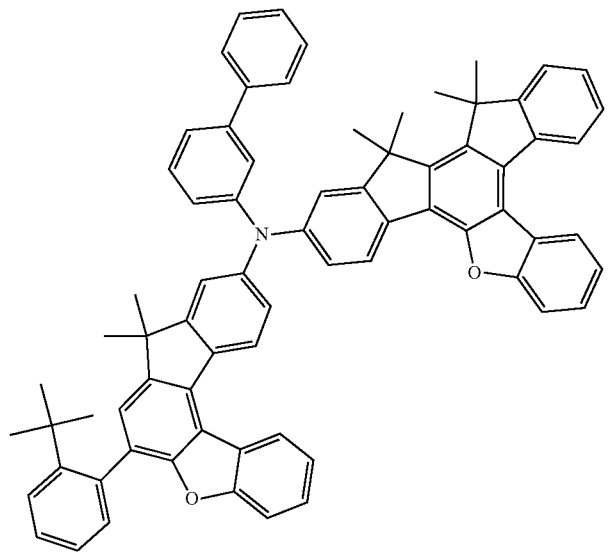 [SMILES: CC(C)(C)c1ccccc1-c1cc2c(c3c1oc1ccccc13)-c1ccc(N(c3cccc(-c4ccccc4)c3)c3ccc4c(c3)C(C)(C)c3c5c(c6c(oc7ccccc76)c3-4)-c3ccccc3C5(C)C)cc1C2(C)C]
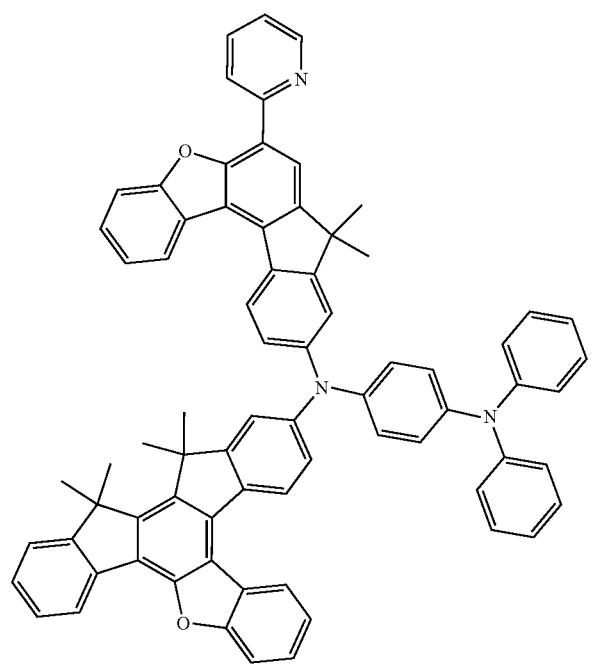 [SMILES: CC1(C)c2cc(N(c3ccc(N(c4ccccc4)c4ccccc4)cc3)c3ccc4c(c3)C(C)(C)c3c5c(c6oc7ccccc7c6c3-4)-c3ccccc3C5(C)C)ccc2-c2c1cc(-c1ccccn1)c1oc3ccccc3c21]

-continued
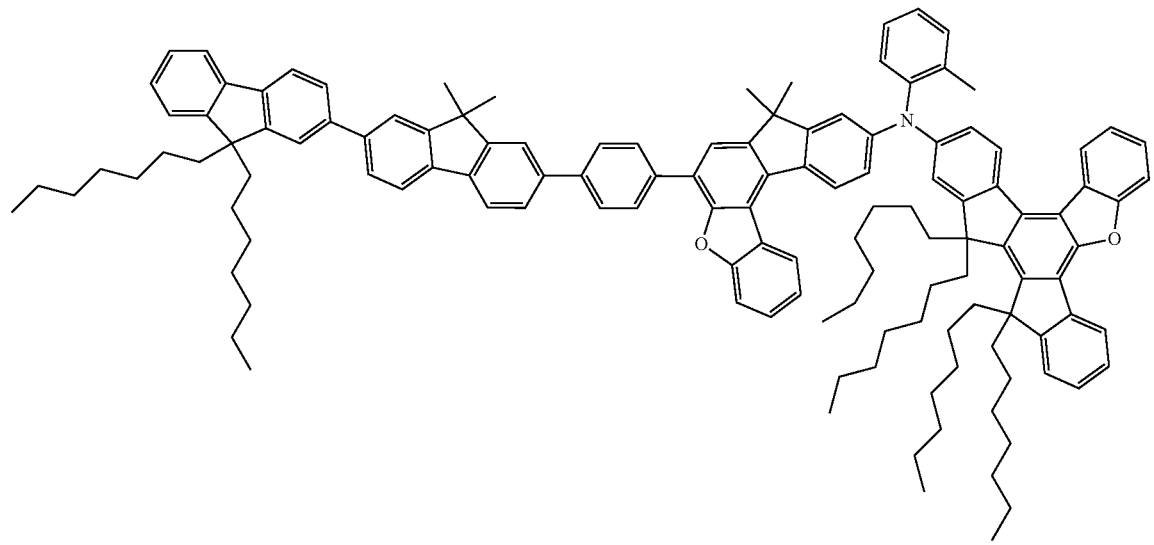 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(CCCCCCC)(CCCCCCC)c8c%10c(c%11oc%12ccccc%12c%11c8-9)-c8ccccc8C%10(CCCCCCC)CCCCCCC)c8ccccc8C)cc6C7(C)C)cc5)ccc3-4)cc21]
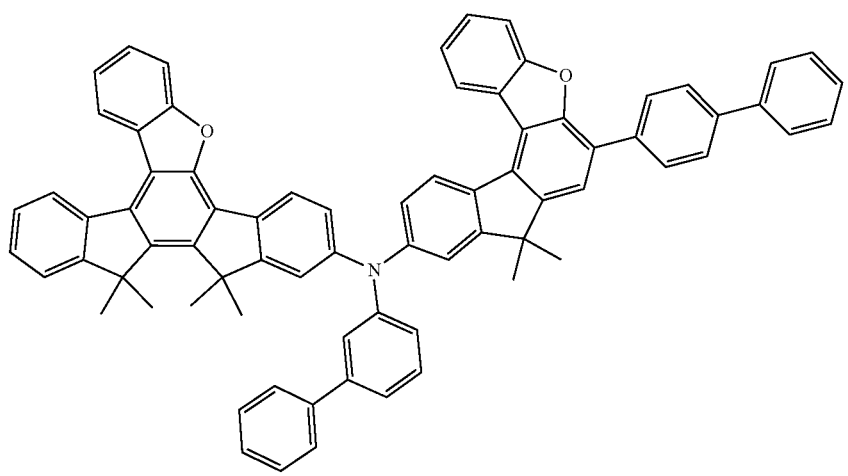 [SMILES: CC1(C)c2cc(N(c3cccc(-c4ccccc4)c3)c3ccc4c(c3)C(C)(C)c3c5c(c6c(oc7ccccc76)c3-4)-c3ccccc3C5(C)C)ccc2-c2c1cc(-c1ccc(-c3ccccc3)cc1)c1oc3ccccc3c21]
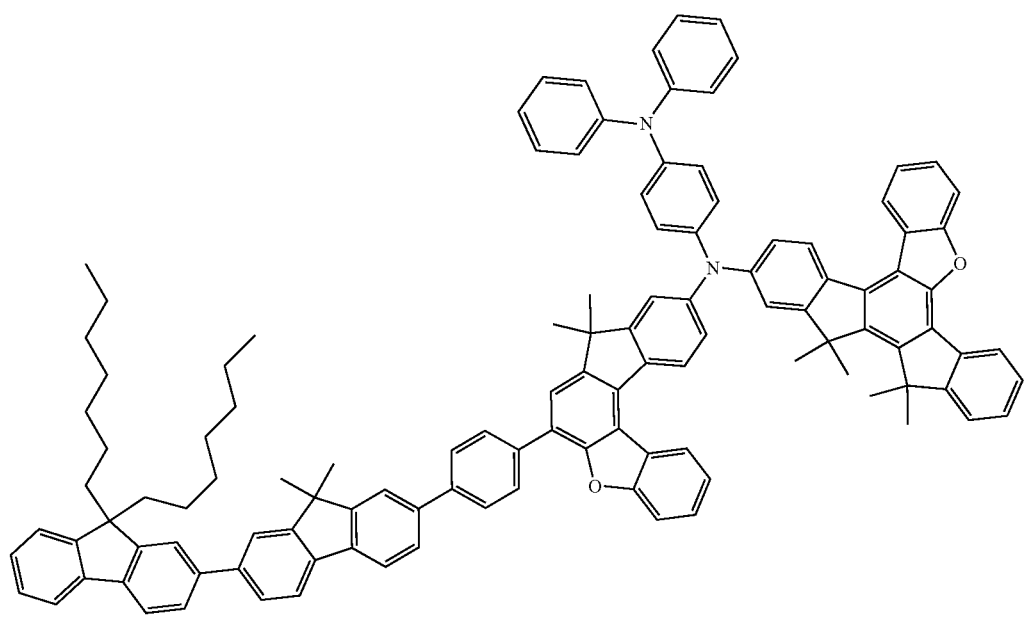 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc(N(c9ccccc9)c9ccccc9)cc8)c8ccc9c(c8)C(C)(C)c8c%10c(c%11oc%12ccccc%12c%11c8-9)-c8ccccc8C%10(C)C)cc6C7(C)C)cc5)ccc3-4)cc21]

-continued
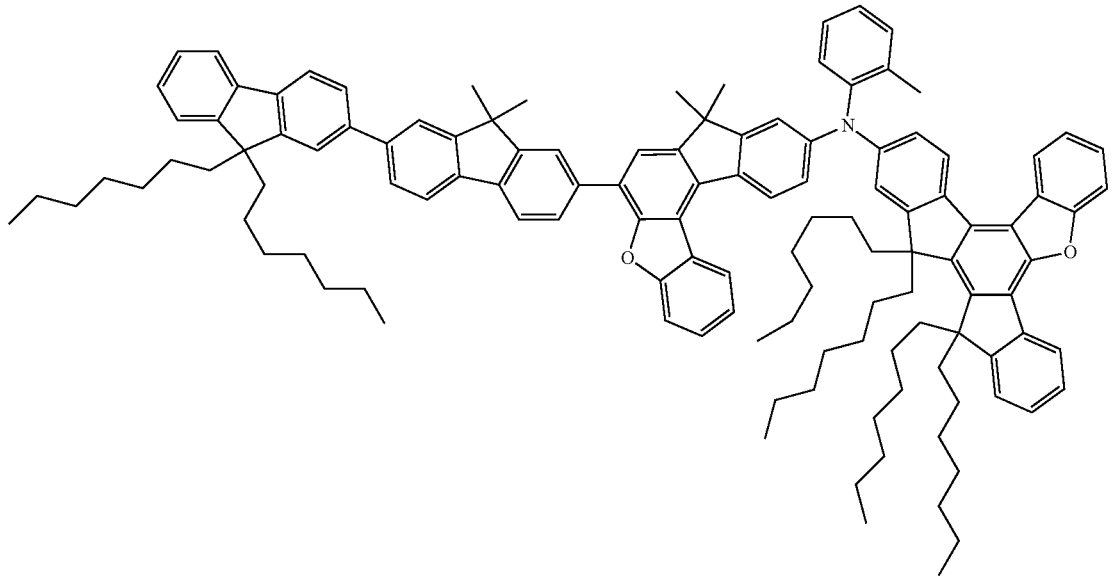 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(CCCCCCC)(CCCCCCC)c7c9c(c%10oc%11ccccc%11c%10c7-8)-c7ccccc7C9(CCCCCCC)CCCCCCC)c7ccccc7C)cc5C6(C)C)ccc3-4)cc21]
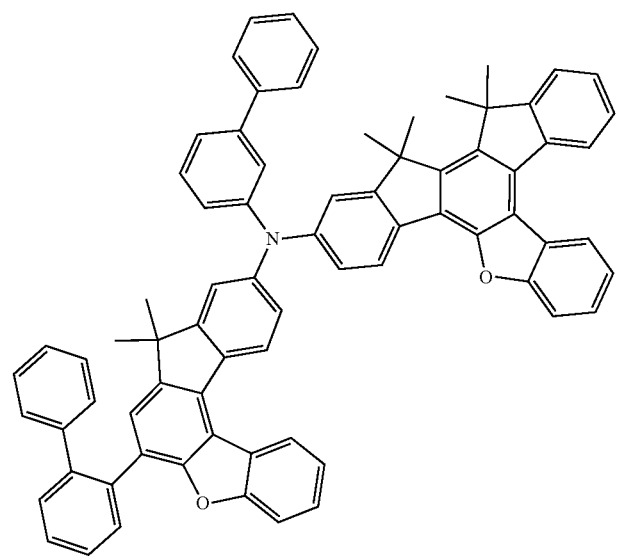 [SMILES: CC1(C)c2cc(N(c3cccc(-c4ccccc4)c3)c3ccc4c(c3)C(C)(C)c3c5c(c6c(oc7ccccc76)c3-4)-c3ccccc3C5(C)C)ccc2-c2c1cc(-c1ccccc1-c1ccccc1)c1oc3ccccc3c21]

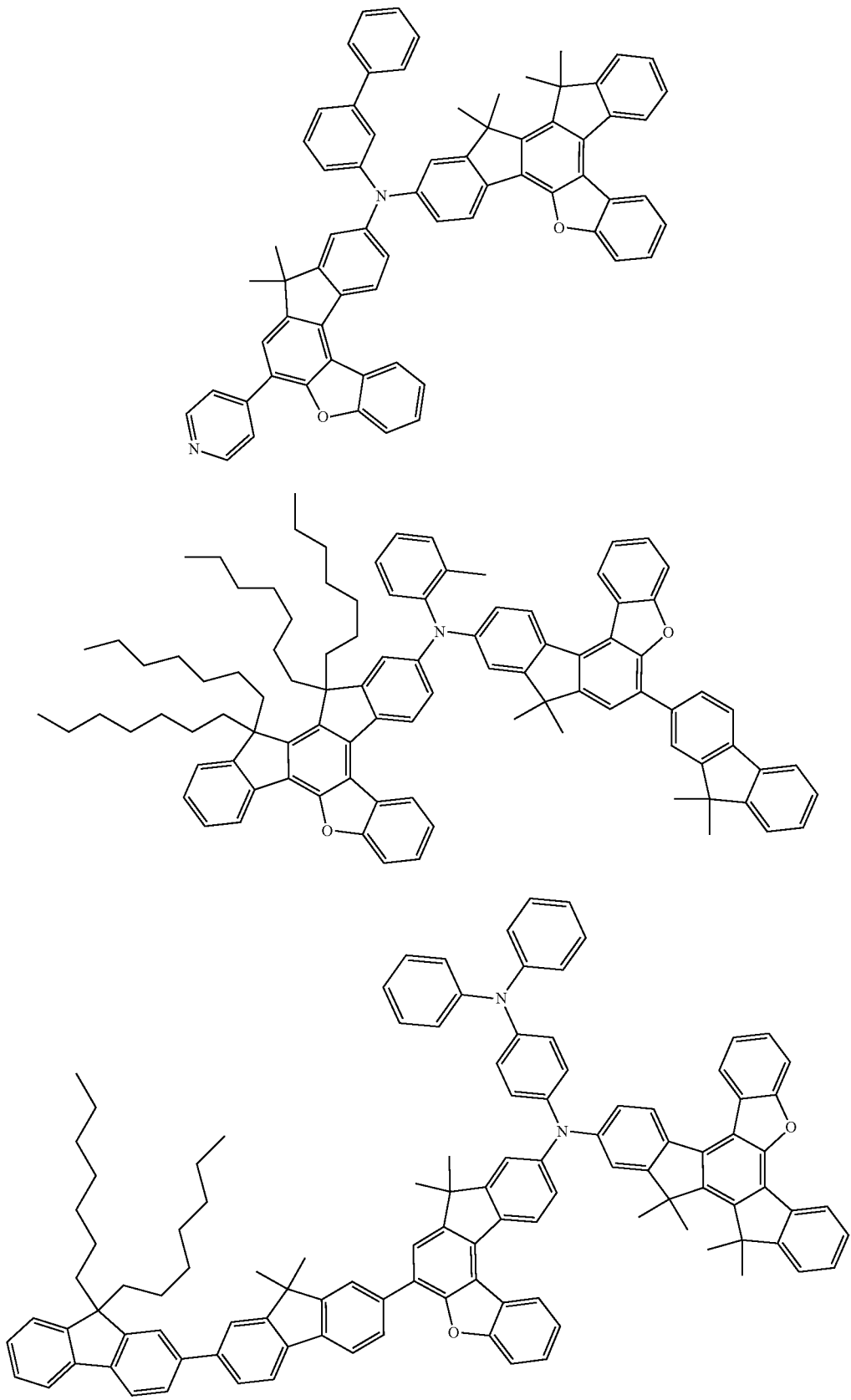

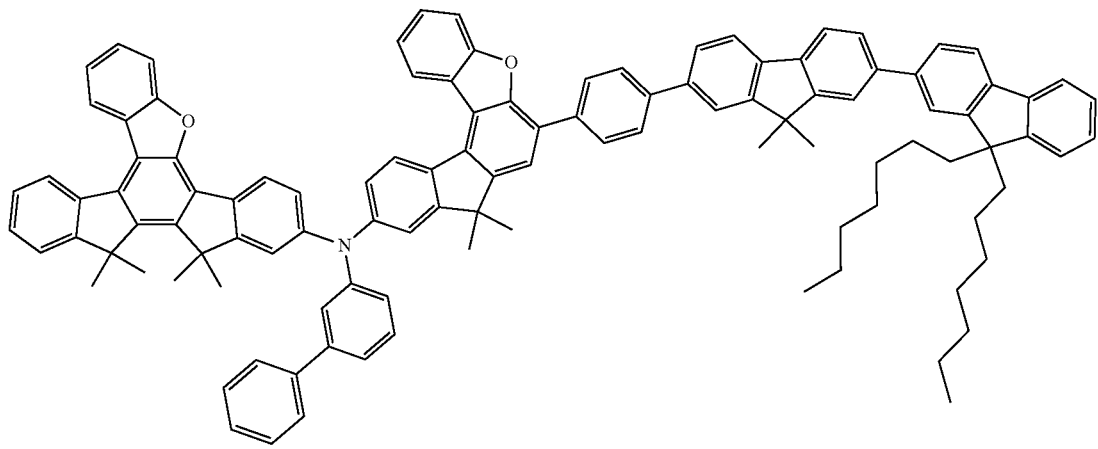 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8cccc(-c9ccccc9)c8)c8ccc9c(c8)C(C)(C)c8c%10c(c%11c(oc%12ccccc%12%11)c8-9)-c8ccccc8C%10(C)C)cc6C7(C)C)cc5)ccc3-4)cc21]
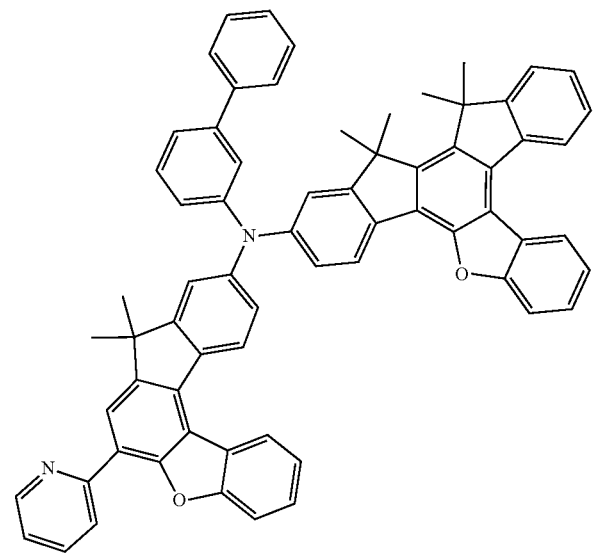 [SMILES: CC1(C)c2cc(N(c3cccc(-c4ccccc4)c3)c3ccc4c(c3)C(C)(C)c3c5c(c6c(oc7ccccc76)c3-4)-c3ccccc3C5(C)C)ccc2-c2c1cc(-c1ccccn1)c1oc3ccccc3c21]
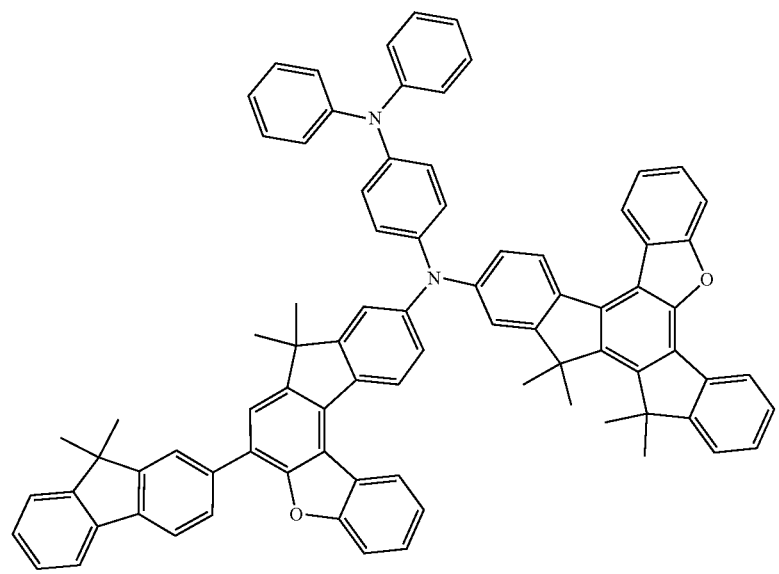 [SMILES: CC1(C)c2ccccc2-c2ccc(-c3cc4c(c5c3oc3ccccc35)-c3ccc(N(c5ccc(N(c6ccccc6)c6ccccc6)cc5)c5ccc6c(c5)C(C)(C)c5c7c(c8oc9ccccc9c8c5-6)-c5ccccc5C7(C)C)cc3C4(C)C)cc21]

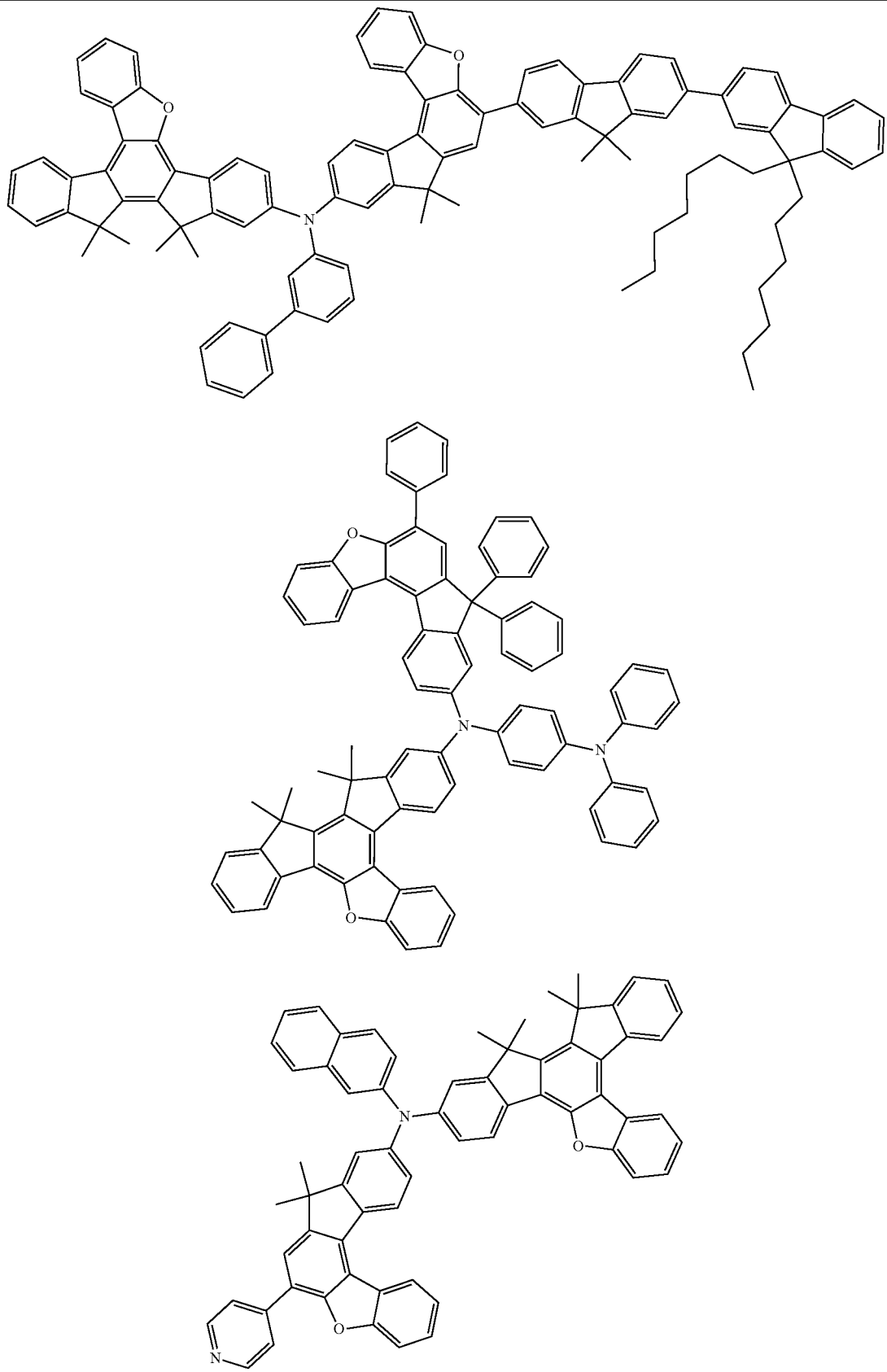

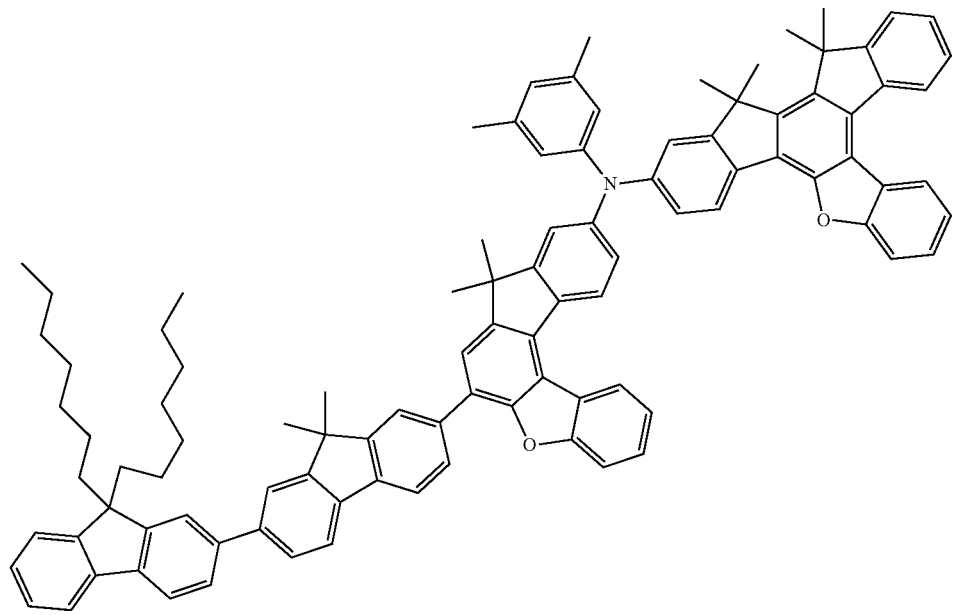 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7cc(C)cc(C)c7)c7ccc8c(c7)C(C)(C)c7c9c(c%10c(oc%11ccccc%11%10)c7-8)-c7ccccc7C9(C)C)cc5C6(C)C)ccc3-4)cc21]
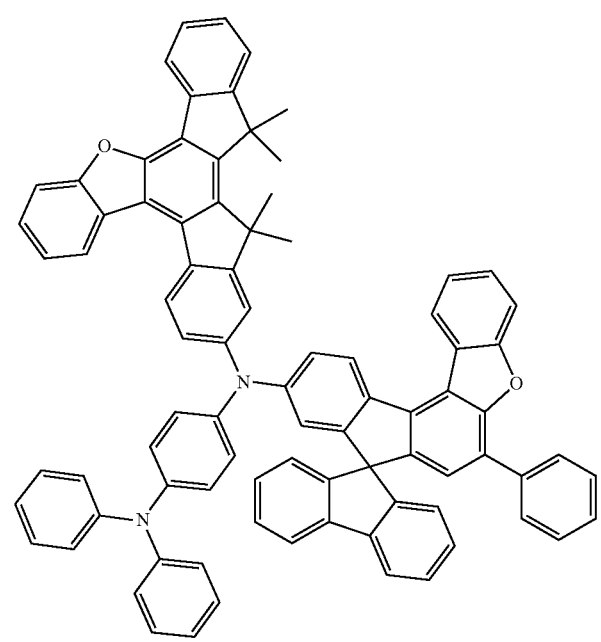 [SMILES: CC1(C)c2ccccc2-c2c1c1c(c3c2oc2ccccc23)-c2ccc(N(c3ccc(N(c4ccccc4)c4ccccc4)cc3)c3ccc4c(c3)C3(c5ccccc5-c5ccccc53)c3cc(-c5ccccc5)c5oc6ccccc6c5c3-4)cc2C1(C)C]

-continued
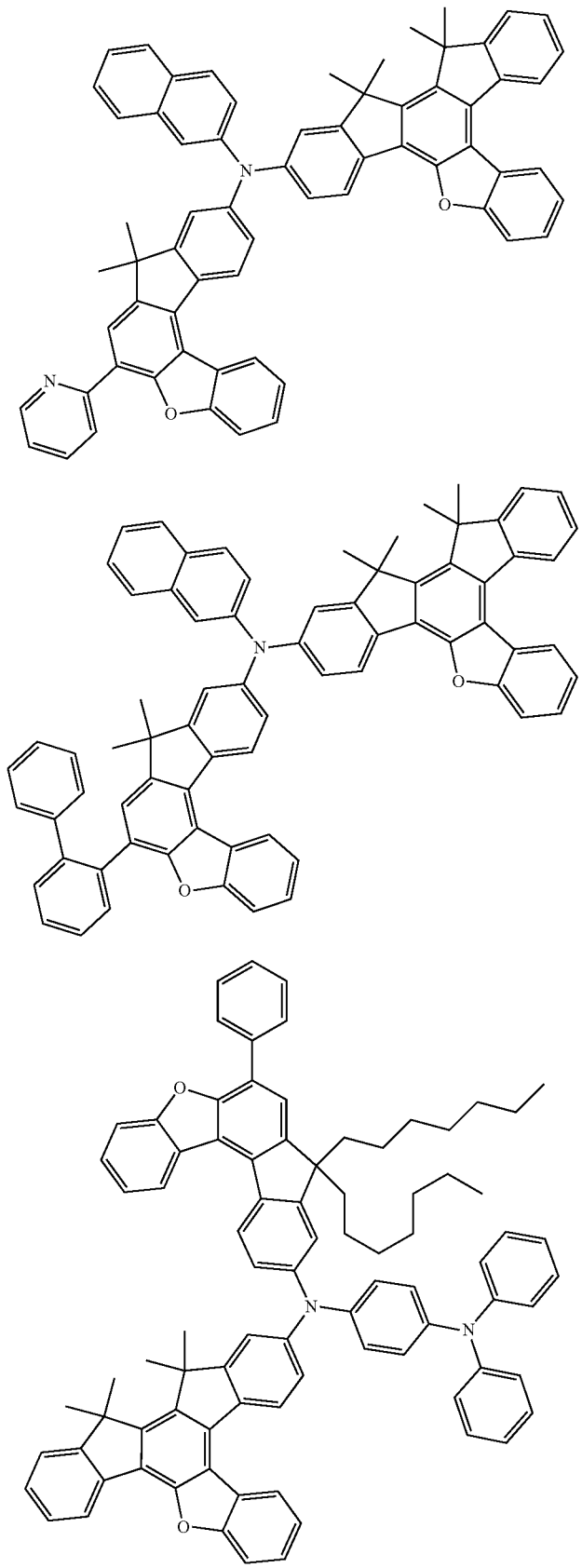

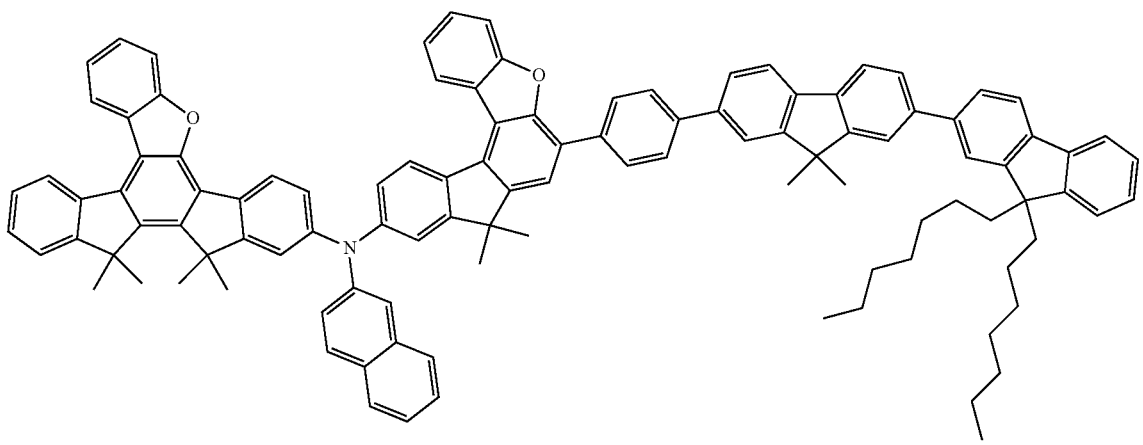 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11c(oc%12ccccc%12%11)c8-9)-c8ccccc8C%10(C)C)c8ccc9ccccc9c8)cc6C7(C)C)cc5)ccc3-4)cc21]
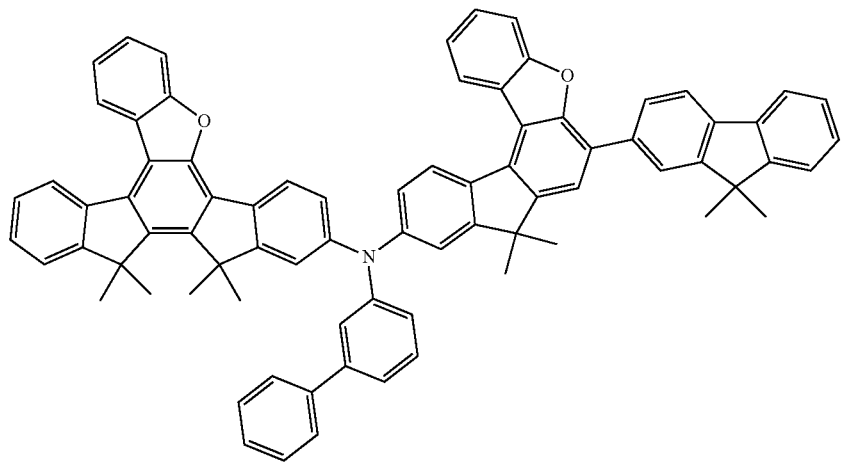 [SMILES: CC1(C)c2ccccc2-c2ccc(-c3cc4c(c5c3oc3ccccc35)-c3ccc(N(c5cccc(-c6ccccc6)c5)c5ccc6c(c5)C(C)(C)c5c7c(c8c(oc9ccccc98)c5-6)-c5ccccc5C7(C)C)cc3C4(C)C)cc21]
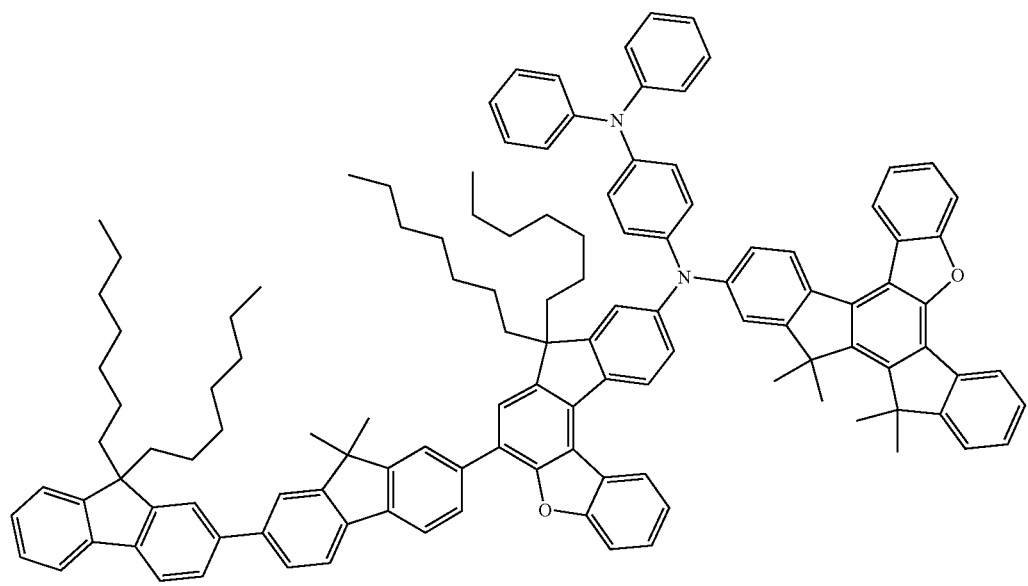 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc(N(c8ccccc8)c8ccccc8)cc7)c7ccc8c(c7)C(C)(C)c7c9c(c%10oc%11ccccc%11c%10c7-8)-c7ccccc7C9(C)C)cc5C6(CCCCCCC)CCCCCCC)ccc3-4)cc21]

-continued
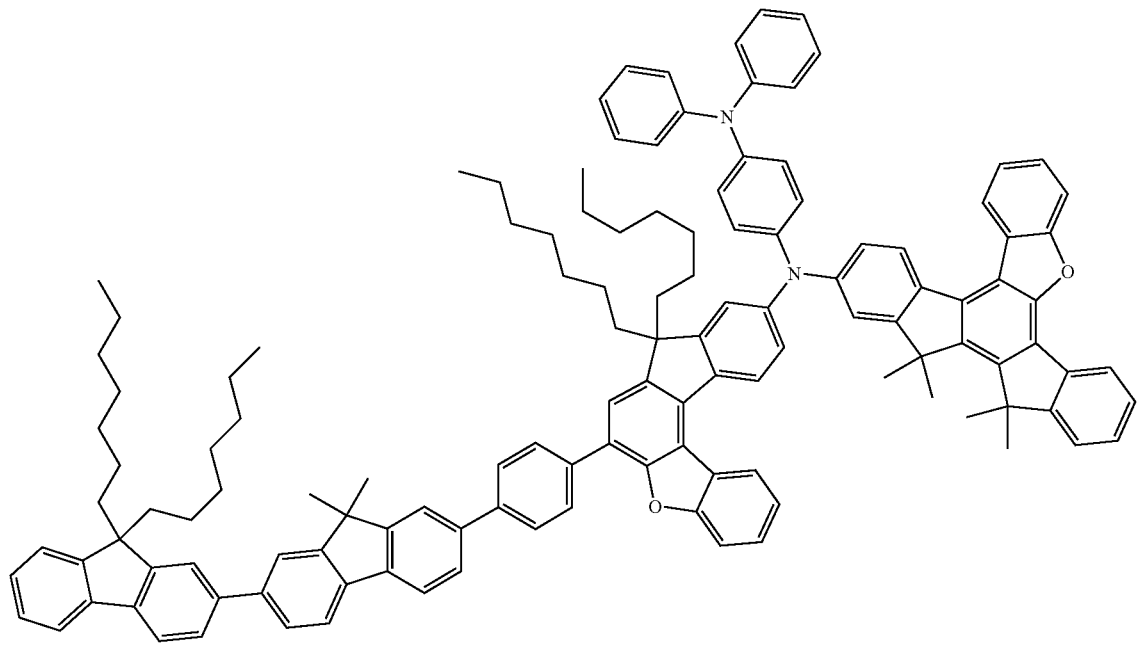 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc(N(c9ccccc9)c9ccccc9)cc8)c8ccc9c(c8)C(C)(C)c8c%10c(c%11oc%12ccccc%12c%11c8-9)-c8ccccc8C%10(C)C)cc6C7(CCCCCCC)CCCCCCC)cc5)ccc3-4)cc21]
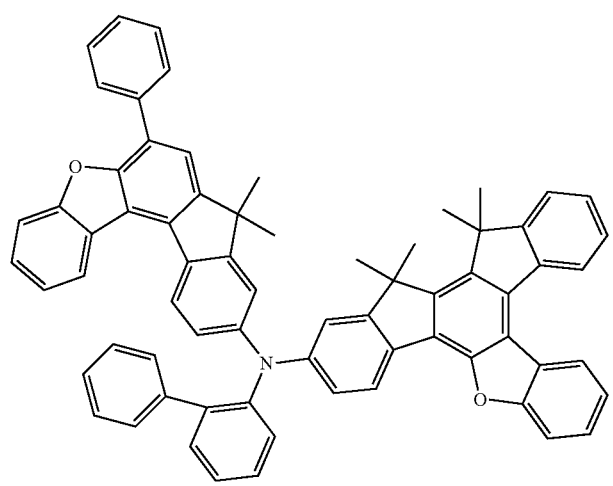 [SMILES: CC1(C)c2cc(N(c3ccc4c(c3)C(C)(C)c3c5c(c6c(oc7ccccc76)c3-4)-c3ccccc3C5(C)C)c3ccccc3-c3ccccc3)ccc2-c2c1cc(-c1ccccc1)c1oc3ccccc3c21]

-continued
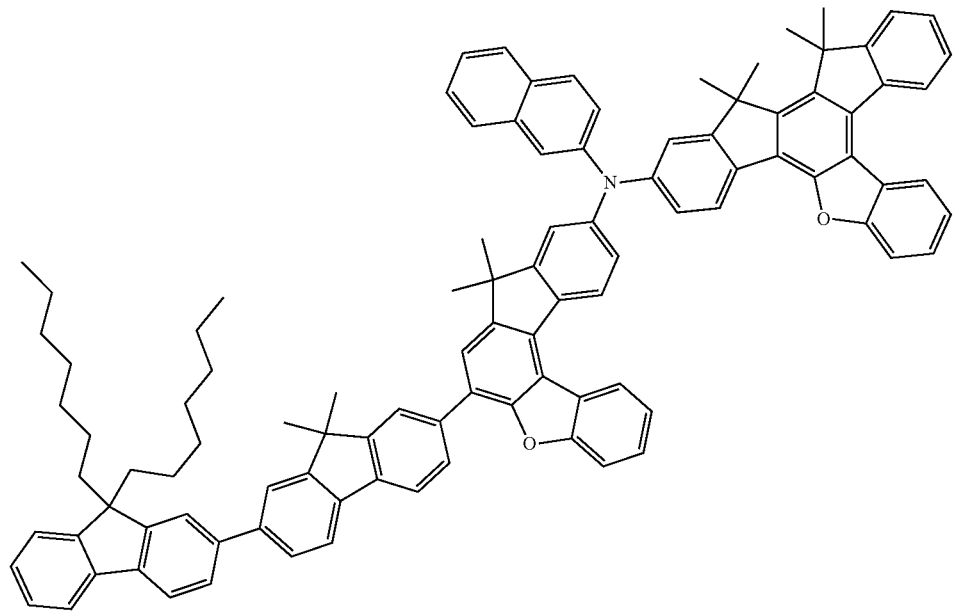 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10c(oc%11ccccc%11%10)c7-8)-c7ccccc7C9(C)C)c7ccc8ccccc8c7)cc5C6(C)C)ccc3-4)cc21]
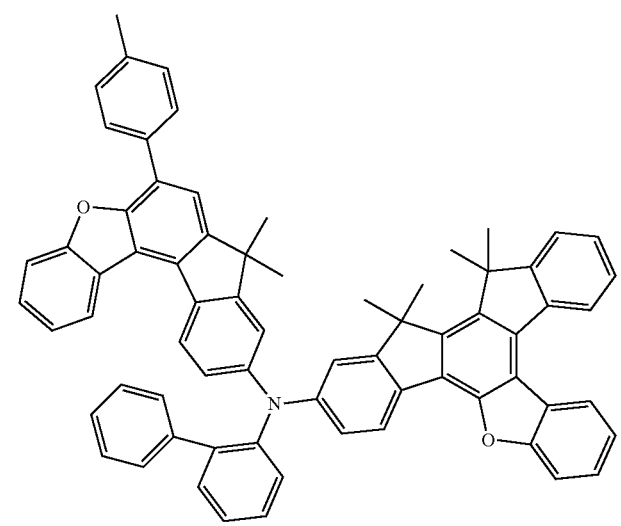 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccccc4-c4ccccc4)cc2C3(C)C)cc1]
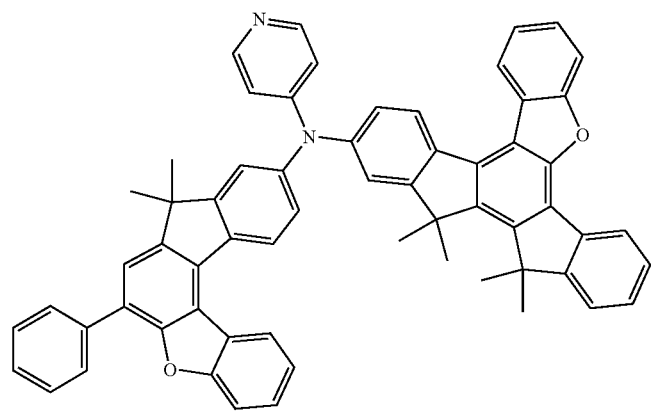 [SMILES: CC1(C)c2cc(N(c3ccncc3)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]

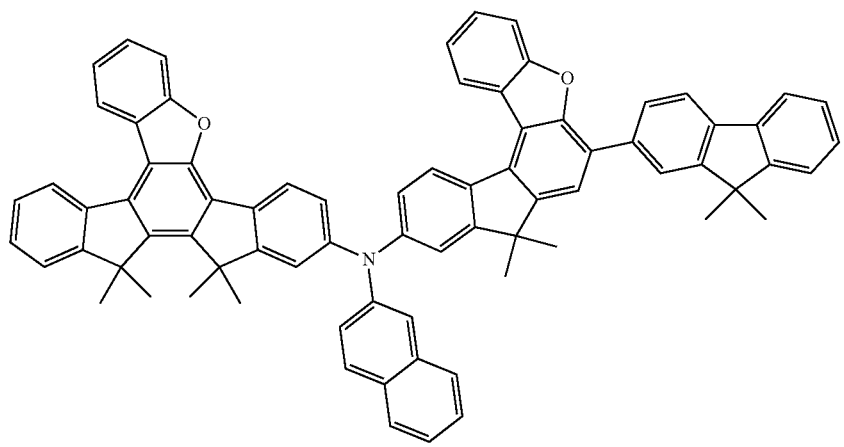 [SMILES: CC1(C)c2ccccc2-c2ccc(-c3cc4c(c5c3oc3ccccc35)-c3ccc(N(c5ccc6c(c5)C(C)(C)c5c7c(c8c(oc9ccccc98)c5-6)-c5ccccc5C7(C)C)c5ccc6ccccc6c5)cc3C4(C)C)cc21]
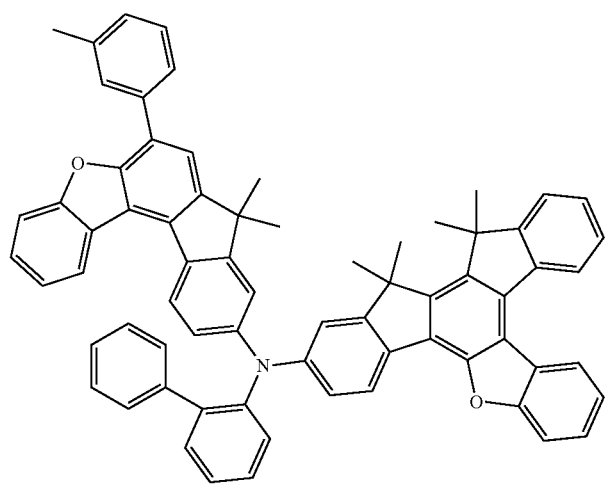 [SMILES: Cc1cccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccccc4-c4ccccc4)cc2C3(C)C)c1]
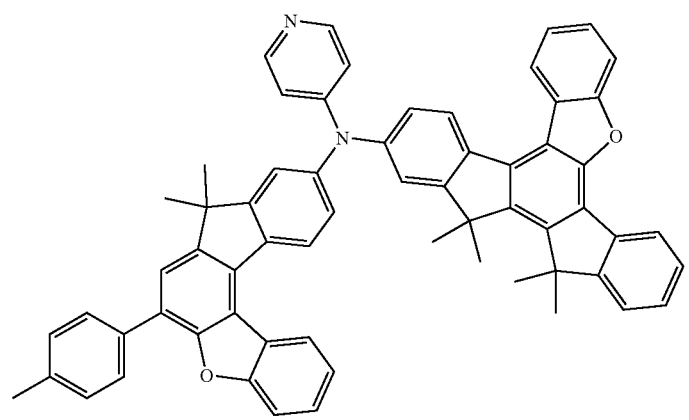 [SMILES: Cc1ccc(-c2cc3c(c4c2oc2ccccc24)-c2ccc(N(c4ccncc4)c4ccc5c(c4)C(C)(C)c4c6c(c7oc8ccccc8c7c4-5)-c4ccccc4C6(C)C)cc2C3(C)C)cc1]

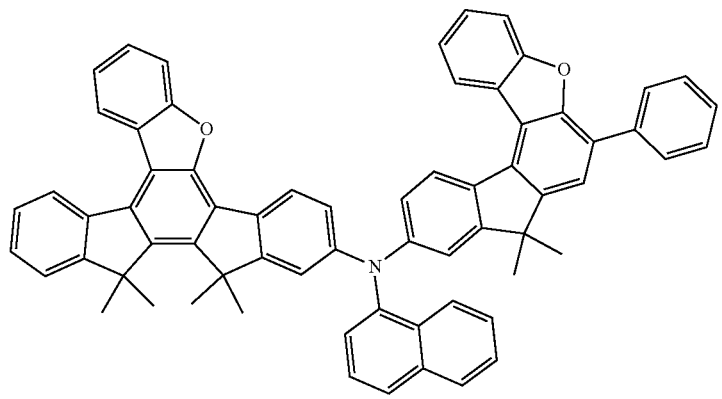 [SMILES: CC1(C)c2cc(N(c3ccc4c(c3)C(C)(C)c3c5c(c6c(oc7ccccc76)c3-4)-c3ccccc3C5(C)C)c3cccc4ccccc34)ccc2-c2c1cc(-c1ccccc1)c1oc3ccccc3c21]
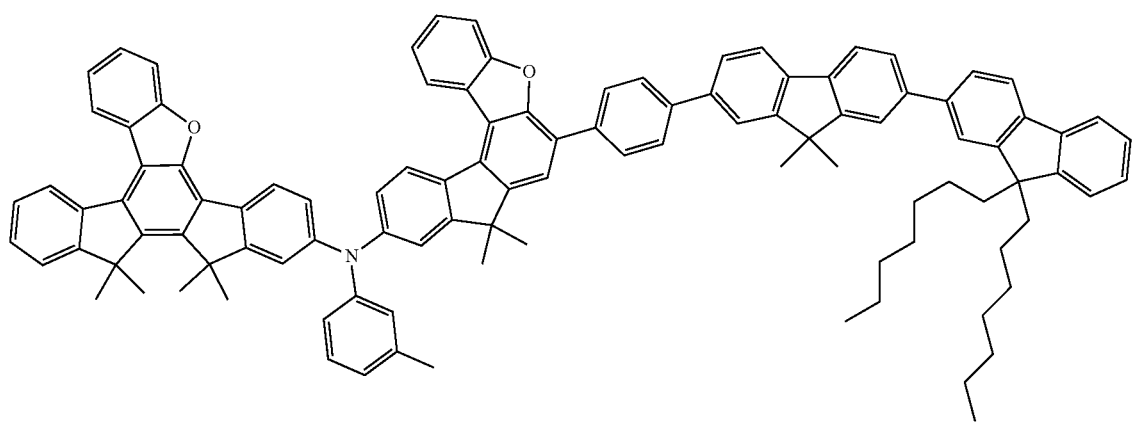 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8cccc(C)c8)c8ccc9c(c8)C(C)(C)c8c%10c(c%11c(oc%12ccccc%12%11)c8-9)-c8ccccc8C%10(C)C)cc6C7(C)C)cc5)ccc3-4)cc21]
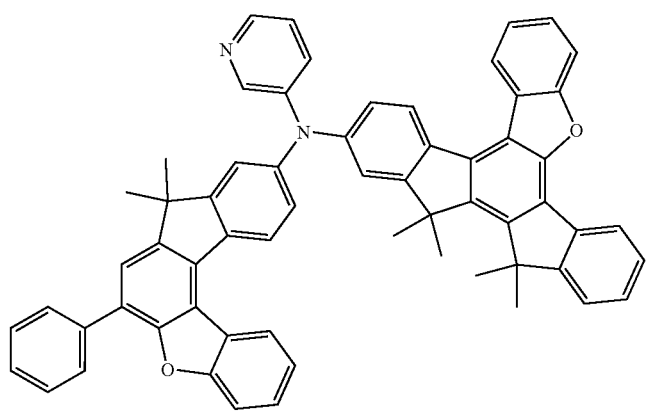 [SMILES: CC1(C)c2cc(N(c3cccnc3)c3ccc4c(c3)C(C)(C)c3c5c(c6oc7ccccc7c6c3-4)-c3ccccc3C5(C)C)ccc2-c2c1cc(-c1ccccc1)c1oc3ccccc3c21]
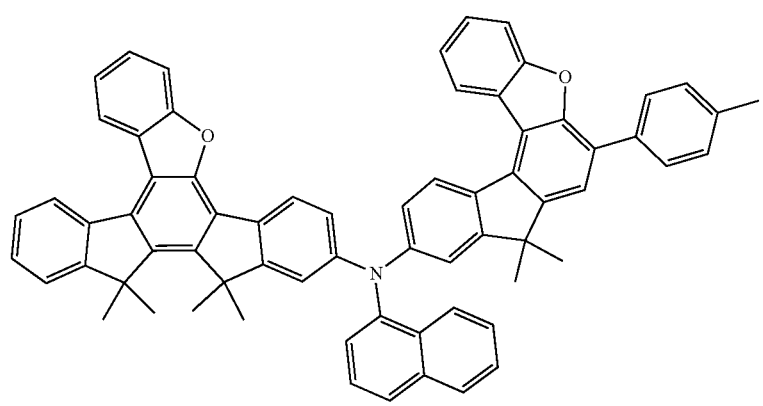 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4cccc5ccccc45)cc2C3(C)C)cc1]

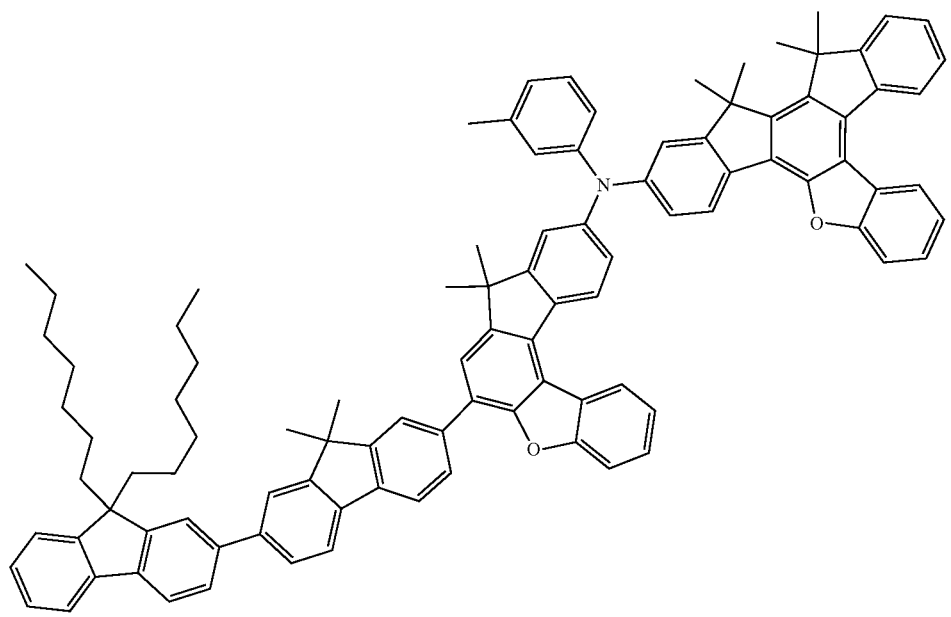 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7cccc(C)c7)c7ccc8c(c7)C(C)(C)c7c9c(c%10c(oc%11ccccc%11%10)c7-8)-c7ccccc7C9(C)C)cc5C6(C)C)ccc3-4)cc21]
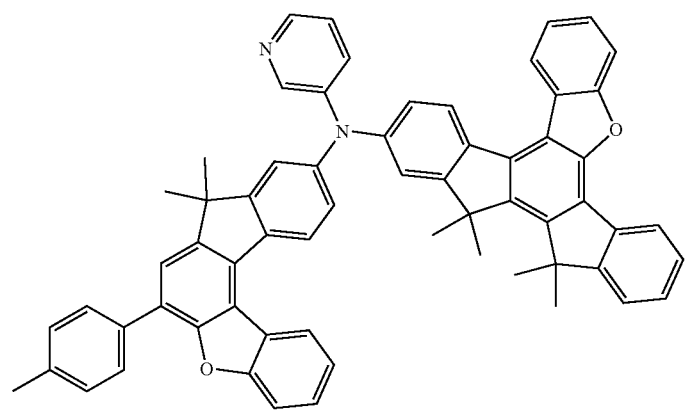 [SMILES: Cc1ccc(-c2cc3c(c4c2oc2ccccc24)-c2ccc(N(c4cccnc4)c4ccc5c(c4)C(C)(C)c4c6c(c7oc8ccccc8c7c4-5)-c4ccccc4C6(C)C)cc2C3(C)C)cc1]
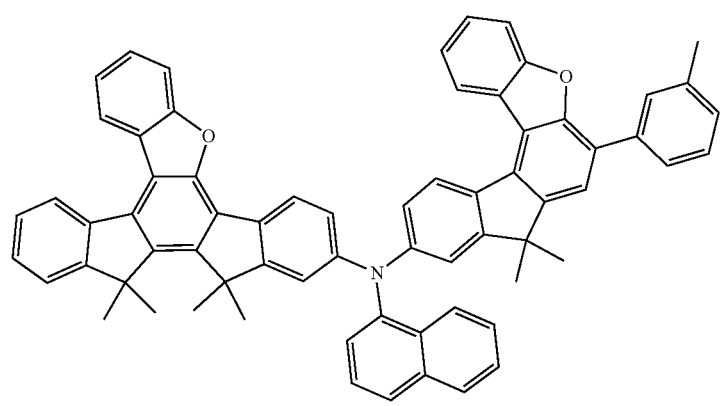 [SMILES: Cc1cccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4cccc5ccccc45)cc2C3(C)C)c1]

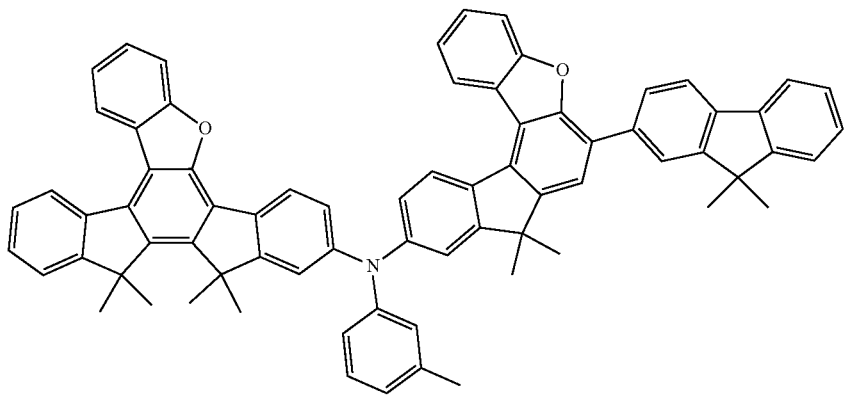 [SMILES: Cc1cccc(N(c2ccc3c(c2)C(C)(C)c2cc(-c4ccc5c(c4)C(C)(C)c4ccccc4-5)c4oc5ccccc5c4c2-3)c2ccc3c(c2)C(C)(C)c2c4c(c5c(oc6ccccc65)c2-3)-c2ccccc2C4(C)C)c1]
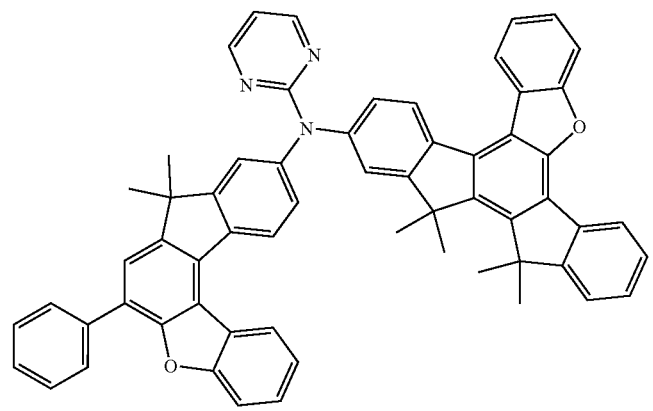 [SMILES: CC1(C)c2cc(N(c3ccc4c(c3)C(C)(C)c3c5c(c6oc7ccccc7c6c3-4)-c3ccccc3C5(C)C)c3ncccn3)ccc2-c2c1cc(-c1ccccc1)c1oc3ccccc3c21]
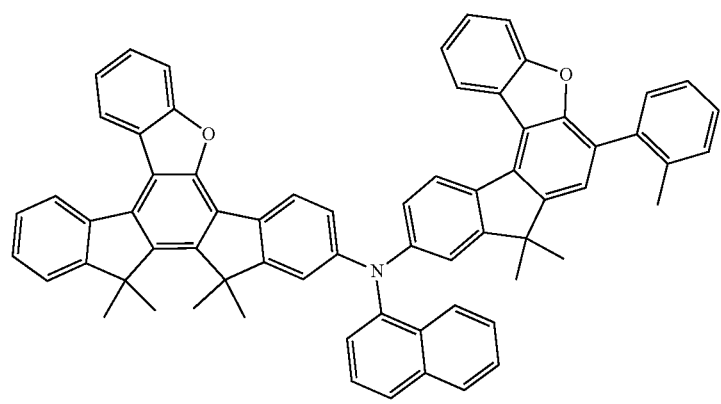 [SMILES: Cc1ccccc1-c1cc2c(c3c1oc1ccccc13)-c1ccc(N(c3ccc4c(c3)C(C)(C)c3c5c(c6c(oc7ccccc76)c3-4)-c3ccccc3C5(C)C)c3cccc4ccccc34)cc1C2(C)C]

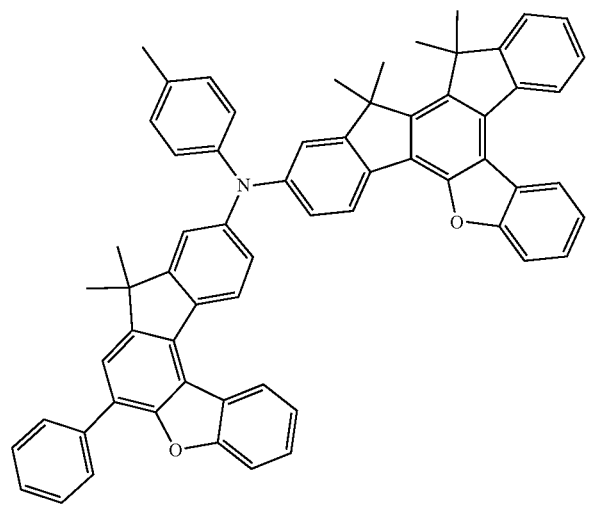 [SMILES: Cc1ccc(N(c2ccc3c(c2)C(C)(C)c2cc(-c4ccccc4)c4oc5ccccc5c4c2-3)c2ccc3c(c2)C(C)(C)c2c4c(c5c(oc6ccccc65)c2-3)-c2ccccc2C4(C)C)cc1]
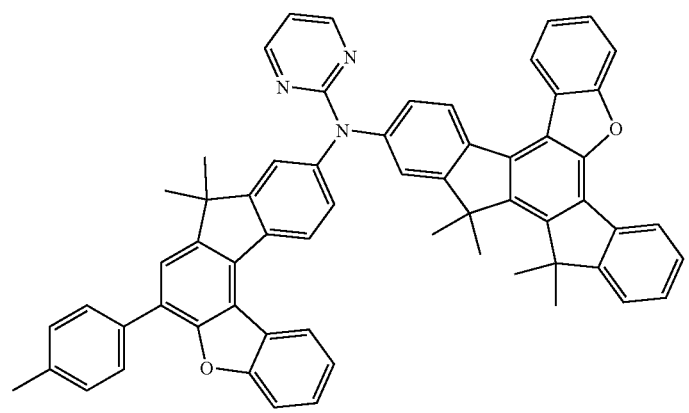 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4ncccn4)cc2C3(C)C)cc1]
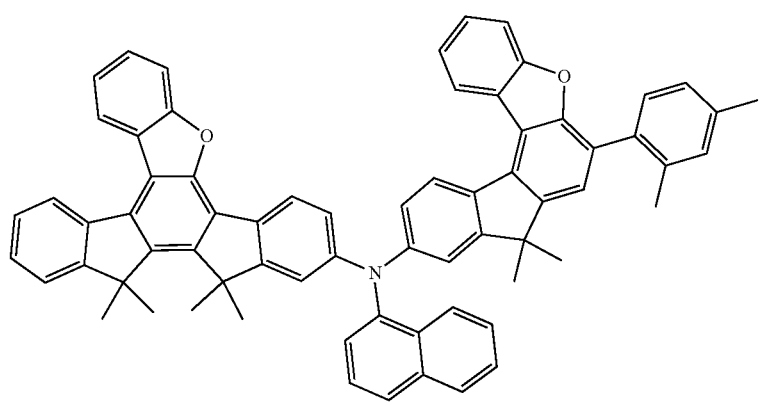 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4cccc5ccccc45)cc2C3(C)C)c(C)c1]

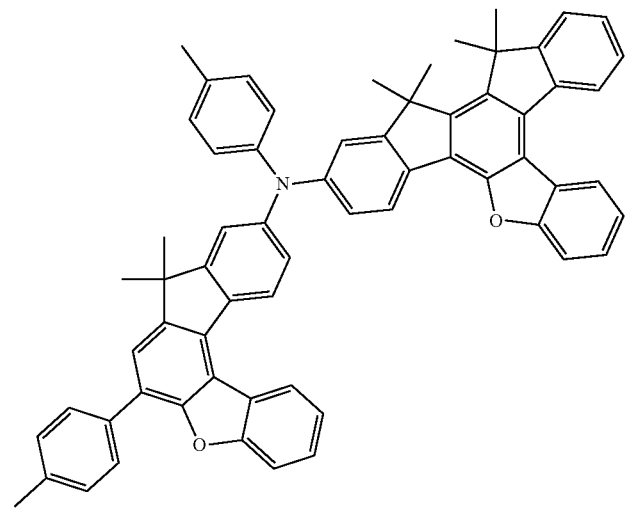 [SMILES: Cc1ccc(-c2cc3c(c4c2oc2ccccc24)-c2ccc(N(c4ccc(C)cc4)c4ccc5c(c4)C(C)(C)c4c6c(c7c(oc8ccccc87)c4-5)-c4ccccc4C6(C)C)cc2C3(C)C)cc1]

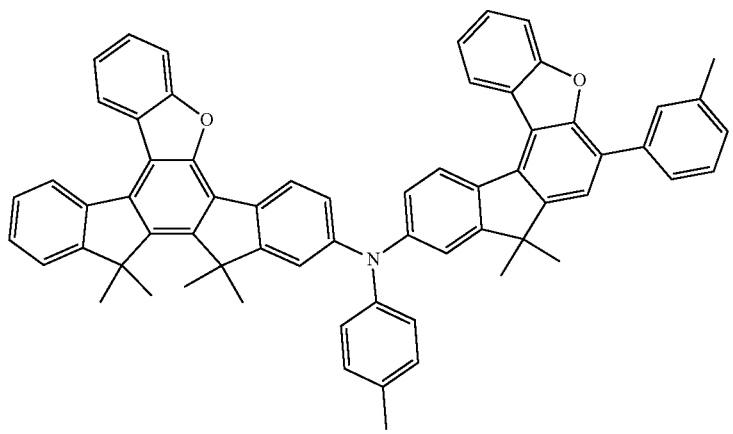 [SMILES: Cc1ccc(N(c2ccc3c(c2)C(C)(C)c2cc(-c4cccc(C)c4)c4oc5ccccc5c4c2-3)c2ccc3c(c2)C(C)(C)c2c4c(c5c(oc6ccccc65)c2-3)-c2ccccc2C4(C)C)cc1]
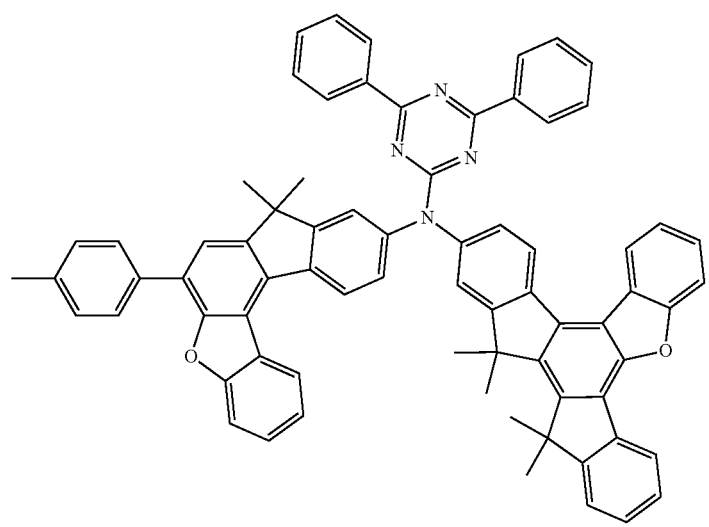 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4nc(-c5ccccc5)nc(-c5ccccc5)n4)cc2C3(C)C)cc1]
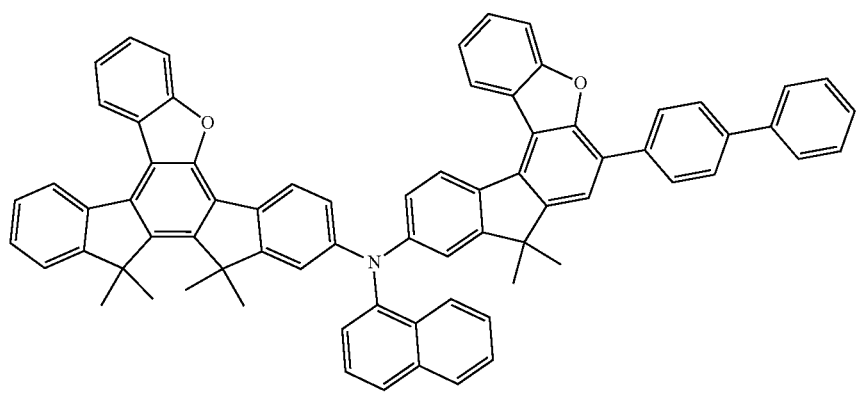 [SMILES: CC1(C)c2cc(N(c3ccc4c(c3)C(C)(C)c3c5c(c6c(oc7ccccc76)c3-4)-c3ccccc3C5(C)C)c3cccc4ccccc34)ccc2-c2c1cc(-c1ccc(-c3ccccc3)cc1)c1oc3ccccc3c21]

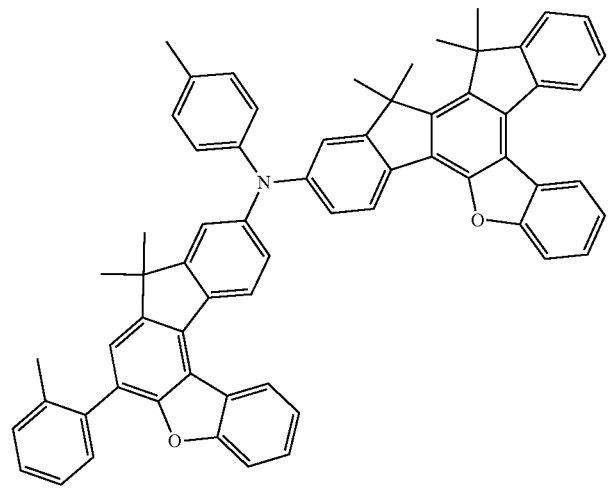 [SMILES: Cc1ccc(N(c2ccc3c(c2)C(C)(C)c2cc(-c4ccccc4C)c4oc5ccccc5c4c2-3)c2ccc3c(c2)C(C)(C)c2c4c(c5c(oc6ccccc65)c2-3)-c2ccccc2C4(C)C)cc1]
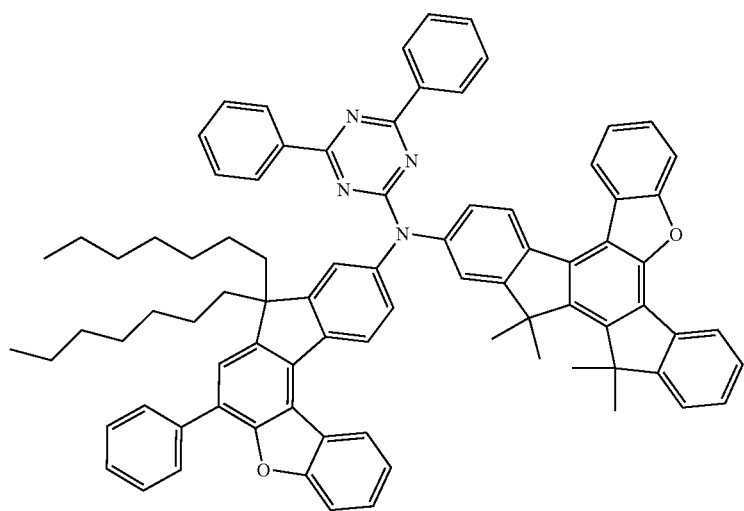 [SMILES: CCCCCCCC1(CCCCCCC)c2cc(N(c3ccc4c(c3)C(C)(C)c3c5c(c6oc7ccccc7c6c3-4)-c3ccccc3C5(C)C)c3nc(-c4ccccc4)nc(-c4ccccc4)n3)ccc2-c2c1cc(-c1ccccc1)c1oc3ccccc3c21]
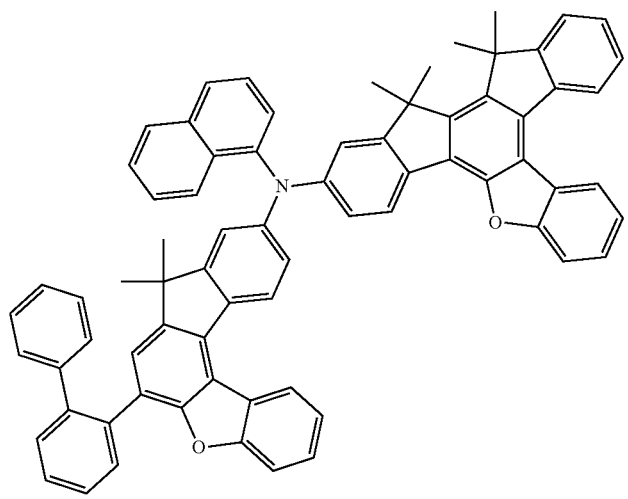 [SMILES: CC1(C)c2cc(N(c3ccc4c(c3)C(C)(C)c3c5c(c6c(oc7ccccc76)c3-4)-c3ccccc3C5(C)C)c3cccc4ccccc34)ccc2-c2c1cc(-c1ccccc1-c1ccccc1)c1oc3ccccc3c21]

-continued
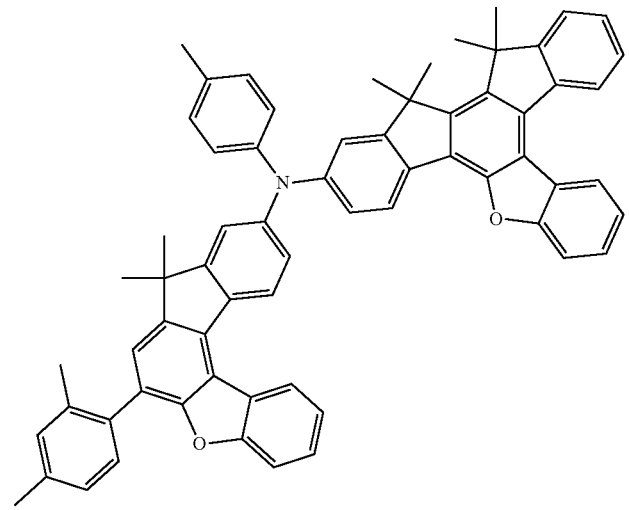 [SMILES: Cc1ccc(N(c2ccc3c(c2)C(C)(C)c2cc(-c4ccc(C)cc4C)c4oc5ccccc5c4c2-3)c2ccc3c(c2)C(C)(C)c2c4c(c5c(oc6ccccc65)c2-3)-c2ccccc2C4(C)C)cc1]
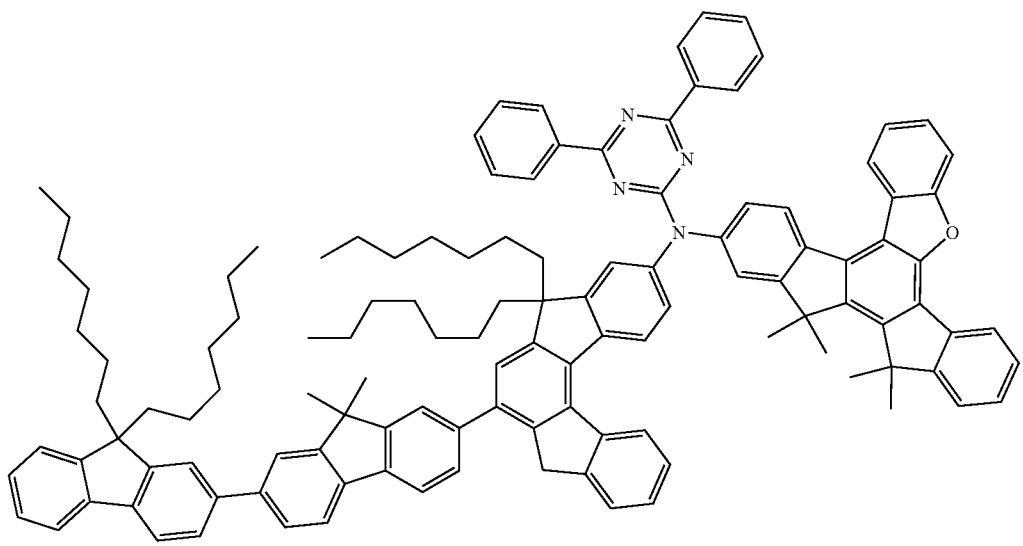 [SMILES: CCCCCCCC1(CCCCCCC)c2ccccc2-c2ccc(-c3ccc4c(c3)C(C)(C)c3cc(-c5cc6c(c7c5Cc5ccccc5-7)-c5ccc(N(c7ccc8c(c7)C(C)(C)c7c9c(c%10oc%11ccccc%11c%10c7-8)-c7ccccc7C9(C)C)c7nc(-c8ccccc8)nc(-c8ccccc8)n7)cc5C6(CCCCCCC)CCCCCCC)ccc3-4)cc21]
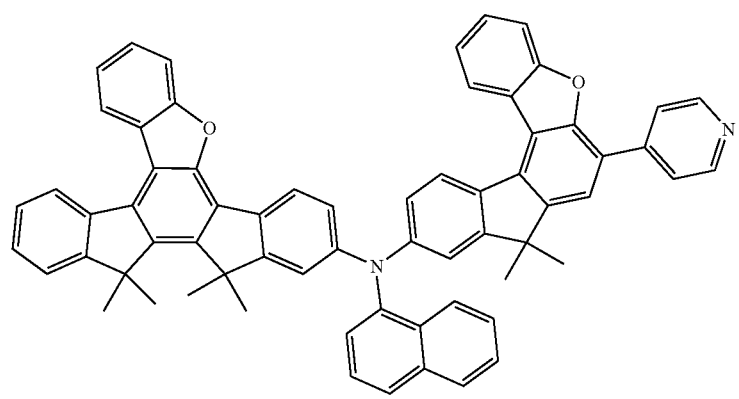 [SMILES: CC1(C)c2cc(N(c3ccc4c(c3)C(C)(C)c3c5c(c6c(oc7ccccc76)c3-4)-c3ccccc3C5(C)C)c3cccc4ccccc34)ccc2-c2c1cc(-c1ccncc1)c1oc3ccccc3c21]

-continued
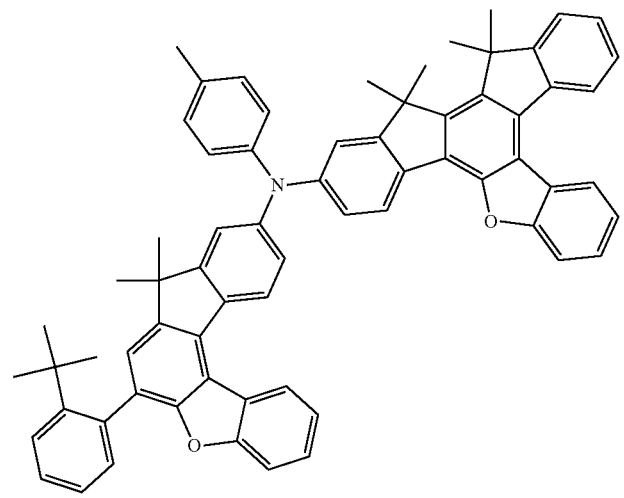 [SMILES: Cc1ccc(N(c2ccc3c(c2)C(C)(C)c2cc(-c4ccccc4C(C)(C)C)c4oc5ccccc5c4c2-3)c2ccc3c(c2)C(C)(C)c2c4c(c5c(oc6ccccc65)c2-3)-c2ccccc2C4(C)C)cc1]
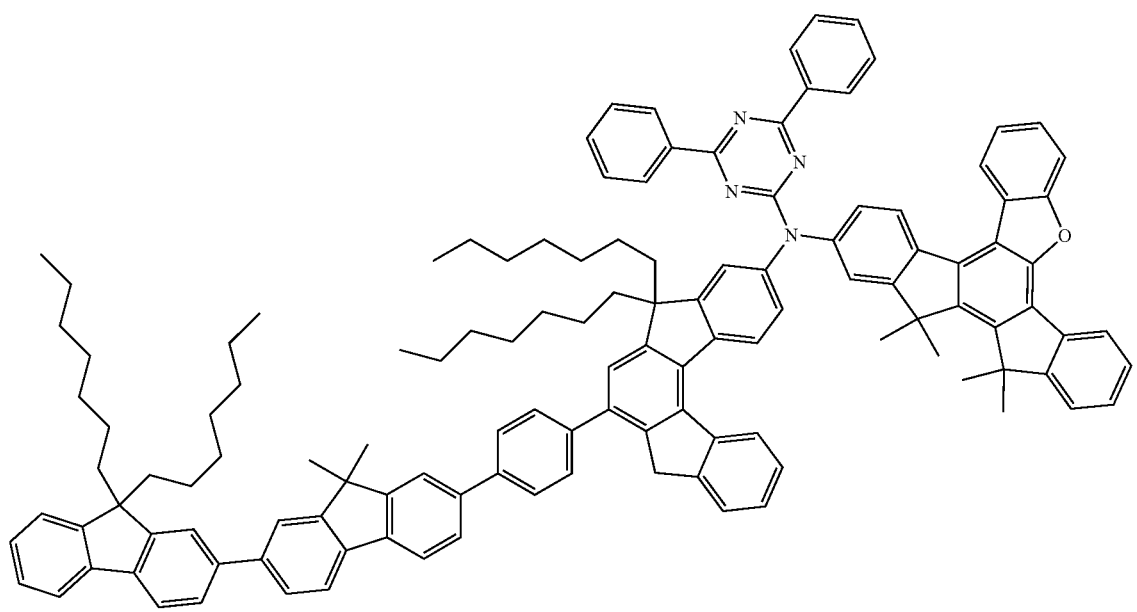 [SMILES: CCCCCCCC1(CCCCCCC)c2ccccc2-c2ccc(-c3ccc4c(c3)C(C)(C)c3cc(-c5ccc(-c6cc7c(c8c6Cc6ccccc6-8)-c6ccc(N(c8ccc9c(c8)C(C)(C)c8c%10c(c%11oc%12ccccc%12c%11c8-9)-c8ccccc8C%10(C)C)c8nc(-c9ccccc9)nc(-c9ccccc9)n8)cc6C7(CCCCCCC)CCCCCCC)cc5)ccc3-4)cc21]
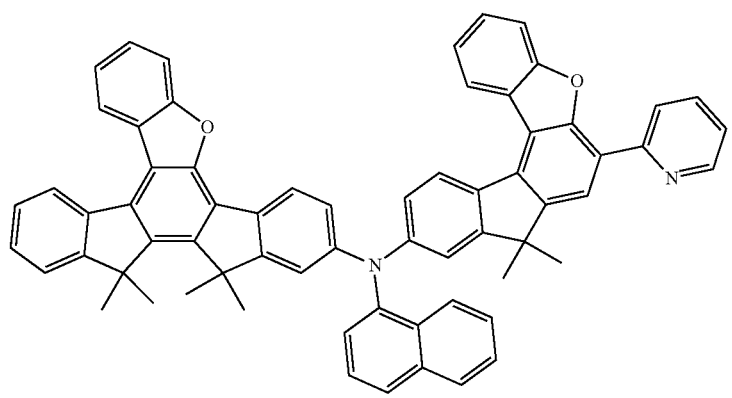 [SMILES: CC1(C)c2cc(N(c3ccc4c(c3)C(C)(C)c3c5c(c6c(oc7ccccc76)c3-4)-c3ccccc3C5(C)C)c3cccc4ccccc34)ccc2-c2c1cc(-c1ccccn1)c1oc3ccccc3c21]

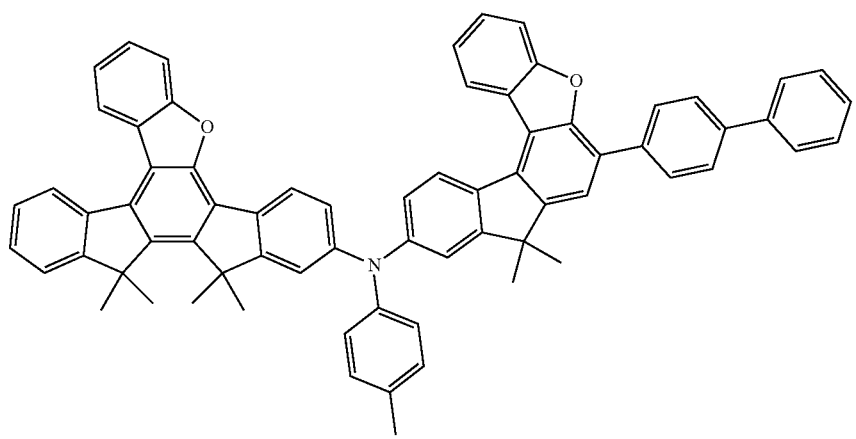 [SMILES: Cc1ccc(N(c2ccc3c(c2)C(C)(C)c2cc(-c4ccc(-c5ccccc5)cc4)c4oc5ccccc5c4c2-3)c2ccc3c(c2)C(C)(C)c2c4c(c5c(oc6ccccc65)c2-3)-c2ccccc2C4(C)C)cc1]
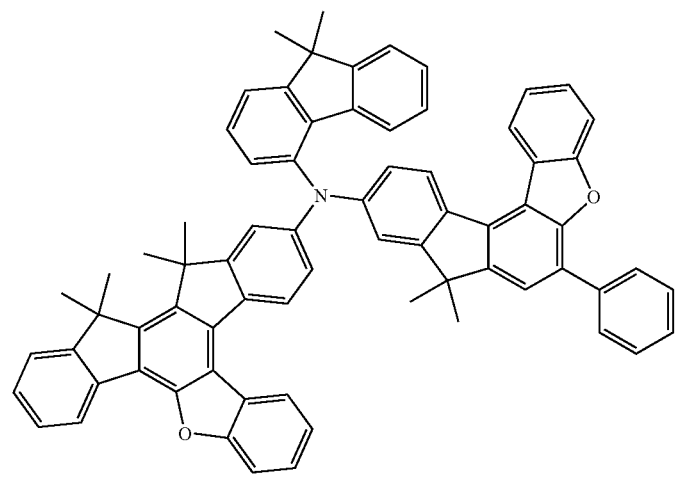 [SMILES: CC1(C)c2ccccc2-c2c(N(c3ccc4c(c3)C(C)(C)c3cc(-c5ccccc5)c5oc6ccccc6c5c3-4)c3ccc4c(c3)C(C)(C)c3c5c(c6oc7ccccc7c6c3-4)-c3ccccc3C5(C)C)cccc21]
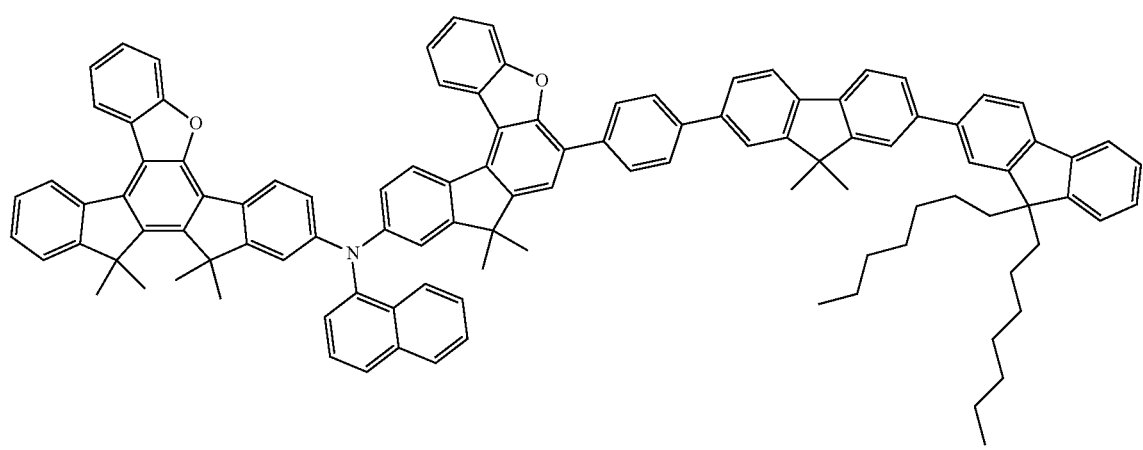 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11c(oc%12ccccc%12%11)c8-9)-c8ccccc8C%10(C)C)c8cccc9ccccc89)cc6C7(C)C)cc5)ccc3-4)cc21]

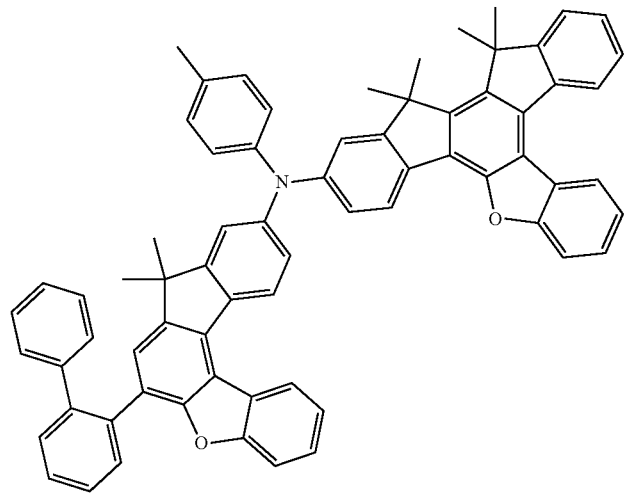 [SMILES: Cc1ccc(N(c2ccc3c(c2)C(C)(C)c2cc(-c4ccccc4-c4ccccc4)c4oc5ccccc5c4c2-3)c2ccc3c(c2)C(C)(C)c2c4c(c5c(oc6ccccc65)c2-3)-c2ccccc2C4(C)C)cc1]
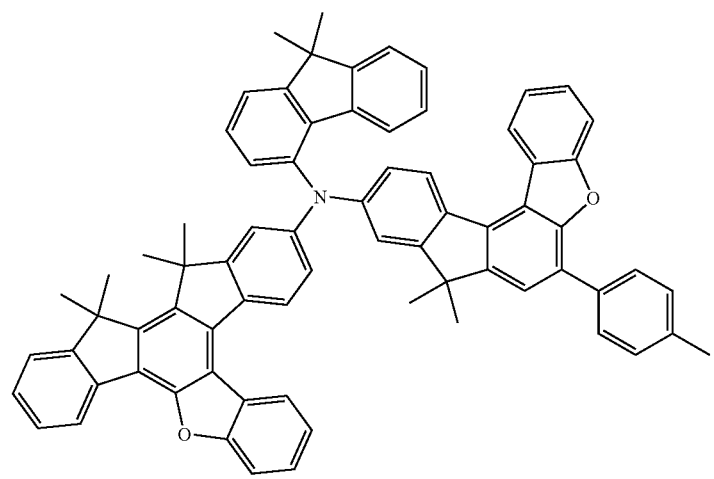 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4cccc5c4-c4ccccc4C5(C)C)cc2C3(C)C)cc1]
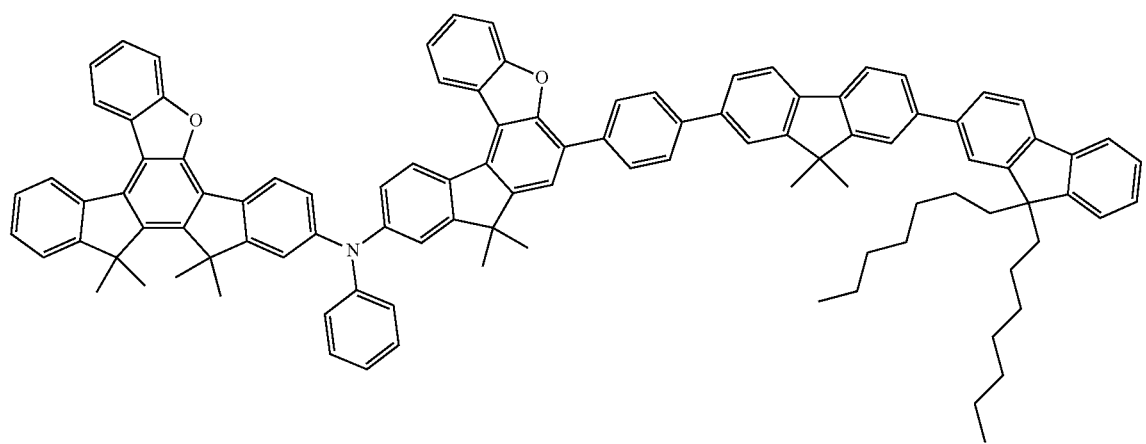 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccccc8)c8ccc9c(c8)C(C)(C)c8c%10c(c%11c(oc%12ccccc%12%11)c8-9)-c8ccccc8C%10(C)C)cc6C7(C)C)cc5)ccc3-4)cc21]

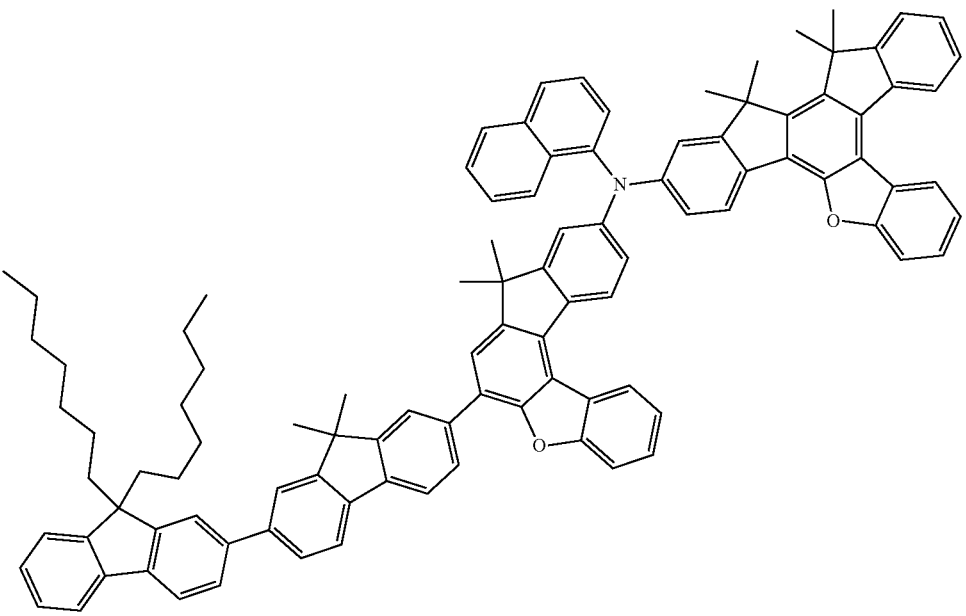 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10c(oc%11ccccc%11%10)c7-8)-c7ccccc7C9(C)C)c7cccc8ccccc78)cc5C6(C)C)ccc3-4)cc21]
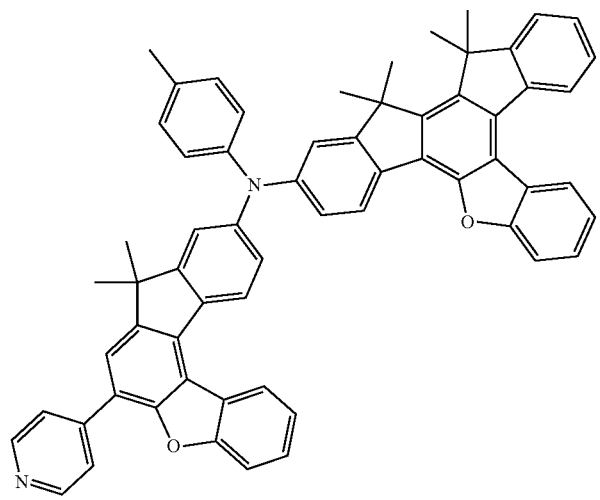 [SMILES: Cc1ccc(N(c2ccc3c(c2)C(C)(C)c2cc(-c4ccncc4)c4oc5ccccc5c4c2-3)c2ccc3c(c2)C(C)(C)c2c4c(c5c(oc6ccccc65)c2-3)-c2ccccc2C4(C)C)cc1]
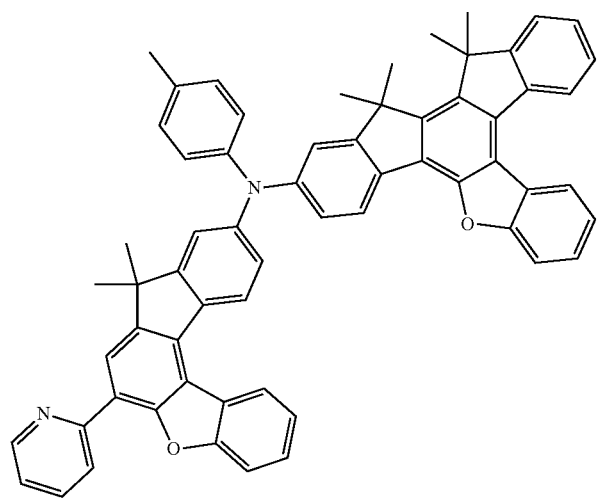 [SMILES: Cc1ccc(N(c2ccc3c(c2)C(C)(C)c2cc(-c4ccccn4)c4oc5ccccc5c4c2-3)c2ccc3c(c2)C(C)(C)c2c4c(c5c(oc6ccccc65)c2-3)-c2ccccc2C4(C)C)cc1]

-continued
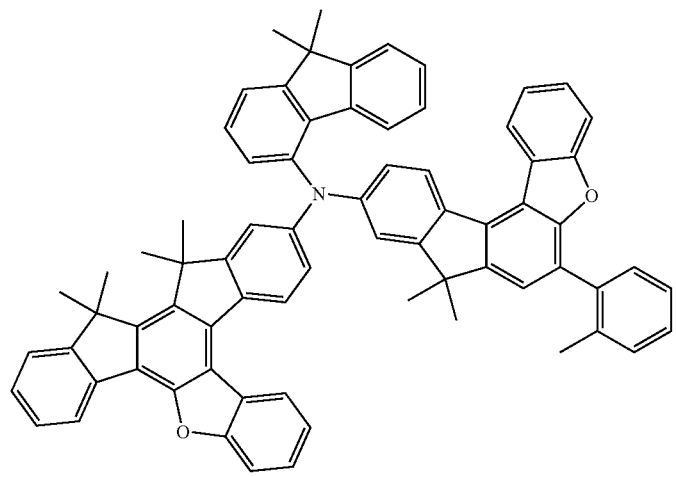 [SMILES: Cc1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3cccc4c3-c3ccccc3C4(C)C)cc1C2(C)C]
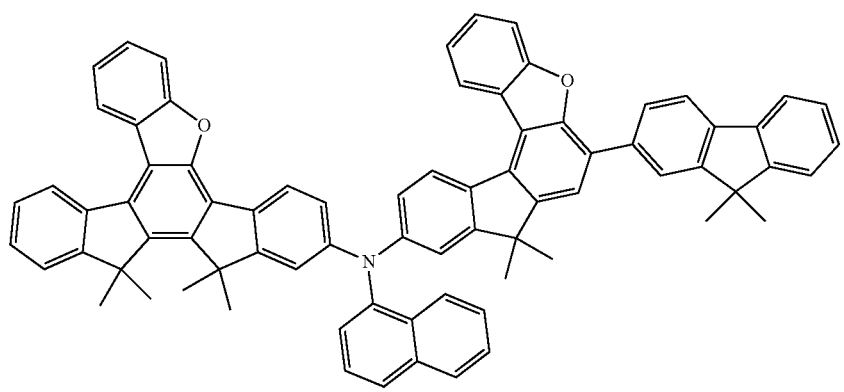 [SMILES: CC1(C)c2ccccc2-c2ccc(-c3cc4c(c5c3oc3ccccc35)-c3ccc(N(c5ccc6c(c5)C(C)(C)c5c7c(c8c(oc9ccccc98)c5-6)-c5ccccc5C7(C)C)c5cccc6ccccc56)cc3C4(C)C)cc21]
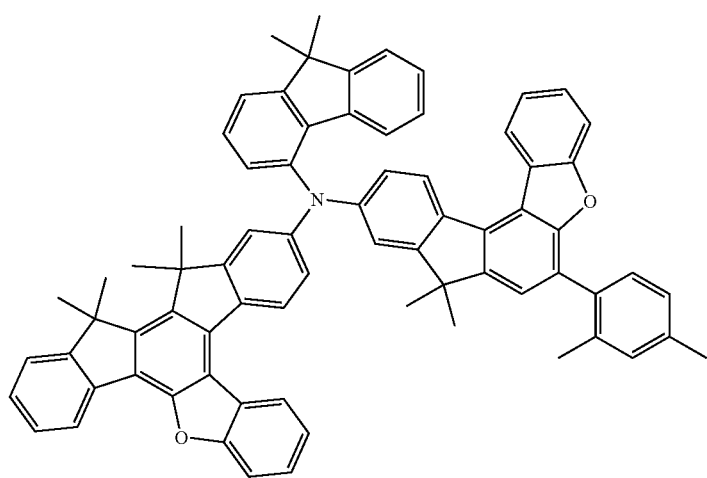 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4cccc5c4-c4ccccc4C5(C)C)cc2C3(C)C)c(C)c1]

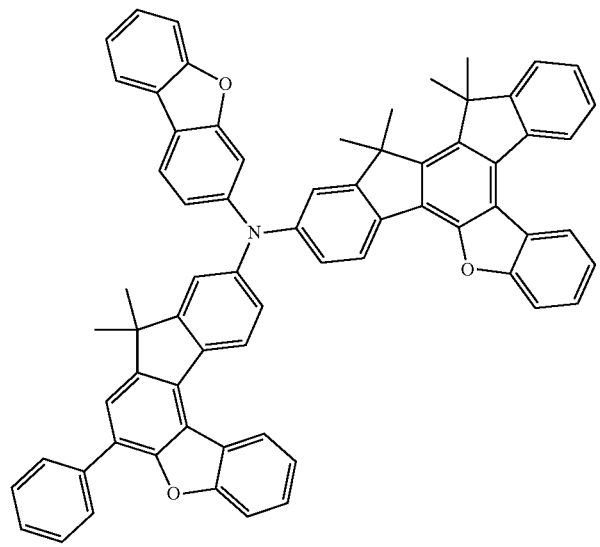 [SMILES: CC1(C)c2cc(N(c3ccc4c(c3)C(C)(C)c3c5c(c6c(oc7ccccc76)c3-4)-c3ccccc3C5(C)C)c3ccc4c(c3)oc3ccccc34)ccc2-c2c1cc(-c1ccccc1)c1oc3ccccc3c21]
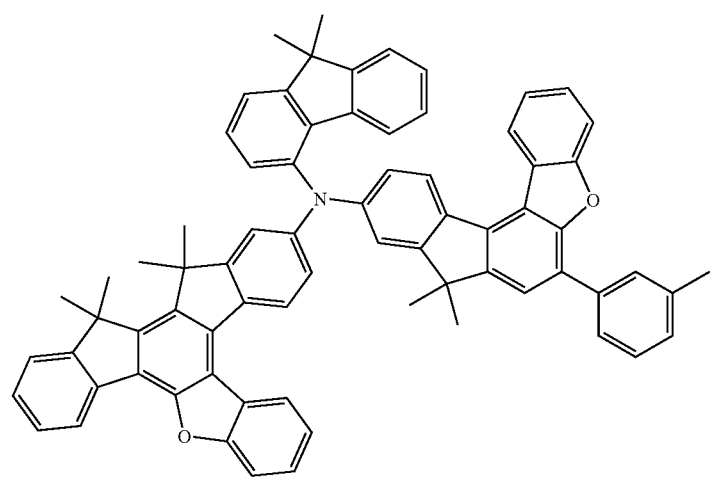 [SMILES: Cc1cccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4cccc5c4-c4ccccc4C5(C)C)cc2C3(C)C)c1]
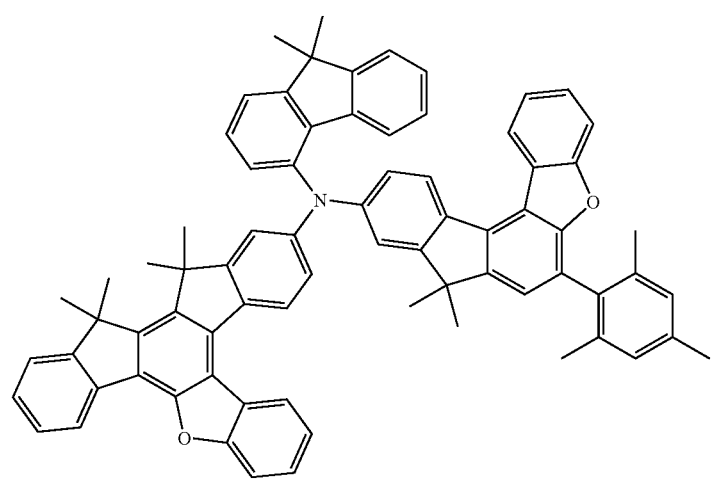 [SMILES: Cc1cc(C)c(-c2cc3c(c4c2oc2ccccc24)-c2ccc(N(c4ccc5c(c4)C(C)(C)c4c6c(c7oc8ccccc8c7c4-5)-c4ccccc4C6(C)C)c4cccc5c4-c4ccccc4C5(C)C)cc2C3(C)C)c(C)c1]

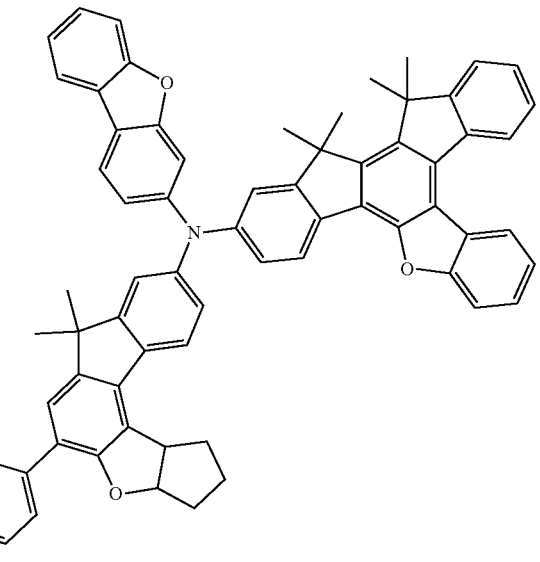
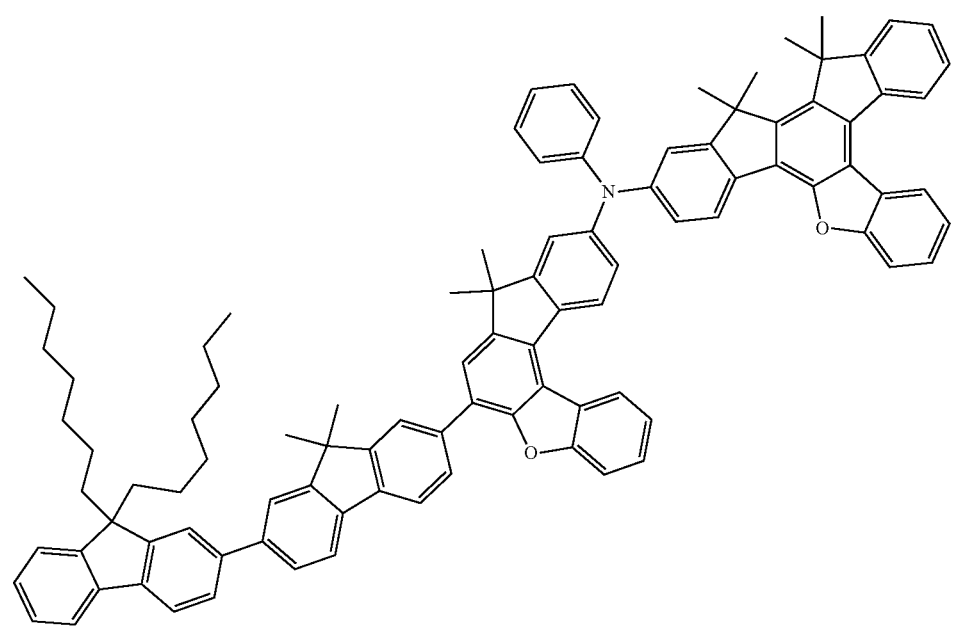 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccccc7)c7ccc8c(c7)C(C)(C)c7c9c(c%10c(oc%11ccccc%11%10)c7-8)-c7ccccc7C9(C)C)cc5C6(C)C)ccc3-4)cc21]
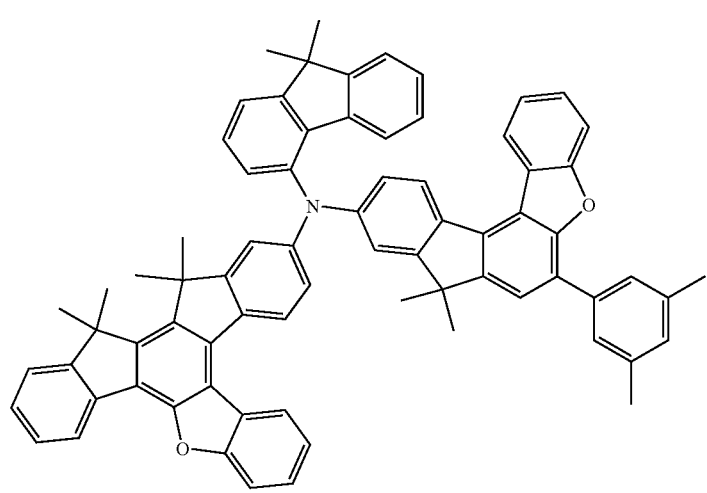 [SMILES: Cc1cc(C)cc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4cccc5c4-c4ccccc4C5(C)C)cc2C3(C)C)c1]

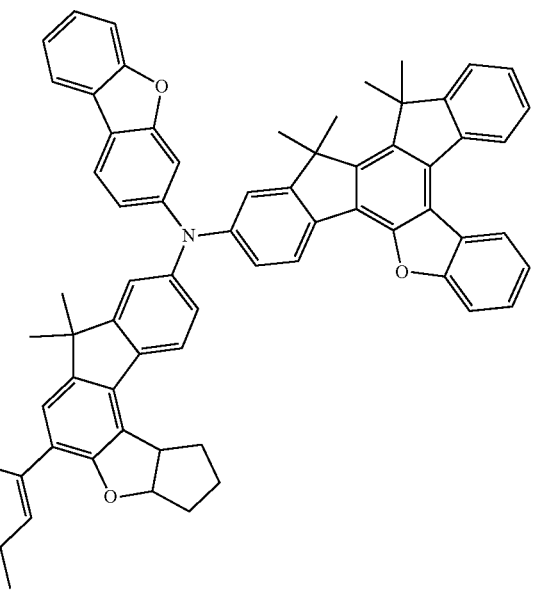
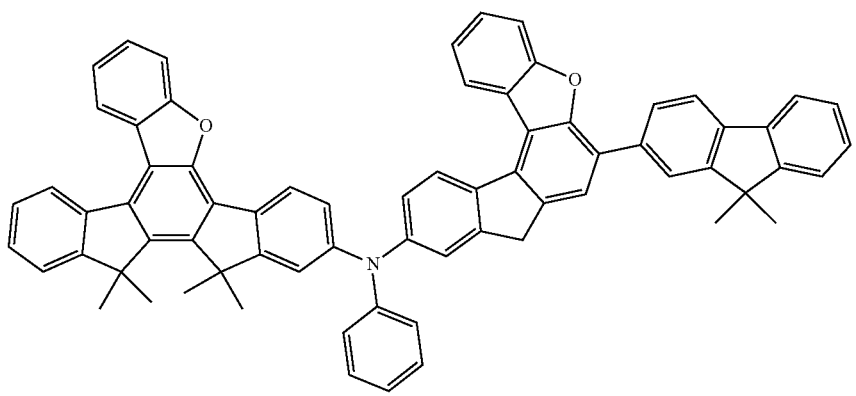 [SMILES: CC1(C)c2ccccc2-c2ccc(-c3cc4c(c5c3oc3ccccc35)-c3ccc(N(c5ccccc5)c5ccc6c(c5)C(C)(C)c5c7c(c8c(oc9ccccc98)c5-6)-c5ccccc5C7(C)C)cc3C4)cc21]
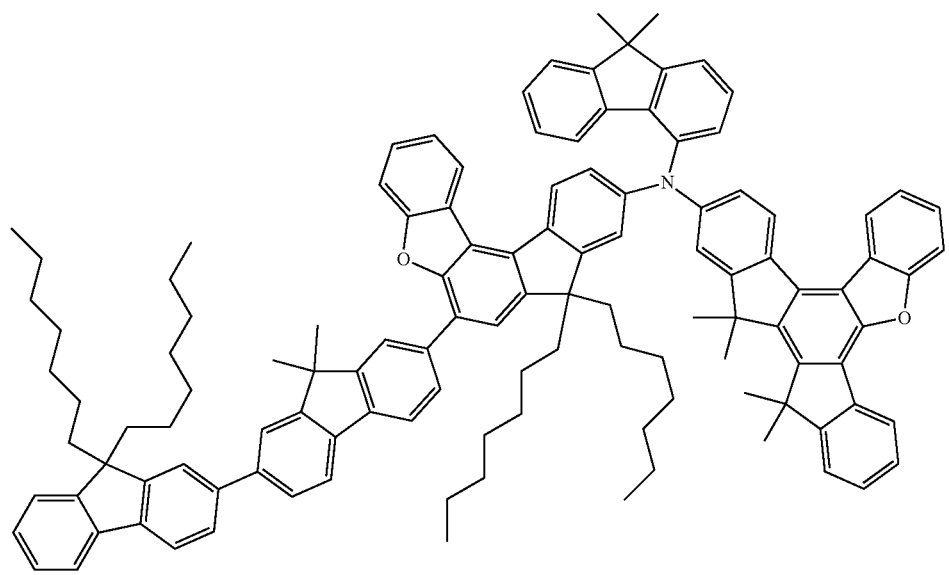 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7cccc8c7-c7ccccc7C8(C)C)cc5C6(CCCCCCC)CCCCCCC)ccc3-4)cc21]

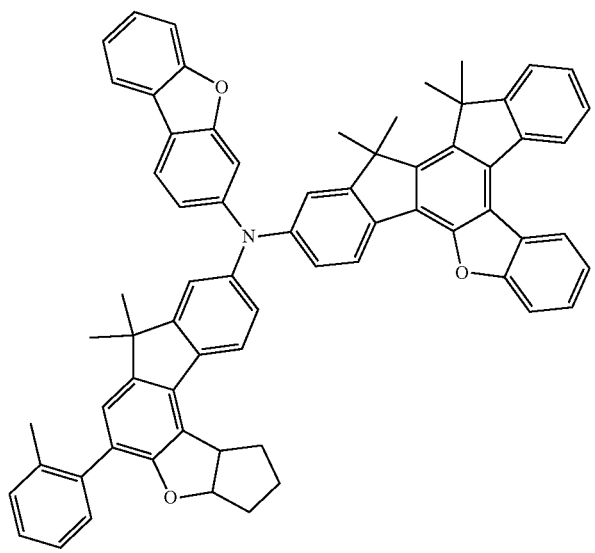 [SMILES: Cc1ccccc1-c1cc2c(c3c1OC1CCCC31)-c1ccc(N(c3ccc4c(c3)C(C)(C)c3c5c(c6c(oc7ccccc76)c3-4)-c3ccccc3C5(C)C)c3ccc4c(c3)oc3ccccc34)cc1C2(C)C]
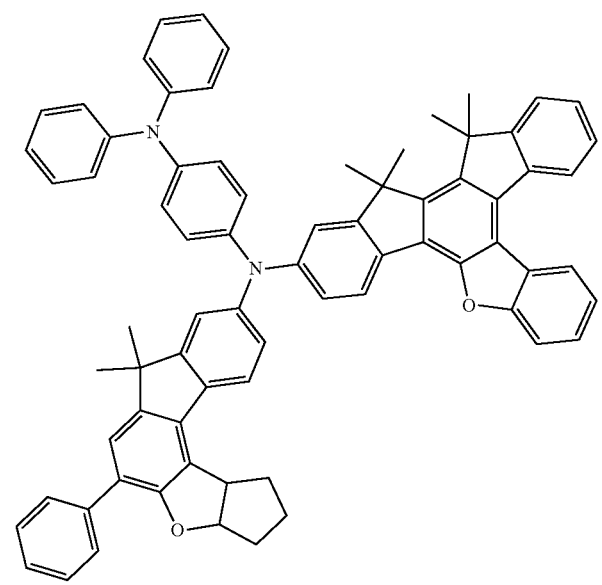 [SMILES: CC1(C)c2cc(N(c3ccc(N(c4ccccc4)c4ccccc4)cc3)c3ccc4c(c3)C(C)(C)c3c5c(c6c(oc7ccccc76)c3-4)-c3ccccc3C5(C)C)ccc2-c2c1cc(-c1ccccc1)c1c2C2CCCC2O1]

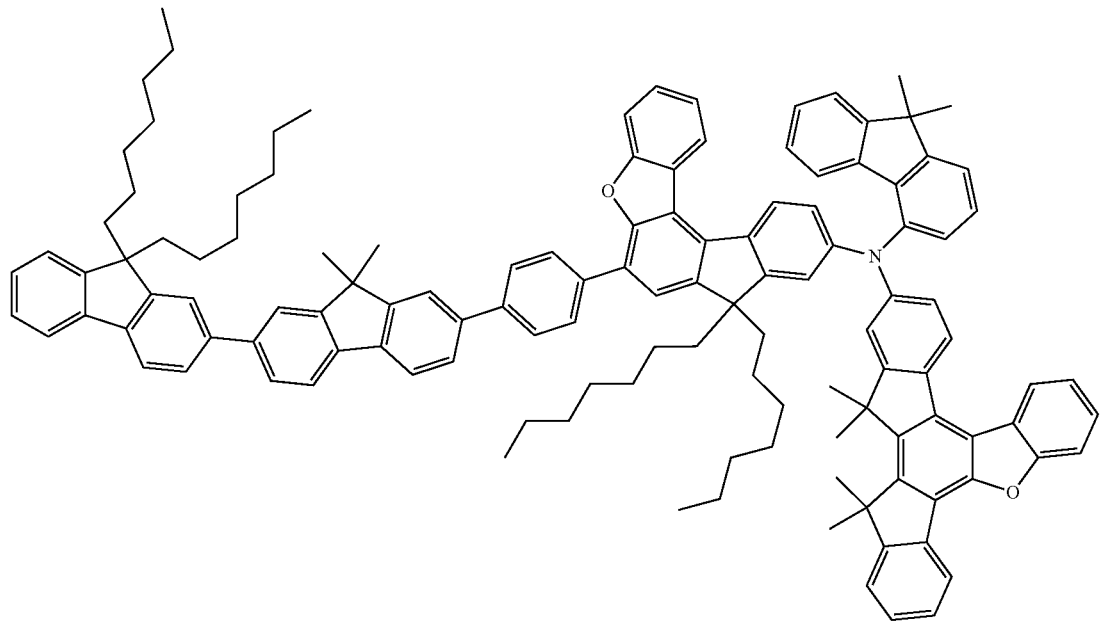 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8cccc9c8-c8ccccc8C9(C)C)cc6C7(CCCCCCC)CCCCCCC)cc5)ccc3-4)cc21]
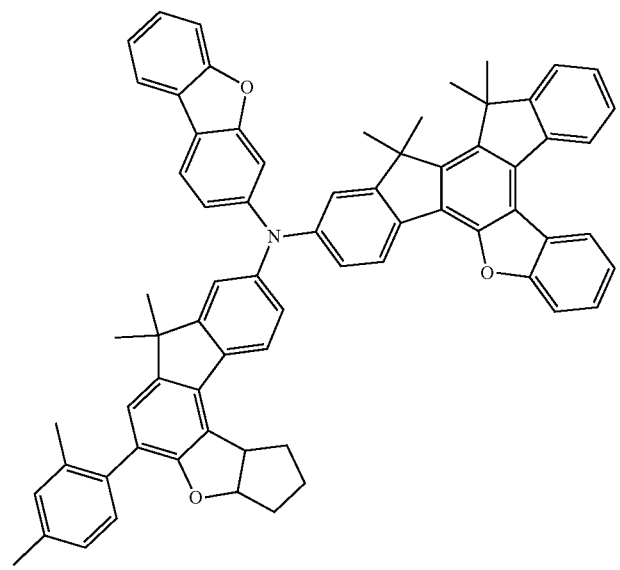 [SMILES: Cc1ccc(-c2cc3c(c4c2OC2CCCC42)-c2ccc(N(c4ccc5c(c4)C(C)(C)c4c6c(c7c(oc8ccccc87)c4-5)-c4ccccc4C6(C)C)c4ccc5c(c4)oc4ccccc45)cc2C3(C)C)c(C)c1]

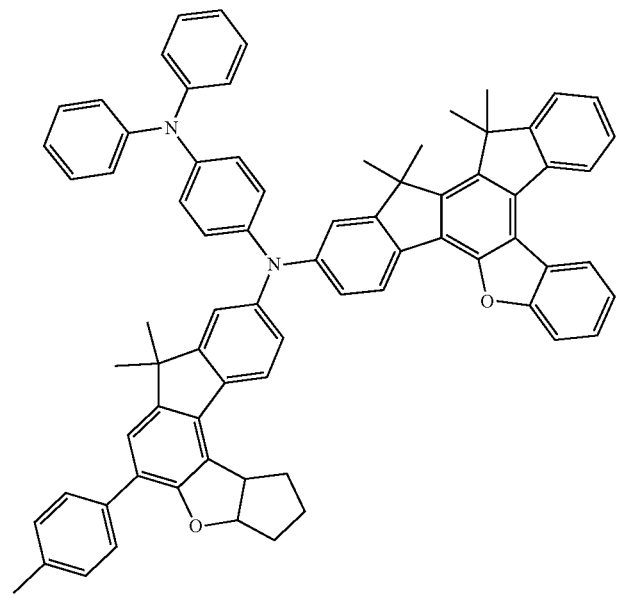 [SMILES: Cc1ccc(-c2cc3c(c4c2OC2CCCC42)-c2ccc(N(c4ccc(N(c5ccccc5)c5ccccc5)cc4)c4ccc5c(c4)C(C)(C)c4c6c(c7c(oc8ccccc87)c4-5)-c4ccccc4C6(C)C)cc2C3(C)C)cc1]
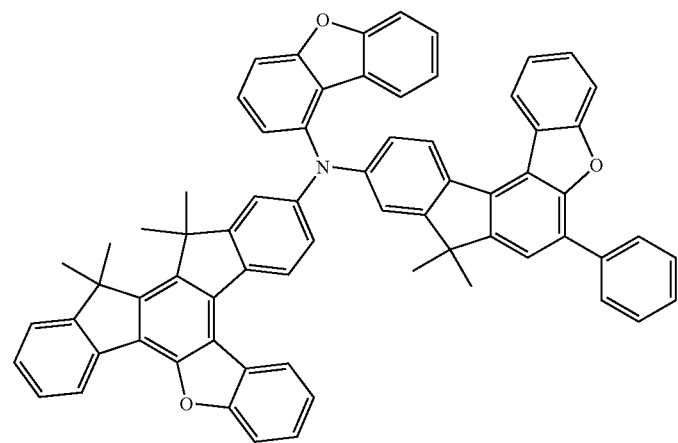 [SMILES: CC1(C)c2cc(N(c3ccc4c(c3)C(C)(C)c3c5c(c6oc7ccccc7c6c3-4)-c3ccccc3C5(C)C)c3cccc4oc5ccccc5c34)ccc2-c2c1cc(-c1ccccc1)c1oc3ccccc3c21]
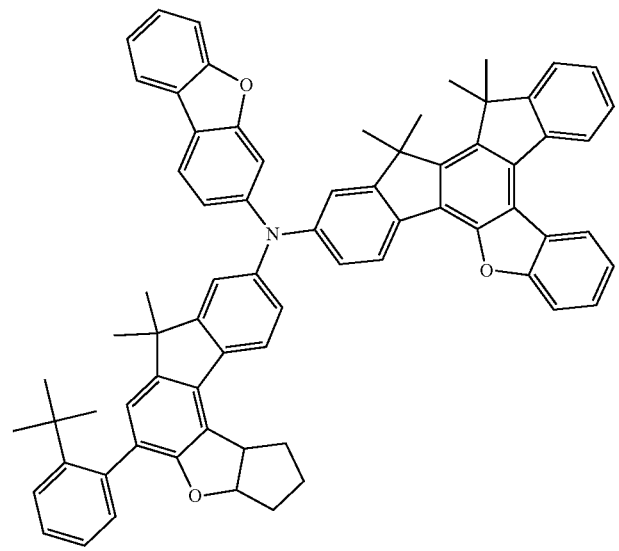 [SMILES: CC(C)(C)c1ccccc1-c1cc2c(c3c1OC1CCCC31)-c1ccc(N(c3ccc4c(c3)C(C)(C)c3c5c(c6c(oc7ccccc76)c3-4)-c3ccccc3C5(C)C)c3ccc4c(c3)oc3ccccc34)cc1C2(C)C]

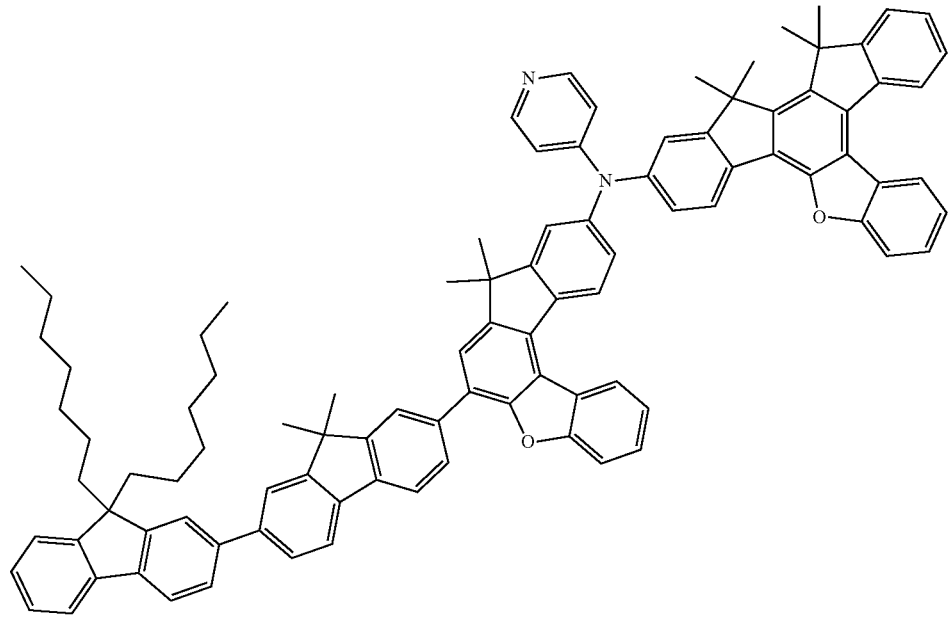 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccncc7)c7ccc8c(c7)C(C)(C)c7c9c(c%10c(oc%11ccccc%11%10)c7-8)-c7ccccc7C9(C)C)cc5C6(C)C)ccc3-4)cc21]
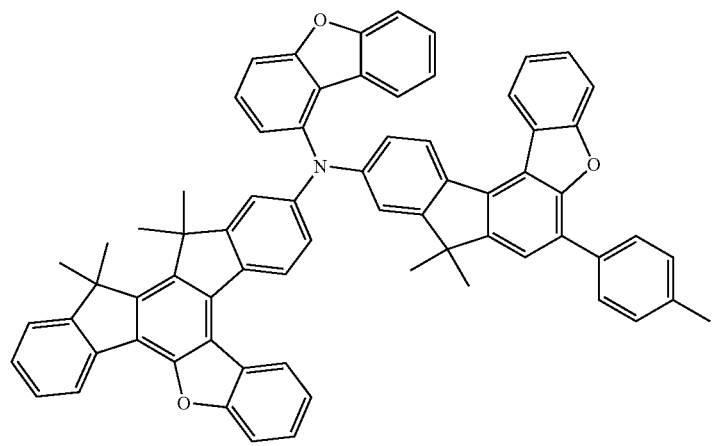 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4cccc5oc6ccccc6c45)cc2C3(C)C)cc1]
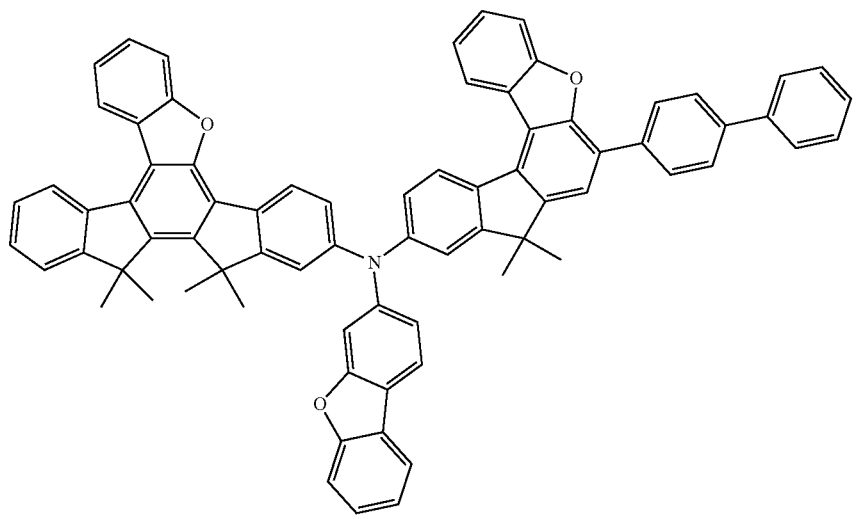 [SMILES: CC1(C)c2cc(N(c3ccc4c(c3)C(C)(C)c3c5c(c6c(oc7ccccc76)c3-4)-c3ccccc3C5(C)C)c3ccc4c(c3)oc3ccccc34)ccc2-c2c1cc(-c1ccc(-c3ccccc3)cc1)c1oc3ccccc3c21]

-continued
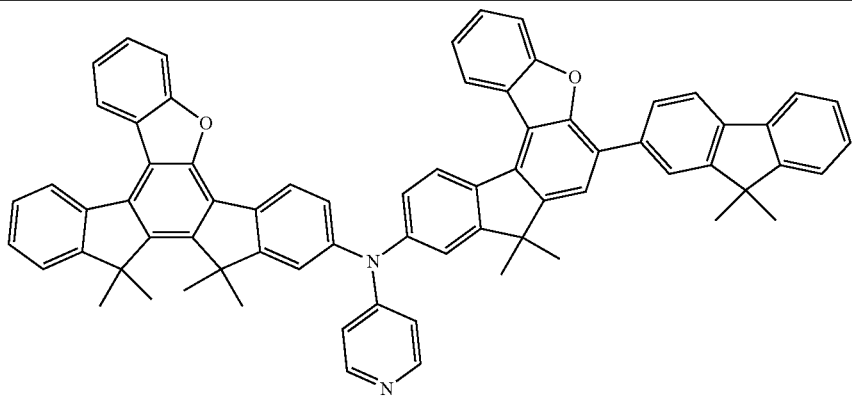
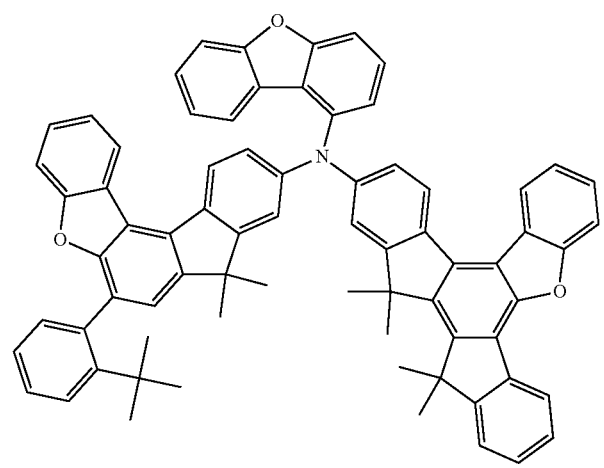 [SMILES: CC(C)(C)c1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3cccc4oc5ccccc5c34)cc1C2(C)C]
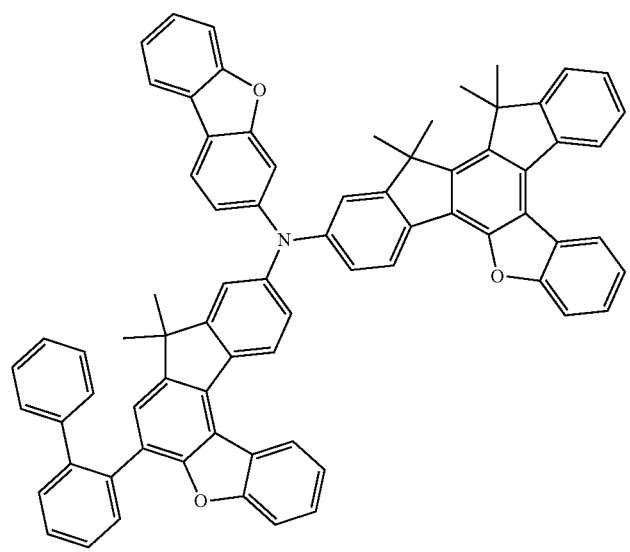 [SMILES: CC1(C)c2cc(N(c3ccc4c(c3)C(C)(C)c3c5c(c6c(oc7ccccc76)c3-4)-c3ccccc3C5(C)C)c3ccc4c(c3)oc3ccccc34)ccc2-c2c1cc(-c1ccccc1-c1ccccc1)c1oc3ccccc3c21]

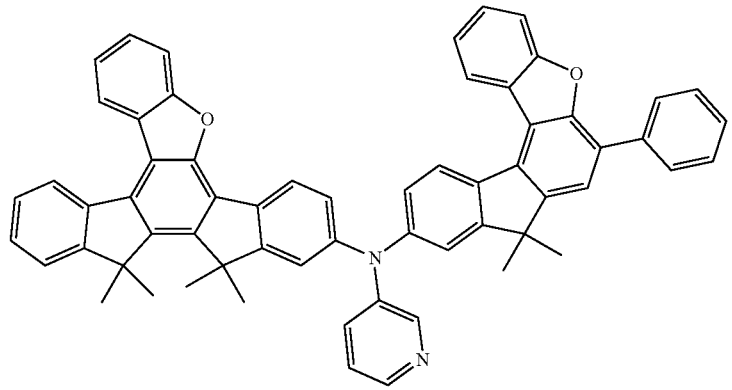 [SMILES: CC1(C)c2cc(N(c3cccnc3)c3ccc4c(c3)C(C)(C)c3c5c(c6c(oc7ccccc76)c3-4)-c3ccccc3C5(C)C)ccc2-c2c1cc(-c1ccccc1)c1oc3ccccc3c21]
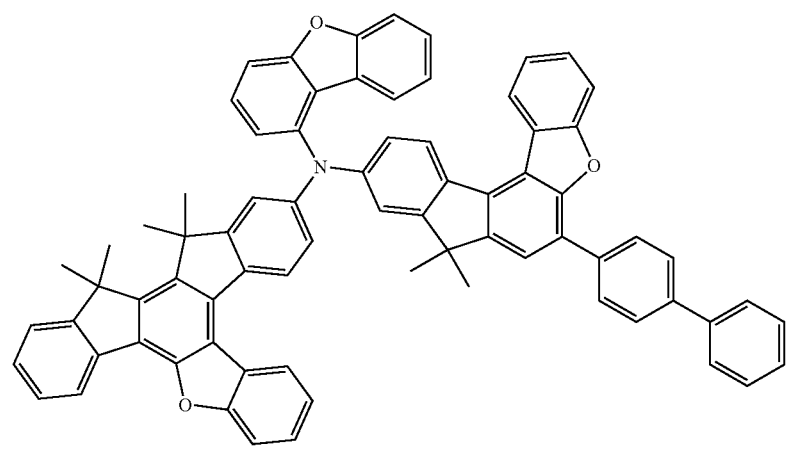 [SMILES: CC1(C)c2cc(N(c3ccc4c(c3)C(C)(C)c3c5c(c6oc7ccccc7c6c3-4)-c3ccccc3C5(C)C)c3cccc4oc5ccccc5c34)ccc2-c2c1cc(-c1ccc(-c3ccccc3)cc1)c1oc3ccccc3c21]
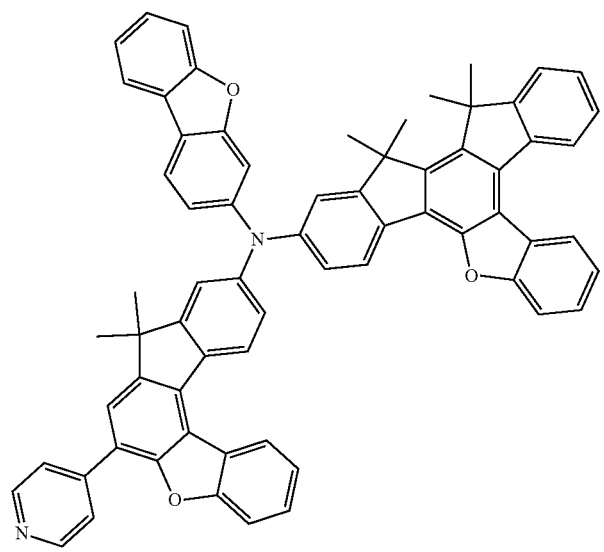 [SMILES: CC1(C)c2cc(N(c3ccc4c(c3)C(C)(C)c3c5c(c6c(oc7ccccc76)c3-4)-c3ccccc3C5(C)C)c3ccc4c(c3)oc3ccccc34)ccc2-c2c1cc(-c1ccncc1)c1oc3ccccc3c21]

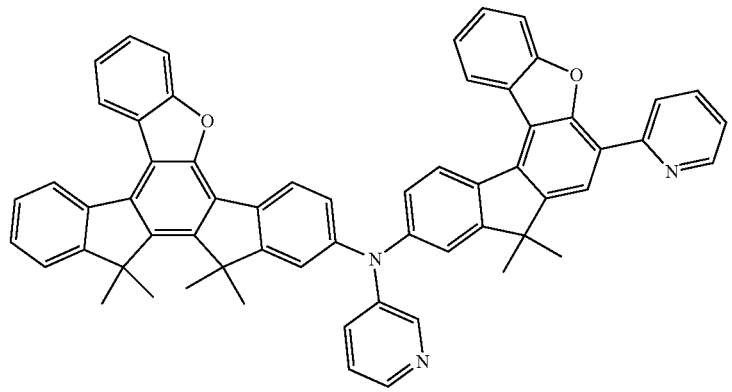
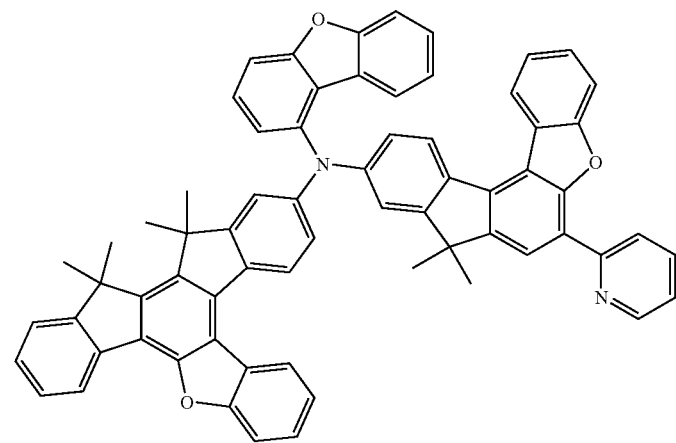 [SMILES: CC1(C)c2cc(N(c3ccc4c(c3)C(C)(C)c3c5c(c6oc7ccccc7c6c3-4)-c3ccccc3C5(C)C)c3cccc4oc5ccccc5c34)ccc2-c2c1cc(-c1ccccn1)c1oc3ccccc3c21]
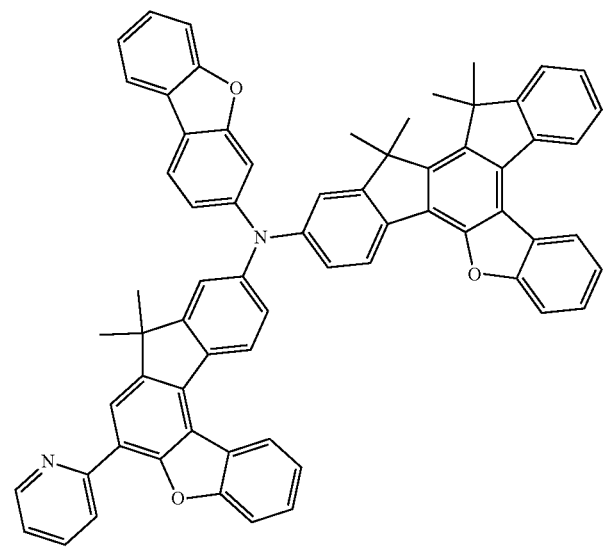 [SMILES: CC1(C)c2cc(N(c3ccc4c(c3)C(C)(C)c3c5c(c6c(oc7ccccc76)c3-4)-c3ccccc3C5(C)C)c3ccc4c(c3)oc3ccccc34)ccc2-c2c1cc(-c1ccccn1)c1oc3ccccc3c21]

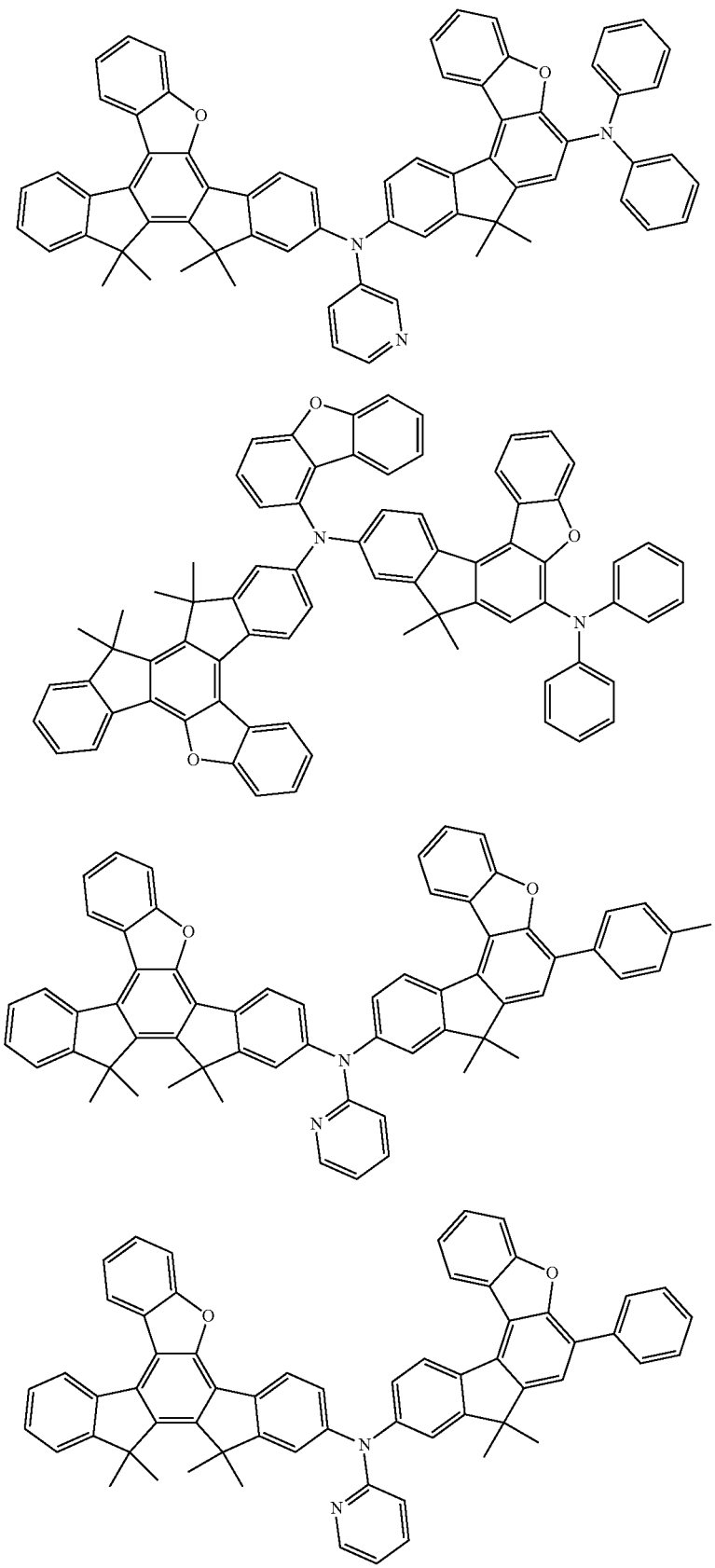

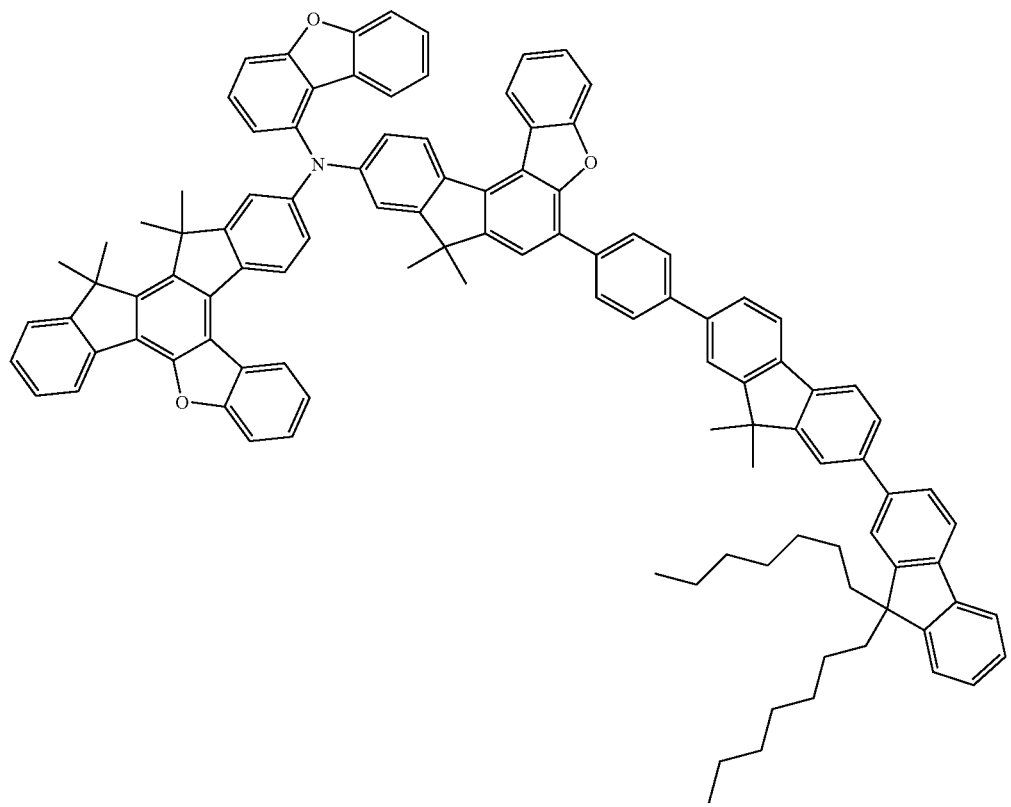 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8cccc9oc%10ccccc%10c89)cc6C7(C)C)cc5)ccc3-4)cc21]
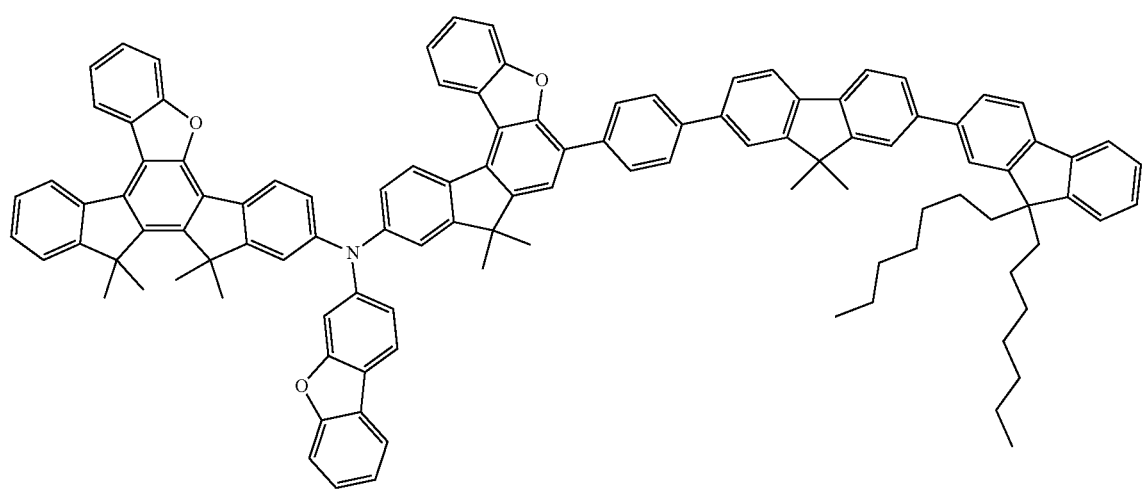 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11c(oc%12ccccc%12%11)c8-9)-c8ccccc8C%10(C)C)c8ccc9c(c8)oc8ccccc89)cc6C7(C)C)cc5)ccc3-4)cc21]

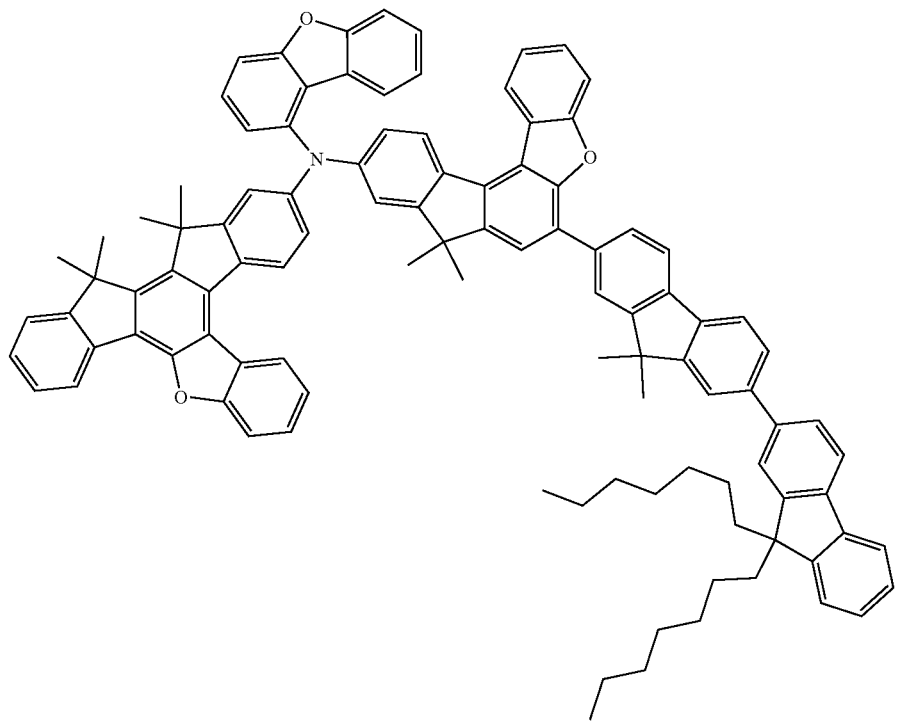 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7cccc8oc9ccccc9c78)cc5C6(C)C)ccc3-4)cc21]
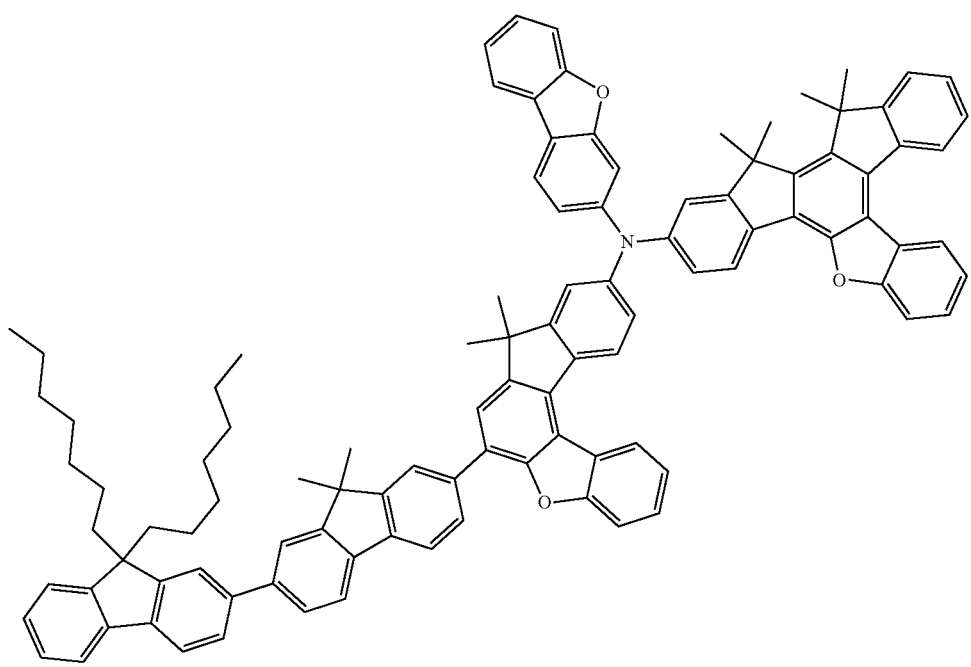 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10c(oc%11ccccc%11%10)c7-8)-c7ccccc7C9(C)C)c7ccc8c(c7)oc7ccccc78)cc5C6(C)C)ccc3-4)cc21]

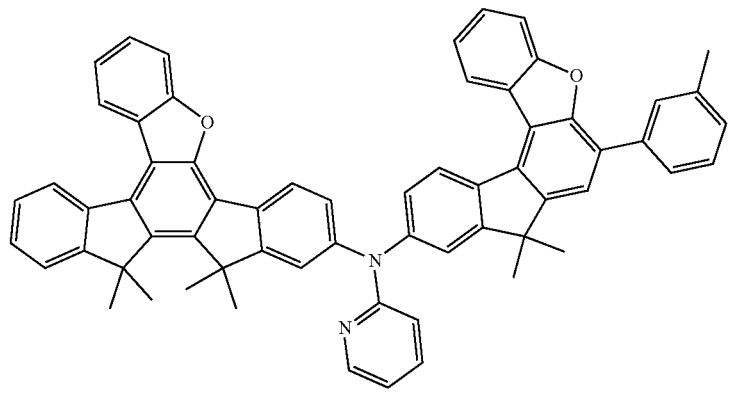 [SMILES: Cc1cccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccccn4)cc2C3(C)C)c1]
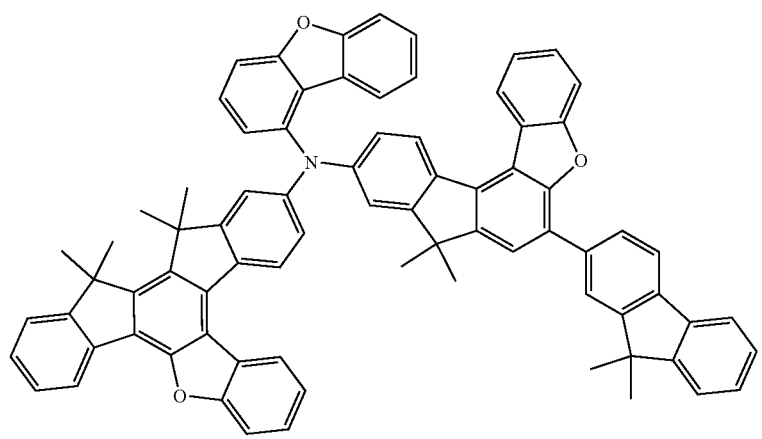 [SMILES: CC1(C)c2ccccc2-c2ccc(-c3cc4c(c5c3oc3ccccc35)-c3ccc(N(c5ccc6c(c5)C(C)(C)c5c7c(c8oc9ccccc9c8c5-6)-c5ccccc5C7(C)C)c5cccc6oc7ccccc7c56)cc3C4(C)C)cc21]
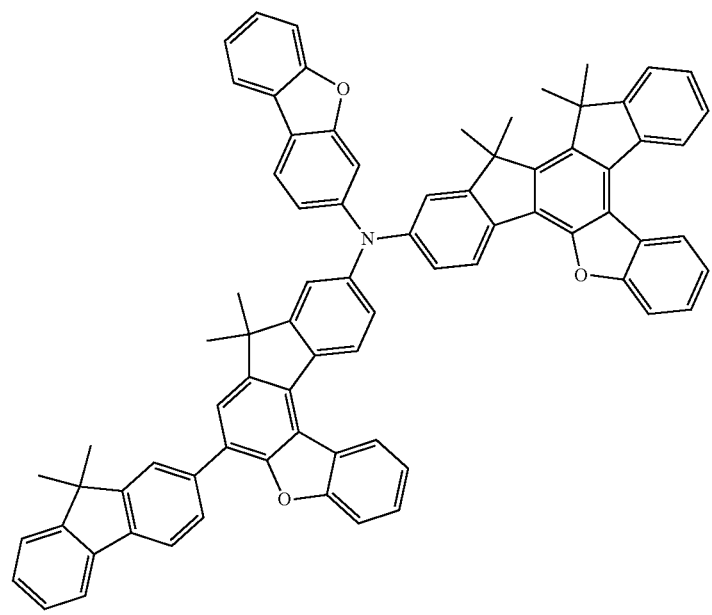 [SMILES: CC1(C)c2ccccc2-c2ccc(-c3cc4c(c5c3oc3ccccc35)-c3ccc(N(c5ccc6c(c5)C(C)(C)c5c7c(c8c(oc9ccccc98)c5-6)-c5ccccc5C7(C)C)c5ccc6c(c5)oc5ccccc56)cc3C4(C)C)cc21]

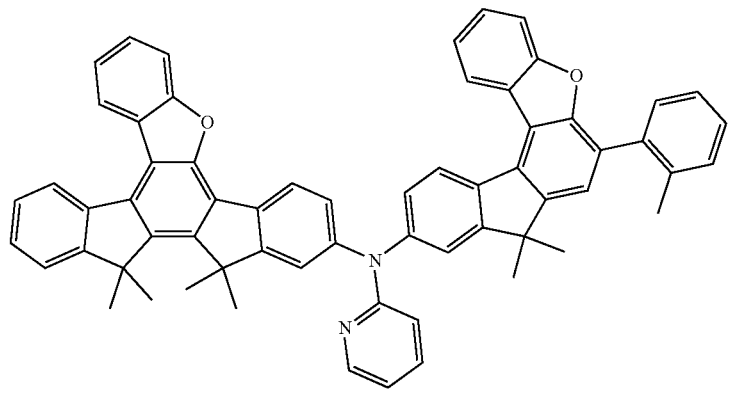 [SMILES: Cc1ccccc1-c1cc2c(c3c1oc1ccccc13)-c1ccc(N(c3ccc4c(c3)C(C)(C)c3c5c(c6c(oc7ccccc76)c3-4)-c3ccccc3C5(C)C)c3ccccn3)cc1C2(C)C]
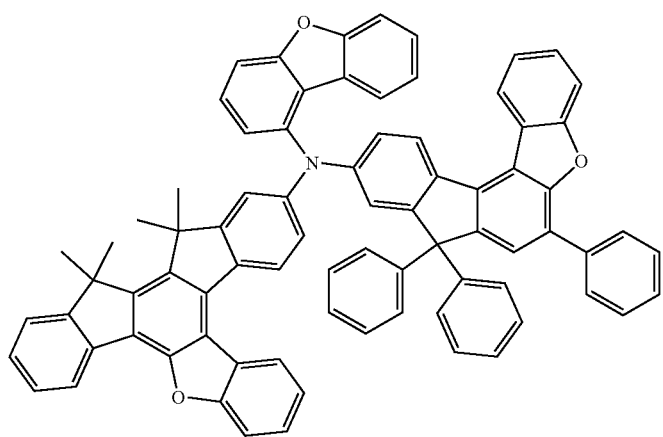 [SMILES: CC1(C)c2ccccc2-c2c1c1c(c3c2oc2ccccc23)-c2ccc(N(c3ccc4c(c3)C(c3ccccc3)(c3ccccc3)c3cc(-c5ccccc5)c5oc6ccccc6c5c3-4)c3cccc4oc5ccccc5c34)cc2C1(C)C]
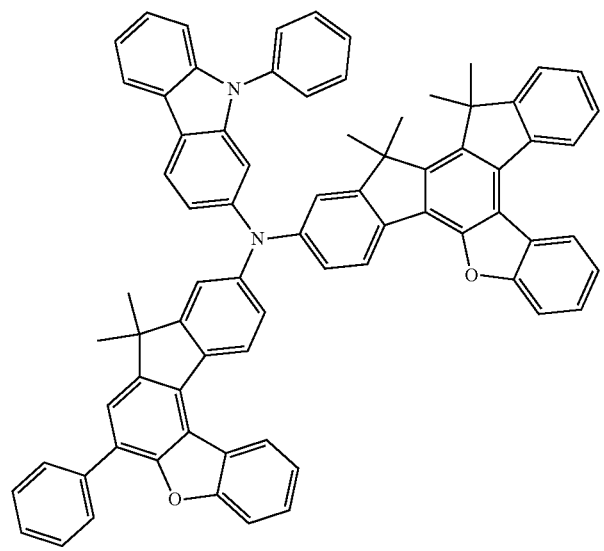 [SMILES: CC1(C)c2cc(N(c3ccc4c(c3)C(C)(C)c3c5c(c6c(oc7ccccc76)c3-4)-c3ccccc3C5(C)C)c3ccc4c5ccccc5n(-c5ccccc5)c4c3)ccc2-c2c1cc(-c1ccccc1)c1oc3ccccc3c21]

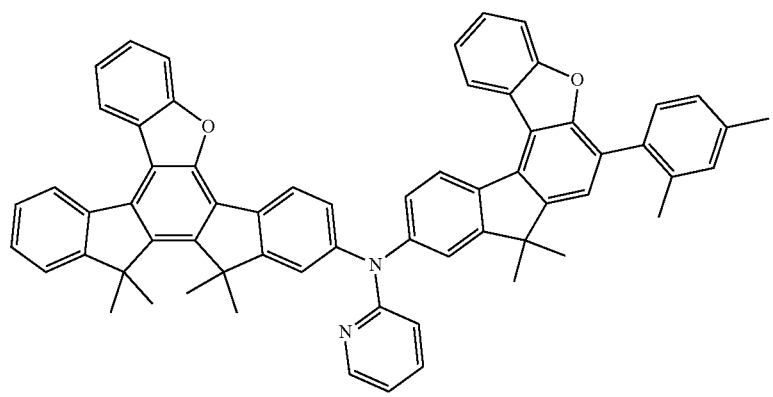 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccccn4)cc2C3(C)C)c(C)c1]
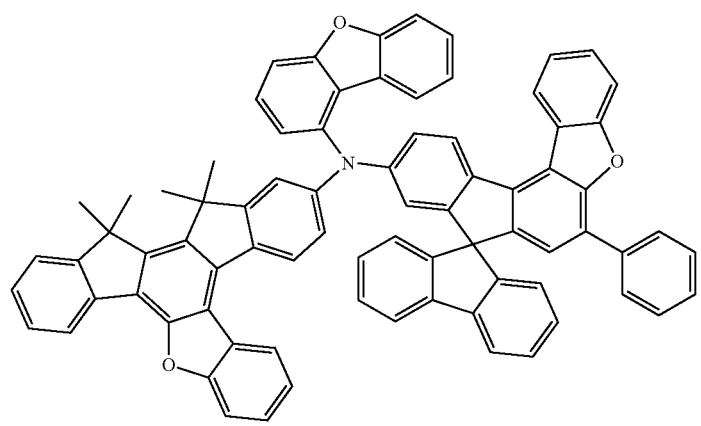 [SMILES: CC1(C)c2ccccc2-c2c1c1c(c3c2oc2ccccc23)-c2ccc(N(c3ccc4c(c3)C3(c5ccccc5-c5ccccc53)c3cc(-c5ccccc5)c5oc6ccccc6c5c3-4)c3cccc4oc5ccccc5c34)cc2C1(C)C]
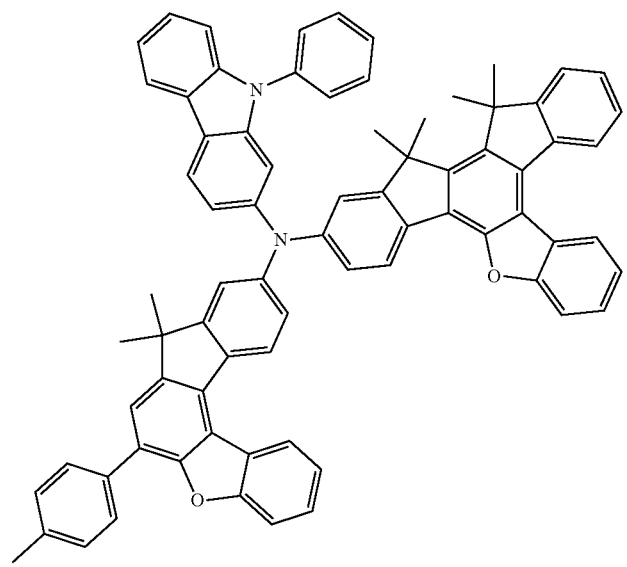 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccc5c6ccccc6n(-c6ccccc6)c5c4)cc2C3(C)C)cc1]

-continued
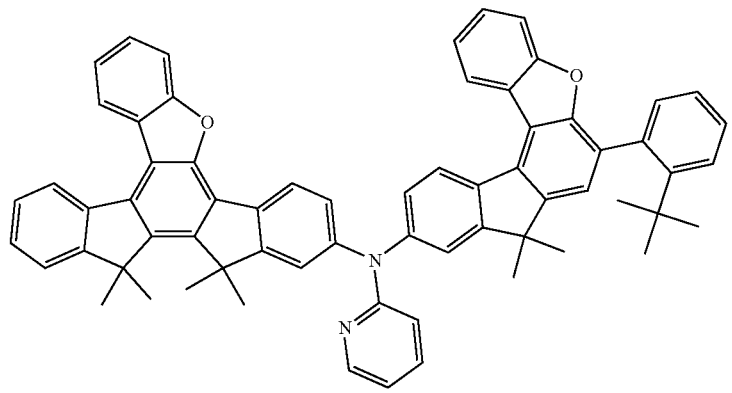 [SMILES: CC(C)(C)c1ccccc1-c1cc2c(c3c1oc1ccccc13)-c1ccc(N(c3ccc4c(c3)C(C)(C)c3c5c(c6c(oc7ccccc76)c3-4)-c3ccccc3C5(C)C)c3ccccn3)cc1C2(C)C]
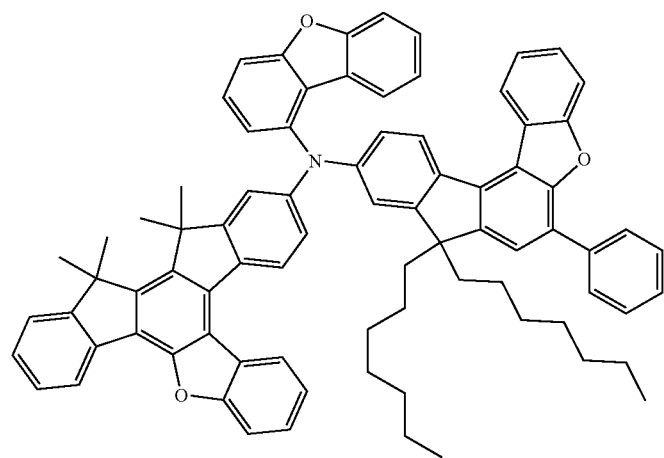 [SMILES: CCCCCCCC1(CCCCCCC)c2cc(N(c3ccc4c(c3)C(C)(C)c3c5c(c6oc7ccccc7c6c3-4)-c3ccccc3C5(C)C)c3cccc4oc5ccccc5c34)ccc2-c2c1cc(-c1ccccc1)c1oc3ccccc3c21]
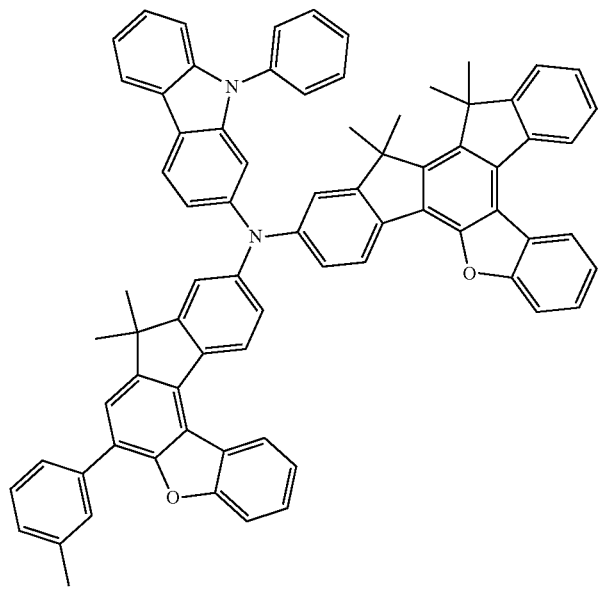 [SMILES: Cc1cccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccc5c6ccccc6n(-c6ccccc6)c5c4)cc2C3(C)C)c1]

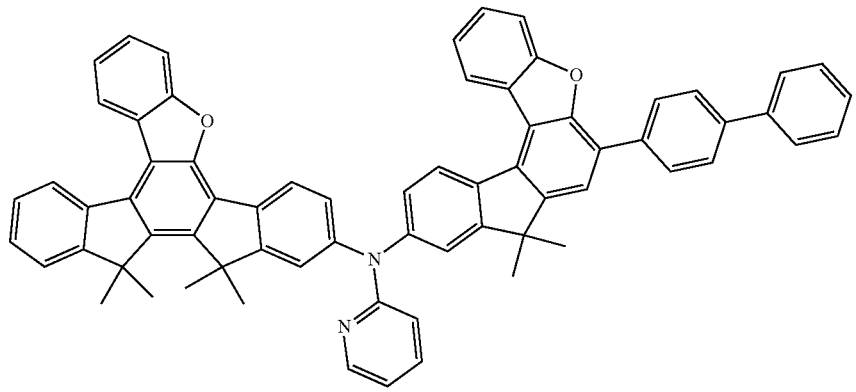 [SMILES: CC1(C)c2cc(N(c3ccc4c(c3)C(C)(C)c3c5c(c6c(oc7ccccc76)c3-4)-c3ccccc3C5(C)C)c3ccccn3)ccc2-c2c1cc(-c1ccc(-c3ccccc3)cc1)c1oc3ccccc3c21]
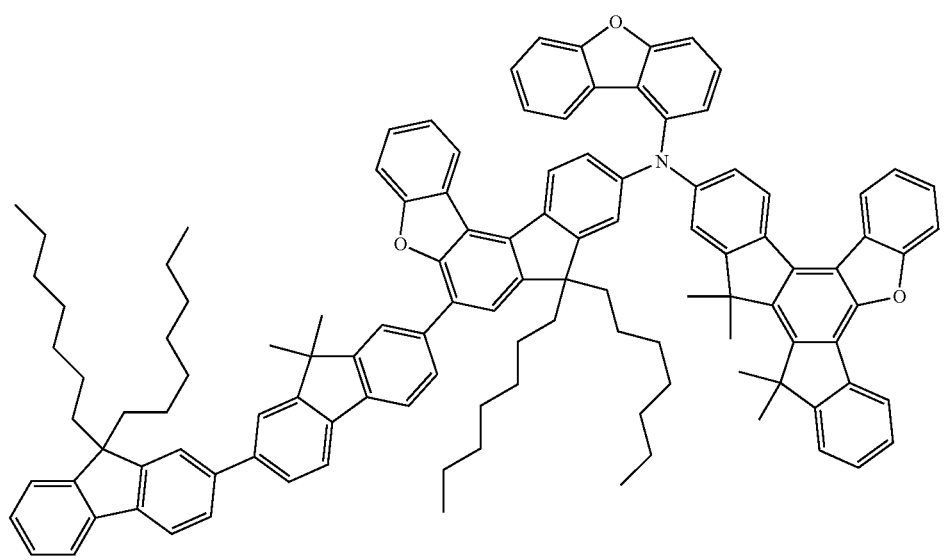 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7cccc8oc9ccccc9c78)cc5C6(CCCCCCC)CCCCCCC)ccc3-4)cc21]
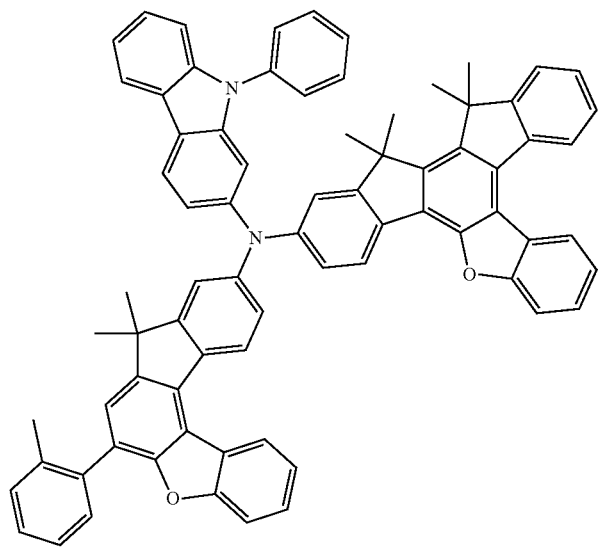 [SMILES: Cc1ccccc1-c1cc2c(c3c1oc1ccccc13)-c1ccc(N(c3ccc4c(c3)C(C)(C)c3c5c(c6c(oc7ccccc76)c3-4)-c3ccccc3C5(C)C)c3ccc4c5ccccc5n(-c5ccccc5)c4c3)cc1C2(C)C]

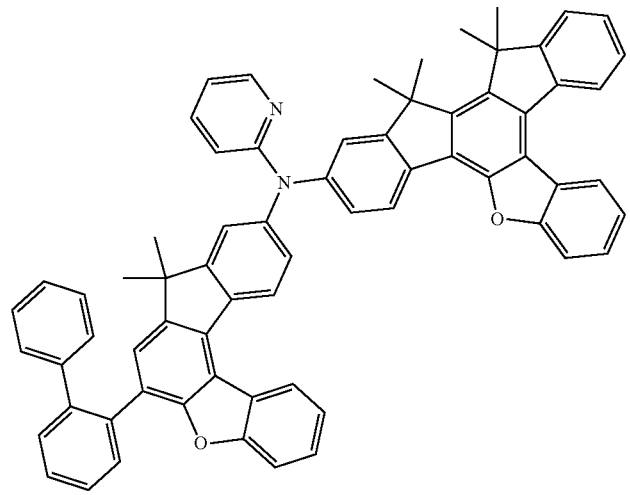 [SMILES: CC1(C)c2cc(N(c3ccc4c(c3)C(C)(C)c3c5c(c6c(oc7ccccc76)c3-4)-c3ccccc3C5(C)C)c3ccccn3)ccc2-c2c1cc(-c1ccccc1-c1ccccc1)c1oc3ccccc3c21]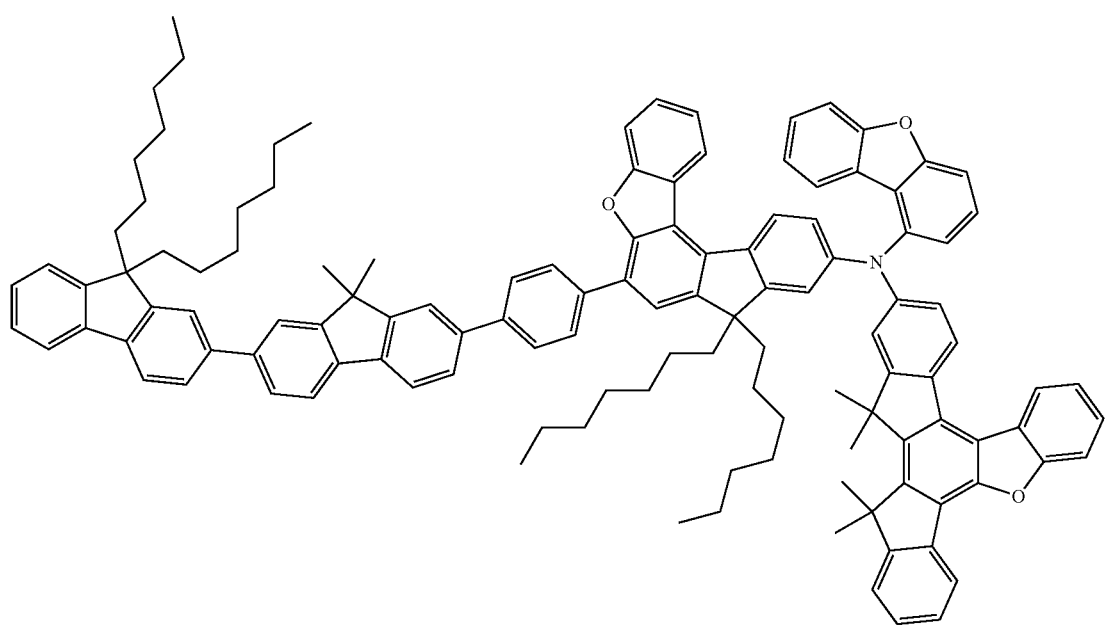 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8cccc9oc%10ccccc%10c89)cc6C7(CCCCCCC)CCCCCCC)cc5)ccc3-4)cc21]

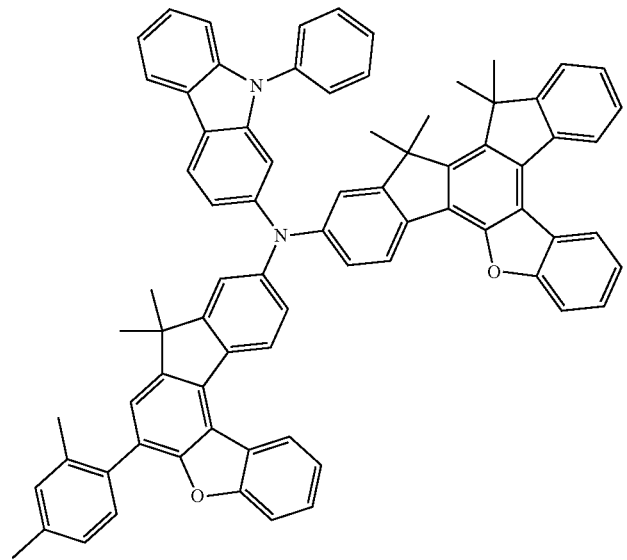 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ccc5c6ccccc6n(-c6ccccc6)c5c4)cc2C3(C)C)c(C)c1]
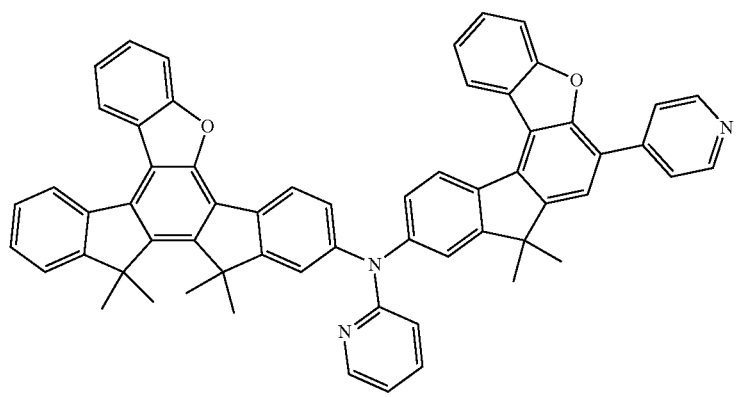 [SMILES: CC1(C)c2cc(N(c3ccc4c(c3)C(C)(C)c3c5c(c6c(oc7ccccc76)c3-4)-c3ccccc3C5(C)C)c3ccccn3)ccc2-c2c1cc(-c1ccncc1)c1oc3ccccc3c21]
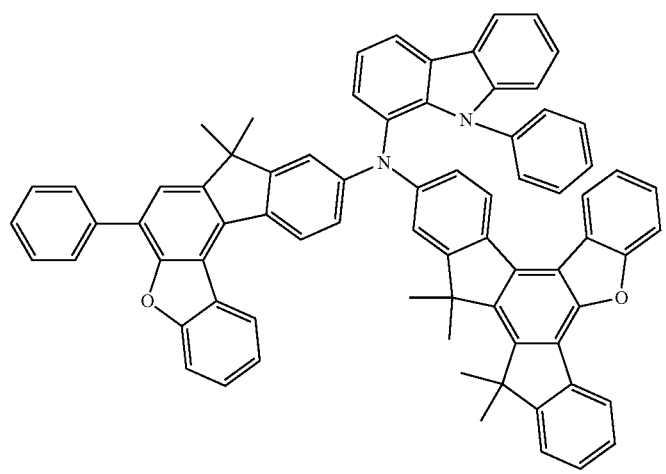 [SMILES: CC1(C)c2cc(N(c3ccc4c(c3)C(C)(C)c3c5c(c6oc7ccccc7c6c3-4)-c3ccccc3C5(C)C)c3cccc4c5ccccc5n(-c5ccccc5)c34)ccc2-c2c1cc(-c1ccccc1)c1oc3ccccc3c21]

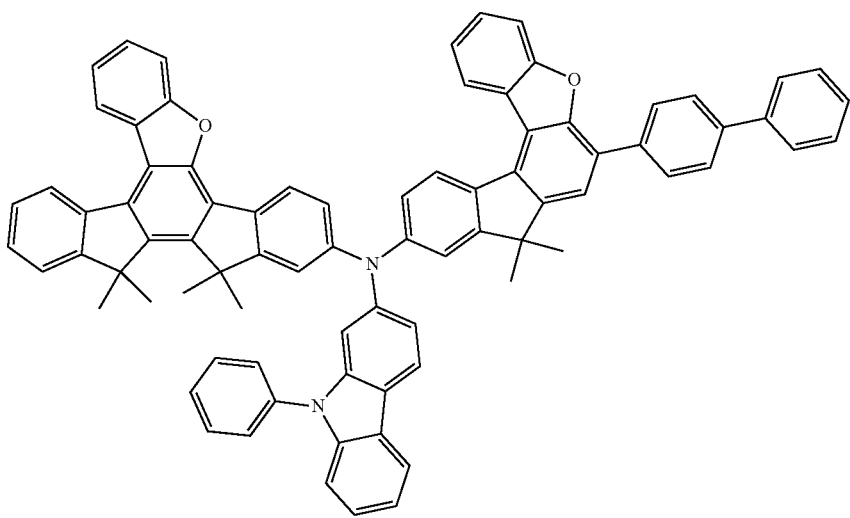 [SMILES: CC1(C)c2cc(N(c3ccc4c(c3)C(C)(C)c3c5c(c6c(oc7ccccc76)c3-4)-c3ccccc3C5(C)C)c3ccc4c5ccccc5n(-c5ccccc5)c4c3)ccc2-c2c1cc(-c1ccc(-c3ccccc3)cc1)c1oc3ccccc3c21]
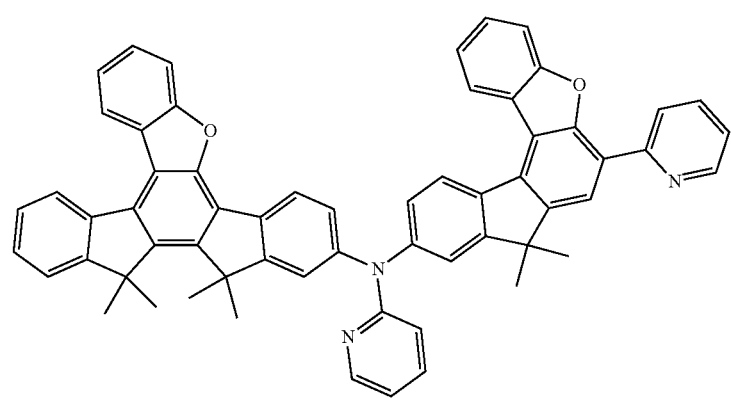 [SMILES: CC1(C)c2cc(N(c3ccc4c(c3)C(C)(C)c3c5c(c6c(oc7ccccc76)c3-4)-c3ccccc3C5(C)C)c3ccccn3)ccc2-c2c1cc(-c1ccccn1)c1oc3ccccc3c21]

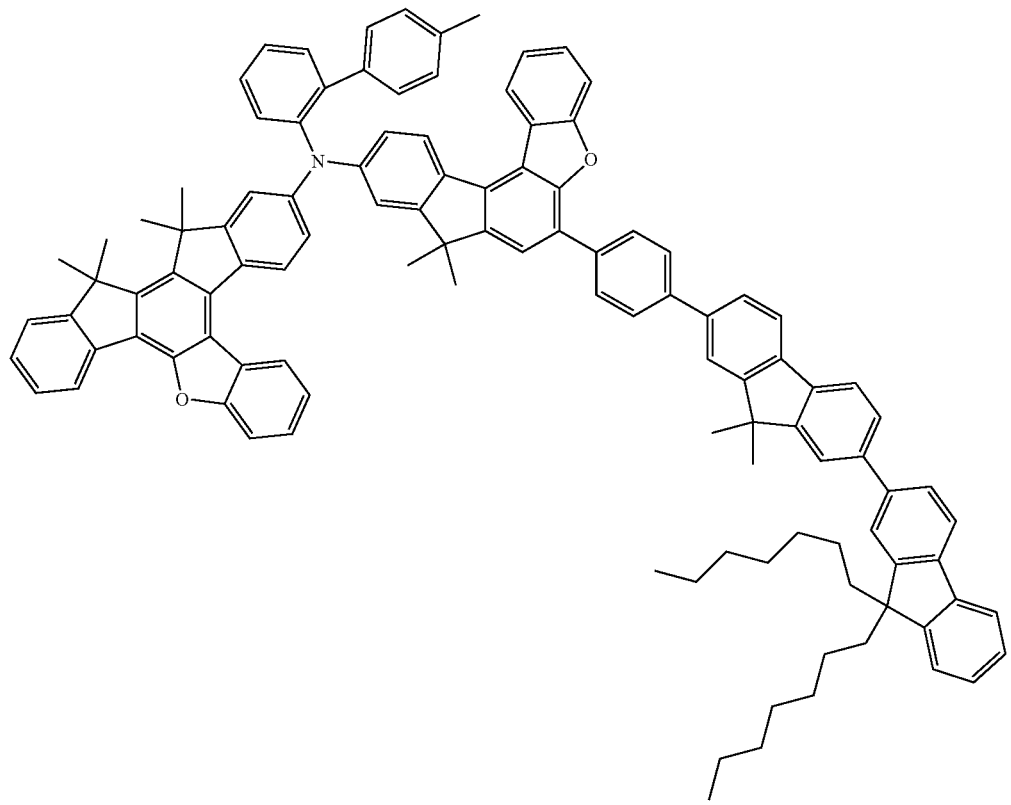 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11oc%12ccccc%12c%11c8-9)-c8ccccc8C%10(C)C)c8ccccc8-c8ccc(C)cc8)cc6C7(C)C)cc5)ccc3-4)cc21]
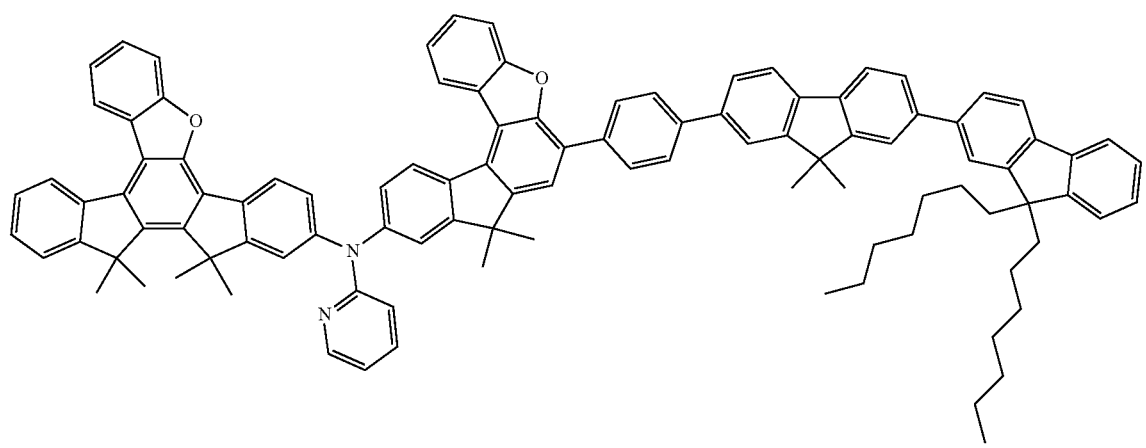 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11c(oc%12ccccc%12%11)c8-9)-c8ccccc8C%10(C)C)c8ccccn8)cc6C7(C)C)cc5)ccc3-4)cc21]

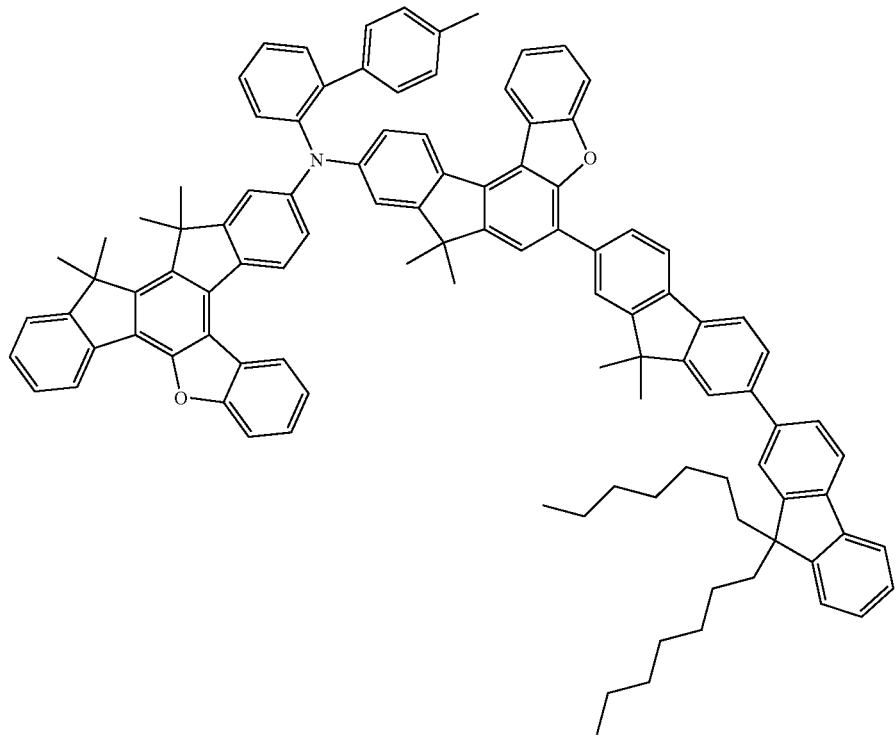 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10oc%11ccccc%11c%10c7-8)-c7ccccc7C9(C)C)c7ccccc7-c7ccc(C)cc7)cc5C6(C)C)ccc3-4)cc21]
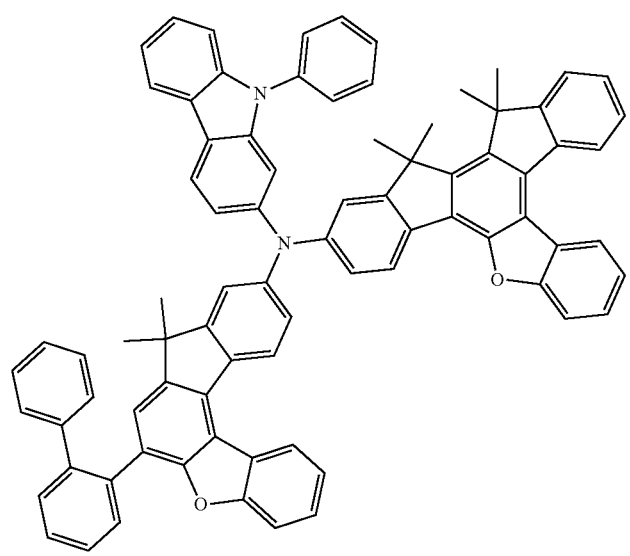 [SMILES: CC1(C)c2cc(N(c3ccc4c(c3)C(C)(C)c3c5c(c6c(oc7ccccc76)c3-4)-c3ccccc3C5(C)C)c3ccc4c5ccccc5n(-c5ccccc5)c4c3)ccc2-c2c1cc(-c1ccccc1-c1ccccc1)c1oc3ccccc3c21]

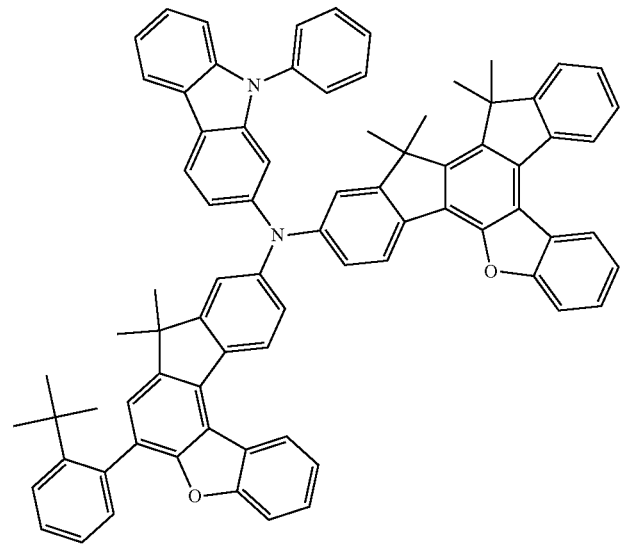 [SMILES: CC(C)(C)c1ccccc1-c1cc2c(c3c1oc1ccccc13)-c1ccc(N(c3ccc4c(c3)C(C)(C)c3c5c(c6c(oc7ccccc76)c3-4)-c3ccccc3C5(C)C)c3ccc4c5ccccc5n(-c5ccccc5)c4c3)cc1C2(C)C]
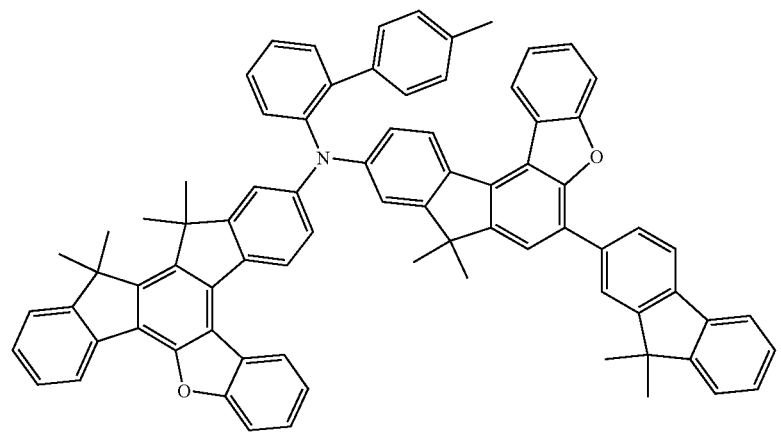 [SMILES: Cc1ccc(-c2ccccc2N(c2ccc3c(c2)C(C)(C)c2cc(-c4ccc5c(c4)C(C)(C)c4ccccc4-5)c4oc5ccccc5c4c2-3)c2ccc3c(c2)C(C)(C)c2c4c(c5oc6ccccc6c5c2-3)-c2ccccc2C4(C)C)cc1]
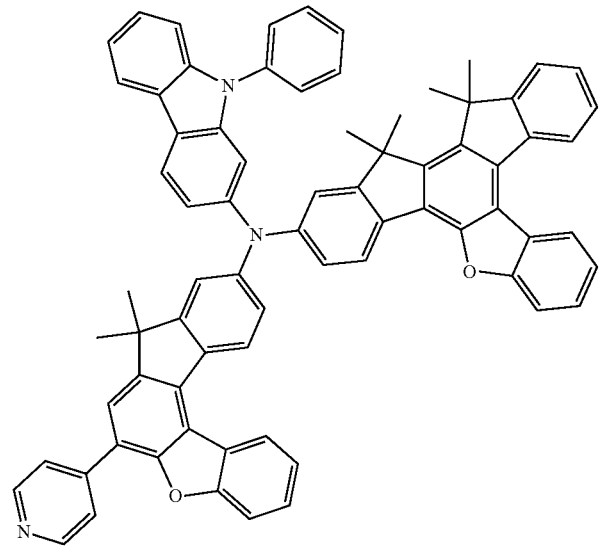 [SMILES: CC1(C)c2cc(N(c3ccc4c(c3)C(C)(C)c3c5c(c6c(oc7ccccc76)c3-4)-c3ccccc3C5(C)C)c3ccc4c5ccccc5n(-c5ccccc5)c4c3)ccc2-c2c1cc(-c1ccncc1)c1oc3ccccc3c21]

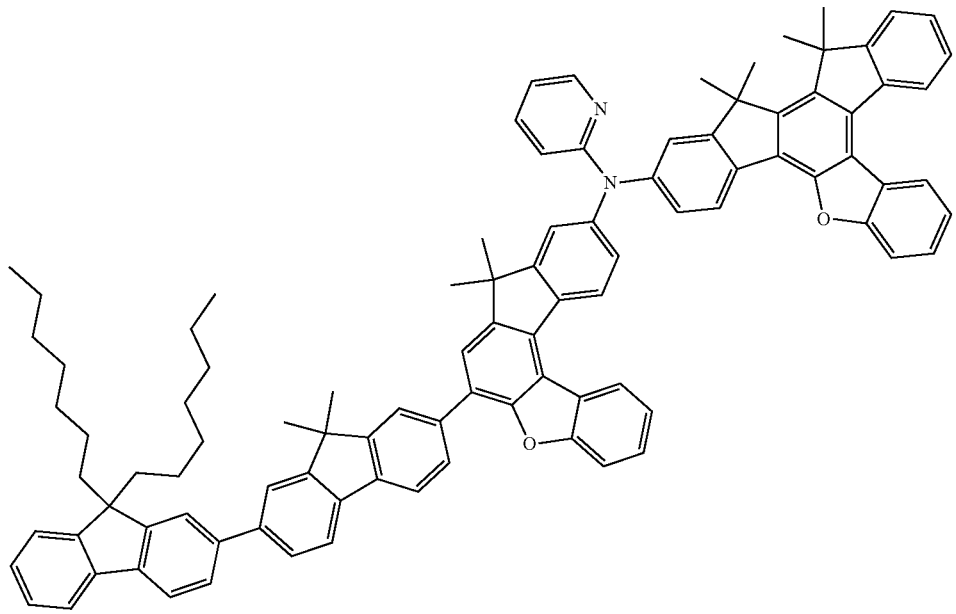 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10c(oc%11ccccc%11%10)c7-8)-c7ccccc7C9(C)C)c7ccccn7)cc5C6(C)C)ccc3-4)cc21]
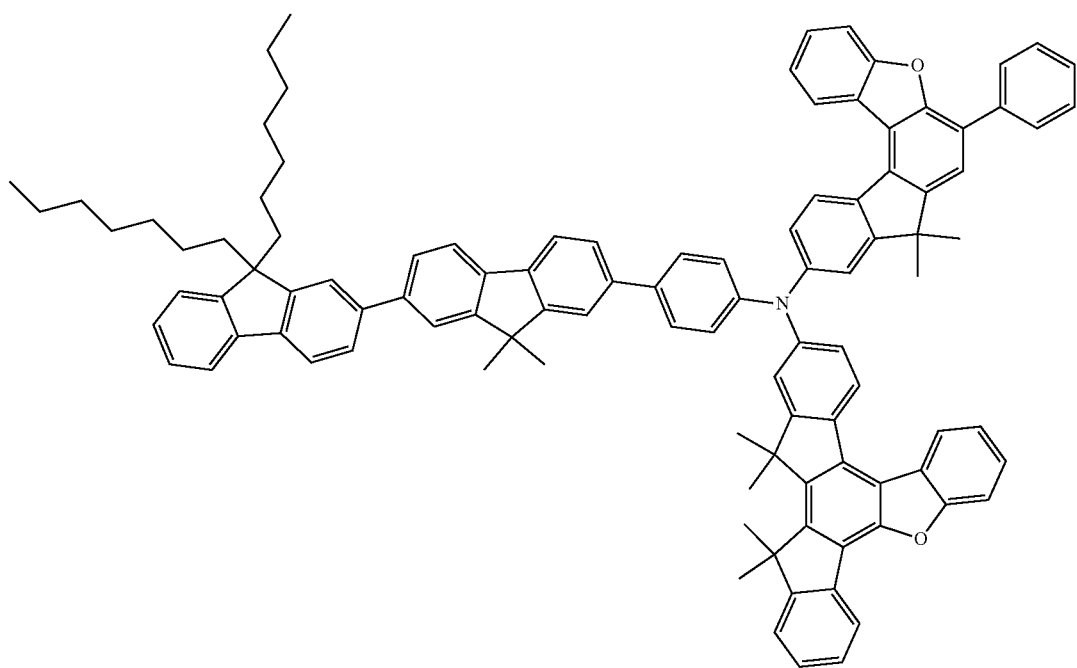 [SMILES: CCCCCCCC1(CCCCCCC)c2ccccc2-c2ccc(-c3ccc4c(c3)C(C)(C)c3cc(-c5ccc(N(c6ccc7c(c6)C(C)(C)c6cc(-c8ccccc8)c8oc9ccccc9c8c6-7)c6ccc7c(c6)C(C)(C)c6c8c(c9oc%10ccccc%10c9c6-7)-c6ccccc6C8(C)C)cc5)ccc3-4)cc21]

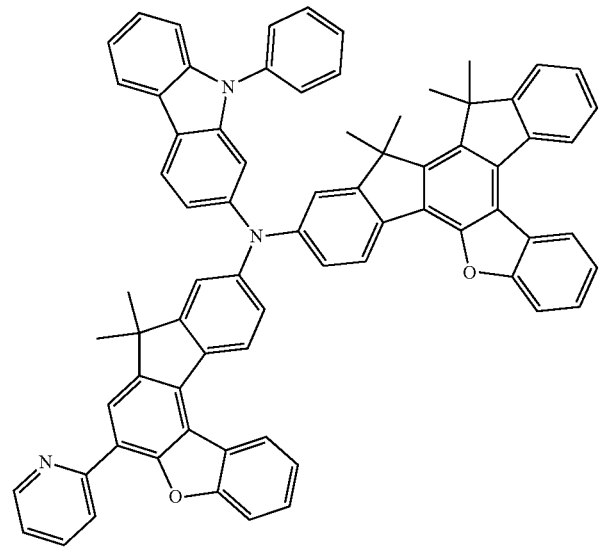 [SMILES: CC1(C)c2cc(N(c3ccc4c(c3)C(C)(C)c3c5c(c6c(oc7ccccc76)c3-4)-c3ccccc3C5(C)C)c3ccc4c5ccccc5n(-c5ccccc5)c4c3)ccc2-c2c1cc(-c1ccccn1)c1oc3ccccc3c21]
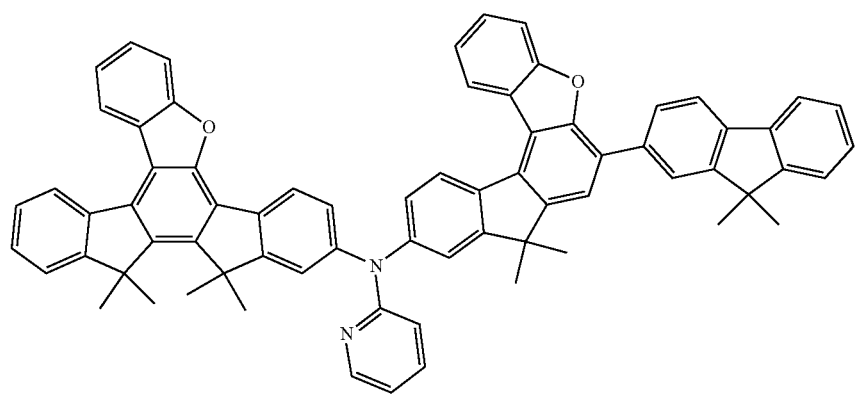 [SMILES: CC1(C)c2ccccc2-c2ccc(-c3cc4c(c5c3oc3ccccc35)-c3ccc(N(c5ccc6c(c5)C(C)(C)c5c7c(c8c(oc9ccccc98)c5-6)-c5ccccc5C7(C)C)c5ccccn5)cc3C4(C)C)cc21]

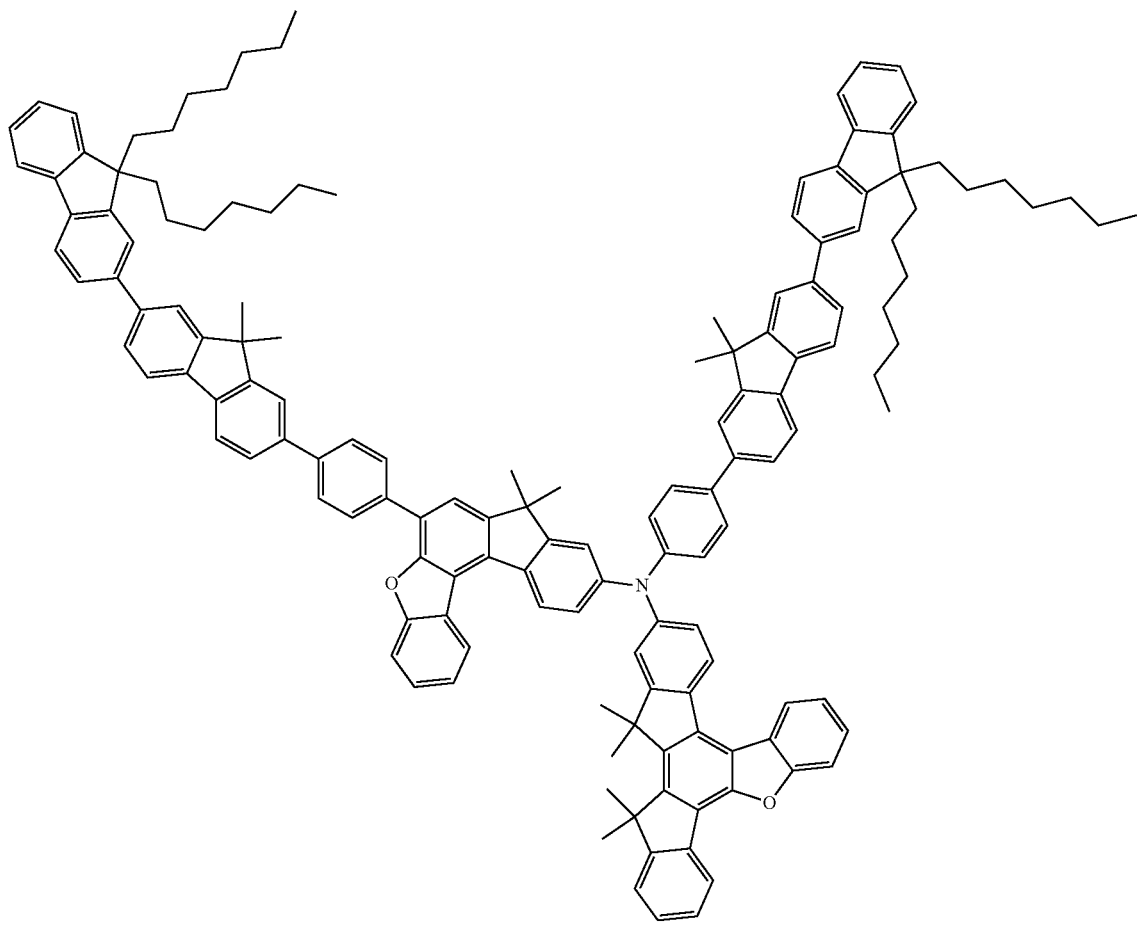 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc(-c9ccc%10c(c9)C(C)(C)c9cc(-c%11ccc%12c(c%11)C(CCCCCCC)(CCCCCCC)c%11ccccc%11-%12)ccc9-%10)cc8)c8ccc9c(c8)C(C)(C)c8c%10c(c%11oc%12ccccc%12c%11c8-9)-c8ccccc8C%10(C)C)cc6C7(C)C)cc5)ccc3-4)cc21]
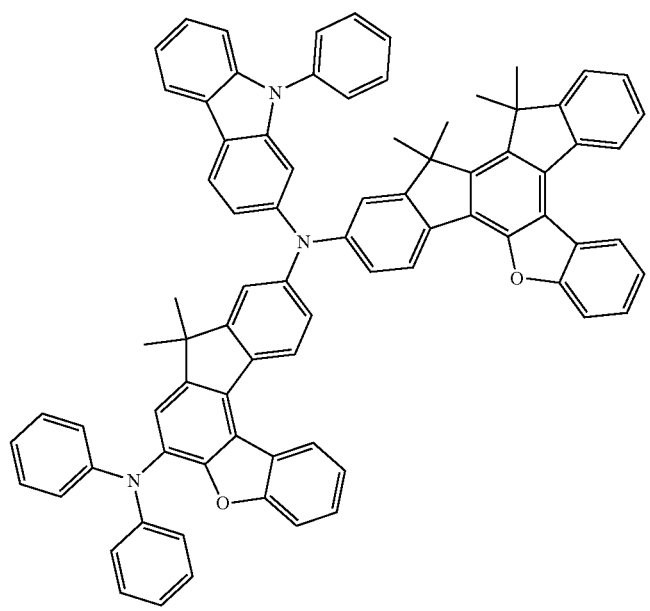 [SMILES: CC1(C)c2cc(N(c3ccc4c(c3)C(C)(C)c3c5c(c6c(oc7ccccc76)c3-4)-c3ccccc3C5(C)C)c3ccc4c5ccccc5n(-c5ccccc5)c4c3)ccc2-c2c1cc(N(c1ccccc1)c1ccccc1)c1oc3ccccc3c21]

-continued
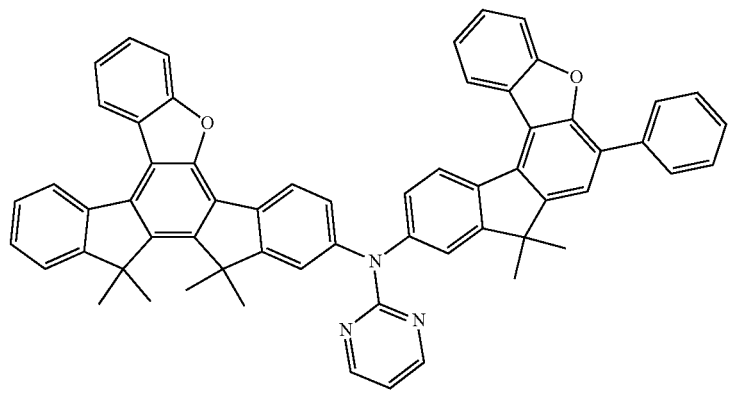 [SMILES: CC1(C)c2cc(N(c3ccc4c(c3)C(C)(C)c3c5c(c6c(oc7ccccc76)c3-4)-c3ccccc3C5(C)C)c3ncccn3)ccc2-c2c1cc(-c1ccccc1)c1oc3ccccc3c21]
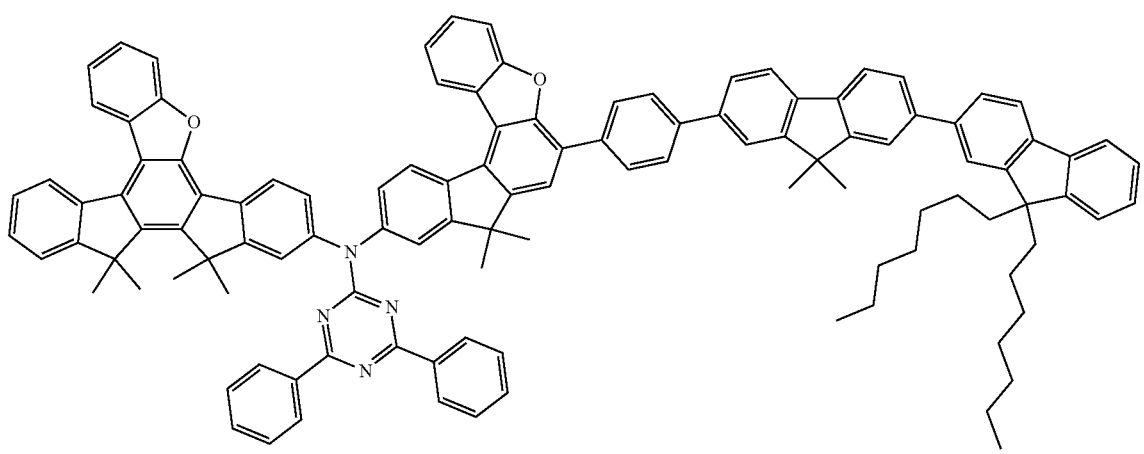 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11c(oc%12ccccc%12%11)c8-9)-c8ccccc8C%10(C)C)c8nc(-c9ccccc9)nc(-c9ccccc9)n8)cc6C7(C)C)cc5)ccc3-4)cc21]
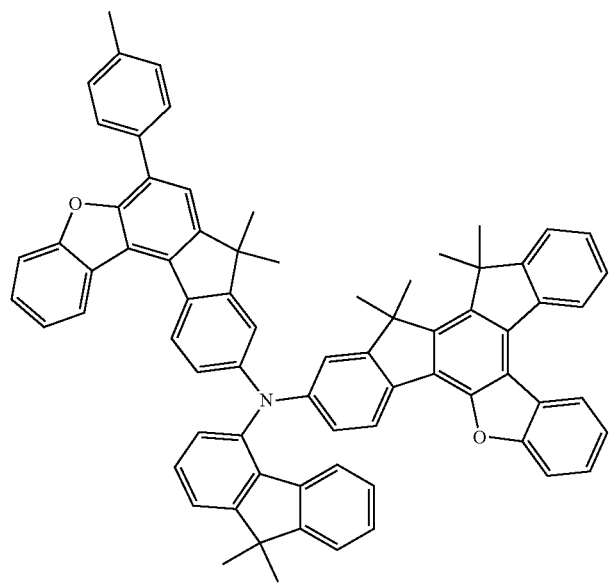 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4cccc5c4-c4ccccc4C5(C)C)cc2C3(C)C)cc1]

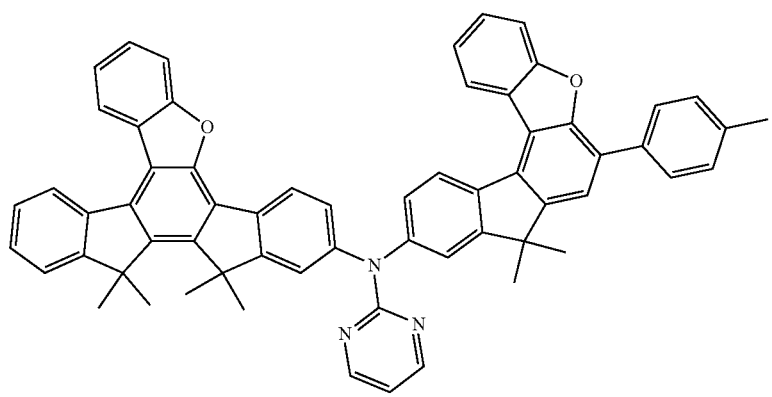 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4ncccn4)cc2C3(C)C)cc1]
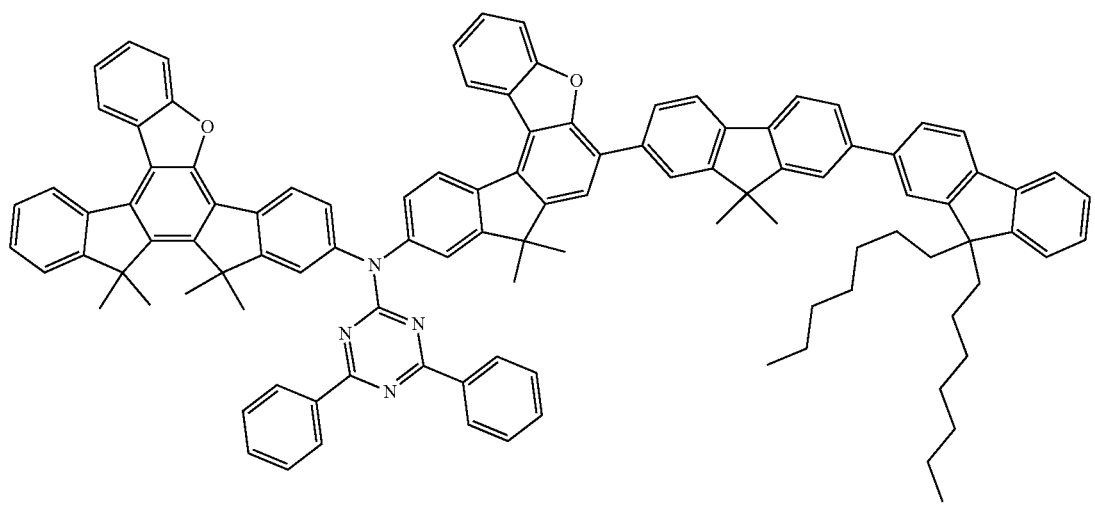 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10c(oc%11ccccc%11%10)c7-8)-c7ccccc7C9(C)C)c7nc(-c8ccccc8)nc(-c8ccccc8)n7)cc5C6(C)C)ccc3-4)cc21]
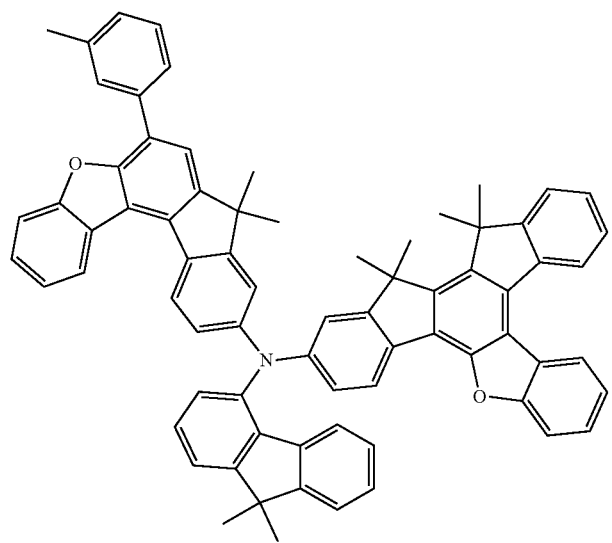 [SMILES: Cc1cccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4cccc5c4-c4ccccc4C5(C)C)cc2C3(C)C)c1]

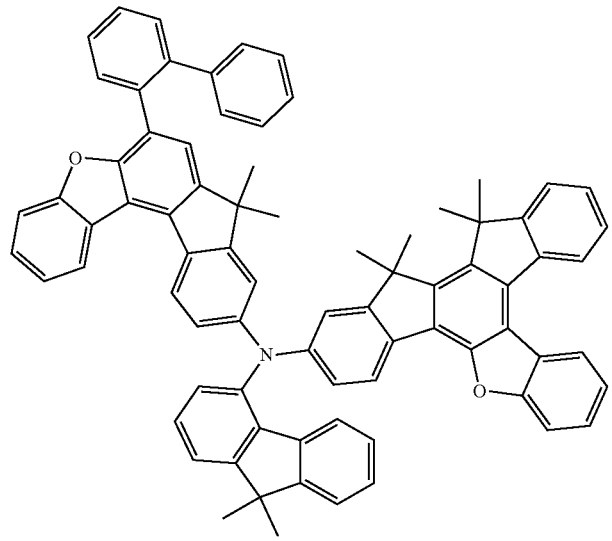 [SMILES: CC1(C)c2ccccc2-c2c(N(c3ccc4c(c3)C(C)(C)c3cc(-c5ccccc5-c5ccccc5)c5oc6ccccc6c5c3-4)c3ccc4c(c3)C(C)(C)c3c5c(c6c(oc7ccccc76)c3-4)-c3ccccc3C5(C)C)cccc21]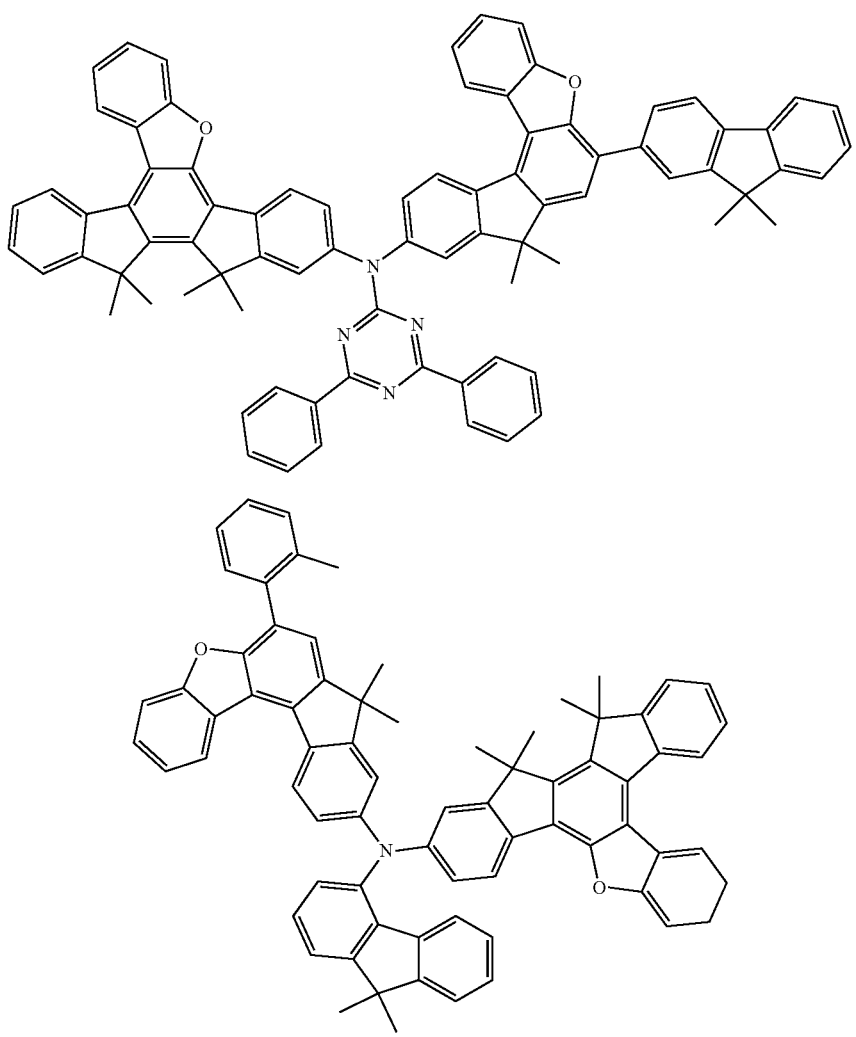

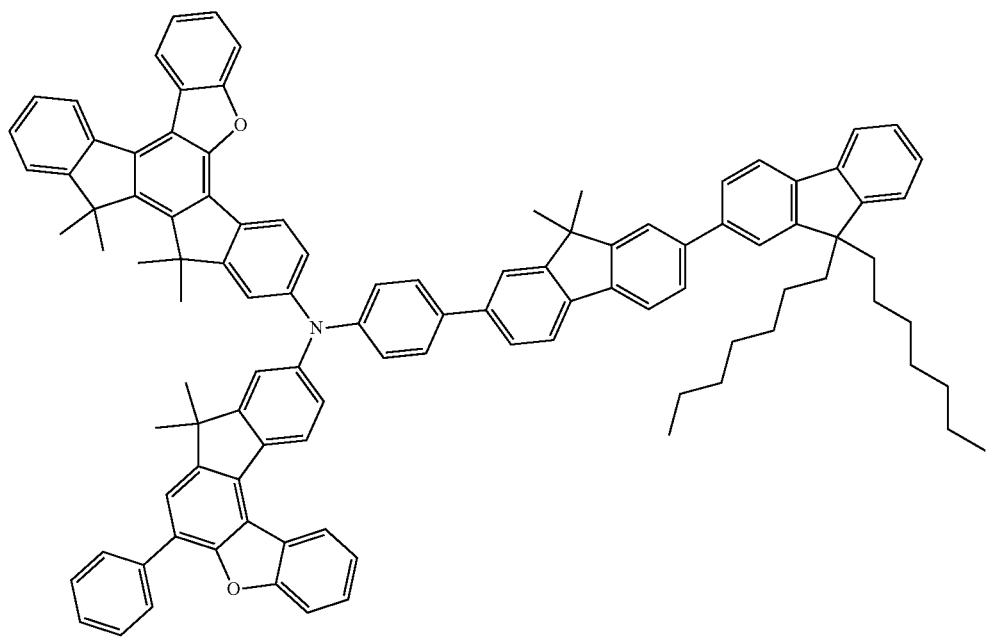 [SMILES: CCCCCCCC1(CCCCCCC)c2ccccc2-c2ccc(-c3ccc4c(c3)C(C)(C)c3cc(-c5ccc(N(c6ccc7c(c6)C(C)(C)c6cc(-c8ccccc8)c8oc9ccccc9c8c6-7)c6ccc7c(c6)C(C)(C)c6c8c(c9c(oc%10ccccc%109)c6-7)-c6ccccc6C8(C)C)cc5)ccc3-4)cc21]
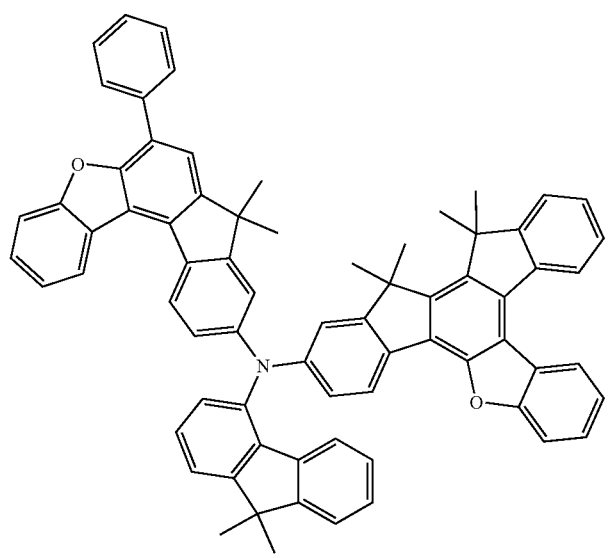 [SMILES: CC1(C)c2ccccc2-c2c(N(c3ccc4c(c3)C(C)(C)c3cc(-c5ccccc5)c5oc6ccccc6c5c3-4)c3ccc4c(c3)C(C)(C)c3c5c(c6c(oc7ccccc76)c3-4)-c3ccccc3C5(C)C)cccc21]

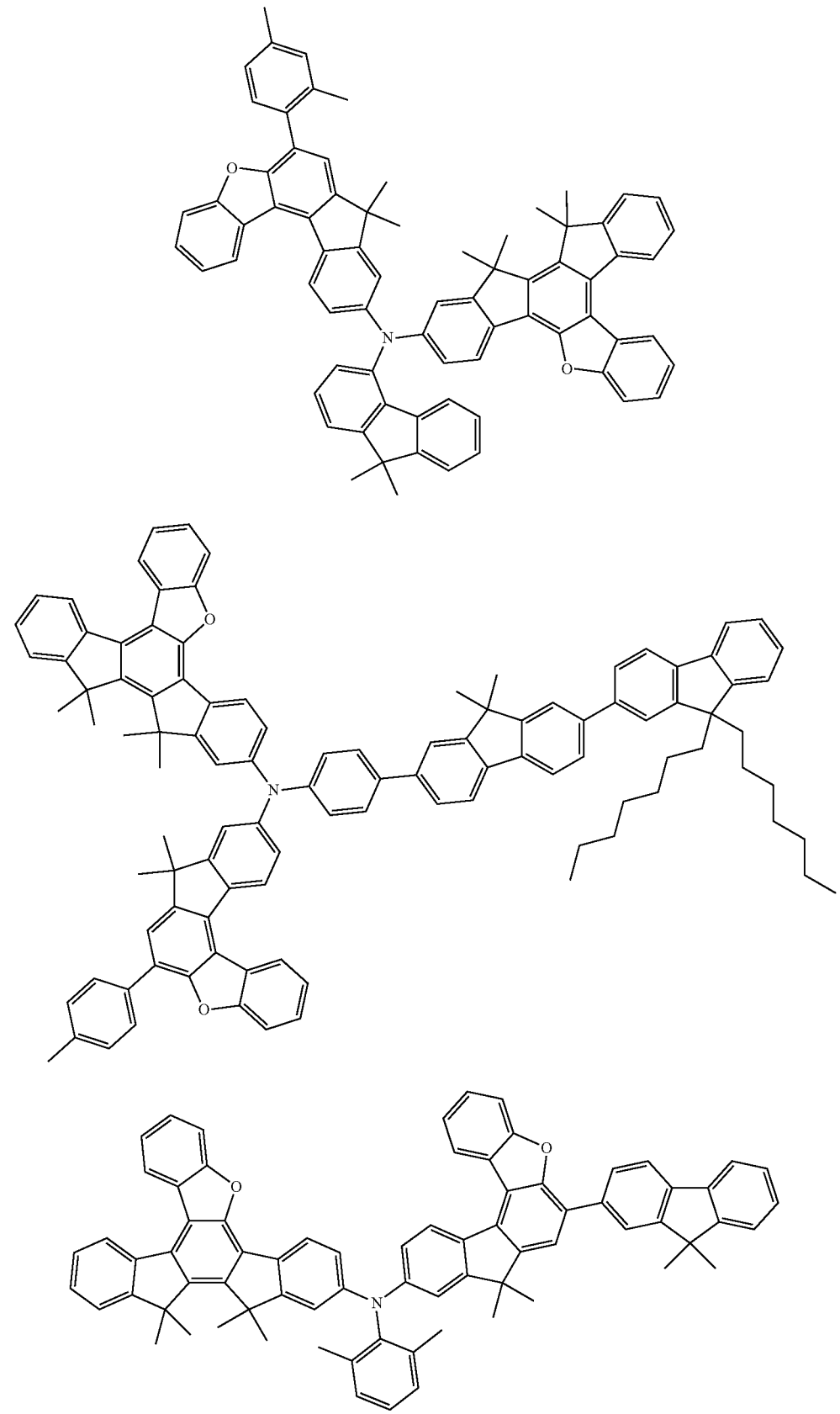

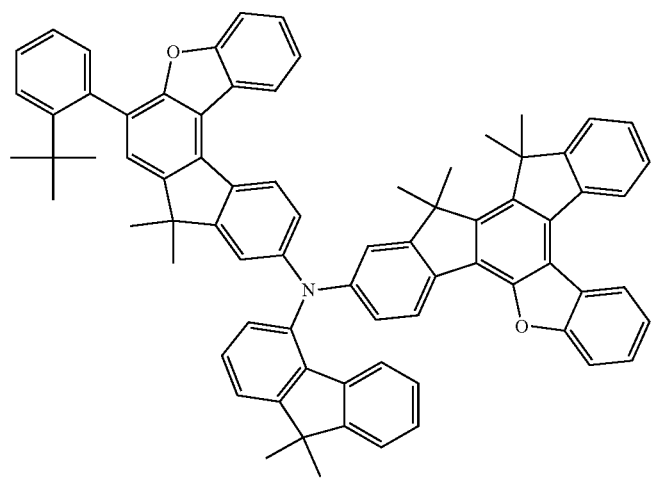 [SMILES: CC(C)(C)c1ccccc1-c1cc2c(c3c1oc1ccccc13)-c1ccc(N(c3ccc4c(c3)C(C)(C)c3c5c(c6c(oc7ccccc76)c3-4)-c3ccccc3C5(C)C)c3cccc4c3-c3ccccc3C4(C)C)cc1C2(C)C]
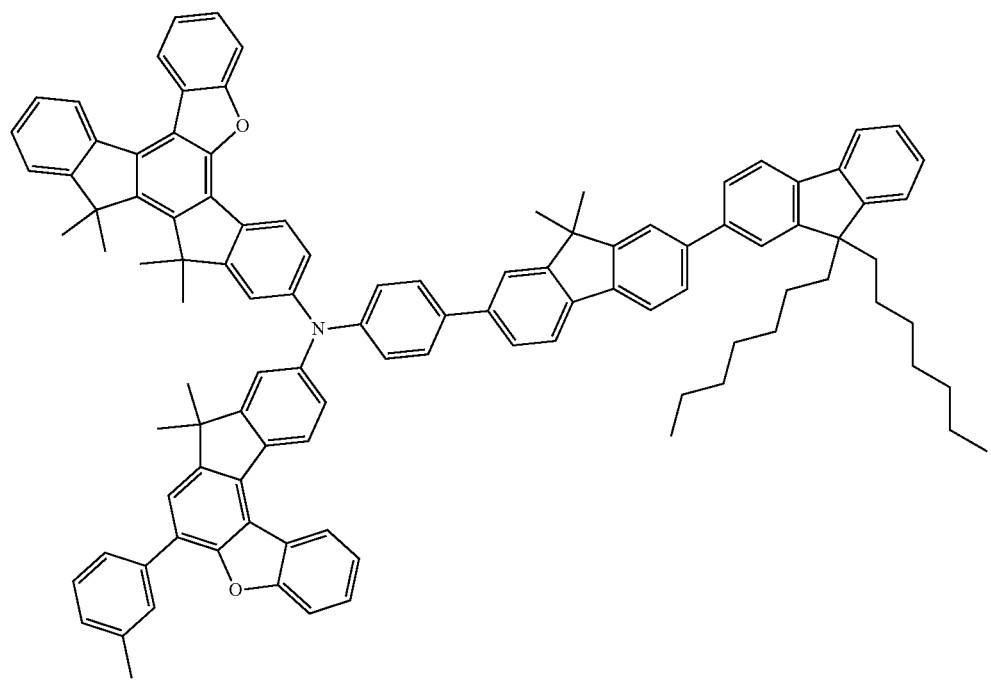 [SMILES: CCCCCCCC1(CCCCCCC)c2ccccc2-c2ccc(-c3ccc4c(c3)C(C)(C)c3cc(-c5ccc(N(c6ccc7c(c6)C(C)(C)c6cc(-c8cccc(C)c8)c8oc9ccccc9c8c6-7)c6ccc7c(c6)C(C)(C)c6c8c(c9c(oc%10ccccc%109)c6-7)-c6ccccc6C8(C)C)cc5)ccc3-4)cc21]

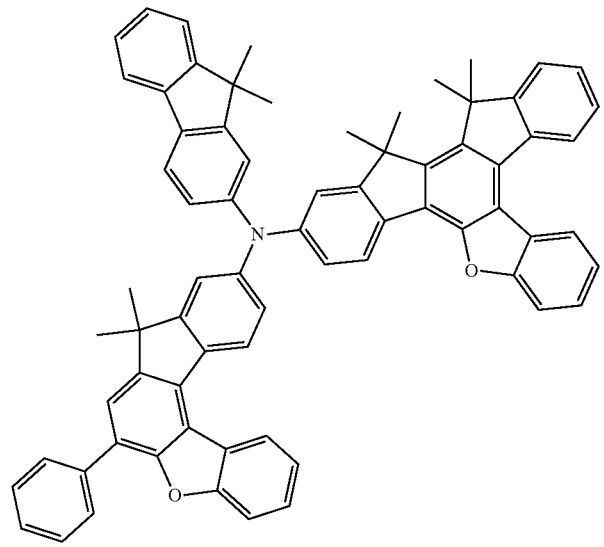 [SMILES: CC1(C)c2ccccc2-c2ccc(N(c3ccc4c(c3)C(C)(C)c3cc(-c5ccccc5)c5oc6ccccc6c5c3-4)c3ccc4c(c3)C(C)(C)c3c5c(c6c(oc7ccccc76)c3-4)-c3ccccc3C5(C)C)cc21]
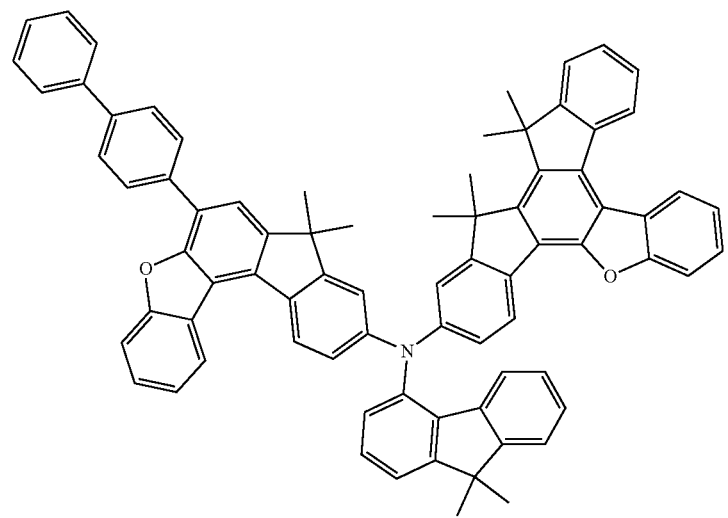 [SMILES: CC1(C)c2ccccc2-c2c(N(c3ccc4c(c3)C(C)(C)c3cc(-c5ccc(-c6ccccc6)cc5)c5oc6ccccc6c5c3-4)c3ccc4c(c3)C(C)(C)c3c5c(c6c(oc7ccccc76)c3-4)-c3ccccc3C5(C)C)cccc21]

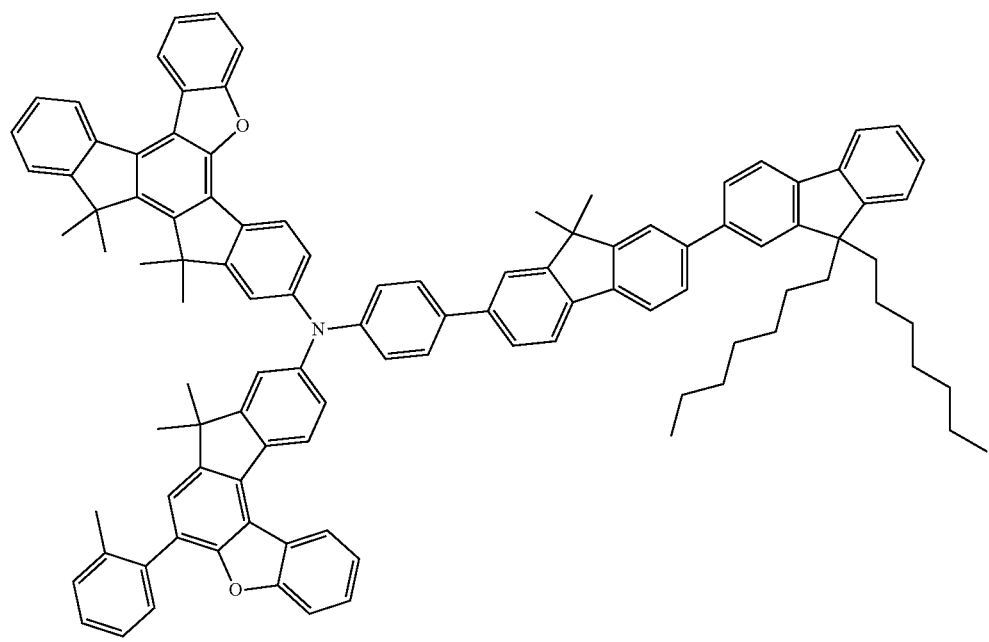 [SMILES: CCCCCCCC1(CCCCCCC)c2ccccc2-c2ccc(-c3ccc4c(c3)C(C)(C)c3cc(-c5ccc(N(c6ccc7c(c6)C(C)(C)c6cc(-c8ccccc8C)c8oc9ccccc9c8c6-7)c6ccc7c(c6)C(C)(C)c6c8c(c9c(oc%10ccccc%109)c6-7)-c6ccccc6C8(C)C)cc5)ccc3-4)cc21]
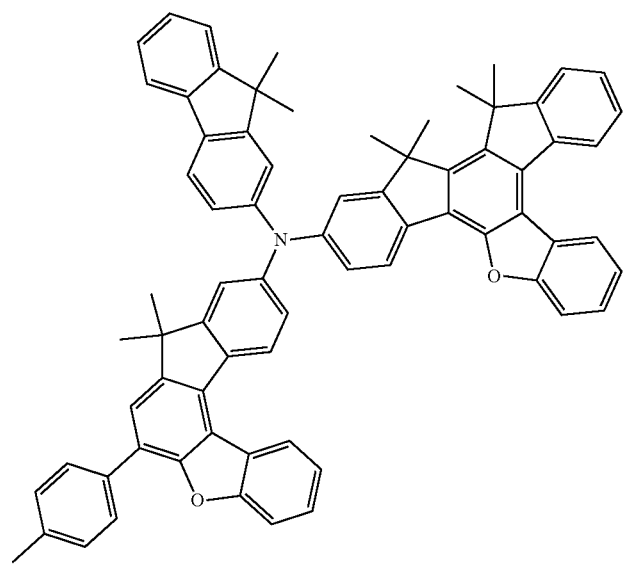 [SMILES: Cc1ccc(-c2cc3c(c4c2oc2ccccc24)-c2ccc(N(c4ccc5c(c4)C(C)(C)c4ccccc4-5)c4ccc5c(c4)C(C)(C)c4c6c(c7c(oc8ccccc87)c4-5)-c4ccccc4C6(C)C)cc2C3(C)C)cc1]

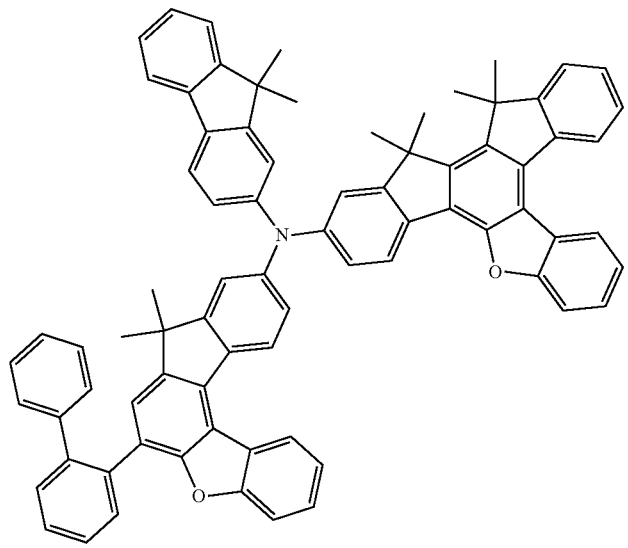 [SMILES: CC1(C)c2ccccc2-c2ccc(N(c3ccc4c(c3)C(C)(C)c3cc(-c5ccccc5-c5ccccc5)c5oc6ccccc6c5c3-4)c3ccc4c(c3)C(C)(C)c3c5c(c6c(oc7ccccc76)c3-4)-c3ccccc3C5(C)C)cc21]
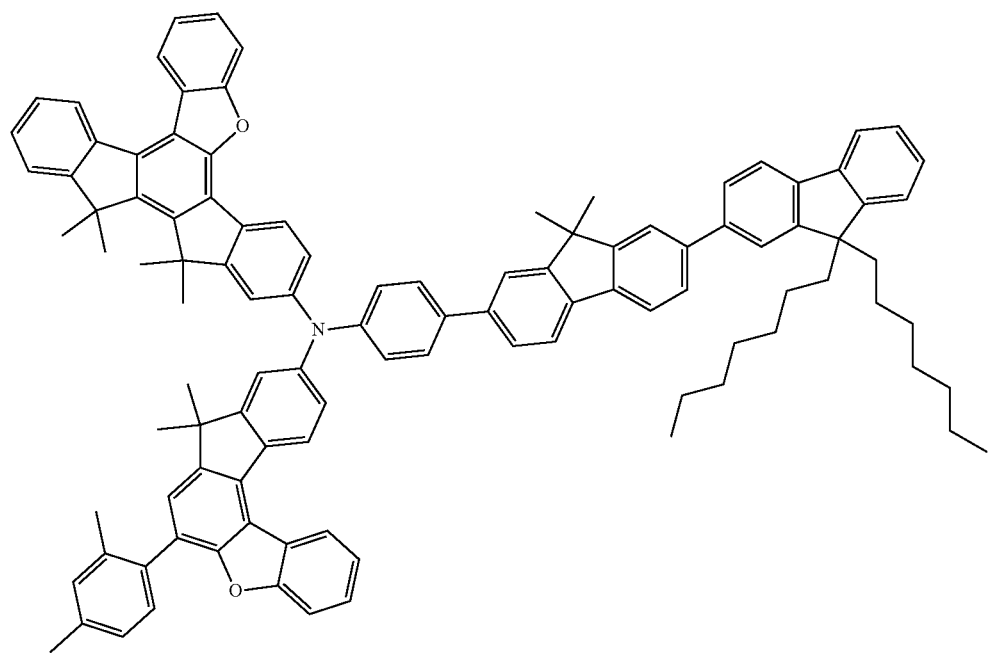 [SMILES: CCCCCCCC1(CCCCCCC)c2ccccc2-c2ccc(-c3ccc4c(c3)C(C)(C)c3cc(-c5ccc(N(c6ccc7c(c6)C(C)(C)c6cc(-c8ccc(C)cc8C)c8oc9ccccc9c8c6-7)c6ccc7c(c6)C(C)(C)c6c8c(c9c(oc%10ccccc%109)c6-7)-c6ccccc6C8(C)C)cc5)ccc3-4)cc21]

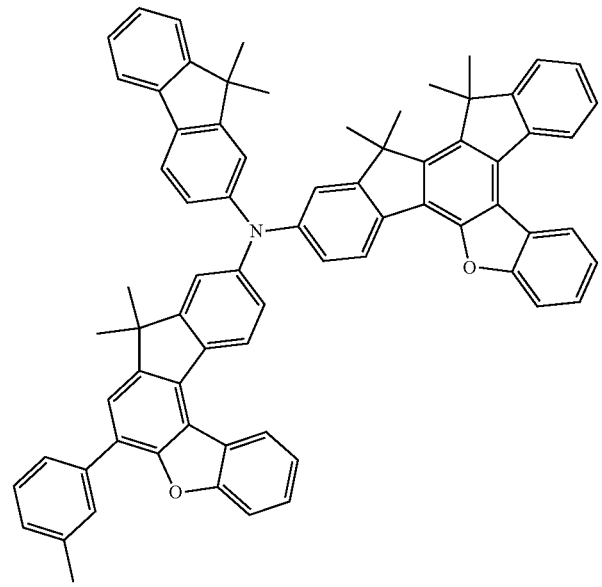 [SMILES: Cc1cccc(-c2cc3c(c4c2oc2ccccc24)-c2ccc(N(c4ccc5c(c4)C(C)(C)c4ccccc4-5)c4ccc5c(c4)C(C)(C)c4c6c(c7c(oc8ccccc87)c4-5)-c4ccccc4C6(C)C)cc2C3(C)C)c1]
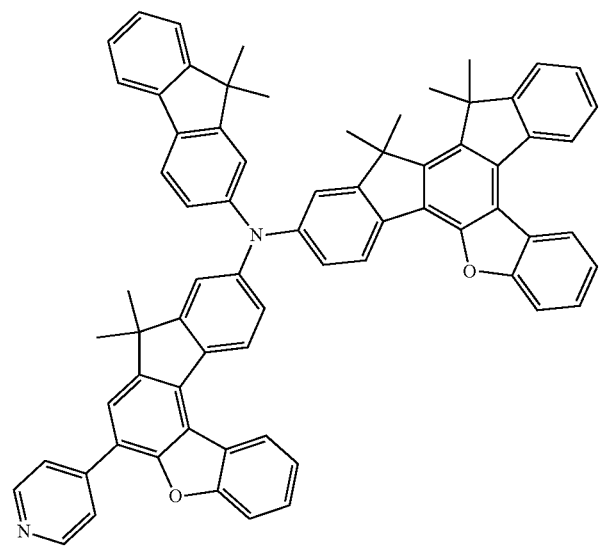 [SMILES: CC1(C)c2ccccc2-c2ccc(N(c3ccc4c(c3)C(C)(C)c3cc(-c5ccncc5)c5oc6ccccc6c5c3-4)c3ccc4c(c3)C(C)(C)c3c5c(c6c(oc7ccccc76)c3-4)-c3ccccc3C5(C)C)cc21]

-continued
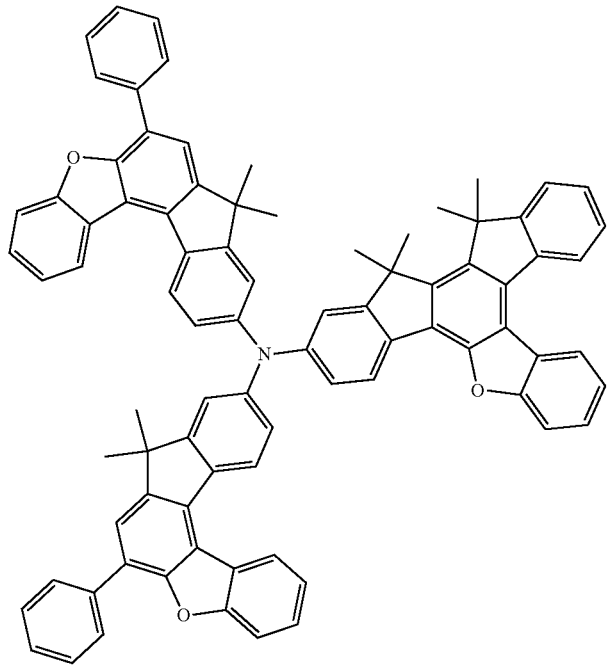 [SMILES: CC1(C)c2cc(N(c3ccc4c(c3)C(C)(C)c3cc(-c5ccccc5)c5oc6ccccc6c5c3-4)c3ccc4c(c3)C(C)(C)c3c5c(c6c(oc7ccccc76)c3-4)-c3ccccc3C5(C)C)ccc2-c2c1cc(-c1ccccc1)c1oc3ccccc3c21]
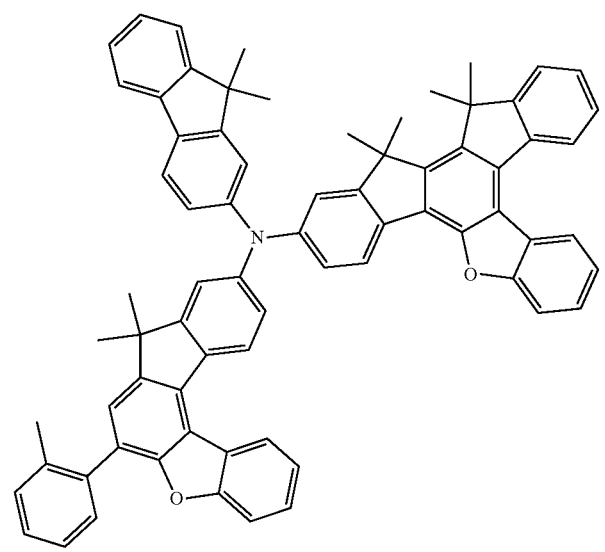 [SMILES: Cc1ccccc1-c1cc2c(c3c1oc1ccccc13)-c1ccc(N(c3ccc4c(c3)C(C)(C)c3ccccc3-4)c3ccc4c(c3)C(C)(C)c3c5c(c6c(oc7ccccc76)c3-4)-c3ccccc3C5(C)C)cc1C2(C)C]

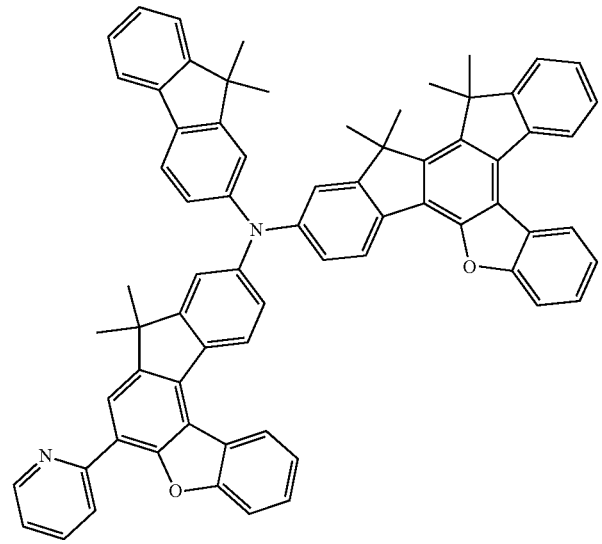 [SMILES: CC1(C)c2ccccc2-c2ccc(N(c3ccc4c(c3)C(C)(C)c3cc(-c5ccccn5)c5oc6ccccc6c5c3-4)c3ccc4c(c3)C(C)(C)c3c5c(c6c(oc7ccccc76)c3-4)-c3ccccc3C5(C)C)cc21]
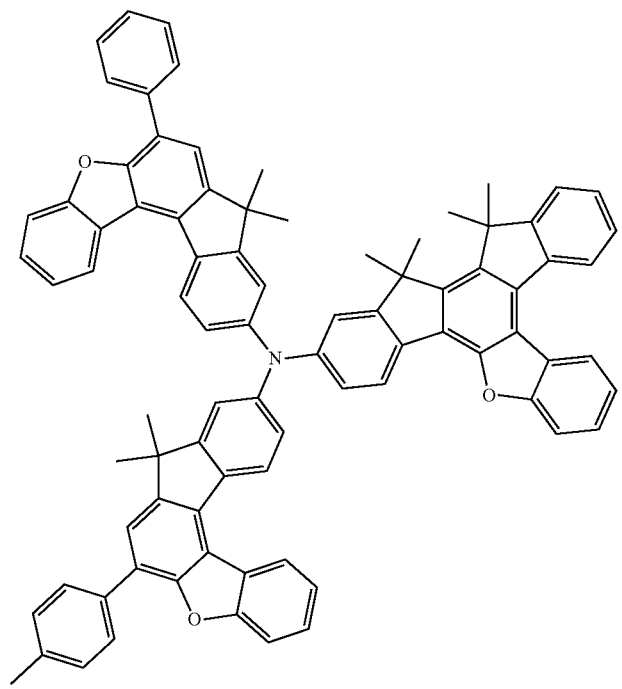 [SMILES: Cc1ccc(-c2cc3c(c4c2oc2ccccc24)-c2ccc(N(c4ccc5c(c4)C(C)(C)c4cc(-c6ccccc6)c6oc7ccccc7c6c4-5)c4ccc5c(c4)C(C)(C)c4c6c(c7c(oc8ccccc87)c4-5)-c4ccccc4C6(C)C)cc2C3(C)C)cc1]

-continued
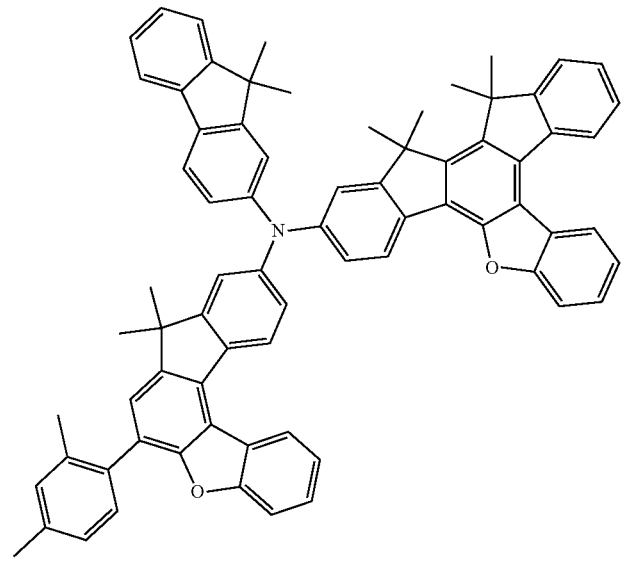 [SMILES: Cc1ccc(-c2cc3c(c4c2oc2ccccc24)-c2ccc(N(c4ccc5c(c4)C(C)(C)c4ccccc4-5)c4ccc5c(c4)C(C)(C)c4c6c(c7c(oc8ccccc87)c4-5)-c4ccccc4C6(C)C)cc2C3(C)C)c(C)c1]
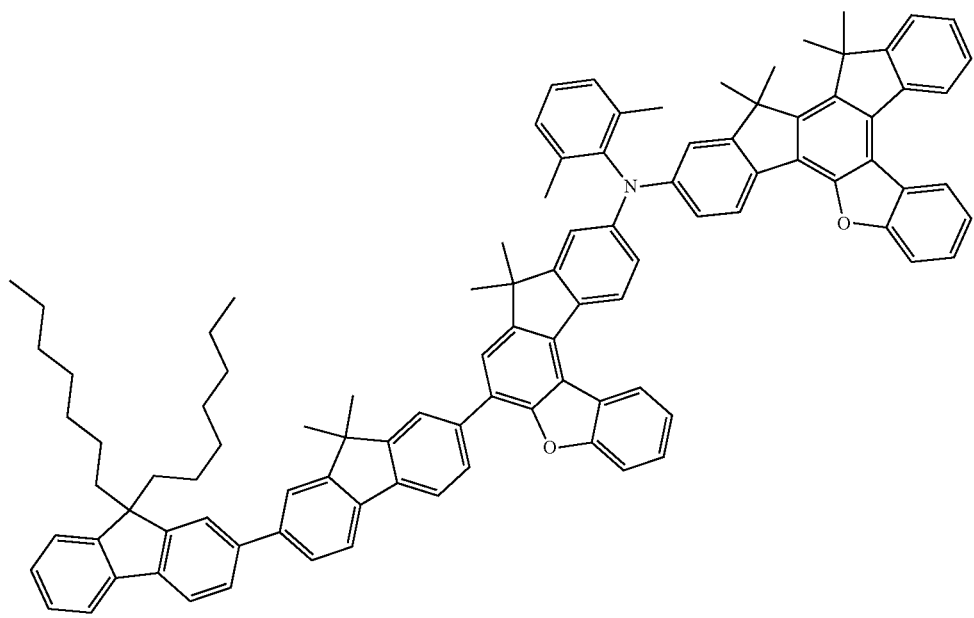 [SMILES: CCCCCCCC1(CCCCCCC)c2ccccc2-c2ccc(-c3ccc4c(c3)C(C)(C)c3cc(-c5cc6c(c7c5oc5ccccc57)-c5ccc(N(c7ccc8c(c7)C(C)(C)c7c9c(c%10c(oc%11ccccc%11%10)c7-8)-c7ccccc7C9(C)C)c7c(C)cccc7C)cc5C6(C)C)ccc3-4)cc21]
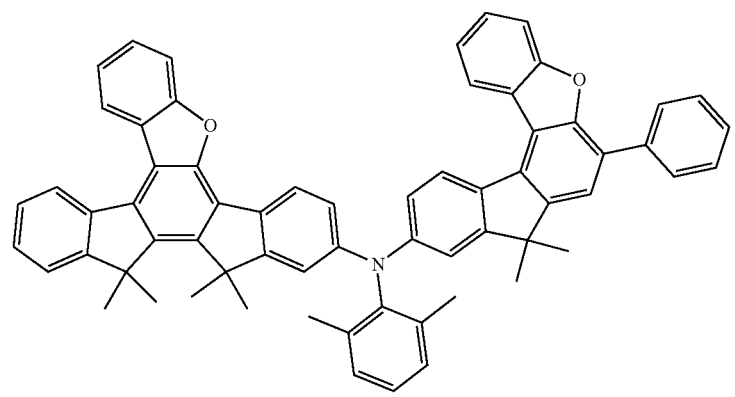 [SMILES: Cc1cccc(C)c1N(c1ccc2c(c1)C(C)(C)c1cc(-c3ccccc3)c3oc4ccccc4c3c1-2)c1ccc2c(c1)C(C)(C)c1c3c(c4c(oc5ccccc54)c1-2)-c1ccccc1C3(C)C]

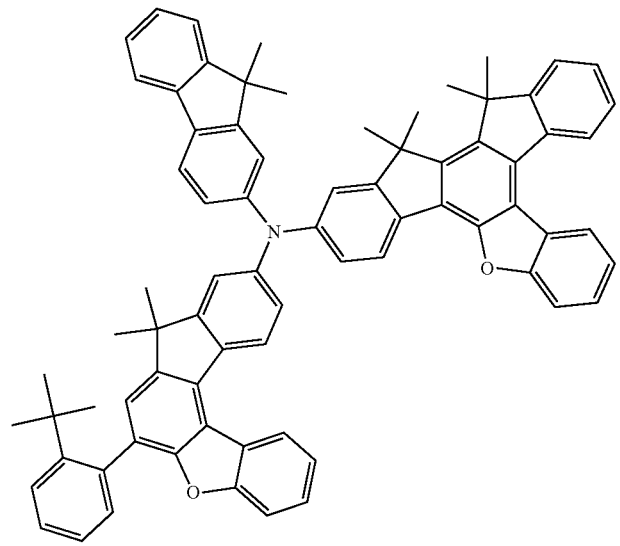 [SMILES: CC(C)(C)c1ccccc1-c1cc2c(c3c1oc1ccccc13)-c1ccc(N(c3ccc4c(c3)C(C)(C)c3ccccc3-4)c3ccc4c(c3)C(C)(C)c3c5c(c6c(oc7ccccc76)c3-4)-c3ccccc3C5(C)C)cc1C2(C)C]
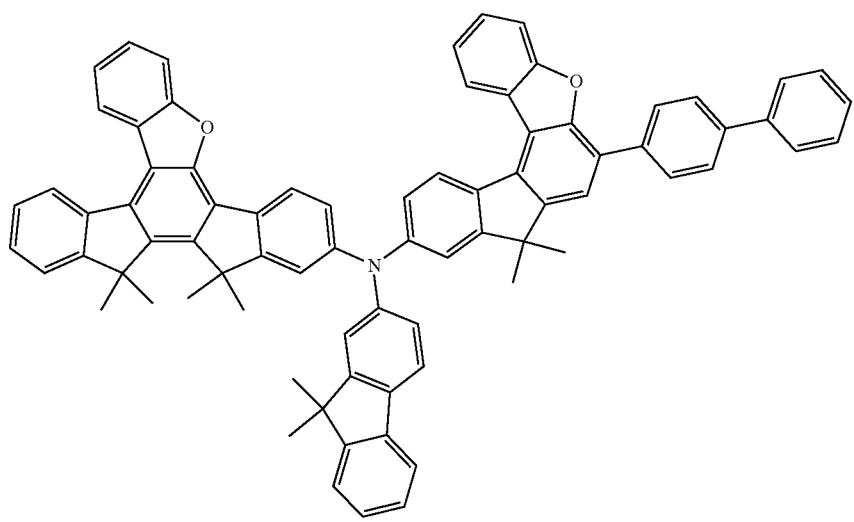 [SMILES: CC1(C)c2ccccc2-c2ccc(N(c3ccc4c(c3)C(C)(C)c3cc(-c5ccc(-c6ccccc6)cc5)c5oc6ccccc6c5c3-4)c3ccc4c(c3)C(C)(C)c3c5c(c6c(oc7ccccc76)c3-4)-c3ccccc3C5(C)C)cc21]
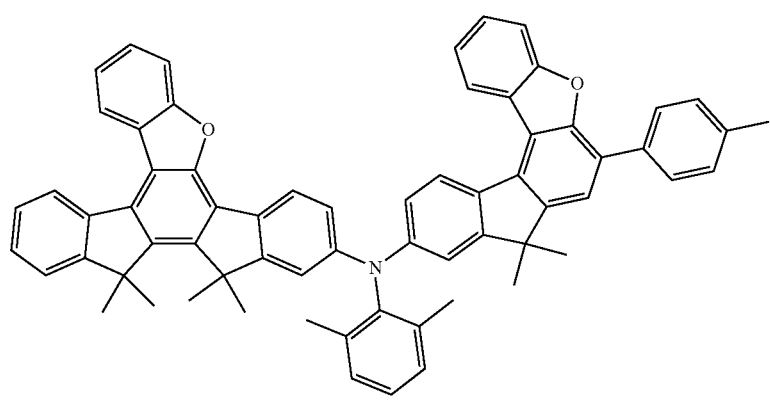 [SMILES: Cc1ccc(-c2cc3c(c4c2oc2ccccc24)-c2ccc(N(c4ccc5c(c4)C(C)(C)c4c6c(c7c(oc8ccccc87)c4-5)-c4ccccc4C6(C)C)c4c(C)cccc4C)cc2C3(C)C)cc1]

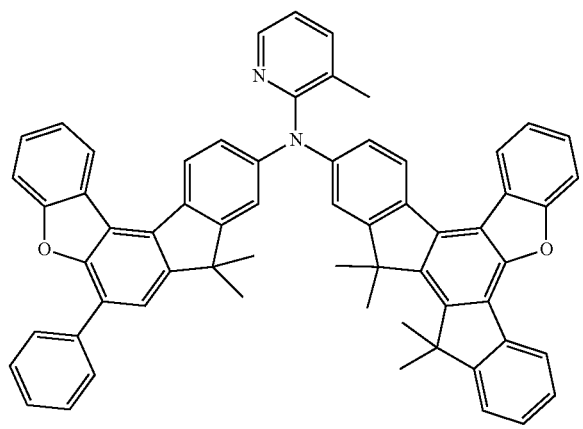 [SMILES: Cc1cccnc1N(c1ccc2c(c1)C(C)(C)c1cc(-c3ccccc3)c3oc4ccccc4c3c1-2)c1ccc2c(c1)C(C)(C)c1c3c(c4oc5ccccc5c4c1-2)-c1ccccc1C3(C)C]
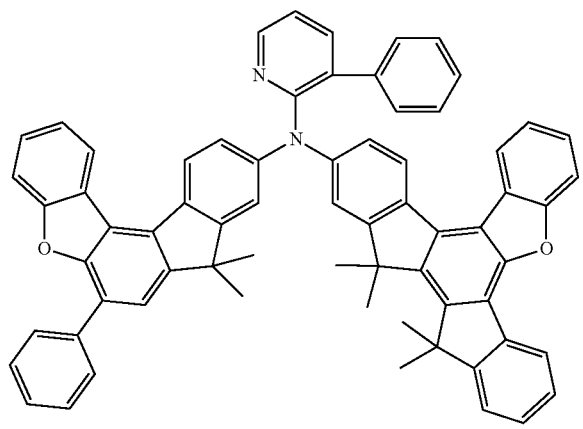 [SMILES: CC1(C)c2cc(N(c3ccc4c(c3)C(C)(C)c3c5c(c6oc7ccccc7c6c3-4)-c3ccccc3C5(C)C)c3ncccc3-c3ccccc3)ccc2-c2c1cc(-c1ccccc1)c1oc3ccccc3c21]
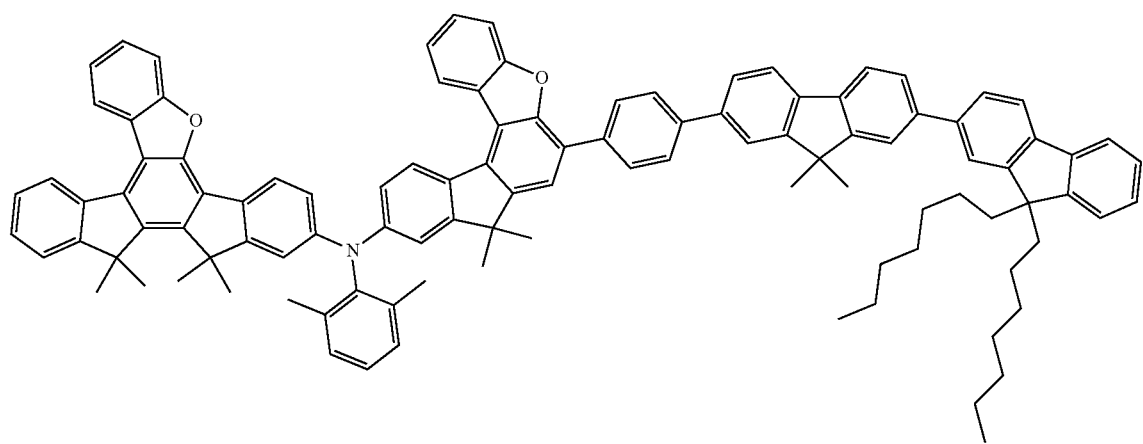 [SMILES: CCCCCCCC1(CCCCCCC)c2ccccc2-c2ccc(-c3ccc4c(c3)C(C)(C)c3cc(-c5ccc(-c6cc7c(c8c6oc6ccccc68)-c6ccc(N(c8ccc9c(c8)C(C)(C)c8c%10c(c%11c(oc%12ccccc%12%11)c8-9)-c8ccccc8C%10(C)C)c8c(C)cccc8C)cc6C7(C)C)cc5)ccc3-4)cc21]

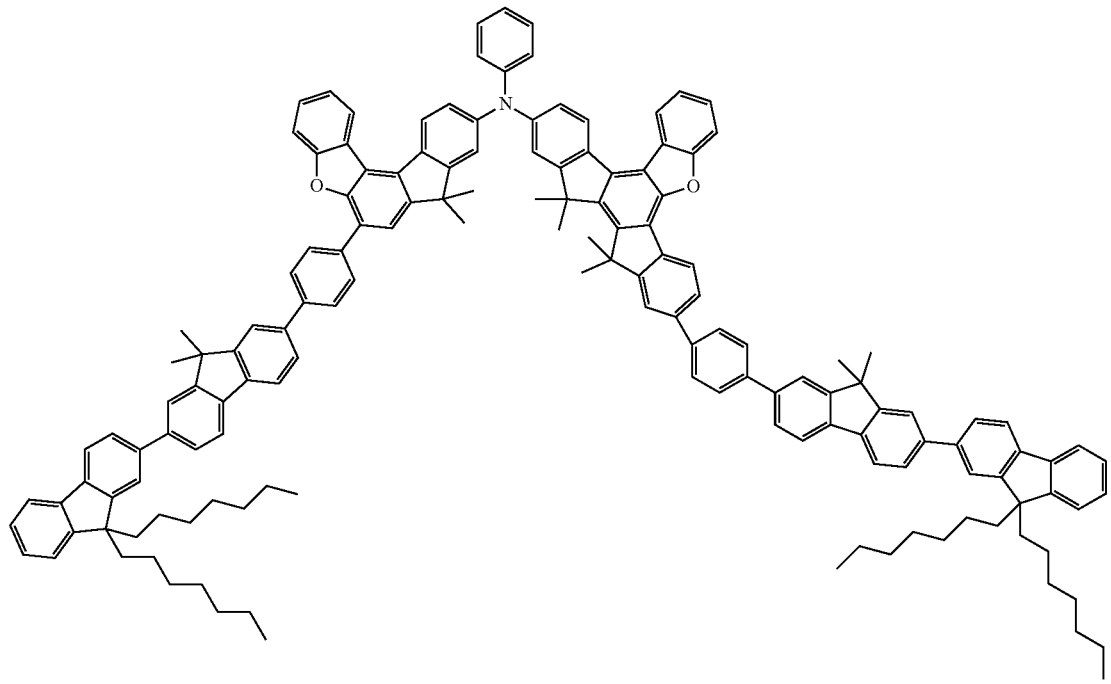 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9c(oc%10ccccc%109)c6-7)-c6ccc(N(c7ccccc7)c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10oc%11ccccc%11c%10c7-9)cc6C8(C)C)cc5)ccc3-4)cc21]
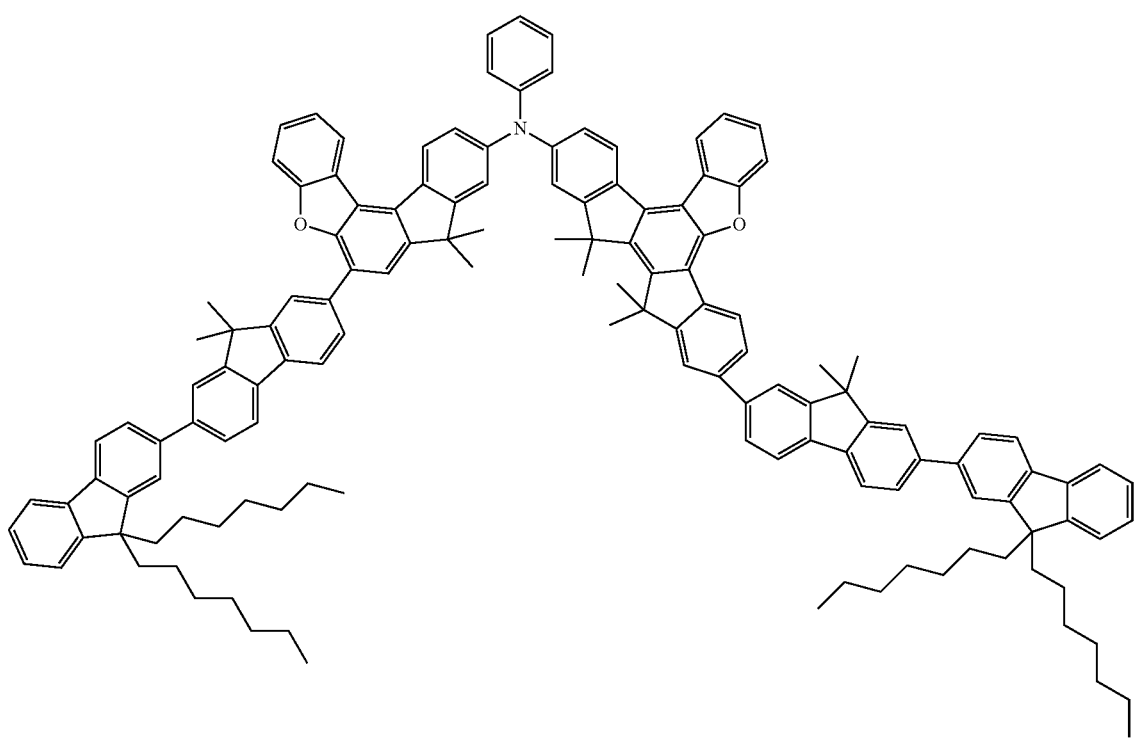 [SMILES: CCCCCCCC1(CCCCCCC)c2ccccc2-c2ccc(-c3ccc4c(c3)C(C)(C)c3cc(-c5ccc6c(c5)C(C)(C)c5c7c(c8c(oc9ccccc98)c5-6)-c5ccc(N(c6ccccc6)c6ccc8c(c6)C(C)(C)c6cc(-c9ccc%10c(c9)C(C)(C)c9cc(-c%11ccc%12c(c%11)C(CCCCCCC)(CCCCCCC)c%11ccccc%11-%12)ccc9-%10)c9oc%10ccccc%10c9c6-8)cc5C7(C)C)ccc3-4)cc21]

705 706
-continued
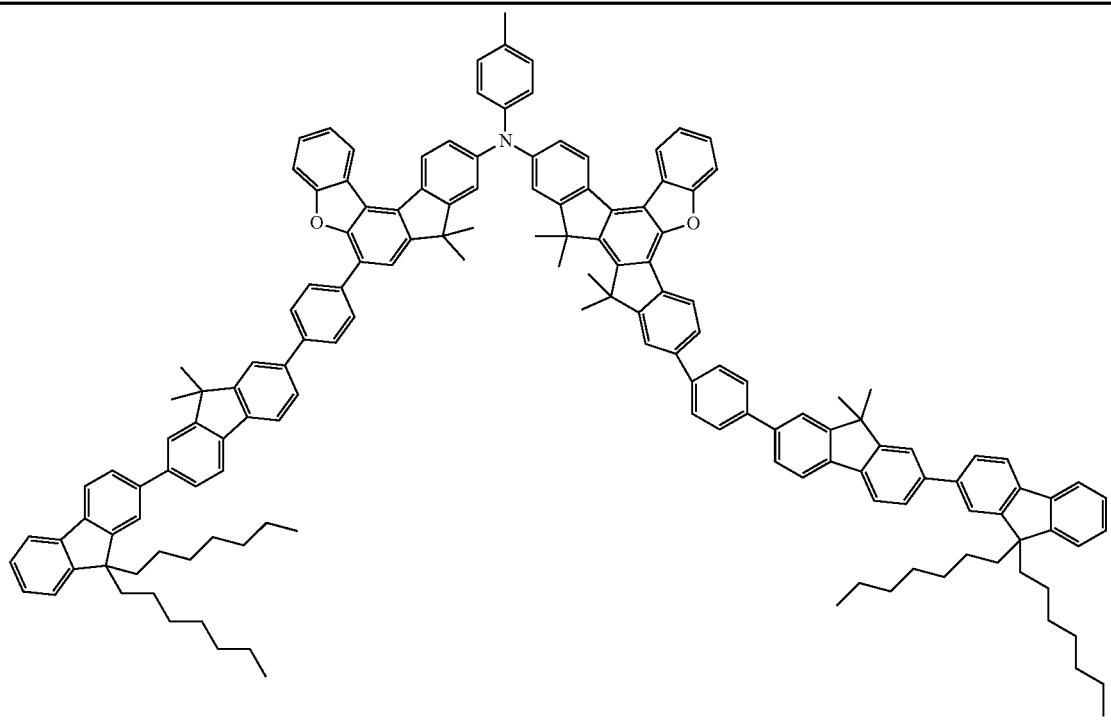
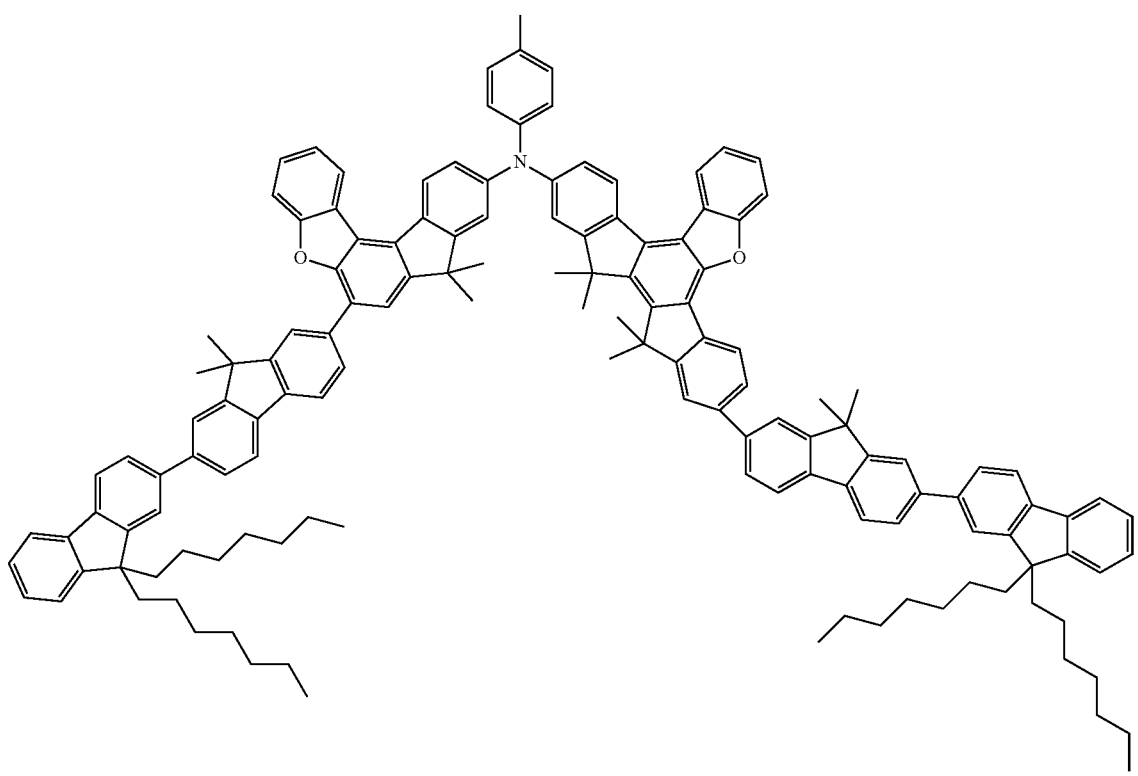 [SMILES: CCCCCCCC1(CCCCCCC)c2ccccc2-c2ccc(-c3ccc4c(c3)C(C)(C)c3cc(-c5ccc6c(c5)C(C)(C)c5c7c(c8c(oc9ccccc98)c5-6)-c5ccc(N(c6ccc(C)cc6)c6ccc8c(c6)C(C)(C)c6cc(-c9ccc%10c(c9)C(C)(C)c9cc(-c%11ccc%12c(c%11)C(CCCCCCC)(CCCCCCC)c%11ccccc%11-%12)ccc9-%10)c9oc%10ccccc%10c9c6-8)cc5C7(C)C)ccc3-4)cc21]

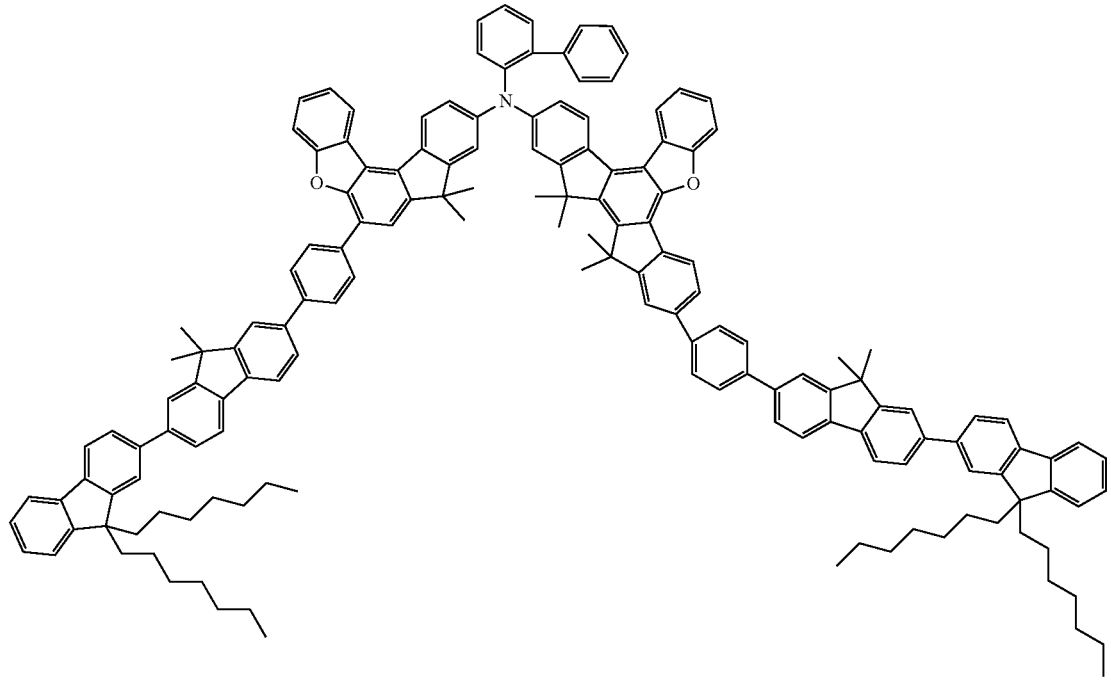 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9c(oc%10ccccc%109)c6-7)-c6ccc(N(c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10oc%11ccccc%11c%10c7-9)c7ccccc7-c7ccccc7)cc6C8(C)C)cc5)ccc3-4)cc21]
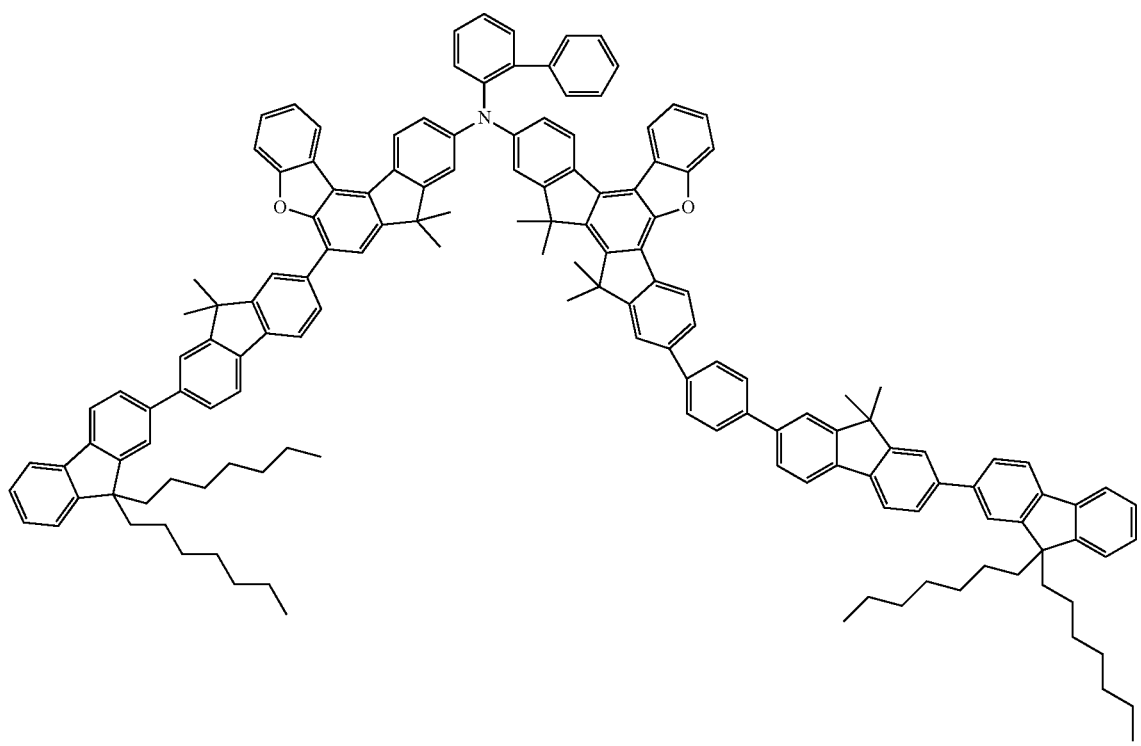 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9c(oc%10ccccc%109)c6-7)-c6ccc(N(c7ccc9c(c7)C(C)(C)c7cc(-c%10ccc%11c(c%10)C(C)(C)c%10cc(-c%12ccc%13c(c%12)C(CCCCCCC)(CCCCCCC)c%12ccccc%12-%13)ccc%10-%11)c%10oc%11ccccc%11c%10c7-9)c7ccccc7-c7ccccc7)cc6C8(C)C)cc5)ccc3-4)cc21]

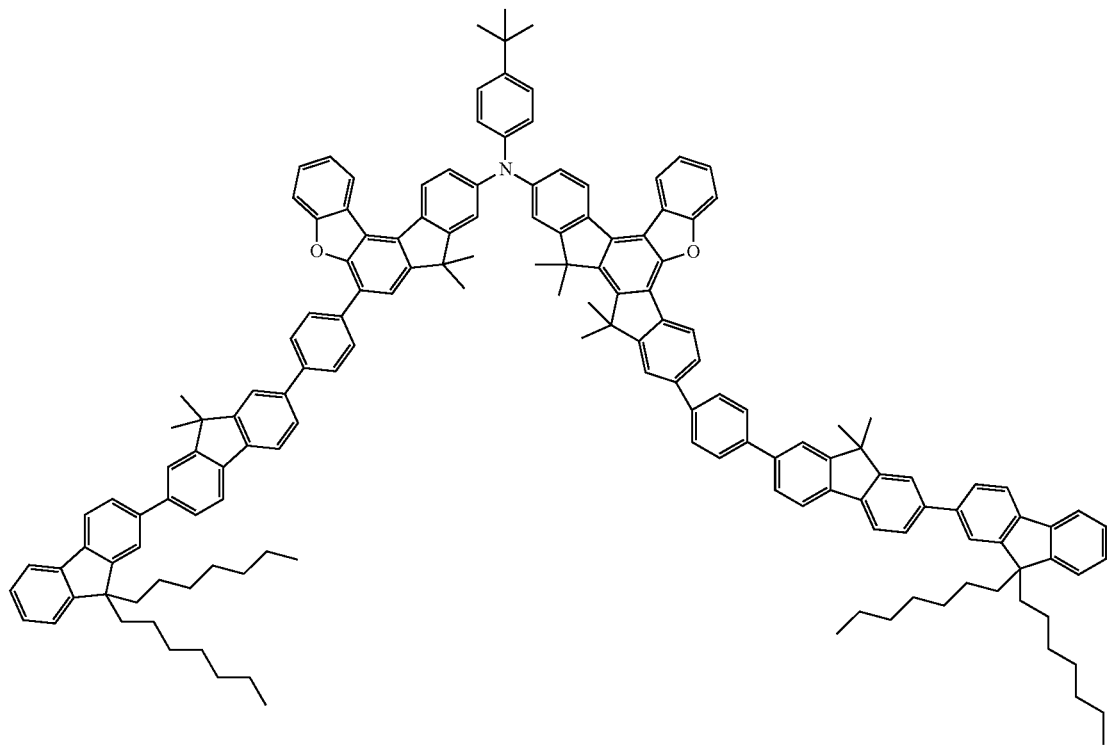 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9c(oc%10ccccc%109)c6-7)-c6ccc(N(c7ccc(C(C)(C)C)cc7)c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10oc%11ccccc%11c%10c7-9)cc6C8(C)C)cc5)ccc3-4)cc21]
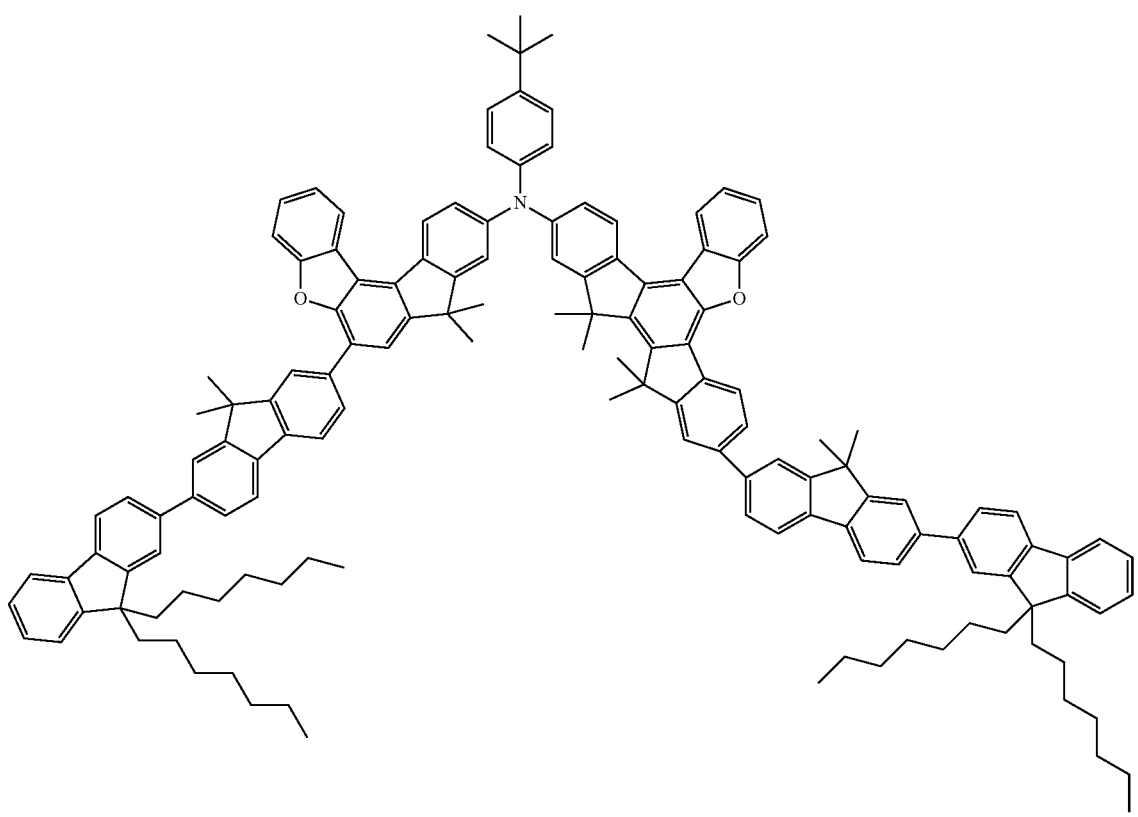 [SMILES: CCCCCCCC1(CCCCCCC)c2ccccc2-c2ccc(-c3ccc4c(c3)C(C)(C)c3cc(-c5ccc6c(c5)C(C)(C)c5c7c(c8c(oc9ccccc98)c5-6)-c5ccc(N(c6ccc(C(C)(C)C)cc6)c6ccc8c(c6)C(C)(C)c6cc(-c9ccc%10c(c9)C(C)(C)c9cc(-c%11ccc%12c(c%11)C(CCCCCCC)(CCCCCCC)c%11ccccc%11-%12)ccc9-%10)c9oc%10ccccc%10c9c6-8)cc5C7(C)C)ccc3-4)cc21]

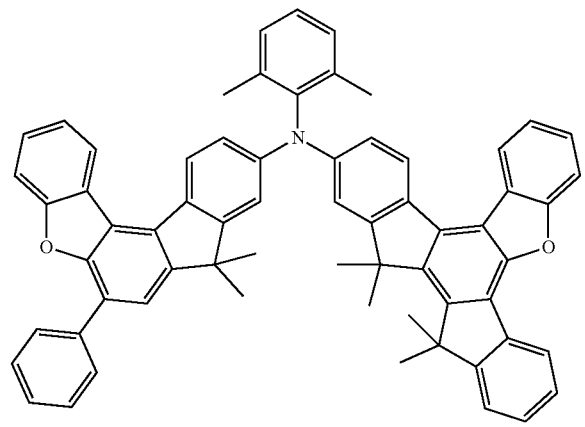 [SMILES: Cc1cccc(C)c1N(c1ccc2c(c1)C(C)(C)c1cc(-c3ccccc3)c3oc4ccccc4c3c1-2)c1ccc2c(c1)C(C)(C)c1c3c(c4oc5ccccc5c4c1-2)-c1ccccc1C3(C)C]
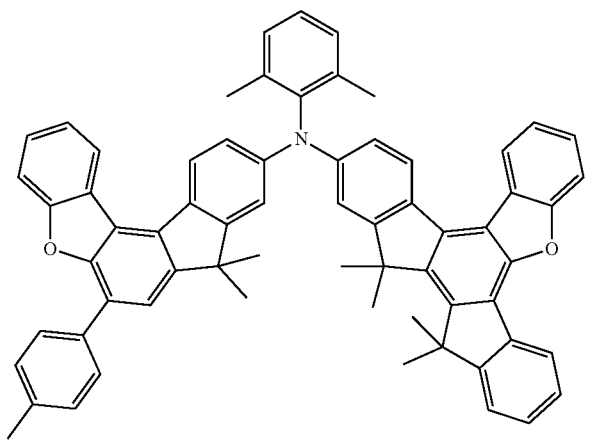 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4c(C)cccc4C)cc2C3(C)C)cc1]
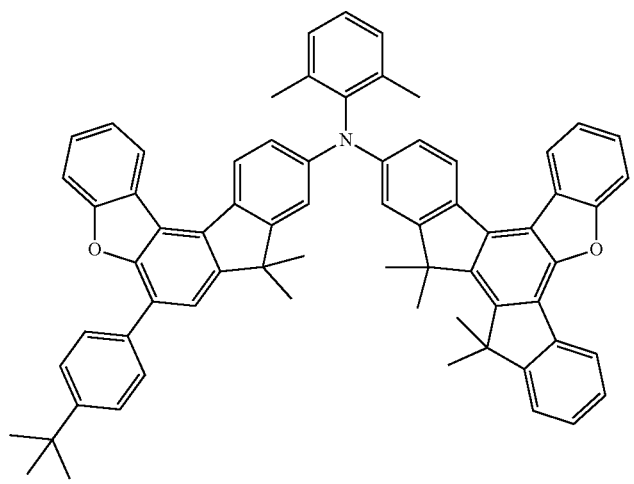 [SMILES: Cc1cccc(C)c1N(c1ccc2c(c1)C(C)(C)c1cc(-c3ccc(C(C)(C)C)cc3)c3oc4ccccc4c3c1-2)c1ccc2c(c1)C(C)(C)c1c3c(c4oc5ccccc5c4c1-2)-c1ccccc1C3(C)C]

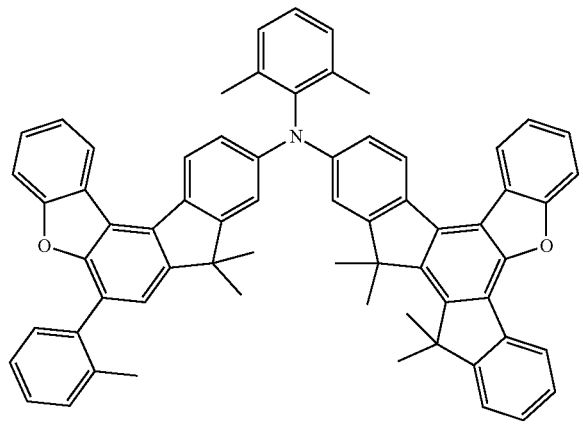 [SMILES: Cc1ccccc1-c1cc2c(c3c1oc1ccccc13)-c1ccc(N(c3ccc4c(c3)C(C)(C)c3c5c(c6oc7ccccc7c6c3-4)-c3ccccc3C5(C)C)c3c(C)cccc3C)cc1C2(C)C]
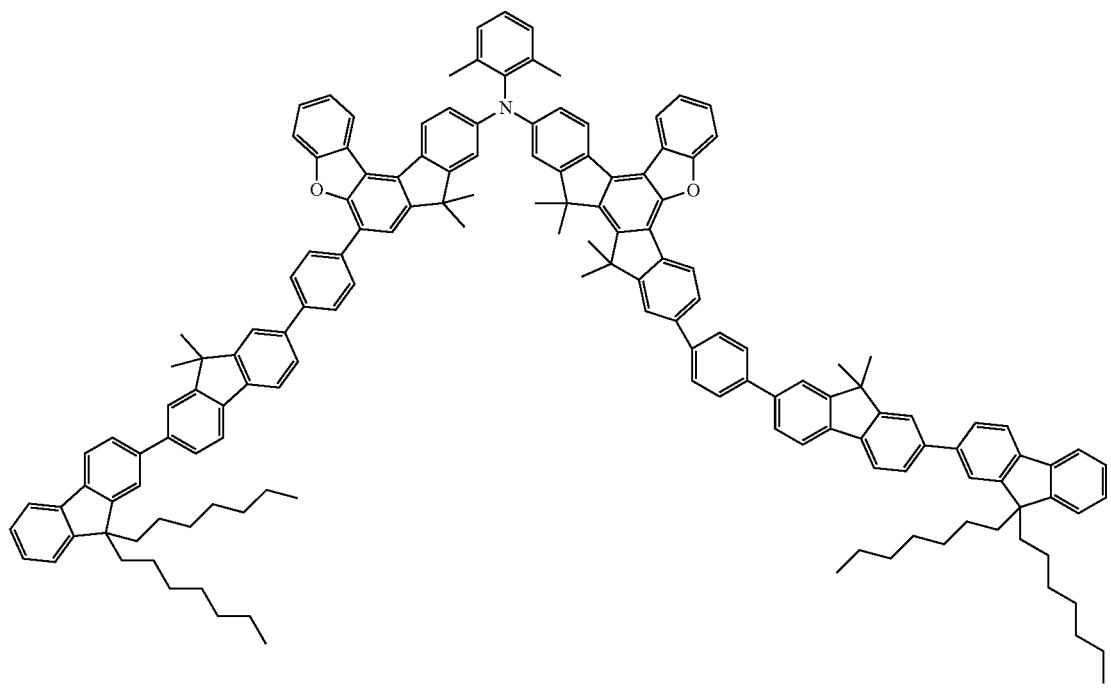 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9c(oc%10ccccc%109)c6-7)-c6ccc(N(c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10oc%11ccccc%11c%10c7-9)c7c(C)cccc7C)cc6C8(C)C)cc5)ccc3-4)cc21]

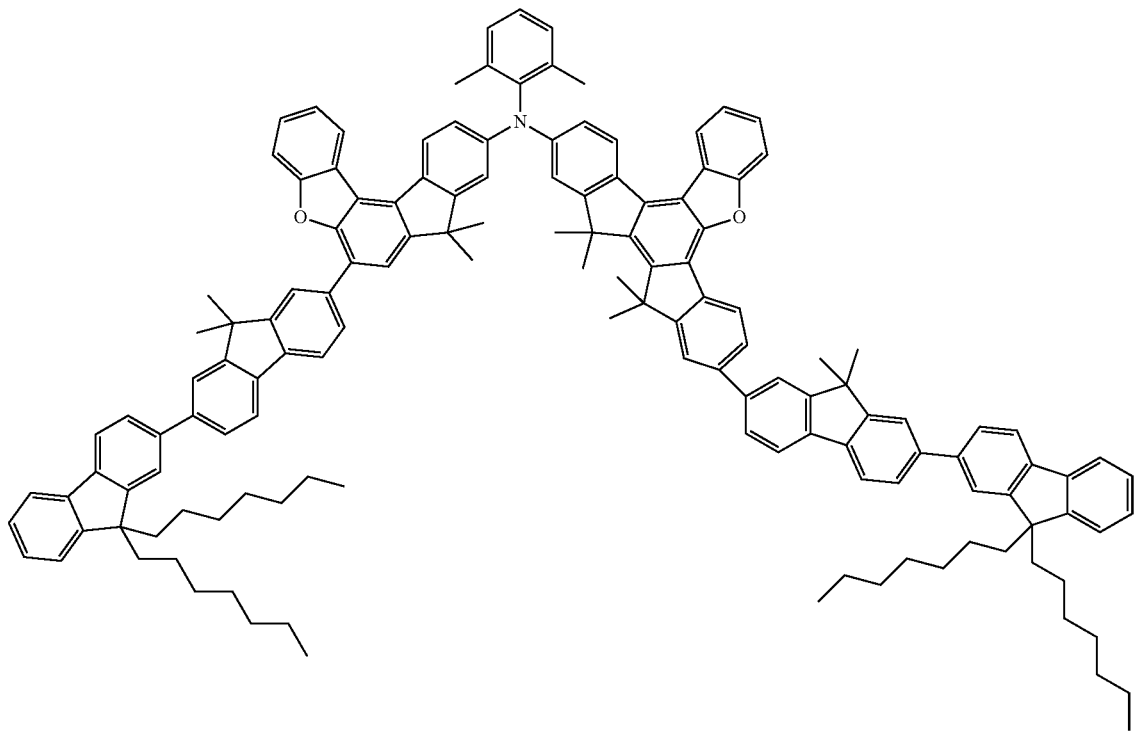 [SMILES: CCCCCCCC1(CCCCCCC)c2ccccc2-c2ccc(-c3ccc4c(c3)C(C)(C)c3cc(-c5ccc6c(c5)C(C)(C)c5c7c(c8c(oc9ccccc98)c5-6)-c5ccc(N(c6ccc8c(c6)C(C)(C)c6cc(-c9ccc%10c(c9)C(C)(C)c9cc(-c%11ccc%12c(c%11)C(CCCCCCC)(CCCCCCC)c%11ccccc%11-%12)ccc9-%10)c9oc%10ccccc%10c9c6-8)c6c(C)cccc6C)cc5C7(C)C)ccc3-4)cc21]
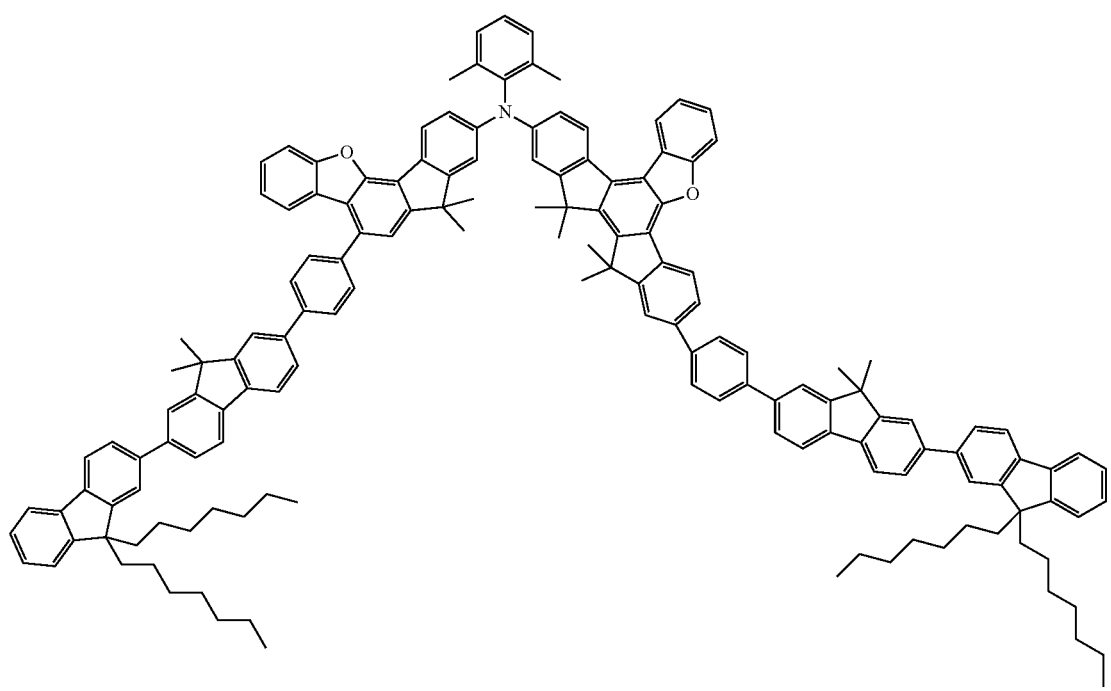 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9c(oc%10ccccc%109)c6-7)-c6ccc(N(c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10c(oc%11ccccc%11%10)c7-9)c7c(C)cccc7C)cc6C8(C)C)cc5)ccc3-4)cc21]

-continued
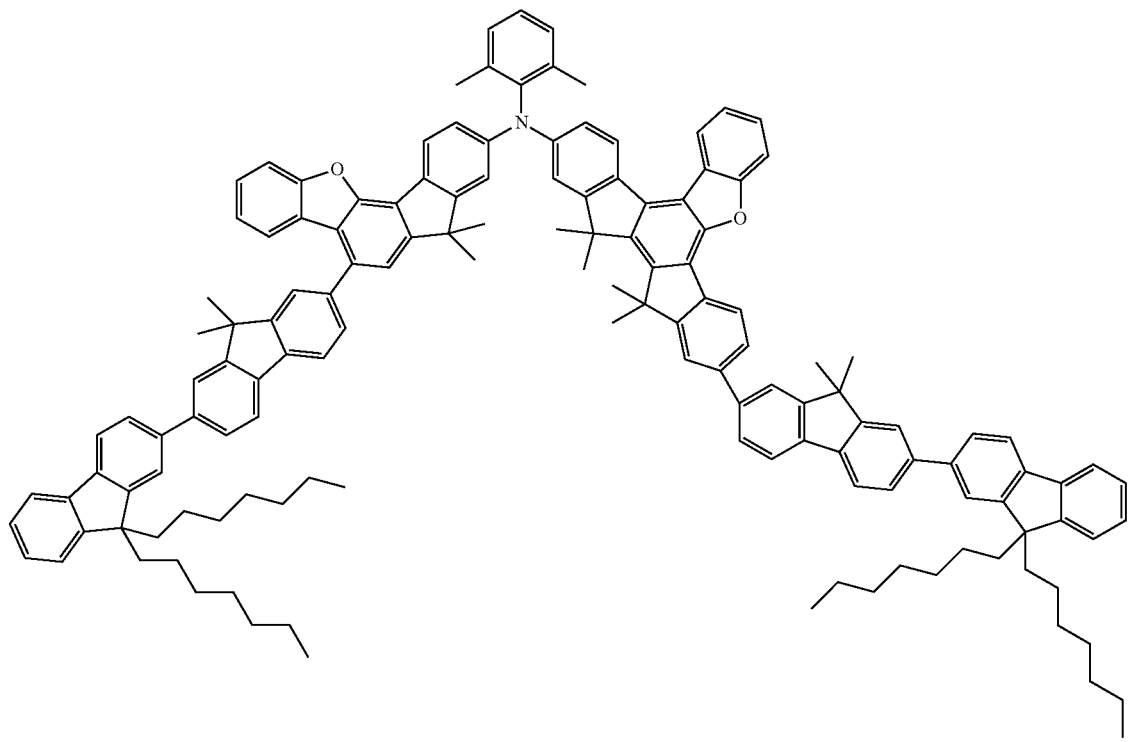 [SMILES: CCCCCCCC1(CCCCCCC)c2ccccc2-c2ccc(-c3ccc4c(c3)C(C)(C)c3cc(-c5ccc6c(c5)C(C)(C)c5c7c(c8c(oc9ccccc98)c5-6)-c5ccc(N(c6ccc8c(c6)C(C)(C)c6cc(-c9ccc%10c(c9)C(C)(C)c9cc(-c%11ccc%12c(c%11)C(CCCCCCC)(CCCCCCC)c%11ccccc%11-%12)ccc9-%10)c9c(oc%10ccccc%109)c6-8)c6c(C)cccc6C)cc5C7(C)C)ccc3-4)cc21]
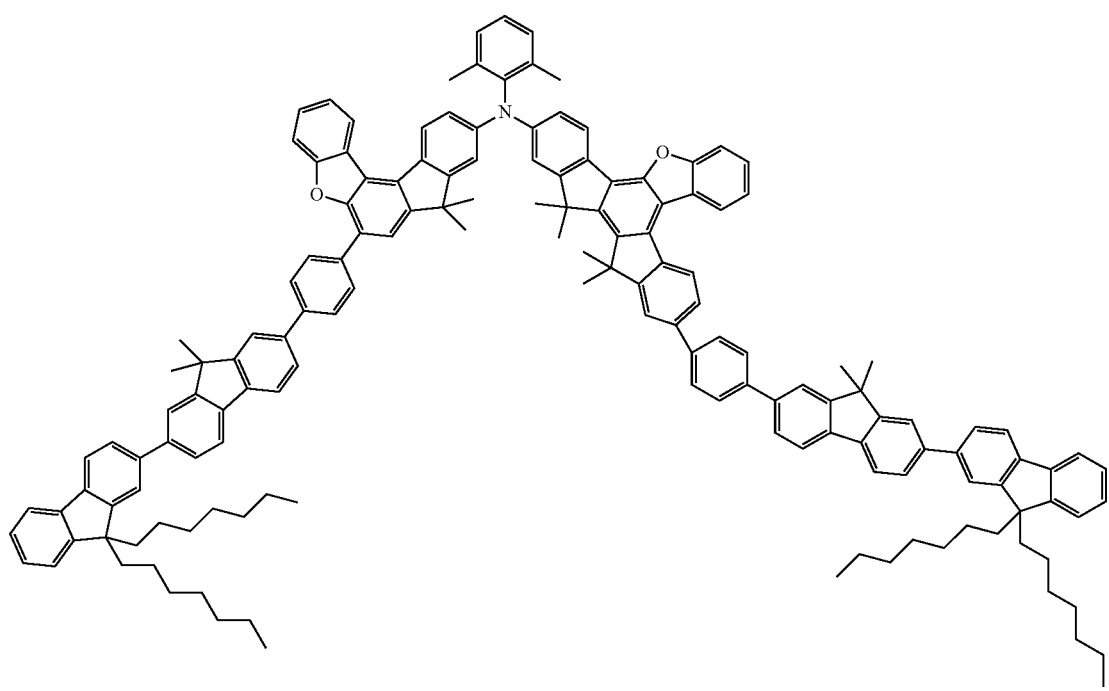 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9oc%10ccccc%10c9c6-7)-c6ccc(N(c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10oc%11ccccc%11c%10c7-9)c7c(C)cccc7C)cc6C8(C)C)cc5)ccc3-4)cc21]

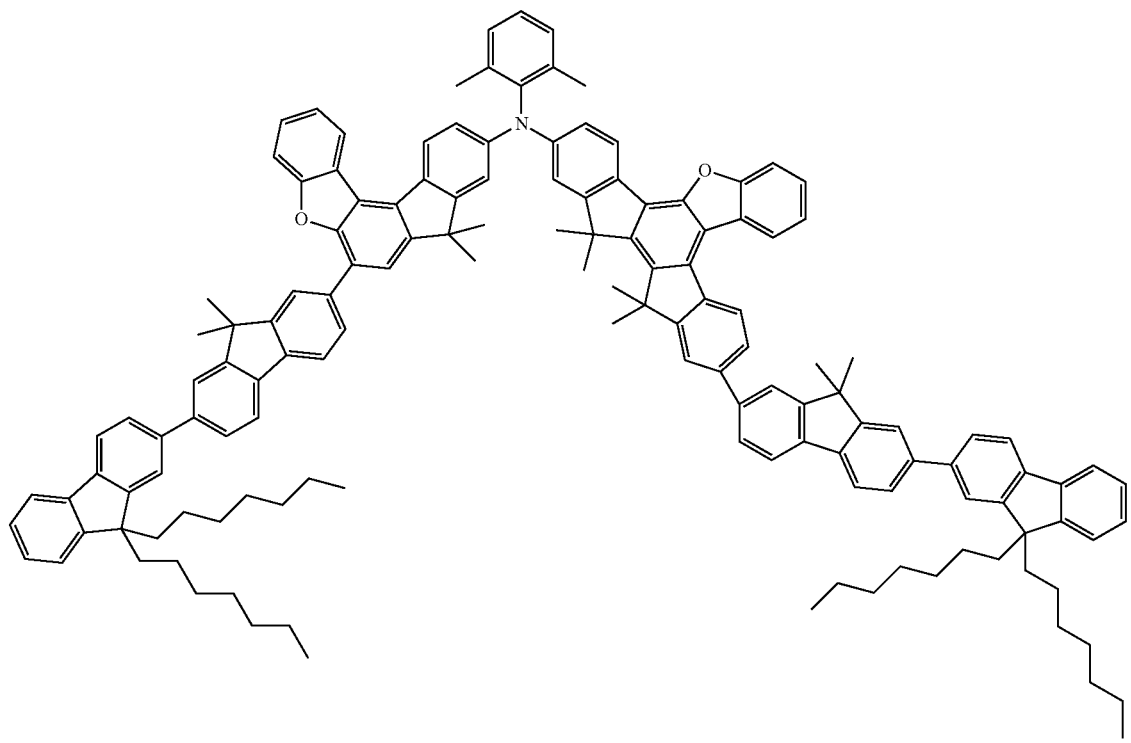 [SMILES: CCCCCCCC1(CCCCCCC)c2ccccc2-c2ccc(-c3ccc4c(c3)C(C)(C)c3cc(-c5ccc6c(c5)C(C)(C)c5c7c(c8oc9ccccc9c8c5-6)-c5ccc(N(c6ccc8c(c6)C(C)(C)c6cc(-c9ccc%10c(c9)C(C)(C)c9cc(-c%11ccc%12c(c%11)C(CCCCCCC)(CCCCCCC)c%11ccccc%11-%12)ccc9-%10)c9oc%10ccccc%10c9c6-8)c6c(C)cccc6C)cc5C7(C)C)ccc3-4)cc21]
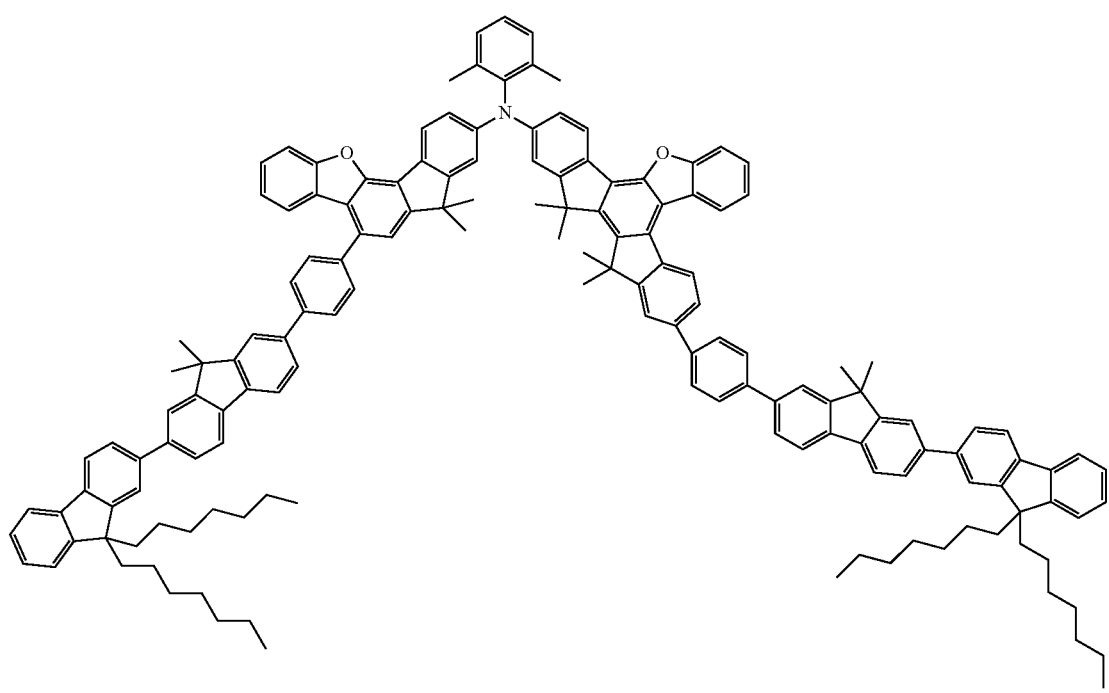 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9oc%10ccccc%10c9c6-7)-c6ccc(N(c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10c(oc%11ccccc%11%10)c7-9)c7c(C)cccc7C)cc6C8(C)C)cc5)ccc3-4)cc21]

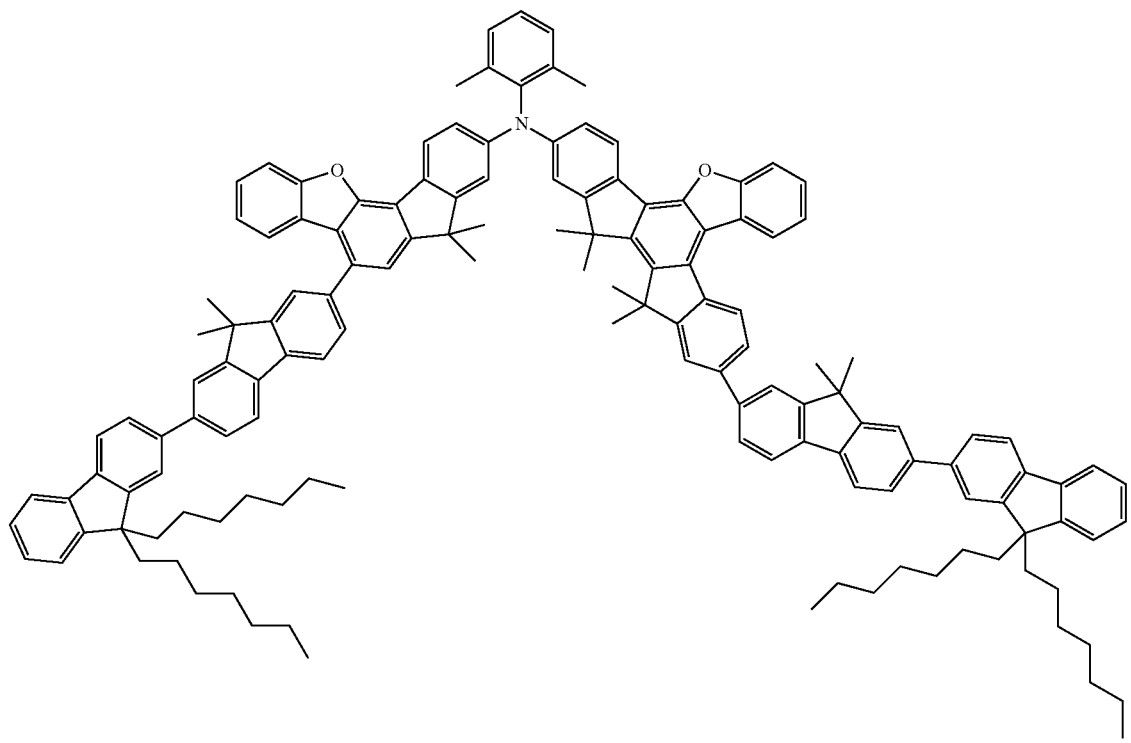 [SMILES: CCCCCCCC1(CCCCCCC)c2ccccc2-c2ccc(-c3ccc4c(c3)C(C)(C)c3cc(-c5ccc6c(c5)C(C)(C)c5c7c(c8oc9ccccc9c8c5-6)-c5ccc(N(c6ccc8c(c6)C(C)(C)c6cc(-c9ccc%10c(c9)C(C)(C)c9cc(-c%11ccc%12c(c%11)C(CCCCCCC)(CCCCCCC)c%11ccccc%11-%12)ccc9-%10)c9c(oc%10ccccc%109)c6-8)c6c(C)cccc6C)cc5C7(C)C)ccc3-4)cc21]
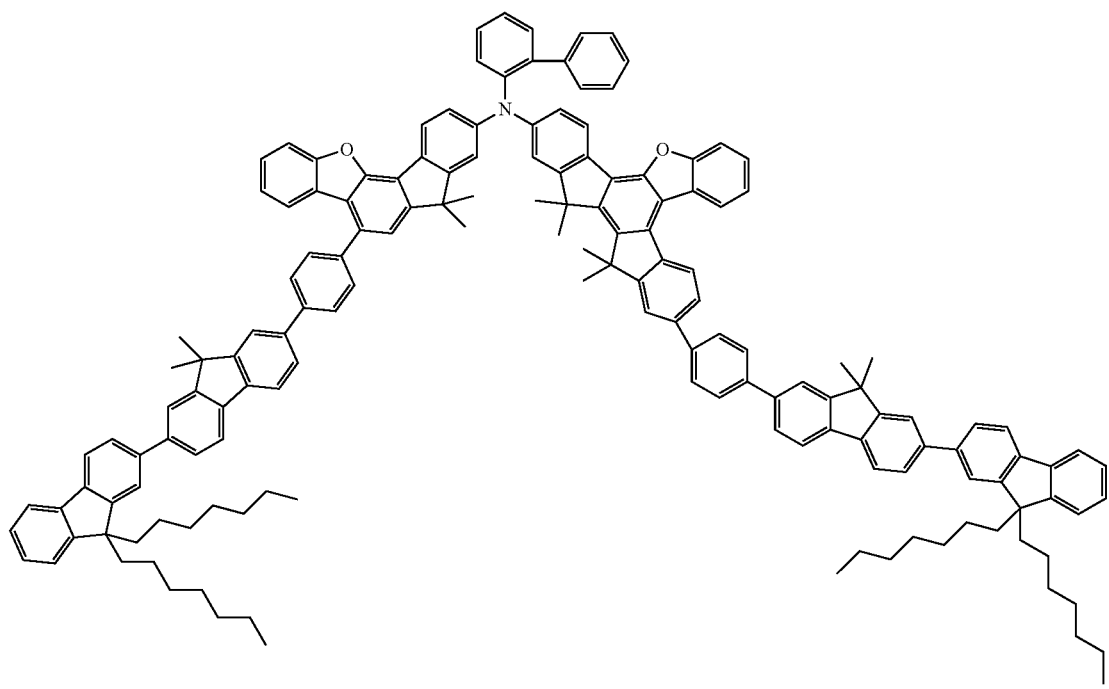 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9oc%10ccccc%10c9c6-7)-c6ccc(N(c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10c(oc%11ccccc%11%10)c7-9)c7ccccc7-c7ccccc7)cc6C8(C)C)cc5)ccc3-4)cc21]

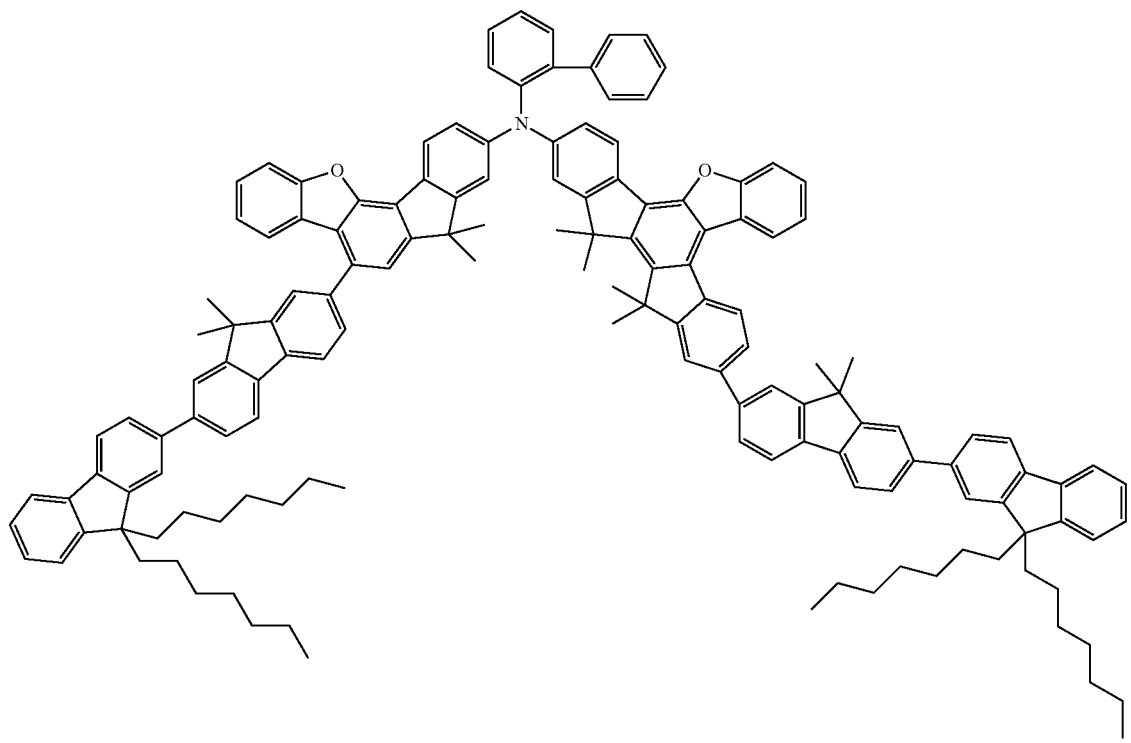 [SMILES: CCCCCCCC1(CCCCCCC)c2ccccc2-c2ccc(-c3ccc4c(c3)C(C)(C)c3cc(-c5ccc6c(c5)C(C)(C)c5c7c(c8oc9ccccc9c8c5-6)-c5ccc(N(c6ccc8c(c6)C(C)(C)c6cc(-c9ccc%10c(c9)C(C)(C)c9cc(-c%11ccc%12c(c%11)C(CCCCCCC)(CCCCCCC)c%11ccccc%11-%12)ccc9-%10)c9c(oc%10ccccc%109)c6-8)c6ccccc6-c6ccccc6)cc5C7(C)C)ccc3-4)cc21]
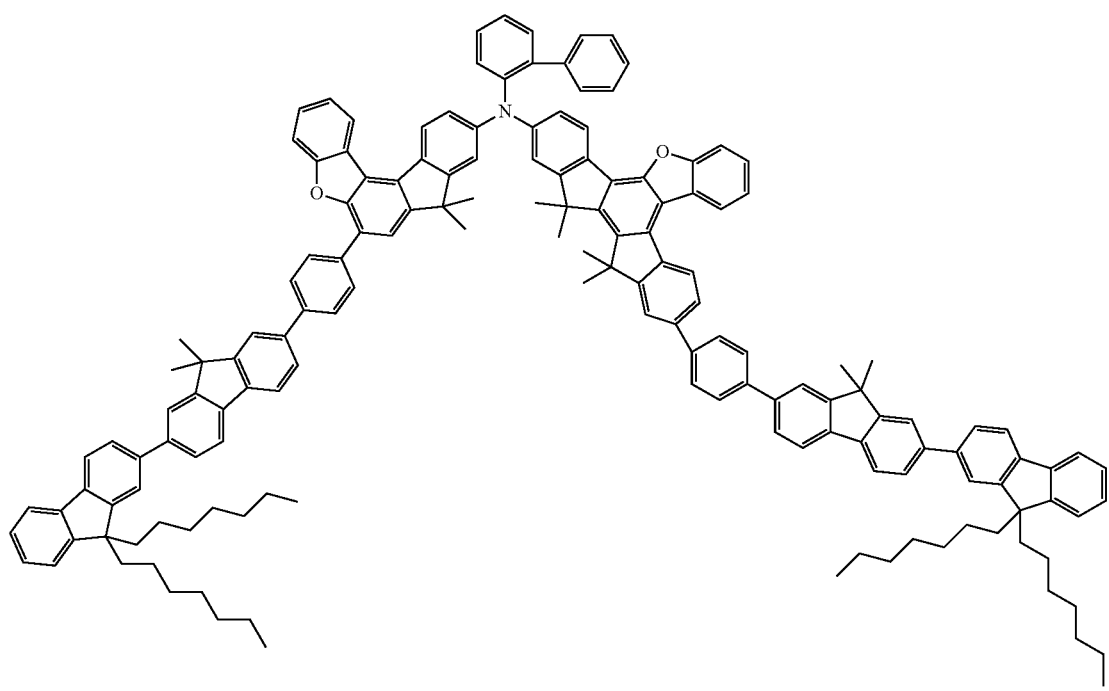 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9oc%10ccccc%10c9c6-7)-c6ccc(N(c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10oc%11ccccc%11c%10c7-9)c7ccccc7-c7ccccc7)cc6C8(C)C)cc5)ccc3-4)cc21]

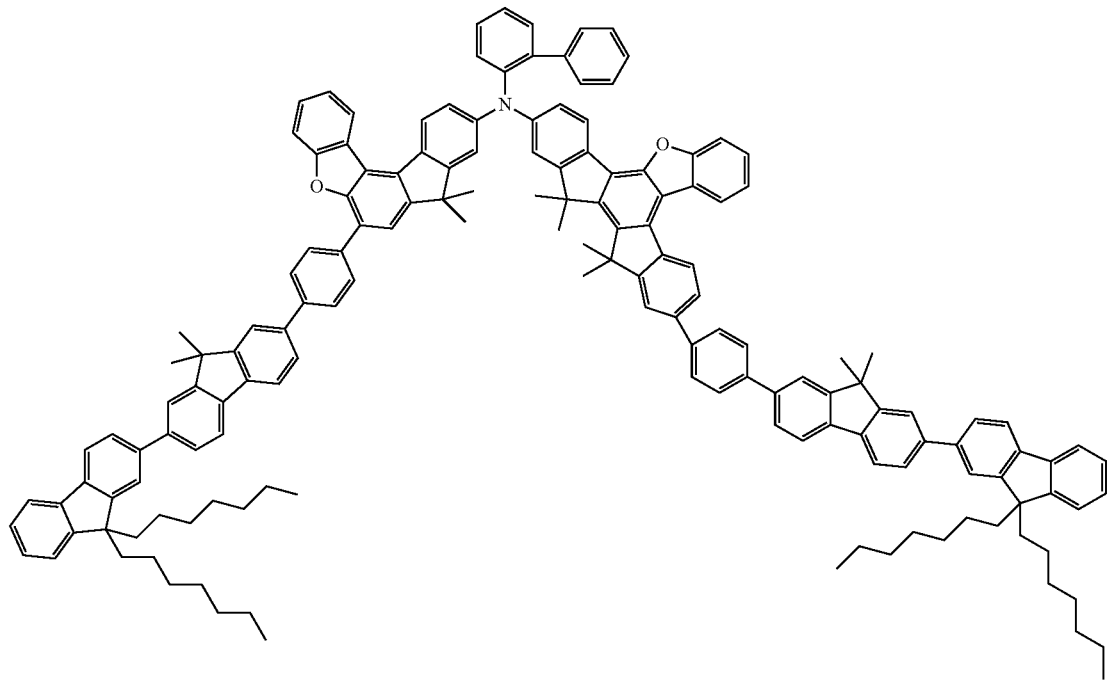 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9oc%10ccccc%10c9c6-7)-c6ccc(N(c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10oc%11ccccc%11c%10c7-9)c7ccccc7-c7ccccc7)cc6C8(C)C)cc5)ccc3-4)cc21]
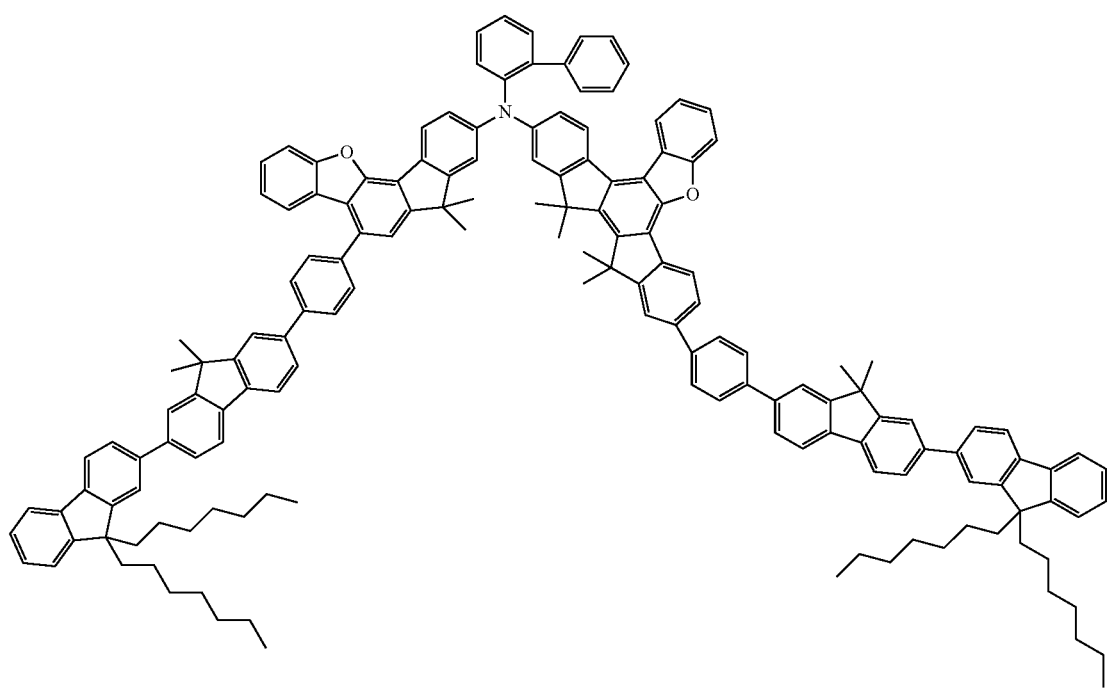 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9c(oc%10ccccc%109)c6-7)-c6ccc(N(c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10c(oc%11ccccc%11%10)c7-9)c7ccccc7-c7ccccc7)cc6C8(C)C)cc5)ccc3-4)cc21]

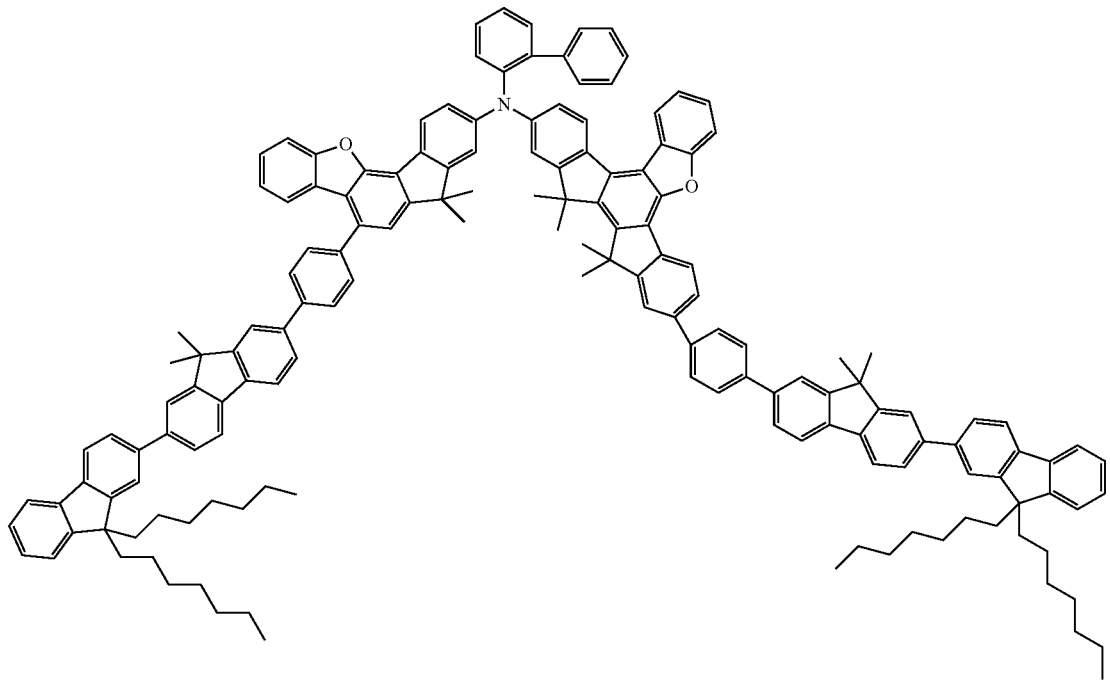 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9c(oc%10ccccc%109)c6-7)-c6ccc(N(c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10c(oc%11ccccc%11%10)c7-9)c7ccccc7-c7ccccc7)cc6C8(C)C)cc5)ccc3-4)cc21]
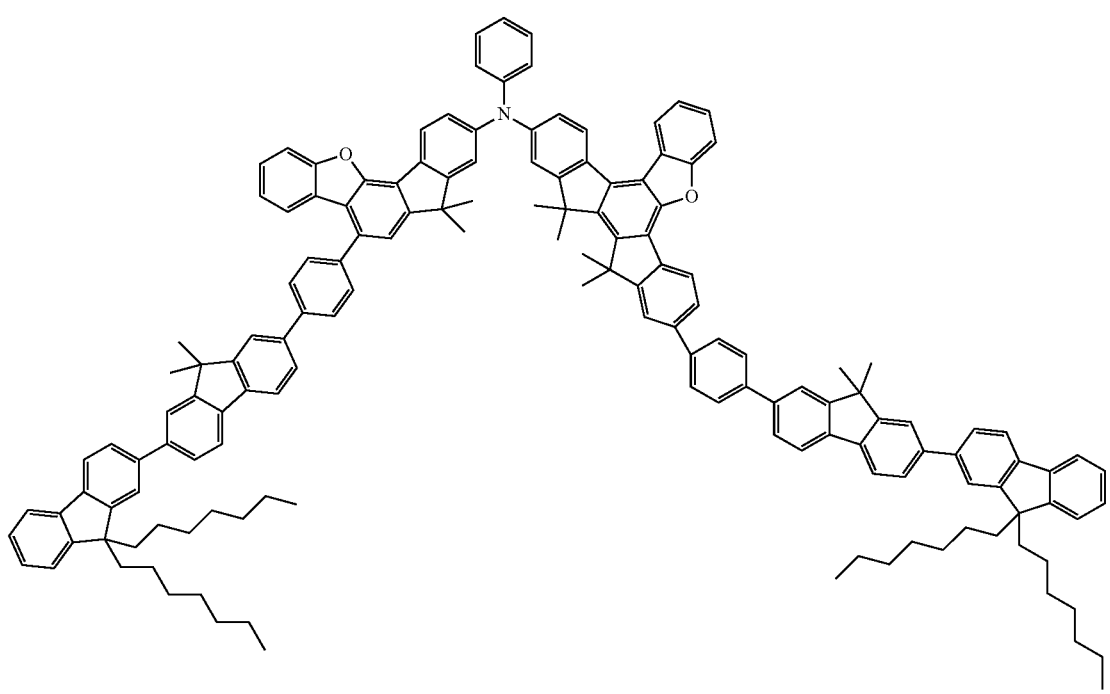 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9c(oc%10ccccc%109)c6-7)-c6ccc(N(c7ccccc7)c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10c(oc%11ccccc%11%10)c7-9)cc6C8(C)C)cc5)ccc3-4)cc21]

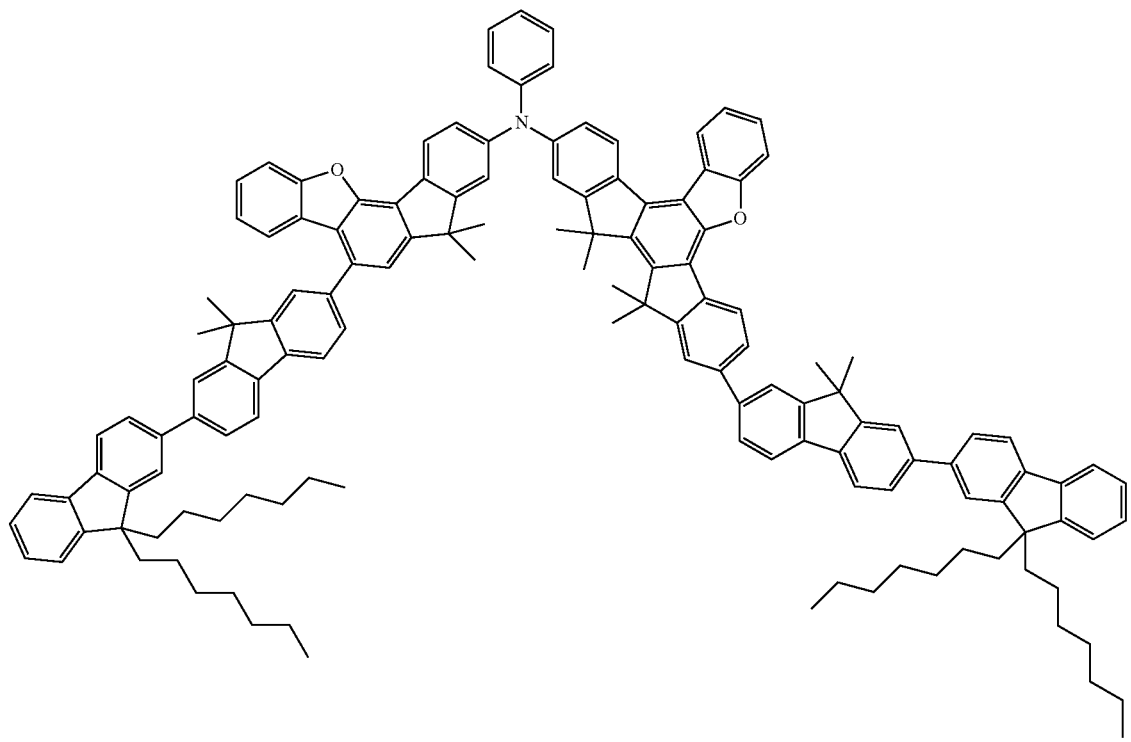 [SMILES: CCCCCCCC1(CCCCCCC)c2ccccc2-c2ccc(-c3ccc4c(c3)C(C)(C)c3cc(-c5ccc6c(c5)C(C)(C)c5c7c(c8c(oc9ccccc98)c5-6)-c5ccc(N(c6ccccc6)c6ccc8c(c6)C(C)(C)c6cc(-c9ccc%10c(c9)C(C)(C)c9cc(-c%11ccc%12c(c%11)C(CCCCCCC)(CCCCCCC)c%11ccccc%11-%12)ccc9-%10)c9c(oc%10ccccc%109)c6-8)cc5C7(C)C)ccc3-4)cc21]
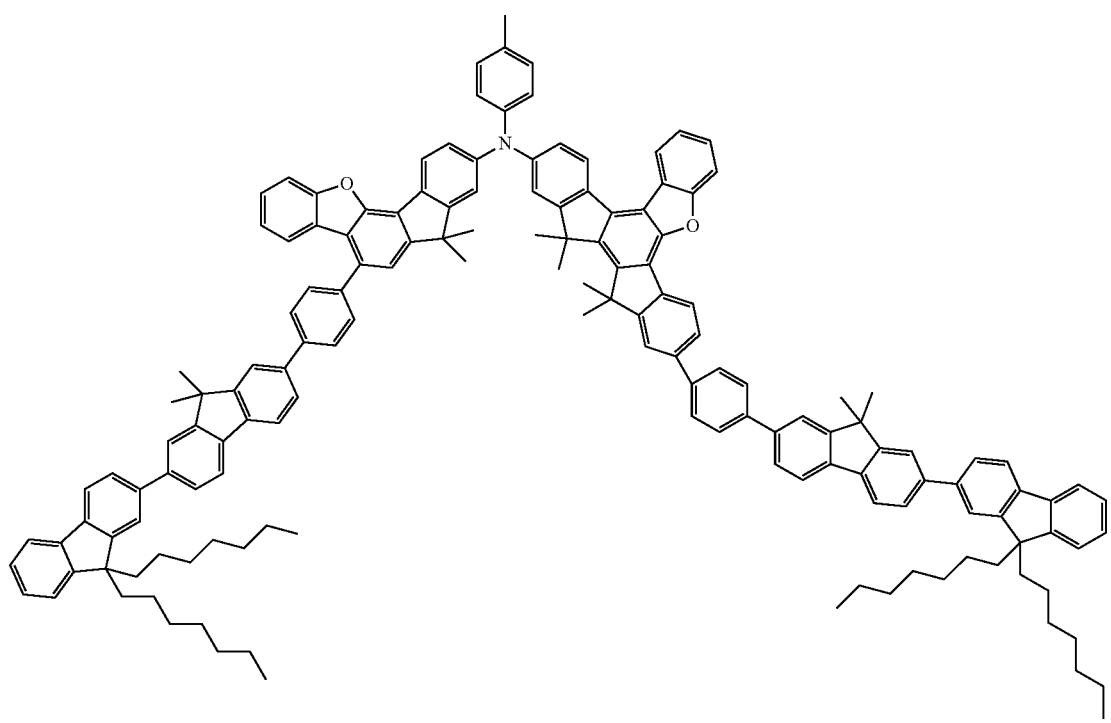 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9c(oc%10ccccc%109)c6-7)-c6ccc(N(c7ccc(C)cc7)c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10c(oc%11ccccc%11%10)c7-9)cc6C8(C)C)cc5)ccc3-4)cc21]

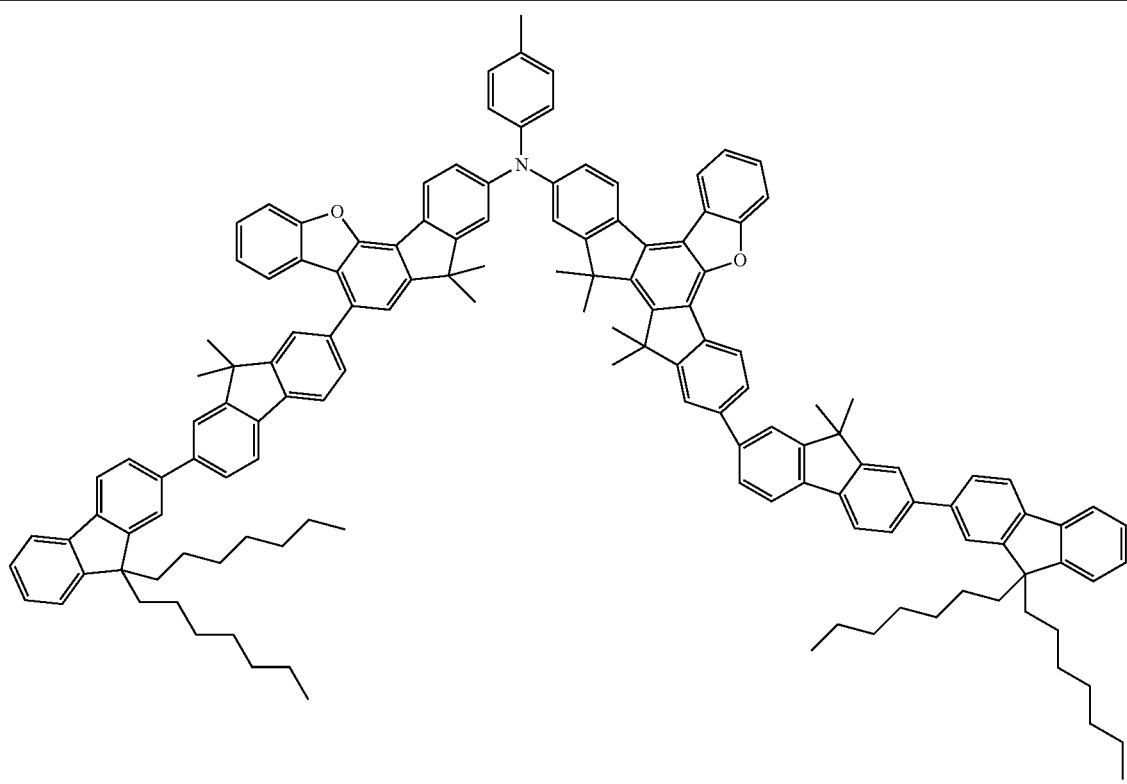
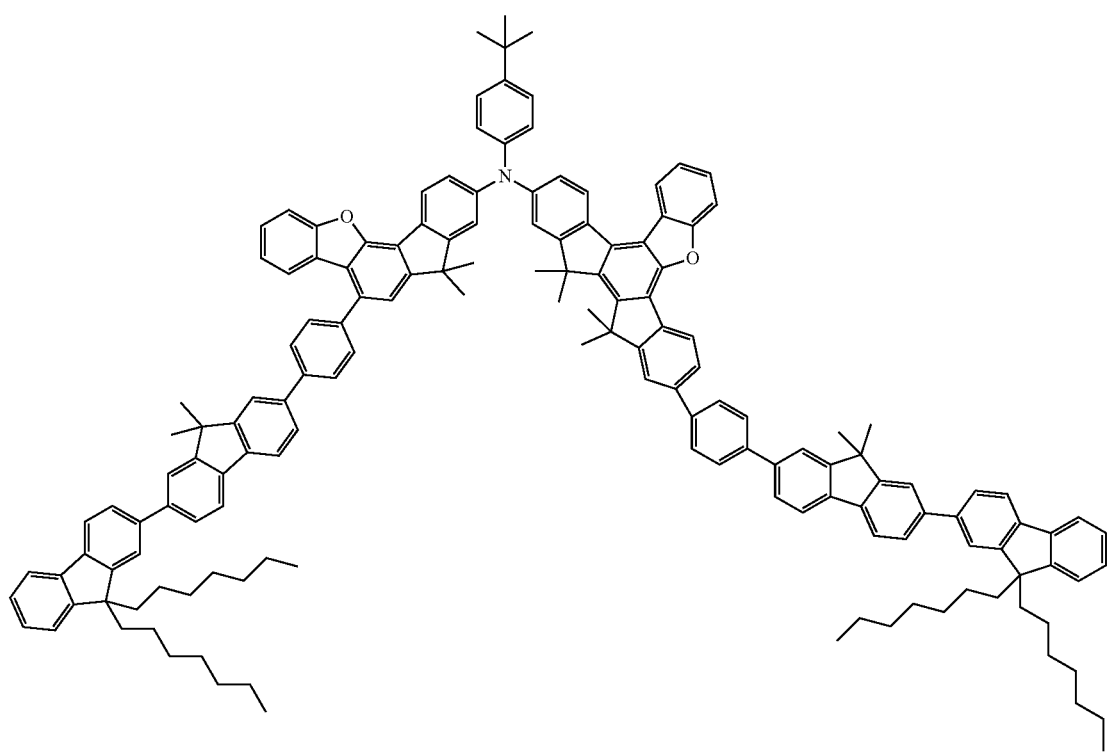 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9c(oc%10ccccc%109)c6-7)-c6ccc(N(c7ccc(C(C)(C)C)cc7)c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10c(oc%11ccccc%11%10)c7-9)cc6C8(C)C)cc5)ccc3-4)cc21]

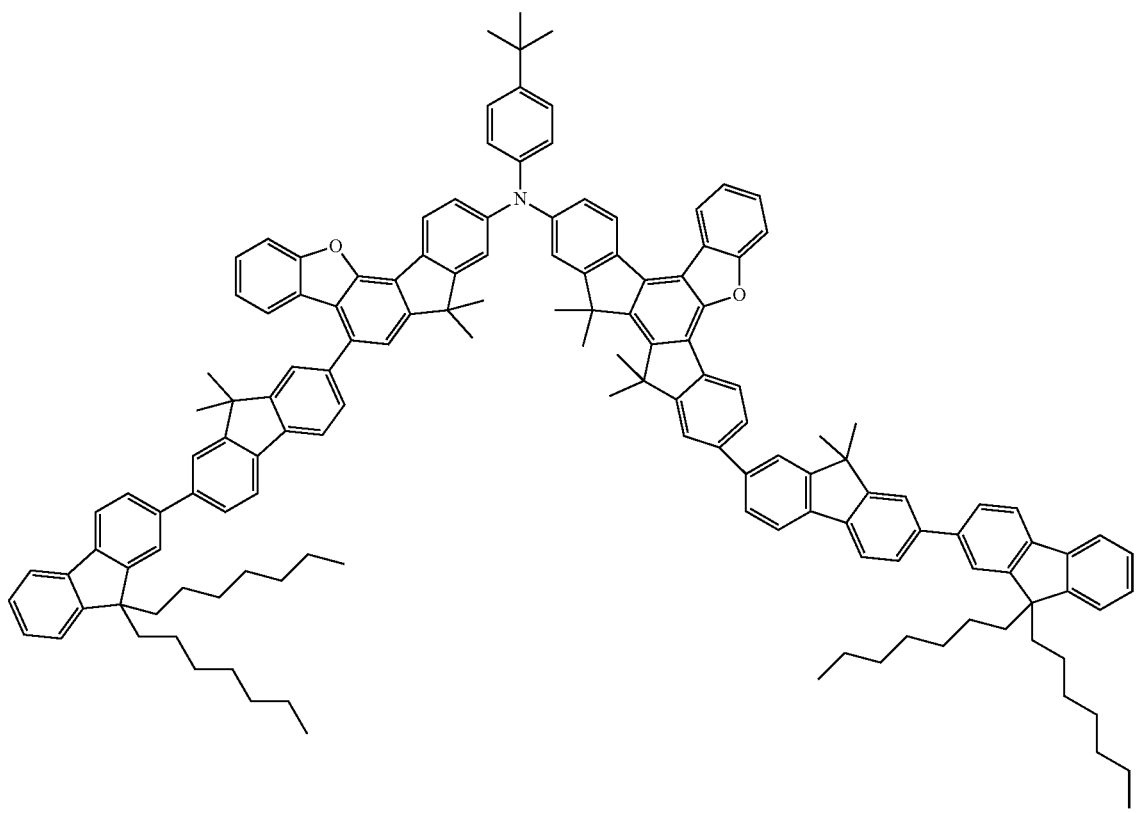 [SMILES: CCCCCCCC1(CCCCCCC)c2ccccc2-c2ccc(-c3ccc4c(c3)C(C)(C)c3cc(-c5ccc6c(c5)C(C)(C)c5c7c(c8c(oc9ccccc98)c5-6)-c5ccc(N(c6ccc(C(C)(C)C)cc6)c6ccc8c(c6)C(C)(C)c6cc(-c9ccc%10c(c9)C(C)(C)c9cc(-c%11ccc%12c(c%11)C(CCCCCCC)(CCCCCCC)c%11ccccc%11-%12)ccc9-%10)c9c(oc%10ccccc%109)c6-8)cc5C7(C)C)ccc3-4)cc21]
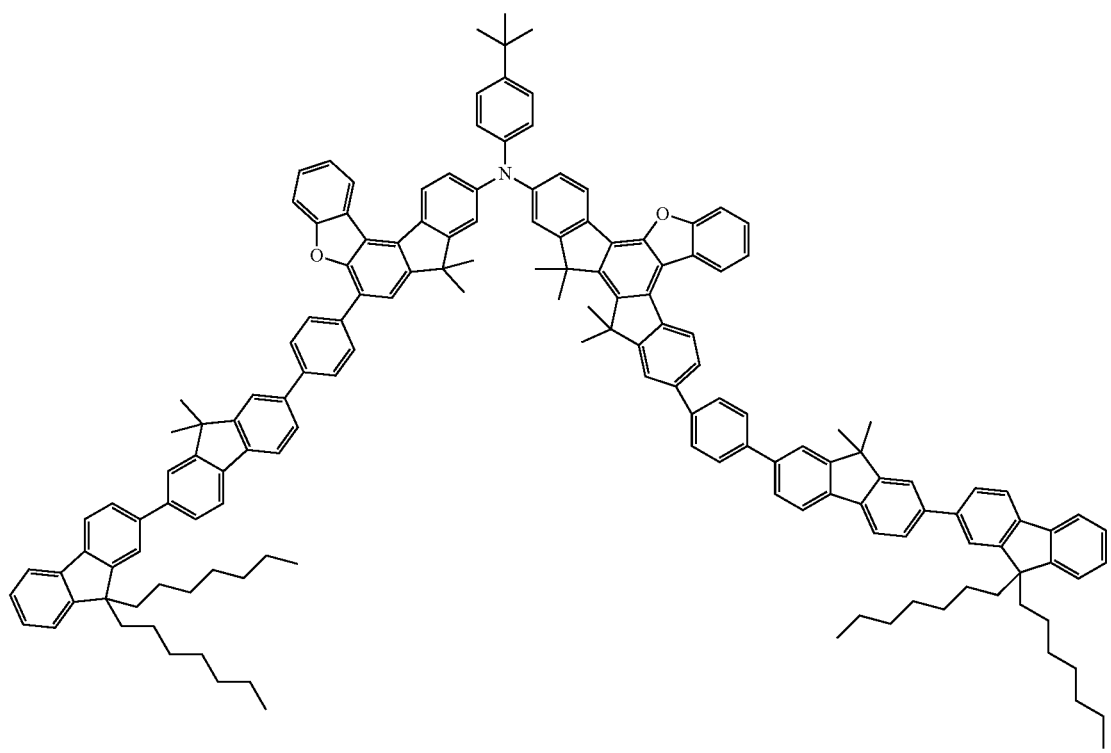 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9oc%10ccccc%10c9c6-7)-c6ccc(N(c7ccc(C(C)(C)C)cc7)c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10oc%11ccccc%11c%10c7-9)cc6C8(C)C)cc5)ccc3-4)cc21]

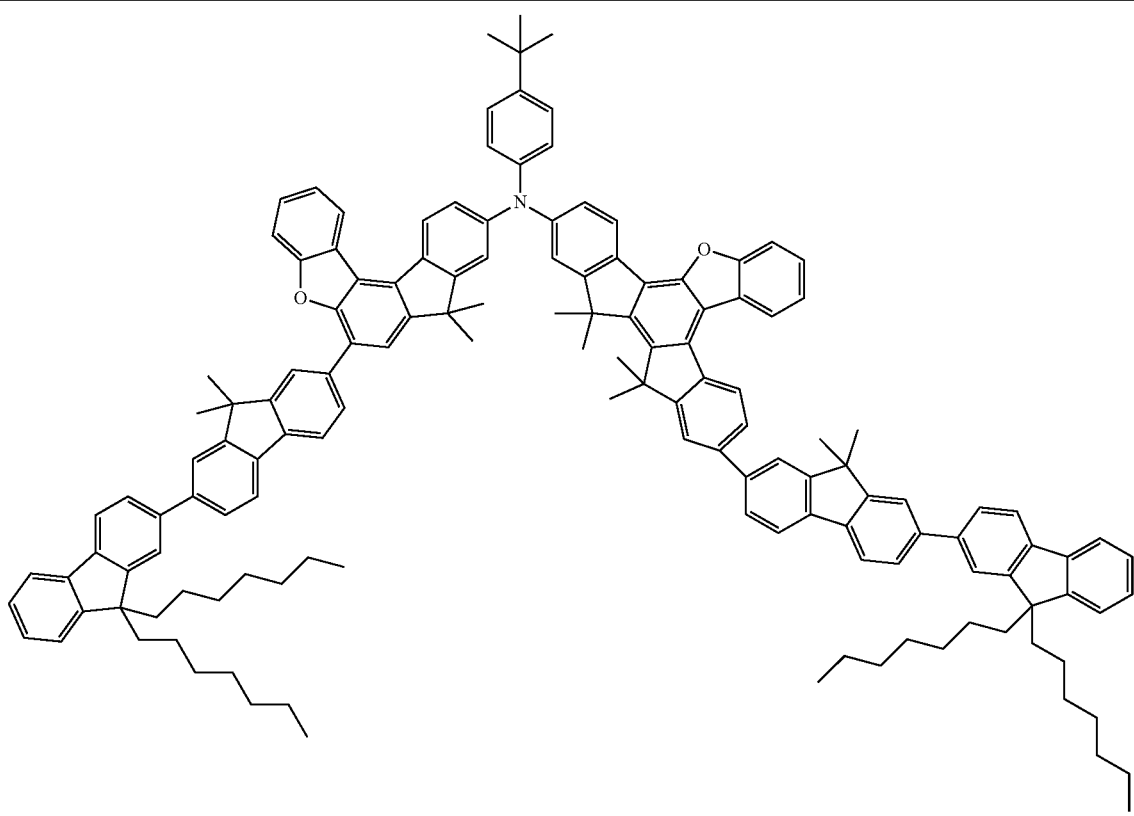
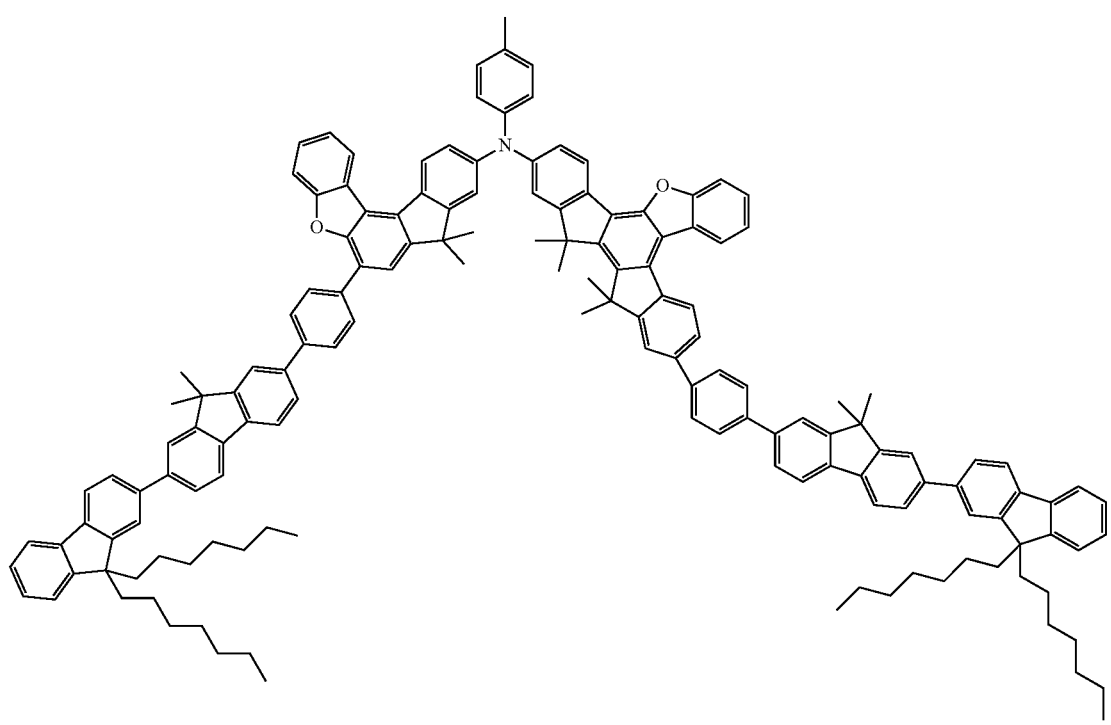 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9oc%10ccccc%10c9c6-7)-c6ccc(N(c7ccc(C)cc7)c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10oc%11ccccc%11c%10c7-9)cc6C8(C)C)cc5)ccc3-4)cc21]

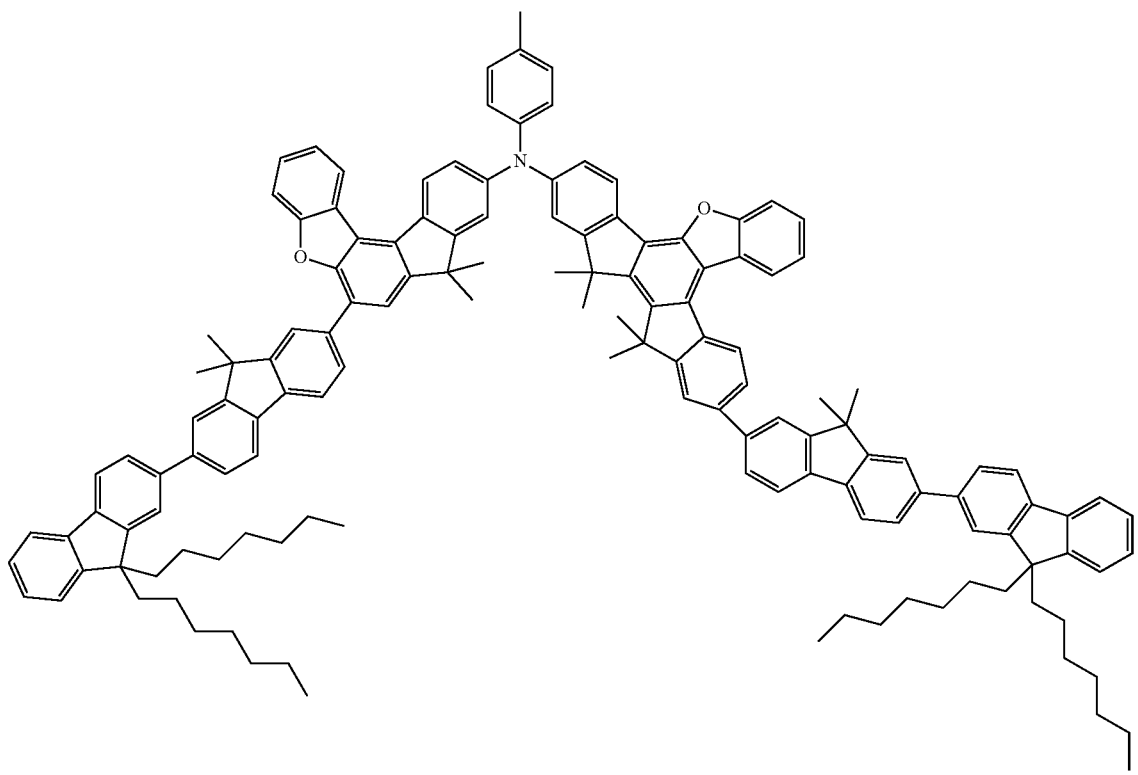 [SMILES: CCCCCCCC1(CCCCCCC)c2ccccc2-c2ccc(-c3ccc4c(c3)C(C)(C)c3cc(-c5ccc6c(c5)C(C)(C)c5c7c(c8oc9ccccc9c8c5-6)-c5ccc(N(c6ccc(C)cc6)c6ccc8c(c6)C(C)(C)c6cc(-c9ccc%10c(c9)C(C)(C)c9cc(-c%11ccc%12c(c%11)C(CCCCCCC)(CCCCCCC)c%11ccccc%11-%12)ccc9-%10)c9oc%10ccccc%10c9c6-8)cc5C7(C)C)ccc3-4)cc21]
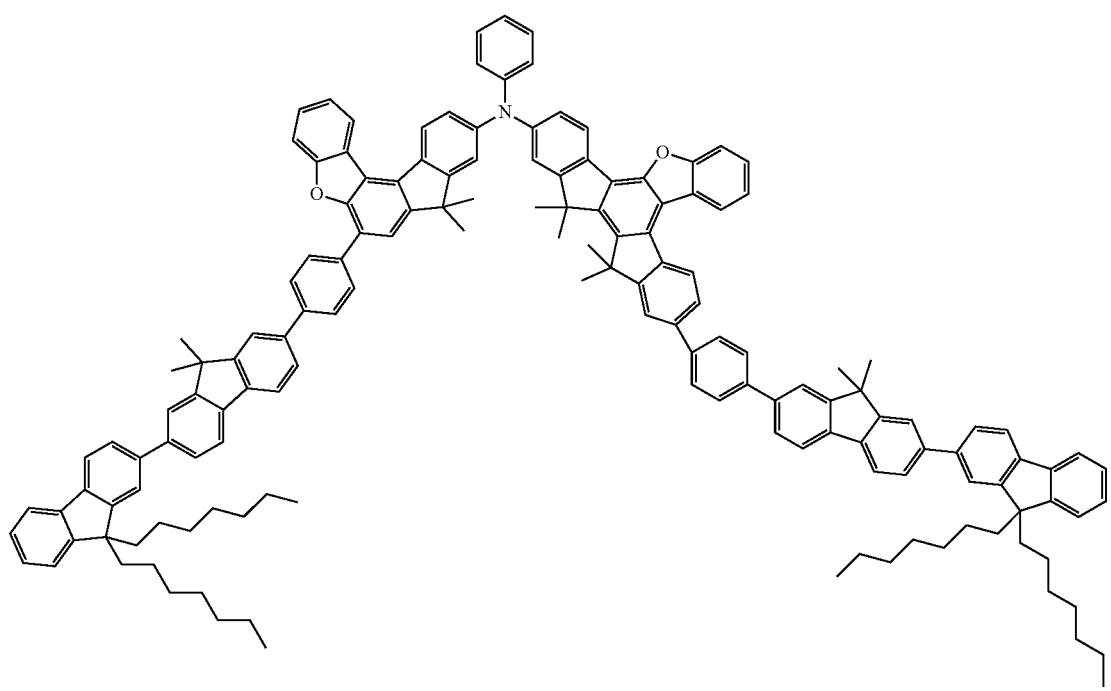 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9oc%10ccccc%10c9c6-7)-c6ccc(N(c7ccccc7)c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10oc%11ccccc%11c%10c7-9)cc6C8(C)C)cc5)ccc3-4)cc21]

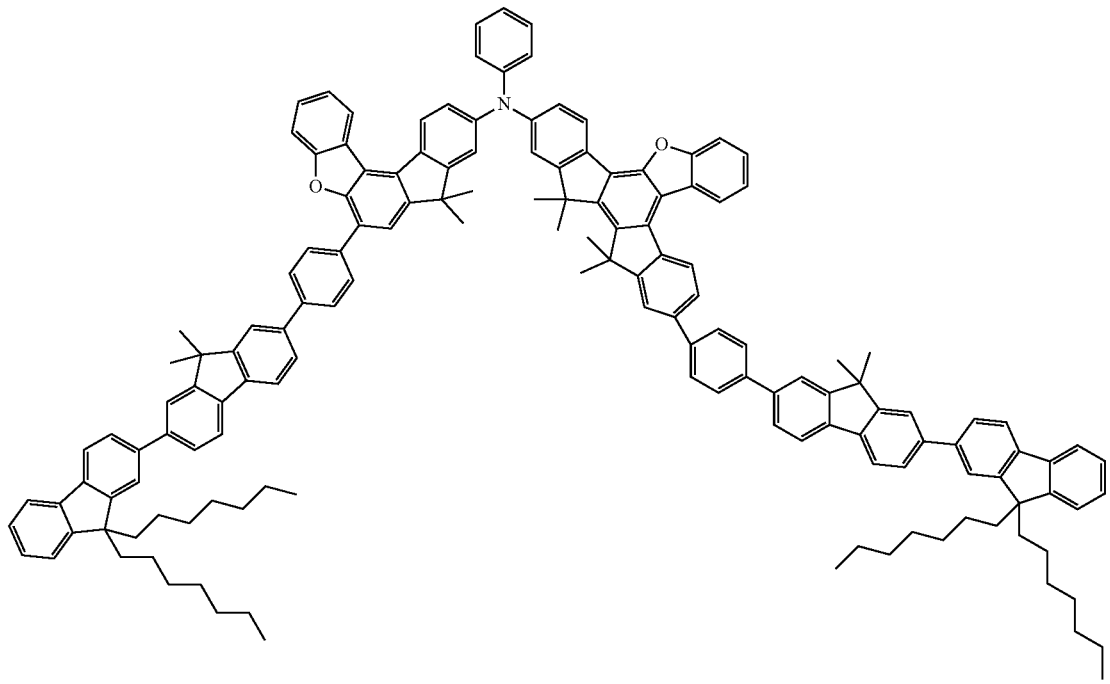 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9oc%10ccccc%10c9c6-7)-c6ccc(N(c7ccccc7)c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10oc%11ccccc%11c%10c7-9)cc6C8(C)C)cc5)ccc3-4)cc21]
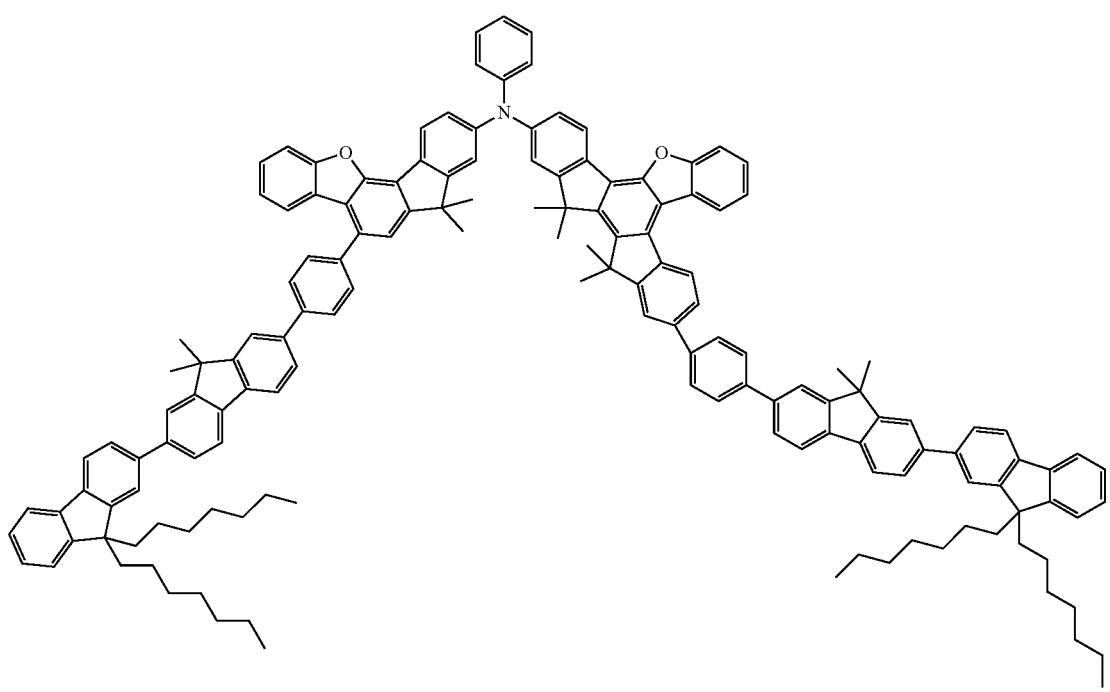 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9oc%10ccccc%10c9c6-7)-c6ccc(N(c7ccccc7)c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10c(oc%11ccccc%11%10)c7-9)cc6C8(C)C)cc5)ccc3-4)cc21]

-continued
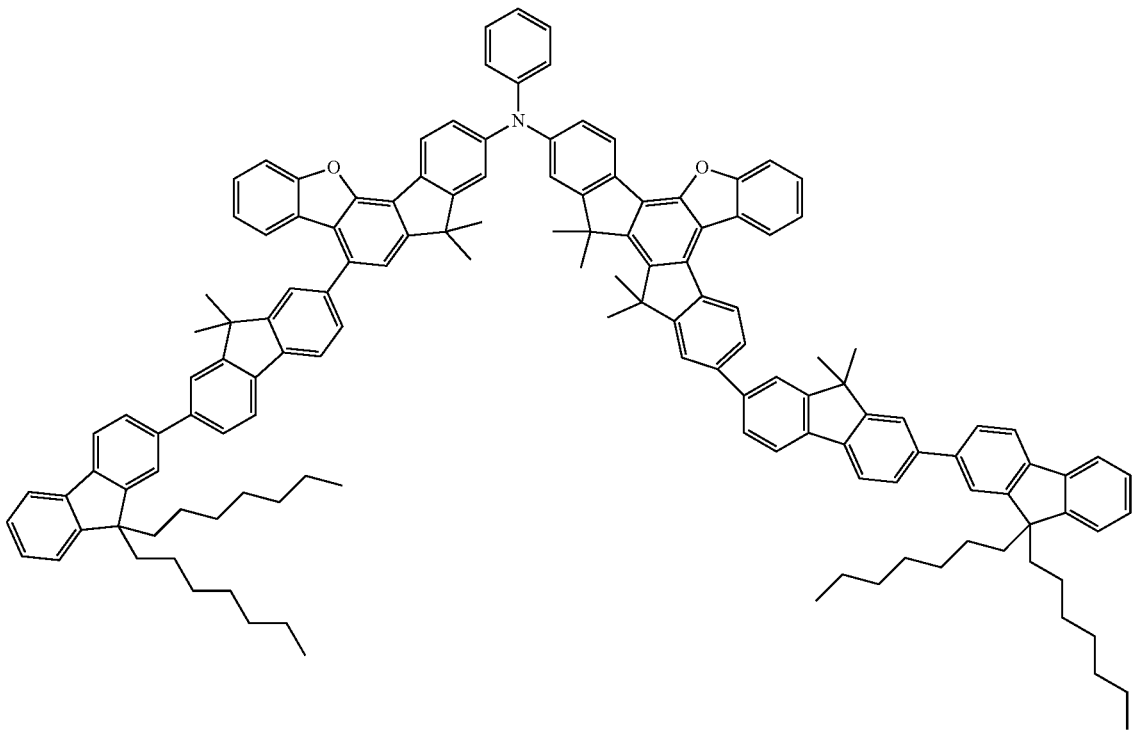 [SMILES: CCCCCCCC1(CCCCCCC)c2ccccc2-c2ccc(-c3ccc4c(c3)C(C)(C)c3cc(-c5ccc6c(c5)C(C)(C)c5c7c(c8oc9ccccc9c8c5-6)-c5ccc(N(c6ccccc6)c6ccc8c(c6)C(C)(C)c6cc(-c9ccc%10c(c9)C(C)(C)c9cc(-c%11ccc%12c(c%11)C(CCCCCCC)(CCCCCCC)c%11ccccc%11-%12)ccc9-%10)c9c(oc%10ccccc%109)c6-8)cc5C7(C)C)ccc3-4)cc21]
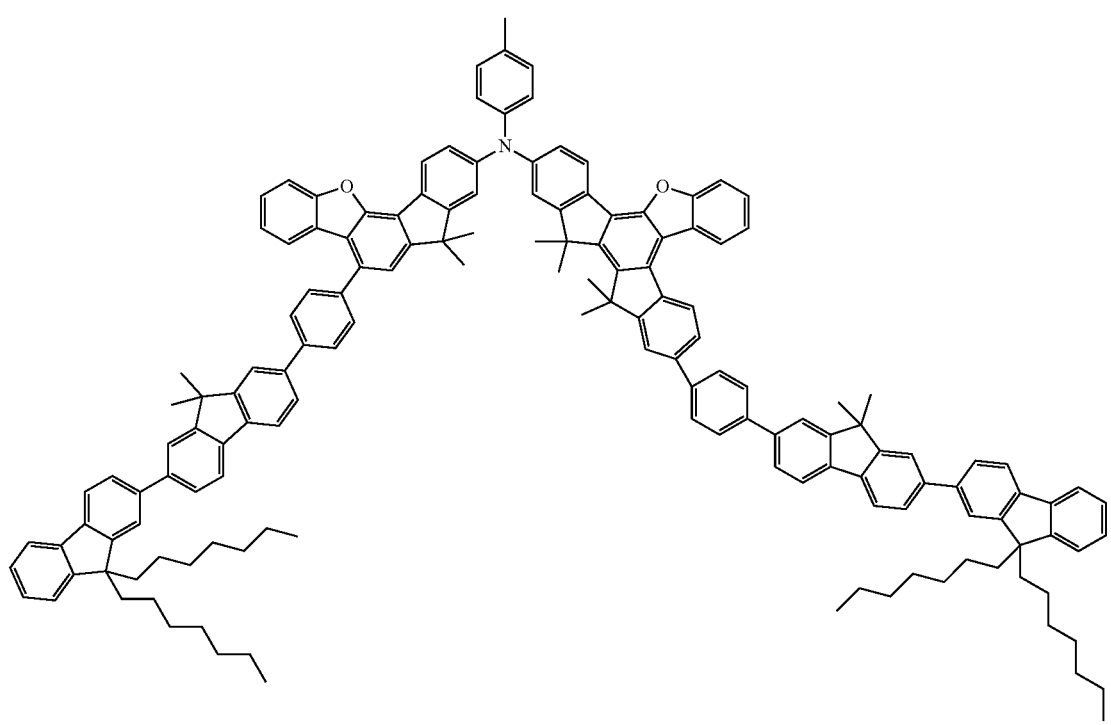 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9oc%10ccccc%10c9c6-7)-c6ccc(N(c7ccc(C)cc7)c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10c(oc%11ccccc%11%10)c7-9)cc6C8(C)C)cc5)ccc3-4)cc21]

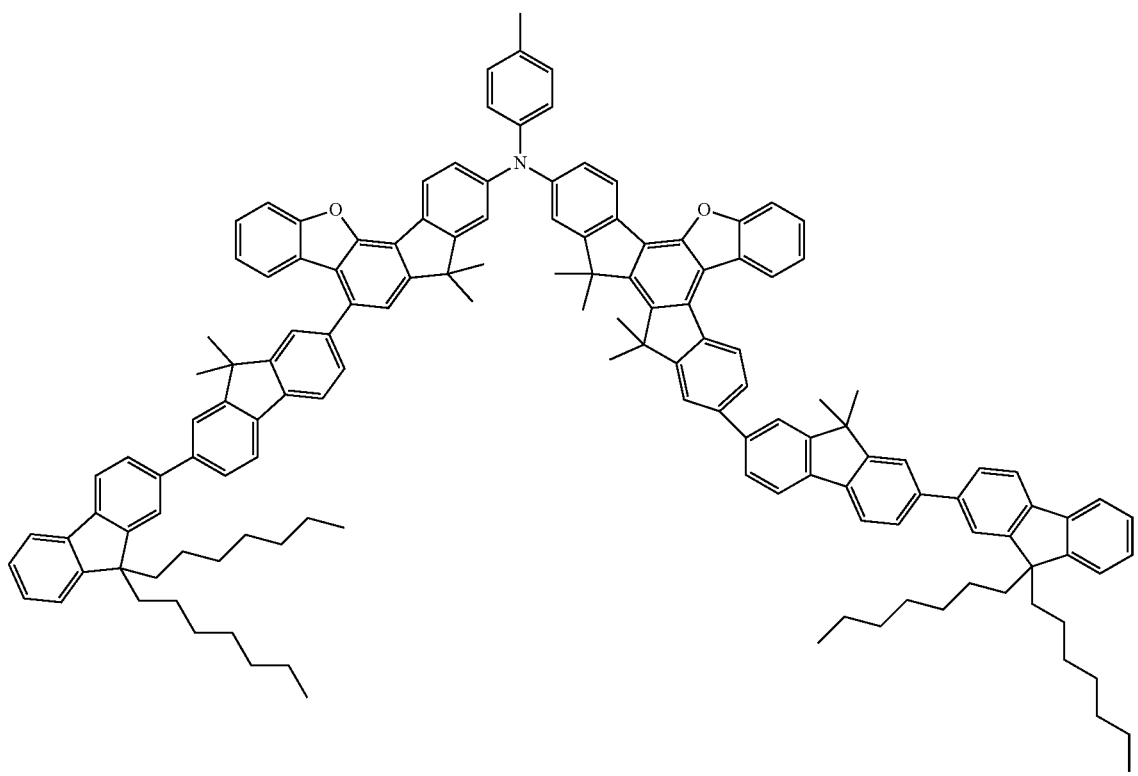 [SMILES: CCCCCCCC1(CCCCCCC)c2ccccc2-c2ccc(-c3ccc4c(c3)C(C)(C)c3cc(-c5ccc6c(c5)C(C)(C)c5c7c(c8oc9ccccc9c8c5-6)-c5ccc(N(c6ccc(C)cc6)c6ccc8c(c6)C(C)(C)c6cc(-c9ccc%10c(c9)C(C)(C)c9cc(-c%11ccc%12c(c%11)C(CCCCCCC)(CCCCCCC)c%11ccccc%11-%12)ccc9-%10)c9c(oc%10ccccc%109)c6-8)cc5C7(C)C)ccc3-4)cc21]
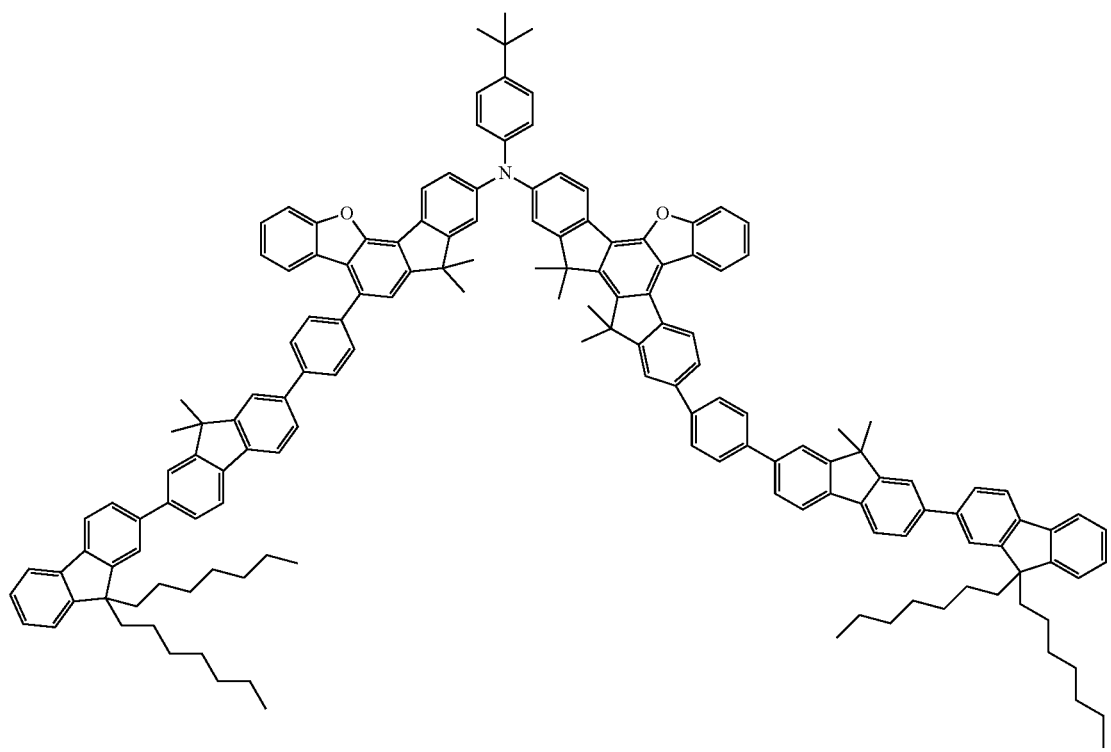 [SMILES: CCCCCCCC1(CCCCCCC)c2ccccc2-c2ccc(-c3ccc4c(c3)C(C)(C)c3cc(-c5ccc(-c6ccc7c(c6)C(C)(C)c6c8c(c9oc%10ccccc%10c9c6-7)-c6ccc(N(c7ccc(C(C)(C)C)cc7)c7ccc9c(c7)C(C)(C)c7cc(-c%10ccc(-c%11ccc%12c(c%11)C(C)(C)c%11cc(-c%13ccc%14c(c%13)C(CCCCCCC)(CCCCCCC)c%13ccccc%13-%14)ccc%11-%12)cc%10)c%10c(oc%11ccccc%11%10)c7-9)cc6C8(C)C)cc5)ccc3-4)cc21]

-continued
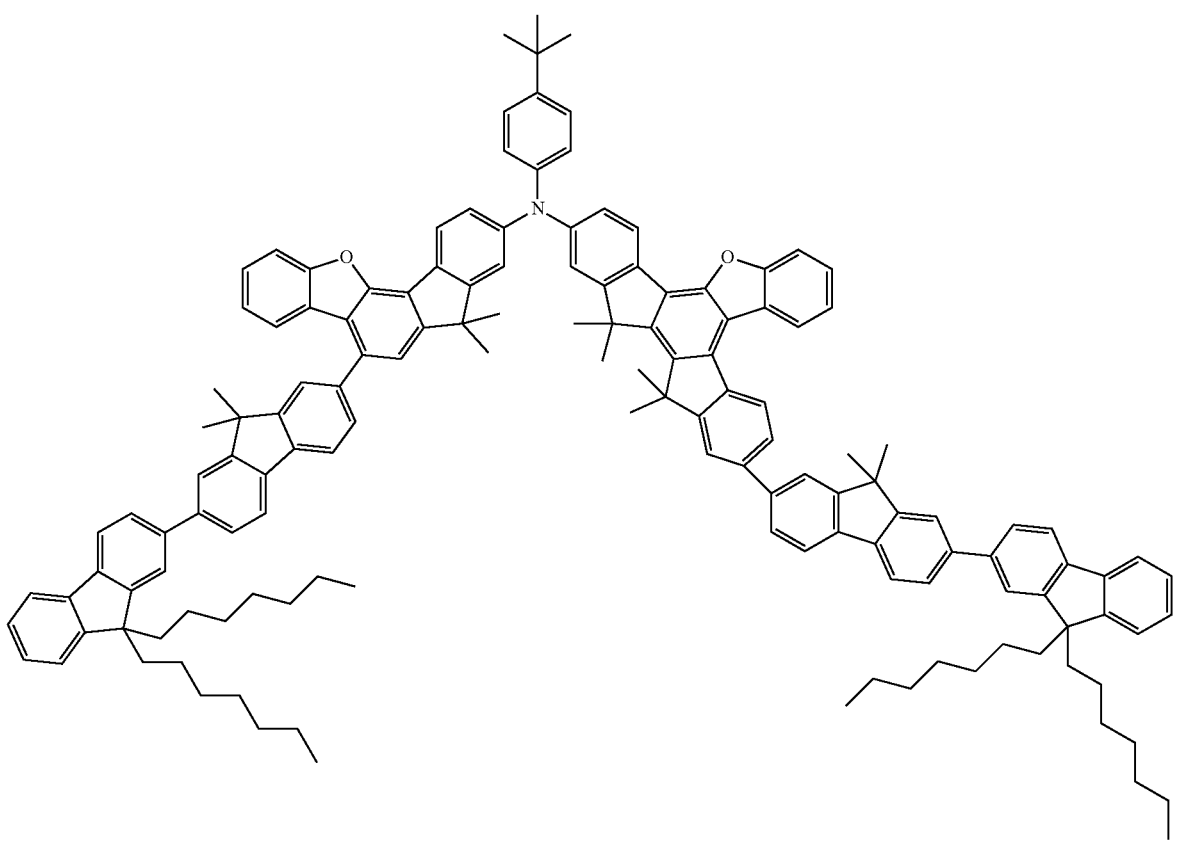 [SMILES: CCCCCCCC1(CCCCCCC)c2ccccc2-c2ccc(-c3ccc4c(c3)C(C)(C)c3cc(-c5ccc6c(c5)C(C)(C)c5c7c(c8oc9ccccc9c8c5-6)-c5ccc(N(c6ccc(C(C)(C)C)cc6)c6ccc8c(c6)C(C)(C)c6cc(-c9ccc%10c(c9)C(C)(C)c9cc(-c%11ccc%12c(c%11)C(CCCCCCC)(CCCCCCC)c%11ccccc%11-%12)ccc9-%10)c9c(oc%10ccccc%109)c6-8)cc5C7(C)C)ccc3-4)cc21]
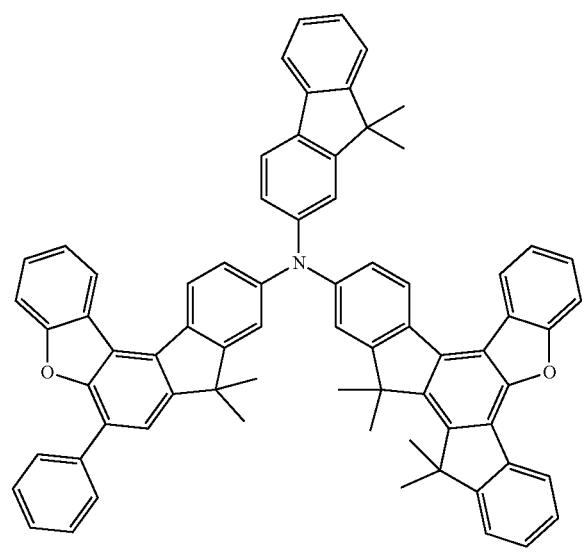 [SMILES: CC1(C)c2ccccc2-c2ccc(N(c3ccc4c(c3)C(C)(C)c3cc(-c5ccccc5)c5oc6ccccc6c5c3-4)c3ccc4c(c3)C(C)(C)c3c5c(c6oc7ccccc7c6c3-4)-c3ccccc3C5(C)C)cc21]

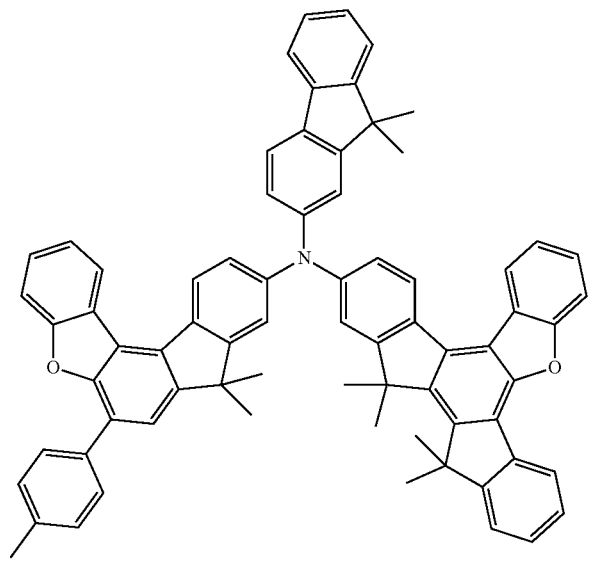 [SMILES: Cc1ccc(-c2cc3c(c4c2oc2ccccc24)-c2ccc(N(c4ccc5c(c4)C(C)(C)c4ccccc4-5)c4ccc5c(c4)C(C)(C)c4c6c(c7oc8ccccc8c7c4-5)-c4ccccc4C6(C)C)cc2C3(C)C)cc1]
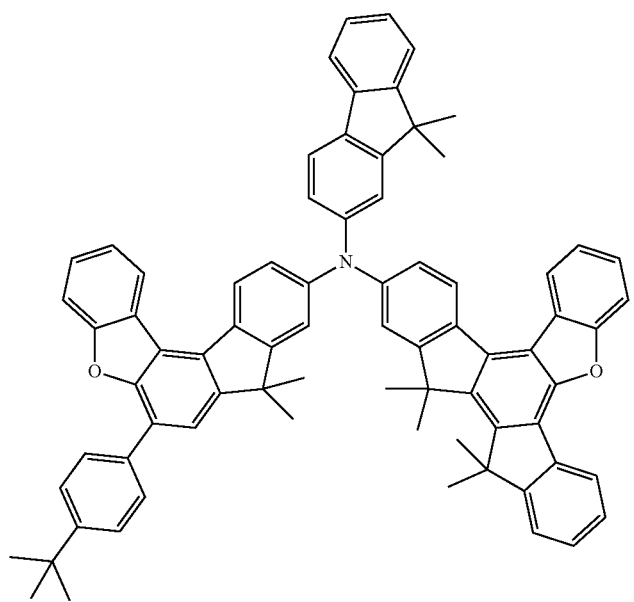 [SMILES: CC(C)(C)c1ccc(-c2cc3c(c4c2oc2ccccc24)-c2ccc(N(c4ccc5c(c4)C(C)(C)c4ccccc4-5)c4ccc5c(c4)C(C)(C)c4c6c(c7oc8ccccc8c7c4-5)-c4ccccc4C6(C)C)cc2C3(C)C)cc1]

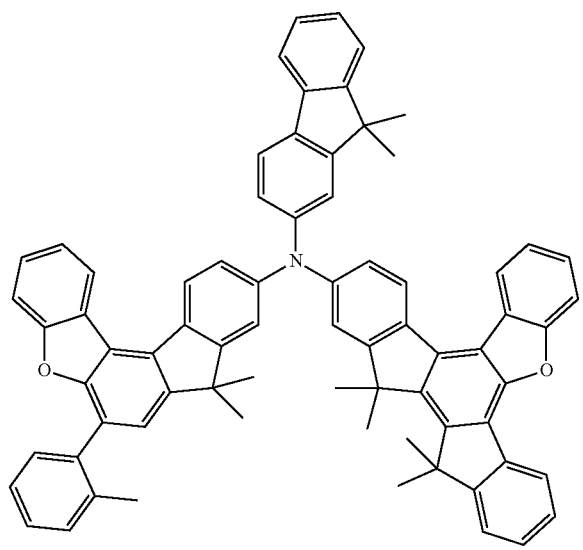 [SMILES: Cc1ccccc1-c1cc2c(c3c1oc1ccccc13)-c1ccc(N(c3ccc4c(c3)C(C)(C)c3ccccc3-4)c3ccc4c(c3)C(C)(C)c3c5c(c6oc7ccccc7c6c3-4)-c3ccccc3C5(C)C)cc1C2(C)C]
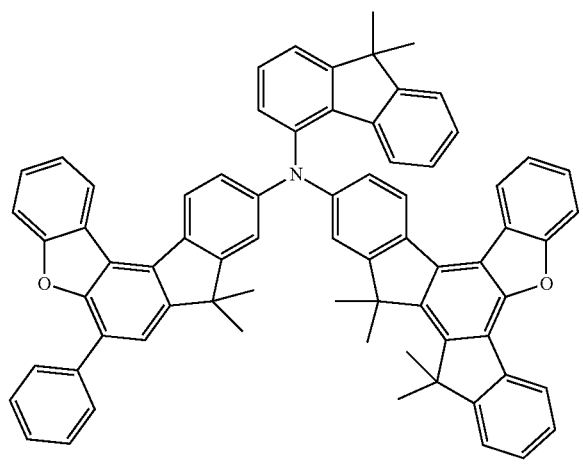 [SMILES: CC1(C)c2ccccc2-c2c(N(c3ccc4c(c3)C(C)(C)c3cc(-c5ccccc5)c5oc6ccccc6c5c3-4)c3ccc4c(c3)C(C)(C)c3c5c(c6oc7ccccc7c6c3-4)-c3ccccc3C5(C)C)cccc21]
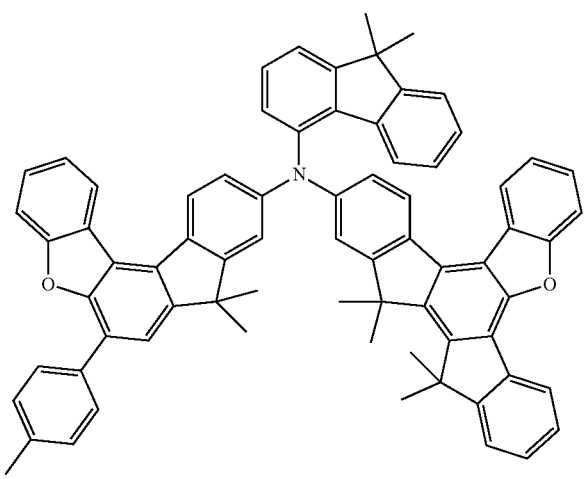 [SMILES: Cc1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4cccc5c4-c4ccccc4C5(C)C)cc2C3(C)C)cc1]

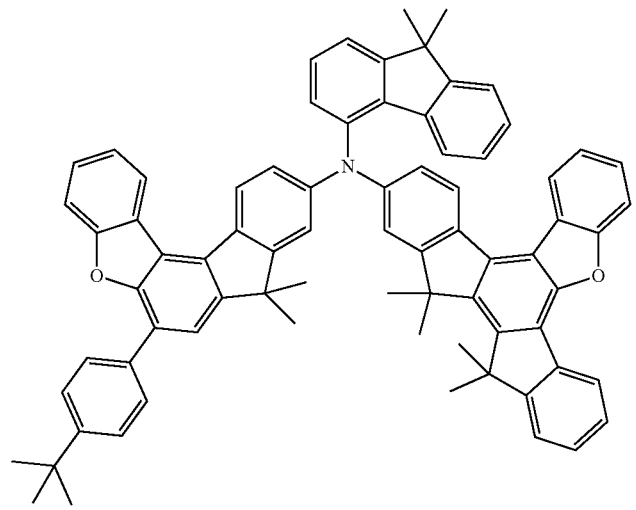 [SMILES: CC(C)(C)c1ccc(-c2cc3c(c4c2oc2ccccc24)-c2ccc(N(c4ccc5c(c4)C(C)(C)c4c6c(c7oc8ccccc8c7c4-5)-c4ccccc4C6(C)C)c4cccc5c4-c4ccccc4C5(C)C)cc2C3(C)C)cc1]
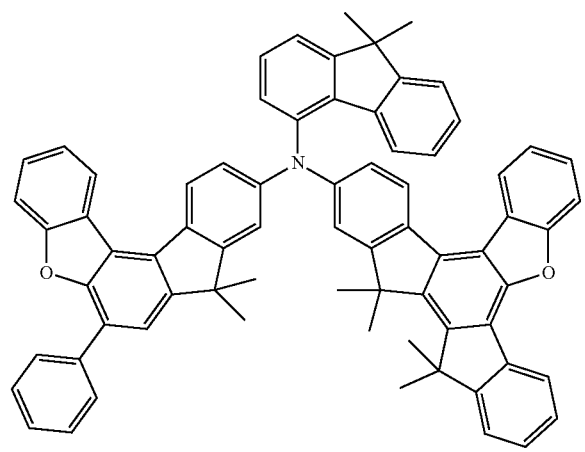 [SMILES: CC1(C)c2ccccc2-c2c(N(c3ccc4c(c3)C(C)(C)c3cc(-c5ccccc5)c5oc6ccccc6c5c3-4)c3ccc4c(c3)C(C)(C)c3c5c(c6oc7ccccc7c6c3-4)-c3ccccc3C5(C)C)cccc21]
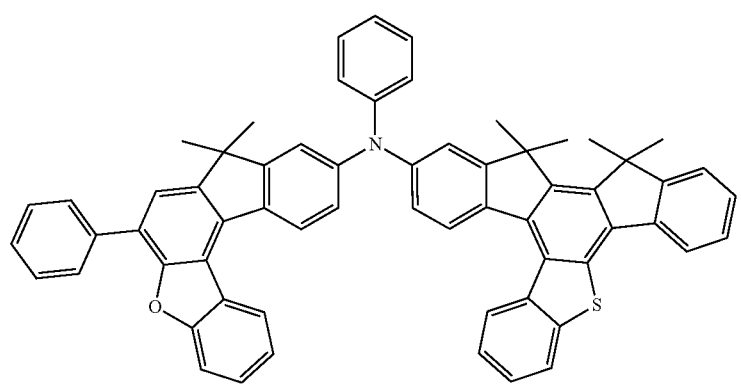

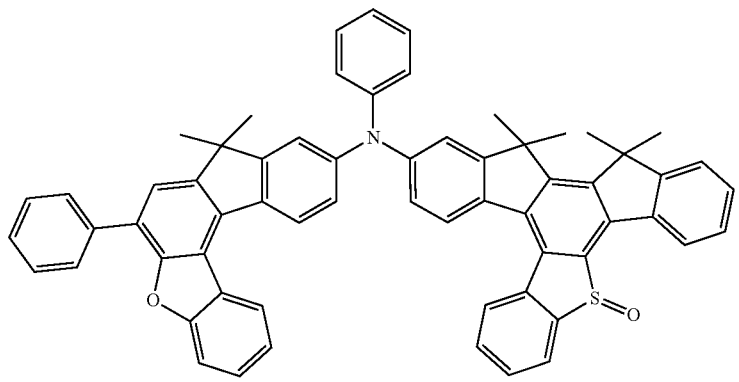 [SMILES: CC1(C)c2cc(N(c3ccccc3)c3ccc4c(c3)C(C)(C)c3c-4c4c(c5c3C(C)(C)c3ccccc3-5)S(=O)c3ccccc3-4)ccc2-c2c1cc(-c1ccccc1)c1oc3ccccc3c21]
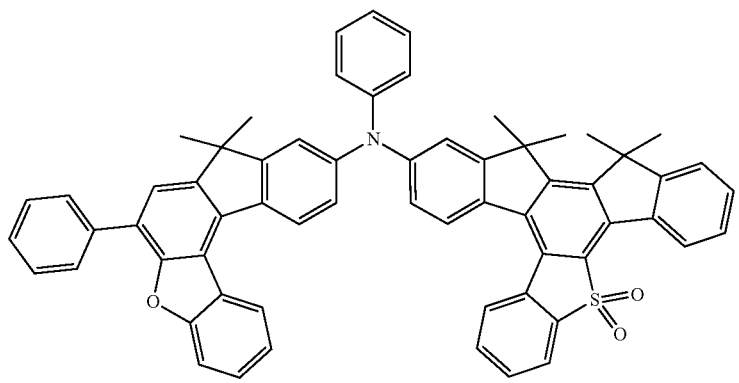 [SMILES: CC1(C)c2cc(N(c3ccccc3)c3ccc4c(c3)C(C)(C)c3c-4c4c(c5c3C(C)(C)c3ccccc3-5)S(=O)(=O)c3ccccc3-4)ccc2-c2c1cc(-c1ccccc1)c1oc3ccccc3c21]
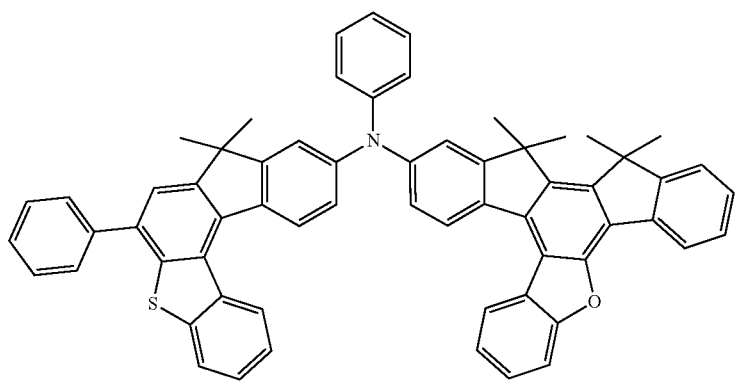
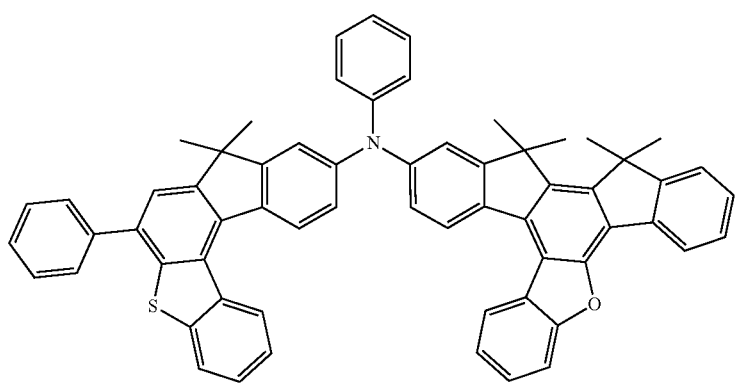 [SMILES: CC1(C)c2cc(N(c3ccccc3)c3ccc4c(c3)C(C)(C)c3c5c(c6oc7ccccc7c6c3-4)-c3ccccc3C5(C)C)ccc2-c2c1cc(-c1ccccc1)c1sc3ccccc3c21]

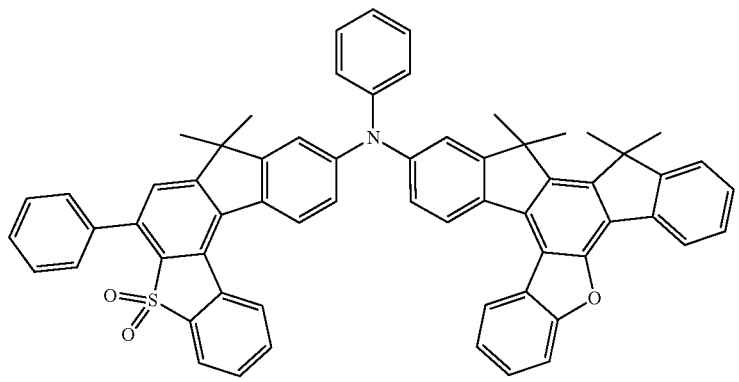 [SMILES: CC1(C)c2cc(N(c3ccccc3)c3ccc4c(c3)C(C)(C)c3c5c(c6oc7ccccc7c6c3-4)-c3ccccc3C5(C)C)ccc2-c2c1cc(-c1ccccc1)c1c2-c2ccccc2S1(=O)=O]
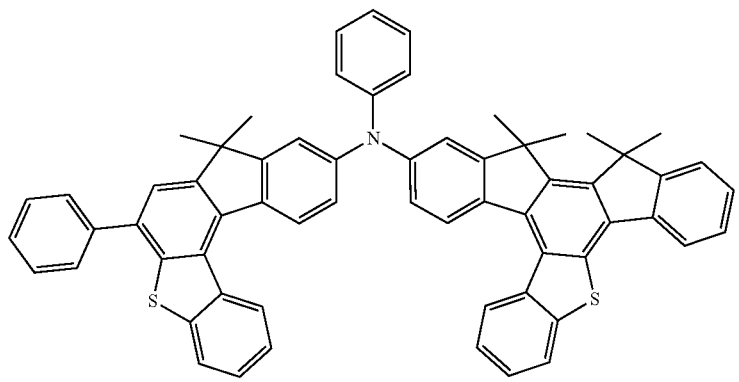
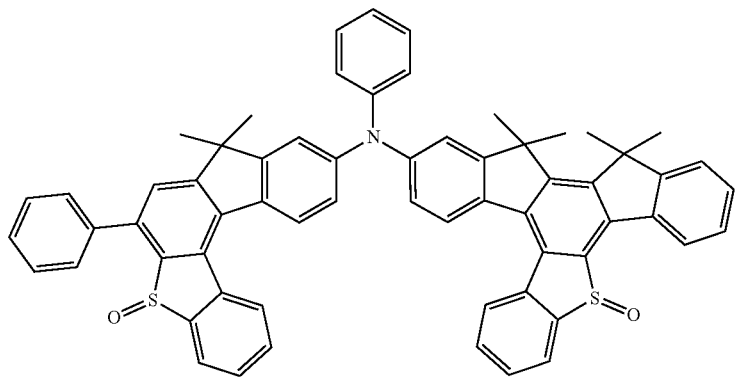 [SMILES: CC1(C)c2cc(N(c3ccccc3)c3ccc4c(c3)C(C)(C)c3c-4c4c(c5c3C(C)(C)c3ccccc3-5)S(=O)c3ccccc3-4)ccc2-c2c1cc(-c1ccccc1)c1c2-c2ccccc2S1=O]
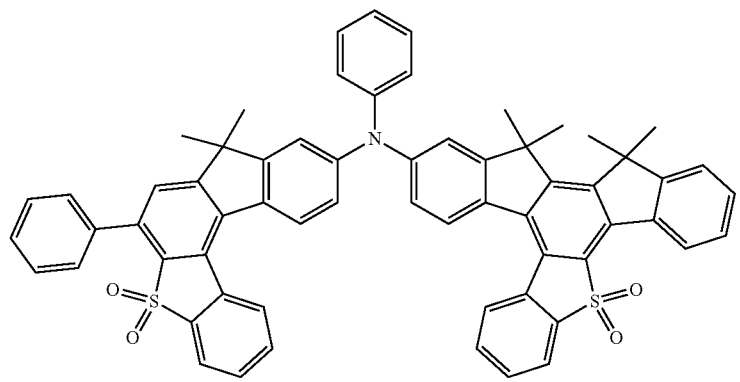 [SMILES: CC1(C)c2cc(N(c3ccccc3)c3ccc4c(c3)C(C)(C)c3c-4c4c(c5c3C(C)(C)c3ccccc3-5)S(=O)(=O)c3ccccc3-4)ccc2-c2c1cc(-c1ccccc1)c1c2-c2ccccc2S1(=O)=O]

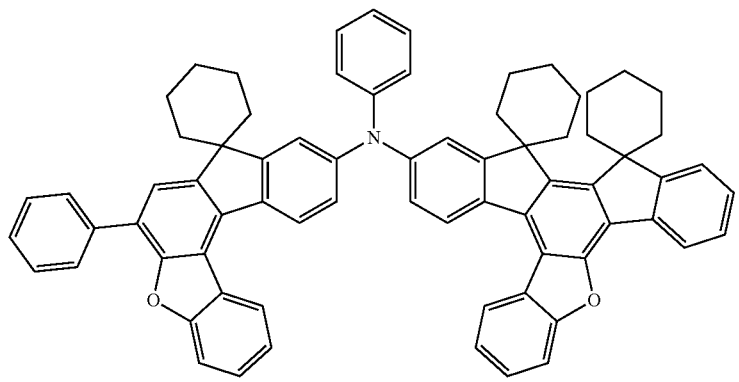 [SMILES: c1ccc(-c2cc3c(c4c2oc2ccccc24)-c2ccc(N(c4ccccc4)c4ccc5c(c4)C4(CCCCC4)c4c6c(c7oc8ccccc8c7c4-5)-c4ccccc4C64CCCCC4)cc2C32CCCCC2)cc1]
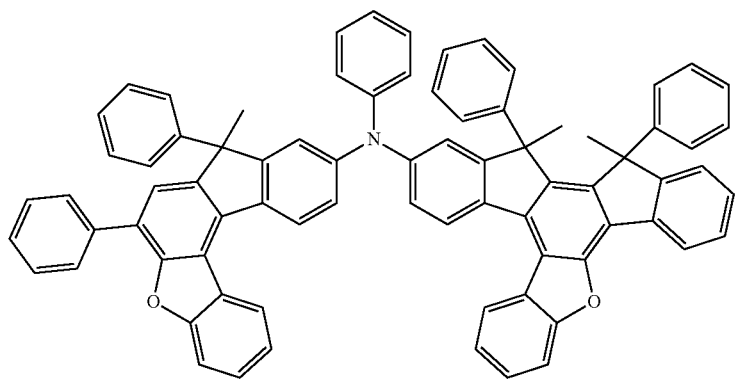 [SMILES: CC1(c2ccccc2)c2cc(N(c3ccccc3)c3ccc4c(c3)C(C)(c3ccccc3)c3c5c(c6oc7ccccc7c6c3-4)-c3ccccc3C5(C)c3ccccc3)ccc2-c2c1cc(-c1ccccc1)c1oc3ccccc3c21]
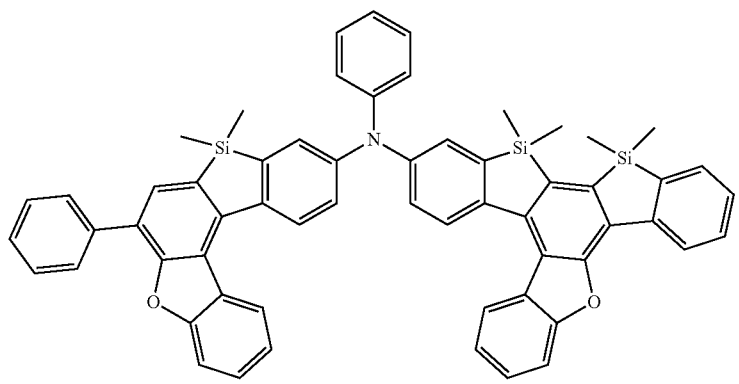 [SMILES: C[Si]1(C)c2cc(N(c3ccccc3)c3ccc4c(c3)[Si](C)(C)c3c5c(c6oc7ccccc7c6c3-4)-c3ccccc3[Si]5(C)C)ccc2-c2c1cc(-c1ccccc1)c1oc3ccccc3c21]
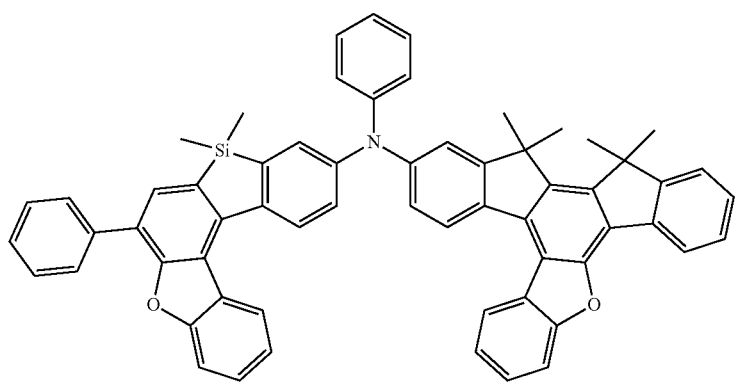 [SMILES: CC1(C)c2ccccc2-c2c1c1c(c3c2oc2ccccc23)-c2ccc(N(c3ccccc3)c3ccc4c(c3)[Si](C)(C)c3cc(-c5ccccc5)c5oc6ccccc6c5c3-4)cc2C1(C)C]

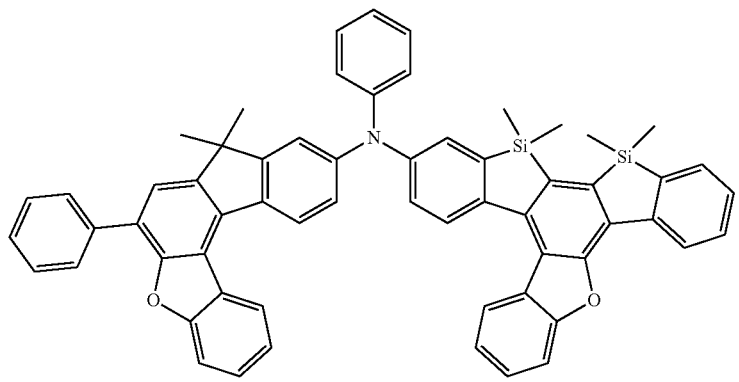 [SMILES: CC1(C)c2cc(N(c3ccccc3)c3ccc4c(c3)[Si](C)(C)c3c5c(c6oc7ccccc7c6c3-4)-c3ccccc3[Si]5(C)C)ccc2-c2c1cc(-c1ccccc1)c1oc3ccccc3c21]
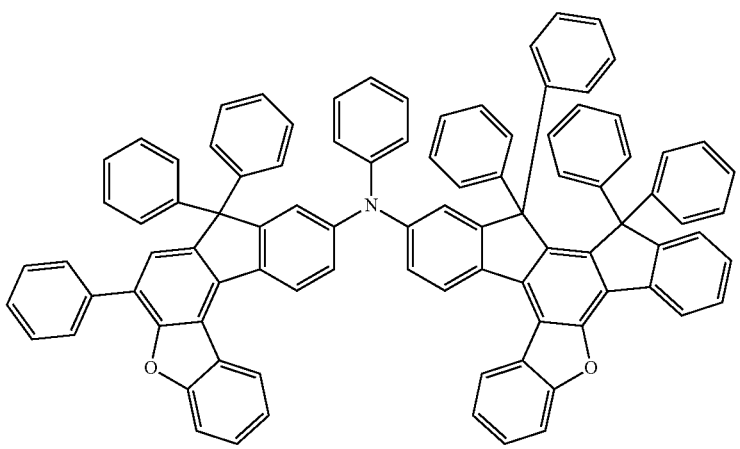 [SMILES: c1ccc(-c2cc3c(c4c2oc2ccccc24)-c2ccc(N(c4ccccc4)c4ccc5c(c4)C(c4ccccc4)(c4ccccc4)c4c6c(c7oc8ccccc8c7c4-5)-c4ccccc4C6(c4ccccc4)c4ccccc4)cc2C3(c2ccccc2)c2ccccc2)cc1]
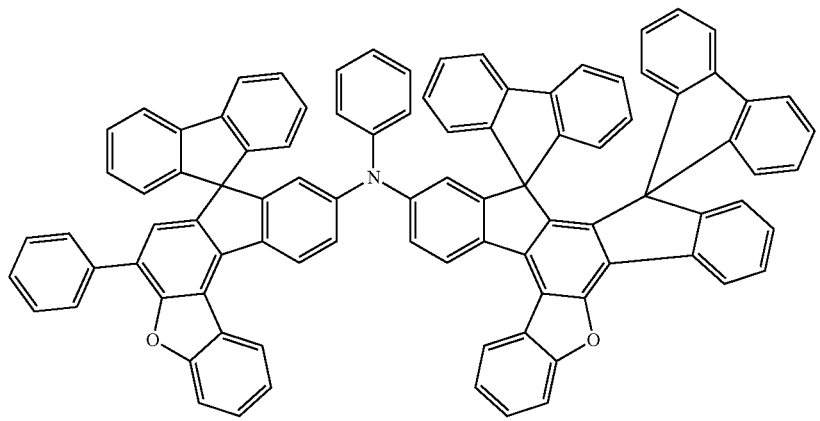 [SMILES: c1ccc(-c2cc3c(c4c2oc2ccccc24)-c2ccc(N(c4ccccc4)c4ccc5c(c4)C4(c6ccccc6-c6ccccc64)c4c6c(c7oc8ccccc8c7c4-5)-c4ccccc4C64c5ccccc5-c5ccccc54)cc2C32c3ccccc3-c3ccccc32)cc1]

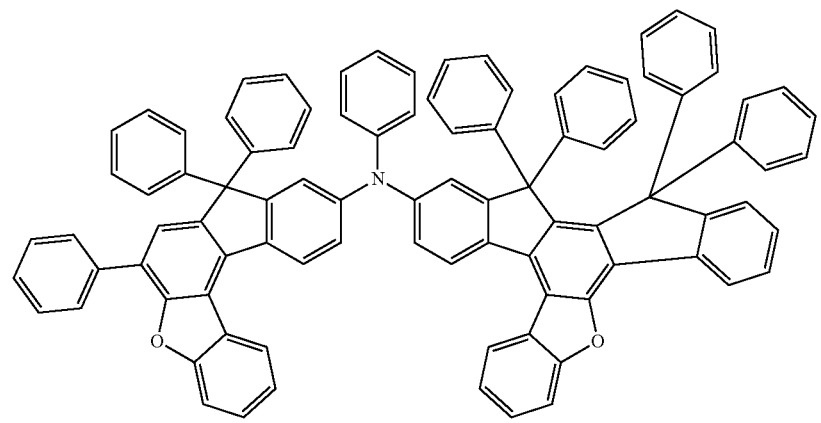 [SMILES: c1ccc(-c2cc3c(c4c2oc2ccccc24)-c2ccc(N(c4ccccc4)c4ccc5c(c4)C(c4ccccc4)(c4ccccc4)c4c6c(c7oc8ccccc8c7c4-5)-c4ccccc4C6(c4ccccc4)c4ccccc4)cc2C3(c2ccccc2)c2ccccc2)cc1]
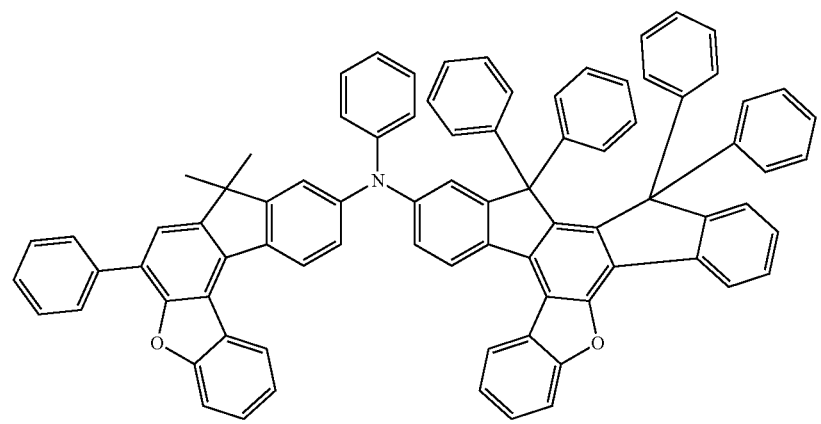 [SMILES: CC1(C)c2cc(N(c3ccccc3)c3ccc4c(c3)C(c3ccccc3)(c3ccccc3)c3c5c(c6oc7ccccc7c6c3-4)-c3ccccc3C5(c3ccccc3)c3ccccc3)ccc2-c2c1cc(-c1ccccc1)c1oc3ccccc3c21]
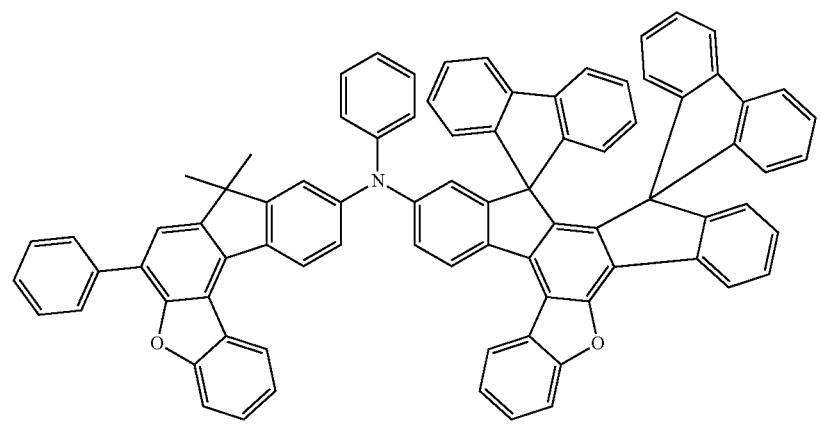 [SMILES: CC1(C)c2cc(N(c3ccccc3)c3ccc4c(c3)C3(c5ccccc5-c5ccccc53)c3c5c(c6oc7ccccc7c6c3-4)-c3ccccc3C53c4ccccc4-c4ccccc43)ccc2-c2c1cc(-c1ccccc1)c1oc3ccccc3c21]

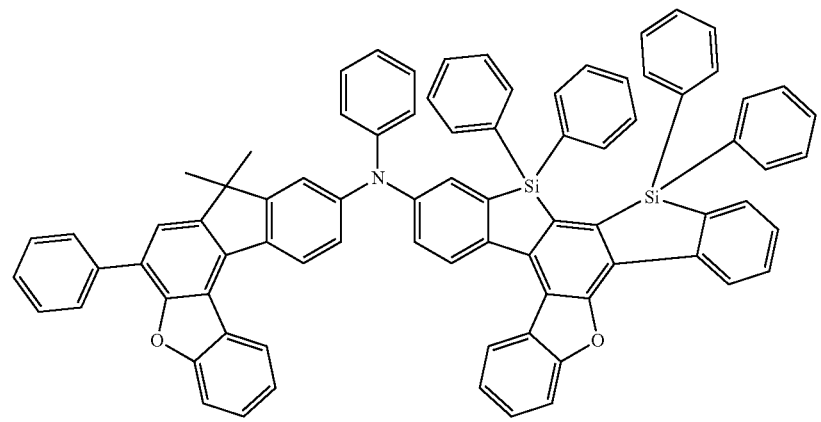 [SMILES: CC1(C)c2cc(N(c3ccccc3)c3ccc4c(c3)[Si](c3ccccc3)(c3ccccc3)c3c5c(c6oc7ccccc7c6c3-4)-c3ccccc3[Si]5(c3ccccc3)c3ccccc3)ccc2-c2c1cc(-c1ccccc1)c1oc3ccccc3c21]
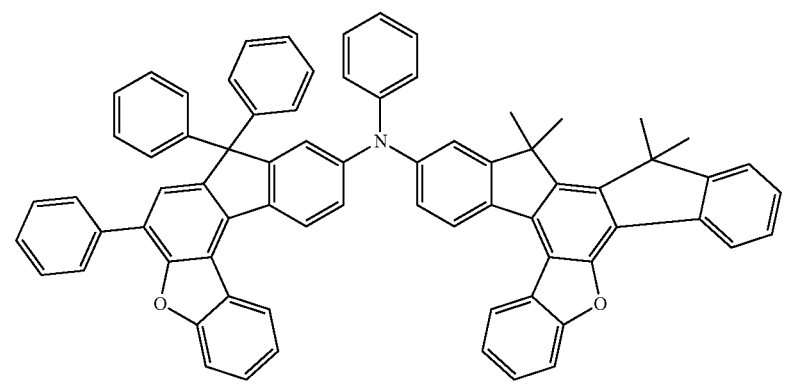
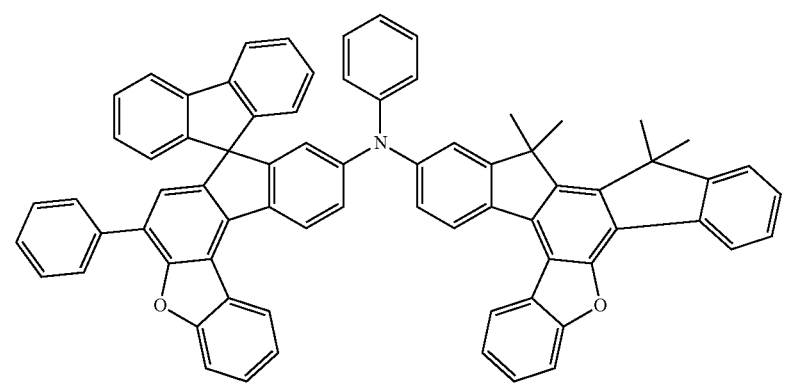 [SMILES: CC1(C)c2ccccc2-c2c1c1c(c3c2oc2ccccc23)-c2ccc(N(c3ccccc3)c3ccc4c(c3)C3(c5ccccc5-c5ccccc53)c3cc(-c5ccccc5)c5oc6ccccc6c5c3-4)cc2C1(C)C]

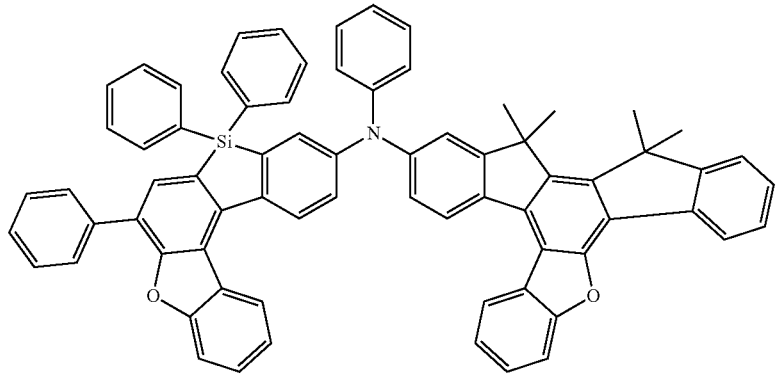 [SMILES: CC1(C)c2ccccc2-c2c1c1c(c3c2oc2ccccc23)-c2ccc(N(c3ccccc3)c3ccc4c(c3)[Si](c3ccccc3)(c3ccccc3)c3cc(-c5ccccc5)c5oc6ccccc6c5c3-4)cc2C1(C)C]
The compounds according to the invention can be prepared by synthesis steps known to the person skilled in the art, such as, for example, bromination, Suzuki coupling, Ullmann coupling, Hartwig-Buchwald coupling, etc. An example of a suitable synthesis process is depicted in general terms in Schemes 1 and 2 below.
Scheme 1
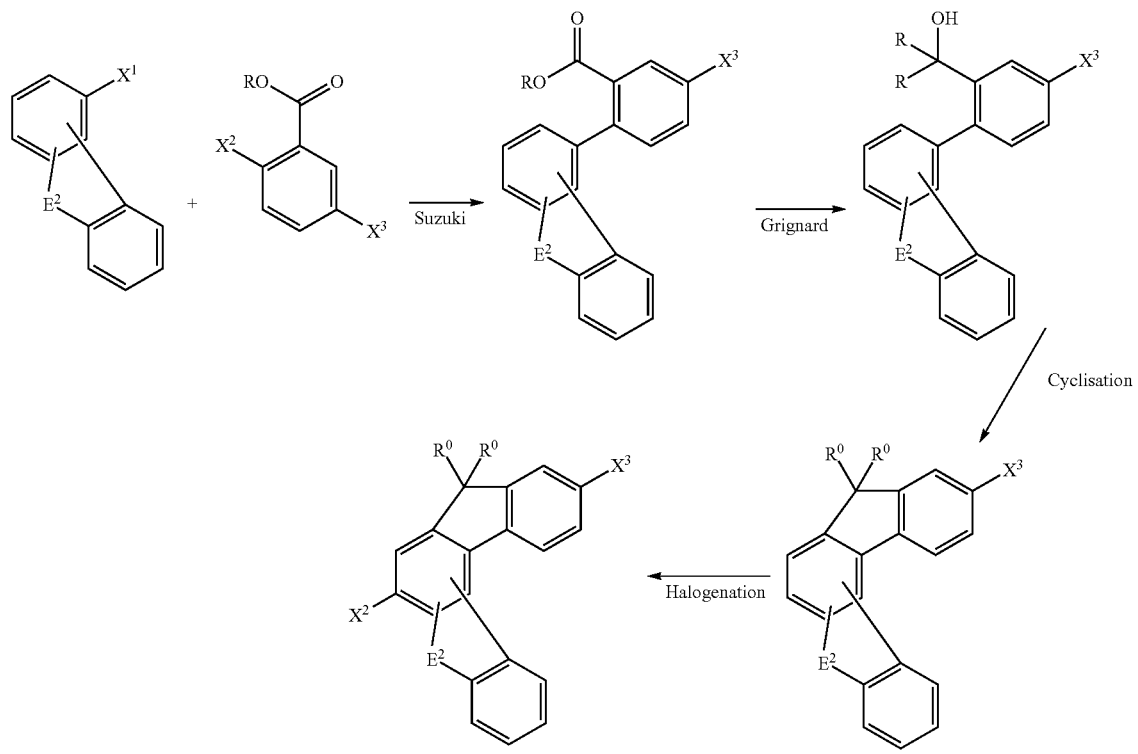

767
Step 1—Synthesis of Intermediate 1
768
Step 3—Synthesis of Compounds of Formula (1)
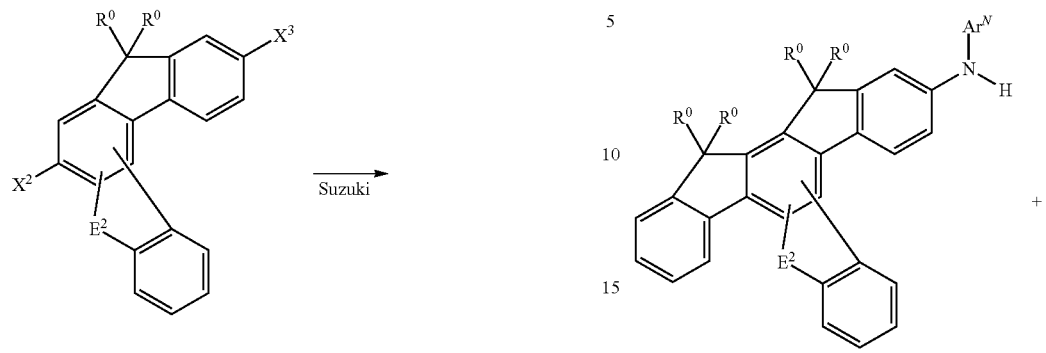
Step 2—Synthesis of Intermediate 2
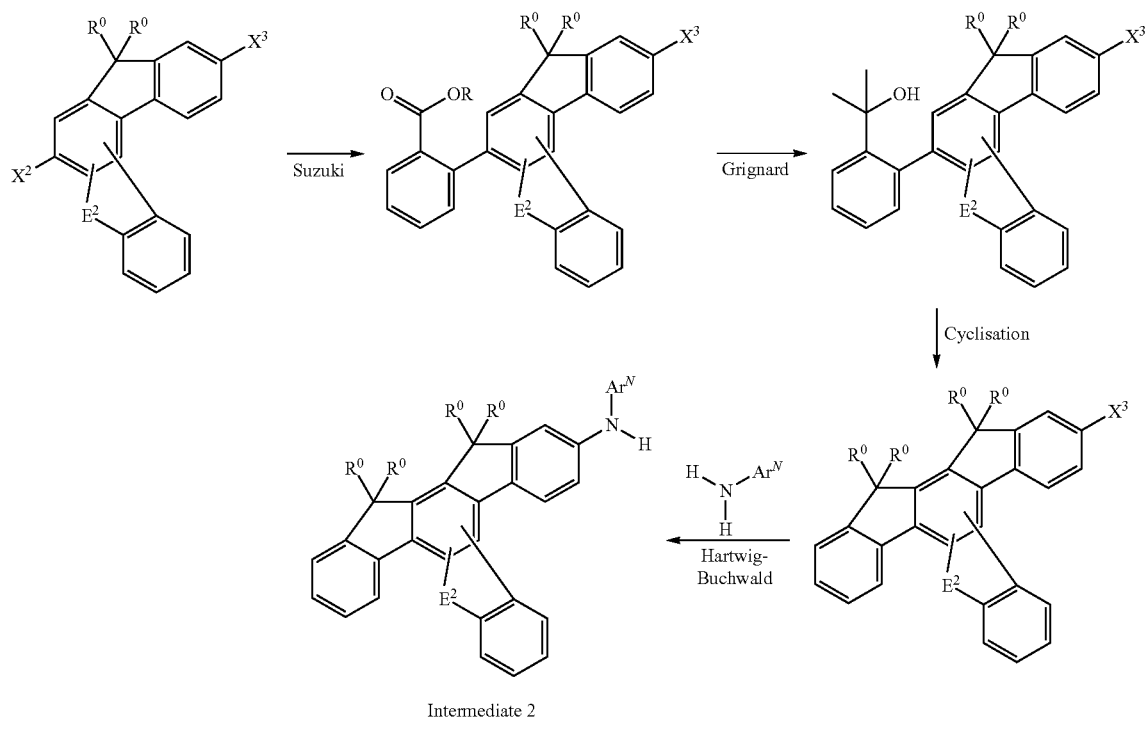

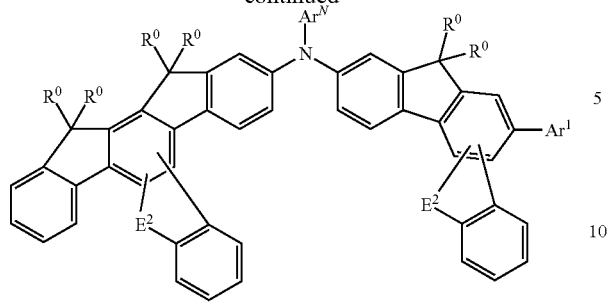
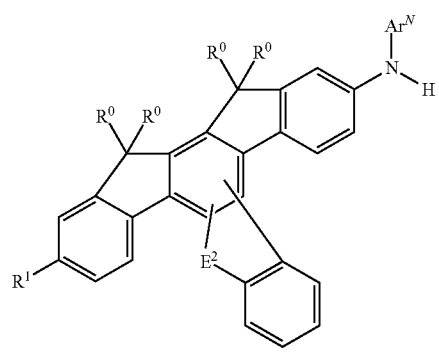
Intermediate 4
Scheme 2
Step 1—Synthesis of Intermediate 1
Same as in Scheme 1
Step 2—Synthesis of Intermediate 3
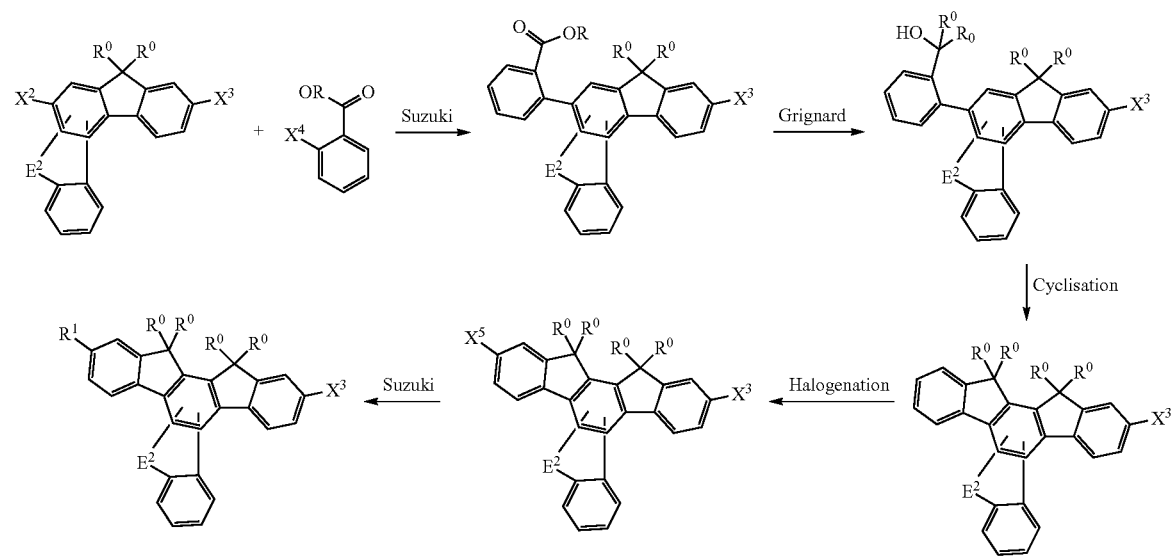
Step 3—Synthesis of Intermediate 4
Step 4—Synthesis of Compounds of Formula (1)
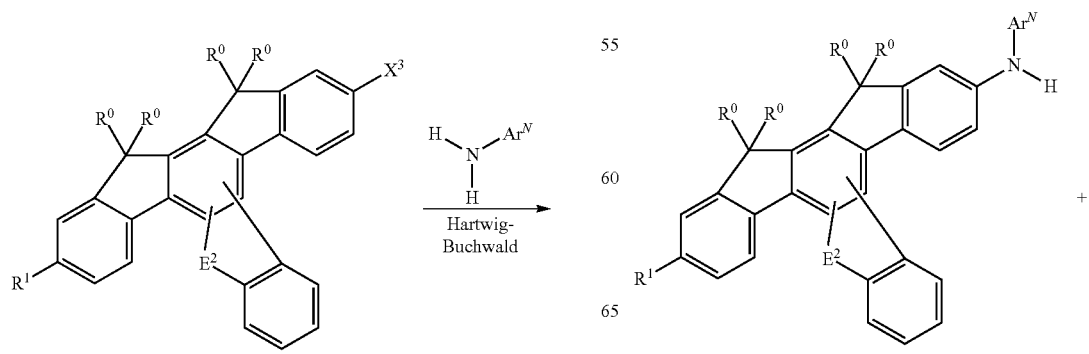

-continued

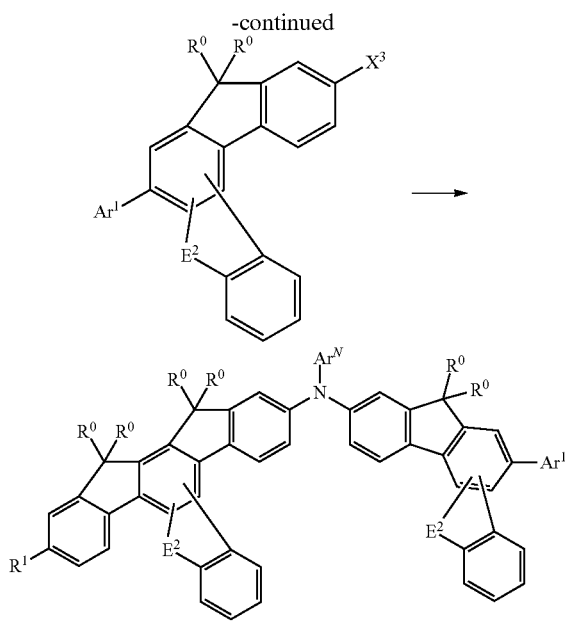

In Schemes 1 and 2, the symbols $Ar^1$, $Ar^N$, $E^2$, R, $R^0$ and $R^1$ have the same meaning as above, the symbols $X^1$ to $X^5$ represent a leaving group (for example a halogen, a boronic ester or a triflate).

The present invention therefore relates to a process for the synthesis of the compounds according to the invention, comprising a step where an aminated oxatruxene derivative reacts with an indenodibenzofuran derivative.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention therefore furthermore relates to a formulation comprising a compound according to the invention and at least one further compound. The further compound may be, for example, a solvent, in particular one of the above-mentioned solvents or a mixture of these solvents. However, the further compound may also be at least one further organic or inorganic compound which is likewise employed in the electronic device, for example an emitting compound, in particular a phosphorescent dopant, and/or a further matrix material. Suitable emitting compounds and further matrix materials are indicated below in connection with the organic electroluminescent device. This further compound may also be polymeric.

The compounds and mixtures according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the compounds or mixtures according to the invention in an electronic device, in particular in an organic electroluminescent device.

The present invention again furthermore relates to an electronic device comprising at least one of the compounds or mixtures according to the invention mentioned above. The preferences stated above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitised solar cells, organic optical detectors, organic photoreceptors, organic field-quench devices (O-FQDs), light-emitting electrochemical cells (LECs), organic laser diodes (O-lasers) and "organic plasmon emitting devices" (D. M. Koller et al., *Nature Photonics* 2008, 1-4), preferably organic electroluminescent devices (OLEDs, PLEDs), in particular phosphorescent OLEDs.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). These can be fluorescent or phosphorescent emission layers or hybrid systems, in which fluorescent and phosphorescent emission layers are combined with one another.

The compound according to the invention in accordance with the embodiments indicated above can be employed in various layers, depending on the precise structure and on the substitution. Preference is given to an organic electroluminescent device comprising a compound of the formula (1) or in accordance with the preferred embodiments as fluorescent emitters, emitters showing TADF (Thermally Activated Delayed Fluorescence), matrix material for fluorescent emitters. Particularly preferred is an organic electroluminescent device comprising a compound of the formula (1) or in accordance with the preferred embodiments as fluorescent emitters, more particularly blue-emitting fluorescent compound.

The compounds of formula (1) can also be employed in an electron-transport layer and/or in an electron-blocking or exciton-blocking layer and/or in a hole-transport layer, depending on the precise substitution. The preferred embodiments indicated above also apply to the use of the materials in organic electronic devices.

The compound according to the invention is particularly suitable for use as blue-emitting emitter compound. The electronic device concerned may comprise a single emitting layer comprising the compound according to the invention or it may comprise two or more emitting layers. The further emitting layers here may comprise one or more compounds according to the invention or alternatively other compounds.

If the compound according to the invention is employed as a fluorescent emitting compound in an emitting layer, it is preferably employed in combination with one or more matrix materials. A matrix material here is taken to mean a material which is present in the emitting layer, preferably as the principal component, and which does not emit light on operation of the device.

The proportion of the emitting compound in the mixture of the emitting layer is between 0.1 and 50.0%, preferably between 0.5 and 20.0%, particularly preferably between 1.0 and 10.0%. Correspondingly, the proportion of the matrix material or matrix materials is between 50.0 and 99.9%, preferably between 80.0 and 99.5%, particularly preferably between 90.0 and 99.0%.

The specifications of the proportions in % are, for the purposes of the present application, taken to mean % by vol. if the compounds are applied from the gas phase and % by weight if the compounds are applied from solution.

Preferred matrix materials for use in combination with fluorescent emitting compounds are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Particularly preferred matrix materials for use in combination with the compounds of the formula (1) in the emitting layer are depicted in the following table.

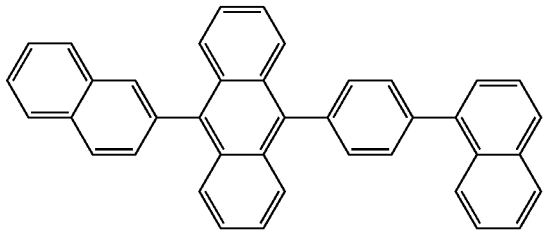 [SMILES: c1ccc2cc(-c3c4ccccc4c(-c4ccc(-c5cccc6ccccc56)cc4)c4ccccc34)ccc2c1]

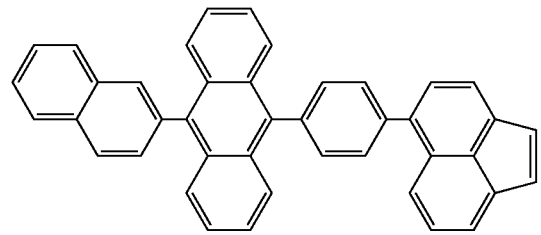 [SMILES: C1=Cc2ccc(-c3ccc(-c4c5ccccc5c(-c5ccc6ccccc6c5)c5ccccc45)cc3)c3cccc1c23]

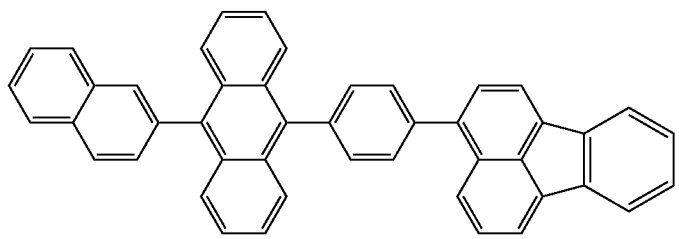 [SMILES: c1ccc2c(c1)-c1cccc3c(-c4ccc(-c5c6ccccc6c(-c6ccc7ccccc7c6)c6ccccc56)cc4)ccc-2c13]

-continued
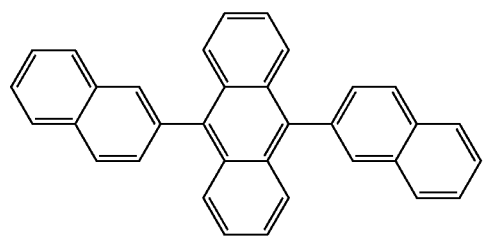 [SMILES: c1ccc2cc(-c3c4ccccc4c(-c4ccc5ccccc5c4)c4ccccc34)ccc2c1]
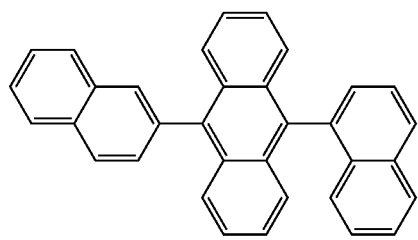 [SMILES: c1ccc2cc(-c3c4ccccc4c(-c4cccc5ccccc45)c4ccccc34)ccc2c1]
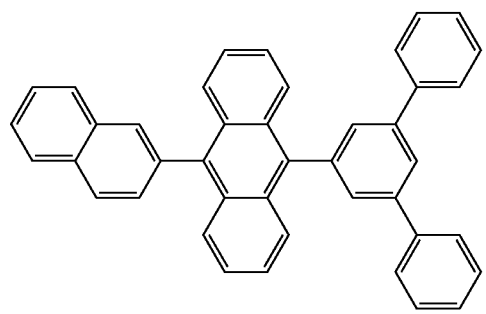 [SMILES: c1ccc(-c2cc(-c3ccccc3)cc(-c3c4ccccc4c(-c4ccc5ccccc5c4)c4ccccc34)c2)cc1]
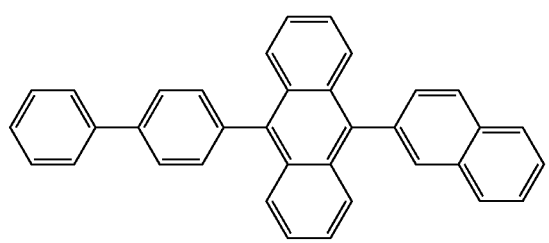 [SMILES: c1ccc(-c2ccc(-c3c4ccccc4c(-c4ccc5ccccc5c4)c4ccccc34)cc2)cc1]
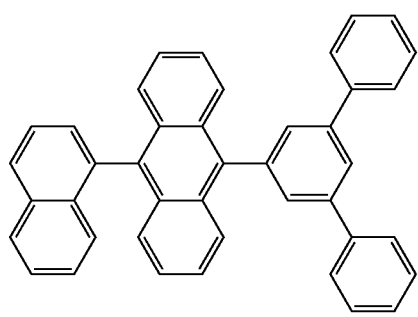 [SMILES: c1ccc(-c2cc(-c3ccccc3)cc(-c3c4ccccc4c(-c4cccc5ccccc45)c4ccccc34)c2)cc1]

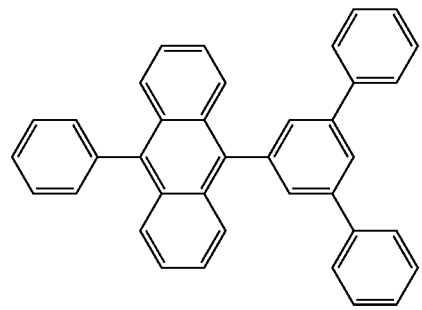 [SMILES: c1ccc(-c2cc(-c3ccccc3)cc(-c3c4ccccc4c(-c4ccccc4)c4ccccc34)c2)cc1]
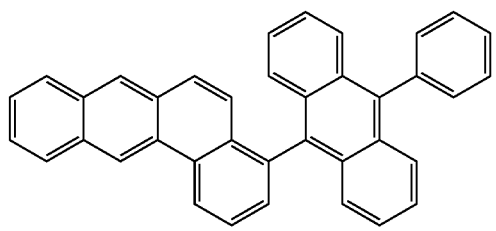 [SMILES: c1ccc(-c2c3ccccc3c(-c3cccc4c3ccc3cc5ccccc5cc34)c3ccccc23)cc1]
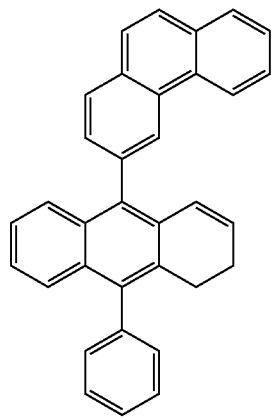 [SMILES: C1=Cc2c(c(-c3ccccc3)c3ccccc3c2-c2ccc3ccc4ccccc4c3c2)CC1]
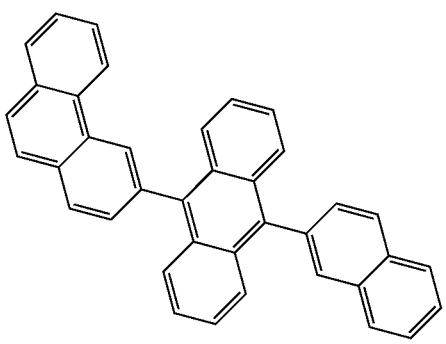 [SMILES: c1ccc2cc(-c3c4ccccc4c(-c4ccc5ccc6ccccc6c5c4)c4ccccc34)ccc2c1]
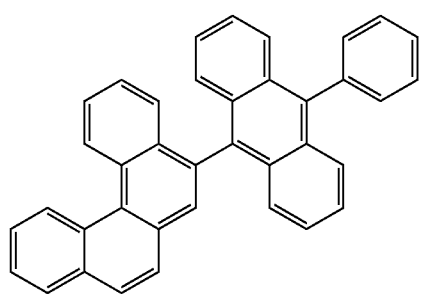 [SMILES: c1ccc(-c2c3ccccc3c(-c3cc4ccc5ccccc5c4c4ccccc34)c3ccccc23)cc1]

-continued
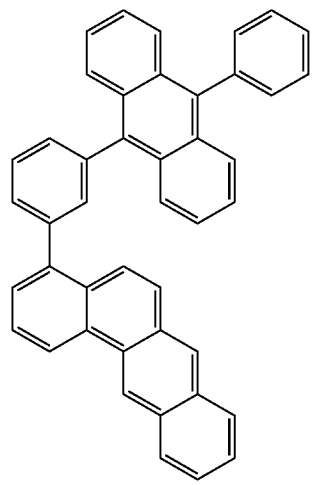 [SMILES: c1ccc(-c2c3ccccc3c(-c3cccc(-c4cccc5c4ccc4cc6ccccc6cc45)c3)c3ccccc23)cc1]

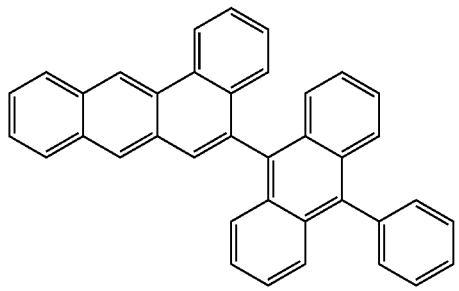 [SMILES: c1ccc(-c2c3ccccc3c(-c3cc4cc5ccccc5cc4c4ccccc34)c3ccccc23)cc1]
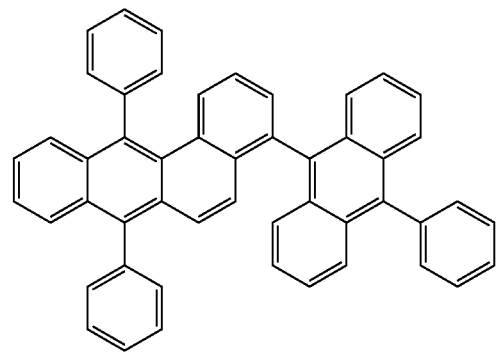 [SMILES: c1ccc(-c2c3ccccc3c(-c3cccc4c3ccc3c(-c5ccccc5)c5ccccc5c(-c5ccccc5)c34)c3ccccc23)cc1]
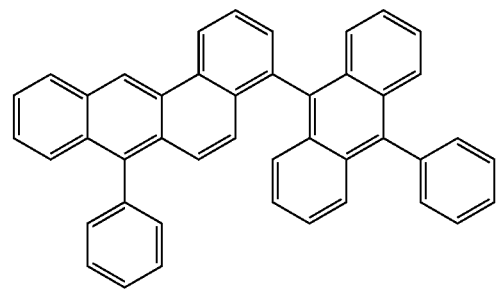 [SMILES: c1ccc(-c2c3ccccc3c(-c3cccc4c3ccc3c(-c5ccccc5)c5ccccc5cc34)c3ccccc23)cc1]
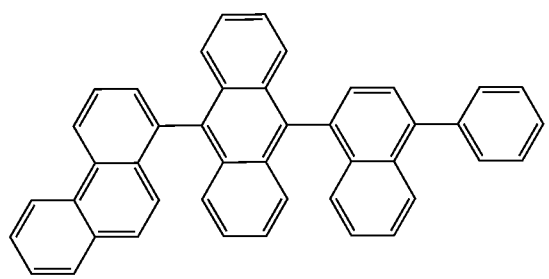 [SMILES: c1ccc(-c2ccc(-c3c4ccccc4c(-c4cccc5c4ccc4ccccc45)c4ccccc34)c3ccccc23)cc1]
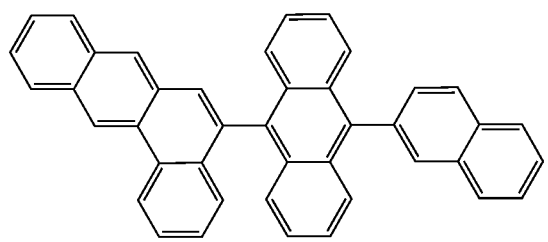 [SMILES: c1ccc2cc(-c3c4ccccc4c(-c4cc5cc6ccccc6cc5c5ccccc45)c4ccccc34)ccc2c1]

-continued
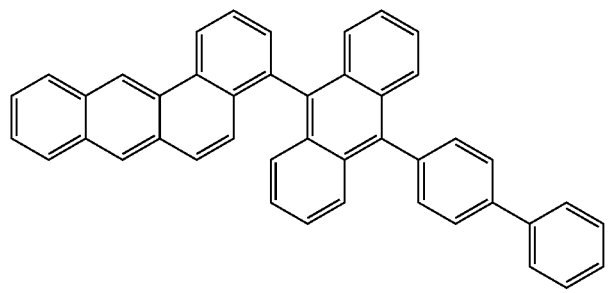 [SMILES: c1ccc(-c2ccc(-c3c4ccccc4c(-c4cccc5c4ccc4cc6ccccc6cc45)c4ccccc34)cc2)cc1]
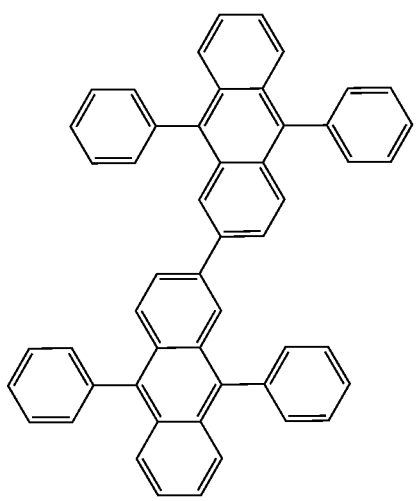 [SMILES: c1ccc(-c2c3ccccc3c(-c3ccccc3)c3cc(-c4ccc5c(-c6ccccc6)c6ccccc6c(-c6ccccc6)c5c4)ccc23)cc1]
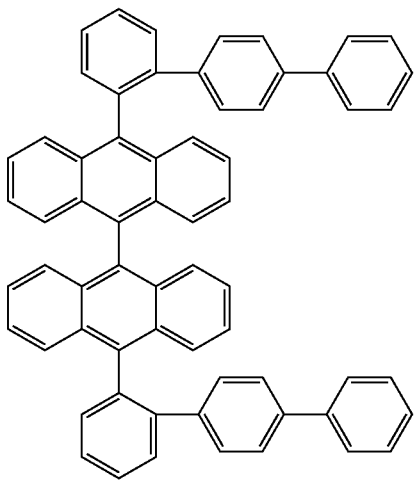 [SMILES: c1ccc(-c2ccc(-c3ccccc3-c3c4ccccc4c(-c4c5ccccc5c(-c5ccccc5-c5ccc(-c6ccccc6)cc5)c5ccccc45)c4ccccc34)cc2)cc1]
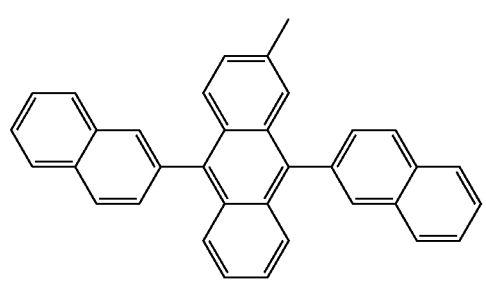 [SMILES: Cc1ccc2c(-c3ccc4ccccc4c3)c3ccccc3c(-c3ccc4ccccc4c3)c2c1]

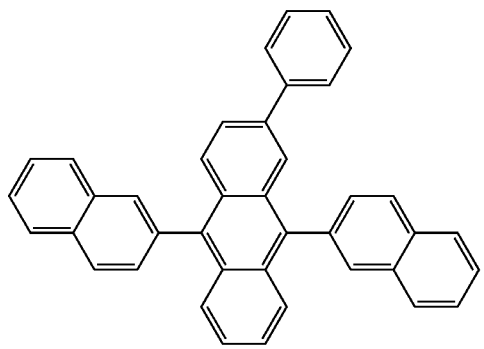 [SMILES: c1ccc(-c2ccc3c(-c4ccc5ccccc5c4)c4ccccc4c(-c4ccc5ccccc5c4)c3c2)cc1]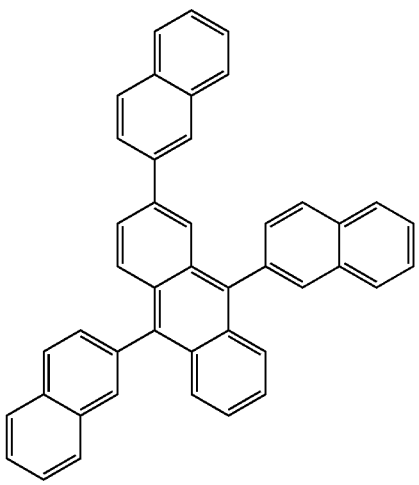 [SMILES: c1ccc2cc(-c3ccc4c(-c5ccc6ccccc6c5)c5ccccc5c(-c5ccc6ccccc6c5)c4c3)ccc2c1]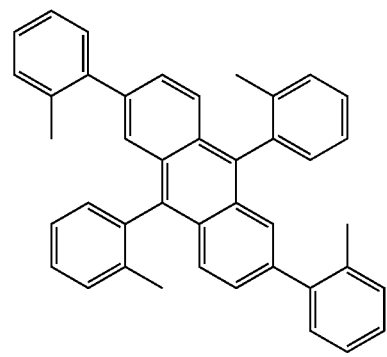 [SMILES: Cc1ccccc1-c1ccc2c(-c3ccccc3C)c3cc(-c4ccccc4C)ccc3c(-c3ccccc3C)c2c1]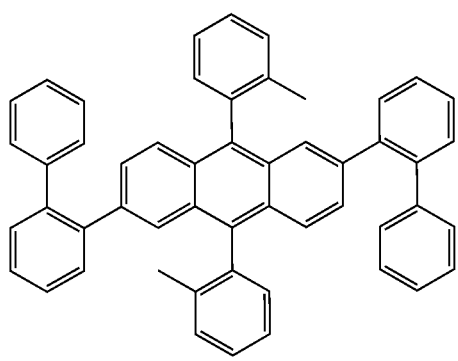 [SMILES: Cc1ccccc1-c1c2ccc(-c3ccccc3-c3ccccc3)cc2c(-c2ccccc2C)c2ccc(-c3ccccc3-c3ccccc3)cc12]

-continued
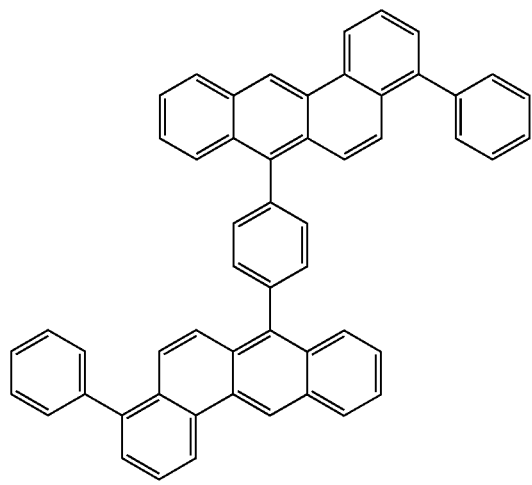 [SMILES: c1ccc(-c2cccc3c2ccc2c(-c4ccc(-c5c6ccccc6cc6c5ccc5c(-c7ccccc7)cccc56)cc4)c4ccccc4cc23)cc1]
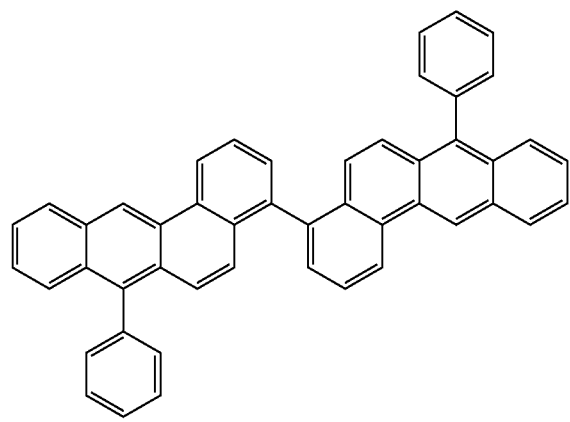 [SMILES: c1ccc(-c2c3ccccc3cc3c2ccc2c(-c4cccc5c4ccc4c(-c6ccccc6)c6ccccc6cc45)cccc23)cc1]
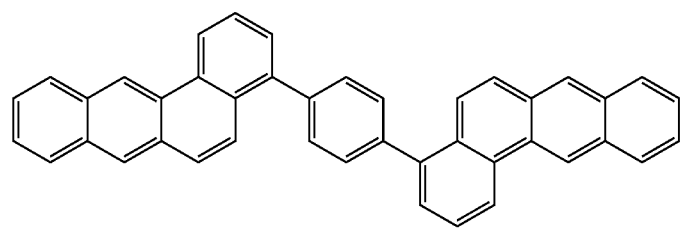 [SMILES: c1ccc2cc3c(ccc4c(-c5ccc(-c6cccc7c6ccc6cc8ccccc8cc67)cc5)cccc43)cc2c1]

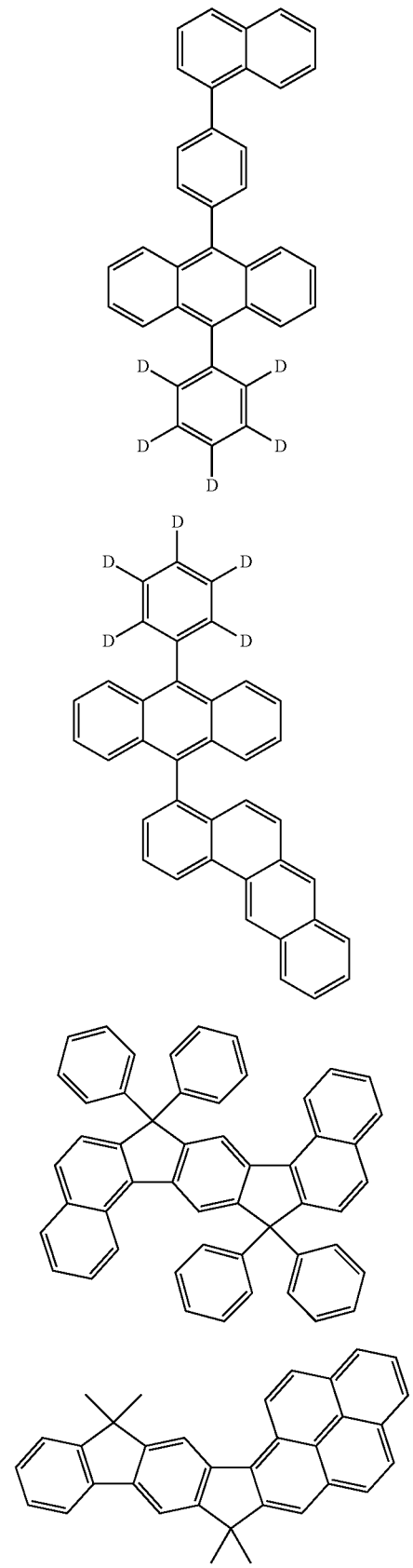

-continued
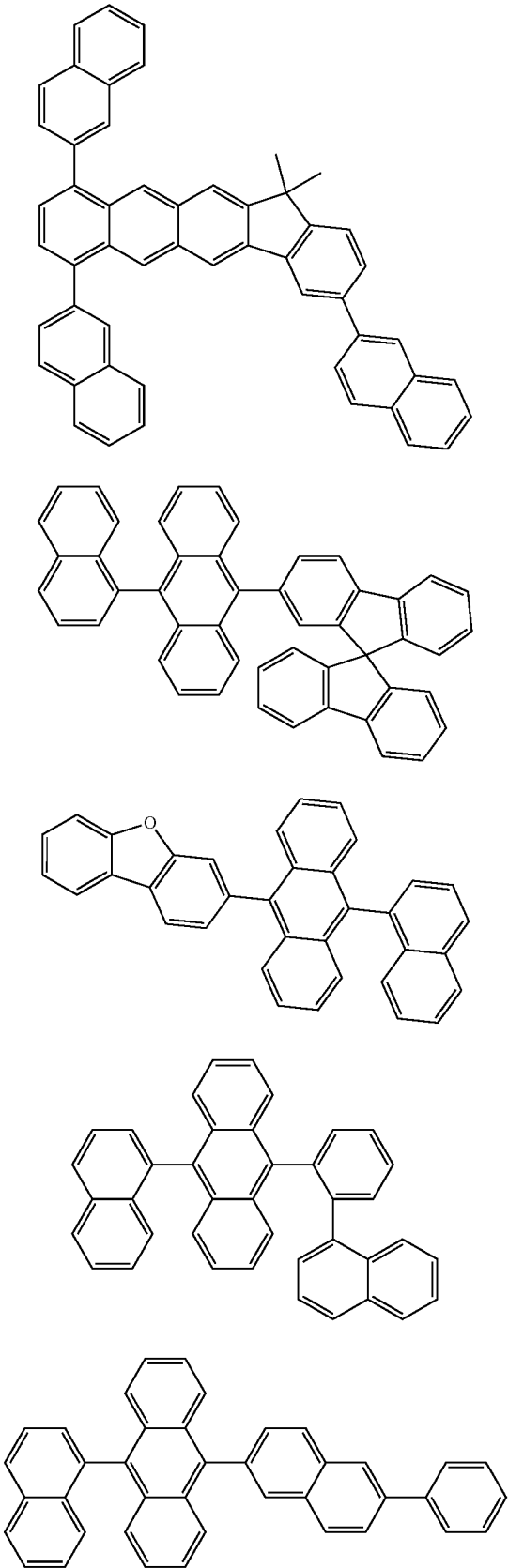

-continued
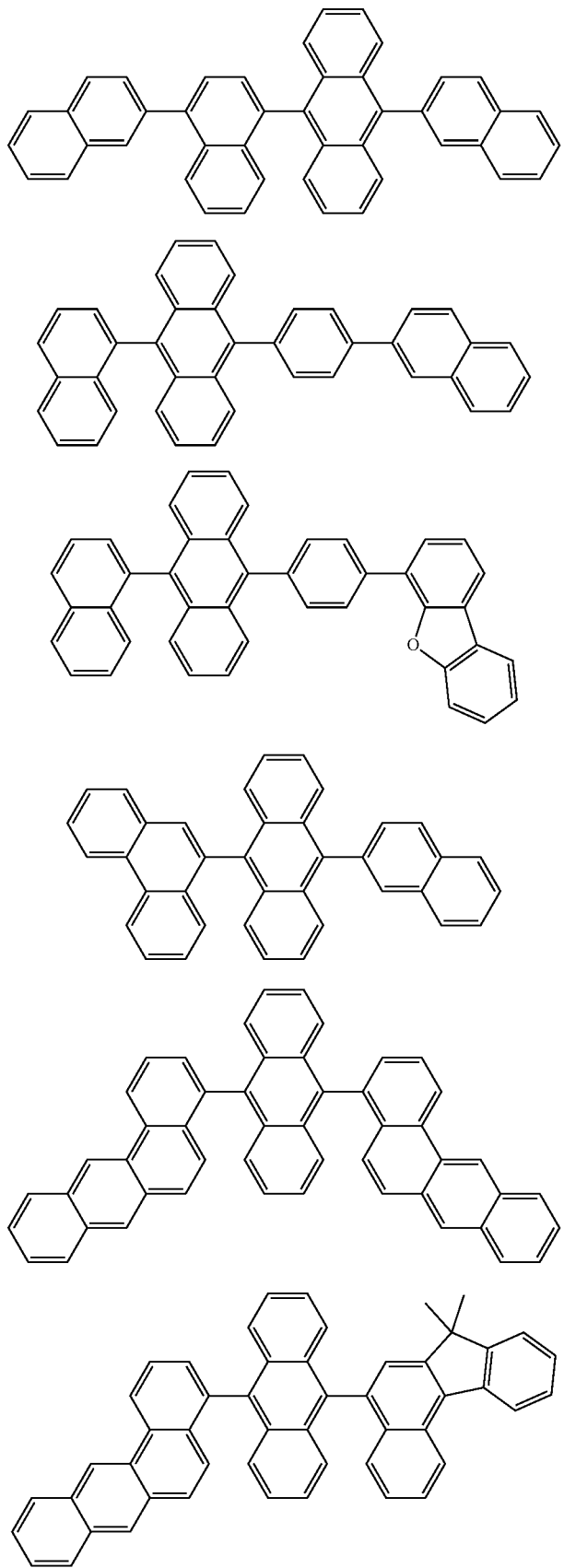

-continued
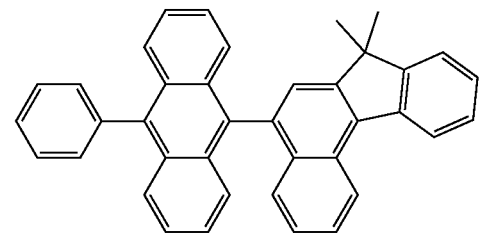 [SMILES: CC1(C)c2ccccc2-c2c1cc(-c1c3ccccc3c(-c3ccccc3)c3ccccc13)c1ccccc21]
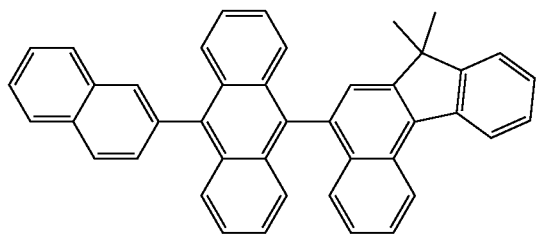 [SMILES: CC1(C)c2ccccc2-c2c1cc(-c1c3ccccc3c(-c3ccc4ccccc4c3)c3ccccc13)c1ccccc21]
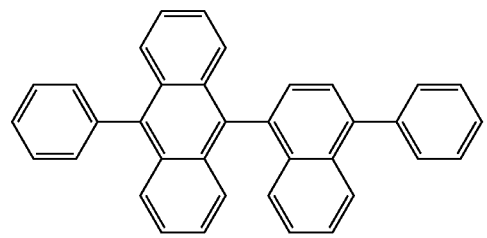 [SMILES: c1ccc(-c2ccc(-c3c4ccccc4c(-c4ccccc4)c4ccccc34)c3ccccc23)cc1]
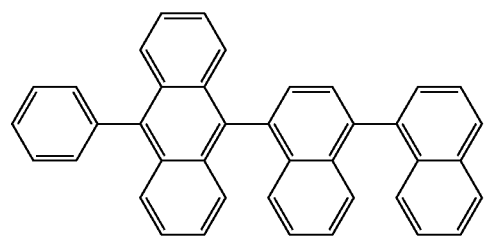 [SMILES: c1ccc(-c2c3ccccc3c(-c3ccc(-c4cccc5ccccc45)c4ccccc34)c3ccccc23)cc1]
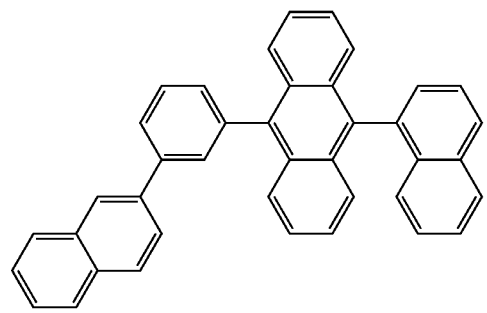 [SMILES: c1cc(-c2ccc3ccccc3c2)cc(-c2c3ccccc3c(-c3cccc4ccccc34)c3ccccc23)c1]
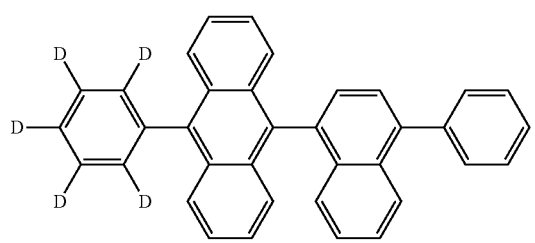 [SMILES: [2H]c1c([2H])c([2H])c(-c2c3ccccc3c(-c3ccc(-c4ccccc4)c4ccccc34)c3ccccc23)c([2H])c1[2H]]

-continued
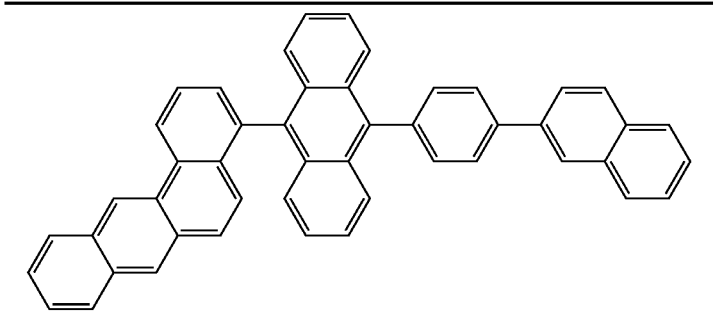
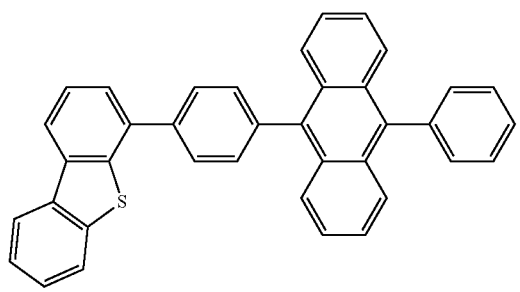 [SMILES: c1ccc(-c2c3ccccc3c(-c3ccc(-c4cccc5c4sc4ccccc45)cc3)c3ccccc23)cc1]
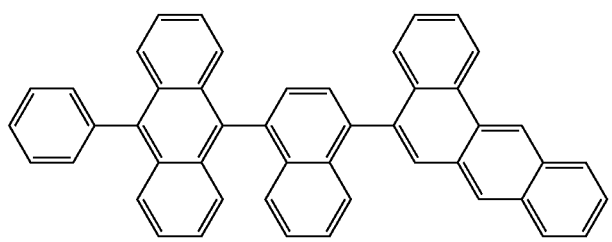 [SMILES: c1ccc(-c2c3ccccc3c(-c3ccc(-c4cc5cc6ccccc6cc5c5ccccc45)c4ccccc34)c3ccccc23)cc1]
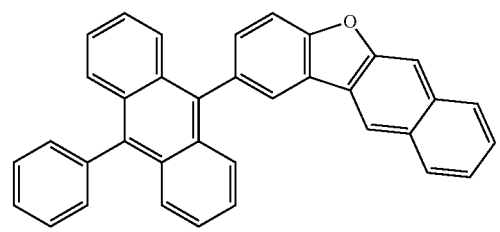 [SMILES: c1ccc(-c2c3ccccc3c(-c3ccc4oc5cc6ccccc6cc5c4c3)c3ccccc23)cc1]
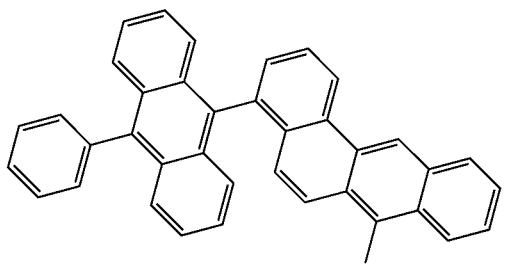 [SMILES: Cc1c2ccccc2cc2c1ccc1c(-c3c4ccccc4c(-c4ccccc4)c4ccccc34)cccc12]
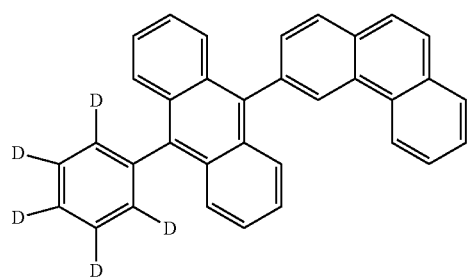 [SMILES: [2H]c1c([2H])c([2H])c(-c2c3ccccc3c(-c3ccc4ccc5ccccc5c4c3)c3ccccc23)c([2H])c1[2H]]

-continued
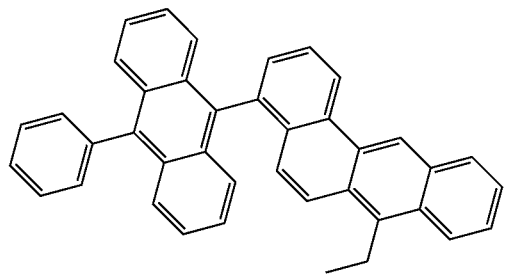 [SMILES: CCc1c2ccccc2cc2c1ccc1c(-c3c4ccccc4c(-c4ccccc4)c4ccccc34)cccc12]
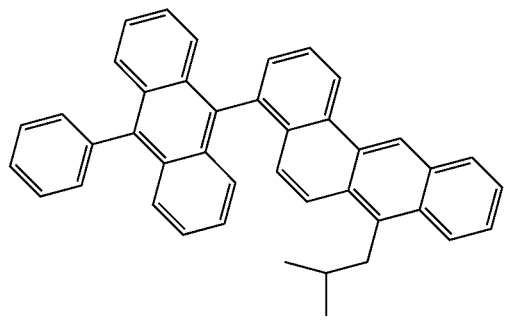 [SMILES: CC(C)Cc1c2ccccc2cc2c1ccc1c(-c3c4ccccc4c(-c4ccccc4)c4ccccc34)cccc12]
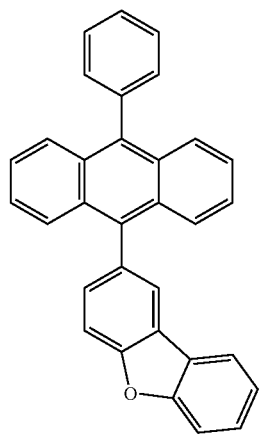 [SMILES: c1ccc(-c2c3ccccc3c(-c3ccc4oc5ccccc5c4c3)c3ccccc23)cc1]
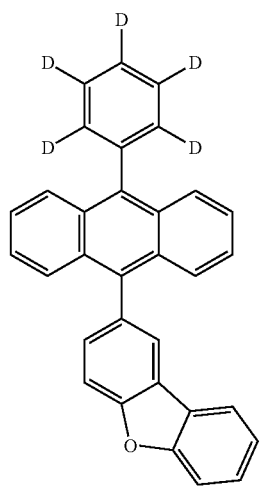 [SMILES: [2H]c1c([2H])c([2H])c(-c2c3ccccc3c(-c3ccc4oc5ccccc5c4c3)c3ccccc23)c([2H])c1[2H]]

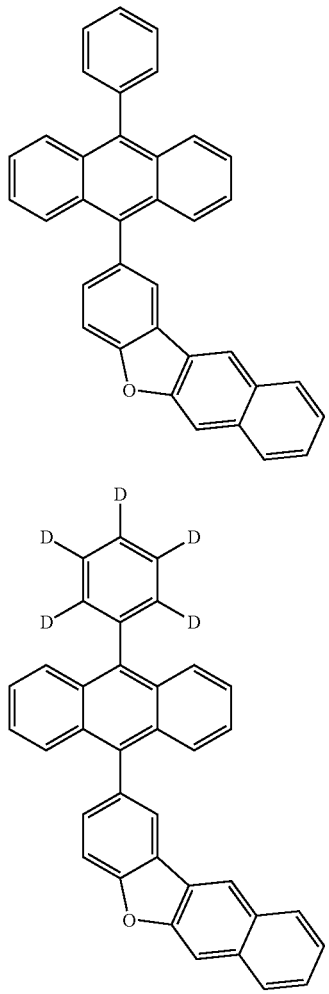

If the compound according to the invention is employed as a fluorescent emitting compound in an emitting layer, it may be employed in combination with one or more other fluorescent emitting compounds.

Preferred fluorescent emitters, besides the compounds according to the invention, are selected from the class of the arylamines. An arylamine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred emitters are indenofluorenamines or indenofluorenediamines, for example in accordance with WO 2006/108497 or WO 2006/122630, benzoindenofluorenamines or benzoindenofluorenediamines, for example in accordance with WO 2008/006449, and dibenzoindenofluorenamines or dibenzoindeno-fluorenediamines, for example in accordance with WO 2007/140847, and the indenofluorene derivatives containing condensed aryl groups which are disclosed in WO 2010/012328. Still further preferred emitters are benzanthracene derivatives as disclosed in WO 2015/158409, anthracene derivatives as disclosed in WO 2017/036573, fluorene dimers like in WO 2016/150544 or phenoxazine derivatives as disclosed in WO 2017/028940 and WO 2017/028941. Preference is likewise given to the pyrenarylamines disclosed in WO 2012/048780 and WO 2013/185871. Preference is likewise given to the benzoindenofluorenamines disclosed in WO 2014/037077, the benzofluorenamines disclosed in WO 2014/106522 and the indenofluorenes disclosed in WO 2014/111269 or WO 2017/036574.

Examples of preferred fluorescent emitting compounds, besides the compounds according to the invention, which can be used in combination with the compounds of the invention in an emitting layer or which can be used in another emitting layer of the same device are depicted in the following table:

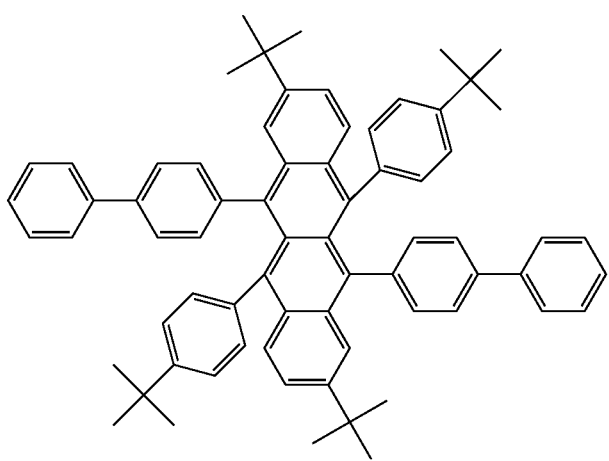

-continued
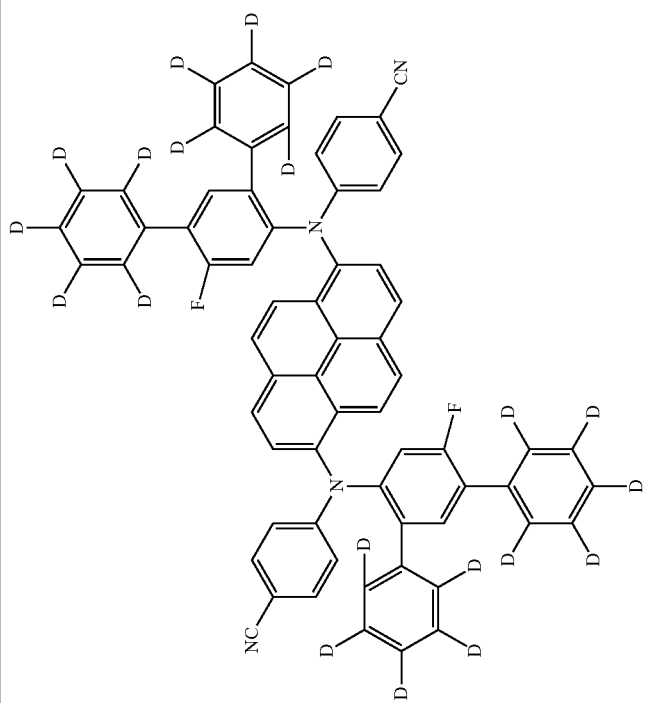

-continued
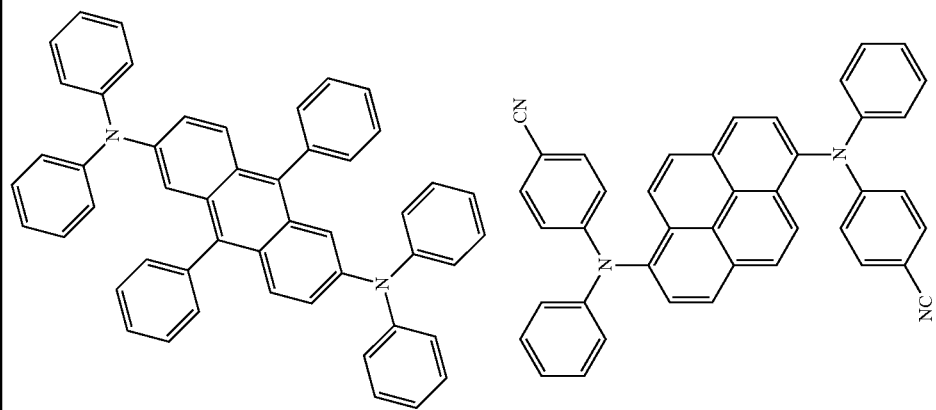

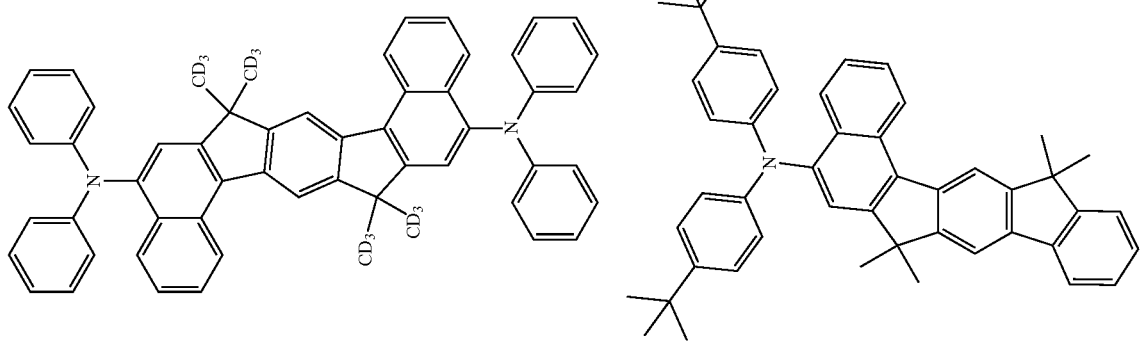

-continued
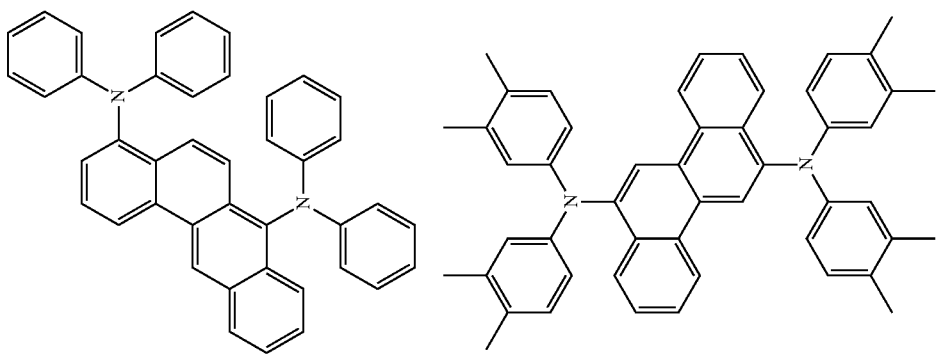

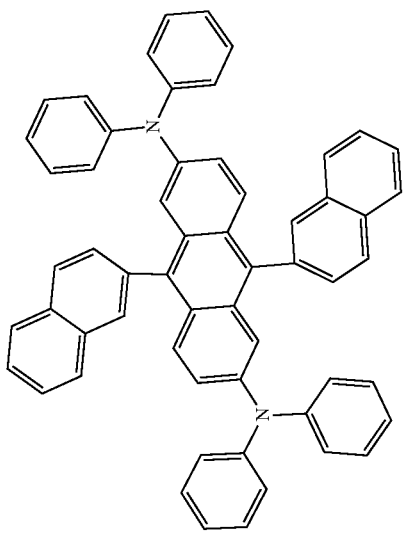

-continued
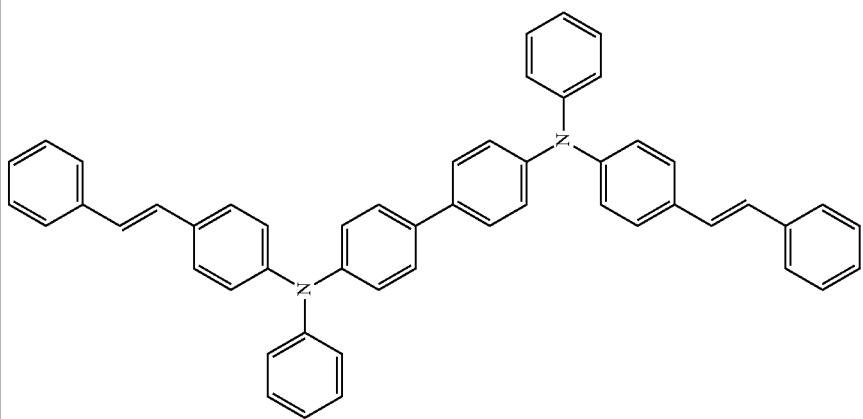

-continued
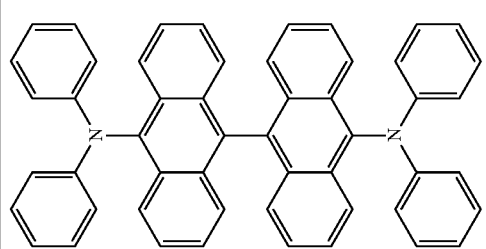
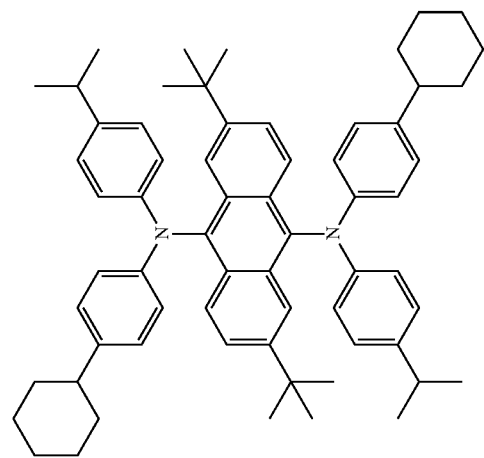

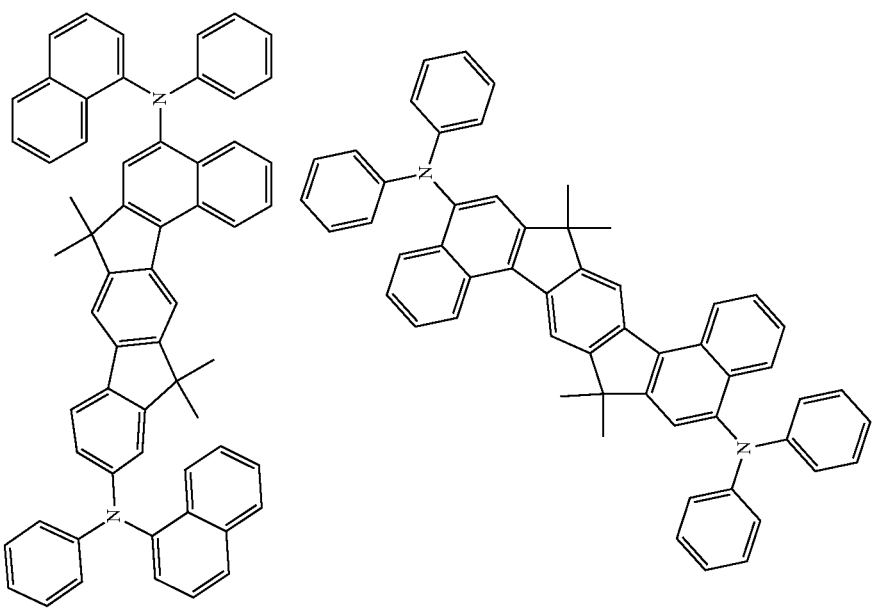

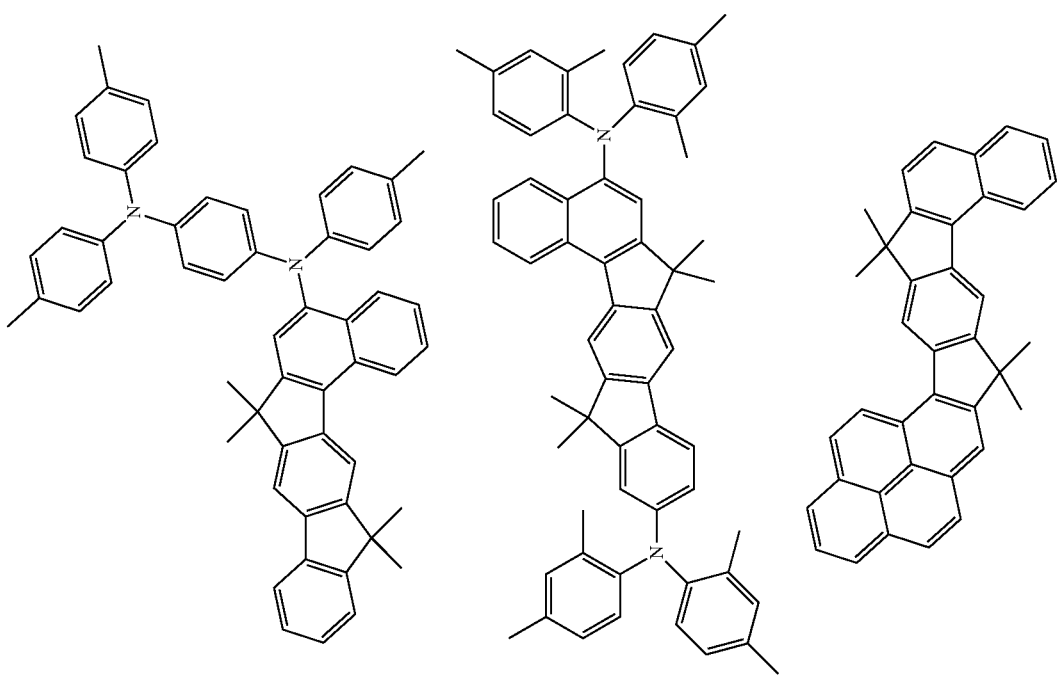

-continued
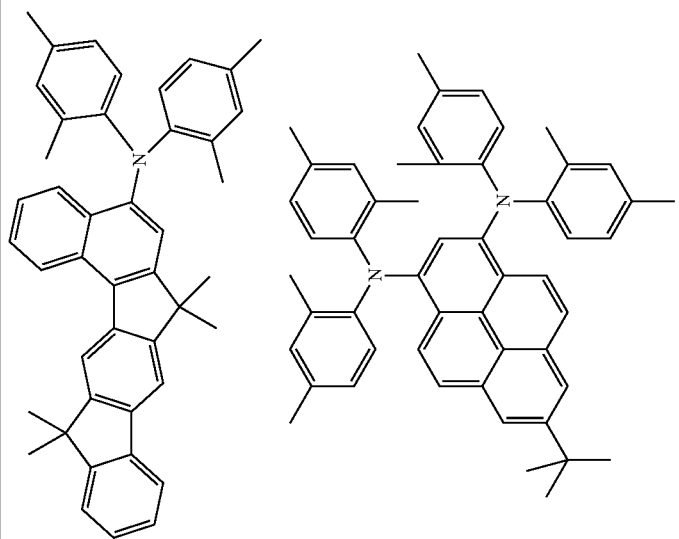

-continued
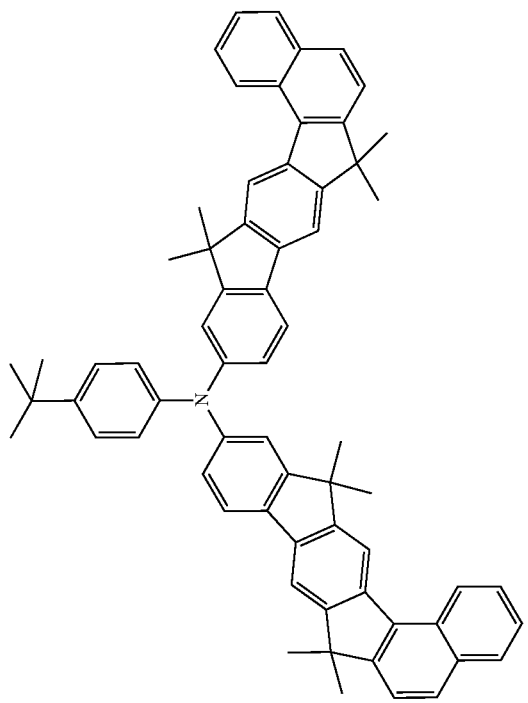
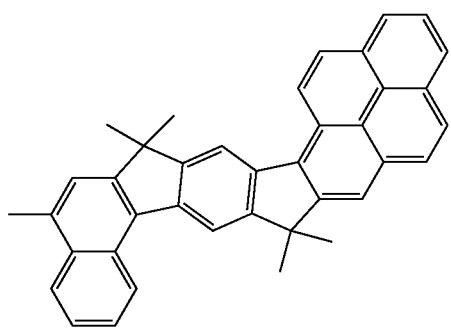

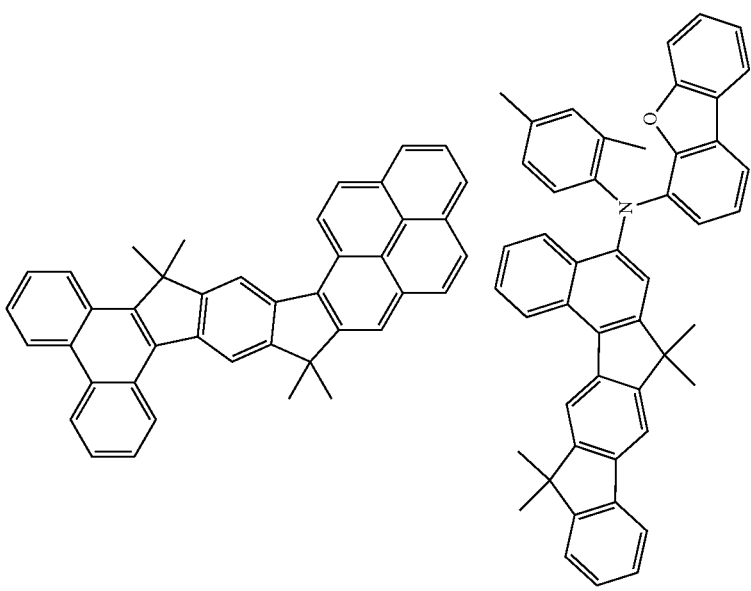

-continued
829 830
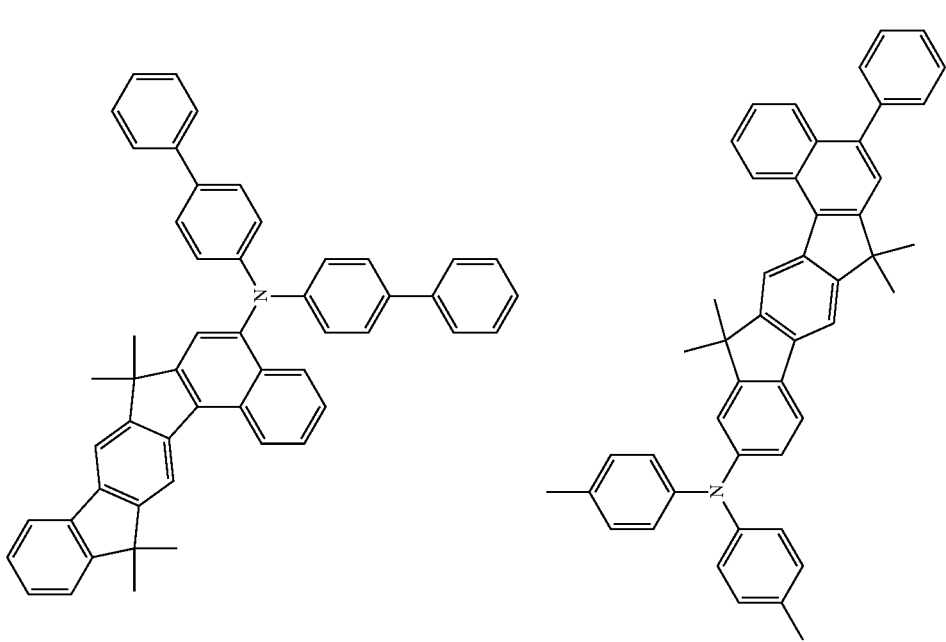

831
832
-continued
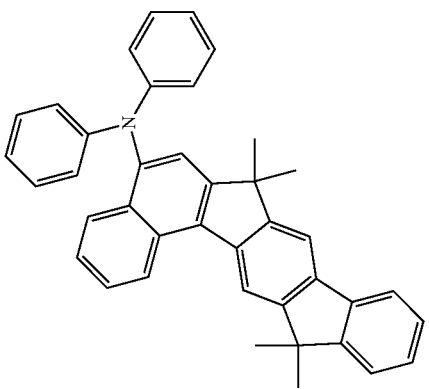
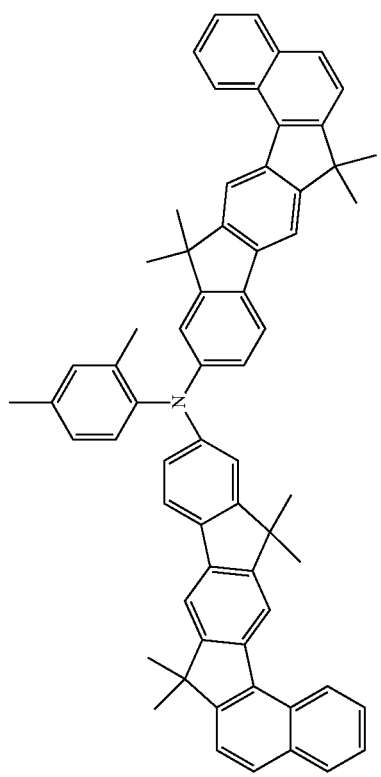

833
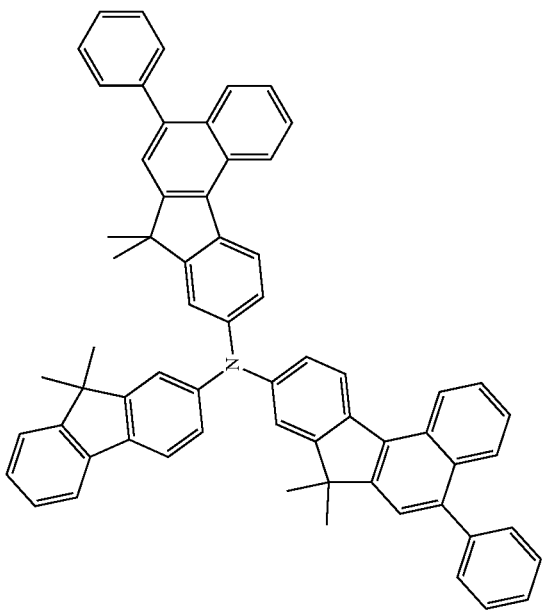
834
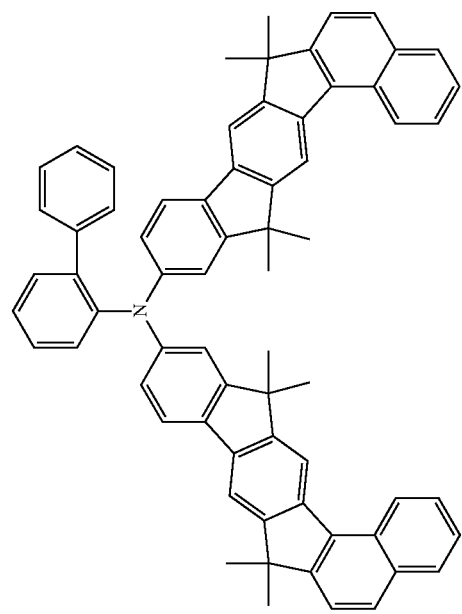

-continued
835 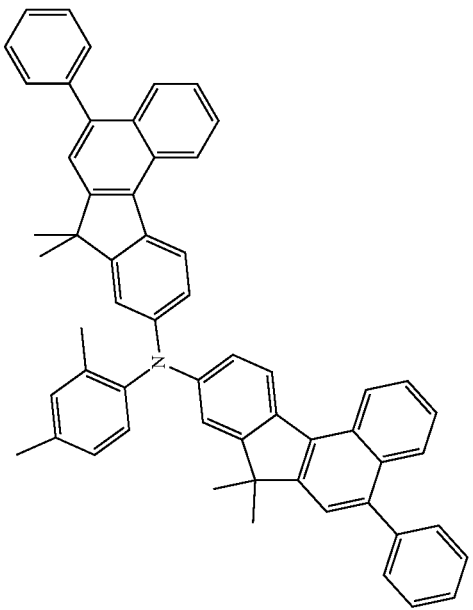
836 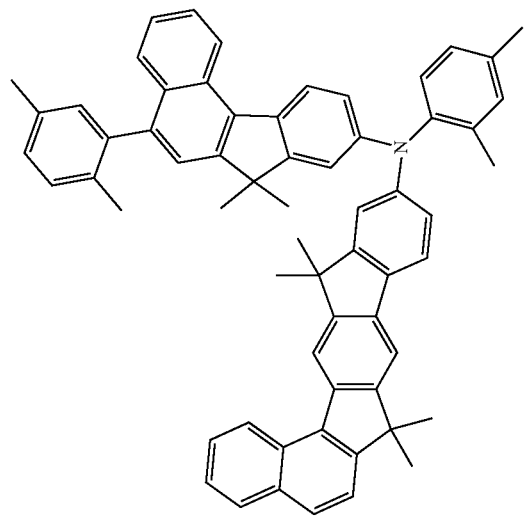

-continued
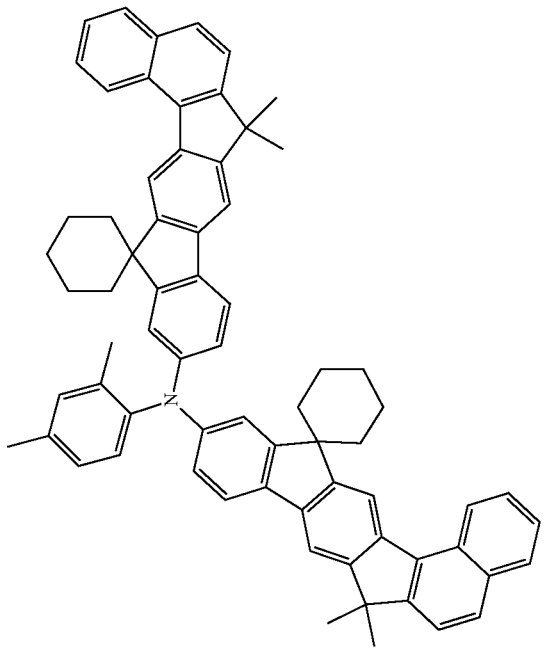 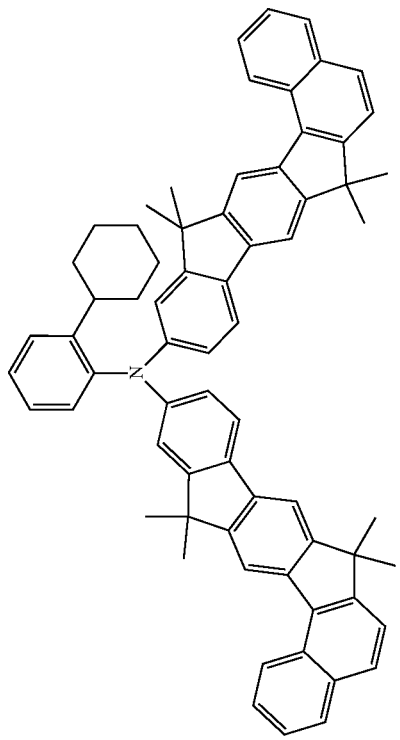

-continued
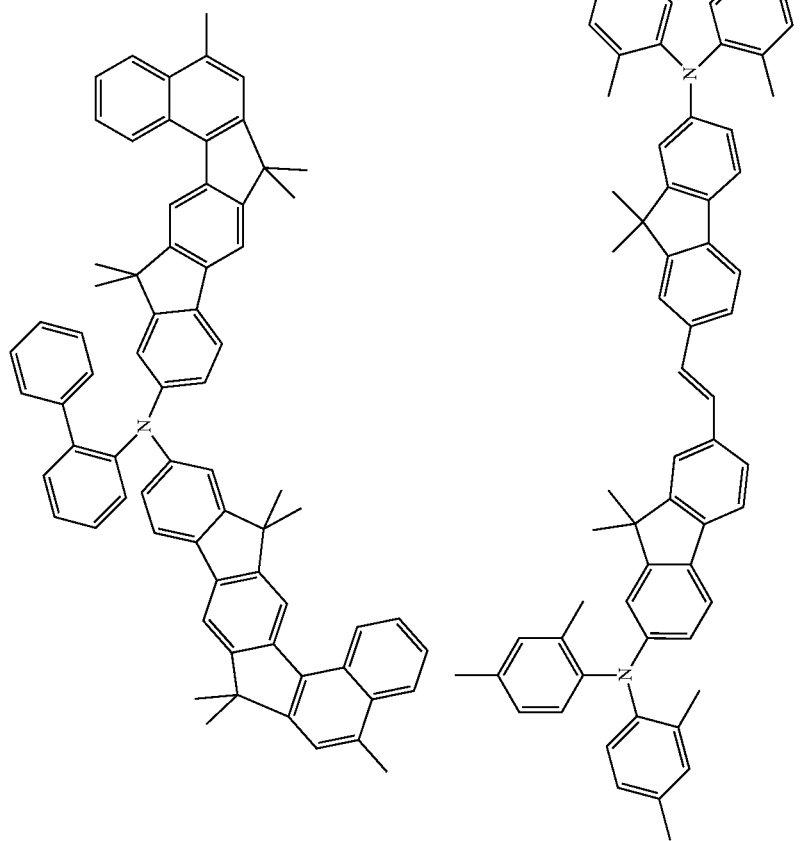

841 842
-continued
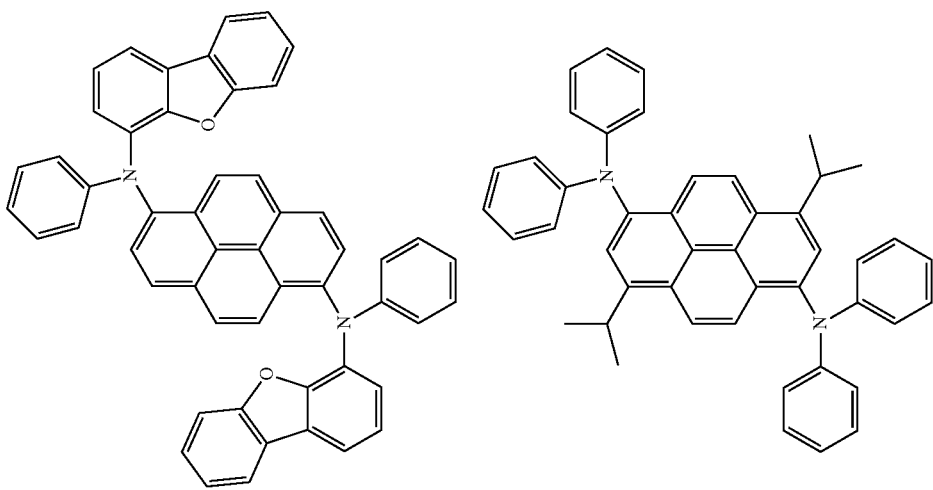

-continued
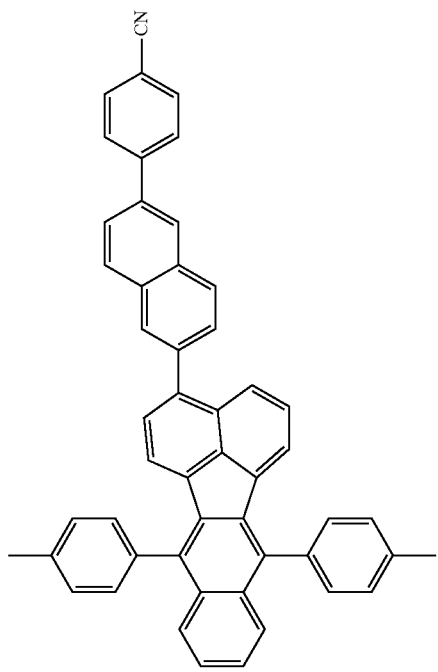 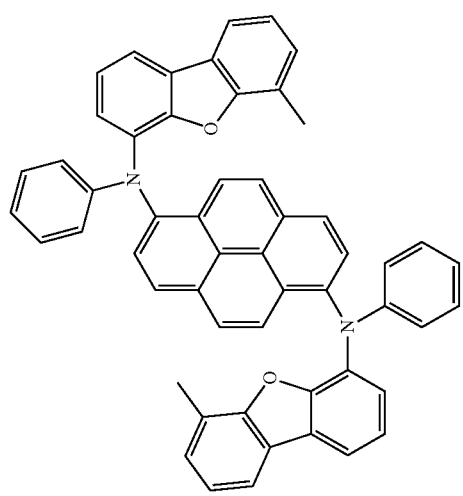

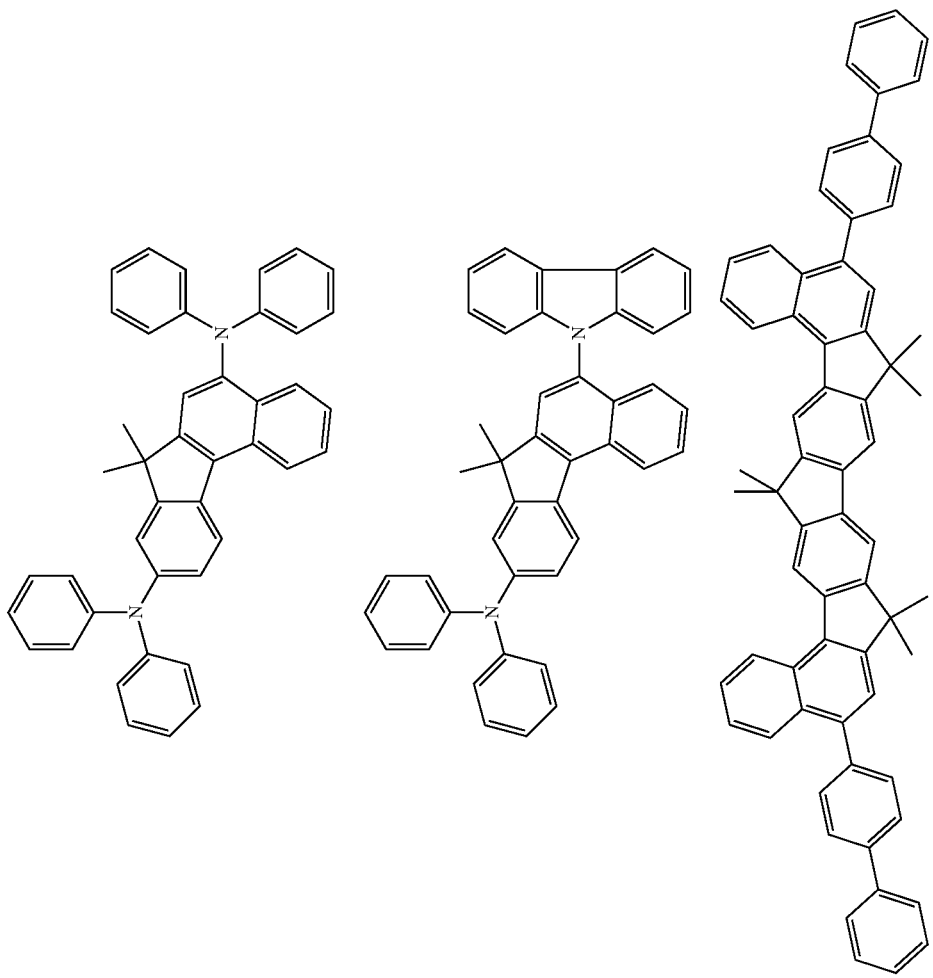

-continued
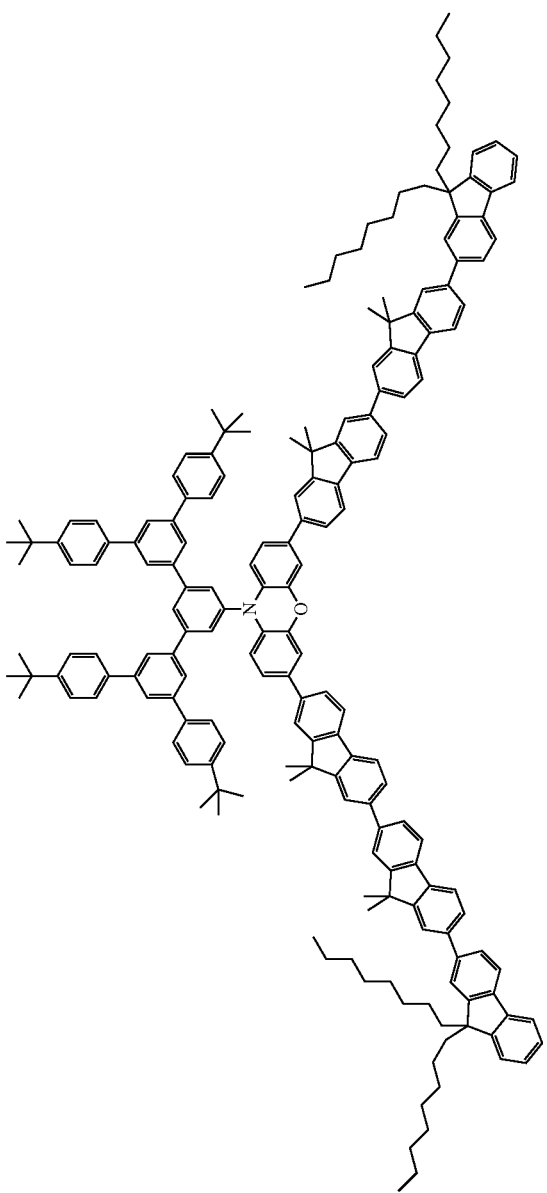
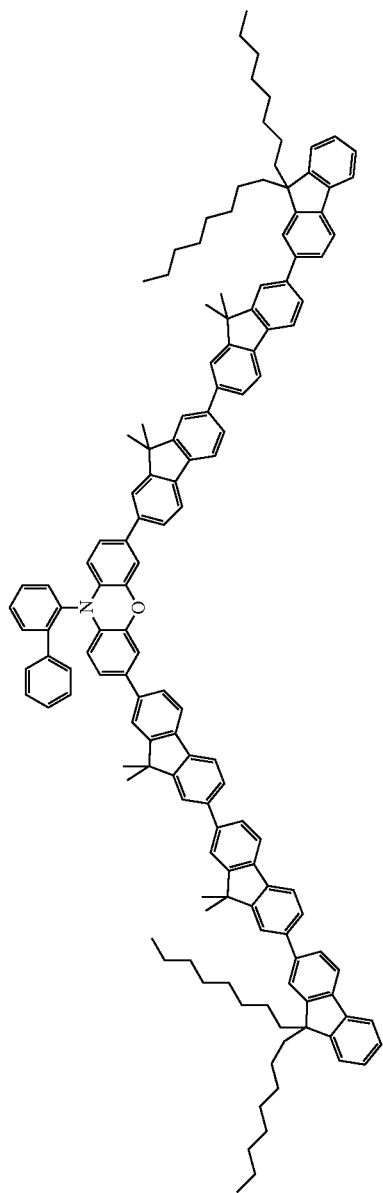

-continued
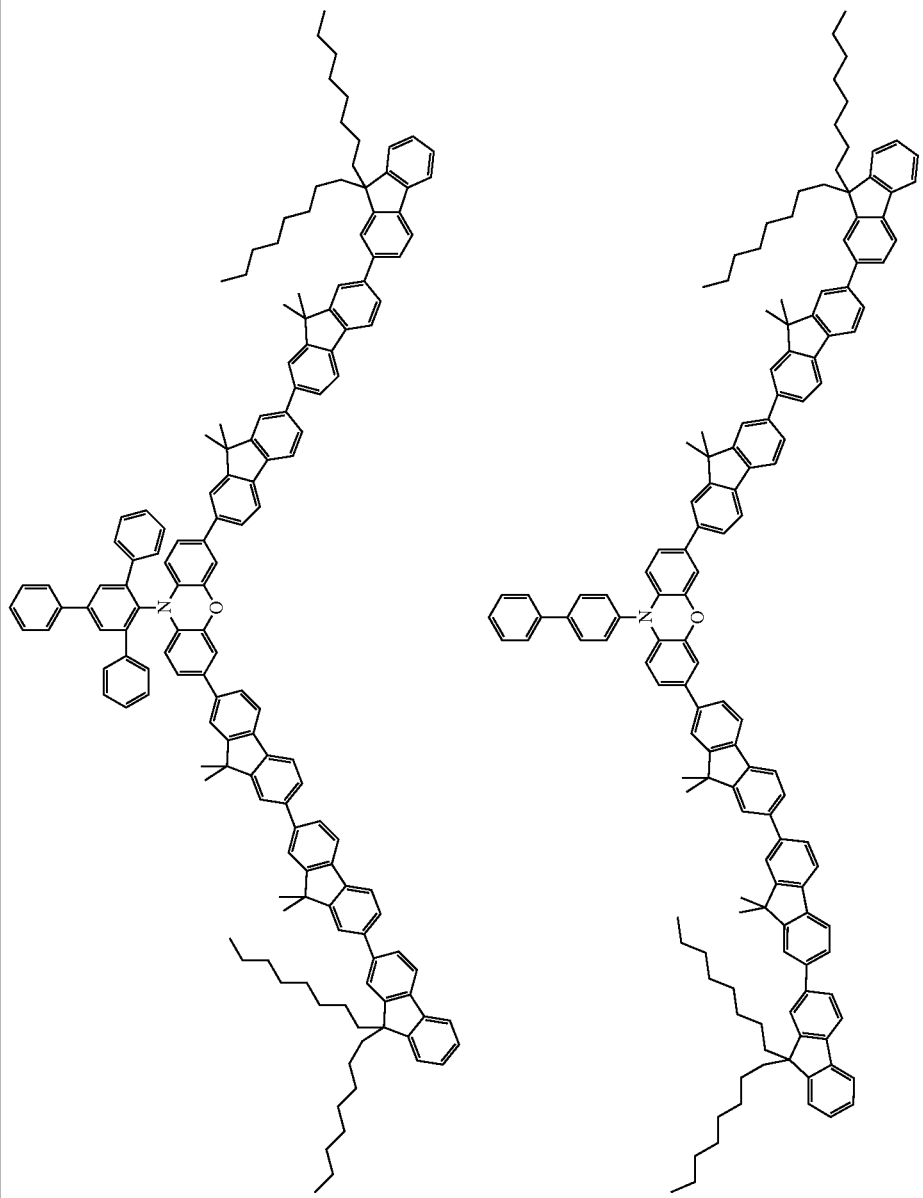

-continued
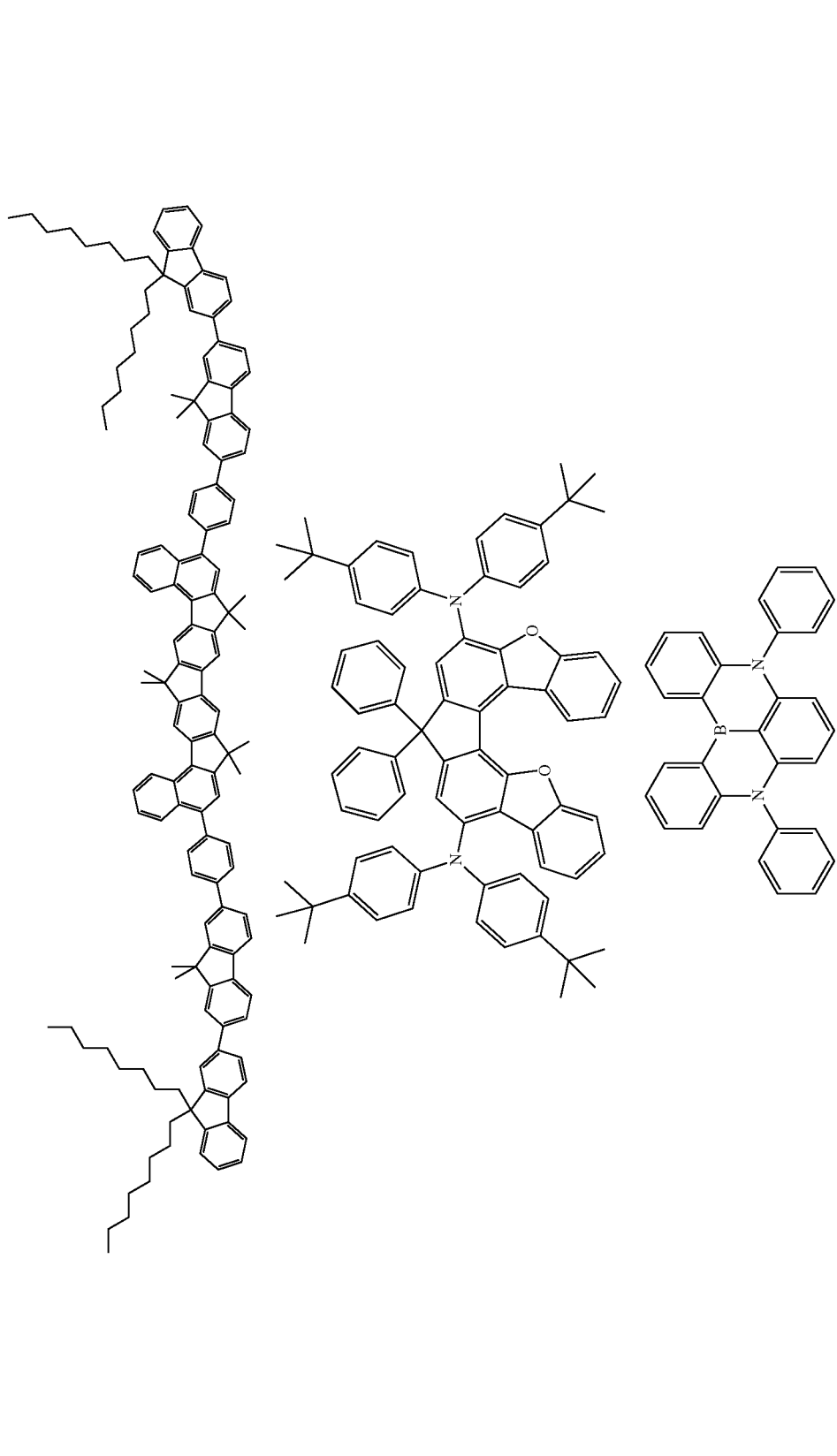

The compounds according to the invention can also be employed in other layers, for example as hole-transport materials in a hole-injection or hole-transport layer or electron-blocking layer or as matrix materials in an emitting layer, preferably as matrix materials for phosphorescent emitters.

If the compound of the formula (I) is employed as hole-transport material in a hole-transport layer, a hole-injection layer or an electron-blocking layer, the compound can be employed as pure material, i.e. in a proportion of 100%, in the hole-transport layer, or it can be employed in combination with one or more further compounds. According to a preferred embodiment, the organic layer comprising the compound of the formula (I) then additionally comprises one or more p-dopants. The p-dopants employed in accordance with the present invention are preferably organic electron-acceptor compounds which are able to oxidise one or more of the other compounds of the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600 and WO 2012/095143.

If the compound of the formula (1) is employed as matrix material in combination with a phosphorescent emitter in an emitting layer, the phosphorescent emitter is preferably selected from the classes and embodiments of phosphorescent emitters indicated below. Furthermore, one or more further matrix materials are preferably present in the emitting layer in this case.

So-called mixed-matrix systems of this type preferably comprise two or three different matrix materials, particularly preferably two different matrix materials. It is preferred here for one of the two materials to be a material having hole-transporting properties and for the other material to be a material having electron-transporting properties. The compound of the formula (1) is preferably the material having hole-transporting properties.

However, the desired electron-transporting and hole-transporting properties of the mixed-matrix components may also be combined mainly or completely in a single mixed-matrix component, where the further mixed-matrix component or components satisfy other functions. The two different matrix materials may be present here in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. Further details on mixed-matrix systems are contained, inter alia, in the application WO 2010/108579.

Particularly suitable matrix materials which can be used as matrix components of a mixed-matrix system in combination with the compounds according to the invention are selected from the preferred matrix materials for phosphorescent emitters indicated below or the preferred matrix materials for fluorescent emitters, depending on what type of emitter compound is employed in the mixed-matrix system.

Generally preferred classes of material for use as corresponding functional materials in the organic electroluminescent devices according to the invention are indicated below.

Suitable phosphorescent emitters are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the phosphorescent emitters described above are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used in accordance with the prior art for phosphorescent OLEDs and as are known to the person skilled in the art in the area of organic electroluminescent devices are suitable for use in the devices according to the invention. The person skilled in the art will also be able to employ further phosphorescent complexes without inventive step in combination with the compounds according to the invention in OLEDs.

Preferred matrix materials for phosphorescent emitters are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109, WO 2011/000455 or WO 2013/041176, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or WO 2012/143080, triphenylene derivatives, for example in accordance with WO 2012/048781, or lactams, for example in accordance with WO 2011/116865 or WO 2011/137951.

Besides the compounds according to the invention, suitable charge-transport materials, as can be used in the hole-injection or hole-transport layer or electron-blocking layer or in the electron-transport layer of the electronic device according to the invention, are, for example, the compounds disclosed in Y. Shirota et al., Chem. Rev. 2007, 107(4), 953-1010, or other materials as are employed in these layers in accordance with the prior art.

Materials which can be used for the electron-transport layer are all materials as are used in accordance with the prior art as electron-transport materials in the electron-transport layer. Particularly suitable are aluminium complexes, for example $Alq_3$, zirconium complexes, for example $Zrq_4$, lithium complexes, for example LiQ, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Furthermore, suitable materials are derivatives of the above-mentioned compounds, as disclosed in JP 2000/053957, WO 2003/060956, WO 2004/028217, WO 2004/080975 and WO 2010/072300.

Preferred hole-transport materials which can be used in a hole-transport, hole-injection or electron-blocking layer in the electroluminescent device according to the invention are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or WO 2013/120577), fluorenamines (for example in accordance with the as applications EP 2875092, EP 2875699 and EP 2875004), spirodibenzopyranamines (for example in accordance with WO 2013/083216) and dihydroacridine derivatives (for example in accordance with WO 2012/150001). The compounds according to the invention can also be used as hole-transport materials.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive doped polymers.

The device is appropriately (depending on the application) structured, pro-vided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

Also possible are hybrid processes, in which, for example, one or more layers are applied from solution and one or more further layers are applied by vapour deposition. Thus, it is possible, for example, to apply the emitting layer from solution and to apply the electron-transport layer by vapour deposition. These processes are generally known to the person skilled in the art and can be applied by him without inventive step to organic electroluminescent devices comprising the compounds according to the invention.

In accordance with the invention, the electronic devices comprising one or more compounds according to the invention can be employed in displays, as light sources in lighting applications and as light sources in medical and/or cosmetic applications (for example light therapy).

The invention will now be explained in greater detail by the following examples, without wishing to restrict it thereby.

A) SYNTHESES EXAMPLES

A-1) Part 1

Synthesis Building Block BB-I

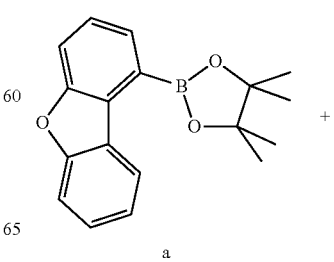

a

857
-continued

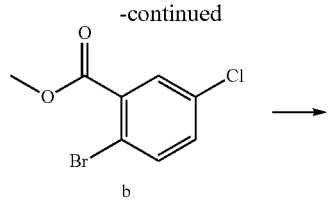
b

858
Synthesis BB-II

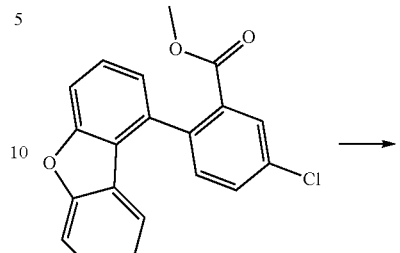
BB-I

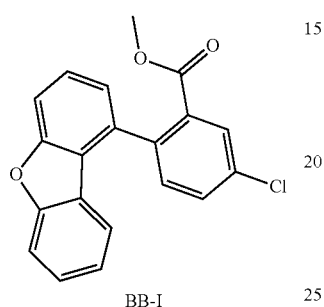
BB-I 117.9 g (401 mmol) starting material a, 100 g (401 mmol) starting material b and 203.1 g (882 mmol) potassium phosphate monohydrate are mixed in 1.6 L toluene/water/dioxane (2:1:1) and degassed. To the mixture, palladium acetate (0.9 g, 4 mmol) and tri-ortho-tolylphosphine (2.44 g, 8 mmol) are added and the mixture is stirred at reflux for 16 h. After cooling the mixture to room temperature, the phases are separated. The aqueous phase is further extracted with ethyl acetate (2×300 mL). The combined organic phases are washed multiple times with water, dried over sodium sulfate and finally removed in vacuum. The crude is filtered over a plug of $SiO_2/Al_2O_3$ using ethyl acetate as solvent. After removing the solvent in vacuum, an oil is obtained in quantitative yield.

The following compounds can be synthesized in an analogous manner:

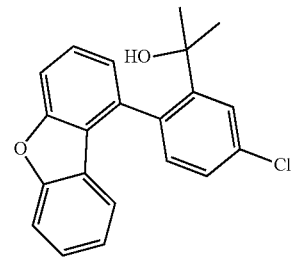
BB-II

MeMgCl (461 mL, 3 M in THF, 1.38 mol) is added dropwise to a pre-cooled THF suspension (0° C., 1.5 L) of compound BB-1 (135 g, 0.4 mol) and $CeCl_3$ (199 g, 0.8 mol). After completion of the reaction, a saturated aqueous solution of $NH_4Cl$ is added to quench the excess of MeMgCl, and the organic phase is extracted three times with ethyl acetate. The organic fractions are combined and washed with water and brine, successively. The volatiles were removed in vacuum to yield the desired product. 129 g (96%).

The following compounds can be synthesized in an analogous manner:

| Compound | Starting material | Starting material | Product |
|---|---|---|---|
| BB-I.a | CAS 912824-85-2 | | |

| Compound | Starting material | Product |
|---|---|---|
| BB-II.a | | |

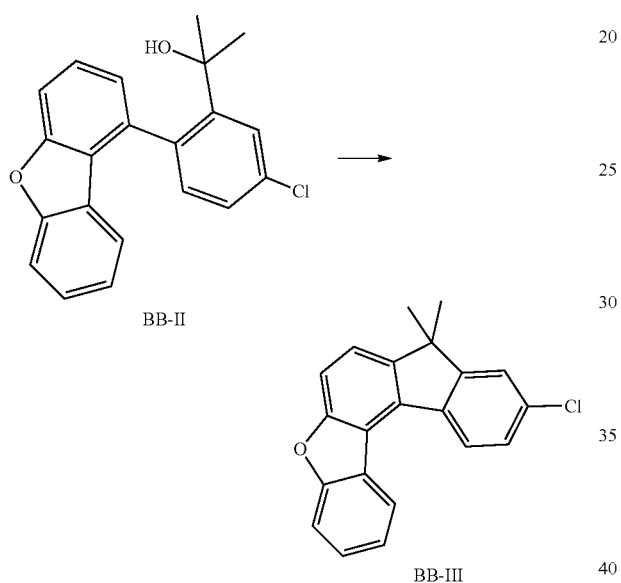

Synthesis of BB-III

To a solution of compound BB-II (129 g, 383 mmol) in toluene (1 L), 50 g of Amberlyst-15 are added. The mixture is stirred at reflux overnight. The mixture is cooled down to room temperature and the Amberlyst-15 filtered off. The solvent is removed in vacuum and the crude product is purified by column chromatography (SiO₂, heptane). Yield: 106.2 g (87%).

The following compounds can be synthesized in an analogous manner:

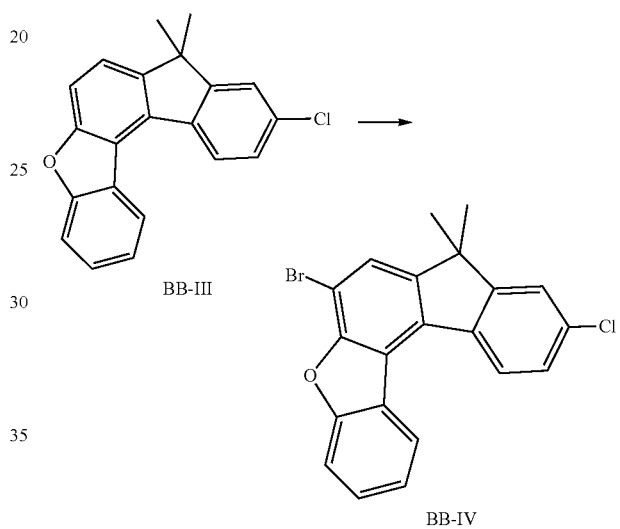

Synthesis BB-IV

To a solution of compound BB-III (100 g, 314 mmol) in $CH_2Cl_2$ (1.2 L), N-bromosuccinimide (55.83 g, 314 mmol) and HBr (32% solution in acetic acid, 0.5 mL) are added. The reaction is heated at 30° C. for 4 days. After completion of the reaction, $Na_2S_2O_3$ (300 mL, saturated aqueous solution) is added and the mixture is stirred vigorously for 30 minutes. The phases are separated and the organic phase is washed several times with water. The solvent is removed in vacuum and the crude product vigorously stirred with ethanol to yield a white solid. Yield: 119.8 g (96%).

The following compounds can be synthesized in an analogous manner:

| Compound | Starting material | Product |
|---|---|---|
| BB-III.a | | |

| Compound | Starting material | Product |
|---|---|---|
| BB-IV.a | | |

Synthesis Intermediate BB-V

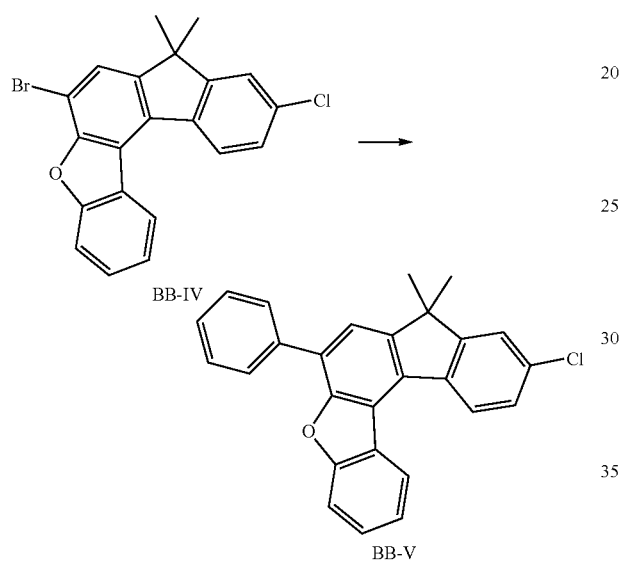

30.0 g (75.4 mmol) BB-IV, 9.2 g (75.4 mmol) phenylboronic acid and 16.0 g (151 mmol) sodium carbonate are mixed in 600 mL toluene/dioxane/water (2:1:2) and degassed. To the mixture, Tetrakis(triphenylphosphine) palladium (2.2 g, 1.9 mmol) is added and the mixture is stirred at reflux for 4 h. After cooling the mixture to room temperature, 400 mL of ethyl acetate is added and the phases are separated. The organic phase is washed multiple times with water and the solvent is removed in vacuum. Afterwards, the organic phase is filtrated over a plug of silica using ethyl acetate as solvent. The solvent is removed in vacuum and the crude product vigorously stirred with ethanol to yield a white solid. Yield: 28.3 g (95%).

The following compounds can be synthesized in an analogous manner:

| Comp. | Starting material | Starting material | Product |
|---|---|---|---|
| BB-V.b | BB-IV.a | | |
| BB-V.c | BB-IV | | |

-continued

| Comp. | Starting material | Starting material | Product |
|---|---|---|---|
| BB-V.d | BB-IV.a | | |
| BB-V.e | BB-IV | | |
| BB-V.f | BB-IV | | |
| BB-V.g | BB-IV | | |
| BB-V.h | BB-IV | | |

-continued
| Comp. | Starting material | Starting material | Product |
|---|---|---|---|
| BB-V.i | BB-IV | CAS 1010100-76-1 | |
| BB-V.j | BB-IV.a | CAS 1010100-76-1 | |
A-2) Part 2
Scheme Synthesis Example of Intermediate VII-a
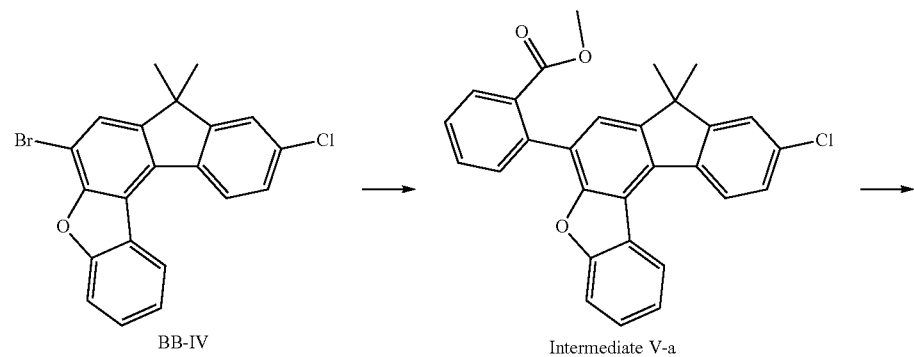

-continued

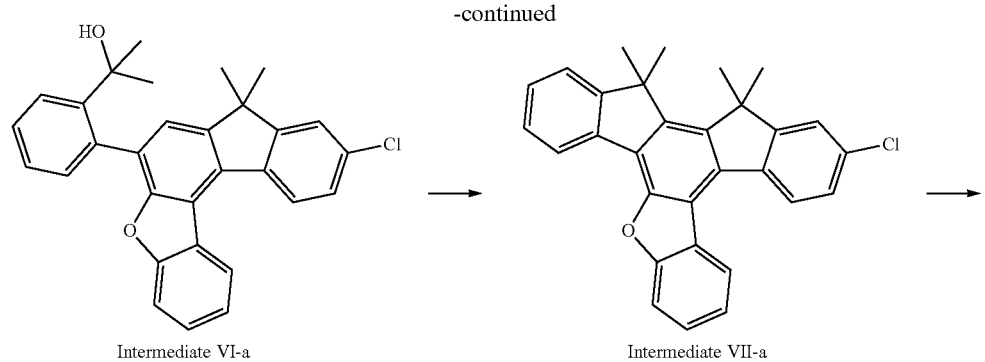

Intermediate VI-a → Intermediate VII-a →

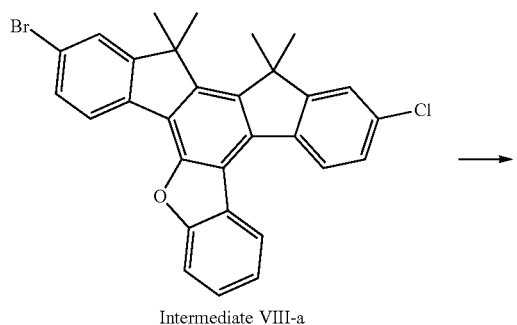

Intermediate VIII-a

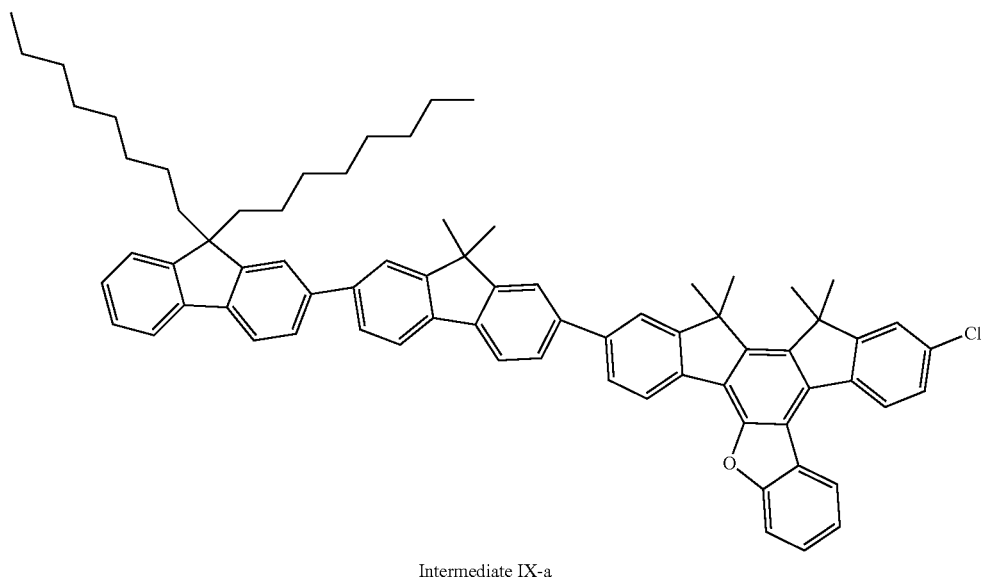

Intermediate IX-a

Synthesis Intermediate V-a 27.5 g (69.1 mmol) BB-IV, 13.1 g (72.6 mmol) (2-methoxycarbonylphenyl)boronic acid and 35.0 g (152.1 mmol) potassium phosphate monohydrate are mixed in 300 mL toluene and degassed. To the mixture, 2-dicyclohexylphosphino-2',4',6'-triisopropyl-1,1'-biphenyl)[2-(2'-amino-1,1'-biphenyl)]palladium(II) methanesulfonate (1.18 g, 2.07 mmol) is added and the mixture is stirred at reflux for 3 h. After cooling the mixture to room temperature, 300 mL water are added and the phases are separated. The organic phase is washed multiple times with water and the solvent is removed in vacuum. Afterwards, the crude product is purified by column chromatography (SiO$_2$, toluene). Yield: 28.2 g (90%).

In a similar manner, the following compounds can also be prepared:

| Examples | Intermediate IV | Intermediate V |
|---|---|---|
| V-b | 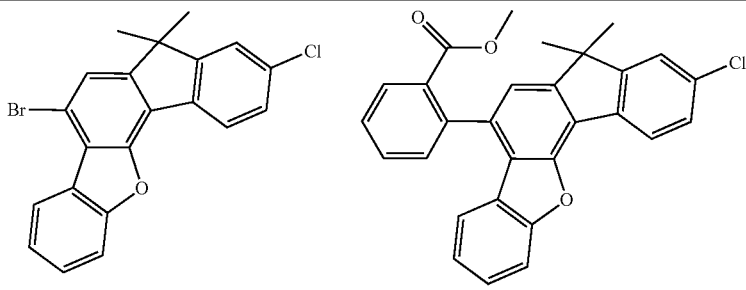 | |

Synthesis Intermediate VI-a

Intermediate VI-a can be prepared in a similar manner as intermediate II-a starting from V-a (28.0 g, 61.8 mmol), MeMgCl (71 mL, 3 M in THF, 213 mmol) and CeCl₃ (30.5 g, 124 mmol) in 350 mL of THF. Yield: 25.5 g (91%).

In a similar manner, the following compounds can also be prepared:

Synthesis Intermediate VII-a

Intermediate VII-a can be synthesized following the same procedure as intermediate III-a starting from 25 g (55 mmol) of VI-a and 12 g of Amberlyst-15 in 300 mL of toluene. Yield: 20.4 g (85%).

In a similar manner, the following compounds can also be prepared:

| Examples | Intermediate V | Intermediate VI |
|---|---|---|
| VI-b | 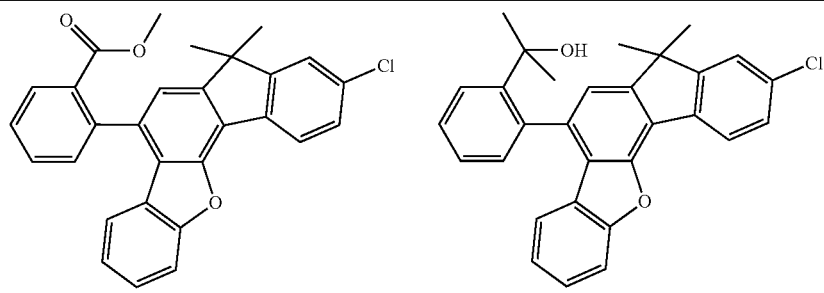 | |
| VI-c | 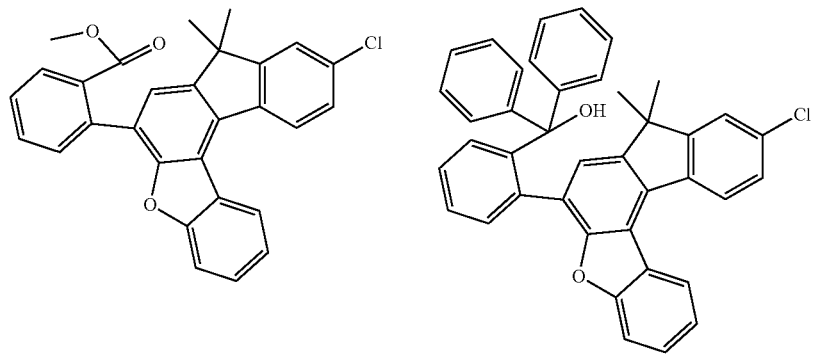 | |

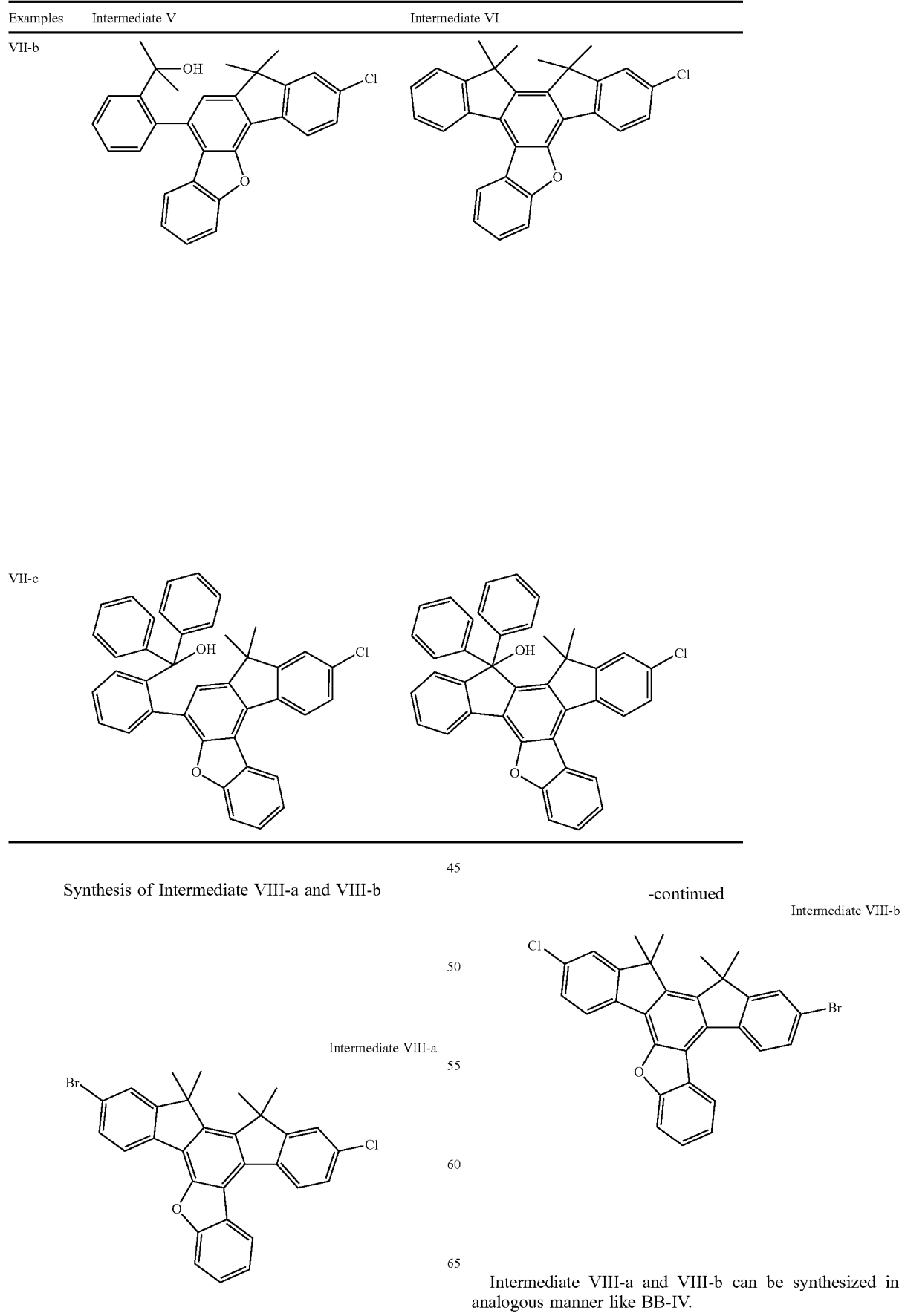
Synthesis of Intermediate VIII-a and VIII-b
Intermediate VIII-a and VIII-b can be synthesized in analogous manner like BB-IV.

Synthesis of Intermediate IX-a and IX-b
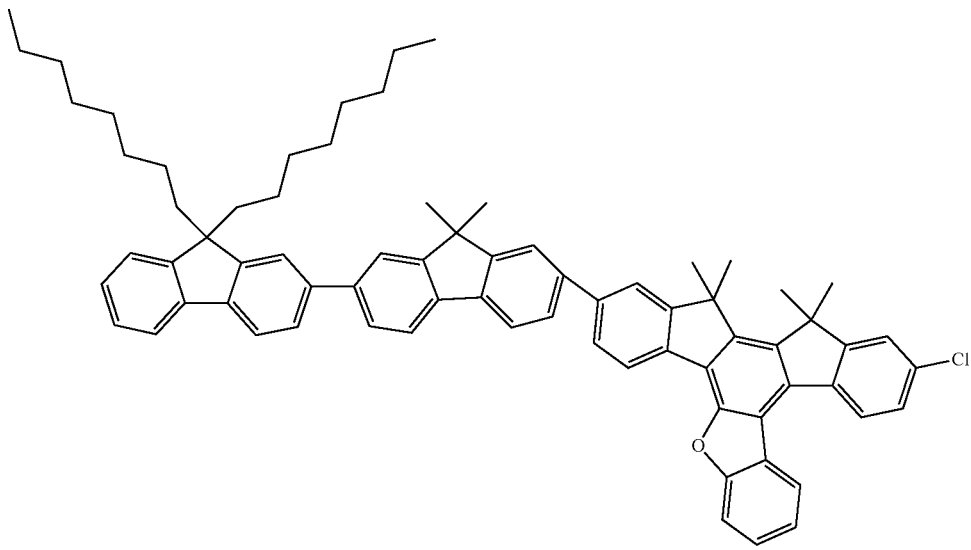
Intermediate IX-a
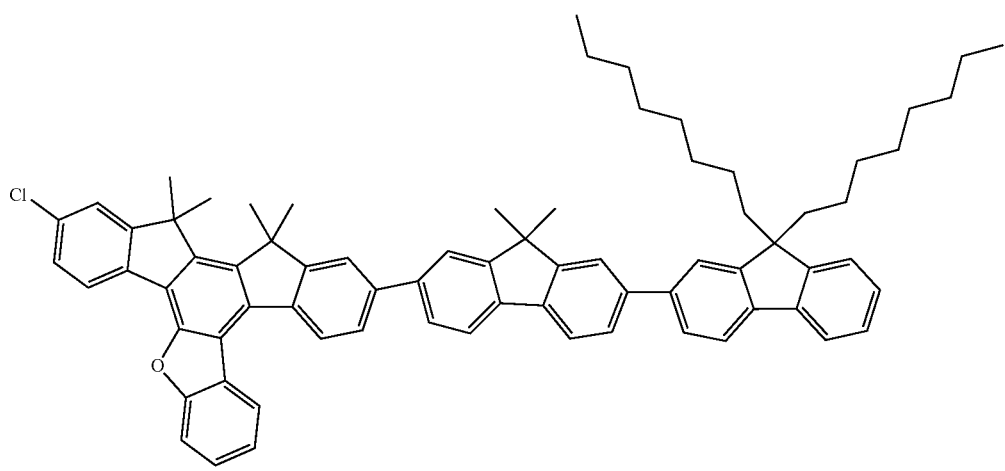
Intermediate IX-b
Intermediate IX-a and IX-b can be synthesized in analogous manner like BB-V by using CAS 1010100-76-1 as boronate ester starting material.

A-3) Part 3

Synthesis of the amine Int1.1

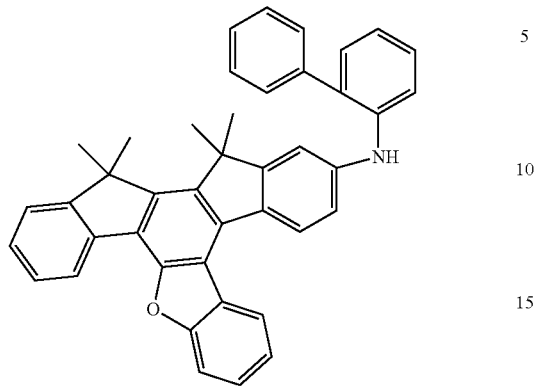

4.41 g (26.0 mmol) biphenyl-2-ylamine, 11.31 g (26.0 mmol) VII-a and 6.82 g (70.9 mmol) sodium tertbutylate are mixed in 300 mL toluene and degassed. Afterwards, 563 mg (1.4 mmol) S-Phos and 151 mg (0.7 mmol) palladium acetate are added and the mixture is stirred at reflux for 16 h. After cooling the mixture at room temperature, 200 mL of water is added and the phases are separated. The crude product is filtrate over a plug of aluminium oxide using toluene as solvent. The product is further purified by recrystallizations from toluene/heptane. Yield: 10.48 g (71%).

The following compounds can be synthesized in an analogous manner:

| Comp. | SM | SM | Product |
|---|---|---|---|
| Int1.2 | VII-a | | |
| Int1.3 | VII-a | | |

-continued
| Comp. | SM | SM | Product |
|---|---|---|---|
| Int1.4 | VII-b | 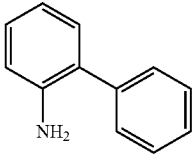 | 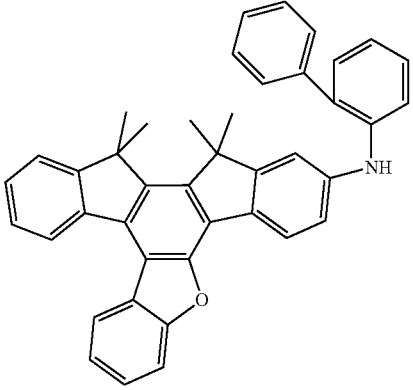 [SMILES: CC1(C)c2cc(Nc3ccccc3-c3ccccc3)ccc2-c2c1c1c(c3c2oc2ccccc23)-c2ccccc2C1(C)C] |
| Int1.6 | VII-a | 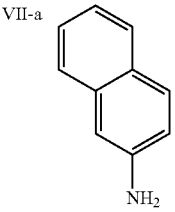 | 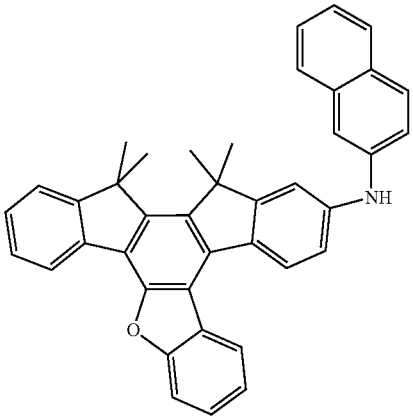 [SMILES: CC1(C)c2ccccc2-c2c1c1c(c3c2oc2ccccc23)-c2ccc(Nc3ccc4ccccc4c3)cc2C1(C)C] |
| Int1.7 | VII-a | 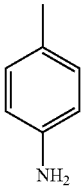 | 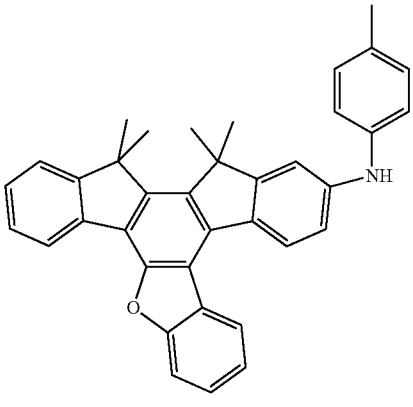 [SMILES: Cc1ccc(Nc2ccc3c(c2)C(C)(C)c2c4c(c5oc6ccccc6c5c2-3)-c2ccccc2C4(C)C)cc1] |

-continued

| Comp. | SM | SM | Product |
|---|---|---|---|
| Int1.8 | IX-a | | |
| Int1.9 | IX-b | | |
| Int1.10 | VII-a | | |
| Int1.11 | VII-c | | |

881

A-4) Part 4

Synthesis of Compound 1

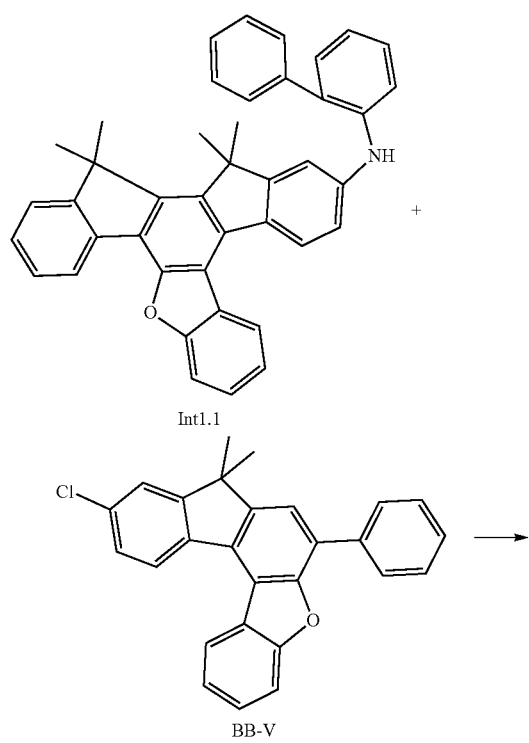

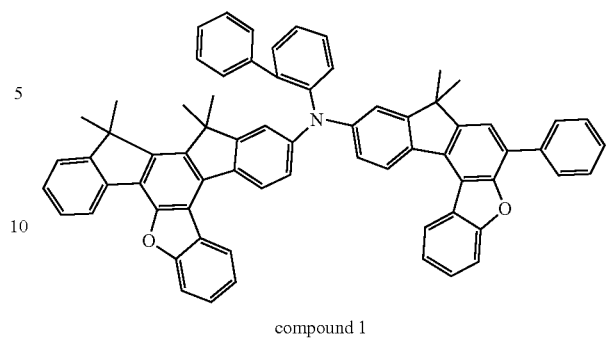

compound 1

17.5 g (30.8 mmol) Int1.1, 12.2 g (30.8 mmol) VII-a and 17.8 g (185 mmol) sodium tertbutylate are mixed in 700 mL toluene and degassed. Afterwards, 1.45 g (3.5 mmol) S-Phos and 389 mg (1.7 mmol) palladium acetate are added and the mixture is stirred at reflux for 16 h. After cooling the mixture at room temperature, 200 mL of water is added and the phases are separated. The crude product is filtrate over a plug of aluminium oxide using toluene as solvent. The product is further purified by recrystallizations from toluene/heptane up to a purity of >99.9% by HPLC. Yield: 13.1 g (46%).

The following compounds can be synthesized in an analogous manner:

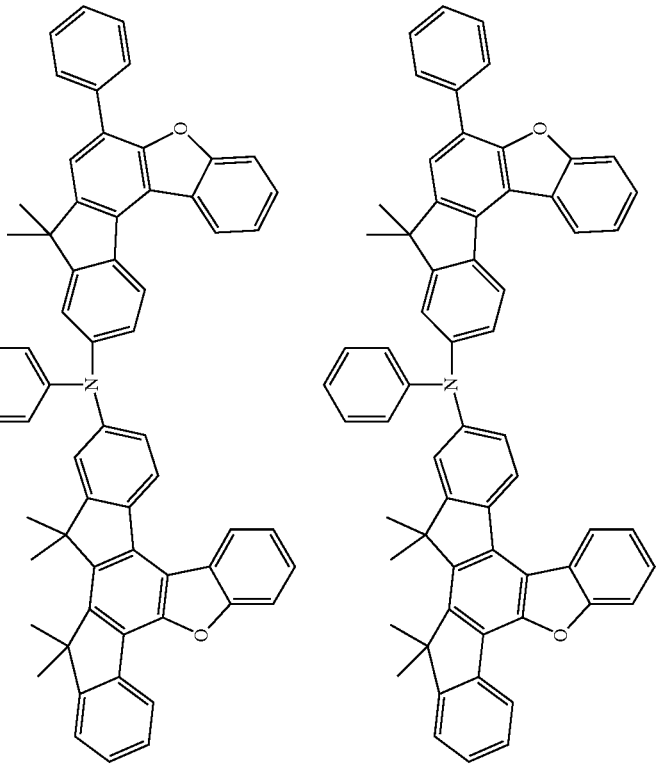
| | SM | Amine | Product |
|---|---|---|---|
| 2 | BB-V | Int1.2 | |
| 3 | BB-V | Int1.3 | |

| | SM | Amine | Product |
|---|---|---|---|
| 4 | BB-V | Int1.4 | 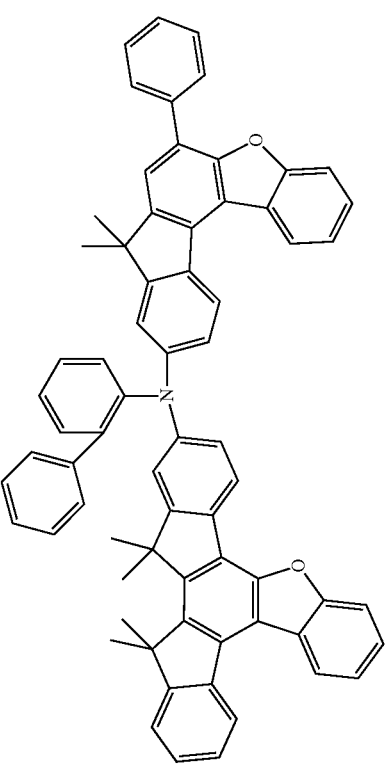 |
| 5 | BB-V | Int1.5 | 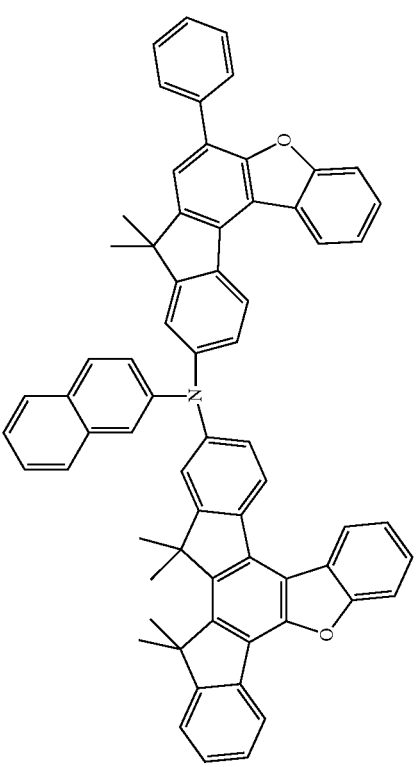 |

-continued

| | SM | Amine | Product |
|---|---|---|---|
| 6 | BB-V | Int1.6 | |
| 7 | BB-V | Int1.7 | |

| | SM | Amine | Product |
|---|---|---|---|
| 8 | BB-V.b | Int1.1 | 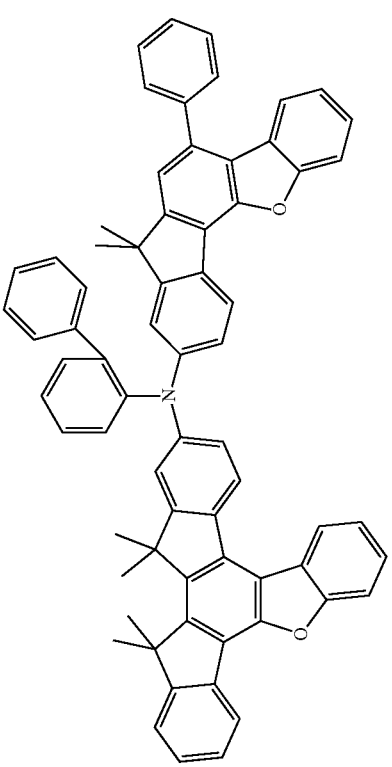 |
| 9 | BB-V.c | Int1.1 | 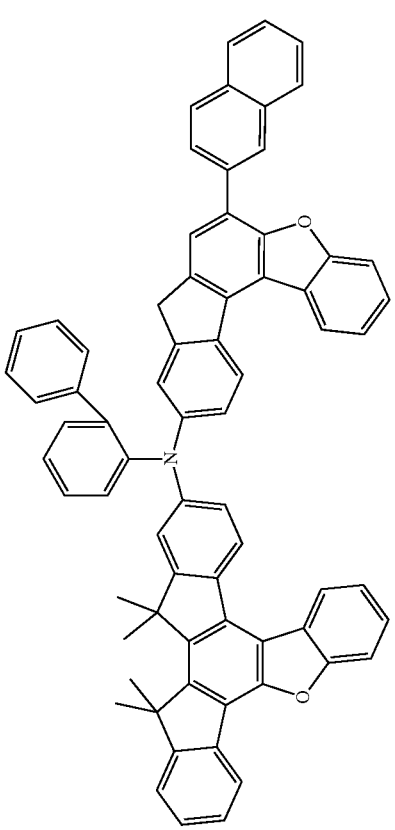 |

-continued

| | SM | Amine | Product |
|---|---|---|---|
| 10 | BB-V.d | Int1.1 | |
| 11 | BB-V.e | Int1.1 | |

-continued

| | SM | Amine | Product |
|---|---|---|---|
| 12 | BB-V.f | Int1.1. | |
| 13 | BB-V.g | Int1.1 | |

-continued

| | SM | Amine | Product |
|---|---|---|---|
| 14 | BB-V.h | Int1.1 | |
| 15 | BB-V.i | Int1.8 | |

-continued
| | SM | Amine | Product |
|---|---|---|---|
| 16 | BB-V.i | Int1.9 | |
| 17 | BB-V.j | Int1.8 | |
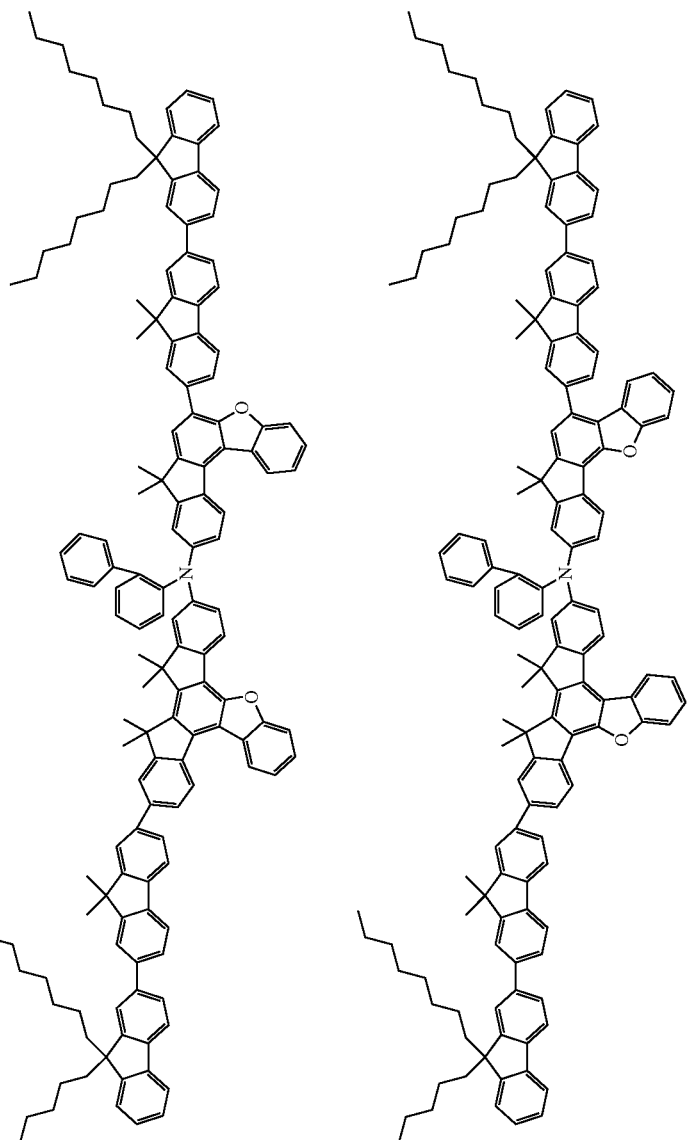

| | SM | Amine | Product |
|---|---|---|---|
| 18 | BB-V.j | Int1.9 | 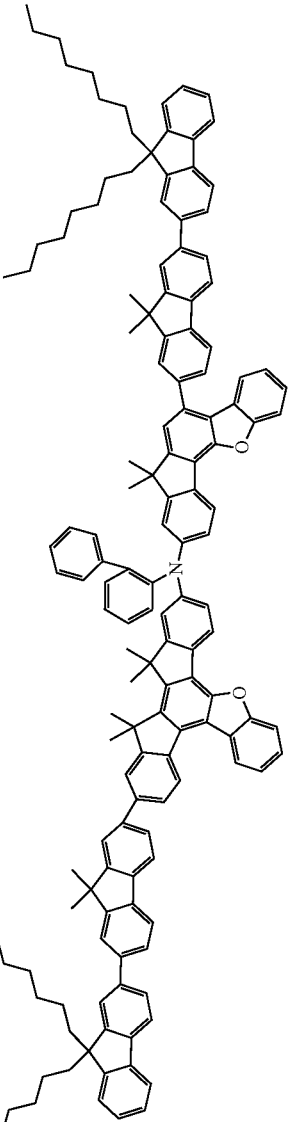 |
| 19 | BB-V | Int1.10 | 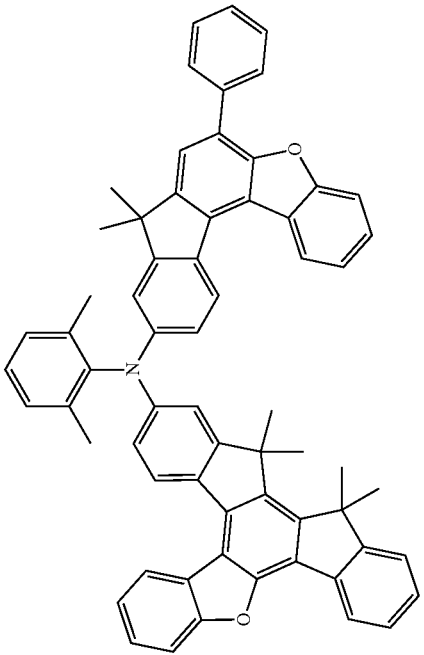 |

| SM | Amine | Product |
|---|---|---|
| 20 BB-V | Int.11 | 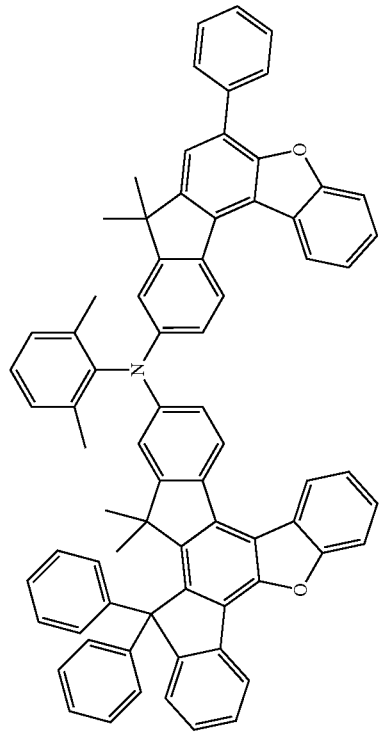 |

B) FABRICATION OF OLEDS

The production of solution-based OLEDs has already been described many times in the literature, for example in WO 2004/037887 and WO 2010/097155. The process is adapted to the circumstances described below (layer-thickness variation, materials).

The inventive material combinations are used in the following layer sequence:
  substrate,
  ITO (50 nm),
  Buffer (40 nm),
  emission layer (EML) (40 nm),
  hole-blocking layer (HBL) (10 nm)
  electron-transport layer (ETL) (30 nm),
  cathode (Al) (100 nm).

Glass plates coated with structured ITO (indium tin oxide) in a thickness of 50 nm serve as substrate. These are coated with the buffer (PEDOT) Clevios P VP AI 4083 (Heraeus Clevios GmbH, Leverkusen). The spin coating of the buffer is carried out from water in air. The layer is subsequently dried by heating at 180° C. for 10 minutes. The emission layers are applied to the glass plates coated in this way.

The emission layer (EML) is composed of the matrix material (host material) H and the emitting dopant (emitter) D. Both materials are present in the emission layer in a proportion of 97% by weight H and 3% by weight D. The mixture for the emission layer is dissolved in toluene. The solids content of such solutions is about 9 mg/ml if, as here, the layer thickness of 40 nm which is typical for a device is to be achieved by means of spin coating. The layers are applied by spin coating in an inert-gas atmosphere and dried by heating at 120° C. for 10 minutes. The materials used in the present case are shown in Table A.

TABLE A

Structural formulae of the solution processed materials in the EML

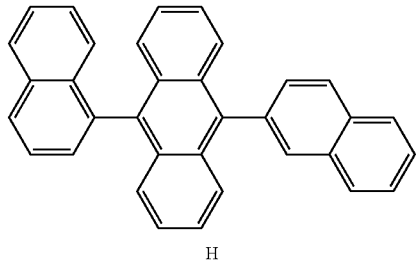

H

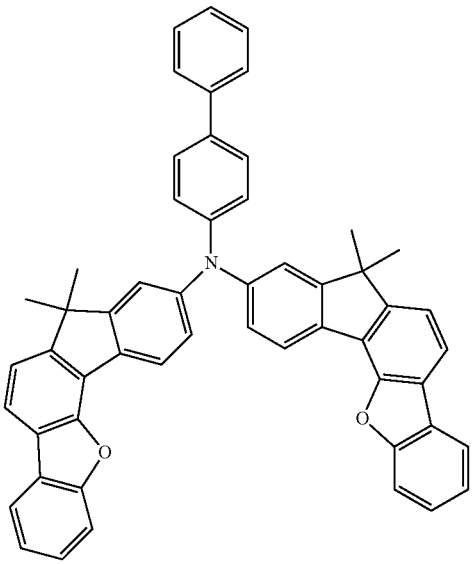 [SMILES: CC1(C)c2cc(N(c3ccc(-c4ccccc4)cc3)c3ccc4c(c3)C(C)(C)c3ccc5c(oc6ccccc65)c3-4)ccc2-c2c1ccc1c2oc2ccccc21]

SdT1

TABLE A-continued
Structural formulae of the solution processed materials in the EML
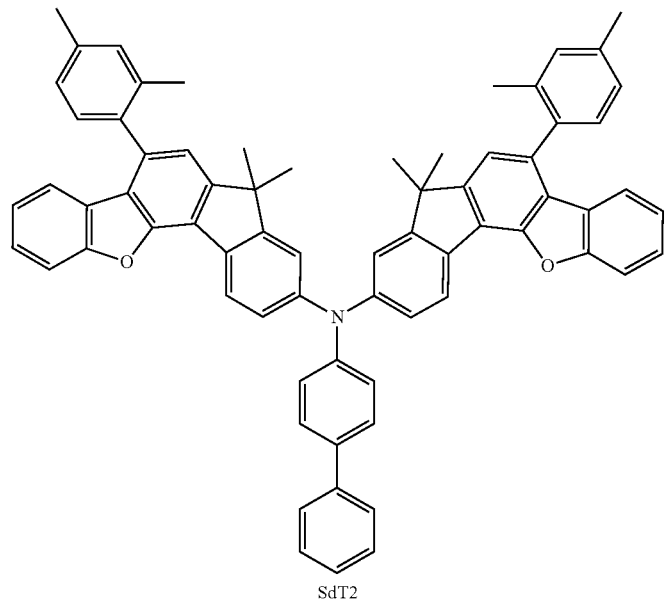
SdT2
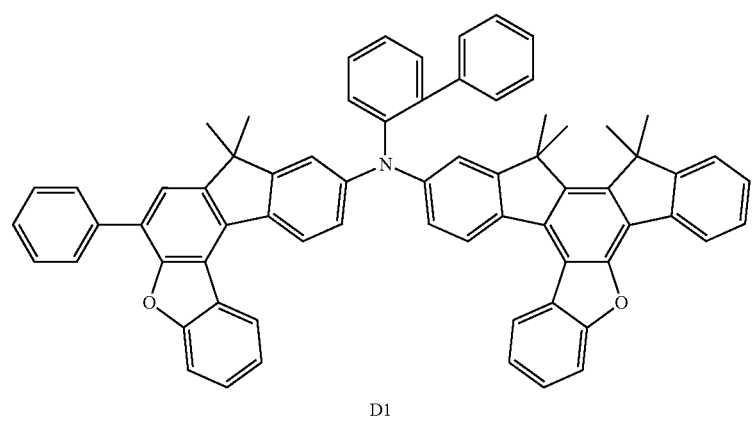
D1

TABLE A-continued

Structural formulae of the solution processed materials in the EML

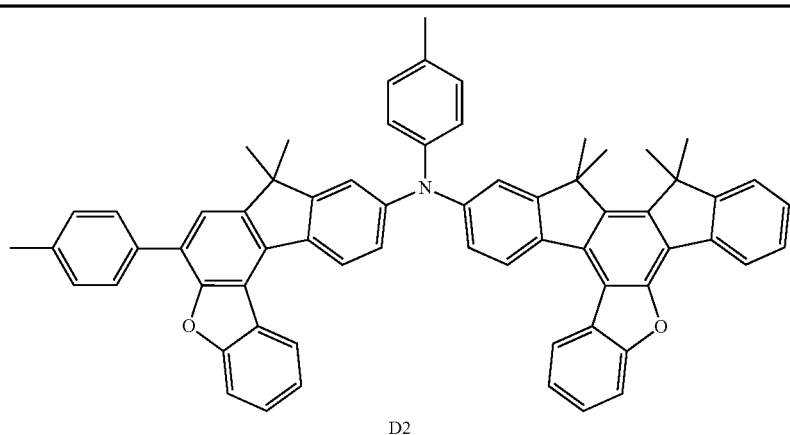

D2

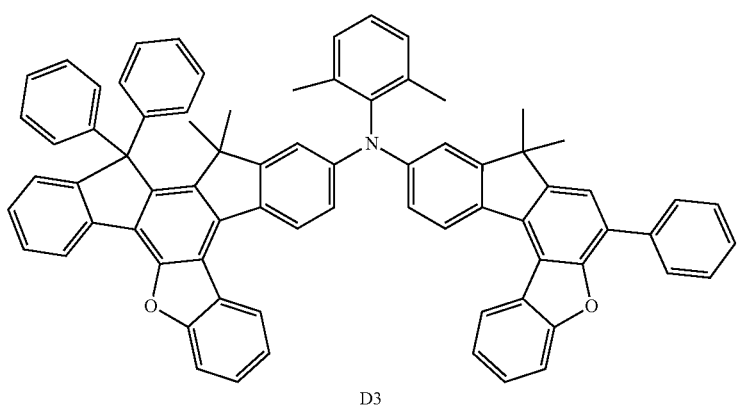

D3

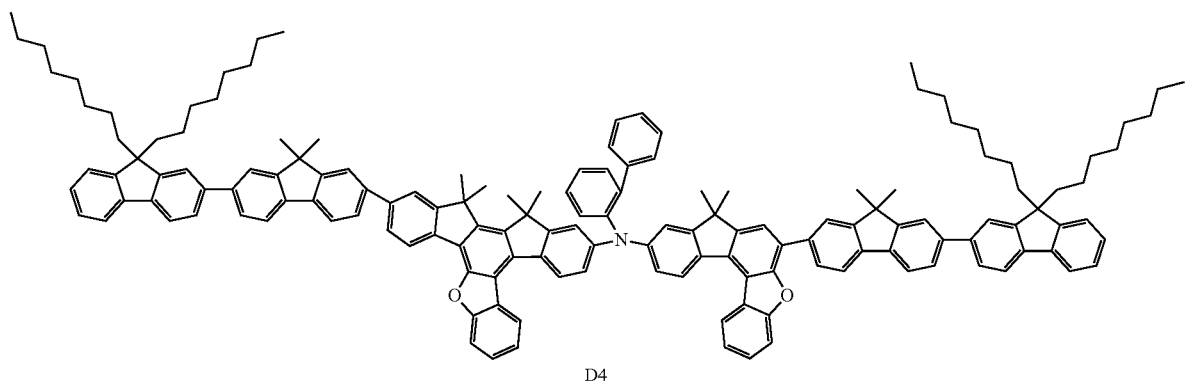

D4

The materials for the hole-blocking layer and electron-transport layer are likewise applied by thermal vapour deposition in a vacuum chamber and are shown in table B. The hole-blocking layer (HBL) consists of ETM. The electron-transport layer (ETL) consists of the two materials ETM and LiQ, which are mixed with one another in a proportion by volume of 50% each by co-evaporation. The cathode is formed by the thermal evaporation of an aluminium layer with a thickness of 100 nm.

TABLE B

Structural formulae of vapor processed OLED materials

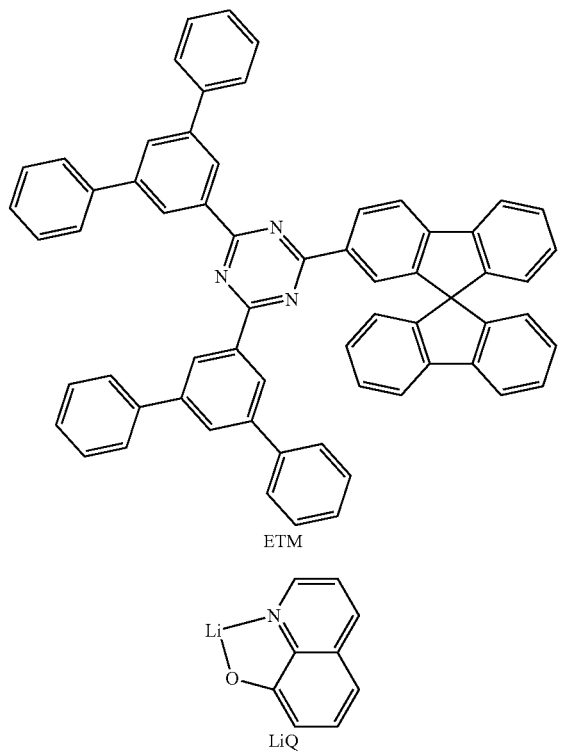

ETM

LiQ

The OLEDs are characterised by standard methods. For this purpose, the electroluminescence spectra are recorded, the current efficiency (measured in cd/A) and the external quantum efficiency (EQE, measured in percent) as a function of the luminous density assuming Lambert emission characteristics are calculated from current/voltage/luminous density characteristic lines (IUL characteristic lines). The electroluminescence spectra are recorded at a luminous density of 1000 cd/m$^2$, and the CIE 1931 x and y colour coordinates are calculated from this data. The term EQE1000 denotes the external quantum efficiency at an operating luminous density of 1000 cd/m$^2$.

The properties of the various OLEDs are summarised in table C. Examples V1 and V2 are the comparative examples, whereas E3 to E6 show properties of OLEDs containing materials of the present invention.

TABLE C

Device data of solution processed OLEDs

| Example | EML host | EML dopant | EQE1000 [%] | CIE x/y |
|---|---|---|---|---|
| V1 | H | SdT1 | 1.9 | 0.15/0.05 |
| V2 | H | SdT2 | 2.6 | 0.16/0.08 |
| E3 | H | D1 | 3.9 | 0.14/0.13 |
| E4 | H | D2 | 4.2 | 0.14/0.14 |
| E5 | H | D3 | 3.7 | 0.14/0.12 |
| E6 | H | D4 | 4.9 | 0.14/0.15 |

Table C shows that use of materials (D1 to D4) according to the present invention give rise to improvements over the prior art (SdT1 and SdT2) when used as fluorescent blue emitters, in particular with respect to efficiency.

The invention claimed is:
1. A compound of the formula (1),

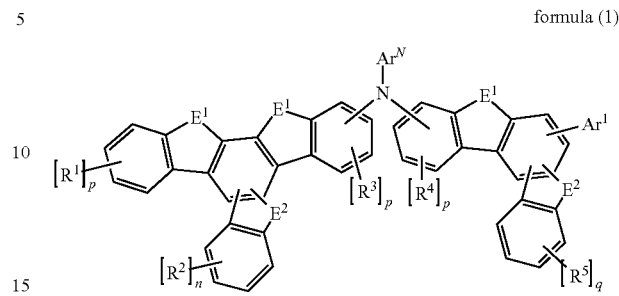

formula (1)

where the following applies to the symbols and indices used:

Ar$^1$, Ar$^N$ are on each occurrence, identically or differently, selected from an aromatic or heteroaromatic ring system having 5 to 60 aromatic ring atoms, which may in each case be substituted by one or more radicals R;

E$^1$ is on each occurrence, identically or differently, selected from —BR$^0$—, —C(R$^0$)$_2$—, —C(R$^0$)$_2$—C(R$^0$)$_2$—, —C(R$^0$)$_2$—O—, —C(R$^0$)$_2$—S—, —R$^0$C=CR$^0$—, —R$^0$C=N—, Si(R$^0$)$_2$, —Si(R$^0$)$_2$—Si(R$^0$)$_2$—, —C(=O)—, —C(=NR$^0$)—, —C(=C(R$^0$)$_2$)—, —O—, —S—, —S(=O)—, —SO$_2$—, —N(R$^0$)—, —P(R$^0$)— and —P((=O)R$^0$)—; or E$^1$ is a group of formula (E-1),

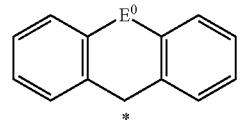

formula (E-1)

where the symbol * in formula (E-1) indicates the corresponding group E$^1$ in formula (1); and E$^0$ is identically or differently on each occurrence, selected from the group consisting of a single bond, —BR$^0$—, —C(R$^0$)$_2$—, —C(R$^0$)$_2$—C(R$^0$)$_2$—, —C(R$^0$)$_2$—O—, —C(R$^0$)$_2$—S—, —R$^0$C=CR$^0$—, —R$^0$C=N—, Si(R$^0$)$_2$, —Si(R$^0$)$_2$—Si(R$^0$)$_2$—, —C(=O)—, —C(=NR$^0$)—, —C(=C(R$^0$)$_2$)—, —O—, —S—, —S(=O)—, —SO$_2$—, —N(R$^0$)—, —P(R$^0$)— and —P((=O)R$^0$)—;

E$^2$ is, identically or differently, on each occurrence, selected from the group consisting of —O—, —S—, —S(=O)— and —SO$_2$—;

R$^0$ to R$^5$ stand on each occurrence, identically or differently, for H, D, F, Cl, Br, I, CHO, CN, N(Ar)$_2$, C(=O)Ar, P(=O)(Ar)$_2$, S(=O)Ar, S(=O)$_2$Ar, NO$_2$, Si(R)$_3$, B(OR)$_2$, OSO$_2$R, a straight-chain alkyl, alkoxy or thioalkyl group having 1 to 40 C atoms or branched or cyclic alkyl, alkoxy or thioalkyl group having 3 to 40 C atoms, each of which may be substituted by one or more radicals R, where in each case one or more non-adjacent CH$_2$ groups may be replaced by RC=CR, C≡C, Si(R)$_2$, Ge(R)$_2$, Sn(R)$_2$, C=O, C=S, C=Se, P(=O)(R), SO, SO$_2$, O, S or CONR and where one or more H atoms may be replaced by D, F, Cl, Br, I, CN or NO$_2$, an aromatic or heteroaromatic ring system having 5 to 60 aromatic ring atoms, which may in each case be substituted by one or more radicals R, or an aryloxy group having 5 to 60 aromatic ring atoms, which may be substituted by one or more radicals R, where two adjacent substituents $R^0$, and/or two adjacent substituents $R^1$, and/or two adjacent substituents $R^2$, and/or two adjacent substituents $R^3$, and/or two adjacent substituents $R^4$, and/or two adjacent substituents $R^5$ may form a mono- or polycyclic, aliphatic ring system or aromatic ring system, which may be substituted by one or more radicals R;

m, n, q stand on each occurrence, identically or differently, for an integer selected from 0, 1, 2, 3 or 4;

p stands on each occurrence, identically or differently, for an integer selected from 0, 1, 2 or 3;

R stands on each occurrence, identically or differently, for H, D, F, Cl, Br, I, CHO, CN, N(Ar)$_2$, C(=O)Ar, P(=O)(Ar)$_2$, S(=O)Ar, S(=O)$_2$Ar, NO$_2$, Si(R')$_3$, B(OR')$_2$, OSO$_2$R—, a straight-chain alkyl, alkoxy or thioalkyl group having 1 to 40 C atoms or branched or cyclic alkyl, alkoxy or thioalkyl group having 3 to 40 C atoms, each of which may be substituted by one or more radicals R', where in each case one or more non-adjacent CH$_2$ groups may be replaced by R'C=CR', C≡C, Si(R')$_2$, Ge(R')$_2$, Sn(R')$_2$, C=O, C=S, C=Se, P(=O)(R'), SO, SO$_2$, O, S or CONR' and where one or more H atoms may be replaced by D, F, Cl, Br, I, CN or NO$_2$, an aromatic or heteroaromatic ring system having 5 to 60 aromatic ring atoms, which may in each case be substituted by one or more radicals R', or an aryloxy group having 5 to 60 aromatic ring atoms, which may be substituted by one or more radicals R', where two adjacent substituents R may form a mono- or polycyclic, aliphatic ring system or aromatic ring system, which may be substituted by one or more radicals R';

Ar is an aromatic or heteroaromatic ring system having 5 to 24 aromatic ring atoms, which may in each case also be substituted by one or more radicals R';

R' stands on each occurrence, identically or differently, for H, D, F, Cl, Br, I, CN, a straight-chain alkyl, alkoxy or thioalkyl group having 1 to 20 C atoms or branched or cyclic alkyl, alkoxy or thioalkyl group having 3 to 20 C atoms, where in each case one or more non-adjacent CH$_2$ groups may be replaced by SO, SO$_2$, O, S and where one or more H atoms may be replaced by D, F, Cl, Br or I, or an aromatic or heteroaromatic ring system having 5 to 24 C atoms.

2. The compound according to claim 1, wherein $Ar^N$ stands for phenyl, biphenyl, fluorene, spirobifluorene, naphthalene, phenanthrene, dibenzofuran, dibenzothiophene, carbazole, pyridine, pyrimidine, pyrazine, pyridazine, triazine, benzopyridine, benzopyridazine, benzopyrimidine or quinazoline, or for a combination of two to six of these groups, each of which may be substituted by one or more radicals R, where R has the same definition as in claim 1.

3. The compound according to claim 1, wherein $Ar^N$ stands for phenyl, biphenyl, fluorene, naphthalene, phenanthrene, dibenzofuran, dibenzothiophene, carbazole, or for a combination of two to six of these groups, each of which may be substituted by one or more radicals R, where R has the same definition as in claim 1.

4. The compound according to claim 1, wherein the compound is selected from selected from compounds of formula (2),

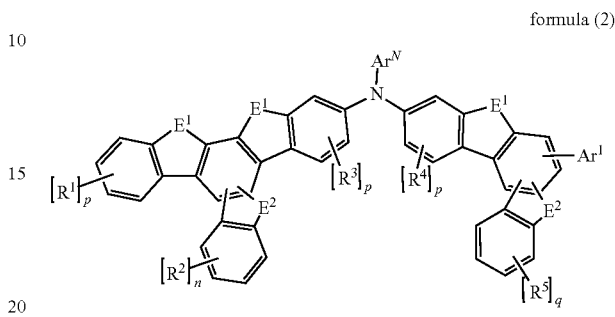

formula (2)

where the symbols $Ar^N$, $E^1$, $E^2$, $Ar^1$, $R^1$ to $R^5$ and the indices m, n, p and q have the same meaning as in claim 1.

5. The compound according to claim 1, wherein the compound is selected from compounds of formula (3),

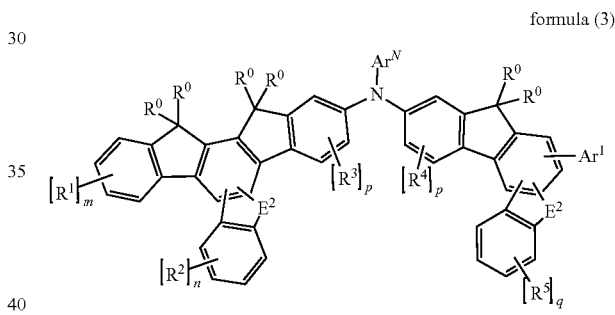

formula (3)

where the symbols $Ar^N$, $E^2$, $Ar^1$, $R^0$, $R^1$ to $R^5$ and the indices m, n, p and q have the same meaning as in claim 1.

6. The compound according to claim 1, wherein the compound is selected from the compounds of formula (4),

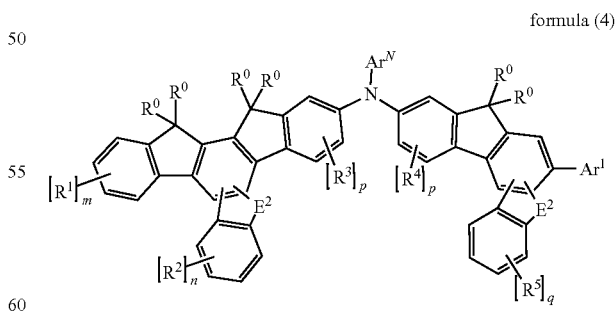

formula (4)

where the symbols $Ar^N$, $E^2$, $Ar^1$, $R^0$, $R^1$ to $R^5$ and the indices m, n, p and q have the same meaning as in claim 1.

7. The compound according to claim 1, wherein the compound is selected from the compounds of formula (4-1) to (4-4),

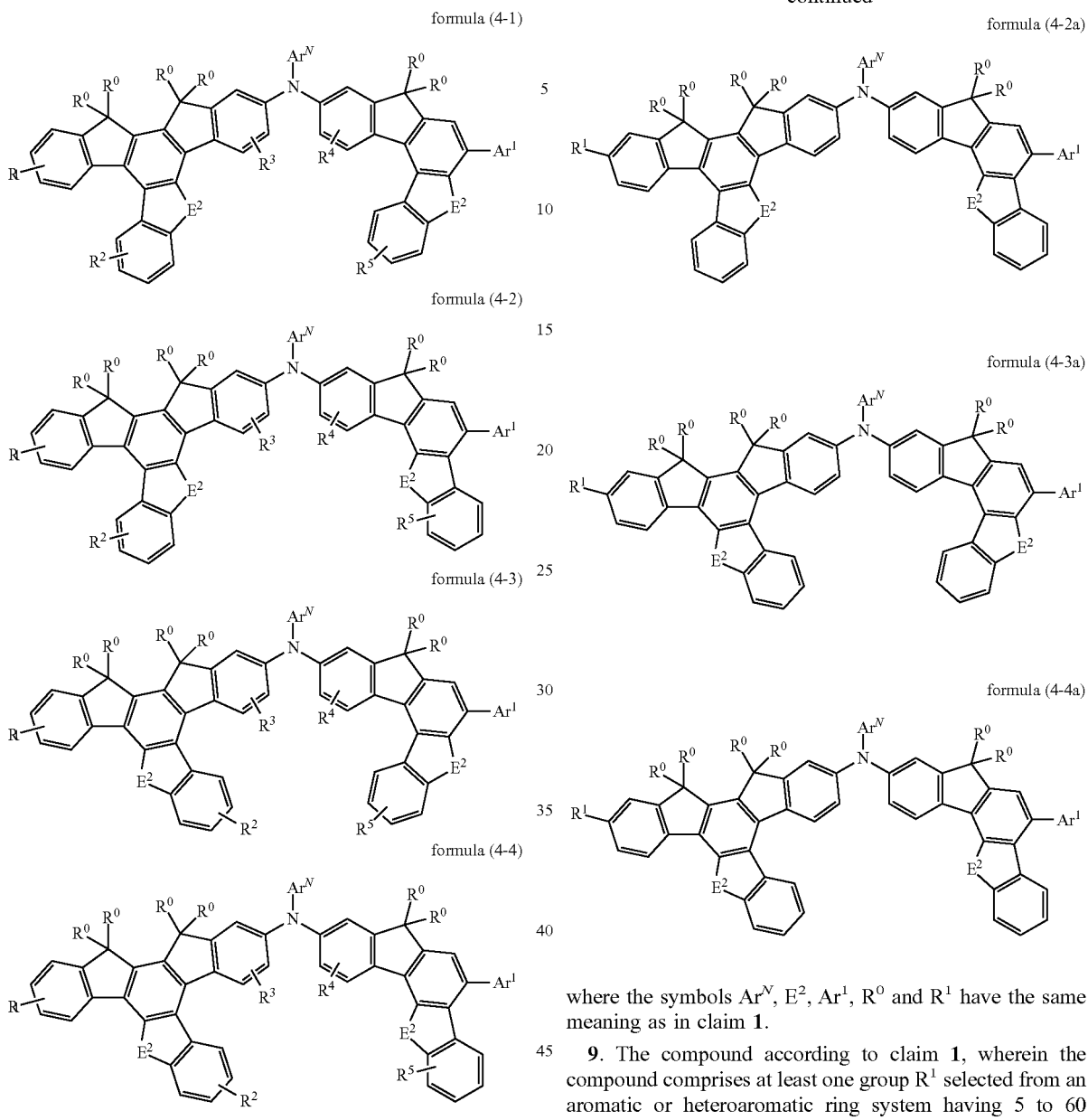

where the symbols $Ar^N$, $E^2$, $Ar^1$, $R^0$, $R^1$ to $R^5$ have the same meaning as in claim 1.

8. The compound according to claim 1, wherein the compound is selected from formulae (4-1a) to (4-4a), where the symbols $Ar^N$, $E^2$, $Ar^1$, $R^0$ and $R^1$ have the same meaning as in claim 1.

9. The compound according to claim 1, wherein the compound comprises at least one group $R^1$ selected from an aromatic or heteroaromatic ring system having 5 to 60 aromatic ring atoms.

10. The compound according to according claim 1, wherein the compound is selected from formulae (4-1b) to (4-4b),

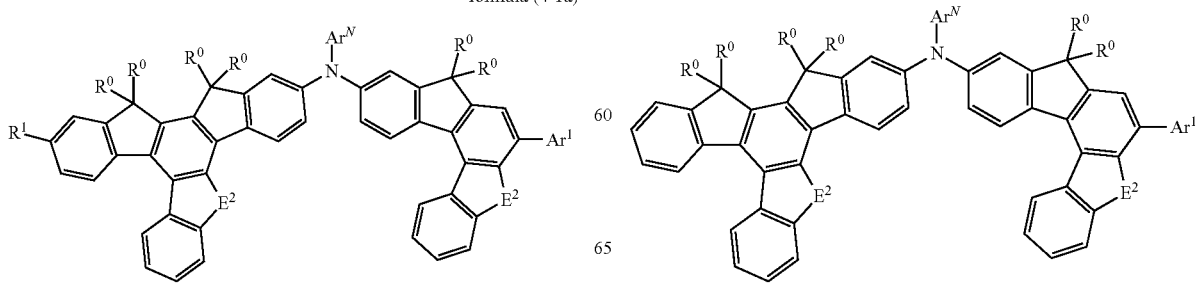

-continued formula (4-2b)

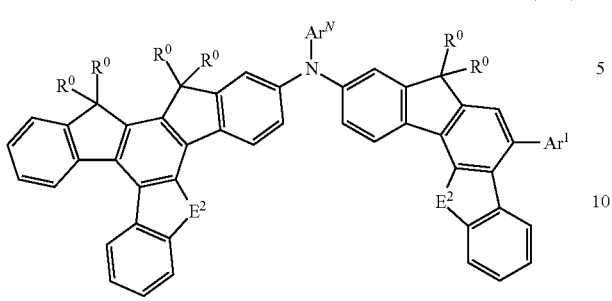

formula (4-3b)

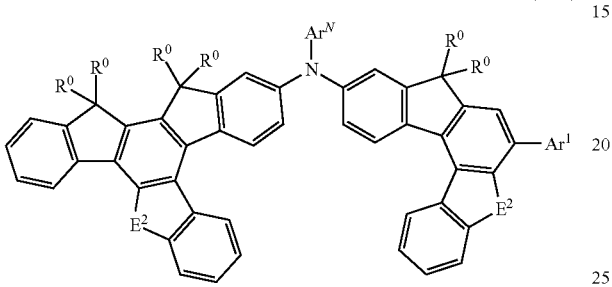

formula (4-4b)

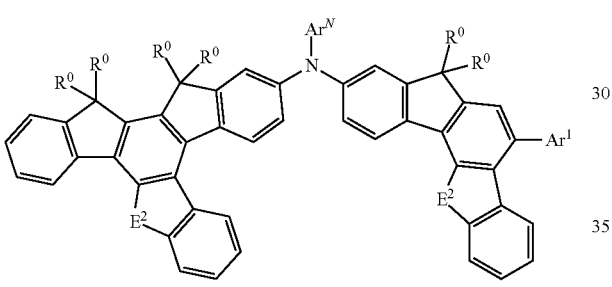

where the symbols Ar$^N$, E$^2$, Ar$^1$ and R$^0$ have the same meaning as in claim 1.

11. The compound according to claim 1, wherein E$^2$ stands for O.

12. The compound according to claim 1, wherein Ar$^1$ stands on each occurrence, identically or differently, for phenyl, biphenyl, fluorene, spirobifluorene, naphthalene, phenanthrene, dibenzofuran, dibenzothiophene, carbazole, pyridine, pyrimidine, pyrazine, pyridazine, triazine, benzopyridine, benzopyridazine, benzopyrimidine, quinazoline, each of which may be substituted by one or more radicals R, or for a combination of two to six of these groups, each of which may be substituted by one or more radicals R, where R has the same meaning as in claim 1.

13. The compound according to claim 1, wherein Ar$^1$ stands on each occurrence, identically or differently, for an aromatic or heteroaromatic ring system selected from phenyl, biphenyl, fluorene or naphthalene, each of which may be substituted by one or more radicals R, or for a combination of two to six groups selected from phenyl, biphenyl, fluorene or naphthalene, each of which may be substituted by one or more radicals R, where R has the same meaning as in claim 1.

14. The compound according to claim 1, wherein Ar$^1$ is selected from the groups of formulae (Ar1-1) to (Ar1-22),

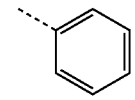 (Ar1-1)

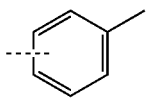 (Ar1-2)

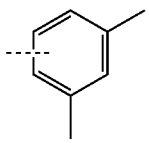 (Ar1-3)

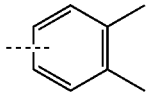 (Ar1-4)

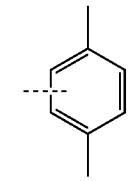 (Ar1-5)

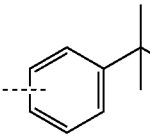 (Ar1-6)

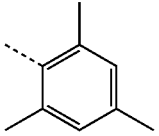 (Ar1-7)

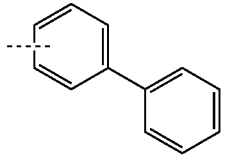 (Ar1-8)

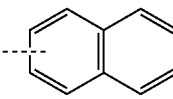 (Ar1-9)

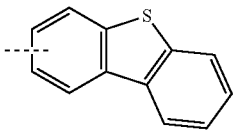 (Ar1-10)

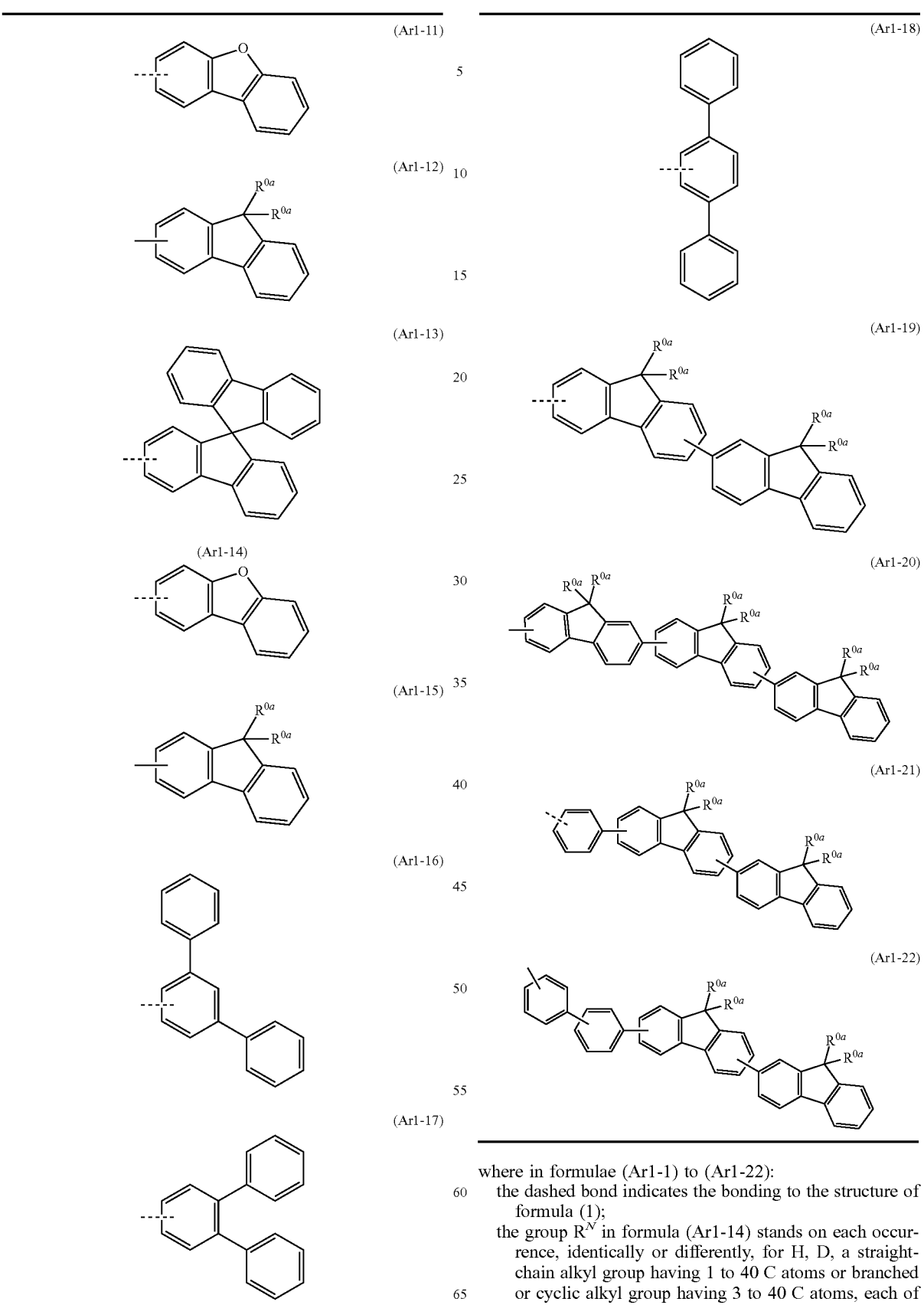

where in formulae (Ar1-1) to (Ar1-22):
the dashed bond indicates the bonding to the structure of formula (1);
the group $R^N$ in formula (Ar1-14) stands on each occurrence, identically or differently, for H, D, a straight-chain alkyl group having 1 to 40 C atoms or branched or cyclic alkyl group having 3 to 40 C atoms, each of which may be substituted by one or more radicals R, where in each case one or more non-adjacent $CH_2$ groups may be replaced by RC=CR, C=O, C=S, SO, SO$_2$, O or S, and where one or more H atoms may be replaced by D, F or CN, an aromatic or heteroaromatic ring system having 5 to 60 aromatic ring atoms, which may in each case be substituted by one or more radicals R, where two adjacent substituents $R^N$ may form a mono- or polycyclic, aliphatic ring system or aromatic ring system, which may be substituted by one or more radicals R, where R has the same meaning as in claim 1;

the group $R^{0a}$ in formulae (Ar1-12) and (Ar1-19) to (Ar1-22) has the same definition as the group $R^0$ as defined in claim 1;

the groups of formulae (Ar1-1) to (Ar1-22) may be substituted at each free position by a group R, which has the same meaning as in claim 1.

15. A polymer, oligomer or dendrimer containing one or more compounds according to claim 1, where the bond(s) to the polymer, oligomer or dendrimer may be localised at any positions in formula (1) which is substituted by $R^0$, $R^1$, $R^2$, $R^3$, $R^4$ or $R^5$.

16. A formulation comprising at least one compound according to claim 1 and at least one solvent.

17. An electronic device comprising at least one compound according to claim 1, wherein the device is selected from the group consisting of organic electroluminescent devices, organic integrated circuits, organic field-effect transistors, organic thin-film transistors, organic light-emitting transistors, organic solar cells, dye-sensitised organic solar cells, organic optical detectors, organic photoreceptors, organic field-quench devices, light-emitting electrochemical cells, organic laser diodes and organic plasmon emitting devices.

18. An organic electroluminescent device, which comprises the compound according to claim 1 is employed as a fluorescent emitter or as a matrix material for fluorescent emitters.

19. A formulation comprising at least one polymer, oligomer or dendrimer according to claim 15 and at least one solvent.

20. An electronic device comprising at least one polymer, oligomer or dendrimer according to claim 15, wherein the device is selected from the group consisting of organic electroluminescent devices, organic integrated circuits, organic field-effect transistors, organic thin-film transistors, organic light-emitting transistors, organic solar cells, dye-sensitised organic solar cells, organic optical detectors, organic photoreceptors, organic field-quench devices, light-emitting electrochemical cells, organic laser diodes and organic plasmon emitting devices.

21. The electronic device as claimed in claim 17, wherein the at least one compound is a blue-emitting emitter compound and is employed in an electron-transport layer and/or in electron-blocking or exciton-blocking layer and/or in a hole-transport layer in the device.

* * * * *